US011773445B1

(12) United States Patent
Marshall-Gradisnik et al.

(10) Patent No.: US 11,773,445 B1
(45) Date of Patent: Oct. 3, 2023

(54) DIAGNOSTIC METHODS

(71) Applicant: GRIFFITH UNIVERSITY, Brisbane (AU)

(72) Inventors: Sonya M. Marshall-Gradisnik, Brisbane (AU); Donald R. Staines, Brisbane (AU); Peter Kenneth Smith, Brisbane (AU)

(73) Assignee: GRIFFITH UNIVERSITY

( * ) Notice: Subject to any disclaimer, the term of this patent is extended or adjusted under 35 U.S.C. 154(b) by 257 days.

(21) Appl. No.: 15/570,628

(22) PCT Filed: Apr. 29, 2016

(86) PCT No.: PCT/AU2016/050313
§ 371 (c)(1),
(2) Date: Oct. 30, 2017

(87) PCT Pub. No.: WO2016/176726
PCT Pub. Date: Nov. 10, 2016

(30) Foreign Application Priority Data

May 1, 2015 (AU) ............................... 2015901567
Dec. 2, 2015 (AU) ............................... 2015904991
Apr. 20, 2016 (AU) ............................... 2016901468

(51) Int. Cl.
*C12Q 1/68* (2018.01)
*C12Q 1/6883* (2018.01)

(52) U.S. Cl.
CPC ...... *C12Q 1/6883* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS 7,888,497 B2    2/2011  Bentwich et al.
2006/0057564 A1 3/2006  Wang

FOREIGN PATENT DOCUMENTS

WO    WO2008/010082       1/2008
WO    WO2010/001419       1/2010
WO    WO 2010/097706 A2   9/2010
WO    WO2010/120746      10/2010

OTHER PUBLICATIONS

Nishizaki and Boyle; Trends Gent. 2017; vol. 33.*
Cabanas et al; Molecular Medicine; 25:14, 2019, pp. 1-15.*
Marshall-Gradisnik et al., "Examination of Single Nucleotide Polymorphisms in Acetylcholine Receptors in Chronic Fatigue Syndrome Patients," Immunology and Immunogenetics Insights. 7:7-20 (May 6, 2015).
Tam et al., "The Role of DNA Copy Number Variation in Schizophrenia," Biological Psychiatry 66:1005-1012 (Dec. 1, 2009) (available online Sep. 12, 2009).
N.N: "Demonstrates that rs4463655 is present on Affymetrix array SNP-5 and SNP-6," (Jan. 1, 2010).
Supplementary Partial European Search Report dated Sep. 25, 2018 for European Application No. EP 16788952.6.
A Scientific Review of Multiple Chemical Sensitivity: Identifying Key Research Needs Report prepared by the National Industrial Chemicals Notification and Assessment Scheme (NICNAS) and the Office of Chemical Safety and Environmental Health (OCSEH) (Nov. 2010).
Aaron LA, Burke MM, Buchwald D. Overlapping conditions among patients with chronic fatigue syndrome, fibromyalgia, and temporomandibular disorder. *Archives of internal medicine.* (Jan. 24, 2000);160(2):221-227.
Abbruscato TJ, Lopez SP, Mark KS, Hawkins BT, Davis TP. Nicotine and cotinine modulate cerebral microvascular permeability and protein expression of ZO-1 through nicotinic acetylcholine receptors expressed on brain endothelial cells. Journal of pharmaceutical sciences. (Jul. 3, 2002);91(12):2525-38. doi:10.1002/jps.10256.
Aboudiab T, Leke L, Skonieczny M, Chouraki JP. [Are IgE-independent food hypersensitivity and chronic fatigue syndrome related?]. Archives de pediatrie: organe officiel de la Societe francaise de pediatrie. (May 13, 2004); 11(8):975-7. doi:10.1016/j.arcped. 2004.05.012. PubMed PMID: 15288095.
Adachi T, Nakanishi M, Otsuka Y, Nishimura K, Hirokawa G, et al. Plasma microRNA 499 as a biomarker of acute myocardial infarction. Clin Chem (Jul. 2010); 56: 1183-1185.
Albuquerque EX, Pereira EF, Alkondon M and Rogers SW. Mammalian nicotinic acetylcholine receptors: from structure to function. *Physiological reviews.* (Jan. 2009); 89: 73-120.
Allantaz F, Cheng DT, Bergauer T, Ravindran P, Rossier MF, et al. Expression profiling of human immune cell subsets identifies miRNA-mRNA regulatory relationships correlated with cell type specific expression. PLoS One (Jan. 20, 2012); 7: e29979.

(Continued)

*Primary Examiner* — Jehanne S Sitton
(74) *Attorney, Agent, or Firm* — Perkins Coie LLP

(57) ABSTRACT

In one aspect the invention relates to the use of single nucleotide polymorphisms (SNPs) in transient receptor potential (TRP) ion channel, acetylcholine receptor (AchR) and/or adrenergic receptor (ADR) genes as probes, tools or reagents for identifying, screening, diagnosing, monitoring or managing/treating subjects with, or predisposed to, medical conditions (or symptoms thereof), such as chronic fatigue syndrome (CFS), myalgic encephalomyelitis (ME), Gulf war syndrome (GWS), irritable bowel syndrome (IBS), multiple chemical sensitivity (MCS), fibromyalgia, and migraine, as well as some medical conditions caused by dysregulation in calcium, acetylcholine, TRP and ADR, and dysregulation in the gastrointestinal, cardiovascular, neurological, genitourinary and immune systems. In another aspect the invention relates to methods, kits and assays for identifying, screening, diagnosing, monitoring or managing/treating subjects with one or more of those medical conditions or symptoms.

1 Claim, 19 Drawing Sheets

Specification includes a Sequence Listing.

(56) References Cited

OTHER PUBLICATIONS

Allen J, Murray A, Di Maria C, Newton JL. Chronic fatigue syndrome and impaired peripheral pulse characteristics on orthostasis—a new potential diagnostic biomarker. Physiological measurement. (Jan. 25, 2012); 33(2):231-41. doi:10.1088/0967-3334/33/2/231.

Alter G, Malenfant JM, Altfeld M. CD107a as a functional marker for the identification of natural killer cell activity. Journal of Immunological Methods. (Sep. 25, 2004);294(1-2):15-22. doi:10.1016/j.jim.2004.08.008.

Ambros V, Lee RC. Identification of microRNAs and other tiny noncoding RNAs by cDNA cloning. Methods Mol Biol (Feb. 2004); 265:131-138.

An J, Lai J, Lehman ML, Nelson CC. miRDeep: an integrated application tool for miRNA identification from RNA sequencing data. Nucleic Acids Res. (Dec. 4, 2012) ;41:727-737.

Anders S, Huber W. Differential expression analysis for sequence count data. Genome Biol (Oct. 27, 2010); 11: R106.

Andersson DA, Gentry C, Alenmyr L, Killander D, Lewis SE, Andersson A, et al. TRPA1 mediates spinal antinociception induced by acetaminophen and the cannabinoid Delta(9)-tetrahydrocannabiorcol. Nature communications. (Nov. 22, 2011); 2:551. doi: 10.1038/ncomms1559. PubMed PMID: 22109525.

Ansel KM. RNA regulation of the immune system. Immunol Rev (May 2013); 253: 5-11.

Aubry JP, Blaecke A, Lecoanet-Henchoz S, Jeannin P, Herbault N, Caron G et al. Annexin V used for measuring apoptosis in the early events of cellular cytotoxicity. Cytometry. (Jul. 29, 1999);37(3):197-204.

Badheka D, Borbiro I and Rohacs T. Transient receptor potential melastatin 3 is a phosphoinositide-dependent ion channel. *The Journal of General Physiology*. (May 21, 2015); 146: 65-77.

Badheka D, Borbiro I, Rohacs T (Feb. 9, 2015) Phosphoinositides as Co-Factors for the Ion Channel TRPM3. Biophysical Journal 108: 283a.

Banerjee K, Biswas PS, Rouse BT. Elucidating the protective and pathologic T cell species in the virus-induced corneal immunoinflammatory condition herpetic stromal keratitis. *Journal of leukocyte biology*. (Oct. 20, 2004);77(1):24-32.

Barbado M, Fablet K, Ronjat M, De Waard M. Gene regulation by voltage-dependent calcium channels.Biochim Biophys Acta. (Mar. 2009);1793(6):1096-104. doi:10.1016/j.bbamcr.2009.02.004. Epub Feb. 27, 2009. Review.

Barber DF, Faure M, Long EO. LFA-1 contributes an early signal for NK cell cytotoxicity. *Journal of immunology* (Baltimore, Md. : 1950). (Jul. 13, 2004);173(6):3653-3659.

Barker E, Fujimura SF, Fadem MB, Landay AL, Levy JA. Immunologic abnormalities associated with chronic fatigue syndrome. Clinical infectious diseases: an official publication of the Infectious Diseases Society of America. (Jan. 1994);18 Suppl 1: S136-41. PubMed PMID: 8148441.

Bautista DM, Pellegrino M, Tsunozaki M. TRPA1: A gatekeeper for inflammation. Annual review of physiology. (Sep. 27, 2012); 75:181-200. doi:10.1146/annurev-physiol-030212-183811. PubMed PMID: 23020579; PubMed Central PMCID: PMC4041114.

Beckmann J, Lips KS. The Non-Neuronal Cholinergic System in Health and Disease. Pharmacology. (Nov. 29, 2013); 92(5-6):286-302. doi:Doi 10.1159/000355835.

Bell DS. *The doctor's guide to chronic fatigue syndrome: understanding, treating, and living with CFIDS*. Da Capo Press; Chapters 1,2, 5, 6, 8 and 9 (1995).

Benhammou K, Lee M, Strook M, Sullivan B, Logel J, Raschen K et al. [H-3]nicotine binding in peripheral blood cells of smokers is correlated with the number of cigarettes smoked per day. Neuropharmacology. (Aug. 14, 2000);39(13):2818-29. doi:Doi10.1016/S0028-3908(00)00153-2.

Berridge MJ, Bootman MD, Roderick HL. Calcium signalling: dynamics, homeostasis and remodelling. Nature reviews Molecular cell biology. (Jul. 2003);4(7):517-29.

Berridge MJ. Elementary and global aspects of calcium signalling. *The Journal of physiology*. (1997);499(2):291-306.

Berthelsen S, Pettinger WA. A functional basis for classification of α-adrenergic receptors. Life sciences. (1977);21(5):595-606.

Blundell S, Ray KK, Buckland M, White PD. Chronic fatigue syndrome and circulating cytokines: A systematic review. *Brain, behavior, and immunity*. (Jul. 3, 2015);50:186-195.

Boeri M, Verri C, Conte D, Roz L, Modena P, et al. MicroRNA signatures in tissues and plasma predict development and prognosis of computed tomography detected lung cancer. Proc Natl Acad Sci U S A (Jan. 12, 2011); 108: 3713-3718.

Boysen NC, Dragon DN and Talman WT. Parasympathetic tonic dilatory influences on cerebral vessels. *Autonomic neuroscience : basic & clinical*. (Jan. 19, 2009); 147: 101-4.

Brann MR, Ellis J, Jørgensen H, Hill-Eubanks D and Jones SP. Muscarinic acetylcholine receptor subtypes: localization and structure/function. *Progress in brain research*. (1993); 98: 121-27.

Brenu EW, Ashton KJ, van Driel M, Staines DR, Peterson D, Atkinson GM, et al. Cytotoxic lymphocyte microRNAs as prospective biomarkers for Chronic Fatigue Syndrome/Myalgic Encephalomyelitis. Journal of affective disorders. (May 8, 2012); 141(2-3):261-9. doi: 10.1016/j.jad.2012.03.037. PubMed PMID: 22572093.

Brenu EW, Hardcastle SL, Atkinson GM, et al. Natural killer cells in patients with severe chronic fatigue syndrome. *Autoimmunity Highlights*. (Apr. 16, 2013);4(3):69-80.

Brenu EW, Huth TK, Hardcastle SL, et al. Role of adaptive and innate immune cells in chronic fatigue syndrome/myalgic encephalomyelitis. *International immunology*. (Dec. 16, 2013);26(4):233-242.

Brenu EW, Staines DR, Baskurt OK, Ashton KJ, Ramos SB, Christy RM et al. Immune and hemorheological changes in chronic fatigue syndrome. Journal of translational medicine. (Jan. 11, 2010); 8(1):1 -10. doi:10.1186/1479-5876-8-1.

Brenu EW, van Driel ML, Staines DR, Ashton KJ, Ramos SB, Keane J et al. Immunological abnormalities as potential biomarkers in Chronic Fatigue Syndrome/Myalgic Encephalomyelitis. Journal of translational medicine. (May 28, 2011); 9:81. doi:10.1186/1479-5876-9-81.

Brenu EW, van Driel ML, Staines DR, et al. Longitudinal investigation of natural killer cells and cytokines in chronic fatigue syndrome/myalgic encephalomyelitis. *Journal of translational medicine*. (May 9, 2012);10:88.

Broderick G, Fuite J, Kreitz A, Vernon SD, Klimas N, Fletcher Ma. A formal analysis of cytokine networks in chronic fatigue syndrome. Brain, behavior, and immunity. (Oct. 2010);24(7):1209-17. doi:10.1016/j.bbi.2010.04.012.

Brown MM, Jason LA. Functioning in individuals with chronic fatigue syndrome: increased impairment with co-occurring multiple chemical sensitivity and fibromyalgia. Dynamic medicine : DM. (May 31, 2007); 6:6. doi: 10.1186/1476-5918-6-6. PubMed PMID: 17540028; PubMed Central PMCID: PMC1890280.

Bruggmann D, Lips KS, Pfeil U, Haberberger RV, Kummer W. Rat arteries contain multiple nicotinic acetylcholine receptor alpha-subunits. *Life sciences*. (2003);72(18-19):2095-2099.

Brunet JL, Fatoohi F, Liaudet AP, Cozon GJ. [Role of pathological delayed-type hypersensitivity in chronic fatigue syndrome: importance of the evaluation of lymphocyte activation by flow cytometry and the measurement of urinary neopterin]. Allergie et immunologie. (Mar. 2002); 34(2):38-44. PubMed PMID: 11933752.

Bryceson YT, Chiang SC, Darmanin S, Fauriat C, Schlums H, Theorell J et al. Molecular mechanisms of natural killer cell activation. J Innate Immun. (Mar. 29, 2011);3(3):216-26. doi:10.1159/000325265.

Bryceson YT, March ME, Barber DF, Ljunggren HG, Long EO. Cytolytic granule polarization and degranulation controlled by different receptors in resting NK cells. The Journal of Experimental Medicine. (Oct. 3, 2005);202(7):1001-12. doi:10.1084/jem.20051143.

Bryceson YT, March ME, Ljunggren H-G, Long EO. Activation, coactivation, and costimulation of resting human natural killer cells. *Immunological reviews*. (2006);214(1):73-91.

(56) References Cited

OTHER PUBLICATIONS

Bryceson YT, March ME, Ljunggren HG, Long EO. Synergy among receptors on resting NK cells for the activation of natural cytotoxicity and cytokine secretion. *Blood.* (Jan. 1, 2006);107(1):159-166.

Caligiuri MA. Human natural killer cells. *Blood.* (Aug. 1, 2008);112(3):461-469.

Cannons JL, Qi H, Lu KT, Dutta M, Gomez-Rodriguez J, et al. Optimal germinal center responses require a multistage T cell:B cell adhesion process involving integrins, SLAM-associated protein, and CD84. Immunity (Feb. 26, 2010); 32: 253-265.

Caraux A, Kim N, Bell SE, et al. Phospholipase C-{gamma}2 is essential for NK cell cytotoxicity and innate immunity to malignant and virally infected cells. *Blood.* (Feb. 1, 2006);107(3):994-1002.

Carreno, O. et al., "SNP variants within the vanilloid TRPV1 and TRPV3 receptor genes are associated with migraine in the Spanish population", American Journal of Medical Genetics Part B: Neuropsychiatric Genetics, (20120000), vol. 159B, No. 1, pp. 94-103 (Dec. 7, 2011).

Carruthers BM, van de Sande MI, De Meirleir KL, Klimas NG, Broderick G, et al. Myalgic encephalomyelitis: International Consensus Criteria. J Intern Med (Aug. 22, 2011); 270: 327-338.

Carruthers BM. Definitions and aetiology of myalgic encephalomyelitis: how the Canadian consensus clinical definition of myalgic encephalomyelitis works. Journal of clinical pathology. (Aug. 25, 2006);60(2):117-9. PubMed PMID: 16935963. Pubmed Central PMCID: 1860613.

Carruthers et al. Myalgic Encephalomyelitis/Chronic Fatigue Syndrome: A Clinical Case Definition and Guidelines for Medical Practitioners. An Overview of the Canadian Consensus Document. Journal of Chronic Fatigue Syndrome. (May 17, 2002);11 (1):7-36.

Cartegni L, Krainer AR. Correction of disease-associated exon skipping by synthetic exon-specific activators. Nature structural biology. (Jan. 13, 2003);10(2): 120-5. doi:10.1038/nsb887.

Caseras X, Mataix-Cols D, Giampietro V, Rimes KA, Brammer M, Zelaya F, et al. Probing the working memory system in chronic fatigue syndrome: a functional magnetic resonance imaging study using the n-back task. Psychosomatic medicine. (Nov. 1, 2006); 68(6):947-55. doi: 10.1097/01.psy.0000242770.50979.5f.PubMed PMID: 17079703.

Caseras X, Mataix-Cols. D, Rimes KA, et al. The neural correlates of fatigue: an exploratory imaginal fatigue provocation study in chronic fatigue syndrome. *Psychological medicine.* (Apr. 30, 2008);38(7):941-951.

Chan A, Hong DL, Atzberger A, Kollnberger S, Filer AD, Buckley CD et al. CD56bright human NK cells differentiate into CD56dim cells: role of contact with peripheral fibroblasts. J Immunol. (Apr. 18, 2007);179(1):89-94.

Changeux J, Edelstein SJ. Allosteric mechanisms in normal and pathological nicotinic acetylcholine receptors. Current opinion in neurobiology. (2001);11(3):369-77.

Changeux JP. The nicotinic acetylcholine receptor: the founding father of the pentameric ligand-gated ion channel superfamily. *The Journal of biological chemistry.* (Nov. 23, 2012); 287: 40207-15.

Chattopadhyay PK, Betts MR, Price DA, Gostick E, Horton H, Roederer M et al. The cytolytic enzymes granyzme A, granzyme B, and perforin: expression patterns, cell distribution, and their relationship to cell maturity and bright CD57 expression. Journal of leukocyte biology. (Aug. 26, 2008);85(1):88-97. doi:10.1189/jlb. 0208107.

Chen CZ, Schaffert S, Fragoso R, Loh C. Regulation of immune responses and tolerance: the microRNA perspective. Immunol Rev (May 2013); 253: 112-128.

Chen et al. Recent progress in α1-adrenergic receptor research. Acta pharmacologica Sinica. (Aug. 28, 2005);26(11):1281-7.

Chen X, Ba Y, Ma L, Cai X, Yin Y, et al. Characterization of microRNAs in serum: a novel class of biomarkers for diagnosis of cancer and other diseases. Cell Res (Sep. 2, 2008);18: 997-1006.

Chen X, Guo X, Zhang H, Xiang Y, Chen J, et al. Role of miR-143 targeting KRAS in colorectal tumorigenesis. Oncogene (Mar. 12, 2009); 28: 1385-1392.

Chen X, Trivedi PP, Ge B, Krzewski K, Stromingcr JL. Many NK cell receptors activate ERK2 and JNK1 to trigger microtubule organizing center and granule polarization and cytotoxicity. *Proceedings of the National Academy of Sciences of the United States of America.* (Apr. 10, 2007);104(15):6329-6334.

Cheng HH, Yi HS, Kim Y, Kroh EM, Chien JW, et al. Plasma Processing Conditions Substantially Influence Circulating microRNA Biomarker Levels. PLoS One (Jun. 7, 2013);8: e64795.

Chen-Izu Y, Xiao R-P, Izu LT, Cheng H, Kuschel M, Spurgeon H, et al. G i-dependent localization of β 2-adrenergic receptor signaling to L-type Ca 2+ channels. Biophysical journal. (Jul. 31, 2000);79(5):2547-56.

Chiang V S-C. Post-harvest consideration factors for microRNA research in cellular, tissue, serum and plasma samples. Cell Biology International (Jul. 31, 2014); 38(12): 1345-54.

Chuderland D, Seger R. Calcium regulates ERK signaling by modulating its protein-protein interactions. *Communicative & Integrative Biology.* (Jun. 9, 2008);1(1):4-5.

Clapham DE. TRP channels as cellular sensors. Nature. (Dec. 4, 2003);426(6966):517-24. doi: 10.1038/nature02196. PubMed PMID: 14654832.

Colomer J, Means AR. Physiological roles of the Ca2+/CaM-dependent protein kinase cascade in health and disease. *Sub-cellular biochemistry.* (2007);45:169-214.

Colsoul B, Nilius B, Vennekens R. On the putative role of transient receptor potential cation channels in asthma. Clinical and experimental allergy : journal of the British Society for Allergy and Clinical Immunology. (2009);39(10):1456-66. PubMed PMID: 19624522.

Colsoul B, Nilius B, Vennekens R. Transient receptor potential (TRP) cation channels in diabetes. Curr Top Med Chem. (2013);13(3):258-69. PubMed PMID: 23432059.

Colsoul B, Vennekens R, Nilius B. Transient receptor potential cation channels in pancreatic beta cells. Reviews of physiology, biochemistry and pharmacology. (Jul. 2011); 161:87-110. doi: 10.1007/112_2011_2. PubMed PMID: 21744203.

Commins SP, Borish L, Steinke JW. Immunologic messenger molecules: cytokines, interferons, and chemokines. *The Journal of allergy and clinical immunology.*(Jul. 10, 2009);125(2 Suppl 2):S53-72.

Conti-Fine BM, Navaneetham D, Lei S, Maus AD. Neuronal nicotinic receptors in non-neuronal cells: new mediators of tobacco toxicity? European journal of pharmacology. (Jan. 21, 2000);393(1-3):279-94.

Cooper MA, Fehniger TA, Caligiuri MA. The biology of human natural killer-cell subsets. vol. 22. England: Elsevier Ltd; (Nov. 2001):633-640.

Cooper MA, Fehniger TA, Turner SC, Chen KS, Ghaheri BA, Ghayur T et al. Human natural killer cells: a unique innate immunoregulatory role for the CD56(bright) subselt. Blood. (May 15, 2001);97(10):3146-51.

Correa SA, Eales KL. The Role of p38 MAPK and Its Substrates in Neuronal Plasticity and Neurodegenerative Disease. Journal of signal transduction. (May 10, 2012);2012:649079.doi:10.1155/2012/649079.

Court JA, Martin-Ruiz C, Graham A and Perry E. Nicotinic receptors in human brain: topography and pathology. *Journal of chemical neuroanatomy.* (Sep. 11, 2000); 20: 281-98.

Crawford DJ, Hoskins AA, Friedman LJ, Gelles J, Moore MJ. Single-molecule colocalization FRET evidence that spliceosome activation precedes stable approach of 5' splice site and branch site. Proceedings of the National Academy of Sciences of the United States of America. (Apr. 23, 2013);110(17):6783-8. doi:10.1073/pnas.1219305110.

Crawford MH, Banerjee P, Demarchi DA, et al. Applications of pooled DNA samples to the assessment of population affinities: short tandem repeats. *Human biology.* (Nov. 8, 2005);77(6):723-733.

Crotty S, Johnston RJ, Schoenberger SP. Effectors and memories: Bcl-6 and Blimp-1 in T and B lymphocyte differentiation. Nat Immunol (Jan. 19, 2010); 11: 114-120.

(56) References Cited

OTHER PUBLICATIONS

Cuenda A, Rousseau S. p38 MAP-kinases pathway regulation, function and role in human diseases. Biochimica et biophysica acta. (Mar. 24, 2007);1773(8):1358-75. doi:10.1016/j.bbamcr.2007.03.010.

Curriu M, Carrillo J, Massanella M, Rigau J, Alegre J, Puig J et al. Screening NK-, B- and T-cell phenotype and function in patients suffering from Chronic Fatigue Syndrome. Journal of translational medicine. (Mar. 20, 2013);11:68. doi:10.1186/1479-5876-11-68.

D'Alessandra Y, Devanna P, Limana F, Straino S, Di Carlo A, et al. Circulating microRNAs are new and sensitive biomarkers of myocardial infarction. Eur Heart J (Jun. 9, 2010); 31: 2765-2773.

De Azua IR, Gautam D, Jain S, Guettier J-M and Wess J. Critical metabolic roles of β-cell M 3 muscarinic acetylcholine receptors. *Life sciences.* (Nov. 27, 2012); 91: 986-91.

De Guire V, Robitaille R, Tetreault N, Guerin R, Menard C, et al. Circulating miRNAs as sensitive and specific biomarkers for the diagnosis and monitoring of human diseases: promises and challenges. Clin Biochem (Apr. 3, 2013); 46: 846-860.

De Petrocellis L, Vellani V, Schiano-Moriello A, Marini P, Magherini PC, Orlando P, et al. Plant-derived cannabinoids modulate the activity of transient receptor potential channels of ankyrin type-1 and melastatin type-8. The Journal of pharmacology and experimental therapeutics. (Mar. 18, 2008); 325(3):1007-15. doi:10.1124/jpet.107.134809. PubMed PMID: 18354058.

DeLuca J, Johnson SK, Beldowicz D, Natelson BH. Neuropsychological impairments in chronic fatigue syndrome, multiple sclerosis, and depression. Journal of neurology, neurosurgery, and psychiatry. (Jan. 1, 1995); 58(1):38-43.

Dinan TG, Clarke G, Quigley EM, Scott LV, Shanahan F, Cryan J et al. Enhanced cholinergic-mediated increase in the pro-inflammatory cytokine IL-6 in irritable bowel syndrome: role of muscarinic receptors. The American journal of gastroenterology. (Jan. 22, 2008);103(10):2570-6. doi:10.1111/j.1572-0241.2008.01871.x.

D'Incamps BL and Ascher P. High affinity and low affinity heteromeric nicotinic acetylcholine receptors at central synapses. *The Journal of physiology.* (May 16, 2014); 592: 4131-6.

Ding S, Liang Y, Zhao M, Liang G, Long H, et al. Decreased microRNA-142-3p/5p expression causes CD4+ T cell activation and B cell hyperstimulation in systemic lupus erythematosus. Arthritis Rheum (Sep. 2012) 64: 2953-2963.

Dolmetsch RE, Xu K and Lewis RS. Calcium oscillations increase the efficiency and specificity of gene expression. *Nature.* (Feb. 12, 1998); 392: 933-6.

Domaica CI, Fuertes MB, Uriarte I, Girart MV, Sardanons J, Comas DI et al. Human natural killer cell maturation defect supports in vivo CD56(bright) to CD56(dim) lineage development. PloS one. (Dec. 11, 2012);7(12):e51677. doi:10.1371/journal.pone.0051677.

Dorn GW, 2nd, Force T. Protein kinase cascades in the regulation of cardiac hypertrophy. *The Journal of clinical investigation.* (Mar. 2005);115(3):527-537.

Drews A, Mohr F, Rizun O, Wagner TF, Dembla S, Rudolph S, et al. Structural requirements of steroidal agonists of transient receptor potential melastatin 3 (TRPM3) cation channels. British journal of pharmacology. (Nov. 13, 2013); 171(4):1019-32. doi: 10.1111/bph.12521. PubMed PMID: 24251620; PubMed Central PMCID: PMC3925040.

Dustin ML, Long EO. Cytotoxic immunological synapses. Immunological reviews. May 2010;235(1):24-34. PubMed PMID: 20536553. Pubmed Central PMCID: Pmc2950621. (2010) Epub Jun. 12, 2010. eng.

Duttagupta R, Jiang R, Gollub J, Getts RC, Jones KW. Impact of cellular miRNAs on circulating miRNA biomarker signatures. PLoS One (Jun. 17, 2011) 6: e20769.

Duttagupta R, Jones KW. The curious case of miRNAs in circulation: potential diagnostic biomarkers? Wiley Interdiscip Rev RNA (Nov. 8, 2012); 4: 129-138.

Elhusseiny A, Hamel E. Muscarinic- but not nicotinic-acetylcholine receptors mediate a nitric oxide-dependent dilation in brain cortical arterioles: a possible role for the M5 receptor subtype. Journal of cerebral blood flow and metabolism : official journal of the International Society of Cerebral Blood Flow and Metabolism. (Feb. 1, 2000); 20(2):298-305. doi:10.1097/00004647-200002000-00011.

Elwary SMA, Hasse S, Schallreuter KU. M2 muscarinic acetylcholine receptor (mAchR) subtype is present in human epidermal keratinocytes in situ and in vitro. Journal of Investigative Dermatology. (Jul. 26, 2004);123(6):1206-7. doi:DOI10.1111/j.0022-202X.2004.23493.x.

Ensembl. Human assembly and gene annotation. (Dec. 2017) (http://uswest.ensembl.org/Homo_sapiens/Info/Annotation) Accessed Apr. 17, 2015.

Fan Y-y, Yang B-y, Wu C-y. Phenotypically and functionally distinct subsets of natural killer cells in human PBMCs. *Cell Biology International.* (Aug. 27, 2007);32(2):188-197.

Fedor MJ. Alternative splicing minireview series: combinatorial control facilitates splicing regulation of gene expression and enhances genome diversity. The Journal of biological chemistry. (Jan. 18, 2008);283(3):1209-10. doi:10.1074/jbc.R700046200.

Felder CC, Bymaster FP, Ward J and DeLapp N. Therapeutic opportunities for muscarinic receptors in the central nervous system. *Journal of medicinal chemistry.* (Nov. 16, 2000); 43: 4333-53.

Felder CC. Muscarinic acetylcholine receptors: signal transduction through multiple effectors. *FASEB journal: official publication of the Federation of American Societies for Experimental Biology.* (May 20, 2014); 9: 619-25.

Fernandez-Sola J, Lluis Padierna M, Nogue Xarau S, Munne Mas P. [Chronic fatigue syndrome and multiple chemical hypersensitivity after insecticide exposure]. Medicina clinica. (Nov. 3, 2004); 124(12):451-3. PubMed PMID: 15826581.

Feske S, Wulff H, Skolnik EY. Ion channels in innate and adaptive immunity. Annu Rev Immunol. (2015);33:291-353. doi: 10.1146/annurev-immunol-032414-112212.

Finn, S. et al., "Expression microarray analysis of papillary thyroid carcinoma and benign thyroid tissue: emphasis on the follicular variant and potential markers of malignancy", Virchows Archiv, (20070000), vol. 450, No. 3, pp. 249-260 (Jan. 25, 2007).

Fischer MJ, Balasuriya D, Jeggle P, Goetze TA, McNaughton PA, Reeh PW, et al. Direct evidence for functional TRPV1/TRPA1 heteromers. Pflugers Archiv : European journal of physiology. (Mar. 2014);466(12):2229-41. doi: 10.1007/S00424-014-1497-z. PubMed PMID: 24643480.

Fletcher MA, Zeng XR, Barnes Z, Levis S, Klimas NG. Plasma cytokines in women with chronic fatigue syndrome. *Journal of translational medicine.* (Nov. 12, 2009);7:96.

Frampton D, Kerr J, Harrison TJ, Kellam P. Assessment of a 44 gene classifier for the evaluation of chronic fatigue syndrome from peripheral blood mononuclear cell gene expression. PLoS One (Mar. 2011); 6: e16872.

Freichel M, Tsvilovskyy V, Camacho-Londono JE. TRPC4- and TRPC4-containing channels. Handbook of experimental pharmacology. (Mar. 29, 2014); 222:85-128. doi: 10.1007/978-3-642-54215-2_5. PubMed PMID: 24756704.

Freud AG, Caligiuri MA. Human Natural Killer Cell Development. Immunological Reviews. (2006);214(1):56-72.

Frevel MA, Bakheet T, Silva AM, Hissong JG, Khabar KS, Williams BR. p38 Mitogen-activated protein kinase-dependent and -independent signaling of mRNA stability of AU-rich element-containing transcripts. Mol Cell Biol. (Oct. 2, 2002);23(2):425-36.

Friedlander MR, Chen W, Adamidi C, Maaskola J, Einspanier R, Knespel S, Rajewsky N. Discovering microRNAs from deep sequencing data using miRDeep. Nat Biotechnol (April 7, 2008); 26:407-415.

Friedlander MR, Mackowiak SD, Li N, Chen W, Rajewsky N. miRDeep2 accurately identifies known and hundreds of novel microRNA genes in seven animal clades. Nucleic Acids Res. (Sep. 12, 2011);40:37-52.

Frühwald J, Camacho Londoño J, Dembla S, et al. Alternative splicing of a protein domain indispensable for function of transient receptor potential melastatin 3 (TRPM3) ion channels. *The Journal of biological chemistry.* (Oct. 26, 2012);287(44):36663-36672.

Fujii T, Harada H, Koyama T, Nakajima Y, Kawashima K. Effects of physostigmine and calcium on acetylcholine efflux from the

(56) References Cited

OTHER PUBLICATIONS hippocampus of freely moving rats as determined by in vivo microdialysis and a radioimmunoassay. Neuroscience letters. (Jun. 17, 2000);289(3):181-184.

Fujii T, Kawashima K. An independent non-neuronal cholinergic system in lymphocytes. Japanese journal of pharmacology. (Aug. 28, 2000);85(1):11-15.

Fujii T, Kawashima K. Calcium signaling and c-Fos gene expression via M3 muscarinic acetylcholine receptors in human T- and B-cells. Japanese journal of pharmacology. (Jul. 3, 2000);84(2):124-132.

Fujii T, Kawashima K. YM905, a novel M3 antagonist, inhibits Ca2+ signaling and c-fos gene expression mediated via muscarinic receptors in human T cells. General pharmacology. (Jul. 1, 2001);35(2):71-75.

Fujii T, Takada-Takatori Y, Kawashima K. Regulatory mechanisms of acetylcholine synthesis and release by T cells. Life sciences. (Apr. 13, 2012);91(21-22):981-5. doi:10.1016/j.lfs.2012.04.031.

Fujii YX, Fujigaya H, Moriwaki Y, et al. Enhanced serum antigen-specific IgG1 and proinflammatory cytokine production in nicotinic acetylcholine receptor alpha7 subunit gene knockout mice. J Neuroimmunol. (Jul. 6, 2007); 189: 69-74.

Fukuchi M, Tabuchi A, Tsuda M. Transcriptional regulation of neuronal genes and its effect on neural functions: cumulative mRNA expression of PACAP and BDNF genes controlled by calcium and cAMP signals in neurons. Journal of pharmacological sciences. (May 12, 2005);98(3):212-8.

Fukuda K, Straus SE, Hickie I, Sharpe MC, Dobbins JG, Komaroff A. The chronic fatigue syndrome: a comprehensive approach to its definition and study. International Chronic Fatigue Syndrome Study Group. Annals of internal medicine. (Dec. 15, 1994);121(12):953-9. PubMed PMID: 7978722.

Furchgott RF. The classification of adrenoceptors (adrenergic receptors). An evaluation from the standpoint of receptor theory. Catecholamines: Springer; (1972). p. 283-335.

Gahring LC, Rogers SW. Neuronal nicotinic acetylcholine receptor expression and function on nonneuronal cells. The AAPS journal. (Jan. 13, 2006);7(4):E885-94. doi:10.1208/aapsj070486.

Garrison SR, Stucky CL. Contribution of transient receptor potential ankyrin 1 to chronic pain in aged mice with complete Freund's adjuvant-induced arthritis. Arthritis & rheumatology. (May 22, 2014); 66(9):2380-90. doi: 10.1002/art.38724. PubMed PMID: 24891324; PubMed Central PMCID: PMC4149259.

Garrison SR, Stucky CL. The dynamic TRPA1 channel: a suitable pharmacological pain target? Current pharmaceutical biotechnology. (Oct. 1, 2011); 12(10):1689-97. PubMed PMID: 21466445; PubMed Central PMCID: PMC3884818.

Gautam D, Han SJ, Hamdan FF, et al. A critical role for beta cell M3 muscarinic acetylcholine receptors in regulating insulin release and blood glucose homeostasis in vivo. Cell metabolism. (Jun. 6, 2006); 3: 449-61.

Gees M, Owsianik G, Nilius B, Voets T. TRP channels. Comprehensive Physiology. (Jan. 2012); 2(1):563-608. doi: 10.1002/cphy.c110026. PubMed PMID: 23728980.

Girod R, Crabtree G, Ernstrom G, Ramirez-Latorre J, McGehee D, Turner J et al. Heteromeric complexes of alpha 5 and/or alpha 7 subunits. Effects of calcium and potential role in nicotine-induced presynaptic facilitation. Annals of the New York Academy of Sciences. (1999);868:578-90.

Git A, Dvinge H, Salmon-Divon M, Osborne M, Kutter C, Hadfield J, Bertone P, Caldas C. Systematic comparison of microarray profiling, real-time PCR, and next-generation sequencing technologies for measuring differential microRNA expression. RNA (May 2010); 16:991-1006.

Gkirtzou et al., "MatureBayes: A Probabilistic Algorithm for Identifying the Mature miRNA within Novel Precursors," PLOSOne. 5(8):e11843 (Aug. 2010).

Gotti C, Moretti M, Maggi R, Longhi R, Hanke W, Klinke N et al. Alpha7 and alpha8 nicotinic receptor subtypes immunopurified from chick retina have different immunological, pharmacological and functional properties. The European journal of neuroscience. (Jan. 22, 1997);9(6):1201-11.

Grafman J, Schwartz V, Dale JK, Scheffers M, Houser C, Straus SE. Analysis of neuropsychological functioning in patients with chronic fatigue syndrome. Journal of neurology, neurosurgery, and psychiatry. (Jun. 1993); 56(6):684-9.

Griendling KK, Sorescu D, Lassègue B, Ushio-Fukai M. Modulation of protein kinase activity and gene expression by reactive oxygen species and their role in vascular physiology and pathophysiology. Arteriosclerosis, thrombosis, and vascular biology. (Aug. 10, 2000);20(10):2175-2183.

Gromada J, Hughes TE. Ringing the dinner bell for insulin: muscarinic M3 receptor activity in the control of pancreatic beta cell function. Cell metabolism. (Jun. 2006);3(6):390-2. doi:10.1016/j.cmet.2006.05.004.

Gronberg A, Ferm MT, Ng J, Reynolds CW, Ortaldo JR. IFN-gamma treatment of K562 cells inhibits natural killer cell triggering and decreases the susceptibility to lysis by cytoplasmic granules from large granular lymphocytes. J Immunol. (Jun. 15, 1988);140(12):4397-402.

Grossman WJ, Verbsky JW, Tollefsen BL, Kemper C, Atkinson JP, Ley TJ. Differential expression of granzymes A and B in human cytotoxic lymphocyte subsets and T regulatory cells. Blood. (Jul. 6, 2004);104(9):2840-8. doi:10.1182/blood-2004-03-0859.

Gu W, Song L, Li XM, Wang D, Guo XJ, Xu WG. Mesenchymal stem cells alleviate airway inflammation and emphysema in COPD through down-regulation of cyclooxygenase-2 via p38 and ERK MAPK pathways. Scientific reports. (Mar. 4, 2015);5:8733. doi:10.1038/srep08733.

Gu Z and Yakel JL. Timing-dependent septal cholinergic induction of dynamic hippocampal synaptic plasticity. Neuron. (Jul. 13, 2011); 71: 155-65.

Gulf War Illness and the Gulf War Veterans, Scientific findings and recommendations, Research Advisory Committee on Gulf War Illness, USA, Washington DC, (Nov. 2008).

Gupta V, Thompson EB, Stock-Novack D, Salmon SE, Pierce HI, Bonnet JD et al. Efficacy of prednisone in refractory multiple myeloma and measurement of glucocorticoid receptors. A Southwest Oncology Group study. Investigational new drugs. (1994);12(2):121-8.

Hackenberg M, Rodriguez-Ezpeleta N, Aransay AM. miRanalyzer: an update on the detection and analysis of microRNAs in high-throughput sequencing experiments. Nucleic Acids Res. (Apr. 22, 2011); 39:W132-W138.

Hackenberg M, Sturm M, Langenberger D, Falcon-Perez JM, Aransay AM. miRanalyzer: a microRNA detection and analysis tool for next-generation sequencing experiments. Nucleic Acids Res (May 11, 2009); 37: W68-76.

Han Z, Boyle DL, Chang L, Bennett B, Karin M, Yang L et al. c-Jun N-terminal kinase is required for metalloproteinase expression and joint destruction in inflammatory arthritis. The Journal of clinical investigation. (May 21, 2001);108(1):73-81. doi:10.1172/JCI12466.

Hardcastle SL, Brenu E, Johnston S, et al. Analysis of the relationship between immune dysfunction and symptom severity in patients with Chronic Fatigue Syndrome/Myalgic Encephalomyelitis (CFS/ME). J Clin Cell Immunol. (Feb. 7, 2014); 5: 4172.

Hardcastle SL, Brenu E, Wong N, Johnston S, Nguyen T, Huth T et al. Serum cytokines in patients with moderate and severe Chronic Fatigue Syndrome/Myalgic Encephalomyelitis (CFS/ME). Cytokine. (2014);70(1):45. doi:10.1016/j.cyto.2014.07.081.

Hardcastle SL, Brenu EW, Johnston S, et al. Characterisation of cell functions and receptors in Chronic Fatigue Syndrome/Myalgic Encephalomyelitis (CFS/ME). BMC Immunol. (Jun. 2, 2015); 16:35.

Hardcastle SL, Brenu EW, Johnston S, et al. Longitudinal analysis of immune abnormalities in varying severities of Chronic Fatigue Syndrome/Myalgic Encephalomyelitis patients. Journal of translational medicine. (Sep. 14, 2015);13:299.

Harfi I, Corazza F, D'Hondt S, Sariban E. Differential calcium regulation of proinflammatory activities in human neutrophils exposed to the neuropeptide pituitary adenylate cyclase-activating protein. Journal of immunology. (Jul. 13, 2005);175(6):4091-102.

(56) References Cited

OTHER PUBLICATIONS

Hasselmo ME. The role of acetylcholine in learning and memory. Current opinion in neurobiology. (Dec. 2006);16(6):710-5.

He C, Li YX, Zhang G, Gu Z, Yang R, Li J, Lu ZJ, Zhou ZH, Zhang C, Wang J. MiRmat: mature microRNA sequence prediction. PLoS One. (Dec. 27, 2012); 7:e51673.

Held K, Kichko T, De Clercq K, Klaassen H, Van Bree R, Vanherck JC et al. Activation of TRPM3 by a potent synthetic ligand reveals a role in peptide release. Proceedings of the National Academy of Sciences of the United States of America. (Mar. 2, 2015);112(11):E1363-72. doi:10.1073/pnas.1419845112.

Hellman B, Dansk H, Grapengiesser E. Activation of alpha adrenergic and muscarinic receptors modifies early glucose suppression of cytoplasmic Ca(2+) in pancreatic beta-cells. Biochemical and biophysical research communications. (Feb. 21, 2014);445(3):629-32. doi:10.1016/j.bbrc.2014.02.056.

Herreros L, Rodriguez-Fernandez JL, Brown MC, Alonso-Lebrero JL, Cabanas C, Sanchez-Madrid F et al. Paxillin localizes to the lymphocyte microtubule organizing center and associates with the microtubule cytoskeleton. The Journal of biological chemistry. (Jun. 5, 2000);275(34):26436-40. doi:10.1074/jbc.M003970200.

Hirosumi J, Tuncman G, Chang L, Gorgun CZ, Uysal KT, Maeda K et al. A central role for JNK in obesity and insulin resistance. Nature. (Nov. 21, 2002);420(6913):333-6. doi:10.1038/nature01137.

Hoad A, Spickett G, Elliott J and Newton J. Postural orthostatic tachycardia syndrome is an under-recognized condition in chronic fatigue syndrome. *QJM: monthly journal of the Association of Physicians*. (Sep. 19, 2008); 101: 961-5.

Hogg RC, Raggenbass M, Bertrand D. Nicotinic acetylcholine receptors: from structure to brain function. Reviews of physiology, biochemistry and pharmacology. (Mar. 20, 2003);147:1-46. doi:10.1007/s10254-003-0005-1.

Holmes GP, Kaplan JE, Gantz NM, Komaroff AL, Schonberger LB, Straus SE, et al. Chronic fatigue syndrome: a working case definition. Annals of internal medicine. (Mar. 1988);108(3):387-9.

Hornig M, Gottschalk G, Peterson DL, et al. Cytokine network analysis of cerebrospinal fluid in myalgic encephalomyelitis/chronic fatigue syndrome. *Molecular psychiatry*.(Mar. 21, 2015);21(2):261-269.

Ho-yen definition: Ho-Yen DO. Patient management of post-viral fatigue syndrome. The British journal of general practice: the journal of the Royal College of General Practitioners. (Jul. 25, 1989);40(330):37-9.

Huijbers MG, Lipka AF, Plomp JJ, Niks EH, van der Maarel SM and Verschuuren JJ. Pathogenic immune mechanisms at the neuromuscular synapse: the role of specific antibody-binding epitopes in myasthenia gravis. *Journal of internal medicine*. (2014);275: 12-26.

Hurst R, Rollema H, Bertrand D. Nicotinic acetylcholine receptors: from basic science to therapeutics. Pharmacology & therapeutics. (Aug. 25, 2012); 137(1):22-54. doi:10.1016/j.pharmthera.2012.08.012.

Huth T, Brenu EW, Nguyen T, et al. Characterization of natural killer cell phenotypes in chronic fatigue syndrome/myalgic encephalomyelitis. *J Clin Cell Immunol*. (Jun. 14, 2014);5(3).

Iacob, E. et al., "Gene expression factor analysis to differentiate pathways linked to fibromyalgia, chronic fatigue syndrome, and depression in a diverse patient sample", Arthritis Care & Research, (20160000), vol. 68, No. 1, pp. 132-140 (Jan. 2016).

International Preliminary Report on Patentability dated Nov. 7, 2017 for International Application No. PCT/AU2016/050313.

International Search Report dated Aug. 16, 2016 International Application No. PCT/AU2016/050313.

Ishii M, Kurachi Y. Muscarinic acetylcholine receptors. Current pharmaceutical design. (2006);12(28):3573-81.

Jaimes M et al (May 27, 2004) Maturation and Trafficking Markers on Rotavirus-Specific B Cells during Acute Infection and Convalescence in Children, J. Virol. 78:10967-10976.

Jansson MD, Lund AH. MicroRNA and cancer. Mol Oncol (Oct. 9, 2012); 6: 590-610.

Jha SK, Jha NK, Kar R, Ambasta RK, Kumar P. p38 MAPK and PI3K/AKT Signalling Cascades in Parkinson's Disease. International journal of molecular and cellular medicine. (Mar. 14, 2015);4(2):67-86.

Johnston RJ, Poholek AC, DiToro D, Yusuf I, Eto D, et al. Bcl6 and Blimp-1 are reciprocal and antagonistic regulators of T follicular helper cell differentiation. Science (Aug. 21, 2009); 325: 1006-1010.

Johnston S, Brenu EW, Staines D, Marshall-Gradisnik S. The prevalence of chronic fatigue syndrome/ myalgic encephalomyelitis: a meta-analysis. Clin Epidemiol (Mar. 25, 2013); 5: 105-110.

Johnston S, Staines D, Marshall-Gradisnik S. Epidemiological characteristics of Chronic Fatigue Syndrome/Myalgic Encephalomyelitis in Australian patients Clinical epidemiology. (May 17, 2016);(Accepted).

Jones CL, Gearheart CM, Fosmire S, Delgado-Martin C, Evensen NA, Bride K et al. MAPK signaling cascades mediate distinct glucocorticoid resistance mechanisms in pediatric leukemia. Blood. (Aug. 31, 2015). doi:10.1182/blood-2015-04-639138.

Jones-Rhoades MW, Bartel DP. Computational identification of plant microRNAs and their targets, including a stress-induced miRNA. Mol. Cell. (Jun. 18, 2004); 14:787-799.

Joyce E, Blumenthal S, Wessely S. Memory, attention, and executive function in chronic fatigue syndrome. Journal of neurology, neurosurgery, and psychiatry. (May 1, 1996); 60(5):495-503.

Kalina U, Kauschat D, Koyama N, Nuernberger H, Ballas K, Koschmieder S et al. IL-18 activates STAT3 in the natural killer cell line 92, augments cytotoxic activity, and mediates IFN-gamma production by the stress kinase p38 and by the extracellular regulated kinases p44erk-1 and p42erk-21. J Immunol. (May 17, 2000);165(3): 1307-13.

Kang SW, Wahl MI, Chu J, et al. PKCbeta modulates antigen receptor signaling via regulation of Btk membrane localization. *The EMBO journal*. (Aug. 24, 2001); 20:5692-702.

Kaushik N, Fear D, Richards SC, McDermott CR, Nuwaysir EF, et al. Gene expression in peripheral blood mononuclear cells from patients with chronic fatigue syndrome. J Clin Pathol (Feb. 10, 2005); 58: 826-832.

Kawashima K, Fujii T, Moriwaki Y and Misawa H. Critical roles of acetylcholine and the muscarinic and nicotinic acetylcholine receptors in the regulation of immune function. *Life sciences*. (May 3, 2012); 91: 1027-32.

Kawashima K, Fujii T, Moriwaki Y, Misawa H and Horiguchi K. Reconciling neuronally and nonneuronally derived acetylcholine in the regulation of immune function. *Annals of the New York Academy of Sciences*. (2012); 1261: 7-17.

Kawashima K, Fujii T. Basic and clinical aspects of non-neuronal acetylcholine: overview of non-neuronal cholinergic systems and their biological significance. *Journal of pharmacological sciences*. (Feb. 16, 2008);106(2):167-173.

Kawashima K, Fujii T. Expression of non-neuronal acetylcholine in lymphocytes and its contribution to the regulation of immune function. *Front Biosci*. (Sep. 1, 2004);9(2):063.

Kawashima K, Fujii T. Extraneuronal cholinergic system in lymphocytes. Pharmacology & therapeutics. (Apr. 5, 2000); 86(1):29-48. doi:Doi 10.1016/S0163-7258(99)00071-6.

Kawashima K, Fujii T. The lymphocytic cholinergic system and its biological function. Life sciences. (Mar. 1, 2003); 72(18-19):2101-9.

Kennedy G, Spence V, Underwood C, Belch JJ. Increased neutrophil apoptosis in chronic fatigue syndrome. J Clin Pathol (Jul. 27, 2004); 57: 891-893.

Kerr JR, Burke B, Petty R, Gough J, Fear D, et al. Seven genomic subtypes of chronic fatigue syndrome/myalgic encephalomyelitis: a detailed analysis of gene networks and clinical phenotypes. J Clin Pathol (Dec. 5, 2007); 61: 730-739.

Kerr JR, Petty R, Burke B, Gough J, Fear D, et al. Gene expression subtypes in patients with chronic fatigue syndrome/myalgic encephalomyelitis. J Infect Dis (Apr. 15, 2008);197: 1171-1184.

Kerr JR. Gene profiling of patients with chronic fatigue syndrome/myalgic encephalomyelitis. Curr Rheumatol Rep (Dec. 2008); 10: 482-491.

(56) References Cited

OTHER PUBLICATIONS

Khaiboullina SF, DeMeirleir KL, Rawat S, et al. Cytokine expression provides clues to the pathophysiology of Gulf War illness and myalgic encephalomyelitis. *Cytokine*. (Mar. 2015);72(1):1-8.
Khan F, Kennedy G, Spence VA, Newton DJ, Belch JJ. Peripheral cholinergic function in humans with chronic fatigue syndrome, Gulf War syndrome and with illness following organophosphate exposure. Clinical science. (Feb. 1, 2004); 106(2):183-9. doi:10.1042/CS20030246.
Kim H, Kim J, Jeon JP, Myeong J, Wie J, Hong C et al. The roles of G proteins in the activation of TRPC4 and TRPC5 transient receptor potential channels. Channels. (Sep. 1, 2012, 2012);6(5):333-43. doi:10.4161/chan.21198.
Kim, S.-C. et al., "Constitutive activation of extracellular signal-regulated kinase in human acute leukemias: combined role of activation of MEK, hyperexpression of extracellular signal-regulated kinase, and downregulation of a phosphatase, PAC1", Blood, (19990000), vol. 93, No. 11, pp. 3893-3899 (Jun. 1, 1999).
Kimura H. Physiological role of hydrogen sulfide and polysulfide in the central nervous system. Neurochemistry international. (Sep. 11, 2013);63(5):492-7. doi:10.1016/j.neuint.2013.09.003.
Kimura R, Ushiyama N, Fujii T, Kawashima K. Nicotine-induced Ca2+ signaling and down-regulation of nicotinic acetylcholine receptor subunit expression in the CEM human leukemic T-cell line. *Life sciences*. (2003);72(18-19):2155-2158.
Kirschner MB, Edelman JJ, Kao SC, Vallely MP, van Zandwijk N, et al. The Impact of Hemolysis on Cell-Free microRNA Biomarkers. Front Genet (May 24, 2013); 4: 94.
Kirschner MB, van Zandwijk N, Reid G. Cell-free microRNAs: potential biomarkers in need of standardized reporting. Front Genet (Apr. 19, 2013); 4: 56.
Klein U, Dalla-Favera R. Germinal centres: role in B-cell physiology and malignancy. Nat Rev Immunol (Feb. 2008); 8: 22-33.
Klimas NG, Salvato FR, Morgan R, Fletcher MA. Immunologic abnormalities in chronic fatigue syndrome. Journal of clinical microbiology. (Jun. 1990); 28(6):1403-10.
Knowlton KU, Michel M, Itani M, Shubeita H, Ishihara K, Brown J, et al. The alpha 1A-adrenergic receptor subtype mediates biochemical, molecular, and morphologic features of cultured myocardial cell hypertrophy. Journal of Biological Chemistry. (Apr. 5, 1993);268(21):15374-80.
Kotecha N, Krutzik PO, Irish JM. Web-based analysis and publication of flow cytometry experiments. Current protocols in cytometry / editorial board, J Paul Robinson, managing editor [et al]. (Jul. 2010);Chapter 10:Unit10 7.doi:10.1002/0471142956.cy1017s53.
Koval L, Lykhmus O, Zhmak M, et al. Differential involvement of alpha4beta2, alpha7 and alpha9alpha10 nicotinic acetylcholine receptors in B lymphocyte activation in vitro. *The international journal of biochemistry & cell biology*. (Dec. 10, 2010); 43: 516-24.
Kovanen PE, Leonard WJ. Cytokines and immunodeficiency diseases: critical roles of the gamma(c)-dependent cytokines interleukins 2, 4, 7, 9, 15, and 21, and their signaling pathways. *Immunological reviews*. (2004);202:67-83.
Krupp LB, Sliwinski M, Masur DM, Friedberg F, Coyle PK. Cognitive functioning and depression in patients with chronic fatigue syndrome and multiple sclerosis. Archives of neurology. (Jul. 1994); 51(7):705-10.
Krutzik PO, Irish JM, Nolan GP, Perez OD. Analysis of protein phosphorylation and cellular signaling events by flow cytometry: techniques and clinical applications. Clin Immunol. (Nov. 10, 2003);110(3):206-21. doi:10.1016/j.clim.2003.11.009.
Kuersten S and Goodwin EB. The power of the 3' UTR: translational control and development. *Nature reviews Genetics*. (Aug. 2003); 4: 626-37.
Kuo YP, Lucero L, Michaels J, DeLuca D, Lukas RJ. Differential expression of nicotinic acetylcholine receptor subunits in fetal and neonatal mouse thymus. Journal of neuroimmunology. (Jun. 25, 2002);130(1-2):140-54. doi:Pii S0165-5728(02)00220-5 Doi 10.1016/S0165-5728(02)00220-5.
Kurzen H, Wessler I, Kirkpatrick CJ, Kawashima K, Grando SA. The non-neuronal cholinergic system of human skin. Hormone and metabolic research=Hormon- und Stoffwechselforschung=Hormones et metabolisme. (Mar. 16, 2006);39(2):125-35. doi:10.1055/s-2007-961816.
Lakhan SE, Kirchgessner A. Gut inflammation in chronic fatigue syndrome. Nutrition & metabolism. (Oct. 12, 2010); 7:79. doi: 10.1186/1743-7075-7-79. PubMed PMID: 20939923; PubMed Central Pmcid: PMC2964729.
Landmark-Høyvik, H. et al., "Alterations of gene expression in blood cells associated with chronic fatigue in breast cancer survivors", The Pharmacogenomics Journal, (20090000), vol. 9, No. 5, pp. 333-340 (Jun. 23, 2009).
Lanier LL. NK cell recognition. *Annual review of immunology*. 2005;23:225-274. (Nov. 11, 2004).
Lanier LL. Up on the Tightrope: Natural Killer Cell Activation and Inhibition. Nat Immunol. (May 2008);9(5):495-502. doi:10.1038/ni1581.
Lanzafame AA, Christopoulos A, Mitchelson F. Cellular signaling mechanisms for muscarinic acetylcholine receptors. Receptors & channels. (Nov. 6, 2002); 9(4):241-60.
Lattie EG, Antoni MH, Fletcher MA, et al. Stress management skills, neuroimmune processes and fatigue levels in persons with chronic fatigue syndrome. Brain, behavior, and immunity. (Aug. 2012);26(6):849-858.
Lavergne MR, Cole DC, Kerr K, Marshall LM. Functional impairment in chronic fatigue syndrome, fibromyalgia, and multiple chemical sensitivity. Canadian family physician Medecin de famille canadien. (Feb. 2010); 56(2):e57-65. PubMed PMID: 20154232; PubMed Central PMCID: PMC2821254.
Leclercq M, Diallo AB, Blanchette. Computational prediction of the localization of microRNAs within their pre-miRNA. Nucleric Acids Res. (Jun. 8, 2013); 41(15):7200-7211.
Lendvai B and Vizi ES. Nonsynaptic chemical transmission through nicotinic acetylcholine receptors. *Physiological reviews*. (Apr. 2008); 88: 333-49.
Lerner MR, Boyle JA, Hardin JA, Steitz JA. Two novel classes of small ribonucleoproteins detected by antibodies associated with lupus erythematosus. Science (Jan. 23, 1981); 211: 400-402.
Levine PH, Whiteside TL, Friberg D, Bryant J, Colclough G, Herberman RB. Dysfunction of natural killer activity in a family with chronic fatigue syndrome. Clinical immunology and immunopathology. Jul. 1998;88(1):96-104. PubMed PMID: 9683556. (Mar. 23, 1998) Epub 1998/07/31. eng.
Lewis I, Pairman J, Spickett G, Newton JL. Clinical characteristics of a novel subgroup of chronic fatigue syndrome patients with postural orthostatic tachycardia syndrome. Journal of internal medicine. (May 2013);273(5):501-10. doi:10.1111/joim.12022.
Lewis RS. Calcium signaling mechanisms in T lymphocytes. Annual review of immunology. (Feb. 2001); 19:497-521. doi: 10.1146/annurev.immunol.19.1.497. PubMed PMID: 11244045.
Li C, Ge B, Nicotra M, Stern JN, Kopcow HD, Chen X et al. JNK MAP kinase activation is required for MTOC and granule polarization in NKG2D-mediated NK cell cytotoxicity. Proc Natl Acad Sci U S A. (Feb. 26, 2008);105(8):3017-22. doi:10.1073/pnas.0712310105.
Li Q, Li L, Wang F, Chen J, Zhao Y, Wang P, et al. Dietary capsaicin prevents nonalcoholic fatty liver disease through transient receptor potential vanilloid 1-mediated peroxisome proliferator-activated receptor delta activation. Pflugers Arch. (Apr. 21, 2013);465(9):1303-16. PubMed PMID: 23605066.
Li W, Llopis J, Whitney M, Zlokarnik G and Tsien RY. Cell-permeant caged InsP3 ester shows that Ca2+ spike frequency can optimize gene expression. Nature. (Feb. 12, 1998); 392: 936-41.
Lieberman J. Anatomy of a Murder: How Cytotoxic T cells and NK Cells are Activated, Develop, and Eliminate their Targets. Immunol Rev. (2010);235(1):5-9. doi:10.1111/j.0105-2896.2010.00914.x.
Light, A. et al., "Gene expression alterations at baseline and following moderate exercise in patients with Chronic Fatigue Syndrome and Fibromyalgia Syndrome", Journal of Internal Medicine, (20120000), vol. 271, No. 1, pp. 64-81 (Jan. 2012).

(56) References Cited

OTHER PUBLICATIONS

Liman ER. TRP Channels: Pain enters through the side door. Nature chemical biology. (Mar. 2014);10(3):171-2. doi:10.1038/nchembio. 1470.

Lind R, Berstad A, Hatlebakk J, Valeur J. Chronic fatigue in patients with unexplained self-reported food hypersensitivity and irritable bowel syndrome: validation of a Norwegian translation of the Fatigue Impact Scale. Clinical and experimental gastroenterology. (Jul. 3, 2013); 6:101-7. doi: 10.2147/CEG.S45760. PubMed PMID: 23869173; PubMed Central PMCID: PMC3706251.

Lindstrom JM. Acetylcholine receptors and myasthenia. Muscle & nerve. (Dec. 16, 1999);23(4):453-77.

Liu B, Qin F. Functional control of cold- and menthol-sensitive TRPM8 ion channels by phosphatidylinositol 4,5-bisphosphate. *The Journal of neuroscience: the official journal of the Society for Neuroscience.* (Feb. 16, 2005);25(7):1674-1681.

Liu D, Martina JA, Wu XS, Hammer JA, 3rd, Long EO. Two modes of lytic granule fusion during degranulation by natural killer cells. Immunol Cell Biol. (Apr. 12, 2011);89(6):728-38. doi:10.1038/icb. 2010.167.

Liu D, Xu L, Yang F, Li D, Gong F, Xu T. Rapid biogenesis and sensitization of secretory lysosomes in NK cells mediated by target-cell recognition. Proc Natl Acad Sci U S A. (Jan. 4, 2005);102(1):123-7. doi:10.1073/pnas.0405737102.

Liu L, Yu X, Guo X, Tian Z, Su M, et al. miR-143 is downregulated in cervical cancer and promotes apoptosis and inhibits tumor formation by targeting Bcl-2. Mol Med Rep (Dec. 1, 2011); 5: 753-760.

Liu Y, Shepherd EG, Nelin LD. MAPK phosphatases—regulating the immune response. Nature reviews Immunology. (Mar. 2007);7(3):202-12. doi:10.1038/nri2035.

Lloyd et al. Prevalence of chronic fatigue syndrome in an Australian population. The Medical journal of Australia. (Dec. 1990);153(9):522-8.

Loebel M, Grabowski P, Heidecke H, et al. Antibodies to β adrenergic and muscarinic cholinergic receptors in patients with Chronic Fatigue Syndrome. *Brain, behavior, and immunity.* (Sep. 21, 2015); 52: 32-9.

Lomasney JW, Cotecchia S, Lorenz W, Leung WY, Schwinn DA, Yang-Feng TL, et al. Molecular cloning and expression of the cDNA for the alpha 1A-adrenergic receptor. The gene for which is located on human chromosome 5. Journal of Biological Chemistry. (Oct. 19, 1990);266(10):6365-9.

Long JM, Lahiri DK. Advances in microRNA experimental approaches to study physiological regulation of gene products implicated in CNS disorders. Exp Neurol (Jun. 2012); 235: 402-418.

Love MI, Huber W, Anders S. Moderated estimation of fold change and dispersion for RNA-seq data with DESeq2. *Genome Biology.* (Dec. 5, 2014);15(12):1-21.

Lucas M, Schachterle W, Oberle K, Aichele P, Diefenbach A. Dendritic cells prime natural killer cells by trans-presenting interleukin 15. *Immunity.* (Apr. 2007);26(4):503-517.

Lukas RJ, Changeux J-P, le Novère N, Albuquerque EX, Balfour DJ, Berg DK, et al. International Union of Pharmacology. XX. Current status of the nomenclature for nicotinic acetylcholine receptors and their subunits. Pharmacol Rev. (1999);51(2):397-401.

Lykhmus O, Gergalova G, Koval L, Zhmak M, Komisarenko S, Skok M. Mitochondria express several nicotinic acetylcholine receptor subtypes to control various pathways of apoptosis induction. *The international journal of biochemistry & cell biology.* (May 24, 2014);53:246-252.

Lyubchenko TA, Wurth GA, Zweifach A. Role of calcium influx in cytotoxic T lymphocyte lytic granule exocytosis during target cell killing. *Immunity.* (Nov. 2001);15(5):847-859.

Ma A, Koka R, Burkett P. Diverse functions of IL-2, IL-15, and IL-7 in lymphoid homeostasis. *Annual review of immunology.* (Jan. 16, 2006);24:657-679.

Mace EM, Dongre P, Hsu HT, Sinha P, James AM, Mann SS et al. Cell biological steps and checkpoints in accessing NK cell cytotoxicity. Immunol Cell Biol. (Jan. 21, 2014);92(3):245-55. doi:10.1038/icb.2013.96.

Macian F. NFAT proteins: key regulators of T-cell development and function.Nat Rev Immunol. (Jun. 2005);5(6):472-84. Review.

Macklin KD, Maus AD, Pereira EF, Albuquerque EX, Conti-Fine BM. Human vascular endothelial cells express functional nicotinic acetylcholine receptors. *The Journal of pharmacology and experimental therapeutics.* (Apr. 30, 1998);287(1):435-439.

Maclennan CA, Vincent A, Marx A, et al. Preferential expression of AChR epsilon-subunit in thymomas from patients with myasthenia gravis. *J Neuroimmunol.* (Jun. 17, 2008);201-202:28-32.

Maes M, Twisk FN, Kubera M, Ringel K. Evidence for inflammation and activation of cell-mediated immunity in Myalgic Encephalomyelitis/Chronic Fatigue Syndrome (ME/CFS): increased interleukin-1, tumor necrosis factor-alpha, PMN-elastase, lysozyme and neopterin. Journal of affective disorders. (Oct. 4, 2011);136(3):933-9. doi:10.1016/j.jad.2011.09.004.

Maes M, Twisk FN, Ringel K. Inflammatory and cell-mediated immune biomarkers in myalgic encephalomyelitis/chronic fatigue syndrome and depression: inflammatory markers are higher in myalgic encephalomyelitis/chronic fatigue syndrome than in depression. *Psychotherapy and psychosomatics.* (Jul. 20, 2012);81(5):286-295.

Maher KJ, Klimas NG, Fletcher MA. Chronic fatigue syndrome is associated with diminished intracellular perforin. Clinical and experimental immunology. (Aug. 8, 2005);142(3):505-11. doi:10.1111/j.1365-2249.2005.02935.x.

Mainiero F, Gismondi A, Soriani A, Cippitelli M, Palmieri G, Jacobelli J et al. Integrin-mediated ras-extracellular regulated kinase (ERK) signaling regulates interferon gamma production in human natural killer cells. The Journal of Experimental Medicine. (Oct. 5, 1998);188(7):1267-75.

Manna PR, Stocco DM. The role of specific mitogen-activated protein kinase signaling cascades in the regulation of steroidogenesis. Journal of signal transduction. (Nov. 28, 2010);2011:821615. doi:10.1155/2011/821615.

Manning G, Whyte DB, Martinez R, Hunter T, Sudarsanam S. The protein kinase complement of the human genome. *Science* (New York, N.Y.). (Dec. 6, 2002);298(5600):1912-1934.

March ME, Long EO. beta2 integrin induces TCRzeta-Syk-phospholipase C-gamma phosphorylation and paxillin-dependent granule polarization in human NK cells. *Journal of immunology* (Baltimore, Md. : 1950). (Jan. 26, 2011);186(5):2998-3005.

Marincsak R, Toth BI, Czifra G, Szabo T, Kovacs L, Biro T. The analgesic drug, tramadol, acts as an agonist of the transient receptor potential vanilloid-1. Anesthesia and analgesia. (Feb. 15, 2008); 106(6):1890-6. doi: 10.1213/ane.0b013e318172fefc. PubMed PMID: 18499628.

Maroney PA, Chamnongpol S, Souret F, Nilsen TW. A rapid, quantitative assay for direct detection of microRNAs and other small RNAs using splinted ligation. RNA (Apr. 24, 2007);13:930-936.

Maroney PA, Chamnongpol S, Souret F, Nilsen TW. Direct detection of small RNAs using splinted ligation. Nat Protoc (Jan. 31, 2008); 3:279-287.

Marshall-Gradisnik, S. et al., "Examination of single nucleotide polymorphisms (SNPs) in transient receptor potential (TRP) ion channels in chronic fatigue syndrome patients", Immunology and Immunogenetics Insights, (20150000), vol. 7, pp. 1-6 (Apr. 15, 2015).

Marshall-Gradisnik, S. et al., "Genotype Frequencies of Transient Receptor Potential Melastatin M3 Ion Channels and Acetylcholine Muscarinic M3 Receptor Gene Polymorphisms in Chronic Fatigue Syndrome/Myalgic Encephalomyelitis Patients", Immunology and Immunogenetics Insights, (20160000), vol. 8, pp. 1-2 (Dec. 21, 2015).

Marshall-Gradisnik, S. et al., "Natural killer cells and single nucleotide polymorphisms of specific ion channels and receptor genes in myalgic encephalomyelitis/chronic fatigue syndrome", The Application of Clinical Genetics, (20160331), vol. 9, pp. 37-47 (2016).

(56) References Cited

OTHER PUBLICATIONS

Mas VR, Dumur CI, Scian MJ, Gehrau RC, Maluf DG. MicroRNAs as biomarkers in solid organ transplantation. Am J Transplant (Sep. 23, 2012); 13: 11-19.

Maslinski W. Cholinergic receptors of lymphocytes. *Brain, behavior, and immunity*. (Feb. 9, 1988);3(1):1-14.

Mathelier A, Carbone A. MIReNA: finding microRNAs with high accuracy and no learning at genome scale and from deep sequencing data. Bioinformatics. (Jun. 30, 2010); 26:2226-2234.

Matteoli G, Boeckxstaens GE. The vagal innervation of the gut and immune homeostasis. Gut. (Sep. 29, 2012);62(8):1214-22. doi:DOI 10.1136/gutjnl-2012-302550.

Mattick P, Parrington J, Odia E, Simpson A, Collins T, Terrar D. Ca2+-stimulated adenylyl cyclase isoform AC1 is preferentially expressed in guinea-pig sino-atrial node cells and modulates the l(f) pacemaker current. The Journal of physiology. (Jun. 1, 2007);582(Pt 3):1195-203. doi:10.1113/jphysiol.2007.133439.

Maul-Pavicic A, Chiang SC, Rensing-Ehl A, et al. ORAI1-mediated calcium influx is required for human cytotoxic lymphocyte degranulation and target cell lysis. *Proceedings of the National Academy of Sciences of the United States of America*. (Feb. 22, 2011);108(8):3324-3329.

Maus AD, Pereira EF, Karachunski PI, Horton RM, Navaneetham D, Macklin K et al. Human and rodent bronchial epithelial cells express functional nicotinic acetylcholine receptors. Molecular pharmacology. (Jul. 28, 1998);54(5):779-88.

Mavropoulos A, Sully G, Cope AP, Clark AR. Stabilization of IFN-gamma mRNA by MAPK p38 in IL-12- and IL-18-stimulated human NK cells. Blood. (Sep. 2, 2004);105(1):282-8. doi:10.1182/blood-2004-07-2782.

Mayerhofer A, Fritz S. Ovarian acetylcholine and muscarinic receptors: hints of a novel intrinsic ovarian regulatory system. Microscopy research and technique. (2002);59(6):503-8. doi:10.1002/jemt.10228.

McAlexander MA, Phillips MJ, Witwer KW. Comparison of Methods for miRNA Extraction from Plasma and Quantitative Recovery of RNA from Cerebrospinal Fluid. Front Genet (May 16, 2013); 4: 83.

McDonald E, Cope H, David A. Cognitive impairment in patients with chronic fatigue: a preliminary study. Journal of neurology, neurosurgery, and psychiatry. (Jul. 1993); 56(7):812-5.

McGehee DS, Role LW. Physiological diversity of nicotinic acetylcholine receptors expressed by vertebrate neurons. Annual review of physiology. (1995);57(1):521-46.

McKemy DD. How cold is it? TRPM8 and TRPA1 in the molecular logic of cold sensation. *Molecular pain*. (Apr. 22, 2005);1:16.

Medow MS, Stewart JM. The postural tachycardia syndrome. Cardiology in review. (Mar. 2007); 15(2):67-75. doi:10.1097/01.crd.0000233768.68421.40.

Meeus M, Nijs J. Central sensitization: a biopsychosocial explanation for chronic widespread pain in patients with fibromyalgia and chronic fatigue syndrome. Clinical rheumatology. (Nov. 18, 2006); 26(4):465-73. doi: 10.1007/s10067-006-0433-9. PubMed PMID: 17115100; PubMed Central PMCID: PMC1820749.

Mentlik AN, Sanborn KB, Holzbaur EL, Orange JS. Rapid lytic granule convergence to the MTOC in natural killer cells is dependent on dynein but not cytolytic commitment. Molecular biology of the cell. (Jul. 1, 2010);21(13):2241-56. doi:10.10 91/mbc.E0 9-11-0930.

Merkerova M, Belickova M, Bruchova H. Differential expression of microRNAs in hematopoietic cell lineages. Eur J Haematol (Jun. 5, 2008); 81: 304-310.

Merriam LA, Roman CW, Baran CN, Girard BM, May V, Parsons RL. Pretreatment with nonselective cationic channel inhibitors blunts the PACAP-induced increase in guinea pig cardiac neuron excitability. Journal of molecular neuroscience: MN. (Nov. 2012);48(3):721-9. doi:10.1007/s12031-012-9763-z.

Middlebrook AJ, Martina C, Chang Y, Lukas RJ, DeLuca D. Effects of nicotine exposure on T cell development in fetal thymus organ culture: Arrest of T cell maturation. Journal of immunology. (Jun. 25, 2002);169(6):2915-24.

Minnerman "α1-adrenergic receptor subtypes, inositol phosphates and sources of cell Ca2+," Pharmacological reviews. 40(2):87-112 (1988).

Mo YY. MicroRNA regulatory networks and human disease. Cell Mol Life Sci (Nov. 2012); 69: 3529-3531.

Mocsai A, Abram CL, Jakus Z, Hu Y, Lanier LL, Lowell CA. Integrin signaling in neutrophils and macrophages uses adaptors containing immunoreceptor tyrosine-based activation motifs. *Nature immunology*. (Dec. 2006);7(12):1326-1333.

Molina J, Rodriguez-Diaz R, Fachado A, Jacques-Silva MC, Berggren PO and Caicedo A. Control of insulin secretion by cholinergic signaling in the human pancreatic islet. *Diabetes*. (Mar. 15, 2014); 63: 2714-26.

Möller MJ, Kammerer R, von Kleist S. A distinct distribution of natural killer cell subgroups in human tissues and blood. *International Journal of Cancer*. (Jun. 8, 1998);78(5):533-538.

Montag DT, Lotze MT. Successful simultaneous measurement of cell membrane and cytokine induced phosphorylation pathways [CIPP] in human peripheral blood mononuclear cells. J Immunol Methods. (May 2, 2006);313(1-2):48-60. doi:10.1016/j.jim.2006.03.014.

Moran MM, McAlexander MA, Biro T, Szallasi A. Transient receptor potential channels as therapeutic targets. Nature reviews Drug discovery. (Aug. 1, 2011);10(8):601-20. doi: 10.1038/nrd3456. PubMed PMID: 21804597.

Moretta A, Bottino C, Vitale M, Pende D, Cantoni C, Mingari MC et al. Activating receptors and coreceptors involved in human natural killer cell-mediated cytolysis. Annu Rev Immunol. (2001);19:197-223. doi:10.1146/annurev.immunol.19.1.197.

Morris G, Maes M. Mitochondrial dysfunctions in Myalgic Encephalomyelitis/chronic fatigue syndrome explained by activated immuno-inflammatory, oxidative and nitrosative stress pathways. Metab Brain Dis. (Sep. 10, 2013);29(1):19-36. doi:DOI 10.1007/s11011-013-9435-x.

Mosakhani N, Sarhadi VK, Borze I, Karjalainen-Lindsberg ML, Sundstrom J, et al. MicroRNA profiling differentiates colorectal cancer according to KRAS status. Genes Chromosomes Cancer (Sep. 15, 2011); 51: 1-9.

Nairn AC, Picciotto MR. Calcium/calmodulin-dependent protein kinases. *Seminars in cancer biology*. (1994);5(4):295-303.

Nakamoto M, Jin P, O'Donnell WT, Warren ST. Physiological identification of human transcripts translationally regulated by a specific microRNA. Hum Mol Genet (Oct. 20, 2005); 14: 3813-3821.

Nakatomi Y, Mizuno K, Ishii A, Wada Y, Tanaka M, Tazawa S, et al. Neuroinflammation in Patients with Chronic Fatigue Syndrome/Myalgic Encephalomyelitis: An 11C-(R)-PK11195 PET Study. Journal of nuclear medicine: official publication, Society of Nuclear Medicine. (Mar. 24, 2014); 55(6):945-50. doi: 10.2967/jnumed.113.131045. PubMed PMID: 24665088.

Nam JW, Shin KR, Han JJ, Lee Y, Kim VN, Zhang BT. Human microRNA prediction through a probabilistic co-learning model of sequence and structure. Nucleic Acids Res. (Jun. 6, 2005); 33:3570-3581.

Naranjo JR, Mellström B. Ca2+-dependent Transcriptional Control of Ca2+ Homeostasis. Journal of Biological Chemistry. 287(38):316714-31680 (Sep. 14, 2012).

Nassini R, Materazzi S, Vriens J, Prenen J, Benemei S, De Siena G, et al. The 'headache tree' via umbellulone and TRPA1 activates the trigeminovascular system. Brain : a journal of neurology. (Oct. 27, 2011); 135(Pt 2):376-90. doi: 10.1093/brain/awr272. PubMed PMID: 22036959.

Navarrete M, Perea G, de Sevilla DF, et al. Astrocytes mediate in vivo cholinergic-induced synaptic plasticity. *PLoS-Biology*. (Feb. 14, 2012); 10: 402.

NCBI. CHRM3 cholinergic receptor, muscarinic 3 [*Homo sapiens* (human)]. Updated on Mar. 4, 2018 (https://www.ncbi.nlm.nih.gov/gene/1131) Accessed 2015.

(56) References Cited

OTHER PUBLICATIONS

Ncbi. TRPM3 transient receptor potential cation channel, subfamily M, member 3 [*Homo sapiens* (human)]. Updated on Mar. 4, 2018 (https://www.ncbi.nlm.nih.gov/gene/80036) Accessed 2015.
Ndoye A, Buchli R, Greenberg B, Nguyen VT, Zia S, Rodriguez JG et al. Identification and mapping of keratinocyte muscarinic acetylcholine receptor subtypes in human epidermis. The Journal of investigative dermatology. (Apr. 29, 1998);111(3):410-6. doi:10.1046/j.1523-1747.1998.00299.x.
Nedergaard M, Verkhratsky A. Calcium dyshomeostasis and pathological calcium signalling in neurological diseases. *Cell calcium.* (Feb. 2010);47(2):101.
Negulescu PA, Shastri N and Cahalan MD. Intracellular calcium dependence of gene expression in single T lymphocytes. *Proceedings of the National Academy of Sciences of the United States of America.* (Sep. 8, 1993); 91: 2873-7.
Neu D, Mairesse O, Montana X, et al. Dimensions of pure chronic fatigue: psychophysical, cognitive and biological correlates in the chronic fatigue syndrome. *European journal of applied physiology.* (May 31, 2014);114(9):1841-1851.
Nieto-Posadas A, Jara-Oseguera A, Rosenbaum T. TRP channel gating physiology. Current topics in medicinal chemistry. (Sep. 2011); 11(17):2131-50. PubMed PMID: 21671880.
Nilius B and Biro T. TRPV3: a 'more than skinny' channel. *Experimental dermatology.* (Jul. 2013); 22: 447-52.
Nilius B and Owsianik G. The transient receptor potential family of ion channels. *Genome biology.* (Mar. 17, 2011); 12: 218.
Nilius B and Szallasi A. Transient receptor potential channels as drug targets: from the science of basic research to the art of medicine. *Pharmacological reviews.* (Jul. 2014); 66: 676-814.
Nilius B and Voets T. The puzzle of TRPV4 channelopathies. *EMBO reports.* (Jan. 11, 2013); 14: 152-63.
Nilius B, Appendino G, Owsianik G. The transient receptor potential channel TRPA1: from gene to pathophysiology. Pflugers Archiv : European journal of physiology. (Sep. 22, 2012);464(5):425-58. doi:10.1007/s00424-012-1158-z.
Nilius B, Biro T, Owsianik G. TRPV3: time to decipher a poorly understood family member! The Journal of physiology. (Jul. 7, 2014); 592(Pt 2):295-304. doi: 10.1113/jphysiol.2013.255968. PubMed PMID: 23836684; PubMed Central PMCID: PMC3922494.
Nilius B, Flockerzi V. Mammalian transient receptor potential (TRP) cation channels. Preface. Handbook of experimental pharmacology. (2014);223:v-vi. PubMed PMID: 25296415.
Nilius B, Owsianik G, Voets T and Peters JA. Transient receptor potential cation channels in disease. *Physiological reviews.* (Jan. 2007); 87: 165-217.
Nilius B, Owsianik G. Transient receptor potential channelopathies. Pflugers Archiv : European journal of physiology. (Feb. 4, 2010); 460(2):437-50. doi: 10.1007/s00424-010-0788-2. PubMed PMID: 20127491.
Nilius B, Prenen J, Owsianik G. Irritating channels: the case of TRPA1. The Journal of physiology. (Nov. 15, 2011); 589(Pt 7):1543-9. doi: 10.1113/jphysiol.2010.200717. PubMed PMID: 21078588; PubMed Central PMCID: PMC3099014.
Nilius B, Voets T. A TRP channel-steroid marriage. Nature cell biology. (Dec. 1, 2008); 10(12):1383-4. doi: 10.1038/ncb1208-1383. PubMed PMID: 19043430.
Nisenbaum R, Reyes M, Mawle AC and Reeves WC. Factor analysis of unexplained severe fatigue and interrelated symptoms: overlap with criteria for chronic fatigue syndrome. *American journal of epidemiology.* (Nov. 19, 1997); 148: 72-7.
Numaga T1, Nishida M, Kiyonaka S, Kato K, Katano M, Mori E, Kurosaki T, Inoue R, Hikida M, Putney JW Jr, Mori Y. Ca2+ influx and protein scaffolding via TRPC3 sustain PKCbeta and ERK activation in B cells. J Cell Sci. (Dec. 18, 2009;123(Pt 6):927-38. doi: 10.1242/jcs.061051. Epub Feb. 23, 2010. Article I.
Nurieva RI, Chung Y, Martinez GJ, Yang XO, Tanaka S, et al. Bcl6 mediates the development of T follicular helper cells. Science (Aug. 21, 2009); 325: 1001-1005.

Oakley BR, Paolillo V, Zheng Y. gamma-Tubulin complexes in microtubule nucleation and beyond. *Molecular biology of the cell.* (Sep. 1, 2015);26(17):2957-2962.
Oberwinkler J, Lis A, Giehl KM, Flockerzi V, Philipp SE. Alternative splicing switches the divalent cation selectivity of TRPM3 channels. *Journal of Biological Chemistry.* (Jun. 10, 2005);280(23):22540-22548.
Oberwinkler J, Philipp SE. Trpm3. Handbook of experimental pharmacology. (Mar. 29, 2014); 222:427-59. doi: 10.1007/978-3-642-54215-2_17. PubMed PMID: 24756716.
Ocon AJ, Medow MS, Taneja I, Clarke D, Stewart JM. Decreased upright cerebral blood flow and cerebral autoregulation in normocapnic postural tachycardia syndrome. American journal of physiology Heart and circulatory physiology. (Jun. 5, 2009); 297(2):H664-73. doi:10.1152/ajpheart.00138.2009.
Oeth P, Beaulieu M, Park C, Kosman D, del Mistro G, van den Boom D et al. iPLEX™ assay: increased plexing efficiency and flexibility for MassARRAY® system through single base primer extension with mass-modified terminators. Sequenom application note. (Apr. 28, 2005): 8876-006.
Ojo-Amaize EA, Conley EJ, Peter JB. Decreased natural killer cell activity is associated with severity of chronic fatigue immune dysfunction syndrome. Clinical infectious diseases : an official publication of the Infectious Diseases Society of America. (Jan. 1994);18 Suppl 1:S157-9. PubMed PMID: 8148445. Epub Jan. 1, 1994. eng.
Oki T, Takagi Y, Inagaki S, et al. Quantitative analysis of binding parameters of [3H]N-methylscopolamine in central nervous system of muscarinic acetylcholine receptor knockout mice. *Brain research. Molecular brain research.* (Sep. 8, 2004);133(1):6-11.
Oki T, Takagi Y, Inagaki S, Taketo MM, Manabe T, Matsui M et al. Quantitative analysis of binding parameters of [3H]N-methylscopolamine in central nervous system of muscarinic acetylcholine receptor knockout mice. Brain research Molecular brain research. (Jan. 1, 2005); 133(1):6-11. doi:10.1016/j.molbrainres.2004.09.012.
Olson CM, Hedrick MN, Izadi H, Bates TC, Olivera ER, Anguita J. p38 mitogen-activated protein kinase controls NF-kappaB transcriptional activation and tumor necrosis factor alpha production through RelA phosphorylation mediated by mitogen- and stress-activated protein kinase 1 in response to Borrelia burgdorferi antigens. *Infection and immunity.*(Oct. 30, 2006);75(1):270-277.
O'Neil D, Glowatz H, Schlumpberger M, Ribosomal RNA Depletion for Efficient Use of RNA-Seq Capacity. Curr Protoc Mol Biol (Jul. 2013); Chapter 4: Unit4 19.
Ornstein BW, Hill EB, Geurs TL, French AR. Natural Killer Cell Functional Defects in Pediatric Patients With Severe and Recurrent Herpesvirus Infections. The Journal of Infectious Diseases. (Nov. 21, 2012);207(3):458-68. PubMed PMID: PMC3693586.
Pagani F, Baralle FE. Genomic variants in exons and introns: identifying the splicing spoilers. Nature reviews Genetics. (May 2004);5(5):389-96. doi:10.1038/nrg1327.
Paldiharis P, Szelenyi JG, Nguyen TH, Hollan SR. Changes in the Expression of the Cholinergic Structures of Human Lymphocytes-T Due to Maturation and Stimulation. Thymus. (Jan. 13, 1990);16(2):119-22.
Pall GS, Codony-Servat C, Byrne J, Ritchie L, Hamilton A. Carbodiimide-mediated cross-linking of RNA to nylon membranes improves the detection of siRNA, miRNA and piRNA by northern blot. Nucleic Acids Res (Apr. 2, 2007); 35:e60.
Pan Q, Shai O, Lee LJ, Frey BJ, Blencowe BJ. Deep surveying of alternative splicing complexity in the human transcriptome by high-throughput sequencing. Nature genetics. (Nov. 2, 2008);40(12):1413-5. doi:10.1038/ng.259.
Park C-K, Kim MS, Fang Z, et al. Functional Expression of Thermo-transient Receptor Potential Channels in Dental Primary Afferent Neurons Implication for Tooth Pain. *Journal of Biological Chemistry.* (Jun. 23, 2006);281 (25):17304-17311.
Park K, Haberberger RV, Gordon TP and Jackson MW. Antibodies interfering with the type 3 muscarinic receptor pathway inhibit gastrointestinal motility and cholinergic neurotransmission in Sjogren's syndrome. *Arthritis and rheumatism.* (Jan. 27, 2011); 63: 1426-34.

(56) References Cited

OTHER PUBLICATIONS

Park, D.-J et al., "Polymorphisms of the TRPV2 and TRPV3 genes associated with fibromyalgia in a Korean population", Rheumatology, (20160000), vol. 55, No. 8, pp. 1518-1527 (Apr. 13, 2016).
Parnavelas JG, Mione MC, Lavdas A. The cell lineage of neuronal subtypes in the mammalian cerebral cortex. Ciba Foundation symposium. (1995);193:41-58; discussion 9-70.
Parpart S, Wang XW. microRNA Regulation and Its Consequences in Cancer. Curr Pathobiol Rep (Mar. 2013); 1: 71-79.
Peschiaroli A, Giacobbe A, Formosa A, Markert EK, Bongiorno-Borbone L, et al. miR-143 regulates hexokinase 2 expression in cancer cells. Oncogene (Apr. 2, 2012); 32: 797-802.
Peterson D, Brenu EW, Gottschalk G, et al. Cytokines in the cerebrospinal fluids of patients with chronic fatigue syndrome/myalgic encephalomyelitis. *Mediators of inflammation*. (Feb. 26, 2015);2015:929720.
Phelan KD, Mock MM, Kretz O, Shwe UT, Kozhemyakin M, Greenfield LJ et al. Heteromeric canonical transient receptor potential 1 and 4 channels play a critical role in epileptiform burst firing and seizure-induced neurodegeneration. Molecular pharmacology. (Mar. 1, 2012); 81 (3):384-92. doi:10.1124/mol.111.075341.
Phelan KD, Shwe UT, Abramowitz J, Wu H, Rhee SW, Howell MD et al. Canonical transient receptor channel 5 (TRPC5) and TRPC1/4 contribute to seizure and excitotoxicity by distinct cellular mechanisms. Molecular pharmacology. (Mar. 1, 2012); 83(2):429-38. doi:10.1124/mol.112.082271.
Poli A, Michel T, Theresine M, Andres E, Hentges F, Zimmer J. CD56bright natural killer (NK) cells: an important NK cell subset. Immunology. (Nov. 26, 2008);126(4):458-65. doi:10.1111/j.1365-2567.2008.03027.x.
Pores-Fernando AT, Zweifach A. Calcium influx and signaling in cytotoxic T-lymphocyte lytic granule exocytosis. Immunological reviews. (2009);231(1):160-73. PubMed PMID: 19754896. Epub 2009/09/17. eng.
Price DT, Lefkowitz RJ, Caron MG, Berkowitz D, Schwinn DA. Localization of mRNA for three distinct alpha 1-adrenergic receptor subtypes in human tissues: implications for human alpha-adrenergic physiology. Molecular pharmacology. (Nov. 15, 1993);45(2):171-5.
Prins JB, van der Meer JW, Bleijenberg G. Chronic fatigue syndrome. Lancet (Jan. 28, 2006); 367: 346-355.
Pritchard CC, Cheng HH, Tewari M. MicroRNA profiling: approaches and considerations. Nat Rev Genet (Apr. 18, 2012); 13: 358-369.
Pritchard CC, Kroh E, Wood B, Arroyo JD, Dougherty KJ, et al. Blood cell origin of circulating microRNAs: a cautionary note for cancer biomarker studies. Cancer Prev Res (Phila) (Mar. 2012); 5: 492-497.
Qiu C, Chen G, Cui Q. Towards the understanding of microRNA and environmental factor interactions and their relationships to human diseases. Sci Rep (Mar. 16, 2012); 2: 318.
Racké K, Juergens UR and Matthiesen S. Control by cholinergic mechanisms. *European journal of pharmacology*. (Feb. 3, 2006); 533: 57-68.
Rah SY, Kwak JY, Chung YJ, Kim UH. ADP-ribose/TRPM2-mediated Ca2+ signaling is essential for cytolytic degranulation and antitumor activity of natural killer cells. *Scientific reports*. (Mar. 25, 2015);5:9482.
Rainville P. Brain mechanisms of pain affect and pain modulation. Current opinion in neurobiology. (Apr. 2002); 12(2):195-204. PubMed PMID: 12015237.
Reefman E, Kay JG, Wood SM, Offenhauser C, Brown DL, Roy S et al. Cytokine secretion is distinct from secretion of cytotoxic granules in NK cells. J Immunol. (Apr. 5, 2010);184(9):4852-62. doi:10.4049/jimmunol.0803954.
Reeves WC, Wagner D, Nisenbaum R, Jones JF, Gurbaxani B, Solomon L, et al. Chronic fatigue syndrome—a clinically empirical approach to its definition and study. BMC medicine. (Dec. 15, 2005);3:19.
Reiter Z. Interferon—a major regulator of natural killer cell-mediated cytotoxicity. Journal of interferon research. (May 3, 1993);13(4):247-57.

Ricci R, Sumara G, Sumara I, Rozenberg I, Kurrer M, Akhmedov A et al. Requirement of JNK2 for scavenger receptor A-mediated foam cell formation in atherogenesis. Science. (Nov. 26, 2004);306(5701):1558-61. doi:10.1126/science.1101909.
Richardson CE, Morgan JM, Jasani B, Green JT, Rhodes J, Williams GT et al. Effect of smoking and transdermal nicotine on colonic nicotinic acetylcholine receptors in ulcerative colitis. Qjm-Int J Med. (Nov. 4, 2002);96(1):57-65. doi:Doi 10.1093/Qjmed/Hcg007.
Richman DP, Arnason BGW. Nicotinic Acetylcholine-Receptor—Evidence for a Functionally Distinct Receptor on Human-Lymphocytes. Proceedings of the National Academy of Sciences of the United States of America. (Jun. 21, 1979);76(9):4632-5. doi:DOI 10.1073/pnas.76.9.4632.
Robertson LK, Ostergaard HL. Paxillin associates with the microtubule cytoskeleton and the immunological synapse of CTL through its leucine-aspartic acid domains and contributes to microtubule organizing center reorientation. J Immunol. (Oct. 31, 2011);187(11):5824-33. doi:10.4049/jimmunol.1003690.
Robertus JL, Harms G, Blokzijl T, Booman M, de Jong D, et al. Specific expression of miR-17-5p and miR-127 in testicular and central nervous system diffuse large B-cell lymphoma. Mod Pathol (Mar. 13, 2009); 22: 547-555.
Rouvier E, Luciani M, Golstein P. Fas involvement in Ca (2+)independent T cell-mediated cytotoxicity. *The Journal of experimental medicine*. (Jan. 1993);177(1):195-200.
Roux PP, Blenis J. Erk and p38 MAPK-activated protein kinases: a family of protein kinases with diverse biological functions. Microbiol Mol Biol Rev. (Jun. 2004);68(2):320-44. doi:10.1128/MMBR.68.2.320-344.2004.
Sacks DB. The role of scaffold proteins in MEK/ERK signalling. Biochemical Society transactions. (Jun. 29, 2006);34(Pt 5):833-6. doi:10.1042/BST0340833.
Saito Y, Liang G, Egger G, Friedman JM, Chuang JC, et al. Specific activation of microRNA-127 with downregulation of the proto-oncogene BCL6 by chromatin-modifying drugs in human cancer cells. Cancer Cell (Jun. 13, 2006); 9: 435-443.
Saito Y, Suzuki H, Tsugawa H, Imaeda H, Matsuzaki J, et al. Overexpression of miR-142-5p and miR-155 in gastric mucosa-associated lymphoid tissue (MALT) lymphoma resistant to Helicobacter pylori eradication. PLoS One (Nov. 28, 2012) 7:e47396.
Sanchez G, Colettis N, Vazquez P, Cervenansky C, Aguirre A, Quillfeldt JA et al. Muscarinic inhibition of hippocampal and striatal adenylyl cyclase is mainly due to the M(4) receptor. Neurochemical research. (Feb. 4, 2009);34(8): 1363-71. doi:10.1007/S11064-009-9916-9.
Sanchez-Mejorada G, Rosales C. Signal transduction by immunoglobulin Fc receptors. *Journal of leukocyte biology*. (Jan. 22, 1998);63(5):521-533.
Sato KZ, Fujii T, Watanabe Y, Yamada S, Ando T, Kazuko F et al. Diversity of mRNA expression for muscarinic acetylcholine receptor subtypes and neuronal nicotinic acetylcholine receptor subunits in human mononuclear leukocytes and leukemic cell lines. Neuroscience letters. (Apr. 30, 1999); 266(1):17-20. (Abstract only).
Schutz M, Oertel BG, Heimann D, Doehring A, Walter C, Dimova V, et al. Consequences of a human TRPA1 genetic variant on the perception of nociceptive and olfactory stimuli. PloS one. (Apr. 21, 2014); 9(4):e95592. doi:10.1371/journal.pone.0095592. PubMed PMID: 24752136; PubMed Central PMCID: PMC4005389.
Scully P, McKernan DP, Keohane J, Groeger D, Shanahan F, Dinan TG et al. Plasma cytokine profiles in females with irritable bowel syndrome and extra-intestinal comorbidity. The American journal of gastroenterology. (Apr. 20, 2010);105(10):2235-43. doi:10.1038/ajg.2010.159.
See DM, Cimoch P, Chou S, Chang J, Tilles J. The in vitro immunomodulatory effects of glyconutrients on peripheral blood mononuclear cells of patients with chronic fatigue syndrome. Integr Physiol Behav Sci (Jul. 1998); 33: 280-287.
Seigneur J, Kroeger D, Nita DA and Amzica F. Cholinergic action on cortical glial cells in vivo. *Cerebral cortex*. (Aug. 10, 2005); 16: 655-68.
Senatore et al. Calcium Channels: Regulation of GeneTranscription (Mar. 14, 2008) Title: Encyclopedia of Neuroscience.

(56) References Cited

OTHER PUBLICATIONS

Sewards TV, Sewards MA. The medial pain system: neural representations of the motivational aspect of pain. Brain research bulletin. (Jul. 24, 2002); 59(3):163-80. PubMed PMID: 12431746.

Shafi G, Aliya N, Munshi A. MicroRNA signatures in neurological disorders. Can J Neurol Sci (Mar. 2010); 37: 177-185.

Sharma G, Vijayaraghavan S. Nicotinic cholinergic signaling in hippocampal astrocytes involves calcium-induced calcium release from intracellular stores. Proceedings of the National Academy of Sciences of the United States of America. (Mar. 27, 2001); 98(7):4148-53. doi:10.1073/pnas.071540198.

Sharpe MC, Archard LC, Banatvala JE, Borysiewicz LK, Clare AW, David A, et al. A report—chronic fatigue syndrome: guidelines for research. Journal of the Royal Society of Medicine. (Feb. 1991);84(2):118-21.

Shaul YD, Seger R. The MEK/ERK cascade: from signaling specificity to diverse functions. Biochimica et biophysica acta. (Oct. 19, 2006);1773(8):1213-26. doi:10.1016/j.bbamcr.2006.10.005.

Shcherbakova I, Hoskins AA, Friedman LJ, et al. Alternative spliceosome assembly pathways revealed by single-molecule fluorescence microscopy. *Cell reports*. (Oct. 17, 2013);5(1):151-165.

Shen JX and Yakel JL. Nicotinic acetylcholine receptor-mediated calcium signaling in the nervous system. *Acta pharmacologica Sinica*. (May 18, 2009); 30: 673-80.

Shigetomi E, Jackson-Weaver O, Huckstepp RT, O'Dell TJ, Khakh BS. TRPA1 channels are regulators of astrocyte basal calcium levels and long-term potentiation via constitutive D-serine release. The Journal of neuroscience: the official journal of the Society for Neuroscience. (Jun. 12, 2013); 33(24):10143-53. doi:10.1523/JNEUROSCI.5779-12.2013.

Shigetomi E, Tong X, Kwan KY, Corey DP, Khakh BS. TRPA1 channels regulate astrocyte resting calcium and inhibitory synapse efficacy through GAT-3. Nature neuroscience. (Dec. 11, 2011); 15(1):70-80. doi: 10.1038/nn.3000. PubMed PMID: 22158513; PubMed Central PMCID: PMC3282183.

Skok M, Grailhe R and Changeux JP. Nicotinic receptors regulate B lymphocyte activation and immune response. *European journal of pharmacology*. (Jun. 16, 2005); 517: 246-51.

Skok MV, Kalashnik EN, Koval LN, Tsetlin VI, Utkin YN, Changeux JP et al. Functional nicotinic acetylcholine receptors are expressed in B lymphocyte-derived cell lines. Molecular pharmacology. (Jul. 3, 2003);64(4):885-9. doi:Doi 10.1124/Mol.64.4.885.

Slaby O, Svoboda M, Fabian P, Smerdova T, Knoflickova D, et al. Altered expression of miR-21, miR-31, miR-143 and miR-145 is related to clinicopathologic features of colorectal cancer. Oncology (Aug. 10, 2007); 72: 397-402.

Slezak S, Jin P, Caruccio L, Ren J, Bennett M, et al. Gene and microRNA analysis of neutrophils from patients with polycythemia vera and essential thrombocytosis: down-regulation of micro RNA-1 and -133a. J Transl Med (Jun. 4, 2009); 7: 39.

Smith RS, Weitz CJ, Araneda RC. Excitatory actions of noradrenaline and metabotropic glutamate receptor activation in granule cells of the accessory olfactory bulb. Journal of neurophysiology. (May 27, 2009);102(2):1103-14.

Sommerfeldt, L. et al., "Polymorphisms of adrenergic cardiovascular control genes are associated with adolescent chronic fatigue syndrome", Acta Paediatrica, (20110000), vol. 100, No. 2, pp. 293-298 (Oct. 22, 2010).

Spence VA, Khan F, Kennedy G, Abbot NC, Belch JJ. Acetylcholine mediated vasodilatation in the microcirculation of patients with chronic fatigue syndrome. Prostaglandins, leukotrienes, and essential fatty acids. (Dec. 18, 2003); 70(4):403-7. doi:10.1016/j.plefa.2003.12.016.

Stocks MB, Moxon S, Mapleson D, Woolfenden HC, Mohorianu I, et al. The UEA sRNA workbench: a suite of tools for analysing and visualizing next generation sequencing microRNA and small RNA datasets. Bioinformatics (May 24, 2012); 28:2059-2061.

Straus, S. E. (Aug. 1992). Defining the chronic fatigue syndrome. *Archives of internal medicine*, 152(8), 1569.

Strehler EE. Plasma membrane calcium ATPases as novel candidates for therapeutic agent development.J Pharm Pharm Sci. (Dec. 20, 2013);16(2):190-206. Review.

Su TT, Guo B, Kawakami Y, et al. PKC-beta controls I kappa B kinase lipid raft recruitment and activation in response to BCR signaling. *Nature immunology*. (Jun. 26, 2002); 3: 780-6.

Sun JC, Lanier LL. NK cell development, homeostasis and function: parallels with CD8+ T cells. *Nature Reviews Immunology*. (Aug. 26, 2011);11 (10):645-657.

Sun W, Julie Li YS, Huang HD, Shyy JY, Chien S. microRNA: a master regulator of cellular processes for bioengineering systems. Annu Rev Biomed Eng (Apr. 20, 2010); 12: 1-27.

Tanoue A, Koshimizu T-a, Shibata K, Nasa Y, Takeo S, Tsujimoto G. Insights into α 1 adrenoceptor function in health and disease from transgenic animal studies. Trends in Endocrinology & Metabolism. (Apr. 2003);14(3):107-13.

Tassi I, Presti R, Kim S, Yokoyama WM, Gilfillan S, Colonna M. Phospholipase C-gamma 2 is a critical signaling mediator for murine NK cell activating receptors. *Journal of immunology* (Baltimore, Md. : 1950). (May 5, 2005);175(2):749-754.

Thiel G, Muller I, Rossler OG. Signal transduction via TRPM3 channels in pancreatic beta-cells. Journal of molecular endocrinology. (Mar. 19, 2013); 50(3):R75-83. doi: 10.1530/JME-12-0237. PubMed PMID: 23511953.

Tobin G, Giglio D and Lundgren O. Muscarinic receptor subtypes in the alimentary tract. *Journal of physiology and pharmacology : an official journal of the Polish Physiological Society*. (Feb. 20, 2009); 60: 3-21.

Toth BL, Konrad M, Ghosh D, et al. Regulation of the transient receptor potential channel TRPM3 by phosphoinositides. *The Journal of general physiology*. (May 18, 2015);146(1):51-63.

Trapani JA. Granzymes: A Family of Lymphocyte Granule Serine Proteases. Genome Biol. (Nov. 23, 2001);2(12):3014.1-.7.

Trotta R, Fettucciari K, Azzoni L, et al. Differential role of p38 and c-Jun N-terminal kinase 1 mitogen-activated protein kinases in NK cell cytotoxicity. *Journal of immunology* (Baltimore, Md. : 1950). (May 26, 2000);165(4):1782-1789.

Tsvilovskyy VV, Zholos AV, Aberle T, Philipp SE, Dietrich A, Zhu MX et al. Deletion of TRPC4 and TRPC6 in mice impairs smooth muscle contraction and intestinal motility in vivo. Gastroenterology. (Oct. 2009);137(4):1415-24. doi:10.1053/j.gastro.2009.06.046.

Turchinovich A, Weiz L, Langheinz A, Burwinkel B. Characterization of extracellular circulating microRNA. Nucleic Acids Res (Apr. 5, 2011); 39: 7223-7233.

Üstün T. Measuring health and disability: Manual for WHO disability assessment schedule WHODAS 2.0. In: World Health Organization. (2010).

Van Borren MM, Verkerk AO, Wilders R, Hajji N, Zegers JG, Bourier J et al. Effects of muscarinic receptor stimulation on Ca2+ transient, cAMP production and pacemaker frequency of rabbit sinoatrial node cells. Basic research in cardiology. (Jul. 29, 2009);105(1):73-87 .doi:10.1007/s00395-009-0048-9.

Varallyay E, Burgyan J, Havelda Z. Detection of microRNAs by Northern blot analyses using LNA probes. Methods (Jun. 1, 2007); 43:140-145.

Veldhuis NA, Poole DP, Grace M, McIntyre P, Bunnett NW. The G protein-coupled receptor-transient receptor potential channel axis: molecular insights for targeting disorders of sensation and inflammation. Pharmacological reviews. (Jan. 2015); 67(1):36-73. doi:10.1124/pr.114.009555.

Vennekens R, Menigoz A, Nilius B. TRPs in the Brain. Reviews of physiology, biochemistry and pharmacology. (Nov. 2012); 163:27-64. doi:10.1007/112_2012_8. PubMed PMID: 23184016.

Verhagen AP, Pruijn GJ. Are the Ro RNP-associated Y RNAs concealing microRNAs? Y RNA-derived miRNAs may be involved in autoimmunity. Bioessays (Jul. 7, 2011); 33: 674-682.

Vijayaraghavan S and Sharma G. Editorial: Brain cholinergic mechanisms. *Frontiers in synaptic neuroscience*. (Sep. 15, 2015); 7: 14.

Visser M, Kayser M, Palstra RJ. HERC2 rs12913832 modulates human pigmentation by attenuating chromatin-loop formation between a long-range enhancer and the OCA2 promoter. Genome research. (Jan. 6, 2012) (3):446-55. PubMed PMID: 22234890. Pubmed Central PMCID: 3290780.

(56) References Cited

OTHER PUBLICATIONS

Vivier E, Tomasello E, Baratin M, Walzer T, Ugolini S. Functions of Natural Killer Cells. Nat Immunol. (Apr. 18, 2008);9(5):503-10. doi:10.1038/ni1582.

Vojdani A, Mordechai E, Brautbar N. Abnormal apoptosis and cell cycle progression in humans exposed to methyl tertiary-butyl ether and benzene contaminating water. Hum Exp Toxicol (Sep. 1, 1997); 16: 485-494.

Von Spiczak, S. et al., "Association study of TRPC4 as a candidate gene for generalized epilepsy with photosensitivity", Neuromolecular Medicine, (20100000), vol. 12, No. 3, pp. 292-299 (Jun. 24, 2010).

Vriens J, Held K, Janssens A, Toth BI, Kerselaers S, Nilius B et al. Opening of an alternative ion permeation pathway in a nociceptor TRP channel. Nature chemical biology. (Jan. 5, 2014);10(3):188-95. doi:10.1038/nchembio.1428.

Vriens J, Owsianik G, Hofmann T, Philipp SE, Stab J, Chen X et al. TRPM3 is a nociceptor channel involved in the detection of noxious heat. Neuron. (May 12, 2011);70(3):482-94. doi:10.1016/j.neuron.2011.02.051.

Wagner TF, Drews A, Loch S, Mohr F, Philipp SE, Lambert S, et al. TRPM3 channels provide a regulated influx pathway for zinc in pancreatic beta cells. Pflugers Archiv : European journal of physiology. (Apr. 18, 2010); 460(4):755-65. doi: 10.1007/S00424-010-0838-9. PubMed PMID: 20401728.

Wagner TF, Loch S, Lambert S, Straub I, Mannebach S, Mathar I, et al. Transient receptor potential M3 channels are ionotropic steroid receptors in pancreatic beta cells. Nature cell biology. (Nov. 2, 2008); 10(12):1421-30. doi: 10.1038/ncb1801. PubMed PMID: 18978782.

Wang H, Lu Y, Wang Z. Function of cardiac M3 receptors. Autonomic & autacoid pharmacology. (Aug. 2, 2006);27(1):1-11. doi:10.1111/j.1474-8673.2006.00381.x.

Wang N, Orr-Urtreger A, Chapman J, Ergun Y, Rabinowitz R, Korczyn AD. Hidden function of neuronal nicotinic acetylcholine receptor beta2 subunits in ganglionic transmission: comparison to alpha5 and beta4 subunits. Journal of the neurological sciences. (Jan. 20, 2005);228(2):167-77. doi:10.1016/j.jns.2004.11.050.

Wang R, Jaw JJ, Stutzman NC, Zou Z, Sun PD. Natural killer cell-produced IFN-gamma and TNF-alpha induce target cell cytolysis through up-regulation of ICAM-1. Journal of leukocyte biology. (Oct. 10, 2011);91(2):299-309. doi:10.1189/jlb.0611308.

Wang S, Dai Y, Fukuoka T, Yamanaka H, Kobayashi K, Obata K, et al. Phospholipase C and protein kinase A mediate bradykinin sensitization of TRPA1: a molecular mechanism of inflammatory pain. Brain: a journal of neurology. (Mar. 20, 2008);131 (Pt 5):1241-51. doi: 10.1093/brain/awn060. PubMed PMID: 18356188.

Wang S, Han HM, Jiang YN, et al. Activation of cardiac M3 muscarinic acetylcholine receptors has cardioprotective effects against ischaemia-induced arrhythmias. *Clinical and experimental pharmacology & physiology*. (Jan. 2, 2012); 39: 343-9.

Wang X, Schwarz TL. The mechanism of Ca2+ -dependent regulation of kinesin-mediated mitochondrial motility. *Cell*. (Jan. 9, 2009);136(1):163-174.

Wang X, Zhang J, Li F, Gu J, He T, Zhang X, Li Y. MicroRNA identification based on sequence and structure alignment. Bioinformatics. (Jun. 30, 2005); 21:3610-3614.

Wang Y, Pereira EF, Maus AD, et al. Human bronchial epithelial and endothelial cells express alpha7 nicotinic acetylcholine receptors. *Molecular pharmacology*. (Jul. 3, 2001);60(6):1201-1209.

Wang ZZ, Hardy SF, Hall ZW. Assembly of the nicotinic acetylcholine receptor. The first transmembrane domains of truncated alpha and delta subunits are required for heterodimer formation in vivo. The Journal of biological chemistry. (Nov. 1, 1996);271(44):27575-84.

Ware Jr JE, Cd. S. The MOS 36-item short-form health survey (SF-36): I. Conceptual framework and item selection. In: Medical care. (Jun. 1992). p. 473-83.

Wei S, Gamero AM, Liu JH, et al. Control of Lytic Function by Mitogen-activated Protein Kinase/Extracellular Regulatory Kinase 2 (ERK2) in a Human Natural Killer Cell Line: Identification of Perforin and Granzyme B Mobilization by Functional ERK2. *The Journal of experimental medicine*. (Jun. 1, 1998) 1998;187(11):1753-1765.

Wess J, Duttaroy A, Zhang W, Gomeza J, Cui Y, Miyakawa T et al. M1-M5 muscarinic receptor knockout mice as novel tools to study the physiological roles of the muscarinic cholinergic system. Receptors & channels. (Apr. 2003); 9(4):279-90.

Wess J. Molecular biology of muscarinic acetylcholine receptors. Critical reviews in neurobiology. (Feb. 1996);10(1):69-99. .

Wessler IK and Kirkpatrick CJ. Activation of muscarinic receptors by non-neuronal acetylcholine. *Handbook of experimental pharmacology*. (2012): 469-91.

White, A. et al., "Differences in metabolite-detecting, adrenergic, and immune gene expression following moderate exercise in chronic fatigue syndrome, multiple sclerosis and healthy controls", Psychosomatic Medicine, (20120000), vol. 74, No. 1, pp. 46-54 (Jan. 2012).

Whiteside TL, Friberg D. Natural killer cells and natural killer cell activity in chronic fatigue syndrome. The American journal of medicine. Sep. 28, 1998;105(3a):27s-34s. PubMed PMID: 9790479. (Sep. 28, 1998) Epub 1998)/10/28. eng.

Wilson SR, Gerhold KA, Bifolck-Fisher A, Liu Q, Patel KN, Dong X, et al. TRPA1 is required for histamine-independent, Mas-related G protein-coupled receptor-mediated itch. Nature neuroscience. (Apr. 3, 2011);14(5):595-602. doi: 10.1038/nn.2789. PubMed PMID: 21460831; PubMed Central PMCID: PMC3181150.

Wu S, Jin L, Vence L, Radvanyi LG. Development and application of 'phosphoflow' as a tool for immunomonitoring. Expert Rev Vaccines. (Jun. 2010);9(6):631-43. doi:10.1586/erv.10.59.

Wyller VB, Godang K, Morkrid L, Saul JP, Thaulow E, Walloe L. Abnormal thermoregulatory responses in adolescents with chronic fatigue syndrome: relation to clinical symptoms. Pediatrics. (Jul. 2007); 120(1):e129-37. doi: 10.1542/peds.2006-2759. PubMed PMID: 17606539.

Xiao C, Rajewsky K. MicroRNA control in the immune system: basic principles. Cell (Jan. 9, 2009); 136: 26-36.

Xuan P, Guo MZ, Huang YC, Li WB, Huang YF. MaturePred: efficient identification of microRNAs within novel plant pre-miRNAs. PLoS One. (Nov. 16, 2011); 6:e27422.

Yan HD, Villalobos C, Andrade R. TRPC Channels Mediate a Muscarinic Receptor-Induced Afterdepolarization in Cerebral Cortex. The Journal of neuroscience: the official journal of the Society for Neuroscience. (Aug. 12, 2009); 29(32):10038-46. doi: 10.1523/JNEUROSCI.1042-09.2009. PubMed PMID: 19675237; PubMed Central PMCID: PMC2747319.

Yim, Y.-R et al., "Polymorphisms of Transient Receptor Potential Vanilloid (TRPV) 2 and TRPV3 Gene Polymorphisms Were Associated with Fibromyalgia in a Korean Population", Arthritis & Rheumatology, (20150929), vol. 67, No. supplement 10 (Oct. 2015).

Yu CR, Role LW. Functional contribution of the alpha5 subunit to neuronal nicotinic channels expressed by chick sympathetic ganglion neurones. The Journal of physiology. (Mar. 10, 1998);509 ( Pt 3):667-81.

Yu TK, Caudell EG, Smid C, Grimm EA. IL-2 activation of NK cells: involvement of MKK1/2/ERK but not p38 kinase pathway. *Journal of immunology* (Baltimore, Md. : 1950). (Apr. 6, 2000);164(12):6244-6251.

Zamudio-Bulcock PA, Everett J, Harteneck C, Valenzuela CF. Activation of steroid-sensitive TRPM3 channels potentiates glutamatergic transmission at cerebellar Purkinje neurons from developing rats. Journal of neurochemistry. (Sep. 28, 2011); 119(3):474-85. doi: 10.1111/j.1471-4159.2011.07441.x. PubMed PMID: 21955047; PubMed Central PMCID: PMC3192925.

Zanovello P, Rosato A, Bronte V, et al. Interaction of lymphokine-activated killer cells with susceptible targets does not induce second messenger generation and cytolytic granule exocytosis. *The Journal of Experimental Medicine*. (Apr. 21, 1989);170(3):665-677.

Zhang M, March ME, Lane WS, Long EO. A signaling network stimulated by beta2 integrin promotes the polarization of lytic granules in cytotoxic cells. *Science signaling*. (Oct. 22, 2014);7(346):ra96.

(56) References Cited

OTHER PUBLICATIONS

Zhang Y, Wang Z, Chen M, Peng L, Wang X, et al. MicroRNA-143 targets MACC1 to inhibit cell invasion and migration in colorectal cancer. Mol Cancer (Apr. 25, 2012); 11:23.

Zhang Z, Reboreda A, Alonso A, Barker PA, Seguela P. TRPC channels underlie cholinergic plateau potentials and persistent activity in entorhinal cortex. Hippocampus. (Jan. 15, 2010); 21(4):386-97. doi: 10.1002/hipo.20755. PubMed PMID: 20082292.

Zhang Z, Seguela P. Metabotropic induction of persistent activity in layers II/III of anterior cingulate cortex. Cerebral cortex. (Mar. 26, 2010); 20(12):2948-57. doi: 10.1093/cercor/bhq043. PubMed PMID: 20348157.

Zheng X, Wang Y, Wei H, Sun R, Tian Z. LFA-1 and CD2 synergize for the Erk1/2 activation in the Natural Killer (NK) cell immunological synapse. *J Biol Chem.* (Jun. 4, 2009);284(32):21280-21287.

Zhu, G. et al., "Association of TRPV4 gene polymorphisms with chronic obstructive pulmonary disease", Human Molecular Genetics, (20090000), vol. 18, No. 11, pp. 2053-2062 (Mar. 11, 2009).

Extended European Search Report dated Feb. 18, 2019 for European Application No. 16788952.6.

Guha et al., "Implications for health and disease in the genetic signature of the Ashkenazi Jewish population," Genome Biology 13:R2 (publication date: Jan. 25, 2012).

N.N.: "Demonstrates rs2673930 is on the Illumina Human 660W array," (publication date: Oct. 14, 2010).

N.N.: "Demonstrates rs655207 is on the Illumina Human 660W array," (publication date: Oct. 14, 2010).

N.N.: "Demonstrates rs7860377 is on the Illumina Human 660W array," (publication date: Oct. 14, 2010).

N.N.: "Demonstrates that Illumina array HumanOmni2.5 comprises probes for rs6650469," (publication date: Jun. 16, 2010).

N.N.: "Demonstrates that Illumina HumanHap 650 array detects rs603955," (publication date: Jan. 25, 2012).

N.N.: "Demonstrates that Illumina HumanHap 650 array detects rs612308," (publication date: Jan. 25, 2012).

N.N.: "Demonstrates that rs11142508 is present on Affymetrix array SNP-5 and SNP-6," (publication date: Dec. 1, 2009).

N.N.: "Demonstrates that rs12682832 is present on Affymetrix array SNP-5 and SNP-6," (publication date: Dec. 1, 2009).

\* cited by examiner

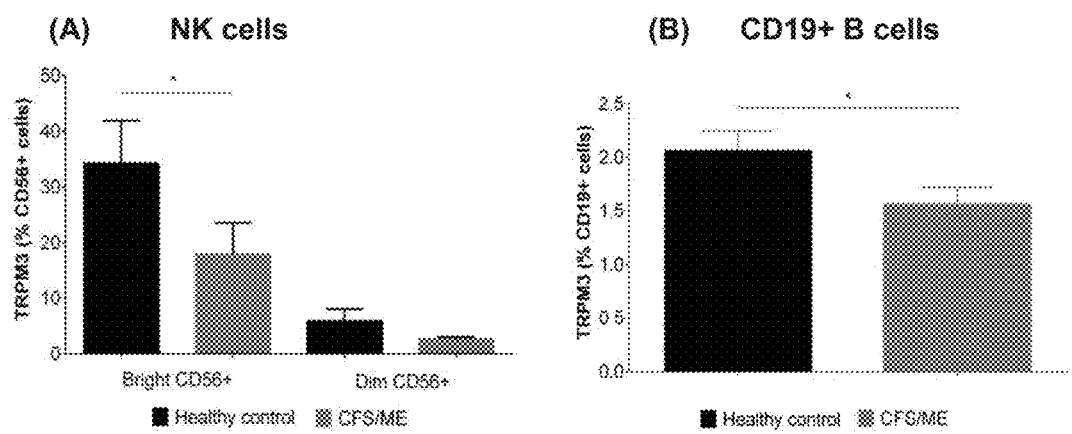
Figure 3
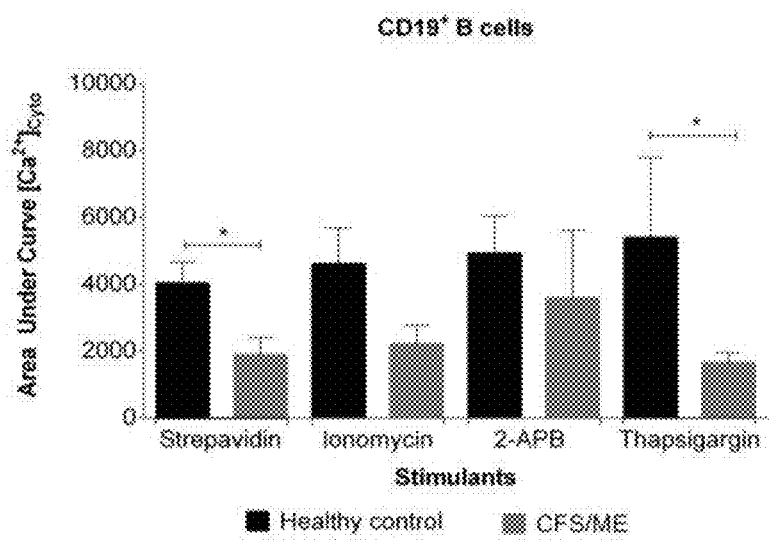
Figure 4 (A) CD19$^+$ B cells

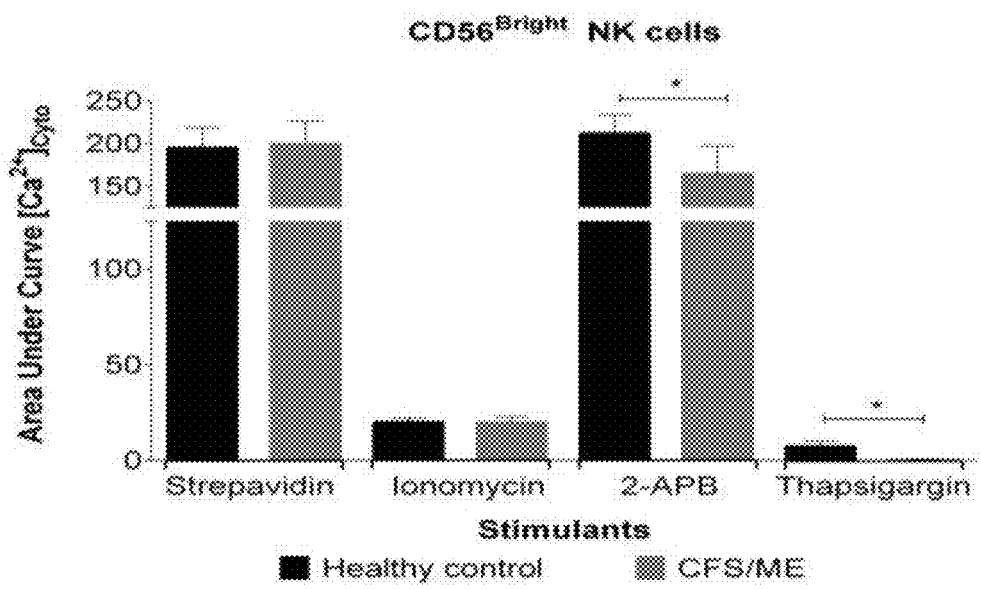
Figure 4 (B)   CD56$^{Bright}$ NK cells
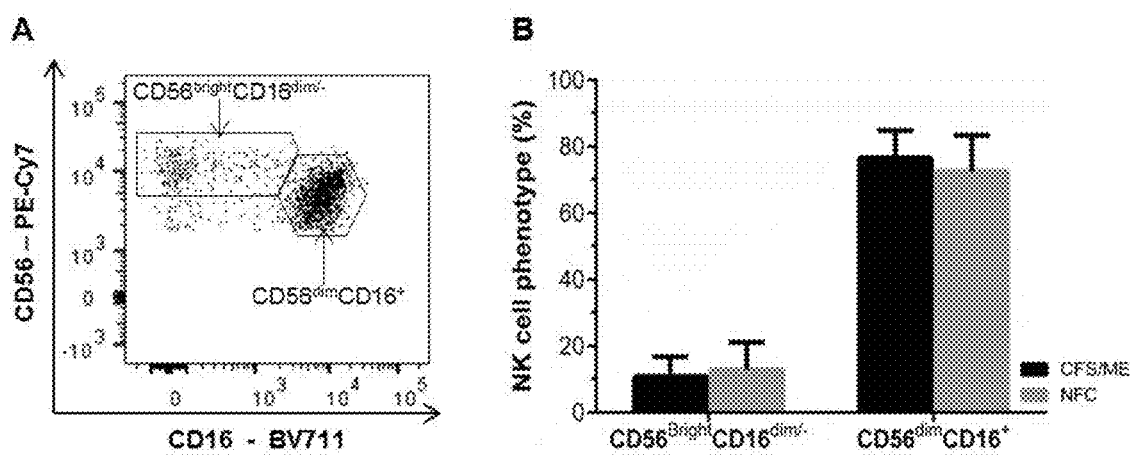
Figure 5

DIAGNOSTIC METHODS

TECHNICAL FIELD

In some aspects the present invention broadly relates to the use of single nucleotide polymorphisms (SNPs) in transient receptor potential (TRP) ion channel, acetylcholine receptor (AchR) and/or adrenergic receptor (ADR) genes as probes, tools or reagents for identifying, screening, diagnosing, monitoring or managing/treating subjects with, or predisposed to, medical conditions (or symptoms thereof), such as chronic fatigue syndrome (CFS), myalgic encephalomyelitis (ME), Gulf war syndrome (GWS), irritable bowel syndrome (IBS), multiple chemical sensitivity (MCS), fibromyalgia, and migraine, as well as some medical conditions caused by dysregulation in calcium, acetylcholine, TRP and ADR, and dysregulation in the gastrointestinal, cardiovascular, neurological, genitourinary and immune systems.

In other aspects the present invention relates to the use of calcium metabolism testing for identifying, screening, diagnosing, monitoring or managing/treating a subject having, or at risk of developing, a medical condition or symptom thereof. This aspect may involve testing any suitable calcium-dependent biochemical process.

In other aspects the present invention relates to identifying or diagnosing a subject having a medical condition or symptom thereof, by testing cells obtained from the subject for dysfunctional signalling through the Mitogen-Activated Protein Kinase (MAPK) pathway, including signalling via the MAPK kinase (MAPKK/MEK1/2) and extracellular signal-regulated kinase (ERK)1/2 as well as p38.

In other aspects the present invention relates to the use of one or more differentially regulated calcium-dependent kinase genes for identifying, screening, diagnosing or monitoring a subject having, or at risk of developing, a medical condition or symptom thereof.

Other aspects concern probes, tools or reagents based on, or developed from, the various aspects of the invention described above.

Yet other aspects relate to methods, kits and assays for identifying, screening, diagnosing, monitoring or managing/treating subjects with one or more of those medical conditions or symptoms.

BACKGROUND ART

It will be clearly understood that, if a prior art publication is referred to herein, this reference does not constitute an admission that the publication forms part of the common general knowledge in the art in Australia or in any other country.

Chronic fatigue syndrome/myalgic encephalomyelitis (CFS/ME) is known to affect about 1-4% of individuals worldwide [1a, 2a]. CFS/ME has an unknown aetiology and there is no specific diagnostic test. Chronic fatigue syndrome (CFS) is an unexplained disorder with multiple physiological impairments. The illness is characterised by significant impairment in physical activity and debilitating fatigue accompanied by impairment in memory, cognition and concentration, enhanced experience of pain as well as dysregulation of the gastrointestinal, cardiovascular and immune systems [14a-31a]. Research to date suggests significant immune impairment. However, the mechanism of this disorder remains to be determined. CFS patients may have reactions to a number of environmental and biological factors [11a-13a]. Moreover, there is evidence to suggest that CFS may have an allergic component [14a-16a].

Gulf war syndrome (GWS) is a serious condition that affects at least a quarter of the 697,000 US veterans who served in the 1900-1991 Gulf war [1e]. GWS comprises a complex of multiple concurrent symptoms, being typified by persistent memory and concentration problems, chronic headaches, wide-spread pain, gastrointestinal problems and other chronic abnormalities, not explained but well established by diagnoses. No effective treatments have been identified for GWS and studies indicate that few veterans recover over time.

Irritable bowel syndrome (IBS) is characterised by abnormally-increased motility of the small and large intestines of unknown origins. Most patients are young adults who complain of diarrhoea and occasionally pain in the lower abdomen. No organic disease has been identified in IBS to date.

Multiple chemical sensitivity (MCS) is the most common term used to describe a condition presenting as a complex array of symptoms linked to low level chemical exposures [2e]. The underlying mode(s) of action of MCS, i.e. the biological mechanisms by which the chemical sensitivity occurs, remain uncertain. In terms of sensitivities involving chemicals, the terms "MCS" and "chemical sensitivity" (sometimes known as "chemical intolerance") are often used interchangeably. However, "chemical sensitivity" in its wider context can describe several distinct types of reactions encompassing classical adverse toxicological reactions, immunological "allergic" sensitivities, individual chemical idiosyncrasies and intolerances through to aversions to particular odours. Broadly, on the basis of Consensus Criteria, MCS is distinguished from other types of chemical sensitivities or intolerances predominantly on the basis of reactions to multiple, diverse chemical substances, the wide spectrum of non-specific symptoms reported in multiple organ systems and the extremely low levels of environmental exposures linked to responses. Symptoms include headache, fatigue, confusion, depression, shortness of breath, arthralgia, myalgia, nausea, dizziness, memory problems, gastrointestinal symptoms and respiratory symptoms. Medical conditions caused by dysregulation in calcium, (especially in respect of CFS, ME, GWS, IBS, MCS, fibromyalgia and migraine), are typified by specific symptoms or dysregulation, including: significant impairment in physical activity; debilitating fatigue accompanied by impairment in memory, cognition and concentration; enhanced experience of pain; dysregulation of the gastrointestinal, cardiovascular and immune systems; respiratory symptoms and immunological "allergic" sensitivities; headache; fatigue; confusion; depression; shortness of breath; arthralgia; myalgia; nausea; dizziness; memory problems; and gastrointestinal symptoms.

Medical conditions caused by dysregulation in acetylcholine are typified by specific symptoms or dysregulation, including: significant impairment in physical activity; debilitating fatigue accompanied by impairment in memory, cognition and concentration; enhanced experience of pain; dysregulation of the gastrointestinal, cardiovascular and immune systems; headache; fatigue; confusion; depression; shortness of breath; arthralgia; myalgia; nausea; dizziness; memory problems; gastrointestinal symptoms; respiratory symptoms; and dysregulation of the gastrointestinal, cardiovascular and immune systems.

Medical conditions caused by dysregulation in TRP are typified by specific symptoms or dysregulation, including: significant impairment in physical activity; debilitating fatigue accompanied by impairment in memory, cognition and concentration; enhanced experience of pain; dysregulation of the gastrointestinal, cardiovascular and immune systems; headache; fatigue; confusion; depression; shortness of breath; arthralgia; myalgia; nausea; dizziness; memory problems; gastrointestinal symptoms; respiratory symptoms; and dysregulation of the gastrointestinal, cardiovascular and immune systems.

Medication conditions caused by dysregulation in ADR are typified by specific symptoms such as respiratory difficulties including shortness or breath, air hunger, colds and nasalpharynx congestion, cardiovascular conditions such as hypertension, and palpitations, gastrointestinal illness, kidney disease, diabetes, and autonomic function including sweating episodes.

Medical conditions caused by dysregulation of the gastrointestinal, cardiovascular, neurological, genitourinary and immune systems are typified by specific symptoms or dysregulation, including: significant impairment in physical activity; debilitating fatigue accompanied by impairment in memory, cognition and concentration; enhanced experience of pain; headache; fatigue; confusion; depression; shortness of breath; arthralgia; myalgia; nausea; dizziness; memory problems; gastrointestinal symptoms; urinary frequency or discomfort and respiratory symptoms.

Transient receptor potential (TRP) ion channels are expressed on almost all cells and have a significant effect on physiological functions [3b]. A number of channelopathies have been associated with TRP genes as these have consequences for cellular function [4b, 18b, 19b]. Dysregulation in TRPs has been associated with pathological conditions and diseases including chronic pain, overactive bladder, diabetes, chronic obstructive pulmonary disease, cardiac hypertrophy, familial Alzheimer's disease, skin diseases, skeletal dysplasias, motor neuropathies, neuro-sensory neuropathies (including Charcot-Marie-Tooth disease (type 2C) and cancer [4b-8b]. TRP ion channels have an important role in $Ca^{2+}$ signalling. TRP ion channels are activated following fluctuations or deviations in the cellular environment. Factors that may influence these changes are stressors including pathogens, temperature, pressure, chemicals, oxidation/reduction, toxins, osmolarity and pH [9b, 10b]. TRP ion channels are activated in the presence of irritants, inflammatory products, and xenobiotic toxins.

Mammalian TRPs are comprised of six main groups including the TRPA (ankyrin), TRPC (canonical), TRPM (melastatin), TRPML (mucolipin), TRPP (polycystin) and TRPV (vanilloid) [1b, 2b]. Generally, the TRPC channels are nonselective cation channels, only two are highly permeable $Ca^{2+}$ channels and two are impermeable for $Ca^{2+}$. Several TRPs are permeable for $Mg^{2+}$ and $Zn^{2+}$ [3b].

Acetylcholine is principally a neurotransmitter. The physiological functions of acetylcholine (ACh) are mediated by two membrane proteins, namely the muscarinic (mAChR) and nicotinic receptors (nAChR). Both receptor types have numerous subtypes and are located in the central and peripheral nervous system including the autonomic system. Furthermore, ACh performs non-neuronal functions, termed the non-neuronal cholinergic system (NNCS), where ACh performs endocrine functions of tissue located on smooth muscle, β pancreatic cells, glial cells, lymphocytes, ocular lens cells and brain vascular endothelium [1c] as well as in the CNS [2c-6c]. The degradation of ACh into choline and acetate is catalysed by the enzymes acetylcholinesterase (AChE) [7c, 8c].

There are five main mAChR subtypes—M1, M2, M3, M4 and M5, where M2 and M4 are inhibitory receptors, and M1, M2 and M3 are excitatory receptors [7c, 8c]. mAChRs are G protein coupled receptors that regulate intracellular signalling second messengers as well as ion channel activities. Once activated each subtype has distinctive functions—M1, M3 and M5 receptors form inositol 1,4,5-triphosphate (IP3) and 1,2 diacylglycerol (DAG), resulting in increased intracellular calcium. Activated M2 and M4 receptors inhibit adenylate cyclase activity as well as mediating function of non-selective cation channels, transient receptor potential channels and potassium channels [7c-10c].

nAChRs are fast ionotropic cationic nicotinic receptor channels which allow for the influx of cations such as potassium, calcium and sodium ions into the cell. nAChRs are comprised of different subunits: α subunits ($\alpha_1$-$\alpha_{10}$), β subunits ($\beta_1$-$\beta_4$), one δ submits, one γ subunit and one ε subunit [11c]. Depending upon combinational subunit binding AChRs can form either heteromers or homomers [11c].

Previous research has reported anomalies in acetylcholine signalling in CFS/ME patients. Peripheral cholinergic function is noted to be abnormal in CFS/ME patients exposed to ACh challenge whereby blood flow peaks take a longer time to return to normal. Increased sensitivity to ACh is noted in peripheral vascular endothelium [30c, 31c]. Moreover it is documented that ACh influences immune cell function [32c] and is manufactured and secreted by a wide range of immune cells including lymphocytes [33c, 34c, 32c, 35c]. The present inventors, along with others, have previously reported profound changes in immune cell and function as well as noting cardiac and neurological effects in CFS/ME patients [14c-16c, 18c-20c, 22c, 24c, 26c, 27c, 29c].

Single nucleotide polymorphisms (SNPs) occur in coding sequences of genes, non-coding regions of genes, or in the intergenic regions of genes. SNPs located within a coding sequence may or may not necessarily change the amino acid sequence of the protein that is produced. As such SNPs that do not alter the polypeptide sequence are termed synonymous (sometimes called silent variants) while SNPs that result in different polypeptide sequences are referred to as non-synonymous. Non-synonymous single nucleotide polymorphisms (nsSNPs) result in changes to protein expression that may result in aberrant signalling, such as loss or gain of function in their effect. Importantly, silent variants have been reported to affect splicing and may lead to human disease [10d, 11d]. Splicing affecting gene variants can induce exon skipping and activate alternate splice isoforms of the gene transcript, potentially resulting in altered gene transcripts and disease phenotypes.

Despite intensive research, to date, the pathophysiology of CFS/ME is not yet fully understood and clear diagnostic tools remain elusive. Therefore, there remains a need for rapid, cost-effective and reliable means for identifying, screening, diagnosing, monitoring, and/or managing/treating individuals having, or at risk of developing, a medical condition such as CFS/ME.

SUMMARY OF INVENTION

The present invention, in a first aspect, broadly concerns the use of one or more single nucleotide polymorphisms (SNPs) in one or more transient receptor potential (TRP) ion channel, acetylcholine receptor (AChR) or adrenergic receptor (ADR) genes as probes, tools or reagents for identifying, screening, diagnosing, monitoring or managing/treating subjects with, or predisposed to, medical conditions or specific symptoms thereof, such as chronic fatigue syndrome (CFS), myalgic encephalomyelitis (ME), Gulf war syndrome (GWS), irritable bowel syndrome (IBS), multiple chemical sensitivity (MCS), fibromyalgia, or migraine, as well as some medical conditions caused by dysregulation in calcium, acetylcholine, TRP or ADR, and dysregulation in the gastrointestinal, cardiovascular, neurological, genitourinary or immune systems.

In a second aspect, the present invention broadly relates to the use of calcium metabolism testing for identifying, screening, diagnosing, monitoring or managing/treating a subject having, or at risk of developing, a medical condition or symptom thereof.

In a third aspect, the present invention broadly relates to identifying, screening, diagnosing, monitoring or managing/treating a subject having a medical condition or symptom thereof, by testing cells obtained from the subject for dysfunctional signalling through the Mitogen-Activated Protein Kinase (MAPK) pathway, including signalling via the MARK kinase (MAPKK/MEK1/2) and extracellular signal-regulated kinase (ERK)1/2 as well as p38.

In a fourth aspect, the present invention broadly relates to the use of at least one differentially regulated calcium-dependent kinase gene for identifying, screening, diagnosing, monitoring or managing/treating a subject having, or at risk of developing, a medical condition or symptom thereof.

In a fifth aspect, the invention broadly concerns at least one probe, toot or reagent based on or developed from any one of the first to fourth aspects, for identifying, screening, diagnosing, monitoring at managing/treating the medical condition or symptom thereof.

In a sixth aspect, the present invention broadly concerns methods, kits or assays based on or developed from any one of the first to fifth aspects, for identifying, screening, diagnosing, monitoring or managing/treating subjects with one or more of the medical conditions or symptom thereof.

Preferred features, embodiments and variations of the invention may be discerned from the following Detailed Description which provides sufficient information for those skilled in the art to perform the invention. The Detailed Description is not to be regarded as limiting the scope of the preceding Summary of Invention in any way. The Detailed Description will make reference to a number of drawings as follows.

BRIEF DESCRIPTION OF THE DRAWINGS

FIG. 3. TRPM3 expression (%) on B lymphocytes and NK cells gated from HC (n=19) and CFS/ME (n=18) peripheral mononuclear cells. (A) NK cells subsets were characterized as $CD56^{Bright}$ NK cells and $CD56^{Dim}$ NK cells. Identification of TRPM3 surface expression on the NK cell subsets was analyzed using indirect flow cytometry. (B) B cells were characterized as total B cells ($CD3^-CD19^+$) and indirect flow cytometry was employed to identify TRPM3 surface expression on B cells. Histograms report the means±SEM. *Denotes p<0.05. HC: healthy controls; CFS: Chronic Fatigue Syndrome, ME: myalgic encephalomyelitis.

FIG. 4: Fura-AM cytoplasmic calcium influx in $CD19^+B$ cells and $CD56^{Bright}$ NK cells. (A). $CD19^+$ B cells calcium influx response curve reported as area under the curve was measured during Anti-IgM and anti-CD21 conjugated biotins were cross-linked with streptavidin or in the presence of ionomycin, 2-APB or Thapsigargin using flow cytometry. (B). Fura-AM cytoplasmic calcium influx response during $CD56^{Bright}$ NK cell receptors, Anti-CD314 and anti-CD335 conjugated biotins were cross-linked with streptavidin or in the presence of ionomycin, 2-APB or Thaosigargin using flow cytometry. Histograms report the means± SEM. *Denotes statistically significance at p<0.05.

FIG. 5: Representative flow cytometric plot of $CD56^{bright}CD16^{dim/-}$ and $CD56^{dim}CD16^+$ NK cell phenotypes (A). Comparisons of $CD56^{bright}CD16^{dim/-}$ and $CD56^{dim}CD16^+$ NK cell phenotypes between CFS/ME and NFC revealed no significant differences (B). Data are presented as median percentage with interquartile range.

DETAILED DESCRIPTION

Figure 1:
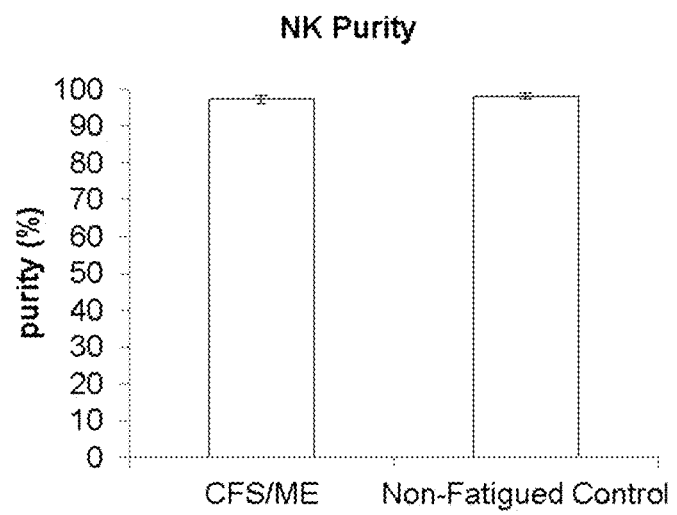
FIG. 1: Natural Killer Cell Purity. The purity of NK cells represents contamination from other cells types. Data shown for ME/CFS (n=39), and non-fatigued controls (n+30), and presented as mean±SEM.

Chronic fatigue syndrome (CFS) and myalgic encephalomyelitis (ME) are significantly debilitating medical conditions characterised by persistent fatigue and other specific symptoms that last for a minimum of six months. CFS and ME are often used interchangeably to describe the same illness, although this need not be the case. The fatigue experienced by human subjects suffering from CFS is not due to exertion or caused by other medical condition, and is not significantly relieved by rest. It is a complex disease involving dysregulation of immune and central nervous systems, dysfunction of cellular energy metabolism and ion transport, and cardiovascular abnormalities.

CFS/ME patients may further be categorised into mild, moderate, severe or very severely affected by their illness. Mild CFS/ME patients are mobile and often still employed, moderate CFS/ME patients have reduced mobility and are restricted in daily tasks, such as household chores, severe CFS/ME patients are only able to perform minimal necessary hygiene-related tasks and are wheelchair dependent while those with very severe CFS/ME are unable to carry out any daily task for themselves and are essentially bedridden [3e]. The ICC is the most recent and accurate set of criteria used for CFS/ME diagnosis and contains reference to these severity subgroups of CFS/ME patients, although it is not a necessary component of the guidelines [4e].

A number of healthcare initiatives have been undertaken to advance research into the likely cause(s), mechanism, preventive measures and potential therapeutic strategies for CFS/ME. Presently, none of these initiatives has been successful and the medical community remains baffled by the illness.

Currently there are no commercially available diagnostic tests or definitive methods for screening of CFS/ME.

The most puzzling aspect of CFS/ME is its multifactorial, multi-symptom nature and resulting difficulty in the diagnosis of CFS/ME. The current method of diagnosis is to rule out other potential causes of the symptoms presented by the patients. When symptoms are attributable to certain other conditions, the diagnosis of CFS/ME is excluded. As a result, there is a prolonged 'elimination' process often including several attempted unsuccessful treatment strategies. This process can often take from 6 to 18 months. Accordingly, it is a serious financial burden to the subject and to the healthcare system and economy.

Although there is no specific treatment for CFS/ME, it can be appropriately managed once a patient is diagnosed as suffering from CFS. Additionally, there is some evidence to suggest that earlier a management regime is adopted the greater the chance of improvement, although no cure exists and improvements are largely empirically based. A diagnostic/screening test would significantly help in diagnosis/screening of CFS/ME, thereby reducing the patient suffering and healthcare costs associated with waiting for many months before being diagnosed with CFS/ME.

The present invention is described in more detail below.

The present inventors have, for the first time, identified SNPs of TRP ion channel, ACh receptor and ADR genes that correlate with CFS and ME or specific symptoms thereof. The inventors believe that the identified SNPs of TRP ion channel, ACh receptor and ADR genes also correlate with other medical conditions or symptoms thereof such as IBS, MCS, fibromyalgia, and migraine, as well as some medical conditions caused by dysregulation in calcium, acetylcholine, TRP and ADR, and dysregulation in the gastrointestinal, cardiovascular, neurological, genitourinary and immune systems.

"Medical condition" as used hereon in the specification can include (but is not limited to): CFS or specific symptoms thereof; ME or specific symptoms thereof; GWS, IBS; MCS; non-allergic rhinitis; fibromyalgia; migraine; or rheumatoid arthritis. "Medical condition" as used hereon in the specification can also include (but is not limited to) conditions or symptoms: caused by dysregulation in calcium (especially in respect of CFS, ME, GWS, IBS, MCS, fibromyalgia or migraine); caused by dysregulation in acetylcholine (especially in respect of CFS, ME, GWS, IBS, MCS, fibromyalgia or migraine); caused by dysregulation in TRP (especially in respect of CFS, ME, GWS, IBS, MCS, fibromyalgia or migraine); caused by dysregulation in ADR; caused by dysregulation of the gastrointestinal, cardiovascular, neurological, genitourinary and immune systems (especially in respect of CFS, ME, GWS, IBS, MCS, non-allergic rhinitis, fibromyalgia or migraine).

Preferably, the medical condition is CFS or ME.

Specific symptoms of CFS or ME include: neuromuscular fatigue, particularly fatigue upon exertion; memory and concentration difficulties; muscle and joint pain; altered blood pressure, particularly postural orthostatic tachycardia syndrome; headache; immunological dysregulation; sore throat; swollen lymph nodes/glands; gastrointestinal symptoms including IB, diarrhoea, constipation and abdominal pain; chemical sensitives; and intolerances to drugs and chemicals.

MCS conditions/symptoms are characterised by reactions to multiple diverse chemical substances, the wide spectrum of non-specific symptoms reported in multiple organ systems, and the extremely low levels of environmental exposures linked to responses. Symptoms include: headache; fatigue; confusion; depression; shortness of breath; arthralgia; myalgia; nausea; dizziness; memory problems; gastrointestinal symptoms; or respiratory symptoms.

Medical conditions caused by dysregulation in calcium, (especially in respect of CPS, ME, GWS, IBS, MCS, fibromyalgia or migraine), are typified by specific symptoms or dysregulation such as: significant impairment in physical activity; debilitating fatigue accompanied by impairment in memory, cognition and concentration; enhanced experience of pain; dysregulation of the gastrointestinal, cardiovascular and immune systems; headache; fatigue; confusion; depression; shortness of breath; arthralgia; myalgia; nausea; dizziness; memory problems; gastrointestinal symptoms; respiratory symptoms; and immunological "allergic" sensitivities.

Medical conditions caused by dysregulation in acetylcholine, (especially in respect of CFS, ME, GWS, IBS, MCS, fibromyalgia or migraine), are typified by specific symptoms or dysregulation such as: significant impairment in physical activity; debilitating fatigue accompanied by impairment in memory, cognition and concentration; enhanced experience of pain; dysregulation of the gastrointestinal, cardiovascular and immune systems; headache; fatigue; confusion; depression; shortness of breath; arthralgia; myalgia; nausea; dizziness; memory problems; gastrointestinal symptoms; respiratory symptoms; and dysregulation of the gastrointestinal, cardiovascular and immune systems (immunological "allergic" sensitivities).

Medical conditions caused by dysregulation in TRP are typified by specific symptoms or dysregulation, including: significant impairment in physical activity; debilitating fatigue accompanied by impairment in memory, cognition and concentration; enhanced experience of pain; dysregulation of the gastrointestinal, cardiovascular and immune systems; headache; fatigue; confusion; depression; shortness of breath; arthralgia; myalgia; nausea; dizziness; memory problems; gastrointestinal symptoms; respiratory symptoms; and dysregulation of the gastrointestinal, cardiovascular and immune systems (immunological "allergic" sensitivities).

Medication conditions caused by dysregulation in ADR are typified by specific symptoms such as respiratory difficulties including shortness or breath, air hunger, colds and nasalpharynx congestion, cardiovascular conditions such as hypertension, and palpitations, gastrointestinal illness, kidney disease, diabetes, and autonomic function including sweating episodes.

Medical conditions caused by dysregulation of the gastrointestinal, cardiovascular, neurological, genitourinary and immune systems, (especially in respect of CFS, ME, GWS, IBS, MCS, fibromyalgia or migraine), are typified by specific symptoms or dysregulation, including: significant impairment in physical activity; debilitating fatigue accompanied by impairment in memory, cognition and concentration; enhanced experience of pain; headache; fatigue; confusion; depression; shortness of breath; arthralgia; myalgia; nausea; dizziness; memory problems; gastrointestinal symptoms; urinary frequency or discomfort; respiratory symptoms; and immunological "allergic" sensitivities.

Therefore, one or more of those SNPs can be used for identifying, screening, diagnosing or monitoring subjects with, or predisposed to, those medical conditions or symptoms thereof.

Moreover, yet one or more other TRP ion channel, ACh receptor or ADR gene/allele-based or gene product-based probes, tools, reagents, methods and assays can be used for identifying, screening, diagnosing, monitoring or managing/ treating subjects with, or predisposed to, those medical conditions or symptoms thereof.

The TRP ion channel can be selected from one or more of the following: TRPC4, TRPA1 (ankyrin), TRPM3 (melastatin) and TRPM4. The TRP ion channel gene can be selected from one or more of the following genes: Gene ID 80036, 7223, 101927086 and 54795. (Searchable at the ncbi.nlm.nih.gov.website.)

The at least one SNP of a TRP ion channel gene can be selected front a SNP listed in one or more of the Tables, such as Tables 1, 3, 4, 7, 9, 10, 12, 13, 15, 16, 17, 26, 27, 34a and 34b.

The at least one SNP of a TRP ion channel gene can be one or more (eg. 1, 2, 3, 4, 5, 6, 7, 8, 9, 10, 11, 12 or 13) of the following SNPs: rs12682832, rs11142508, rs1160742, rs4454352, rs1328123, rs3763619, rs7865858, rs1504401 or rs10115622 of TRPM3; rs2383844 or rs4738202 of TRPA1; or rs6650469 or rs655207 of TRPC4.

The ACh receptor can be selected from one or more of the following: muscarinic acetylcholine receptor, especially mAChRM3; and nicotinic acetylcholine alpha receptors, especially nAChRα2, nAChRα5 or nAChRα10. The AChR gene can be selected from one or more of the following genes: Gene ID 1131, 417, 4928, 57053, 100873984, 1138 and 1142.

The at least one SNP of an ACh receptor gene can be selected from a SNP listed in one or more of the Tables, such as Tables 2, 5, 6, 7, 9, 10, 12, 13, 14, 16, 17, 26, 28, 34a and 34b.

The at least one SNP of an ACh receptor gene can be one or more (eg. 1, 2, 3, 4, 5, 6, 7, 8, 9, 10, 11, 12, 13, 14, 15, 16, or 17) of the following SNPs: rs4463655, rs589962, rs1072320, rs7543259, rs6661621, rs7520974, rs726169, rsrs6669810 or rsrs6429157 of mAChRM3; rs2672211, rs2672214, rs2741868, rs2741870 or rs2741862 of nACh alpha 10; rs951266 or rs7180002 of nACh alpha 5; or rs2565048 of nACh alpha 2.

The ADR may be any suitable member of the adrenergic receptor family, such as α or β, or any suitable subtype thereof. (See Protein Sci. 1993 August; 2(8): 1198-1209, for example.)

The ADR can be adrenergic receptor α1 (ADRA1A), Gene ID. 148. (Searchable at the ncbi.nlm.nih.gov website.)

The at least one SNP of the ADRA1A gene can be rs2322333.

The at least one SNP of an ADR gene can be selected from a SNP listed in a Table, such as Table 34a or 34b.

The at least one SNP can be one or more non-synonymous SNPs. The non-synonymous SNP can be located in an intron, exon or regulatory region.

More information about the aforementioned SNPs/polymorphisms as well as other polymorphisms in the TRP ion channel, ACh receptor and ADR genes can be found in the NCBI SNP database, searchable at the ncbi.nim.nih.gov website.

The at least one probe, tool or reagent based on or developed from a TRP ion channel, ACh receptor or ADR gene or gene product can, for example, specifically bind, detect, identify, characterise or quantify the gene or part of the gene, the RNA gene product or part of the RNA gene product (RNA transcript), the polypeptide gene product or part of the polypeptide gene product (protein).

Of course, in an embodiment, the at least one probe, tool or reagent can identify a TRP ion channel, ACh receptor or ADR gene SNP of interest.

The probe, tool or reagent can be, but is not limited to, an oligonucleotide, primer, nucleic acid, polynucleotide, DNA, cDNA, RNA, peptide or polypeptide. These can be, for example, single stranded or double stranded, naturally occurring, isolated, purified, chemically modified, recombinant or synthetic.

The probe, tool or reagent can be, but is not limited to, an antibody or other type of molecule or chemical entity capable of detecting the gene or gene product (RNA or polypeptide).

The at least one probe, tool or reagent can be any number or combination of the above, and the number and combination will depend on the desired result to be achieved—eg. detection of a polymorphism at the genomic level (genotyping), at the RNA transcription level or translation polypeptide level, or quantitative or qualitative measurement of RNA transcription or translation.

In one preferred embodiment, the at least one probe, tool or reagent is for detection of a polymorphism at the genomic level, at the transcription level or polypeptide level.

In another preferred embodiment, the at least one probe, tool or reagent is for quantitative or qualitative measurement of RNA transcription or translation.

In yet another preferred embodiment, the at least one probe, tool or reagent is for assaying TRP ion channel, or ACh receptor protein/polypeptide expression on the surface of cells, preferably blood cells such as NK, T and/or B cells.

In yet another preferred embodiment, the at least one probe, tool or reagent is for assaying ADR protein/polypeptide expression in or on cells.

In a preferred embodiment, the probe, tool or reagent is for detecting at least one polymorphism as listed in a Table, such as any one of Tables 1 to 7, 9, 10, 12 to 17, 26 to 28, 34a and 34b.

The probe, tool or reagent can be derived from or based on one or more SNPs recited in a Table, such as any one of Tables 1 to 7, 9, 10, 12 to 17, 26 to 28, 34a and 34b.

The probe, tool or reagent can be derived from or based on any relevant region or regions of the TRP ion channel, ACh receptor or ADR genes. This includes the promoter region, 5' UTR, coding region (exon), intronic region or 3' UTR.

The probe, tool or reagent (1) can have a sequence as listed in Table 35 or Table 36, or (2) can have a sequence substantially identical to that shown In Table 35 or Table 36, or (3) can have a reverse complementary sequence to (1) or (2). The at least one probe, tool or reagent can, for example, be used to specifically bind, detect, identify, amplify, characterise or quantify the gene or part of the gene, the RNA gene product or part of the RNA gene product, or any synthetic or recombinant nucleic acid based on these.

With the foregoing in view, the present invention, in a preferred first form, resides broadly in at least one SNP of a TRP ion channel, ACh receptor and/or ADR gene for use as an indicator of a medical condition or symptom thereof.

For clarity, the term "indicator" signifies that the SNP positively correlates with the medical condition or symptom thereof.

For clarity, the expression "TRP ion channel, ACh receptor and/or ADR" and like expressions as used herein mean any individual gene/protein or any combination of 2 genes/proteins, or the combination of 3 genes/proteins.

In a second form, the present invention resides broadly in at least one probe, tool or reagent based on or developed from a TRP ion channel, ACh receptor and/or ADR gene or gene product for use as an indicator of a medical condition or symptom thereof.

For clarity, the term "indicator" signifies that a result produced by the probe, tool or reagent positively correlates with the medical condition or symptom thereof.

In a third form, the present invention resides in the use of at least one SNP of a TRP ion channel, ACh receptor and/or ADR gene for identifying, screening, diagnosing or monitoring a subject having, or at risk of developing, a medical condition or symptom thereof.

In a first preferred form, the present invention resides in a method of evaluating a subject for a medical condition or symptom thereof, or predisposition to a medical condition or symptom thereof, said method comprising:
(a) genotyping said subject for at least one polymorphism in a TRP ion channel, ACh receptor and/or ADR gene to obtain a result; and
(b) employing said result to provide an evaluation of the subject for the medical condition or symptom thereof.

In another preferred form, the present invention resides in a method of evaluating a subject for a medical condition or symptom thereof, or predisposition to a medical condition or symptom thereof, said method comprising:
(a) testing said subject for a TRP ion channel, ACh receptor and/or ADR gene product to obtain a result; and
(b) employing said result to provide an evaluation of the subject for the medical condition or symptom thereof.

The TRP ion channel, ACh receptor or ADR gene product may be transcribed RNA, nascent RNA, mRNA or polypeptide. Testing may involve, for example, detecting aberrant mRNA or a difference in the level of gene expression (ie. deregulation).

Testing may involve, for example, assaying TRP ion channel and/or ACh receptor expression on the surface of cells, preferably blood cells such as NK, T and/or B cells, whereby altered or reduced expression of TRP ion channel and/or ACh receptor is indicative of the subject having the medical condition or symptom thereof or a predisposition to the medical condition or symptom thereof.

Testing may involve, for example, assaying ADR expression in or on cells whereby altered or reduced expression of ADR is indicative of the subject having the medical condition or symptom thereof or a predisposition to the medical condition or symptom thereof.

In a fourth form, the present invention resides broadly in the use of at least one probe, tool or reagent based on or developed from a TRP ion channel, ACh receptor and/or ADR gene or gene product for identifying, screening, diagnosing, monitoring or managing/treating a subject having, or at risk of developing, a medical condition or symptom thereof.

In a fifth form, the present invention resides in at least one SNP of a TRP ion channel, ACh receptor and/or ADR gene when used as an indicator of a medical condition or symptom thereof, when used for identifying, screening, diagnosing or monitoring a subject having the medical condition or symptom thereof, or when used for identifying a subject at risk of developing a medical condition or symptom thereof.

In a sixth form, the present invention resides in at least one probe, tool or reagent based on or developed from a TRP ion channel, ACh receptor and/or ADR gene or gene product when used as an indicator of a medical condition or symptom thereof, when used in identifying, screening, diagnosing, monitoring or managing/treating a subject having a medical condition or symptom thereof, or when used for identifying a subject at risk of developing a medical condition or symptom thereof.

In a seventh form, the present invention resides in a method of identifying a subject at risk of developing, or diagnosing a subject having, a medical condition or symptom thereof, said method comprising the step of testing the subject for at least one SNP of a TRP ion channel, ACh receptor and/or ADR gene known to correlate with the medical condition or symptom thereof.

Preferably, this method comprises the step of testing a biological sample obtained from the subject for the at least one SNP of a TRP ion channel, ACh receptor and/or ADR gene known to correlate with the medical condition or symptom thereof.

In an eighth form, the present invention resides in a method of identifying a subject at risk of developing, or diagnosing a subject having, a medical condition or symptom thereof, said method comprising the step of assaying the subject for a property of a TRP ion channel, ACh receptor and/or ADR gene or gene product known to correlate with the medical condition or symptom thereof.

Preferably, this method comprises the step of testing a biological sample obtained from the subject for the property.

The property may be a polymorphism as the genomic level, at the transcription level or polypeptide level. That is, the property may relate to a polymorphism at the genomic level, or altered RNA, altered mRNA or altered polypeptide/protein expression.

The method may involve, for example, assaying TRP ion channel and/or ACh receptor expression on the surface of cells (such as blood cells), whereby altered or reduced expression of TRP ion channel and/or ACh receptor is indicative of the subject having the medical condition or symptom thereof.

The method may involve, for example, assaying ADR expression in or on cells whereby altered or reduced expression of ADR is indicative of the subject having the medical condition or symptom thereof.

In a ninth form, the present invention resides in a method of screening subjects for a prevalence of a medical condition or symptom thereof, or a method of identifying subjects at risk of developing a medical condition or symptom thereof, said method comprising the step of testing the subjects for at least one SNR of a TRP ion channel, ACh receptor and/or ADR gene known to correlate with the medical condition or symptom thereof.

Preferably, this method comprises the step of testing a biological sample obtained from each of the subjects for the at least one SNP of a TRP ion channel, ACh receptor and/or ADR gene.

In a tenth form, the present invention resides in a method of screening subjects for a prevalence of a medical condition or symptom thereof, or a method of identifying subjects at risk of developing a medical condition or symptom thereof, said method comprising the step of assaying each of the subjects for a property of a TRP ion channel, ACh receptor and/or ADR gene or gene product known to correlate with the medical condition or symptom thereof.

Preferably, this method comprises the step of testing a biological sample obtained from each of the subjects for the property.

Again, as for other forms of the invention, the property may be a polymorphism at the genomic level, at the transcription level or polypeptide level. That is, the property may relate to a polymorphism at the genomic level, or altered RNA or mRNA, or altered polypeptide/protein expression. The method may involve, for example, assaying TRP ion channel and/or ACh receptor expression on the surface of cells (such as blood cells), whereby altered or reduced expression of TRP ion channel and/or ACh receptor is indicative of the subject having the medical condition or symptom thereof. The method may involve, for example, assaying ADR expression in or on cells, whereby altered or reduced ADR is indicative of the subject having the medical condition or symptom thereof.

In view of the fact that SNPs/genes for the medical condition or symptom thereof have been discovered and characterised, this enables management/treatment of a subject that has been identified as having the medical condition or symptom thereof, and identifying whether a subject having the medical condition or symptom thereof is likely to respond to, or is responding to, management/treatment of that illness.

In an eleventh form, the present invention resides in a method of managing a subject with a medical condition or symptom thereof, or at risk of developing a medical condition or symptom thereof, said method comprising the steps of:

(1) testing the subject for at least one SNP of a TRP ion channel, ACh receptor and/or ADR gene known to correlate with the medical condition or symptom thereof; and (2) managing the subject if the subject has been found to have the at least one SNP of a TRP ion channel, ACh receptor and/or ADR gene known to correlate with the medical condition or symptom thereof.

Preferably, this method comprises the step of testing a biological sample obtained from the subject for the at least one SNP.

In a twelfth form, the present invention resides in a method of managing a subject with a medical condition or symptom thereof, or at risk of developing a medical condition or symptom thereof, said method comprising the steps of:

(1) assaying the subject for a property of a TRP ion channel, ACh receptor and/or ADR gene or gene product known to correlate with the medical condition or symptom thereof; and (2) managing the subject if the subject has been found to have the property of the TRP ion channel, ACh receptor and/or ADR gene or gene product known to correlate with the medical condition or symptom thereof.

Preferably, this method comprises the step of assaying a biological sample obtained from the subject for the property.

The property may relate to a polymorphism at the genomic level, or altered mRNA or altered polypeptide/protein expression. The method may involve, for example, assaying TRP ion channel and/or ACh receptor expression on the surface of cells (such as blood cells), whereby altered or reduced expression of TRP ion channel and/or ACh receptor is indicative of the subject having the medical condition or symptom thereof. The method may involve, for example, assaying ADR expression in or on cells, whereby altered or reduced ADR is indicative of the subject having the medical condition or symptom thereof.

In a thirteenth form, the present invention resides in a method of identifying or diagnosing a subject having a medical condition or symptom thereof, or at risk of developing a medical condition or symptom thereof, said method comprising the steps of:

(a) measuring the level of expression of at least one gene marker in a biological sample obtained from the subject that is differentially expressed in the medical condition or symptom thereof; and (b) comparing the level of expression of the at least one gene marker in the biological sample relative to a reference, wherein the at least one gene marker is a TRP ion channel, ACh receptor and/or ADR gene, and detection of an alteration in the level of gene expression of the at least one gene marker in the biological sample relative to the reference indicates that the subject has the medical condition or symptom thereof, or is at risk of developing the medical condition or symptom thereof.

In some embodiments, measuring the level of expression may involve measuring RNA, mRNA or polypeptide/protein expression. Measuring the level of expression may involve, for example, assaying TRP ion channel and/or ACh receptor expression on the surface of cells, preferably blood cells such as NK, T and/or B cells, whereby altered or reduced expression of TRP ion channel and/or ACh receptor is indicative of the subject having the medical condition or symptom thereof or a predisposition to the medical condition or symptom thereof. Measuring the level of expression may involve, for example, assaying ADR expression in or on cells, whereby altered or reduced ADR is indicative of the subject having the medical condition or symptom thereof or a predisposition to the medical condition or symptom thereof.

In some embodiments, measuring the level of expression may involve immunocytochemistry and/or flow cytometry.

In a fourteenth form, the present invention resides in a method of identifying whether a subject having a medical condition or symptom thereof ("illness") is responding to management of that illness, said method comprising the steps of:

optionally, isolating a biological sample from the subject prior to management of the illness and during and/or after management of the illness;

measuring the level of expression in the biological samples of at least one gene marker that is differentially expressed in the illness; and comparing the level of expression of the gene marker in the biological samples before and during and/or after management of the illness, wherein the at least one gene marker is a TRP ion channel, ACh receptor and/or ADR gene, and a change in the level of expression of the gene marker identifies the subject as having responded to the management of the illness.

In some embodiments, measuring the level of expression may involve measuring RNA, mRNA or polypeptide/protein expression. In some embodiments, measuring the level of expression may involve, for example, assaying TRP ion channel and/or ACh receptor expression on the surface of cells, preferably blood cells such as NK, T and/or B cells. In some embodiments, measuring the level of expression may involve, for example, assaying ADR expression on or in cells.

In a fifteenth form, the present invention resides in a TRP ion channel, ACh receptor and/or ADR gene-based or gene-product-based probe, tool or reagent for identifying a subject having a medical condition or symptom thereof, or a TRP ion channel, ACh receptor and/or ADR gene-based or gene-product-based probe, tool or reagent for use in identifying a subject having a medical condition or symptom thereof.

In a sixteenth form, the present invention resides in a TRP ion channel, ACh receptor and/or ADR gene-based or gene-product-based probe, tool or reagent for identifying a subject at risk of developing a medical condition or symptom thereof, or a TRP ion channel, ACh receptor and/or ADR gene-based or gene-product-based probe, tool or reagent for use in identifying a subject at risk of developing a medical condition or symptom thereof.

In a seventeenth form, the present invention resides in a TRP ion channel, ACh receptor and/or ADR gene-based or gene-product-based probe, tool or reagent when used for identifying a subject having, or at risk of developing, a medical condition or symptom thereof.

In an eighteenth form, the present invention resides in a kit or assay for identifying a subject having a medical condition or symptom thereof or at risk of developing a medical condition or symptom thereof, said kit or assay comprising one or more probes, tools or reagents for assaying or characterising a TRP ion channel, ACh receptor and/or ADR gene or gene product using a biological sample derived from the subject.

In a nineteenth form, the present invention resides in a biological sample comprising at least a TRP ion channel, ACh receptor and/or ADR gene or gene product, when isolated for the purpose for testing the biological sample for a medical condition or symptom thereof.

In a twentieth form, the present invention resides in an array of oligonucleotide probes suitable for determining a TRP ion channel, ACh receptor and/or ADR gene/allele or gene product in a biological sample.

In a twenty-first form, the present invention resides in a microarray comprising oligonucleotide probes suitable for determining a TRP ion channel, ACh receptor and/or ADR gene/allele or gene product in a biological sample.

In a twenty-second form, the present invention resides in a biochip comprising a solid substrate and at least one oligonucleotide probe suitable for determining a TRP ion channel, ACh receptor and/or ADR gene/allele or gene product in a biological sample.

In a twenty-third form, the present invention resides in an article of manufacture comprising: (1) non-naturally occurring polynucleotide, recombinant polynucleotide, oligonucleotide or cDNA form of a TRP ion channel, ACh receptor and/or ADR gene or a fragment thereof; or (2) a polynucleotide or an oligonucleotide that is complementary to the gene of (1) or fragment thereof; or (3) an expression vector, recombinant cell or biological sample, tool, reagent, kit or assay comprising (1) or (2) or fragment thereof.

In a twenty-fourth form, the present invention resides in a TRP ion channel, ACh receptor and/or ADR gene SNP as shown in a Table, such as any one of Tables 1 to 7, 9, 10, 12 to 17, 26 to 28, 34a and 34b.

In a twenty-fifth form, the present invention resides in a nucleotide sequence as shown or substantially as shown in Table 35 or Table 36 (SEQ ID Nos. 1 to 64), or a complementary sequence thereof.

By "substantially as shown", the sequence has sequence identity preferably of between 80-99%, including 81, 82, 83, 84, 85, 86, 87, 88, 89, 90, 91, 92, 93, 94, 95, 96, 97, 98 and 99%.

The expression "at least one"—context allowing—means 2, 3, 4, 5, 6, 7, 8, 9, 10, 11, 12, 13, 14, 15, 16, 17, 18, 19, 20 or more.

Since the inventors have found SNPs in the TRP ion channel, ACh receptor or ADR gene to correlate with calcium metabolic changes/regulation (including calcium ion changes), it follows that those changes can also be used, for example, to identify, screen, diagnose or monitor subjects with, or predisposed to, one or more of the medical conditions or specific symptoms thereof described above.

It also follows that since the inventors have found SNPs in the TRP ion channel, ACh receptor or ADR gene to correlate with yet other changes, those changes can also be used, for example, to identify, screen, diagnose or monitor subjects with, or predisposed to, one or more of the medical conditions or specific symptoms thereof described above. For the sake of convenience, however, only calcium ion/ metabolic changes/testing will be further expanded upon below. Those of skill in the art will appreciate what those other changes/tests could be and may include but not be limited to calcium metabolic co-factors or transcription factors such as calmodulin, calcineurin, nuclear factor of activated T cells (NFAT), IP3, DAG, ORAI, ATPases in all their forms or iso-types.

Accordingly, in a twenty-sixth form, the present invention resides in the use of calcium metabolism testing for identifying, screening, diagnosing or monitoring a subject having, or at risk of developing, a medical condition or symptom thereof. The medical condition or symptom thereof may be attributable to at least one SNP in a TRP ion channel, ACh receptor and/or ADR gene, but it need not be attributable to the at least one SNP in a TRP ion channel, ACh receptor and/or ADR gene.

In a twenty-seventh form, the present invention resides broadly in calcium metabolism testing when used as an indicator of a medical condition or symptom thereof, when used for identifying, screening, diagnosing or monitoring a subject having the medical condition or symptom thereof, or when used for identifying a subject at risk of developing a medical condition or symptom thereof. The medical condition or symptom thereof is preferably attributable to at least one SNP in a TRP ion channel, ACh receptor and/or ADR gene.

In a twenty-eighth form, the present invention resides in a method of identifying a subject at risk of developing, or diagnosing a subject having, a medical condition or symptom thereof, said method comprising the step of testing or assaying the subject for a change in calcium metabolism. The medical condition or symptom thereof is preferably attributable to at least one SNP in a TRP ion channel, ACh receptor and/or ADR gene.

In a twenty-ninth form, the present invention resides in a method of screening subjects for a prevalence of a medical condition or symptom thereof, or a method of identifying subjects at risk of developing a medical condition or symptom thereof, said method comprising the step of assaying each of the subjects for a change in calcium metabolism. The medical condition or symptom thereof is preferably attributable to at least one SNP in a TRP ion channel, ACh receptor and/or ADR gene.

In a thirtieth form, the present invention resides in a method of managing a subject with a medical condition or symptom thereof, or at risk of developing a medical condition or symptom thereof, said method comprising the steps of:

(1) testing the subject for a change in calcium metabolism; and (2) managing the subject if the subject has been found to have said change in calcium metabolism. The medical condition or symptom thereof is preferably attributable to at least one SNP in a TRP ion channel, ACh receptor and/or ADR gene.

In a thirty-first form, the present invention resides in a kit or assay for identifying a subject having a medical condition or symptom thereof or at risk of developing a medical condition or symptom thereof, said kit or assay comprising one or more probes, tools or reagents for assaying calcium metabolic change in the subject. The medical condition or symptom thereof is preferably attributable to at least one SNP in a TRP ion channel, ACh receptor and/or ADR gene.

In a thirty-second form, the present invention resides in a kit or method for testing, screening or managing/treating a subject having a medical condition or symptom thereof or at risk of developing a medical condition or symptom thereof for any calcium metabolite which may include but not be limited to calcium metabolic co-factors or transcription factors such as calmodulin, calcineurin, nuclear factor of activated T cells (NFAT), IP3, DAG, ORAI, ATPases in all their forms or iso-types. The medical condition or symptom thereof is preferably attributable to at least one SNP in a TRP ion channel, ACh receptor and/or ADR gene.

The inventors have also discovered that calcium-dependent protein kinase genes may be differentially regulated in patients having particular medical conditions or symptoms thereof compared to healthy individuals. For example, in severe CFS/ME patients, dysfunction in $Ca^{2+}$ dependent protein kinase genes contribute to the pathomechanism of that illness.

In a thirty-third form, the present invention resides in at least one differentially regulated calcium-dependent kinase gene for use as an indicator of a medical condition or symptom thereof.

In a thirty-fourth form, the present invention resides in at least one probe, tool or reagent based on or developed from at least one differentially regulated calcium-dependent kinase gene for use as an indicator of a medical condition or symptom thereof.

In a thirty-fifth form, the present invention resides in the use of at least one differentially regulated calcium-dependent kinase gene for identifying, screening, diagnosing or monitoring a subject having, or at risk of developing, a medical condition or symptom thereof.

In a thirty-sixth form, the present invention resides in a method of evaluating a subject for a medical condition or symptom thereof, or predisposition to a medical condition or symptom thereof, said method comprising:
 (a) testing a subject for differential regulation of at least one calcium-dependent kinase gene to obtain a result; and
 (b) employing said result to provide an evaluation of the subject for the medical condition or symptom thereof.

In a thirty-seventh form, the present invention resides in at least one differentially regulated calcium-dependent kinase gene for identifying, screening, diagnosing, monitoring or managing/treating a subject having, or at risk of developing, a medical condition or symptom thereof.

In a thirty-eighth form, the present invention resides in at least one differentially regulated calcium-dependent kinase gene when used as an indicator of a medical condition or symptom thereof, when used for identifying, screening, diagnosing, monitoring or managing/treating a subject having the medical condition or symptom thereof, or when used for identifying a subject at risk of developing a medical condition or symptom thereof.

In a thirty-ninth form, the present invention resides in at least one probe, tool or reagent based on or developed from at least one differentially regulated calcium-dependent kinase gene when used as an indicator of a medical condition or symptom thereof, when used in identifying, screening, diagnosing, monitoring or managing/treating a subject having a medical condition or symptom thereof, or when used for identifying a subject at risk of developing a medical condition or symptom thereof.

In a fortieth form, the present invention resides in a method of identifying a subject at risk of developing, or diagnosing a subject having, a medical condition or symptom thereof, said method comprising the step of testing the subject for at least one differentially regulated calcium-dependent kinase gene known to correlate with the medical condition or symptom thereof.

In a forty-first form, the present invention resides in a method of screening subjects for a prevalence of a medical condition or symptom thereof, or a method of identifying subjects at risk of developing a medical condition or symptom thereof, said method comprising the step of testing the subjects for at least one differentially regulated calcium-dependent kinase gene known to correlate with the medical condition or symptom thereof.

In a forty-second form, the present invention resides in a method of managing a subject with a medical condition or symptom thereof or at risk of developing a medical condition or symptom thereof said method comprising the steps of:
(1) testing the subject for differential regulation of at least one calcium-dependent kinase gene known to correlate with the medical condition or symptom thereof; and
(2) managing the subject if the subject has been found to have the at least one differentially regulated calcium-dependent kinase gene known to correlate with the medical condition or symptom thereof.

In a forty-third form, the present invention resides in a method of identifying or diagnosing a subject having a medical condition or symptom thereof or at risk of developing a medical condition or symptom thereof said method comprising the steps of:
(a) measuring the level of expression of at least one calcium-dependent kinase gene marker in a biological sample obtained from the subject that is differentially expressed in the medical condition or symptom thereof; and
(b) comparing the level of expression of the at least one gene marker in the biological sample relative to a reference, wherein detection of an alteration in the level of gene expression of the at least one gene marker in the biological sample relative to the reference indicates that the subject has the medical condition or symptom thereof, or is at risk of developing the medical condition or symptom thereof.

In a forty-fourth form, the present invention resides in a method of identifying whether a subject having a medical condition or symptom thereof ("illness") is responding to management of that illness, said method comprising the steps of:
optionally, isolating a biological sample from the subject prior to management of the illness and during and/or after management of the illness;
measuring the level of expression in the biological samples of at least one calcium-dependent kinase gene marker that is differentially expressed in the illness; and
comparing the level of expression of the at least one gene marker in the biological samples before and during and/or after management of the illness, wherein a change in the level of expression of the at least one gene marker identifies the subject as having responded to the management of the illness.

In a forty-fifth form, the present invention resides in at least one calcium-dependent kinase gene-based or gene-product-based probe, tool or reagent for identifying a subject having a medical condition or symptom thereof, or at least one calcium-dependent kinase gene-based or gene-product-based probe, tool or reagent for use in identifying a subject having a medical condition or symptom thereof.

In a forty-sixth form, the present invention resides in at least one calcium-dependent kinase gene-based or gene-product-based probe, tool or reagent for identifying a subject at risk of developing a medical condition or symptom thereof, or at least one calcium-dependent kinase gene-based or gene-product-based probe, tool or reagent for use in identifying a subject at risk of developing a medical condition or symptom thereof.

In a forty-seventh form, the present invention resides in at least one calcium-dependent kinase gene-based or gene-product-based probe, tool or reagent when used for identifying a subject having, or at risk of developing, a medical condition or symptom thereof.

In a forty-eighth form, the present invention resides in a kit or assay for identifying a subject having a medical condition or symptom thereof or at risk of developing a medical condition or symptom thereof, said kit or assay comprising one or more probes, tools or reagents for assaying or characterizing at least one calcium-dependent kinase gene product using a biological sample derived from the subject.

In a forty-ninth form, the present invention resides in a biological sample comprising at least at least one calcium-dependent kinase gene or gene product, when isolated for the purpose for testing the biological sample for a medical condition or symptom thereof.

In a fiftieth form, the present invention resides in an array of oligonucleotide probes suitable for determining at least one calcium-dependent kinase gene product in a biological sample.

In a fifty-first form, the present invention resides in a microarray comprising oligonucleotide probes suitable for determining at least one calcium-dependent kinase gene product in a biological sample.

In a fifty-second form, the present invention resides in a biochip comprising a solid substrate and at least one oligonucleotide probe suitable for determining at least one calcium-dependent kinase gene product in a biological sample.

In a fifty-third form, the present invention resides in an article of manufacture comprising: (1) non-naturally occurring polynucleotide, recombinant polynucleotide, oligonucleotide or cDNA form of at least one calcium-dependent kinase gene or a fragment thereof; or (2) a polynucleotide or an oligonucleotide that is complementary to the gene of (1) or fragment thereof; or (3) an expression vector, recombinant cell or biological sample, tool, reagent, kit or assay comprising (1) or (2) or fragment thereof.

In a fifty-fourth form, the present invention resides in the use of calcium metabolism testing for identifying, screening, diagnosing or monitoring a subject having, or at risk of developing, a medical condition or symptom thereof, wherein said medical condition or symptom thereof is attributable to differential regulation of at least one calcium-dependent kinase gene.

In a fifty-fifth form, the present invention resides in calcium metabolism testing when used as an indicator of a medical condition or symptom thereof, when used for identifying, screening, diagnosing or monitoring a subject having the medical condition or symptom thereof, or when used for identifying a subject at risk of developing a medical condition or symptom thereof, wherein said medical condition or symptom thereof is attributable to at least one differentially regulated calcium-dependent kinase gene.

In a fifty-sixth form, the present invention resides in a method of identifying a subject at risk of developing, or diagnosing a subject having, a medical condition or symptom thereof, said method comprising the step of testing the subject for a change in calcium metabolism, wherein said medical condition or symptom thereof is attributable to at least one differentially regulated calcium-dependent kinase gene.

In a fifty-seventh form, the present invention resides in a method of screening subjects for a prevalence of a medical condition or symptom thereof, or a method of identifying subjects at risk of developing a medical condition or symptom thereof, said method comprising the step of assaying each of the subjects for a change in calcium metabolism, wherein said medical condition or symptom thereof is attributable to at least one differentially regulated calcium-dependent kinase gene.

In a fifty-eighth form, the present invention resides in a method of managing a subject with a medical condition or symptom thereof, or at risk of developing a medical condition or symptom thereof, said method comprising the steps of:
(1) testing the subject for a change in calcium metabolism, wherein said medical condition or symptom thereof is attributable to at least one differentially regulated calcium-dependent kinase gene; and
(2) managing the subject if the subject has been found to have said change in calcium metabolism.

In a fifty-ninth form, the present invention resides in a kit or assay for identifying a subject having a medical condition or symptom thereof or at risk of developing a medical condition or symptom thereof, said kit or assay comprising one or more probes, tools or reagents for assaying calcium metabolic change in the subject, wherein said medical condition or symptom thereof is attributable to at least one differentially regulated calcium-dependent kinase gene.

In a sixtieth form, the present invention resides in a kit or method for testing, screening or treating a subject having a medical condition or symptom thereof or at risk of developing a medical condition or symptom thereof, for any calcium metabolite which may include but not be limited to calcium metabolic co-factors or transcription factors wherein said medical condition or symptom thereof is attributable to at least one differentially regulated calcium-dependent kinase gene.

For the thirty-third to sixtieth forms of the invention, preferably the medical condition or symptom thereof is: CFS and/or ME; severe CFS and/or ME (subjects are only able to perform minimal necessary hygiene-related tasks and are wheelchair dependent); or very severe CFS and/or ME (subjects are unable to carry out any daily task for themselves and are essentially bedridden) or symptom thereof.

For the thirty-third to sixtieth forms of the invention, preferably the at least one differentially regulated calcium-dependent kinase gene is a gene selected from a Table, such as Table 31 or Table 32.

For the thirty-third to sixtieth forms of the invention, preferably the at least one differentially regulated calcium-dependent kinase gene is selected from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91 or 92 genes shown in a Table, such as Table 31 or Table 32.

For clarity, the testing of at least one differentially regulated calcium-dependent kinase gene may involve testing one gene or a group of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 71, 72, 73, 74, 75, 76, 77, 78, 79, 80, 81, 82, 83, 84, 85, 86, 87, 88, 89, 90, 91 or 92 genes.

For the thirty-third to sixtieth forms of the invention, preferably the at least one differentially regulated calcium-dependent kinase gene is upregulated in gene expression.

For the thirty-third to sixtieth forms of the invention, preferably the at least one differentially regulated calcium-dependent kinase gene is downregulated in expression.

For the thirty-third to sixtieth forms of the invention the calcium-dependent kinase gene may be isolated from or tested in any suitable cell type or tissue. The calcium-dependent kinase gene may be of peripheral blood mononuclear cell original, although this need not be the case. The calcium-dependent kinase gene may be of Natural Killer cell origin.

For the thirty-third to sixtieth forms of the invention, preferably the biological sample contains peripheral blood mononuclear cells, including Natural Killer cells.

For the thirty-third to sixtieth forms of the invention, in some embodiments, the testing or measuring involves testing or measuring altered transcription/mRNA expression. In other embodiments, the testing or measuring involves testing or measuring altered translation/protein expression or another property or characteristic of the gene product/RNA/protein. Of course, determining differential regulation of a calcium-dependent kinase gene can be carried out as described for the first to thirty-second forms of the invention.

The inventors have also discovered that dysfunctional signalling through the Mitogen-Activated Protein Kinase (MAPK) pathway of cells (such as NK cells), including signalling via the MAPK kinase (MAPKK/MEK1/2) and extracellular signal-regulated kinase (ERK)1/2 as well as p38, may be used as an indicator that a subject has a particular medical condition or symptom thereof.

In a sixty-first form, the present invention resides in a method of identifying or diagnosing a subject having a medical condition or symptom thereof, comprising the step of testing a biological sample obtained from the subject for dysfunctional signalling through the Mitogen-Activated Protein Kinase (MAPK) pathway, including signaling via the MAPK kinase (MAPKK/MEK1/2) and extracellular signal-regulated kinase (ERK)1/2 as well as p38, wherein dysfunctional signalling through the MAPK pathway, including signalling via the MAPK kinase (MAPKK/MEK1/2) and extracellular signal-regulated kinase (ERK) 1/2 as well as p38, indicates that the subject has the medical condition or symptom thereof.

In a sixty-second form, the present invention resides in a method of identifying or diagnosing a subject having a medical condition or symptom thereof, said method comprising the steps of:
  (a) obtaining at least one biological sample from the subject; and
  (b) testing the biological sample for dysfunctional signalling through the Mitogen-Activated Protein Kinase (MAPK) pathway, including signalling via the MAPK kinase (MAPKK/MEK1/2) and extracellular signal-regulated kinase (ERK)1/2 well as p38, wherein dysfunctional signalling through the MAPK pathway, including signalling via the MAPK kinase (MAPKK/MEK1/2) and extracellular signal-regulated kinase (ERK)1/2 as well as p38, indicates that the subject has the medical condition or symptom thereof.

In a sixty-third form, the present invention resides in a method of identifying whether a subject having a medical condition or symptom thereof ("illness") is responding to management of that illness, said method comprising the steps of:
  (a) obtaining at least one biological sample from the subject; and
  (b) testing the at least one biological sample for dysfunctional signalling through the Mitogen-Activated Protein Kinase (MAPK) pathway, including signalling via the MAPK kinase (MAPKK/MEK1/2) and extracellular signal-regulated kinase (ERK)1/2 as well as p38, wherein dysfunctional signalling through the MAPK pathway indicates that the subject has the medical condition or symptom thereof, and wherein no or less dysfunctional signalling through the MAPK pathway indicates that the subject is responding to management of the illness.

In a sixty-fourth form, the present invention resides in at least one probe, tool or reagent for identifying a subject having a medical condition or symptom thereof, said at least one probe, tool or reagent being for assaying or characterising the Mitogen-Activated Protein Kinase (MAPK) pathway, including signalling via the MAPK kinase (MAPKK/MEK1/2) and extracellular signal-regulated kinase (ERK) 1/2 as well as p38, using a biological sample derived from the subject.

In a sixty-fifth form, the present invention resides in a kit or assay for identifying a subject having a medical condition or symptom thereof, said kit or assay comprising one or more probes, tools or reagents for assaying or characterising the Mitogen-Activated Protein Kinase (MAPK) pathway, including signalling via the MAPK kinase (MAPKK/MEK1/2) and extracellular signal-regulated kinase (ERK) 1/2 as well as p38, using a biological sample derived from the subject.

For the sixtieth to sixty-fifth forms of the invention, the MAPK pathway of any suitable cell or tissue type may be tested/assayed. For example, in some embodiments, the biological sample may contain peripheral blood mononuclear cells. For example, in some embodiments, the biological sample may include Natural Killer cells.

Testing for dysfunctional signalling may be carried out in any suitable way. For example, dysfunctional signalling may be typified by reduced or increased phosphorylation, so phosphorylation of dephosphorylation may be tested. In other embodiments, the level of gene expression (RNA or protein) may be tested, or a property of the protein or biochemical function may be tested, as described for other forms of the invention as well as elsewhere in this specification.

For the sixtieth to sixty-fifth forms of the invention, preferably dysfunctional signalling is typified by reduced phosphorylation of ERK1/2. Preferably dysfunctional signalling is typified by increased phosphorylation of MEK1/2 and p38. Preferably dysfunctional signalling is typified by reduced phosphorylation of ERK1/2 in conjunction with increased phosphorylation of MEK1/2 and p38.

For the sixtieth to sixty-fifth forms of the invention, preferably dysfunctional signalling is typified by reduced phosphorylation of ERK1/2 in $CD56^{dim}CD16^+$ NK cells in conjunction with increased phosphorylation of MEK1/2 and p38 in $CD56^{bright}CD16^{dim/-}$ NK cells.

For the sixtieth to sixty-fifth forms of the invention, preferably the medical condition or symptom is: chronic fatigue syndrome (CFS) or symptom thereof; or, myalgic encephalomyelitis (ME) or symptom thereof. The CFS/ME may or may not be linked to a single nucleotide polymorphism (SNP) in a transient receptor potential (TRP) ion channel, acetylcholine receptor (AchR) and/or ADR gene.

In a sixty-sixth form, the present invention resides in the use of calcium metabolism testing for identifying, screening, diagnosing or monitoring, a subject having, or at risk of developing, a medical condition or symptom thereof, wherein said medical condition or symptom thereof is optionally attributable to: at least one SNP of at least one transient receptor potential (TRP) ion channel, acetylcholine receptor (AchR) and/or adrenergic receptor (ADR) gene; a polymorphism at the genomic level, altered RNA expression, altered polypeptide/protein expression, or an altered biological function of at least one transient receptor potential (TRP) ion channel, acetylcholine receptor (AchR) and/or adrenergic receptor (ADR) gene; differential regulation of at least one calcium-dependent kinase gene; and/or dysfunctional signalling through the Mitogen-Activated Protein Kinase (MAPK) pathway, including signalling via the MAPK kinase (MAPKK/MEK1/2) and extracellular signal-regulated kinase (ERK)1/2 as well as p38.

In a sixty-seventh form, the present invention resides in calcium metabolism testing when used as an indicator of a medical condition or symptom thereof, when used for identifying, screening, diagnosing or monitoring a subject having the medical condition or symptom thereof, or when used for identifying a subject at risk of developing a medical condition or symptom thereof, wherein said medical condition or symptom thereof is optionally attributable to: at least one SNP of at least one transient receptor potential (TRP) ion channel, acetylcholine receptor (AchE) and/or adrenergic receptor (ADR) gene; a polymorphism at the genomic level, altered RNA expression, altered polypeptide/protein expression, or an altered biological function of at least one transient receptor potential (TRP) ion channel, acetylcholine receptor (AchR) and/or adrenergic receptor (ADR) gene; differential regulation of at least one calcium-dependent kinase gene; and/or dysfunctional signalling through the Mitogen-Activated Protein Kinase (MAPK) pathway, including signalling via the MAPK kinase (MAPKK/MEK1/2) and extracellular signal-regulated kinase (ERK)1/2 as well as p38.

In a sixty-eighth form, the present invention resides in a method of identifying a subject at risk of developing, or diagnosing a subject having, a medical condition or symptom thereof, said method comprising the step of testing the subject for a change in calcium metabolism, wherein said medical condition or symptom thereof is optionally attributable to: at least one SNP of at least one transient receptor potential (TRP) ion channel, acetylcholine receptor (AchR) and/or adrenergic receptor (ADR) gene; a polymorphism at the genomic level, altered RNA expression, altered polypeptide/protein expression, or an altered biological function of at least one transient receptor potential (TRP) ion channel, acetylcholine receptor (AchR) and/or adrenergic receptor (ADR) gene; differential regulation of at least one calcium-dependent kinase gene; and/or dysfunctional signalling through the Mitogen-Activated Protein Kinase (MARK) pathway, including signalling via the MAPK kinase (MAPKK/MEK1/2) and extracellular signal-regulated kinase (ERK)1/2 as well as p38.

In a sixty-ninth form, the present invention resides in a method of screening subjects for a prevalence of a medical condition or symptom thereof, or a method of identifying subjects at risk of developing a medical condition or symptom thereof, said method comprising the step of assaying each of the subjects for a change in calcium metabolism, wherein said medical condition or symptom thereof is optionally attributable to: at least one SNP of at least one transient receptor potential (TRP) ion channel, acetylcholine receptor (AchR) and/or adrenergic receptor (ADR) gene; a polymorphism at the genomic level, altered RNA expression, altered polypeptide/protein expression, or an altered biological function of at least one transient receptor potential (TRP) ion channel, acetylcholine receptor (AchR) and/or adrenergic receptor (ADR) gene; differential regulation of at least one calcium-dependent kinase gene; and/or dysfunctional signalling through the Mitogen-Activated Protein Kinase (MAPK) pathway, including signalling via the MAPK kinase (MAPKK/MEK1/2) and extracellular signal-regulated kinase (ERK)1/2 as well as p38.

In a seventieth form, the present invention resides in a method of managing a subject with a medical condition or symptom thereof, or at risk of developing a medical condition or symptom thereof, said method comprising the steps of: (1) testing the subject for a change in calcium metabolism; and (2) managing the subject if the subject has been found to have said change in calcium metabolism, wherein said medical condition or symptom thereof is optionally attributable to: at least one SNP of at least one transient receptor potential (TRP) ion channel, acetylcholine receptor (AchR) and/or adrenergic receptor (ADR) gene; a polymorphism at the genomic level, altered RNA expression, altered polypeptide/protein expression, or an altered biological function of at least one transient receptor potential (TRP) ion channel, acetylcholine receptor (AchR) and/or adrenergic receptor (ADR) gene; differential regulation of at least one calcium-dependent kinase gene; and/or dysfunctional signalling through the Mitogen-Activated Protein Kinase (MAPK) pathway, including signalling via the MAPK kinase (MAPKK/MEK1/2) and extracellular signal-regulated kinase (ERK)1/2 as well as p38.

In a seventy-first form, the present invention resides in a kit or assay for identifying a subject having a medical condition or symptom thereof or at risk of developing a medical condition or symptom thereof, said kit or assay comprising one or more probes, tools or reagents for assaying calcium metabolic change in the subject, wherein said medical condition or symptom thereof is optionality attributable to: at least one SNP of at least one transient receptor potential (TRP) ion channel, acetylcholine receptor (AchR) and/or adrenergic receptor (ADR) gene; a polymorphism at the genomic level, altered RNA expression, altered polypeptide/protein expression, or an altered biological function of at least one transient receptor potential (TRP) ion channel, acetylcholine receptor (AchR) and/or adrenergic receptor (ADR) gene; differential regulation of at least one calcium-dependent kinase gene; and/or dysfunctional signalling through the Mitogen-Activated Protein Kinase (MAPK) pathway, including signalling via the MARK kinase (MAPKK/MEK1/2) and extracellular signal-regulated kinase (ERK)1/2 as well as p38.

In a seventy-second form, the present invention resides in a kit or method for testing, screening or treating a subject having a medical condition or symptom thereof or at risk of developing a medical condition or symptom thereof, for any calcium metabolite, wherein said medical condition or symptom thereof is optionally attributable to: at least one SNP of at least one transient receptor potential (TRP) ion channel, acetylcholine receptor (AchR) and/or adrenergic receptor (ADR) gene; a polymorphism at the genomic level, altered RNA expression, altered polypeptide/protein expression, or an altered biological function of at least one transient receptor potential (TRP) ion channel, acetylcholine receptor (AchR) and/or adrenergic receptor (ADR) gene; differential regulation of at least one calcium-dependent kinase gene; and/or dysfunctional signalling through the Mitogen-Activated Protein Kinase (MAPK) pathway, including signalling via the MAPK kinase (MARKK/MEK1/2) and extracellular signal-regulated kinase (ERK)1/2 as well as p38.

The sixty-fifth to seventy-second forms of the invention can have features as described for the earlier forms of the invention.

Further features of all forms of the invention, including the first to seventy-second forms of the invention, are explained below.

Definitions

The term 'oligonucleotide' refers to a single-stranded sequence of ribonucleotide or deoxyribonucleotide bases, known analogues of natural nucleotides, or mixtures thereof. An oligonucleotide comprises a nucleic-acid based molecule including DNA, RNA, PNA, LNA, UNA or any combination thereof. Oligonucleotides are typically less than about 50 nucleotides in length and may be prepared by direct chemical synthesis or cloning and restriction of appropriate sequences.

The term 'polynucleotide' refers to a single- or double-stranded polymer of deoxyribonucleotide, ribonucleotide bases or known analogues of natural nucleotides, or mixtures thereof. A polynucleotide comprises a nucleic-acid based molecule including DNA, RNA, PNA, LNA, UNA or any combination thereof. The term includes reference to the specified sequence as well as to the sequence complimentary thereto, unless otherwise indicated. The term 'polynucleotide' includes chemically modified variants, as realised by those skilled in the art.

The term 'complementary' refers to the ability of two single-stranded nucleotide sequences to base pair, typically according to the Watson-Crick base pairing rules. For two nucleotide molecules to be complementary they need not display 100% complementarity across the base pairing regions, but rather there must be sufficient complementarity to enable base pairing to occur. Thus a degree of mismatching between the sequences may be tolerated and the sequences may still be complementary.

'Nucleic acid' as used herein includes 'polynucleotide', 'oligonucleotide', and 'nucleic acid molecule', and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide.

As used herein, the term 'recombinant' refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The terms 'isolated', 'purified' and 'substantially purified' as used herein mean essentially free of association with other biological components/contaminants, e.g., as a naturally occurring protein that has been separated from cellular and other contaminants by the use of antibodies or other methods or as a purification product of a recombinant host cell culture.

'Probe' as used herein may mean an oligonucleotide capable of binding to a target nucleic acid/RNA of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind. Probes may be used for screening and diagnostic methods, as described herein. The probes may be attached or immobilized to a solid substrate or apparatus, such as a biochip.

'Target' as used herein (context allowing) can mean an oligonucleotide or portions or fragments thereof, which may be bound by one or more probes under stringent hybridization conditions.

Subject

The subject can be any mammal. Mammals include humans, primates, livestock and farm animals (eg. horses, sheep and pigs), companion animals (eg. dogs and cats), and laboratory test animals (eg. rats, mice and rabbits). The subject is preferably human.

Human subjects having CFS and/or ME can be defined as per the American CDC 1994 case definition [26a] and in the following citations [75a, 76a, 77a, 78a, 79a, 80a, 81a, 82a].

Non-fatigued/healthy controls/subjects (eg. not having CFS/ME) preferably have no medical history or symptoms of persistent fatigue or illness. Human subjects also preferably exclude individuals who were smokers, pregnant/breast-feeding or immobile, or bad autoimmune, thyroid or cardiac related disorders prior to the onset of CFS/ME.

General Techniques Overview

The steps/techniques of isolating a biological sample from a subject, processing a biological sample, genomic DNA extraction, RNA extraction, polypeptide extraction, DNA detection and characterisation, RNA detection and characterisation, polypeptide detection and characterisation, DNA sequencing, DNA sequence analyses, SNP genotyping studies, RNA location and identification, RNA profiling, RNA screening, RNA sequencing, RNA sequence analyses, measuring a level of expression of RNA, comparing expression levels (differential expression or dysregulation) of an RNA, polypeptide isolation, polypeptide sequencing and characterisation, measuring a level of polypeptide expression, comparing expression levels (differential expression or dysregulation) of a polypeptide, characterisation of dysfunctional signalling through the Mitogen-Activated Protein Kinase pathway of cells (such as PBMCs or NK cells), and detecting changes in calcium-dependent kinase pathways can be carried out in any suitable way.

It is to be appreciated that methodologies generally described for SNPs, such as differential expression or characterisation of RNA or protein or protein function etc, may equally apply to other forms of the invention, such as testing for changes in calcium metabolism, testing for dysfunctional signalling through the Mitogen-Activated Protein Kinase pathway or detecting changes in calcium-dependent kinase pathways.

It is also to be appreciated that methodologies generally described for any one form of the invention may equally be applicable to one or more other forms of the invention.

Biological Sample

Any biological sample that comprises nucleic acid/a polynucleotide (eg. genomic DNA or RNA) from the subject is suitable for use in the methods of the invention. The biological sample can be processed so as to isolate the nucleic acid/polynucleotide. Alternatively, whole cells or other biological samples can be used without isolation of the nucleic acid/polynucleotides contained therein.

Any biological sample that comprises polypeptide/protein from the subject is suitable for use in the methods of the invention. The biological sample can be processed so as to isolate the polypeptide/protein. Alternatively, whole cells or other biological samples can be used without isolation of the nucleic polypeptide/protein contained therein.

Some forms of the invention concern a biological sample or a step of isolating one or more biological samples from a subject. Typically, any form of the invention concerning testing of a subject etc. may involve the step of isolating one or more biological samples from the subject and testing that/those. For example, testing for differences in gene expression/gene products may involve isolating more than one biological sample, even from different tissues of that subject.

The biological sample can be any suitable sample derived from the subject—obtained either non-invasively or invasively. It can be cellular- or extracellular-derived, or both. For example: 1. Buccal (mouth) cells—obtained by swishing mouthwash in the mouth or by swabbing or brushing the inside of the cheek with a swab or brush; 2. Blood—obtained by pricking the finger and collecting the drops (dried blood spot) or by venepuncture (whole blood); 3. Skin—obtained by a (punch) biopsy; 4. Organ tissue—obtained by biopsy; 5. Plasma—obtained by blood plasma fractionation; 6. Urine—obtained by urination; 7. Faeces—obtained by stool sample; 8. Cerebrospinal fluid—obtained by spinal tap; and 9. Sputum—obtained by expectoration or nasotracheal suctioning.

Techniques for biological sample collection are well known to skilled persons.

In some embodiments, the biological sample can be a biofluid such as blood, plasma, serum, other blood isolate/component, urine, sputum, cerebrospinal fluid, or ductal fluid, and can be fresh, frozen or fixed. In some preferred embodiments, for example, biofluid or biological sample comprising plasma or serum can be removed surgically and preferably by extraction, e.g. by hypodermic or other types of needles.

The biofluid typically will contain at least one SNP/gene/gene product (RNA and/or polypeptide) of interest, and will be relatively stable.

In some embodiments, plasma harvesting is employed. Plasma harvesting/extraction can be performed in any suitable way, but preferably immediately after peripheral blood collection. Plasma harvesting can involve a centrifugation step so as to separate the plasma from other blood components, and frozen storage of that plasma.

In some embodiments, different biological samples can be obtained from different tissues from one and the same subject.

Subject Management

As used herein, the term 'managing' (or 'treating') a subject or 'management' is such that the medical condition or at least one symptom of the medical condition is cured, healed, alleviated, relieved, altered, remedied, ameliorated, or improved. Management can include administering one or more therapeutic compounds in an amount effective to alleviate, relieve, alter, remedy, ameliorate, improve, affect the illness or a symptom of the illness. The terms can also refer to providing the subject with a management regime which can comprise, for example, psychological counselling and/or administration of one or more therapeutic compounds by any appropriate route to achieve the desired effect. Administration can include, but is not limited to, oral, sublingual, parenteral (e.g., intravenous, subcutaneous, intracutaneous, intramuscular, intraarticular, intraarterial, intrasynovial, intrasternal, intrathecal, intralesional or intracranial injection), transdermal, topical, buccal, rectal, vaginal, nasal, ophthalmic, via inhalation, and implants. [Johnston, S., Staines, D., Brenu, E., & Marshall-Gradisnik, S. (2014). Management of Chronic Fatigue Syndrome: Current Approaches and Future Directions. In Chronic Fatigue Syndrome: Risk Factors, Management and Impacts on Dally Life (pp. 79-90). United States: Nova Science Publishers.]

In some embodiments, obtainment of the genotype from the biological sample being assayed, the genotype can be evaluated to determine if the subject is predisposed to the medical condition or symptom thereof, or to determine a treatment/management of the subject that is suffering from the medical condition or symptom thereof. In certain embodiments, the obtained genotype may be compared with a reference or control to make a diagnosis.

When comparing a subject sample to a reference or control, the reference can be any suitable control sample known in the art, such as, for example, a sample from a normal, healthy subject. In some embodiments, the reference can be a sample from the same subject prior to demonstration of illness symptoms or prior to identification with the medical condition or symptom thereof.

In some embodiments, the reference can be a 'standardised' sample, such as a sample comprising material or data from several samples, preferably also from several subjects.

Detection of Polymorphism Overview

Detection of a target polymorphism (SNP) in a polynucleotide sample derived from an individual can be accomplished by any means known in the art, including, but not limited to, amplification of a sequence with specific primers; determination of the nucleotide sequence of the polynucleotide sample; hybridization analysis; single strand conformational polymorphism analysis; denaturing gradient gel electrophoresis; mismatch cleavage detection; exome sequencing and the like.

Detection of a target polymorphism can also be accomplished by detecting an alteration in the level of an RNA/mRNA transcript of the gene; aberrant modification of the corresponding gene, e.g., an aberrant methylation pattern; the presence of a non-wild-type splicing pattern of the corresponding transcript/mRNA; an alteration in the expression or translation level of the corresponding polypeptide; an alteration in the length of the corresponding polypeptide; and/or an alteration in corresponding polypeptide activity.

Polymorphism Detection Methodologies

As mentioned, detection of a target polymorphism by analyzing a polynucleotide sample can be conducted in a number of ways. A test nucleic acid sample can be amplified with primers which amplify a region known to comprise the target polymorphism(s). Genomic DNA or mRNA can be used directly. Alternatively, the region of interest can be cloned into a suitable vector and grown in sufficient quantity for analysis. The nucleic acid may be amplified by conventional techniques, such as a polymerase chain reaction (PCR), to provide sufficient amounts for analysis. The use of the polymerase chain reaction is described in a variety of publications, including, e.g., "PCR Protocols (Methods in Molecular Biology)" (2000) J. M. S. Bartlett and D. Stirling, eds, Humana Press; and "PCR Applications: Protocols for Functional Genomics" (1999) Innis, Gelfaund, and Sninsky, eds., Academic Press. Once the region comprising a target polymorphism has been amplified, the target polymorphism can be detected in the PCR product by nucleotide sequencing, by Single Strand Conformation Polymorphism (SSCP) analysis, or any other method known in the art. In performing SSCP analysis, the PCR product may be digested with a restriction endonuclease that recognizes a sequence within the PCR product generated by using as a template a reference sequence, but does not recognize a corresponding PCR product generated by using as a template a variant sequence by virtue of the fact that the variant sequence no longer contains a recognition site for the restriction endonuclease.

PCR can also be used to determine whether a polymorphism is present by using a primer that is specific for the polymorphism. Such methods can comprise the steps of collecting from a subject a biological sample comprising the subject's genetic material as template, optionally isolating template nucleic acid (genomic DNA, mRNA, or both) from the biological sample, contacting the template nucleic acid sample with one or more primers that specifically hybridize with a target polymorphic nucleic acid molecule under conditions such that hybridization and amplification of the template nucleic acid molecules in the sample occurs, and detecting the presence, absence, and/or relative amount of an amplification product and comparing the length to a control sample. Observation of an amplification product of the expected size is an indication that the target polymorphism contained within the target polymorphic primer is present in the test nucleic acid sample. Parameters such as hybridization conditions, polymorphic primer length, and position of the polymorphism within the polymorphic primer can be chosen such that hybridization will not occur unless a polymorphism present in the primer(s) is also present in the sample nucleic acid. Those of ordinary skill in the art are well aware of how to select and vary such parameters. See, e.g., Saiki et al. (1986) Nature 324:163; and Saiki et al (1989) Proc. Natl. Acad. Sci USA 86:6230.

Alternatively, various methods are known in the art that utilize oligonucleotide ligation as a means of detecting polymorphisms. See, e.g., Riley et al. (1990) Nucleic Acids Res. 18:2887-2890; and Delahunty et al. (1996) Am. J. Hum. Genet. 58:1239-1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2,7'-dimethoxy-4,5'-dichloro-6-carboxyfluorescein (JOE), 6-carboxy-X-rhodamine (ROX), 6-carboxy-2', 4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid can be sequenced by a dideoxy chain termination method or other well-known methods. Genomic DNA or mRNA may be used directly. If mRNA is used, a cDNA copy may first be made. If desired, the sample nucleic acid can be amplified using a PCR step. A variety of sequencing reactions known in the art can be used to directly sequence the relevant gene, or a portion thereof in which a specific polymorphism is known to occur, and detect polymorphisms by comparing the sequence of the sample nucleic acid with a reference polynucleotide that contains a target polymorphism. Any of a variety of automated sequencing procedures can be used. See, e.g., WO 94/16101; Cohen et al. (1996) Adv. Chromatography 36:127-162.

Hybridization with the variant sequence can also be used to determine the presence of a target polymorphism. Hybridization analysis can be carried out in a number of different ways, including, but not limited to Southern blots, Northern blots, dot blots, microarrays, etc. The hybridization pattern of a control and variant sequence to an array of oligonucleotide probes immobilized on a solid support, as described in U.S. Pat. No. 5,445,934, or in WO 95/35505, may also be used as a means of detecting the presence of variant sequences. Identification of a polymorphism in a nucleic acid sample can be performed by hybridizing a sample and control nucleic acids to high density arrays containing hundreds or thousands of oligonucleotide probes. Cronin et al. (1996) Human Mutation 7:244-255; and Kozai et al. (1996) Nature Med. 2:753-759.

Single strand conformational polymorphism (SSCP) analysis; denaturing gradient gel electrophoresis (DGGE); mismatch cleavage detection and heteroduplex analysis in gel matrices can also be used to detect polymorphisms. Alternatively, where a polymorphism creates or destroys a recognition site for a restriction endonuclease (restriction fragment length polymorphism, RFLP), the sample is digested with that endonuclease, and the products size fractionated to determine whether the fragment was digested. Fractionation is performed by gel or capillary electrophoresis, particularly actylamide or agarose gels. The aforementioned techniques are well known in the art. Detailed description of these techniques can be found in a variety of publications, including, e.g., "Laboratory Methods for the Detection of Mutations and Polymorphisms in DNA" (1997) G. R. Taylor, ed., CRC Press, and references cited therein.

SNP Detection

As mentioned above, various methods can be used to determine the presence or absence of a SNP in a subject/biological sample. Genotype can be determined, for example, by microarray analysis, sequencing, primer extension, ligation of allele specific oligonucleotides, mass determination of primer extension products, restriction length polymorphism analysis, single strand conformational polymorphism analysis, pyrosequencing, dHPLC or denaturing gradient gel electrophoresis (DGGE). Furthermore, having sequenced nucleic acid of a subject or sample, the sequence information can be retained and subsequently searched without recourse to the original nucleic acid itself. Thus, for example, a sequence alteration or mutation may he identified by scanning a database of sequence information using a computer or other electronic means.

In general, nucleic acid regions which contain the SNPs of interest (target regions) are preferably subjected to an amplification reaction. Any suitable technique or method may be used for amplification. In general, where multiple SNPs are to be analysed, it is preferable to simultaneously amplify all of the corresponding target regions (comprising the nucleotide variations).

Some embodiments of the invention can comprise determining the binding of an oligonucleotide probe to a genomic sample. The probe can comprise a nucleotide sequence which binds specifically to a particular SNP. Suitable oligonucleotide probes can be derived based on the SNP and nucleotide sequences of any one of Tables 1 to 7, 9, 10, 12 to 17, 26 to 28, and 34 to 36. The oligonucleotide probe may comprise a label and binding of the probe can be determined by detecting the presence of the label.

Some embodiments of the invention can comprise hybridising of one, two or more oligonucleotide probes or primers to target nucleic acid. Where the nucleic acid is double-stranded DNA, hybridisation will generally be preceded by denaturation to produce single-stranded DNA. The hybridisation can be as part of an amplification, e.g. PCR procedure, or as part of a probing procedure not involving amplification, e.g. PCR. An example procedure would be a combination of PCR and low stringency hybridisation. Any suitable screening procedure can be used to identify successful hybridisation events and isolated hybridised nucleic acid.

Binding of a probe to target nucleic acid (e.g. DNA) can be measured using any of a variety of techniques. For instance, probes may be radioactively, fluorescently or enzymatically labelled. Other methods not employing labelling of probe include examination of restriction fragment length polymorphisms, amplification using, PCR, RNase cleavage and allele specific oligonucleotide probing. Probing can employ the standard Southern blotting technique. For instance, DNA can be extracted from cells and digested with different restriction enzymes. Restriction fragments can then be separated by electrophoresis on an agarose gel, before denaturation and transferred to a nitrocellulose filter. Labelled probe can be hybridised to the DNA fragments on the filter and binding determined. DNA for probing can be prepared from RNA preparations from cells. Suitable stringency for selective hybridisation, oligonucleotide length, base composition and temperature can be readily determined by the skilled addressee.

For example, suitable selective hybridisation conditions for oligonucleotides of 17 to 30 bases include hybridization overnight at 42° C. in 6× SSC and washing in 6× SSC at a series of increasing temperatures from 42° C. to 65° C. Other suitable conditions and protocols are described in Molecular Cloning: a Laboratory Manual: 2nd edition, Sambrook et al., 1989, Cold Spring Harbor Laboratory Press and Current Protocols in Molecular Biology, Ausubel et al. eds., John Wiley & Sons, 1992.

An oligonucleotide for use in nucleic acid amplification can be about 30 or fewer nucleotides in length (e.g. 18, 20, 22, 24 or 26). Generally, specific primers are upwards of 14 nucleotides in length. Those skilled in the art are well versed in the design of primers for use in processes such as PCR. Suitable oligonucleotides can be designed based on the SNPs or sequences of any one of Tables 1 to 7, 9, 10, 12 to 17, 26 to 28, and 34 to 36. Various techniques for synthesizing oligonucleotide primers are well known in the art, including phosphotriester and phosphodiester synthesis methods. Primers and primer pairs suitable for amplification of nucleic acid regions comprising the sequences in Tables 1 to 7, 9, 10, 12 to 17, 26 to 28 and 34 can be readily developed by those of skill in the art. For examples, see Tables 35 and 36.

Nucleic acid can also be screened using a variant- or allele-specific probe. Such a probe can correspond in sequence to a region of genomic nucleic acid, or its complement, which contains one or more of the SNPs of interest. Under suitably stringent conditions, specific hybridisation of such a probe to test nucleic acid is indicative of the presence of the sequence alteration in the test nucleic acid. For efficient screening purposes, more than one probe can be used on the same test sample. Suitable probes can be designed based on the SNPs or sequences of any one of Tables 1 to 7, 9, 10, 12 to 17, 26 to 28 and 34 to 36.

Nucleic acid in a test sample, which can be a genomic sample or an amplified region thereof, can be sequenced to identify or determine the identity of a polymorphic allele. The allele of the SNP in the test nucleic acid can therefore be compared with the SNP as described herein in Tables 1 to 7, 9, 10, 12 to 17, 26 to 28 and 34 to determine whether the test nucleic acid contains one or more alleles which are associated with the medical condition or symptom thereof.

Since it will not generally be time- or labour-efficient to sequence all nucleic acid in a test sample, a specific amplification reaction such as PCR using one or more pairs of primers can be employed to amplify the region of interest in the nucleic acid, for instance the particular region in which the SNPs of interest occur. The amplified nucleic acid can then be sequenced as above, and/or tested in any other way to determine the presence or absence of a particular nucleotide. Nucleic acid for testing can be prepared from nucleic acid removed from cells or in a library using a variety of other techniques such as restriction enzyme digest and electrophoresis.

Sequencing of an amplified product can involve precipitation with isopropanol, resuspension and sequencing using a TaqFS+ Dye terminator sequencing kit. Extension products may be electrophoresed on an ABI 377 DNA sequencer and data analysed using Sequence Navigator software.

Nucleic acid in a test sample can be probed under conditions for selective hybridisation and/or subjected to a specific nucleic acid amplification reaction such as the polymerase chain reaction (PCR) (reviewed for instance in "PCR protocols; A Guide to Methods and Applications", Eds. Innis et al, 1990, Academic Press, New York, Mullis et al, Cold Spring Harbor Symp. Quant. Biol., 51 :263, (1987), Ehrlich (ed), PCR technology, Stockton Press, NY, 1989, and Ehrlich et al, Science, 252:1643-1650, (1991)). PCR comprises steps of denaturation of template nucleic acid (if double-stranded), annealing of primer to target, and polymerisation. The nucleic acid probed or used as template in the amplification reaction may be genomic DNA, cDNA or RNA.

Other specific nucleic acid amplification techniques include strand displacement activation, the QB replicase system, the repair chain reaction, the ligase chain reaction, rolling circle amplification and ligation activated transcription. Methods of the present invention may therefore comprise amplifying the region in said genomic sample containing the one or more positions of single nucleotide polymorphism of interest.

Allele-specific oligonucleotides can be used in PCR to specifically amplify particular sequences if present in a test sample. Assessment of whether a PCR band contains a gene variant may be carried out in a number of ways familiar to those skilled in the art. The PCR product may for instance be treated in a way that enables one to display the polymorphism on a denaturing polyacrylamide DNA sequencing gel, with specific bands that are linked to the gene variants being selected.

In some embodiments, the region of genomic sample comprising a polymorphism can be amplified using a pair of oligonucleotide primers, of which the first member of the pair comprises a nucleotide sequence which hybridises to a complementary sequence which is proximal to and 5' of the position of single nucleotide polymorphism, and the second member of the primer pair comprises a nucleotide sequence which hybridises to a complementary sequence which is proximal to and 3' of the position of single nucleotide polymorphism.

In other embodiments, the first member of the pair of oligonucleotide primers can comprise a nucleotide sequence which hybridises to a complementary sequence which is proximal to and 5' or 3' of the polymorphism, and the second member of the pair can comprise a nucleotide sequence which hybridises under stringent conditions to a particular allele of the polymorphism and not to other alleles, such that amplification only occurs in the presence of the particular allele.

A further aspect of the present invention provides a pair of oligonucleotide amplification primers. A suitable pair of amplification primers according to this aspect can have a first member comprising a nucleotide sequence which hybridises to a complementary sequence which is proximal to and 5' of a single nucleotide polymorphism and a second member comprising a nucleotide sequence which hybridises to a complementary sequence which is proximal to and 3' of the single nucleotide polymorphism.

The allele of the at least one polymorphism (i.e. the identity of the nucleotide at the position of single nucleotide polymorphism) can then be determined by determining the binding of an oligonucleotide probe to the amplified region of the genomic sample. A suitable oligonucleotide probe comprises a nucleotide sequence which binds specifically to a particular allele of the at least one polymorphism and does not bind specifically to other alleles of the at least one polymorphism Other suitable pairs of amplification primers can have a first member comprising a nucleotide sequence which hybridises to a complementary sequence which is proximal to and 5' or 3' of a single nucleotide polymorphism and a second member of the pair comprising a nucleotide sequence which hybridises under stringent conditions to a particular allele of the polymorphism and not to other alleles, such that amplification only occurs in the presence of the particular allele.

PCR primers suitable for amplification of target DNA regions comprising the SNPs in Tables 1 to 7, 9, 10, 12 to 17, 26 to 28 and 34 or sequences of Tables 35 and 36 can be readily prepared by the skilled addressee. A further aspect of the present invention provides an oligonucleotide which hybridises specifically to a nucleic acid sequence which comprises a particular allele of a polymorphism selected from the group consisting of any one of the single nucleotide polymorphisms shown in Tables 1 to 7, 9, 10, 12 to 17, 26 to 28 and 34, and does not bind specifically to other alleles of the SNP. Hybridisation may be determined under suitable selective hybridisation conditions as described herein.

Such oligonucleotides may be used in a method of nucleic acid.

In some preferred embodiments, oligonucleotides according to the present invention are at least about 10 nucleotides in length, more preferably at least about 15 nucleotides in length, more preferably at least about 20 nucleotides in length. Oligonucleotides may be up to about 100 nucleotides in length, more preferably up to about 50 nucleotides in length, more preferably up to about 30 nucleotides in length. The boundary value 'about X nucleotides' as used above includes the boundary value 'X nucleotides'.

Approaches which rely on hybridisation between a probe and test nucleic acid and subsequent detection of a mismatch may be employed. Under appropriate conditions (temperature, pH etc.), an oligonucleotide probe will hybridise with a sequence which is not entirely complementary. The degree of base-pairing between the two molecules will be sufficient for them to anneal despite a mis-match. Various approaches are well known in the art for detecting the presence of a mis-match between two annealing nucleic acid molecules.

For instance, RNase A cleaves at the site of a mis-match. Cleavage can be detected by electrophoresis test nucleic acid to which the relevant probe or probe has annealed and looking for smaller molecules (i.e. molecules with higher electrophoretic mobility) than the full length probe/test hybrid.

Genotype analysis may be carried out by microarray analysis. Any suitable microarray technology may be used. Preferably the methodology reported in International Patent Application No. PCT/IB2006/00796 filed 12 Jan. 2006 (the contents of which are hereby incorporated by reference) is used. This technology uses a low-density DNA array and hybridisation to allele-specific oligonucleotide probes to screen for SNPs.

Typically in this technology, nucleic acid regions which contain the SNPs of interest (target regions) may be subjected to an amplification reaction. Any suitable technique or method may be used for amplification. In general, where multiple SNPs are to be analysed, it is preferable to simultaneously amplify all of the corresponding target regions (comprising the variations).

For example, multiplex PCR may be carried out, using appropriate pairs of oligonucleotide PCR primers. Any suitable pair of primers which allow specific amplification of a target region may be used. In one aspect, the primers allow amplification in the fewest possible number of PCR reactions.

Following amplification, the amplified nucleic acid may undergo fragmentation, e.g. by digestion with a suitable nuclease such as DNAse 1. Typically the amplified (optionally fragmented) DNA is then labelled. Suitable labels are known in the art.

A microarray typically comprises a plurality of probes deposited on a solid support. In general the solid support comprises oligonucleotide probes suitable for discrimination between possible nucleotides at each SNP variable to be determined in the method. The microarray typically also comprises additional positive and/or negative controls.

Typically, for a SNP with the possible alleles A and B, there will be at least one probe which is capable of hybridising specifically to allele A (probe 1) and one probe which is capable of hybridising specifically to allele B (probe 2) under the selected hybridisation conditions. These probes form a probe pair. Typically the probes can be used to discriminate between A and B (e.g. the wildtype and mutant alleles). The probes may examine either the sense or the antisense strand. Typically, probes 1 and 2 examine the same nucleic acid strand (e.g. the sense strand or antisense strand) although in some cases the probes may examine different strands. In one aspect probes 1 and 2 have the same sequence except for the site of the genetic variation.

In one instance, the probes in a probe pair have the same length. In some aspects, where two or more pairs of probes are provided for analysis of a genetic variation, the probes may all have the same length.

Preferably more than one probe pair is provided for detection of each genetic variation. Thus, at least 2, 3, 4, 5, 6, 7, 8, 9, 10 or more probe pairs may be provided per genetic variation. In one aspect, (at least) 2 probe pairs are provided. The aim is to reduce the rate of false positives and negatives in the present methods.

For example, for a given genetic variation there may be:
Probe 1 which is capable of hybridising to genetic variation A (e.g. a normal allele)
Probe 2 which is capable of hybridising to genetic variation B (e.g. a mutant allele)

Probe 3 which is capable of hybridising to genetic variation A (e.g. a normal allele)

Probe 4 which is capable of hybridising to genetic variation B (e.g. a mutant allele).

The probes may examine the same or different strands. Thus in one embodiment, probes 3 and 4 are the complementary probes of probes 1 and 2 respectively and are designed to examine the complementary strand. In one aspect it is preferred that the probes provided for detection of each genetic variation examine both strands.

More than 2 pairs of probes may be provided for analysis of a genetic variation as above. For example, where a genetic variation exists as any one of 4 bases in the same strand (e.g. there are three mutant possibilities), at least one pair of probes may be provided to detect each possibility. Preferably, at least 2 pairs of probes are provided for each possibility.

A number of methods are known in the art for designing oligonucleotide probes suitable for use in DNA-chips. These include "standard tiling", "alternative tiling" "block tiling" and "alternative block tiling". Any one or more of these strategies may be used to design probes for the present invention. Preferably standard tiling is used, in particular with 2 pairs of probes e.g. 2 pairs of complementary probes as above. Thus it is preferable that the oligonucleotide sequence is complementary to the target DNA or sequence in the regions flanking the variable nucleotide(s). However, in some cases, one or more mismatches may be introduced. The oligonucleotide probes for use in the present invention typically present the base to be examined (the site of the genetic variation) at the centre of the oligonucleotide.

In general the probes for use in the present invention comprise or in some embodiments consist (essentially) of 17 to 27 nucleotides, for example, 19, 21, 23, or 25 nucleotides or 18, 20, 22, 24 or 26 nucleotides.

The probes provided for detection of each genetic variation (as described above) are typically capable of discriminating between genetic variants A and B (e.g. the normal and mutant alleles) under the selected hybridisation conditions. Preferably the discrimination capacity of the probes is substantially 100%. If the discrimination capacity is not 100%, the probes are preferably redesigned. Preferably the melting temperature of the probe/target complexes is in the range of 75-85° C.

In general probes are provided on the support in replicate. Typically, at least 4, 6, 8, 10, 12, 14, 16, 18 or 20 replicates are provided of each probe, in particular, 6, 8 or 10 replicates. Thus for example, the support (or DNA-chip) may comprise or include 10 replicates for each of (at least) 4 probes used to detect each genetic variation (i.e. 40 probes). Alternatively the support (or DNA-chip) may comprise or include 8 replicates for each of (at least) 4 probes used to detect each genetic variation (i.e. 32 probes). Still further the support (or DNA-chip) may comprise or include 6 replicates or each of (at least) 4 probes used to detect each genetic variation (i.e. 24 probes). In general the support also comprises one or more control oligonucleotide probes which are useful as positive and/or negative controls of the hybridisation reactions. These are also provided in replicate as above.

Typically the chip or array will include positive control probes, e.g., probes known to be complementary and hybridisable to sequences in the target polynucleotide molecules, probes known to hybridise to an external control DNA, and negative control probes, e.g., probes known to not be complementary and hybridizable to sequences in the target polynucleotide molecules. The chip may have one or more controls specific for each target, for example, 2, 3, or more controls. There may also be at least one control for the array.

Positive control probes are generally designed to hybridise equally, to all target DNA samples and provide a reference signal intensity against which hybridisation of the target DNA (sample) to the test probes can be compared. Negative controls comprise either "blanks" where only solvent (DMSO) has been applied to the support or control oligonucleotides that have been selected to show no, or only minimal, hybridisation to the target, e.g. human, DNA (the test DNA). The intensity of any signal detected at either blank or negative control oligonucleotide features is an indication of non-specific interactions between the sample DNA and the array and is thus a measure of the background signal against which the signal from real probe-sample interactions must be discriminated.

Desirably, the number of sequences in the array will be such that where the number of nucleic acids suitable for detection of genetic variations is n, the number of positive and negative control nucleic acids is n', where n' is typically from 0.01 to 0.4n.

One example of a DNA chip/microarray which may be used is Fibrochip.

A Fibro-chip comprises oligonucleotide probes suitable for detection of some or all of the genetic variations (SNPs) in Tables 1 to 7, 9, 10, 12 to 17, 26 to 28 and 34.

In general an array comprises a support or surface with an ordered array of binding (e.g. hybridisation) sites or probes. Each probe (i.e. each probe replicate) is located at a known predetermined position on the solid support such that the identity (i.e. the sequence) of each probe can be determined from its position in the array. Preferably, the probes deposited on the support, although they maintain a predetermined arrangement, are not grouped by genetic variation but have a random distribution. Typically they are also not grouped within the same genetic variation. If desired, this random distribution can be always the same. Probes may be arranged on the support in subarrays.

The support, on which the plurality of probes is deposited, can be any solid support to which oligonucleotides can be attached. For example, the said support can be of a non-porous material, for example, glass, silicon, plastic, or a porous material such as a membrane or filter (for example, nylon, nitrocellulose) or a gel. In one embodiment, the said support is a glass support, such as a glass slide.

Probes may be attached to the support using conventional techniques for immobilization of oligonucleotides on the surface of the supports.

In one embodiment, the support is a glass slide and in this case, the probes, in the number of established replicates (for example, 6, 8 or 10) are printed on pre-treated glass slides, for example coated with aminosilanes, using equipment for automated production of DNA-chips by deposition of the oligonucleotides on the glass slides ("micro-arrayer"). Deposition is carried out under appropriate conditions, for example, by means of crosslinking with ultraviolet radiation and heating (80° C.), maintaining the humidity and controlling the temperature during the process of deposition, typically at a relative humidity of between 40-50% and typically at a temperature of 20° C.

The replicate probes are distributed uniformly amongst the areas or sectors (sub-arrays), which typically constitute a DNA-chip. The number of replicas and their uniform distribution across the DNA-chip minimizes the variability arising from the printing process that can affect experimental results. Likewise, positive and negative hybridisation controls (as described herein) may be printed.

To control the quality of the manufacturing process of the DNA-chip, in terms of hybridization signal, background noise, specificity, sensitivity and reproducibility of each replica as well as differences caused by variations in the morphology of the spotted probe features after printing, a commercial DNA can be used. For example, as a quality control of the printing of the DNA-chips, hybridization may be carried out with a commercial DNA (e.g. k562 DNA High Molecular Weight, Promega)

In general, methods for using microarrays for genotyping are known in the art.

In one aspect the data from the present microarrays may be analysed and used to determine genotype according to the methods in International Patent Application No. PCT/IB2006/00796 filed 12 Jan. 2006, the contents of which are hereby incorporated by reference. Typically, following amplification of the target DNA and optional fragmentation (e.g. by digestion with DNase 1), the target DNA is labelled as described herein.

The labelled DNA may then be hybridised with a microarray under suitable hybridisation conditions which may be determined by the skilled person. For example, an automatic hybridisation station may be used.

In general the microarray is then scanned and the label intensities at the specific probe positions determined in order to determine which allele is present in the target DNA hybridised to the array.

In one aspect, following hybridisation, the signal intensity of the label is detected at each probe position on the microarray to determine extent of hybridisation at each position. This may be done by any means suitable for detecting and quantifying the given label. For example, fluorescent labels may be quantified using a confocal fluorescent scanner.

This signal intensity value is typically corrected to eliminate background noise by means of controls on the array. Where a microarray includes probe pairs and probe replicates as described herein, a hybridisation signal mean can then be calculated for each probe (based on the signals from the probes replicates). The ratio of the hybridisation signal mean of the A allele to the sum of the hybridisation signal means of the A and B alleles can then be defined for each probe pair used for genotyping of each SNP (ratios 1 and 2).

The 2 ratio values corresponding to each of the 3 possible genotypes (AA, AB and BB) may be calculated using target DNA from control individuals of each genotype identified previously by, e.g. sequence analysis (at least 10 per genotype).

By comparison of test DNA results with the control ratios, a genotype may be assigned to a test individual. This may be done using the MG 1.0 software.

As mentioned above, genotyping may also be carried out using sequencing methods. Typically, nucleic acid comprising the SNPs of interest is isolated and amplified as described herein. Primers complementary to the target sequence are designed so that they are a suitable distance (e.g. 50-400 nucleotides) from the polymorphism. Sequencing is then carried out using conventional techniques. For example, primers may be designed using software that aims to select sequence(s) within an appropriate window which have suitable Tm values and do not possess secondary structure or that will hybridise to non-target sequence.

Additional references describing various protocols for detecting the presence of a target polymorphism include, but are not limited to, those described in: U.S. Pat. Nos. 6,703, 228; 6,692,909; 6,670,464; 6,660,476; 6,653,079; 6,632,606; 6,573,049; the disclosures of which are herein incorporated by reference.

Exome Sequencing

SNPs can be identified and characterised using exome sequencing. Exome sequencing (also known as Whole Exome Sequencing or WES) is a technique for sequencing all the protein-coding genes in a genome (known as the exome). It consists of first selecting only the subset of DNA that encodes proteins (known as exons), and then sequencing that DNA using any high throughput DNA sequencing technology. Different target-enrichment techniques are briefly described below:

PCR—PCR is technology to amplify specific DNA sequences. It uses a single stranded piece of DNA as a start for DNA amplification. Uniplex PCR uses only one starting point (primer) for amplification and multiplex PCR uses multiple primers.

Molecular inversion probes (MIP)—Molecular inversion probe uses probes of singe stranded DNA oligonucleotides flanked by target-specific ends. The gaps between the flanking sequences are filled and ligated to form a circular DNA fragment. Probes that did not undergo reaction remain linear and are removed using exonucleases.

Hybrid capture—Microarrays contain single-stranded oligonucleotides with sequences from the human genome to tile the region of interest fixed to the surface. Genomic DNA is sheared to form double-stranded fragments. The fragments undergo end-repair to produce blunt ends and adaptors with universal priming sequences are added. These fragments are hybridized to oligos on the microarray. Unhybridized fragments are washed away and the desired fragments are eluted. The fragments are then amplified using PCR.

In-solution capture—To capture genomic regions of interest using in-solution capture, a pool of custom oligonucleotides (probes) is synthesized and hybridized in solution to a fragmented genomic DNA sample. The probes (labeled with beads) selectively hybridize to the genomic regions of interest after which the beads (now including the DNA fragments of interest) can be pulled down and washed to clear excess material. The beads are then removed and the genomic fragments can be sequenced allowing for selective DNA sequencing of genomic regions (e.g., exons) of interest.

Sequencing—Sequencing platforms include the classical Sanger sequencing, the Roche 454 sequencer, the Illumina Genome Analyzer 11 and the Life Technologies SOLiD & Ion Torrent—all of which have been used for exome sequencing.

Sequencing types: Sanger sequencing; SNP sequencing of exome; pyrosequencing; RNA sequencing; and, protein sequencing.

Expression Level Detection Methodologies

Biochemical studies may be performed to determine whether a sequence polymorphism in a coding region or control region of interest is associated with the medical condition. Condition-associated polymorphisms may include deletion or truncation of the gene, mutations that alter expression level, that affect the activity of the polypeptide, etc.

A number of methods are available for determining the expression level of a polymorphic nucleic acid molecule, e.g., RNA/mRNA or a polymorphic polypeptide (protein) in a particular sample. Diagnosis may be performed by a number of methods to determine the absence or presence or altered amounts of normal or abnormal RNA/mRNA or polypeptide in a patient sample.

Characterisation of RNA Expression

Methods of the subject invention in which the level of (polymorphic) gene expression is of interest will typically involve comparison of the relevant nucleic acid abundance of a sample of interest with that of a control value to determine any relative differences, where the difference may be measured qualitatively and/or quantitatively, which differences are then related to the presence or absence of an abnormal gene expression pattern.

A variety of different methods for determining the nucleic acid abundance in a sample are known to those of skill in the art, where particular methods of interest include those described in: Pieta et al., Genome Res. (June 1996) 6: 492-503; Zhao et at., Gene (Apr. 24, 1995) 156: 207-213; Soares, Curr. Opin. Biotechnol. (October 1997) 8: 542-546; Raval, J. Pharmacol Toxicol Methods (November 1994) 32: 125-127; Chalifour et al., Anal. Biochem (Feb. 2, 1994) 216: 299-304; Stolz & Tuan, Mol. Biotechnol. (December 1996 0 6: 225-230; Hong et al., Bioscience Reports (1982) 2: 907; and McGraw, Anal. Biochem. (1984) 143: 298. Also of interest are the methods disclosed in WO 97/27317, the disclosure of which is herein incorporated by reference.

RNA manipulation techniques are described, for example, in the following references, the entire contents of which are incorporated herein:

PureLink (Invitiogen), Trizol reagent (Invitrogen), Stratagene (total and small RNA), TRI-Reagent (Sigma-Aldrich), Nucleospin (Machery-Nagel) and RNA-Bee (Tel-test). Reference [89a].

The degree to which RNA expression differs need only be large enough to quantify via standard characterization techniques such as expression arrays, RT-qPCR, Northern analysis and RNase protection.

Blotting and hybridization assays: [103a, 104a].

Microarrays: [105a].

Next generation assays covering all platforms: [107a].

Different ways of assaying expression: Real time PCR, Affymetrix, Agilent, Illumina, and Nanostring.

Profiling methods: Agilent microarray, exiqon array, exiqon microarray, miRCURY LNA ncode array, LC Sciences array ABI Taqman array, affymetrix, illumine array, SOLID ligation sequencing, Illumina HiSeq and TaqMan miR assay.

Tools or reagents for assaying for RNA differential expression: SYBR green probes and TaqMan probes.

Radiolabeled splinted ligation detection: [110a, 111a].

Preferably, for one or more methods of the present invention, the level of RNA expression or differential expression can be carried out using: Northern analysis and a probe that specifically binds to the RNA; RNase protection; or, reverse transcription-polymerase chain reaction (RT-PCR) using one or more oligonucleotides/primers that will amplify transcribed RNA. A universal primer can be used in combination with the one or more oligonucleotides/primers that will amplify transcribed RNA. Preferably, RT-qPCR is used. Preferably, for one or more methods of the present invention, the method/s can comprise the step of statistical analysis so as to identify differential expression.

In some embodiments, RNA can be extracted from plasma using a commercially available kit. The size, quantity and quality of the extracted RNA can be assessed using a small RNA chip on an Agilent 2100 Bioanalyzer (Agilent Technologies, Palo Alto, Calif.).

RNA profiling and sequencing can be carried out in any suitable way. Preferably high throughput sequencing (HTS) is utilised. RNA libraries can be constructed using the TruSeq Small RNA Sample Preparation kit (Illumina, San Diego, Calif.). RNA samples can be ligated with 5' and 3' adapters, followed by reverse transcription-polymerase chain reaction (RT-PCR) for cDNA library construction and incorporation of index tags. The cDNA library fragments can be separated and size fractioned. cDNA library samples can be pooled in equimolar amounts and used for cluster generation and sequence analysis.

Sequence data that has been generated can be analysed in any suitable way. In some embodiments, raw FASTQ sequences can be generated.

In some embodiments, reverse transcription-quantitative polymerase chain reaction (RT-qPCR) may be used for expression and comparison.

Polypeptide Characterisation

One may screen for polymorphisms at the protein level. Screening for mutations in a polymorphic polypeptide may be based on the functional or antigenic characteristics of the protein. Functional assays include cofactor binding assays, enzyme activity assays, substrate binding assays or surface expression assays. For example, protein truncation assays are useful in detecting deletions that may affect the biological activity of the protein. The activity of the encoded a polymorphic polypeptide may be determined by comparison with a reference polypeptide lacking a specific polymorphism. Alternatively, the three-dimensional structure of the protein may be assayed, for example by fluorescence polarization or circular dichroism spectroscopy, wherein the three-dimensional structure of the encoded a polymorphic polypeptide may be determined by comparison with purified protein carrying the opposing allele of the polymorphism.

Alternatively, various immunoassays designed to detect polymorphisms in polymorphic polypeptides may be used. The absence or presence of antibody binding to a polymorphic polypeptide may be determined by various methods, including flow cytometry of dissociated cells, microscopy, radiography, scintillation counting, etc. Immunocytochemistry and flow cytometry, particularly fluorescence-activated cell sorting (FACS), can be used to evaluate cell-surface expression of proteins on cells, including on the different types of blood cells.

Detailed descriptions of how to make antibodies, including antibodies that are specific for epitopes, for example, single amino acid substitutions within epitopes, can be found in a variety of publications, including, e.g. "Making and using Antibodies: A Practical Handbook" (2006) G. C. Howard and M. R. Kaser, eds. CRC Press; "Antibody Engineering: Methods and Protocols" (2004) B. K. C. Lo, ed, Humana Press; and U.S. Pat. No. 6,054,632, the disclosure of which is herein incorporated by reference.

Methods for performing protein sequencing include: Edman degradation; peptide mass fingerprinting; mass spectrometry; and, protease digests. For example, detection may utilize staining of cells or histological sections with labeled antibodies, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a fluorescent compound, e.g. fluorescein, rhodamine, Texas red, etc. Final detection uses a substrate that undergoes a color change in the presence of the peroxidase.

The absence or presence of antibody binding may be determined by various methods, including flow cytometry of dissociated cells, microscopy, radiography, scintillation counting, etc. Detailed descriptions of how to make antibodies can be found in a variety of publications, including, e.g. "Making and using Antibodies: A Practical Handbook" (2006) G. C. Howard and M. R. Kaser, eds. CRC Press; "Antibody Engineering: Methods and Protocols" (2000 B .K. C. Lo, ed, Humana Press.

The techniques described above can be used to assay TRP ion channel, ACh receptor and/or ADR expression in or on the surface of cells, preferably blood cells such as NK, T and/or B cells for TRP and ACh receptor, whereby reduced expression of TRP ion channel, ACh receptor and/or ADR is typically indicative of the subject having the medical condition or symptom thereof or a predisposition to the medical condition or symptom thereof.

Calcium Testing

Testing for a change in calcium metabolism/calcium metabolic change in a subject can be achieved in any suitable way. For example, all calcium-dependent biochemical processes and genes can be assessed/tested. For example, detection of Ca++ and its signaling mechanisms in all cells and tissues of the body may be utilised. For example, the effects of Ca++ on gene expression may be assessed. For example, the effects of Ca++ on all transcription factors in all cells and tissues of the body and their associated genes can be assessed. For example, testing can include muscle biopsy, blood samples (e.g. immune cells), radiological investigations, cardiac assessments such as exercise testing which manifest Ca++ signaling or disorders of same. For example, Ca++ regulatory mechanisms including IP3, Calcineurin, Calmodulin, OR1, DAG etc, which may be affected can be assessed. For example: assessment of inter- or intra-calcium wave signaling or other Ca++ signaling mechanisms can be undertaken. [See. references 1f-6f, or example, as well as other references in the Examples.]

Preferably, testing for a change in calcium metabolism involves testing for a change in $Ca^{2+}$ cell signaling.

Testing for a change in calcium metabolism/calcium metabolic change in a subject may involve using calcium channel blockers (CCB), calcium channel antagonists, calcium antagonists or calcium agonists.

Examples of these include:
Amlodipine (Norvasc)
Diltiazem (Cardizem, Tiazac), Cardizem CD, Cardizem SR, Dilacor XR, Diltia XT
Felodipine
Isradipine
Nicardipine (Cardene SR)
Nifedipine (Procardia)
Nisoldipine (Sular)
Verapamil (Calan, Verelan, Covera-HS) Calan SR, Covera-HS, Isoptin, Isoptin SR, Verelan PM
Cardene, Cardene SR (nicardipine)
Sular (nisoldipine)
Vascor (bepridil)

Examples of agonists and antagonists (inhibitors and activators), available from Sigma-Aldrich, include:
A-967079 (Product #SML0085)
AC-265347 (Product #SML0129)
Amiloride hydrochloride hydrate (Product #A7410)
Amiodarone hydrochloride (Product #A8423)
Amlodipine besylate (Product #A5605)
N-(p-Antylcinnamoyl)anthranilic acid (Product #A8486)
AP-18 (Product #A7232)
ASP7663 (Product #SML1467)
Azelnidipine (Product #A7106)
(S)-(−)-Bay K8644 (Product #B133)
(±)-Bay K8644 calcium channel agonist (Product #B112)
Bepridil hydrochloride (Product #B5016)
CaCCinh-A01 (Product #SML0916)
Caged Ca2+ channel antagonist (Product #C235)
Carboxyamidotriazoic (Product #SML0408)
Cilnidipine (Product #C1493)
Cinnarizine (Product #C5270)
Daurisoline (Product #SML0597)
(±)-cis-Diltiazem hydrochloride (Product #D2521)
Efonidipine hydrochloride monoethanolate (Product #E0159)
EVP4593 (Product #SML0579)
Felodipine (Product #F9677)
Fendiline hydrochloride (Product #F7265)
Flavoxate hydrochloride (Product #F8304)
Flunarizine dihydrochloride (Product #F8257)
Fluspirilene (Product #F100)
FPL 64176 (Product #F131)
Gabapentin (Product #G154)
GSK2193874 (Product #SML0942)
HA-1077 (Product #H139)
HC-030031 (Product #H4415)
Isradipine (Product #16658)
KB-R7943 (Product #K4144)
Kurtoxin (Product #K1514)
Lacidipine (Product #SML0946)
Lanthanum(III) chloride heptahydrate (Product #L4131)
Lercanidipine hydrochloride (Product #L6668)
Lidoflazine (Product #L9668)
Lomerizine dihydrochloride (Product #L6295)
Loperamide hydrochloride (Product #L4762)
M8-B hydrochloride (Product #SML0893)
3-MFA (Product #SML0658)
Mibefradil dihydrochloride hydrate (Product #M5441) Ro 40-5967
ML204 (Product #SML0400)
ML218 (Product #SML0385)
ML-SA1 (Product #SNL0627)
MRS 1845 (Product #M1692)
Nateglinide (Product #N3538)
Neomycin trisulfate (Product #N1876)
Nicardipine hydrochloride (Product #N7510)
Nifedipine (Product #N7634)
Nifetepimine (Product #SML1372)
Nilvadipine (Product #SML0945)
Nimodipine (Product #N149)
Nisoldipine (Product #N0165)
Nitrendipine (Product #N144)
NNC 55-0396 hydrate (Product #N0287)
ORM-10103 (Product #SML0972)
Penfluridol (Product #P3371)
PF-05105679 (Product #PZ0245)
Phloretin (Product #P7912)
Polygodial (Product #SML0049)
Pregabalin (Product #PZ0010)
Protopine hydrochloride (Product #P8489)
Pyr10 (Product #SML1243)
Pyr3 (Product #P0032)
Pyr6 (Product #SML1241)
Ruthenium Red (Product #R2751)
N-Salicyloyltryptamine (Product #S6444)

SKA-31 (Product #S5576)
SKF-96365 (Product #S7809)
SNX-482 (Product #S1818)
Tetracaine hydrochloride (Product #T7645)
Thioridazine hydrochloride (Product #T9025)
γ6 TM1a trifluoroacetate salt (Product #T2955) pricing
Tyrphostin A9 (Product #T182)
(−)-Umbellulone (Product #SML0782)
Veratridine (Product #V5754)
YM-58483 (Product #Y4895)

Characterisation of Dysfunctional Signalling Through Tissue or Cell Mitogen-Activated Protein Kinase Pathway Characterisation of dysfunctional signalling through tissue or cell Mitogen-Activated Protein Kinase pathway may be carried out in any suitable manner. For example, cell MAPK phosphorylation studies, including assaying cell cytotoxic activity, cell degranulation, cell lytic proteins and maturation markers and cell cytokines, as well as multiparametric flow cytometry analysis and statistical analysis, may be carried out as previously described [9m, 27m, 29m 38m-45m].

Protein phosphorylation or dephosphorylation can be determined, measured, quantitiated or assayed in any suitable way, including using antibodies, phospho-specific antibodies, FACS, chemiluminescent detection, immunofluorescence, radioactive ligands and electrophoresis. For example, commercial kits for testing the relative phosphorylation of various kinases are available (eg. R&D Systems).

In other embodiments, the level of gene expression (RNA or protein) may be tested, or a property of the protein or biochemical function may be tested, as described for other forms of the invention.

General Techniques

The following general methodologies may be utilised.

1. Recombinant technology:
   a. Expression of a recombinant protein (polypeptide) detected by constructing a plasmid that encodes the desired protein, introducing the plasmid into the required host cell, growing the host cells and inducing protein expression, then lysing the cells, purifying the protein, and performing SDS-PAGE analysis to verify the presence of the protein.
   b. Protein expression using an inducing agent by a raising of the incubation temperature of the medium or by the addition of an inducing chemical to the culture medium.

2. Time-course analysis of protein expression:
   a. To optimize the expression of a given protein construct, a time-course analysis by SDS-PAGE of the level of protein expression could be used. As intracellular protein content is often a balance between the amount of soluble protein in the cells, the formation of inclusion bodies and protein degradation, by checking the protein present at various times after induction, the optimal induction period can be established.

3. Protein purification:
   a. The expression and purification of recombinant proteins facilitates production and detailed characterization of virtually any protein.
   b. Classical purification procedures can be employed, but in most cases recombinant DNA techniques permit the construction of fusion proteins in which specific affinity tags are added to the protein sentience of interest; the use of these affinity tags simplifies the purification of the recombinant fusion proteins by employing affinity chromatography methods.

4. SDS PAGE:
   a. SDS polyacrylamide gel electrophoresis (SDS-PAGE) involves the separation of proteins based on their size. By heating the sample under denaturing and reducing conditions, proteins become unfolded and coated with SDS detergent molecules, acquiring a high net negative charge that is proportional to the length of the polypeptide chain of interest.
   b. Visualization of proteins in SDS-PAGE gels
   Visualization of protein bands is carried out by incubating the gel with a staining solution, such as Coomassie and silver staining. Silver staining is a more sensitive staining method than Coomassie staining, and is able to detect 2-5 ng protein per band on a gel.

5. Western blotting:
   a. Following electrophoresis, proteins in a polyacrylamide gel can be transferred to a positively charged membrane in a buffer-tank-blotting apparatus or by semi-dry electroblotting.
   b. With the semi-dry electroblotting method, the gel and membrane are sandwiched between two stacks of filter paper that have been pre-wet with transfer buffer. The membrane is placed near the anode and the gel is placed near the cathode. SDS-coated, negatively charged proteins are transferred to the membrane when an electric current is applied.
   c. Additionally, a tank-blotting method could be used. This is where a blotting cassette is submerged in a tank for blotting. This can be performed over extended periods since the buffer capacity is far greater than that with semi-dry transfer systems. Results obtained with the tank-blotting method are typically better, with more efficient transfer, particularly of large proteins.

6. Acrylamide concentration:
   a. Low acrylamide concentrations are used to separate high molecular weight proteins, while high acrylamide concentrations are used to separate proteins of low molecular weight.

7. Dot blots:
   a. Dot blotting is a simple, convenient method for detection of proteins in crude lysates or solutions without the need for separation by SDS-PAGE. This method is especially useful as a simple control because it avoids problems that may be due to the western transfer process. Any components that interfere with binding or bind non-specifically, however, will not be spatially separated from the protein and will interfere with the intensity of signals.

8. Protein detection—Specific antibody-mediated detection of proteins on a membrane/Immunodetection using a chemiluminescent method:
   a. Using primary antibody applied to the membrane to bind to the target protein as well as a secondary antibody that chemically coupled to a reporter, which allows detection and visualization of the antibody and the protein of interest. Fluorescing molecules, or enzymes that produce colored or luminescent reaction products, are typically used as reporter groups.
   b. Importantly a primary antibody chemically coupled to a reporter enzyme (termed a conjugate) can be used for direct detection without the use of a secondary antibody.

9. Protein assay—ELISA:
   a. Enzyme-linked immunosorbent assay (ELISA) is a method that is analogous to immunodetection of proteins on a membrane, and is used for the quantitative assay of proteins in solution. In an ELISA, proteins are immobilized on a solid support (e.g., the wells of a 96-well plate) and used as capture molecules to bind the protein that is being assayed. After a wash step to remove nonspecifically bound material, a secondary antibody—specific for the protein being assayed—is added. This secondary antibody is usually conjugated to an enzyme that allows its detection by chromogenic or chemiluminescent methods. ELISA methods can be direct or indirect for the detection of a protein.

10. Quantifying proteins using the Bradford method or UV spectrophotometry:
   a. The Bradford method or UV spectrophotometry methods are a quantitative protein assay method, based on the binding of a dye, Coomassie Brilliant Blue, to a protein sample, and comparing this binding to a standard curve generated by the reaction of known amounts of a standard protein, usually BSA.

11. Quantification of DNA/mRNA and fragments of proteins using Spectrophotometry and fluorometry:
   a. Spectrophotometry and fluorometry are commonly used to measure both genomic and plasmid DNA concentration. Spectrophotometry can be used to measure microgram quantities of pure DNA samples (i.e., DNA that is not contaminated by proteins, phenol, agarose, or RNA). Fluorometry is more sensitive, allowing measurement of nanogram quantities of DNA, and furthermore, the use of Hoechst 33258 dye allows specific analysis of DNA.

12. Ligation of DNA methods:
   a. DNA will be firstly be digested using restriction endonucleases. The individual components of the desired DNA molecule are purified and then combined and treated with DNA ligase. The products of the ligation mixture are introduced into competent *E. coli* cells and transformants are identified by appropriate genetic selection.

13. Analysis of DNA by Southern blotting:
   a. Southern blotting is a widely used technique that allows analysis of specific DNA sequences. DNA is usually first converted into conveniently sized fragments by restriction digestion. The DNA of interest can be identified by hybridization to radioactive or chemiluminescent probes and visualized by autoradiography or stainin.

14. PCR, One step and Two Step Real time PCR, Long range PCR, Single Cell PCR, Fast Cycling PCR, Methylation-specific PCR and Differential display PCR methods.

15. Multiplex PCR and RT-PCR and whole transcriptome amplification:
   There are 3 main PCR-based WGA techniques. These are degenerate oligonucleotide PCR (DOP-PCR) (1), primer extension preamplification (PEP) (2) or derivatives thereof, and adaptor-ligation PCR (3). The main difference between the techniques is that PEP uses a preamplification step to add primer binding sites to small DNA fragments for later WGA by PCR, while adaptor ligation PCR uses adaptors ligated to small DNA fragments to create PCR primer binding sites. PEP utilizes random primers and a low PCR annealing temperature. Less frequently used today, DOP-PCR uses semi-degenerate oligonucleotides and an increasing annealing temperature.

16. RAPD: Rapid amplified polymorphic DNA and RACE: Rapid amplification of cDNA ends analysis.

17. Ext-generation sequencing, Genotyping using microarrays, Comparative genome hybridization studies (CGH), Single nucleotide polymorphism (SNP) genotyping, Sanger sequencing, STR/microsatellite analysis.

18. Haplotyping, Genotying
19. NGS sequencing methods
20. Metagenomics
21. RNA sequencing
   a. RNA sequencing (RNA-seq) is a method of investigating the transcriptome of an organism using deep-sequencing techniques. The RNA content of a sample is directly sequenced after appropriate library construction, providing a rich data set for analysis. The high level of sensitivity and resolution provided by this technique makes it a valuable tool for investigating the entire transcriptional landscape. The quantitative nature of the data and the high dynamic range of the sequencing technology enables gene expression analysis with a high sensitivity. The single-base resolution of the data provides information on single nucleotide polymorphisms (SNPs), alternative splicing, exon/intron boundaries, untranslated regions, and other elements 22. ChIP-Seq:
   a. Chromatin immunoprecipitation (ChIP) is a powerful and versatile method for understanding the mechanisms of gene regulation by transcription factors and modified histones.
   b. It is used to identify chromatin regions which are bound by transcription factors, co-regulators, modified histones, chromatin remodeling proteins, or other nuclear factors from live cells.

23. Flow cytometric analysis:
   Methods using Fluorescence-activated cell sorting.
   a. Fluorophores technology that label a recognised target feature on or in the cell. Use of flurophores may also be attached to a chemical entity with affinity for the cell membrane or another cellular structure.
   b. Quantum dots methods to be in place of traditional fluorophores because of their narrower emission peaks.
   c. Isotope labelling such as Mass cytometry 24. UEP results (SNP results):
   a. Unique-event polymorphisms (UEPs) such as SNPs represent haplogroups. STRs represent haplotypes. The results that comprise the full Y-DNA haplotype from the Y chromosome DNA test can be divided into two parts: the results for UEPs, sometimes loosely called the SNP results as most UEPs are single-nucleotide polymorphisms, and the results for microsatellite short tandem repeat sequences (Y-STRs).
   b. The UEP results represent the inheritance of events it is believed can be assumed to have happened only once in all human history. These can be used to identify the individual's Y-DNA haplogroup, his place in the "family tree" of the whole of humanity. Different Y-DNA haplogroups identify genetic populations that are often distinctly associated with particular geographic regions; their appearance in more recent populations located in different regions represents the migrations tens of thousands of years ago of the direct patrilineal ancestors of current individuals.

25. Y-STR haplotypes:
   a. Genetic results also include the Y-STR haplotype, the set of results from the Y-STR markers tested. Unlike the UEPs, the Y-STRs mutate much more easily, which allows them to be used to distinguish recent genealogy.

Using Haplotype technologies also:
   FAMHAP—FAMHAP is a software for single-marker analysis and, in particular, joint analysis of unphased genotype data from lightly linked markers (haplotype analysis).
   Fague—EM based haplotype estimation and association tests in unrelated and nuclear families.
   HPlus—A software package for imputation and testing of haplotypes association studies using a modified method that incorporates the expectation-maximization algorithm and a Bayesian method known as progressive ligation.
   HaploBlockFinder—A software package for analyses of haplotype block structure.
   Haploscribe—Reconstruction of whole-chromosome haplotypes based on all genotyped positions in a nuclear family, including rare variants.

Haploview—Visualisation of linkage disequilibrium, haplotype estimation and haplotype tagging (Homepage).

HelixTree—Haplotype analysis software-Haplotype Trend Regression (HTR), haplotypic association tests, and haplotype frequency estimation using both the expectation-maximization (EM) algorithm and composite haplotype method (CHM).

PHASE—A software for haplotype reconstruction, and recombination rate estimation from population data.

SHAPEIT—SHAPEIT2 is a program for haplotype estimation of SNP genotypes in large cohorts across whole chromosome.

SNPHAP—EM based software for estimating haplotype frequencies from unphased genotypes.

WHAP—haplotype based association analysis.

26. Microfluorimetry

This is an adaption of fluorimetry for studying the biochemical and biophysical properties of cells by using microscopy to image cell components tagged with fluorescent molecules.

Kits and Assays

The kit or assay for identifying a subject having a medical condition or symptom thereof or at risk of developing a medical condition or symptom thereof can comprise one or more probes, tools or reagents, including nucleic acid oligonucleotides or primers, arrays of nucleic acid probes, antibodies to polymorphic polypeptides (e.g., immobilized on a substrate), signal producing system reagents, labelling and detection means, controls and/or other reagents such as buffers, nucleotides or enzymes e.g. polymerase, nuclease or transferase, depending on the particular protocol to be performed. Other examples of reagents include arrays that comprise probes that are specific for one or more of the genes of interest or one or more polymorphisms thereof, and antibodies to epitopes of the proteins encoded by these genes of interest, wherein the epitope may comprise a polymorphism of interest.

A kit or assay can include one or more articles and/or reagents for performance of the method, such as means for providing the test sample itself, e.g. a swab for removing cells from the buccal cavity or a syringe for removing a blood sample (such components generally being sterile).

In addition to the above components, the kits or assay can further include instructions. These instructions may be present in the subject kits in a variety of forms, one form in which these instructions may be present is as printed information on a suitable medium or substrate, e.g., a piece or pieces of paper on which the information is printed, in the packaging of the kit, in a package insert, etc. Yet another form would be a computer readable medium, e.g., diskette, CD, etc., on which the information has been recorded. Yet another form that may be present is a website address which may be used via the internet to access the information at a removed site.

It is to be appreciated that one or more components of kits and assays generally described for SNPs/polymorphism detection may also be used for one or more other forms of the invention or may include components as described elsewhere in this specification (such as in the Examples), such as testing for differential regulation of calcium-dependent kinase genes, testing for dysfunctional signalling through the Mitogen-Activated Protein Kinase pathway (eg. for determining protein phosphorylation or dephosphorylation), testing for changes in calcium metabolism, or testing for changes in calcium-dependent kinase pathways. Suitable kit components include: a probe, tool or reagent for detection of a polymorphism at the genomic level, at the transcription level or polypeptide level; a probe, tool or reagent for quantitative or qualitative measurement of RNA transcription or translation; or a probe, tool or reagent such as an antibody or other type of molecule or chemical entity capable of detecting the gene or gene product (RNA or polypeptide) or property of the protein or dysfunctional biochemical signalling or pathway.

Biochip

A biochip is also provided. The biochip is an apparatus which, in certain embodiments, comprises a solid substrate comprising an attached probe or plurality of probes/oligonucleotides. The probes may be capable of hybridizing to a target sequence under stringent hybridization conditions. The probes may be attached at spatially defined address on the substrate. More than one probe per target sequence may be used, with either overlapping probes or probes to different sections of a particular target sequence. In an embodiment, two or more probes per target sequence are used. The probes may be capable of hybridizing to different targets, such as a TRP ion channel and/or ACh receptor gene/allele or gene product.

The probes may be attached to the biochip in a wide variety of ways, as will be appreciated by those of skill in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as a flexible foam, including closed cell foams made of particular plastics.

The biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using linkers. The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

A variety of hybridization conditions may be used, including high, moderate and low stringency conditions as outlined above. The assays may be performed under stringency conditions which allow hybridization of the probe only to the target. Stringency can be controlled by altering a step parameter that is a thermodynamic variable, including, but not limited to, temperature, formamide concentration, salt concentration, chaotropic salt concentration pH, or organic solvent concentration.

Hybridization reactions may be accomplished in a variety of ways. Components of the reaction may be added simultaneously, or sequentially, in different orders. In addition, the reaction may include a variety of other reagents. These include salts, buffers, neutral proteins, e.g., albumin, detergents, etc. which may be used to facilitate optimal hybridization and detection, and/or reduce non-specific or background interactions. Reagents that otherwise improve the efficiency of the assay, such as protease inhibitors, nuclease inhibitors and anti-microbial agents may also be used as appropriate, depending on the sample preparation methods and purity of the target.

Exemplary biochips of the present invention include an organized assortment of oligonucleotide probes described above immobilized onto an appropriate platform. Each probe selectively binds a nucleic acid target in a sample.

In accordance with another embodiment, the biochip of the present invention can also include one or more positive or negative controls. For example, oligonucleotides with randomized sentences can be used as positive controls, indicating orientation of the biochip based on where they are placed on the biochip, and providing controls for the detection time of the biochip.

Embodiments of the biochip can be made in the following manner. The oligonucleotide probes to be included in the biochip are selected and obtained. The probes can be selected, for example, based on particular SNPs of interest. The probes can be synthesized using methods and materials known to those skilled in the art, or they can be synthesized by and obtained from a commercial source, such as GeneScript USA (Piscataway, N.J.).

Each discrete probe is then attached to an appropriate platform in a discrete location, to provide an organized array of probes. Appropriate platforms include membranes and glass slides. Appropriate membranes include, for example, nylon membranes and nitrocellulose membranes. The probes are attached to the platform using methods and materials known to those skilled in the art. Briefly, the probes can be attached to the platform by synthesizing the probes directly on the platform, or probe-spotting using a contact or non-contact printing system. Probe-spotting can be accomplished using any of several commercially available systems, such as the GeneMachines(TM) OmniGrid (San Carlos, Calif.).

Particularly preferred embodiments of the invention are defined in the claims.

Any of the features described herein can be combined in any combination with any one or more of the other features described herein within the scope of the invention.

Unless defined otherwise, all technical and scientific terms used herein have the same meaning as commonly understood by one of ordinary skill in the art to which this invention belongs. Although any methods and materials similar or equivalent to those described herein can also be used in the practise or testing of the present invention.

Other forms and advantages of the invention will become apparent from a reading of this specification.

EXAMPLES

The following examples are illustrative only and should not be construed as limiting in any way the general nature of the disclosure of the description throughout this specification.

Example 1: The Role of the Transient Receptor Potential (TRP) Superfamily in CFS The transient receptor potential (TRP) superfamily in humans comprises 27 cation channels with permeability to monovalent and divalent cations. These channels are widely expressed within humans on cells and tissues, and have significant sensory and regulatory roles in most physiological functions.

Methodology

Subjects

The study comprised 115 CFS patients (age=48.68±1.06 years) and 90 non-fatigued controls (age=46.48±1.22 years). CFS patients were defined in accordance with the 1994 CDC criteria for CFS [20b]. 10 mL of whole blood samples were collected from all participants into EDTA tubes.

DNA Extraction

Genomic DNA was extracted from all whole blood samples using the Qiagen DNA blood mini-kit as per manufacturer's instructions (Qiagen). The Nanodrop (Nanodrop) was used to assess the quality and quantity of the DNA extracted. Approximately 2 µg of genomic DNA was used in the SNP assay.

SNP Genotyping Studies

SNP analysis was performed by Geneworks using the MassARRAY iPLEX Gold Assay (Sequenom Inc.) as previously described. Customized assays were developed for 240 SNPs across the 21 TRP genes (TRPA1, TRPC1, TRPC2, TRPC3, TRPC74, TRPC6, TRPC7, TRPM1, TRPM2, TRPM3, TRPM4, TRPM5, TRPM6, TRPM7, TRPM8, TRPV1, TRPV2, TRPV3, TRPV4, TRPV5 and TRPV6). Primers and extension primers were created for each of the SNPs using the Assay Designer (Sequenom Inc.) according to the manufacturer's instructions. Briefly, DNA was amplified via PCR under the follow conditions: 94° C. for 2 minutes, 94° C. for 30 seconds, 56° C. for 30 seconds and 72° C. for 1 minute. Amplification products were then treated with shrimp alkaline phosphatase (SAP) at 37° C. for 40 min, 85° C. for 5 min reaction and a final incubation at 4° C. Extension primers were optimized to control signal-to-noise ratio where un-extended primers (UEPs) were examined on the spectroCHIP and evaluated in Typer 4.0 to enable the division into low mass UEP, medium mass UEP and high mass UEP. To perform the iPLEX extension reaction, a mixture containing iPLEX Gold reaction was carried out using iPLEX Gold Buffer Pins, iPLEX termination mix, iPLEX enzyme and primer mix was prepared. iPLEX reaction was cycled at an initial denaturation of 94° C. for 30 s, annealing at 52° C. for 5 min, extension at 80° C. for 5 min (5 cycles of annealing and extension were performed, however the whole reaction was performed in 40 cycles) and extension again at 72° C. for 3 min. Resin beads were used to rinse all iPLEX Gold reaction products. Following iPLEX Gold reaction, MassARRAY was performed using the MassARRAY mass spectrometer, the data generated was analysed using the TyperAnalyzer software.

Statistical Analysis

The PLINK v1.07 [21.b] whole genome analysis tool set was used to determine associations between the CFS patients and the non-fatigued control group. A two column $\chi 2$ test was used to determine significance where p value of ≤0.05 was determined to be significant.

Results

Participants

Of the 115 CFS patients (age=48.68±1.06 years), 84 (73.04%) were females and 31 (26.96%) were males. The 90 non-fatigued controls (age=46.48±1.22 years) comprised 59

(65.56%) females and 31 (34.44%) males. All participants in the patient and non-fatigued control groups were of European decent and were all residents of Australia at the time of blood collection.

SNP Association Studies

Of the 240 SNPs that were examined in the present study, 233 were successfully identified in both participants groups. Of the 233, thirteen were observed to be significantly associated with CFS (Table 1).

platelets and smooth muscle function. Incidentally, $Ca^+$ is known to be required for the regulation of immune cells as $Ca^{2+}$ acts as a second messenger for most cells, particularly T cells and B cells. Intracellular $Ca^{2+}$ increases when lymphocytes receptors are exposed to antigens [23b]. In CFS patients, there are numerous reports on compromises to immune function although there is limited information on the role of $Ca^{2+}$ in these patients. However, dysregulation in TRPCs may affect intracellular calcium concentration and

TABLE 1

Analysis of the frequency distribution and significance of TRP Single Nucleotide Polymorphisms (SNPs) in CFS patients and non-fatigued controls in rank order significance.

| Gene | Chromosome | RefSNP ID | A1 | A2 | Frequency_A | Frequeney_U | $\chi^2$ | P |
|---|---|---|---|---|---|---|---|---|
| TRPM3 | 9 | rs12682832 | A | G | 0.444 | 0.293 | 8.808 | 0.003 |
| TRPM3 | 9 | rs11142508 | C | T | 0.445 | 0.298 | 8.438 | 0.004 |
| TRPM3 | 9 | rs1160742 | A | G | 0.470 | 0.333 | 7.063 | 0.008 |
| TRPM3 | 9 | rs4454352 | C | T | 0.240 | 0.137 | 6.232 | 0.013 |
| TRPM3 | 9 | rs1328153 | C | T | 0.240 | 0.137 | 6.232 | 0.013 |
| TRPM3 | 9 | rs3763619 | A | C | 0.440 | 0.316 | 5.990 | 0.014 |
| TRPC4 | 13 | rs6650469 | T | C | 0.505 | 0.380 | 5.775 | 0.016 |
| TRPC4 | 13 | rs655207 | G | T | 0.505 | 0.381 | 5.639 | 0.018 |
| TRPA1 | 8 | rs4738202 | A | G | 0.369 | 0.253 | 5.591 | 0.018 |
| TRPM3 | 9 | rs7865858 | A | G | 0.450 | 0.331 | 5.340 | 0.021 |
| TRPA1 | 8 | rs2383844 | G | A | 0.505 | 0.398 | 4.218 | 0.040 |
| TRPM3 | 9 | rs1504401 | T | C | 0.100 | 0.173 | 4.172 | 0.041 |
| TRPM3 | 9 | rs10115622 | A | C | 0.335 | 0.435 | 3.837 | 0.050 |
| TRPM4 | 19 | rs10403114 | G | A | 0.293 | 0.390 | 3.802 | 0.051 |
| TRPV3 | 17 | rs9909424 | G | A | 0.115 | 0.060 | 3.442 | 0.064 |
| TRPC4 | 13 | rs612308 | A | G | 0.439 | 0.537 | 3.393 | 0.065 |
| TRPM3 | 9 | rs7860377 | A | C | 0.350 | 0.262 | 3.314 | 0.069 |
| TRPC7 | 5 | rs2673930 | C | A | 0.200 | 0.280 | 3.218 | 0.073 |
| TRPC4 | 13 | rs603955 | C | T | 0.445 | 0.536 | 3.008 | 0.083 |
| TRPM3 | 9 | rs11142798 | C | G | 0.135 | 0.202 | 2.998 | 0.083 |
| TRPM3 | 9 | rs4744611 | G | A | 0.360 | 0.446 | 2.843 | 0.092 |
| TRPM2 | 21 | rs1785452 | T | C | 0.215 | 0.289 | 2.67 | 0.102 |
| TRPM3 | 9 | rs1566838 | G | T | 0.460 | 0.375 | 2.669 | 0.102 |
| TRPA1 | 8 | rs1384002 | T | C | 0.495 | 0.410 | 2.664 | 0.103 |
| TRPM6 | 9 | rs2274924 | G | A | 0.115 | 0.175 | 2.652 | 0.103 |
| TRPM3 | 9 | rs1394309 | G | A | 0.030 | 0.065 | 2.608 | 0.106 |
| TRPC4 | 13 | rs2985167 | G | A | 0.340 | 0.422 | 2.577 | 0.108 |
| TRPM5 | 11 | rs2301698 | G | T | 0.530 | 0.446 | 2.551 | 0.110 |
| TRPM6 | 9 | rs944857 | C | T | 0.185 | 0.125 | 2.476 | 0.116 |
| TRPM2 | 21 | rs762426 | G | A | 0.160 | 0.223 | 2.325 | 0.127 |

Nine of these SNPs were associated with TRPM3 (rs12682832; p=0.003, rs11142508; p=0.004, rs1160742; p=0.08, rs4454352; p=0.013, rs1328153; p=0013, rs3763619; p=0.014, rs786558; p=0.021, rs1504401; p=0041, rs10115622; p=0.050), while the remainder were associated with TRPA1 (rs2383844; p=0.040, rs4738202; p=0.018) and TRPC4 (rs6650469; p=0.016, rs655207; p=0.018).

Discussion

The purpose of this study was to determine the presence of possible SNP variations in CFS patients with a specific focus on SNPs within the coding sequences of 21 TRP ion channel genes. Out of the 240 SNPs examined, thirteen alleles were found to be significantly associated with CFS patients compared with the non-fatigued controls. These alleles were located in the gene sequence of one of the canonical TRPs ion channels (TRPC4), one ankyrin (TRPA1) and one melastatin TRP ion channel (TRPM3).

There is limited information available on the role of these SNPs, however TRPs may mediate the potential onset of CFS. TRPC4 is activated via receptor-dependent activation of the $G_{q/11}$/PLC β/γ pathway but also via $G_{\alpha i}$ proteins, PI(4,5)$P_2$ proteins and also intracellular $Ca^{2+}$ [22b]. It is mainly involved in vasomotor function, aggregation of incidentally lymphocyte function. Lymphocytes such as Natural Killer (NK) cells and T cells have been shown to be compromised in CFS. In NK cells, $Ca^{2+}$ enhances cytotoxic activity and its depletion or excessive influx may have severe consequences on NK cells function. In CFS reduced cytotoxic activity has been consistently reported [24b-29b] and this may be related to dysregulation in $Ca^{2+}$.

Dysregulation of TRPCs may affect neuronal responses in particular those associated with the stimulation of muscarinic receptors. Following activation of TRPCs by PLCs an influx of $Ca^{2+}$ occurs causing an induction in muscarinic receptors, and maintained incessant neuronal firing [30b, 31b]. Hence, secretion of $Ca^{2+}$ and availability of TRPCs in the neuronal environment is paramount to optimal muscarinic receptor function and overall function of the brain. Importantly, this process is essential for memory, attention, sensory acuity, emotion, pain and motor control [32b, 33b] and occurs in the amygdala, entorhinal cortex, hippocampus and prefrontal cortex [34b]. Neuronal deficits involving memory and attention have been identified in CFS [35b-37b]. Deletion or compromises to TRPC4 may also affect intestinal function. TRPC4 and TRPC6 pair with muscarinic receptors in the intestine activating smooth muscle depolarization, inflow of $Ca^{2+}$ and smooth muscle contraction

[38b]. Intestinal dysfunction is a component of CFS [39b], however the extent of damage to the intestinal wall or the exact role of ion channels in the intestine remains to be determined. TRPC4 may be simultaneously regulated by G protein coupled receptors (GPCRs) Gαi and Gαq [40b].

TRPA1 is a multiple chemical receptor that has been identified on nociceptive sensory neurons (C fibers) and has a role in the regulation of the release of neuropeptides, pain sensation and inflammation [41b]. It may be activated by both exogenous and endogenous inflammatory agents resulting in inflammation and pain [42b]. GPCRs also activate TRPA1 via PLC signalling sensitising the ion channel to various stimuli [43b]. TRPA1 may be activated and subsequently inactivated in the presence of intracellular and extracellular calcium concentrations [44b, 45b]. TRPA1 gene has been proposed to affect sensitivity to nociceptive stimuli [46b], hence CFS patients expressing SNPs in the TRPA1 gene may increase their sensitivity to nociceptive stimuli. In the CNS astrocytes express TRPA1 channels and these channels are necessary for calcium uptake and neuronal regulation in the astrocytes. Changes in the level of calcium may therefore affect the function of astrocytes and interneuron communication [45b, 47b]. Activation of TRPA1 has been shown to induce acute headache and this may occur through the calcitonin gene related peptide (CGRP) causing vasodilation in the meningeal artery [45b, 48b]. Importantly, headache is a prominent symptom of CFS. TRPA1 is also a key player in migraine, neuropathic, joint and muscle pain which is most often experienced by patients with fibromyalgia [49b, 50b]. TRPA1 forms functional heterotetramers with TRPV1 hence variations in the TRPA1 gene may suggest functional deficits to TRPV1 that may not be related to polymorphism in nucleotides [51b]. Analgesics and antinociceptive drugs target TRPV1 and TRPA1 respectively to alleviate pain sensation [52b-54b] and these drugs are routinely prescribed to CFS patients. Perhaps in CFS these drugs may not be effective due to impairments or variations in these ion channels.

TRPM channels are mostly permeable to magnesium and calcium. Only TRPM4 and TRPM5 are impermeable for divalent cations. TRPM3 is permeable for cations including $Ca^{2+}$ and $Zn^{2+}$. However, the permeation profile highly depends on the expressed spliced variant [55b]. No hereditary TRPM3 channelopathy has been described to date. TRPM3 has been implicated in inflammatory pain syndromes, rheumatoid arthritis, and secretion of proinflammatory cytokines. As pancreatic β cells also have a high proportion of TRPM3 channels [45b, 56b-58b], there is the likelihood of perturbations in insulin/glucose regulation in CFS patients. Metabolic disturbance has also long been identified as a cardinal feature of CFS. The most characterised TRPM3 in humans is in the central nervous system (CNS) and eye [55b]. TRPM3 is involved in the detection of heat and in pain transmission. TRPM3-deficient mice exhibit clear deficits in their avoidance responses to noxious heat and in the development of inflammatory heat hyperalgesia [55b]. Dysregulation in thermoregulatory responses has been reported in CFS patients [59b]. Generalised pain is a characteristic of CFS and occurs in the absence of tissue damage and this is suggestive of potential CNS impairments [60b]. As TRPM3 has a role in nociception and thermoregulation, it may have a role in the pathomechansim of CFS. Additionally, TRPM3 is activated by pregnenolone sulfate suggesting that it has neuroendocrine effects [61b, 62b] and might also be involved in the regulation of glutamatergic signalling in the brain [63b].

These findings implicate TRP ion channels (predominantly TRPM3) in the aetiology and pathomechansim of CFS. Dysregulation of TRPs, including the TRPM3 family, is likely pertinent in predisposing CFS patients to calcium metabolism perturbations and aligns with symptom presentation. Potentially, dysregulated influx of calcium ions into cells will impact a number of vital components of cell regulatory machinery. These components include calcium sensitive adenylate cyclases (ACs) and hence cAMP expression and function.

Example 2: The Role of ACh Receptor (nAChRs and mAChRs) SNPs in CFS/ME

Methodology

Subjects

The study comprised 115 CFS/ME patients (age=48.68±1.06 years) and 90 non-fatigued controls (age=46.48±1.22 years). CFS patients were defined in accordance with the 1994 CDC criteria for CFS [36c]. A volume of 10 mL of whole blood was collected from all participants into EDTA tubes.

DNA Extraction

Genomic DNA was extracted from all whole blood samples using the Qiagen DNA blood mini-kit as per manufacturer's instructions (Qiagen). Quality and quantity of the DNA extracted was determined by the Nanodrop (Nanodrop), where approximately 2 μg of genomic DNA was used to perform the SNP assay.

SNP Genotyping Studies

A total of 464 single nucleotide polymorphisms (SNPs) for nine mammalian ACh receptor genes (M1, M2, M3, M4, M5, alpha 2, 5, 7 and 10) were examined via the Agena Biosciences Gold assay. Geneworks completed the SNP analysis as previously defined (MassARRAY iPLEX Gold Assay) [37c]. Customized assays were developed for 464 SNPs across the 9 mammalian acetylcholine receptor genes (M1, M2, M3, M4, M5, alpha 2, 5, 7 and 10). Primers and extension primers were created for each of the SNPs using the Assay Designer [37c] according to the manufacturer's instructions. The amplification of the DNA was as previously described. Briefly, DNA was amplified via PCR under the follow conditions 94° C. for 2 minutes, 94° C. for 30 seconds, 56° C. for 30 seconds and 72° C. for 1 minute. Amplification products were then treated with shrimp alkaline phosphatase (SAP) at 37° C. for 40 min, 85° C. for 5 min reaction and a final incubation at 4° C. Extension primers were optimized to control signal-to-noise ratio where un-extended primers (UEPs) were examined on the spectroCHIP and evaluate in Typer 4.0 to enable the division into low mass UEP, medium mass UEP and high mass UEP. To perform the iPLEX extension reaction, a mixture containing iPLEX Gold reaction was carried out using iPLEX Gold Buffer Plus, iPLEX termination mix, iPLEX enzyme and primer mix was prepared. iPLEX reaction was cycled at an initial denaturation of 94° C. for 30 s, annealing at 52° C. for 5 min, extension at 80° C. for 5 min (5 cycles of annealing and extension were performed, however the whole reaction was performed in 40 cycles) and extension again at 72° C. for 3 min. Resin beads were used to rinse all iPLEX Gold reaction products. Following iPLEX Gold reaction, MassARRAY was performed using the MassARRAY mass spectrometer, the data generated was analysed suing the TyperAnalyzer software.

Statistical Analysis

The PLINK v1.07 [39c] whole genome analysis tool set was implemented to determine associations between the CFS patients and the non-fatigued control group. A two column χ2 test was used where alpha level of significance was set at p value of ≤0.05.

Results

Participants

Of the 115 CFS patients (age=48.68±1.06 years), 84 (73.04%) were females and 31 (26.96%) were males. 90 non-fatigued controls (age=46.48±1.22 years) comprised 59 (65.56%) females and 31 (34.44%) males. All participants in both groups were of European decent. All were residents of Australia at the time of blood collection.

SNP Association Studies

Of the 464 SNPs that were examined in the present study, 393 were successfully identified in both participants groups. Of the 393, seventeen were observed to be significantly associated with CFS (Table 2).

remainder were associated with nACh alpha 10 (rs2672211; p=0.01, rs2672214; p=0.01, rs2741868; p=0.01, rs2741870; p=0.01, rs2741862; p=0.03) alpha 5 (rs951266; p=0.012; rs7180002, p=0.04) and alpha 2 (rs2565048; p=0.0).

Discussion

This study revealed a number of AChR SNP variations in CFS/ME patient., Specifically, within the coding sequences of nine AChR genes out of 464 SNPs examined, 17 significant alleles associated with CFS/ME patients were found compared with the non-fatigued controls. Moreover these alleles were located in the gene sequence of one of the muscarinic acetylcholine receptors (mAChRM3) and three nicotinic acetylcholine alpha receptors (nAChRα2, nAChRα5 and nAChRα10). Interestingly, in Example 1 the inventors identified a number of SNPs in the TRP family, namely TRPC4. The significance of SNPs in mAChRM3

TABLE 2

Analysis of the frequency distribution and significance of acetylcholine receptor Single Nucleotide Polymorphisms (SNPs) in CFS patients and non-fatigued controls in rank order of significance.

| Gene | Chromosome | RefSNP ID | A1 | Frequency_A | Frequency_U | A2 | $\chi^2$ | P |
|---|---|---|---|---|---|---|---|---|
| mAchM3 | 1 | rs4463655 | T | 0.3077 | 0.4671 | C | 8.932 | 0.00 |
| mAchM3 | 1 | rs589962 | C | 0.2416 | 0.3919 | T | 8.539 | 0.00 |
| mAchM3 | 1 | rs1072320 | G | 0.3242 | 0.1842 | A | 8.423 | 0.00 |
| mAchM3 | 1 | rs7543259 | A | 0.3187 | 0.1842 | G | 7.834 | 0.01 |
| mAchM3 | 1 | rs6661621 | C | 0.3022 | 0.1711 | G | 7.755 | 0.01 |
| nAchα10 | 11 | rs2672211 | C | 0.3736 | 0.2434 | T | 6.515 | 0.01 |
| nAchα10 | 11 | rs2672214 | C | 0.3708 | 0.24 | T | 6.498 | 0.01 |
| nAchα5 | 15 | rs951266 | T | 0.3944 | 0.2632 | C | 6.382 | 0.01 |
| nAchα10 | 11 | rs2741868 | T | 0.3693 | 0.24 | A | 6.333 | 0.01 |
| nAchα10 | 11 | rs2741870 | G | 0.3708 | 0.2434 | C | 6.195 | 0.01 |
| nAchα2 | 8 | rs2565048 | C | 0.0989 | 0.1933 | T | 6.034 | 0.01 |
| mAchM3 | 1 | rs7520974 | G | 0.4205 | 0.5533 | A | 5.727 | 0.02 |
| mAchM3 | 1 | rs726169 | G | 0.2833 | 0.4013 | A | 5.132 | 0.02 |
| mAchM3 | 1 | rs6669810 | G | 0.4213 | 0.5467 | C | 5.123 | 0.02 |
| nAchα10 | 11 | rs2741862 | C | 0.2857 | 0.1842 | T | 4.685 | 0.03 |
| nAchα5 | 15 | rs7180002 | T | 0.3846 | 0.2763 | A | 4.359 | 0.043 |
| mAchM3 | 1 | rs6429157 | G | 0.522 | 0.4079 | A | 4.327 | 0.04 |
| nAchα2 | 8 | rs55828312 | G | 0.2386 | 0.1513 | A | 3.914 | 0.05 |
| nAchα5 | 15 | rs2175886 | C | 0.4944 | 0.3867 | T | 3.847 | 0.05 |
| mAchM3 | 1 | rs12036141 | A | 0.4121 | 0.3092 | G | 3.781 | 0.05 |
| mAchM3 | 1 | rs6429147 | C | 0.4444 | 0.34 | G | 3.728 | 0.05 |
| mAchM3 | 1 | rs1594513 | G | 0.2198 | 0.3133 | T | 3.722 | 0.05 |
| nAchα2 | 8 | rs16891561 | T | 0.2472 | 0.1597 | C | 3.696 | 0.05 |
| nAchα10 | 1 | rs2672215 | A | 0.4607 | 0.36 | C | 3.399 | 0.07 |
| nAchα2 | 8 | rs6474413 | C | 0.2308 | 0.1513 | T | 3.336 | 0.07 |
| mAchM3 | 1 | rs10926008 | G | 0.3722 | 0.277 | A | 3.333 | 0.07 |
| nAchα2 | 8 | rs2741343 | C | 0.5337 | 0.4324 | T | 3.317 | 0.07 |
| nAchα5 | 15 | rs7178270 | G | 0.3571 | 0.4539 | C | 3.231 | 0.07 |
| nAchα5 | 15 | rs4243084 | G | 0.3977 | 0.3026 | C | 3.227 | 0.07 |
| nAchα5 | 15 | rs601079 | A | 0.3901 | 0.4868 | T | 3.155 | 0.08 |
| nAchα5 | 15 | rs12911602 | C | 0.3901 | 0.4868 | T | 3.155 | 0.08 |
| nAchα5 | 15 | rs588765 | T | 0.3846 | 0.4803 | C | 3.095 | 0.08 |
| nAchα5 | 15 | rs680244 | A | 0.3846 | 0.4803 | G | 3.095 | 0.08 |
| nAchα5 | 15 | rs6495306 | G | 0.3895 | 0.4863 | A | 3.01 | 0.08 |
| nAchα5 | 15 | rs6495307 | T | 0.4111 | 0.5068 | C | 2.997 | 0.08 |
| mAchM3 | 1 | rs12093821 | A | 0.489 | 0.3947 | G | 2.979 | 0.08 |
| mAchM3 | 1 | rs16838637 | G | 0.4889 | 0.3947 | A | 2.957 | 0.09 |
| nAchα2 | 8 | rs6997909 | A | 0.2333 | 0.1579 | G | 2.945 | 0.09 |
| nAchα10 | 11 | rs2672216 | C | 0.4888 | 0.3947 | T | 2.934 | 0.09 |
| mAchM3 | 1 | rs6429165 | A | 0.2473 | 0.1711 | G | 2.873 | 0.09 |
| nAchα2 | 8 | rs891398 | C | 0.533 | 0.4392 | T | 2.872 | 0.09 |
| nAchα5 | 15 | rs4366683 | G | 0.3956 | 0.4868 | A | 2.802 | 0.09 |
| nAchα2 | 8 | rs6985052 | C | 0.2308 | 0.1579 | T | 2.774 | 0.10 |
| nAchα2 | 8 | rs4950 | C | 0.2308 | 0.1579 | T | 2.774 | 0.10 |

Seventeen SNPs were significantly associated with CFS/ME patients compared with the controls. Nine of these SNPs were associated with mAChRM3 (rs4463655; p=0.00, rs589962; p=0.00, rs1072120; p=0.00, rs7543259; p=0.01, rs6661621; p=0.01, rs7520974; p=0.02, rs726169; p=0.02, rsrs6669810; p=0.02, rsrs6429157; p=0.04), while the and TRPC4 is that the latter couples to mAChRM3 and can be activated by ACh [40c-42c].

There is limited information available on the role of these AChR SNPs, however the role of ACh in calcium ($Ca^{2+}$) cell signalling suggests these AChRs may mediate, in part, the clinical expression of CFS/ME. Moreover, the inventors have shown in Example 1 significant SNPs in the TRP ion channel family, namely TRPA1, TRPM3 and TRPC4, using the same cohort of CFS/ME patients. These findings suggest the potential for significant aberrations in $Ca^{2+}$ cell signalling possibly reflected in the clinical presentation of CFS/ME patients.

mAChR receptors are responsible for initiating smooth muscle contraction, such as in the gastrointestinal and genitourinary tracts, as well as effects in immune cells, epithelial, ovarian and ocular skin cells, respiratory and secretory glands [43c-46c, 33c, 34c, 32c, 47c-52c, 35c, 5c]. nAChRs are also reported on T and B lymphocytes [53c, 54c]. Human T lymphocytes express the α3, α4, α7, β2 and β4 receptor subunits [55c] while in the mouse and human thymus mAChR expression has been found to play a role in T lymphocyte development and proliferation [53c, 56c-58c]. The α4 or α7 subunits have also been reported on B lymphocytes and found to stimulate proliferation, while decreasing antibody production [59c]. Such findings provide possible insight regarding the SNPs characterised in this Example noting that previous investigations have reported compromise to immune function in CFS/ME patients. Significantly, changes in numbers and function of lymphocytes such as Natural Killer (NK) lymphocytes, T and B lymphocytes in these studies suggests increased influx of $Ca^{2+}$.

The mAChRM3 receptors are located in the gastrointestinal tract and are controlled in part by the parasympathetic nervous system, through the vagus nerve [60c]. Where nerve fibres make synapse within the gut wall, the main neurotransmitter, acetylcholine, usually stimulates GI motility. Moreover, clinical data reports nAChRs are involved in inflammatory bowel disease [61c]. Dysregulation of $Ca^{2+}$ mediated channels such as influx or reduction of $Ca^{2+}$ flow could cause significant changes in GI motility. CFS/ME patients often exhibit gastrointestinal associated issues, such as irritable bowel syndrome and constipation [12c, 28c].

Dysregulation of mAChRM3 receptors may affect metabolic and cardiac responses. In normal pancreas, mAChRM3 receptors play a role in regulating insulin and glucagon secretion [62c, 63c]. Muscarinic acetylcholine receptors expressed by pancreatic β-cells have been reported to play significant role in maintaining proper insulin release and in maintaining whole body glucose homeostasis [62c]. Changes in $Ca^{2+}$ mediated channels may result in adverse glucose metabolic outcomes as implied in CFS/ME patients [64c]. AChR SNPs in CFS patients will likely affect $Ca^{2+}$ modulation in intracellular pathways through the influx of $Ca^{2+}$ ions. Pancreatic β-cells rely on a transient decrease in $Ca^{2+}$ to initiate the complex sequence of events resulting in insulin secretion following glucose exposure. Hellman et al. [65c] report that elevation of glucose induces transient inhibition of insulin release by lowering cytoplasmic $Ca^{2+}$ below baseline in pancreatic β-cells. This period was found to coincide with increased glucagon release and hence was asserted to be the starting point for anti-synchronous pulses of insulin and glucagon. They conclude that the period of initial decrease of cytoplasmic calcium ion concentration regulates the subsequent β-cell response to glucose. Thus it may be argued that aberrant elevated intracellular $Ca^{2+}$ concentrations through permissive TRP and AChR activity will impede the usual and necessary sequence of events required to initiate insulin response to glucose in CFS patients.

Cardiac mAChRM3 receptors perform an array of pathological and physiological functions. mAChM2 is not the only muscarinic receptor involved in cardiac function, rather mAChRM3 parasympathetic control of cardiac function is well established [66c]. A report by van Borren et al. [67c] shows the effect of muscarinic AChR stimulation on $Ca^{2+}$ transients, cAMP production and pacemaker frequency in sinoatrial (SA) nodes of the rabbit. They found that the pacemaker slowing effects of muscarinic agonists are augmented by $Ca^{2+}$ transient inhibition, suggesting a negative chronotropic effect of muscarinic agonists is, in part, obtained by $Ca^{2+}$ transient inhibition and subsequent reduction in cAMP. These findings imply that muscarinic agonism will have an effect on SA node function exacerbating disturbances of proper cardio-regulatory mechanisms, particularly in an environment where $Ca^{2+}$ intracellular concentrations are likely to be altered due to direct effects of receptor activity. Clinical consequences such as altered orthostatic cardiovascular responses could be predicted and could align with symptom presentation in CFS/ME [13c, 21c, 25c, 27c, 29c].

In the vascular system, the endothelium contains nAChRs, including α3, α5, α7, α10, β2, β and β4 [68c, 48c, 69c]. Depending upon the type of smooth muscle a specific subtype of nAChR is present; α3 and α5 are found in arteries, while α7 is widespread, although not present in the renal circulatory system. nAChR α5, α7, β2 and β3 have been found in brain endothelial cells [70c] and are an important component of the blood-brain barrier (BBB). nAChR receptor assembly is important for ion permeability and desensitisation. nAChR α7 subunits are known to desensitise rapidly as well as have a high $Ca^{2+}:Na^+$ permeability. A combination of α7 with α5 nAChR subunits results in receptors with distinct desensitisation properties and ion permeability relative to the homomeric α7 nAChR [71c, 72c]. More dramatic changes in nAChR channel kinetics are observed when the α5 nAChR subunit incorporates into receptors with the α3 and β4 nAChR subunits, suggesting subunit conformations may impact on functional properties [73c, 74c] of these receptors. This current Example identified SNPs in α5 and α3 nAChR subunits, implying anomalies of signal transduction in the inventor's patient cohort. nAChRs are reported to be involved in arousal, sleep and fatigue as well as those functions that are responsible for processing of pain, memory and cognition [75c-77c].

Voltage-gated $Ca^{2+}$-selective channels (CaVs) and intracellular $Ca^{2+}$ Signalling Networks and nonselective ion channels are known to play a significant role in cell integrity, function and cell cycle. The results in this current Example suggest there is an intrinsic role between SNPs of both TRP and ACh receptors that may underpin CPS/ME pathology.

Adenylate cyclases (AC) are critical in producing cAMP from ATP through a non-redundant mechanism. $Ca^{2+}$ promotes cAMP production via the $Ca^{2+}$ sensitive AC1 in the guinea pig sinoatrial (SA) node, although the role of the other $Ca^{2+}$-stimulated AC subtype (AC8), in the guinea pig SA node is uncertain [78c]. The five muscarinic ACh receptors (M(1)-M(5)) are differentially expressed in the brain M(2) and M(4) are coupled to inhibition of stimulated adenylyl cyclase, while M(1), M(3) and M(5) are mainly coupled to the phosphoinositide pathway [79c]. However as ACh is largely mediated through $Ca^{2+}$ the question is raised as to whether permissive influx of $Ca^{2+}$ occurs through TRP and AChR SNPs and whether this combination of factors may result in dysregulation of AC activity and cAMP/$Ca^{2+}$ interactions. Support for this argument is highlighted where TRPC4 couples to mAChRM3 and is activated by ACh [40c-42c].

A key component of AC regulation and cAMP production is achieved through two AC stimulating vasoactive neuropeptides, namely vasoactive intestinal peptide (VIP) and the pituitary adenylate cyclase activating polypeptide (PACAP). In cardiac neurons which express TRPC transcripts, PACAP activates calcium-permeable non-selective cationic channels, which are likely members of the TRPC family [80c]. Inhibition of intracellular calcium increases by the application of calcium channel blockers indicates that PACAP acts on calcium influx [81c]. Notably it is calcium ion influx, not release from calcium ion stores, which is required for PACAP-induced increase in excitability in guinea pig intracardiac neurons. Importantly, the expression of PACAP genes is controlled by calcium and cAMP signals in neurons, suggesting that dysregulated calcium influx into cells will have effects on PACAP expression. The activity-dependent gene expression is jointly controlled by $Ca^{2+}$ and cAMP signals not only at the transcriptional level but also at the post-translational level for the cumulative mRNA expression in neurons [82c]. Earlier research has shown in isolated NK lymphocytes a significant increase in VPAC1R numbers for CFS/ME patients compared with controls [15c]. An increase in VPAC1R numbers found on these lymphocytes may have occurred to compensate for impaired AC and cAMP signalling.

In conclusion, the inventors report for the first time the presence of SNPs in receptors for ACh (predominantly M3 and CFS) and in association with TRP SNPs in patients with CFS/ME. Many detrimental consequences for physiological homeostasis are possible through aberrant ACh and TRP function in these patients. These scenarios conceivably are associated with CFS/ME pathomechanisms and symptomatology and require further investigation.

Example 3—Non-Synonymous Single Nucleotide Polymorphisms in AChR and TRP in Myalgic Encephalomyelitis/Chronic Fatigue Syndrome In Examples 1 and 2 the inventors identified single nucleotide polymorphisms (SNPs) in genes for transient receptor potential (TRP) ion channels and acetylcholine receptors (AChRs), which have important roles in calcium ($Ca^{2+}$) and acetylcholine (ACh) signalling. Non-synonymous single nucleotide polymorphisms (nsSNPs) are those SNPs resulting in changes to protein expression of these receptors which may be responsible for aberrant signalling and hence potentially change of function.

In this Example the inventors determine that nsSNPs are present in those SNPs previously identified in TRP ion channel and AChR genes in CFS/ME patients.

Method

Subjects

CFS patients were defined in accordance with the 1994 CDC criteria for CFS [32d]. 115 CFS/ME patients (age=48.68±1.06 years) and 90 non-fatigued controls (age=46.48±1.22 years) were examined for nsSNPs in genes for TRP ion channels and AChRs.

Blood Collection and DNA Extraction

A volume of 10 mL of whole blood was collected from all participants into EDTA tubes. Genomic DMA was extracted from all whole blood samples using the Qiagen DNA blood mini-kit as per manufacturer's instructions (Qiagen). SNP genotyping studies were performed as previously described.

nsSNP Analysis

A total of 81 SNPs were examined in the present study: 53 nsSNPs for four AChR genes (M3, and alpha 2, 5 and 10) and 28 nsSNPs for TRP ion channel genes (TRPA1, TRPC4, TRPM3 and TRPM4).

nsSNP Statistical Analysis

All 81 SNPs resulting from the PLINK analysis with p values of <0.1, were taken and used as input into the Variant Effect Predictor, to determine the effect of the variants. The resulting variants set at an alpha level of p<0.05 and their consequences can be found in Table 3-4 and 5-6 for TRP and AChR, respectively. Analyses were performed at the Australian Genome Research Facility Ltd, The Walter and Eliza Hall institute, Parkville, Victoria, Australia.

TABLE 3

Frequency distribution and significance of Transient Receptor Potential (TRP) nsSNPs in CFS/ME patients and no-fatigued controls in rank order of significance.

| CHR | SNP | BP | A1 | F_A | F_U | A2 | P | Location | Allele | Consequence |
|---|---|---|---|---|---|---|---|---|---|---|
| 9 | rs12682832 | 70605775 | A | 0.4444 | 0.2927 | G | 0.002999 | 9: 70605775-70605775 | G | intron_variant |
| | | | | | | | | 9: 70605775-70605775 | G | intron_variant, non_coding_transcript |
| | | | | | | | | 9: 70605775-70605775 | G | intron_variant |
| | | | | | | | | 9: 70605775-70605775 | G | intron_variant |
| | | | | | | | | 9: 70605775-70605775 | G | downstream_gene_variant |
| | | | | | | | | 9: 70605775-70605775 | G | intron_variant |
| | | | | | | | | 9: 70605775-70605775 | G | intron_variant |
| | | | | | | | | 9: 70605775-70605775 | G | intron_variant |
| | | | | | | | | 9: 70605775-70605775 | G | intron_variant |
| | | | | | | | | 9: 70605775-70605775 | G | intron_variant |
| 9 | rs11142508 | 70616746 | C | 0.445 | 0.2976 | T | 0.003675 | 9: 70616746-70616746 | T | intron_variant |
| | | | | | | | | 9: 70616746-70616746 | T | intron_variant |
| | | | | | | | | 9: 70616746-70616746 | T | intron_variant |
| | | | | | | | | 9: 70616746-70616746 | T | intron_variant |
| | | | | | | | | 9: 70616746-70616746 | T | intron_variant |
| | | | | | | | | 9: 70616746-70616746 | T | intron_variant |
| | | | | | | | | 9: 70616746-70616746 | T | intron_variant |
| | | | | | | | | 9: 70616746-70616746 | T | intron_variant |
| 9 | rs1160742 | 70699095 | A | 0.47 | 0.3333 | G | 0.007871 | 9: 70699095-70699095 | G | intron_variant |
| | | | | | | | | 9: 70699095-70699095 | G | intron_variant |
| | | | | | | | | 9: 70699095-70699095 | G | intron_variant |
| | | | | | | | | 9: 70699095-70699095 | G | intron_variant |
| | | | | | | | | 9: 70699095-70699095 | G | intron_variant |
| | | | | | | | | 9: 70699095-70699095 | G | intron_variant |
| | | | | | | | | 9: 70699095-70699095 | G | intron_variant |
| | | | | | | | | 9: 70699095-70699095 | G | intron_variant |

TABLE 3-continued

Frequency distribution and significance of Transient Receptor Potential (TRP) nsSNPs in CFS/ME patients and no-fatigued controls in rank order of significance.

| | | | | | | | | | |
|---|---|---|---|---|---|---|---|---|---|
| 9 | rs4454352 | 70795494 | C | 0.24 | 0.1369 | T | 0.01254 | 9: 70795494-70795494 | T | intron_variant |
| | | | | | | | | 9: 70795494-70795494 | T | intron_variant |
| | | | | | | | | 9: 70795494-70795494 | T | intron_variant |
| | | | | | | | | 9: 70795494-70795494 | T | intron_variant |
| | | | | | | | | 9: 70795494-70795494 | T | intron_variant |
| | | | | | | | | 9: 70795494-70795494 | T | intron_variant |
| | | | | | | | | 9: 70795494-70795494 | T | intron_variant |
| | | | | | | | | 9: 70795494-70795494 | T | intron_variant |
| | | | | | | | | 9: 70795494-70795494 | T | intron_variant |
| | | | | | | | | 9: 70795494-70795494 | T | intron_variant |

| CHR | SNP | BP | IMPACT | Gene | Feature_type | Feature | BIOTYPE | HGVSc |
|---|---|---|---|---|---|---|---|---|
| 9 | rs12682832 | 70605775 | MODIFIER | 80036 | Transcript | NM_020952.4 | protein_coding | NM_020952.4: c.2173-2305N>C |
| | | | MODIFIER | 101927086 | Transcript | XR_428546.1 | lncRNA | XR_428546.1: n.1265-1283N>G |
| | | | MODIFIER | 80036 | Transcript | NM_001007471.2 | protein_coding | NM_001007471.2: c.2632-2305N>C |
| | | | MODIFIER | 80036 | Transcript | NM_206946.3 | protein_coding | NM_206946.3: c.2248-2305N>C |
| | | | MODIFIER | 101927086 | Transcript | XR_242612.2 | lncRNA | — |
| | | | MODIFIER | 80036 | Transcript | NM_206944.3 | protein_coding | NM_206944.3: c.2143-2305N>C |
| | | | MODIFIER | 80036 | Transcript | NM_024971.5 | protein_coding | NM_024971.5: c.2209-2305N>C |
| | | | MODIFIER | 80036 | Transcript | NM_206947.3 | protein_coding | NM_206947.3: c.2218-2305N>C |
| | | | MODIFIER | 80036 | Transcript | XM_005252218.2 | protein_coding | XM_005252218.2: c.2713-2305N>C |
| | | | MODIFIER | 80036 | Transcript | NM_206945.3 | protein_coding | NM_206945.3: c.2179-2305N>C |
| 9 | rs11142508 | 70616746 | MODIFIER | 80036 | Transcript | NM_020952.4 | protein_coding | NM_020952.4: c.1864-671N>A |
| | | | MODIFIER | 80036 | Transcript | NM_001007471.2 | protein_coding | NM_001007471.2: c.2323-671N>A |
| | | | MODIFIER | 80036 | Transcript | NM_206946.3 | protein_coding | NM_206946.3: c.1939-671N>A |
| | | | MODIFIER | 80036 | Transcript | NM_206944.3 | protein_coding | NM_206944.3: c.1834-671N>A |
| | | | MODIFIER | 80036 | Transcript | NM_024971.5 | protein_coding | NM_024971.5: c.1900-671N>A |
| | | | MODIFIER | 80036 | Transcript | NM_206947.3 | protein_coding | NM_206947.3: c.1909-671N>A |
| | | | MODIFIER | 80036 | Transcript | XM_005252218.2 | protein_coding | XM_005252218.2: c.2404-671N>A |
| | | | MODIFIER | 80036 | Transcript | NM_206945.3 | protein_coding | NM_206945.3: c.1870-671N>A |
| 9 | rs1160742 | 70699095 | MODIFIER | 80036 | Transcript | NM_020952.4 | protein_coding | NM_020952.4: c.814-17517N>C |
| | | | MODIFIER | 80036 | Transcript | NM_001007471.2 | protein_coding | NM_001007471.2: c.1273-17517N>C |
| | | | MODIFIER | 80036 | Transcript | NM_206946.3 | protein_coding | NM_206946.3: c.889-17517N>C |
| | | | MODIFIER | 80036 | Transcript | NM_206944.3 | protein_coding | NM_206944.3: c.814-17517N>C |
| | | | MODIFIER | 80036 | Transcript | NM_024971.5 | protein_coding | NM_024971.5: c.814-17517N>C |
| | | | MODIFIER | 80036 | Transcript | NM_206947.3 | protein_coding | NM_206947.3: c.889-17517N>C |
| | | | MODIFIER | 80036 | Transcript | XM_005252218.2 | protein_coding | XM_005252218.2: c.1354-17517N>C |
| | | | MODIFIER | 80036 | Transcript | NM_206945.3 | protein_coding | NM_206945.3: c.814-17517N>C |
| 9 | rs4454352 | 70795494 | MODIFIER | 80036 | Transcript | NM_020952.4 | protein_coding | NM_020952.4: c.515-11215N>A |
| | | | MODIFIER | 80036 | Transcript | NM_001007470.1 | protein_coding | NM_001007470.1: c.590-11215N>A |
| | | | MODIFIER | 80036 | Transcript | NM_001007471.2 | protein_coding | NM_001007471.2: c.974-11215N>A |
| | | | MODIFIER | 80036 | Transcript | NM_206948.2 | protein_coding | NM_206948.2: c.515-11215N>A |
| | | | MODIFIER | 80036 | Transcript | NM_206946.3 | protein_coding | NM_206946.3: c.590-11215N>A |

TABLE 3-continued

Frequency distribution and significance of Transient Receptor Potential (TRP) nsSNPs in CFS/ME patients and no-fatigued controls in rank order of significance.

| | MODIFIER | 80036 | Transcript | NM_206944.3 | protein_coding | NM_206944.3: c.515−11215N>A |
|---|---|---|---|---|---|---|
| | MODIFIER | 80036 | Transcript | NM_024971.5 | protein_coding | NM_024971.5: c.515−11215N>A |
| | MODIFIER | 80036 | Transcript | NM_206947.3 | protein_coding | NM_206947.3: c.590−11215N>A |
| | MODIFIER | 80036 | Transcript | NM_206945.3 | protein_coding | NM_206945.3: c.515−11215N>A |
| | MODIFIER | 80036 | Transcript | XM_005252218.2 | protein_coding | XM_005252218.2: c.1055−11215N>A |

TABLE 4

Frequency distribution and significance of Transient Receptor Potential (TRP) nsSNPs in CFS/ME patients and non-fatigued controls in rank order of significance.

| CHR | SNP | BP | A1 | F_A | F_U | A2 | P | Location | Allele | Consequence |
|---|---|---|---|---|---|---|---|---|---|---|
| 13 | rs6650469 | 37793812 | T | 0.505 | 0.3795 | C | 0.01625 | 13: 37793812-37793812 | T | intron_variant |
| | | | | | | | | 13: 37793812-37793812 | T | intron_variant |
| | | | | | | | | 13: 37793812-37793812 | T | intron_variant |
| | | | | | | | | 13: 37793812-37793812 | T | intron_variant |
| | | | | | | | | 13: 37793812-37793812 | T | intron_variant |
| | | | | | | | | 13: 37793812-37793812 | T | intron_variant |
| 13 | rs655207 | 37793875 | G | 0.5051 | 0.381 | T | 0.01757 | 13: 37793875-37793875 | T | intron_variant |
| | | | | | | | | 13: 37793875-37793875 | T | intron_variant |
| | | | | | | | | 13: 37793875-37793875 | T | intron_variant |
| | | | | | | | | 13: 37793875-37793875 | T | intron_variant |
| | | | | | | | | 13: 37793875-37793875 | T | intron_variant |
| | | | | | | | | 13: 37793875-37793875 | T | intron_variant |
| 8 | rs4738202 | 72028626 | A | 0.3687 | 0.253 | G | 0.01806 | 8: 72028626-72028626 | G | intron_variant, non_coding_transcript |
| | | | | | | | | 8: 72028626-72028626 | G | intron_variant, non_coding_transcript |
| | | | | | | | | 8: 72028626-72028626 | G | intron_variant |
| 9 | rs7865858 | 70589515 | A | 0.45 | 0.3313 | G | 0.02084 | 9: 70589515-70589515 | G | intron_variant |
| | | | | | | | | 9: 70589515-70589515 | G | intron_variant |
| | | | | | | | | 9: 70589515-70589515 | G | intron_variant |
| | | | | | | | | 9: 70589515-70589515 | G | intron_variant |
| | | | | | | | | 9: 70589515-70589515 | G | intron_variant |
| | | | | | | | | 9: 70589515-70589515 | G | intron_variant |
| | | | | | | | | 9: 70589515-70589515 | G | intron_variant |
| | | | | | | | | 9: 70589515-70589515 | G | regulatory_region_variant |
| 8 | rs2383844 | 72049017 | G | 0.505 | 0.3976 | A | 0.3999 | 8: 72049017-72049017 | A | intron_variant, non_coding_transcript |
| | | | | | | | | 8: 72049017-72049017 | A | intron_variant, non_coding_transcript |
| | | | | | | | | 8: 72049017-72049017 | A | intron_variant |
| 9 | rs1504401 | 71302037 | T | 0.1 | 0.1726 | C | 0.04111 | 9: 71302037-71302037 | C | intron_variant |
| 9 | rs10115622 | 70691635 | A | 0.335 | 0.4345 | C | 0.05014 | 9: 70691635-70691635 | A | intron_variant |
| | | | | | | | | 9: 70691635-70691635 | A | intron_variant |
| | | | | | | | | 9: 70691635-70691635 | A | intron_variant |
| | | | | | | | | 9: 70691635-70691635 | A | intron_variant |
| | | | | | | | | 9: 70691635-70691635 | A | intron_variant |
| | | | | | | | | 9: 70691635-70691635 | A | intron_variant |
| | | | | | | | | 9: 70691635-70691635 | A | intron_variant |
| 19 | rs10403114 | 49200507 | G | 0.2929 | 0.3902 | A | 0.05119 | 19: 49200507-49200507 | G | intron_variant |
| | | | | | | | | 19: 49200507-49200507 | G | intron_variant |
| | | | | | | | | 19: 49200507-49200507 | G | intron_variant |
| | | | | | | | | 19: 49200507-49200507 | G | intron_variant |
| | | | | | | | | 19: 49200507-49200507 | G | intron_variant |

| CHR | SNP | BP | IMPACT | Gene | Feature_type | Feature | BIOTYPE | HGVSc |
|---|---|---|---|---|---|---|---|---|
| 13 | rs6650469 | 37793812 | MODIFIER | 7223 | Transcript | NM_016179.2 | protein_coding | NM_016179.2: c.-27−10452N>A |
| | | | MODIFIER | 7223 | Transcript | NM_003306.1 | protein_coding | NM_003306.1: c.-27−10452N>A |
| | | | MODIFIER | 7223 | Transcript | NM_001135958.1 | protein_coding | NM_001135958.1: c.-27−10452N>A |
| | | | MODIFIER | 7223 | Transcript | NM_001135955.1 | protein_coding | NM_001135955.1: c.-27−10452N>A |

TABLE 4-continued

Frequency distribution and significance of Transient Receptor Potential (TRP) nsSNPs in CFS/ME patients and non-fatigued controls in rank order of significance.

| | | | | | | | |
|---|---|---|---|---|---|---|---|
| | | | MODIFIER | 7223 Transcript | NM_001135956.1 | protein_coding | NM_001135956.1: c.-27-10452N>A |
| | | | MODIFIER | 7223 Transcript | NM_001135957.1 | protein_coding | NM_001135957.1: c.-27-10452N>A |
| 13 | rs655207 | 37793875 | MODIFIER | 7223 Transcript | NM_016179.2 | protein_coding | NM_016179.2: c.-27-10515N>A |
| | | | MODIFIER | 7223 Transcript | NM_003306.1 | protein_coding | NM_003306.1: c.-27-10515N>A |
| | | | MODIFIER | 7223 Transcript | NM_001135958.1 | protein_coding | NM_001135958.1: c.-27-10515N>A |
| | | | MODIFIER | 7223 Transcript | NM_001135955.1 | protein_coding | NM_001135955.1: c.-27-10515N>A |
| | | | MODIFIER | 7223 Transcript | NM_001135956.1 | protein_coding | NM_001135956.1: c.-27-10515N>A |
| | | | MODIFIER | 7223 Transcript | NM_001135957.1 | protein_coding | NM_001135957.1: c.-27-10515N>A |
| 8 | rs4738202 | 72028626 | MODIFIER | 100132891 Transcript | NR_033652.1 | lncRNA | NR_033652.1: n.1029-23913N>G |
| | | | MODIFIER | 100132891 Transcript | NR_033651.1 | lncRNA | NR_033651.1: n.434-23913N>G |
| | | | MODIFIER | 8989 Transcript | NM_007332.2 | protein_coding | NM_007332.2: c.2937+1275N>C |
| 9 | rs7865858 | 70589515 | MODIFIER | 80036 Transcript | NM_020952.4 | protein_coding | NM_020952.4: c.2728+1516N>C |
| | | | MODIFIER | 80036 Transcript | NM_001007471.2 | protein_coding | NM_001007471.2: c.3187+1516N>C |
| | | | MODIFIER | 80036 Transcript | NM_206946.3 | protein_coding | NM_206946.3: c.2803+1516N>C |
| | | | MODIFIER | 80036 Transcript | NM_206944.3 | protein_coding | NM_206944.3: c.2698+1516N>C |
| | | | MODIFIER | 80036 Transcript | NM_024971.5 | protein_coding | NM_024971.5: c.2764+1516N>C |
| | | | MODIFIER | 80036 Transcript | NM_206947.3 | protein_coding | NM_206947.3: c.2773+1516N>C |
| | | | MODIFIER | 80036 Transcript | XM_005252218.2 | protein_coding | XM_005252218.2: c.3268+1516N>C |
| | | | MODIFIER | 80036 Transcript | NM_206945.3 | protein_coding | NM_206945.3: c.2734+1516N>C |
| | | | MODIFIER | — RegulatoryFeature | ENSR00001471087 | promoter_flanking_region | — |
| 8 | rs2383844 | 72049017 | MODIFIER | 100132891 Transcript | NR_033652.1 | lncRNA | NR_033652.1: n.1029-3522N>A |
| | | | MODIFIER | 100132891 Transcript | NR_033651.1 | lncRNA | NR_033651.1: n.434-3522N>A |
| | | | MODIFIER | 8989 Transcript | NM_007332.2 | protein_coding | NM_007332.2: c.1905+1761N>T |
| 9 | rs1504401 | 71302037 | MODIFIER | 80036 Transcript | XM_005252218.2 | protein_coding | XM_005252218.2: c.183+144616N>G |
| 9 | rs10115622 | 70691635 | MODIFIER | 80036 Transcript | NM_020952.4 | protein_coding | NM_020952.4: c.814-10057N>T |
| | | | MODIFIER | 80036 Transcript | NM_001007471.2 | protein_coding | NM_001007471.2: c.1273-10057N>T |
| | | | MODIFIER | 80036 Transcript | NM_206946.3 | protein_coding | NM_206946.3: c.889-10057N>T |
| | | | MODIFIER | 80036 Transcript | NM_206944.3 | protein_coding | NM_206944.3: c.814-10057N>T |
| | | | MODIFIER | 80036 Transcript | NM_024971.5 | protein_coding | NM_024971.5: c.814-10057N>T |
| | | | MODIFIER | 80036 Transcript | NM_206947.3 | protein_coding | NM_206947.3: c.889-10057N>T |
| | | | MODIFIER | 80036 Transcript | XM_005252218.2 | protein_coding | XM_005252218.2: c.1354-10057N>T |
| | | | MODIFIER | 80036 Transcript | NM_206945.3 | protein_coding | NM_206945.3: c.814-10057N>T |
| 19 | rs10403114 | 49200507 | MODIFIER | 54795 Transcript | XM_005259017.1 | protein_coding | XM_005259017.1: c.1491+75N>G |
| | | | MODIFIER | 54795 Transcript | NM_001195227.1 | protein_coding | NM_001195227.1: c.2343+75N>G |
| | | | MODIFIER | 54795 Transcript | XM_005259018.1 | protein_coding | XM_005259018.1: c.1170+75N>G |
| | | | MODIFIER | 54795 Transcript | XM_006723249.1 | protein_coding | XM_006723249.1: c.2523+75N>G |
| | | | MODIFIER | 54795 Transcript | NM_017636.3 | protein_coding | NM_017636.3: c.2778+75N>G |

TABLE 5

Frequency distribution and significance of acetylcholine receptor (AchR) nsSNPs in CFS/ME patients and non-fatigued controls in rank order of significance.

| CHR | SNP | BP | A1 | F_A | F_U | A2 | P | Location | Allele | Consequence |
|---|---|---|---|---|---|---|---|---|---|---|
| 3 | rs4463655 | 239820994 | T | 0.3077 | 0.4671 | C | 0.002803 | 1: 239820994-239820994 | C | intron_variant |
|   |   |   |   |   |   |   |   | 1: 239820994-239820994 | C | intron_variant |
|   |   |   |   |   |   |   |   | 1: 239820994-239820994 | C | intron_variant |
|   |   |   |   |   |   |   |   | 1: 239820994-239820994 | C | intron_variant |
| 3 | rs589962 | 239826664 | C | 0.2416 | 0.3919 | T | 0.003476 | 1: 239826664-239826664 | C | intron_variant |
|   |   |   |   |   |   |   |   | 1: 239826664-239826664 | C | intron_variant |
|   |   |   |   |   |   |   |   | 1: 239826664-239826664 | C | upstream_gene_variant |
|   |   |   |   |   |   |   |   | 1: 239826664-239826664 | C | intron_variant |
|   |   |   |   |   |   |   |   | 1: 239826664-239826664 | C | intron_variant |
| 3 | rs1072320 | 239819076 | G | 0.3242 | 0.1842 | A | 0.003704 | 1: 239819076-239819076 | G | intron_variant |
|   |   |   |   |   |   |   |   | 1: 239819076-239819076 | G | intron_variant |
|   |   |   |   |   |   |   |   | 1: 239819076-239819076 | G | intron_variant |
|   |   |   |   |   |   |   |   | 1: 239819076-239819076 | G | intron_variant |
|   |   |   |   |   |   |   |   | 1: 239819076-239819076 | G | regulatory_region_variant |
| 3 | rs7543259 | 239815886 | A | 0.3187 | 0.1842 | G | 0.005128 | 1: 239815886-239815886 | A | intron_variant |
|   |   |   |   |   |   |   |   | 1: 239815886-239815886 | A | intron_variant |
|   |   |   |   |   |   |   |   | 1: 239815886-239815886 | A | intron_variant |
|   |   |   |   |   |   |   |   | 1: 239815886-239815886 | A | intron_variant |
|   |   |   |   |   |   |   |   | 1: 239815886-239815886 | A | regulatory_region_variant |
| 3 | rs6661621 | 239821503 | C | 0.3022 | 0.1711 | G | 0.005358 | 1: 239821503-239821503 | C | intron_variant |
|   |   |   |   |   |   |   |   | 1: 239821503-239821503 | C | intron_variant |
|   |   |   |   |   |   |   |   | 1: 239821503-239821503 | C | intron_variant |
|   |   |   |   |   |   |   |   | 1: 239905329-239905329 | C | intron_variant |
| 11 | rs2672211 | 3669048 | C | 0.3736 | 0.2434 | T | 0.0107 | 11: 3669048-3669048 | T | downstream_gene_variant |
|   |   |   |   |   |   |   |   | 11: 3669048-3669048 | T | downstream_gene_variant |
|   |   |   |   |   |   |   |   | 11: 3669048-3669048 | T | intron_variant |
|   |   |   |   |   |   |   |   | 11: 3669048-3669048 | T | intron_variant |
|   |   |   |   |   |   |   |   | 11: 3669048-3669048 | T | downstream_gene_variant |
| 11 | rs2672214 | 3670282 | C | 0.3708 | 0.24 | T | 0.0108 | 11: 3670282-3670282 | T | downstream_gene_variant |
|   |   |   |   |   |   |   |   | 11: 3670282-3670282 | T | downstream_gene_variant |
|   |   |   |   |   |   |   |   | 11: 3670282-3670282 | T | downstream_gene_variant |
|   |   |   |   |   |   |   |   | 11: 3670282-3670282 | T | downstream_gene_variant |
|   |   |   |   |   |   |   |   | 11: 3670282-3670282 | T | intron_variant |
|   |   |   |   |   |   |   |   | 11: 3670282-3670282 | T | intron_variant |
|   |   |   |   |   |   |   |   | 11: 3670282-3670282 | T | downstream_gene_variant |
|   |   |   |   |   |   |   |   | 11: 3670282-3670282 | T | downstream_gene_variant |
| 11 | rs2741868 | 3668953 | T | 0.3693 | 0.24 | A | 0.01185 | 11: 3668953-3668953 | T | downstream_gene_variant |
|   |   |   |   |   |   |   |   | 11: 3668953-3668953 | T | downstream_gene_variant |
|   |   |   |   |   |   |   |   | 11: 3668953-3668953 | T | intron_variant |
|   |   |   |   |   |   |   |   | 11: 3668953-3668953 | T | intron_variant |
|   |   |   |   |   |   |   |   | 11: 3668953-3668953 | T | downstream_gene_variant |
| 11 | rs2741870 | 3668879 | G | 0.3708 | 0.2434 | C | 0.01281 | 11: 3668879-3668879 | G | downstream_gene_variant |
|   |   |   |   |   |   |   |   | 11: 3668879-3668879 | G | downstream_gene_variant |
|   |   |   |   |   |   |   |   | 11: 3668879-3668879 | G | intron_variant |
|   |   |   |   |   |   |   |   | 11: 3668879-3668879 | G | intron_variant |
|   |   |   |   |   |   |   |   | 11: 3668879-3668879 | G | downstream_gene_variant |

| CHR | SNP | BP | IMPACT | Gene | Feature_type | Feature | BIOTYPE | HGVSc |
|---|---|---|---|---|---|---|---|---|
| 3 | rs4463655 | 239820994 | MODIFIER | 1131 | Transcript | XM_005273033.1 | protein_coding | XM_005273033.1: c.-146-6258T>C |
|   |   |   | MODIFIER | 1131 | Transcript | XM_005273032.1 | protein_coding | XM_005273032.1: c.-146-6258T>C |
|   |   |   | MODIFIER | 1131 | Transcript | XM_006711732.1 | protein_coding | XM_006711732.1: c.-19-86439T>C |
|   |   |   | MODIFIER | 1131 | Transcript | NM_000740.2 | protein_coding | NM_000740.2: c.-146-6258T>C |
| 3 | rs589962 | 239826664 | MODIFIER | 1131 | Transcript | XM_005273033.1 | protein_coding | XM_005273033.1: c.-146-588T>C |
|   |   |   | MODIFIER | 1131 | Transcript | XM_005273032.1 | protein_coding | XM_005273032.1: c.-146-588T>C |
|   |   |   | MODIFIER | 1131 | Transcript | XM_005273034.1 | protein_coding | — |
|   |   |   | MODIFIER | 1131 | Transcript | XM_006711732.1 | protein_coding | XM_006711732.1: c.-19-80769T>C |
|   |   |   | MODIFIER | 1131 | Transcript | NM_000740.2 | protein_coding | NM_000740.2: c.-146-588T>C |
| 3 | rs1072320 | 239819076 | MODIFIER | 1131 | Transcript | XM_005273033.1 | protein_coding | XM_005273033.1: c.-146-8176A>G |
|   |   |   | MODIFIER | 1131 | Transcript | XM_005273032.1 | protein_coding | XM_005273032.1: c.-146-8176A>G |
|   |   |   | MODIFIER | 1131 | Transcript | XM_006711732.1 | protein_coding | XM_006711732.1: c.-19-88357A>G |

TABLE 5-continued

Frequency distribution and significance of acetylcholine receptor (AchR) nsSNPs in CFS/ME patients and non-fatigued controls in rank order of significance.

| | | | | | | | | |
|---|---|---|---|---|---|---|---|---|
| | | | MODIFIER | 1131 | Transcript | NM_000740.2 | protein_coding | NM_000740.2: c.-146-8176A>G |
| 3 | rs7543259 | 239815886 | MODIFIER | — | RegulatoryFeature | ENSR00000555822 | CTCF_binding_site | — |
| | | | MODIFIER | 1131 | Transcript | XM_005273033.1 | protein_coding | XM_005273033.1: c.-146-11366G>A |
| | | | MODIFIER | 1131 | Transcript | XM_005273032.1 | protein_coding | XM_005273032.1: c.-146-11366G>A |
| | | | MODIFIER | 1131 | Transcript | XM_006711732.1 | protein_coding | XM_006711732.1: c.-19-91547G>A |
| | | | MODIFIER | 1131 | Transcript | NM_000740.2 | protein_coding | NM_000740.2: c.-146-11366G>A |
| | | | MODIFIER | — | RegulatoryFeature | ENSR00000555821 | promoter_flanking_region | — |
| 3 | rs6661621 | 239821503 | MODIFIER | 1131 | Transcript | XM_005273033.1 | protein_coding | XM_005273033.1: c.-146-5749G>C |
| | | | MODIFIER | 1131 | Transcript | XM_005273032.1 | protein_coding | XM_005273032.1: c.-146-5749G>C |
| | | | MODIFIER | 1131 | Transcript | XM_006711732.1 | protein_coding | XM_006711732.1: c.-19-85930G>C |
| | | | MODIFIER | 1131 | Transcript | NM_000740.2 | protein_coding | NM_000740.2: c.-146-5749G>C |
| | | | MODIFIER | 1131 | Transcript | XM_005273033.1 | protein_coding | XM_005273033.1: c.-19-2104G>C |
| 11 | rs2672211 | 3669048 | MODIFIER | 417 | Transcript | XM_005252933.2 | protein_coding | — |
| | | | MODIFIER | 417 | Transcript | NM_004314.2 | protein_coding | — |
| | | | MODIFIER | 57053 | Transcript | NM_020402.2 | protein_coding | NM_020402.2: c.362+148G>A |
| | | | MODIFIER | 417 | Transcript | XM_006718236.1 | protein_coding | XM_006718236.1: c.886+7635C>T |
| | | | MODIFIER | 417 | Transcript | XM_006718237.1 | protein_coding | — |
| 11 | rs2672214 | 3670282 | MODIFIER | 4928 | Transcript | XM_006718241.1 | protein_coding | — |
| | | | MODIFIER | 4928 | Transcript | XM_006718242.1 | protein_coding | — |
| | | | MODIFIER | 4928 | Transcript | NM_016320.4 | protein_coding | — |
| | | | MODIFIER | 4928 | Transcript | XM_006718240.1 | protein_coding | — |
| | | | MODIFIER | 417 | Transcript | XM_006718236.1 | protein_coding | XM_006718236.1: c.886+8869C>T |
| | | | MODIFIER | 57053 | Transcript | NM_020402.2 | protein_coding | NM_020402.2: c.62-341G>A |
| | | | MODIFIER | 4928 | Transcript | XM_005252950.1 | protein_coding | — |
| | | | MODIFIER | 4928 | Transcript | NM_139132.3 | protein_coding | — |
| 11 | rs2741868 | 3668953 | MODIFIER | 417 | Transcript | XM_005252933.2 | protein_coding | — |
| | | | MODIFIER | 417 | Transcript | NM_004314.2 | protein_coding | — |
| | | | MODIFIER | 57053 | Transcript | NM_020402.2 | protein_coding | NM_020402.2: c.362+243T>A |
| | | | MODIFIER | 417 | Transcript | XM_006718236.1 | protein_coding | XM_006718236.1: c.886+7540A>T |
| | | | MODIFIER | 417 | Transcript | XM_006718237.1 | protein_coding | — |
| 11 | rs2741870 | 3668879 | MODIFIER | 417 | Transcript | XM_005252933.2 | protein_coding | — |
| | | | MODIFIER | 417 | Transcript | NM_004314.2 | protein_coding | — |
| | | | MODIFIER | 57053 | Transcript | NM_020402.2 | protein_coding | NM_020402.2: c.362+317G>C |
| | | | MODIFIER | 417 | Transcript | XM_006718236.1 | protein_coding | XM_006718236.1: c.886+7466C>G |
| | | | MODIFIER | 417 | Transcript | XM_006718237.1 | protein_coding | — |

TABLE 6

Frequency distribution and significance of acetylcholine receptor (AChR) nsSNPs in CFS/ME patients and non-fatigued controls in rank order of significance.

| CHR | SNP | BP | A1 | F_A | F_U | A2 | P | Location | Allele | Consequence |
|---|---|---|---|---|---|---|---|---|---|---|
| 3 | rs7520974 | 239903960 | G | 0.4205 | 0.5533 | A | 0.0167 | 1: 239903960-239903960 | A | intron_variant |
| | | | | | | | | 1: 239903960-239903960 | A | intron_variant |
| | | | | | | | | 1: 239903960-239903960 | A | intron_variant |
| | | | | | | | | 1: 239903960-239903960 | A | intron_variant |
| | | | | | | | | 1: 239903960-239903960 | A | upstream_gene_variant |
| | | | | | | | | 1: 239903960-239903960 | A | intron_variant |
| 3 | rs6669810 | 239905329 | G | 0.4213 | 0.5467 | C | 0.02361 | 1: 239905329-239905329 | C | intron_variant |
| | | | | | | | | 1: 239905329-239905329 | C | intron_variant |
| | | | | | | | | 1: 239905329-239905329 | C | intron_variant |
| | | | | | | | | 1: 239905329-239905329 | C | intron_variant |
| 3 | rs7180002 | 78581651 | T | 0.3846 | 0.2763 | A | 0.03682 | 15: 78581651-78581651 | T | intron_variant |
| | | | | | | | | 15: 78581651-78581651 | T | intron_variant |

TABLE 6-continued

Frequency distribution and significance of acetylcholine receptor (AChR) nsSNPs
in CFS/ME patients and non-fatigued controls in rank order of significance.

| | | | | | | | | | | |
|---|---|---|---|---|---|---|---|---|---|---|
| 3 | rs6429157 | 239818343 | G | 0.522 | 0.4079 | A | 0.375 | 1: 239818343-239818343 | G | intron_variant |
| | | | | | | | | 1: 239818343-239818343 | G | intron_variant |
| | | | | | | | | 1: 239818343-239818343 | G | intron_variant |
| | | | | | | | | 1: 239818343-239818343 | G | intron_variant |
| 8 | rs55828312 | 42734459 | G | 0.2386 | 0.1513 | A | 0.04789 | 8: 42734459-42734459 | G | intron_variant |
| 3 | rs12036141 | 239902696 | A | 0.4121 | 0.3092 | G | 0.05184 | 1: 239902696-239902696 | A | intron_variant |
| | | | | | | | | 1: 239902696-239902696 | A | intron_variant |
| | | | | | | | | 1: 239902696-239902696 | A | intron_variant |
| | | | | | | | | 1: 239902696-239902696 | A | upstream_gene_variant |
| | | | | | | | | 1: 239902696-239902696 | A | intron_variant |
| 3 | rs6429147 | 239631494 | C | 0.4444 | 0.34 | G | 0.05349 | 1: 239631494-239631494 | G | intron_variant |
| | | | | | | | | 1: 239631494-239631494 | G | intron_variant |
| | | | | | | | | 1: 239631494-239631494 | G | intron_variant |
| | | | | | | | | 1: 239631494-239631494 | G | intron_variant |
| 8 | rs16891561 | 42724596 | T | 0.2472 | 0.1597 | C | 0.05454 | 8: 42724596-42724596 | C | intron_variant |

| CHR | SNP | BP | IMPACT | Gene | Feature_type | Feature | BIOTYPE | HGVSc |
|---|---|---|---|---|---|---|---|---|
| 3 | rs7520974 | 239903960 | MODIFIER | 1131 | Transcript | XM_005273033.1 | protein_coding | XM_005273033.1: c.-19-3473G>A |
| | | | MODIFIER | 1131 | Transcript | XM_005273032.1 | protein_coding | XM_005273032.1: c.-19-3473G>A |
| | | | MODIFIER | 1131 | Transcript | XM_005273034.1 | protein_coding | XM_005273034.1: c.-19-3473G>A |
| | | | MODIFIER | 1131 | Transcript | XM_006711732.1 | protein_coding | XM_006711732.1: c.-19-3473G>A |
| | | | MODIFIER | 100873984 | Transcript | NR_046582.1 | lncRNA | — |
| | | | MODIFIER | 1131 | Transcript | NM_000740.2 | protein_coding | NM_000740.2: c.-19-3473G>A |
| 3 | rs6669810 | 239905329 | MODIFIER | 1131 | Transcript | XM_005273033.1 | protein_coding | XM_005273033.1: c.-19-2104G>C |
| | | | MODIFIER | 1131 | Transcript | XM_005273034.1 | protein_coding | XM_005273032.1: c.-19-2104G>C |
| | | | MODIFIER | 1131 | Transcript | XM_006711732.1 | protein_coding | XM_006711732.1: c.-19-2104G>C |
| | | | MODIFIER | 1131 | Transcript | NM_000740.2 | protein_coding | NM_000740.2: c.-19-2104G>C |
| 3 | rs7180002 | 78581651 | MODIFIER | 1138 | Transcript | NM_000745.3 | protein_coding | NM_000745.3: c.258+689A>T |
| | | | MODIFIER | 1138 | Transcript | XM_005254142.1 | protein_coding | XM_005254142.1: c.258+689A>T |
| 3 | rs6429157 | 239818343 | MODIFIER | 1131 | Transcript | XM_005273033.1 | protein_coding | XM_005273033.1: c.-146-8909A>G |
| | | | MODIFIER | 1131 | Transcript | XM_005273032.1 | protein_coding | XM_005273032.1: c.-146-8909A>G |
| | | | MODIFIER | 1131 | Transcript | XM_006711732.1 | protein_coding | XM_006711732.1: c.-146-8909A>G |
| | | | MODIFIER | 1131 | Transcript | NM_000740.2 | protein_coding | NM_000740.2: c.-146-8909A>G |
| 8 | rs55828312 | 42734459 | MODIFIER | 1142 | Transcript | NM_000749.3 | protein_coding | NM_000749.3: c.1242+1910A>G |
| 3 | rs12036141 | 239902696 | MODIFIER | 1131 | Transcript | XM_005273033.1 | protein_coding | XM_005273033.1: c.-19-3473G>A |
| | | | MODIFIER | 1131 | Transcript | XM_005273032.1 | protein_coding | XM_005273032.1: c.-19-3473G>A |
| | | | MODIFIER | 1131 | Transcript | XM_005273034.1 | protein_coding | XM_005273034.1: c.-19-3473G>A |
| | | | MODIFIER | 1131 | Transcript | XM_006711732.1 | protein_coding | XM_006711732.1: c.-19-473G>A |
| | | | MODIFIER | 100873984 | Transcript | NR_046582.1 | lncRNA | — |
| | | | MODIFIER | 1131 | Transcript | NM_000740.2 | protein_coding | NM_000740.2: c.-19-4737G>A |
| 3 | rs6429147 | 239631494 | MODIFIER | 1131 | Transcript | XM_005273033.1 | protein_coding | XM_005273033.1: c.-249-46692C>G |
| | | | MODIFIER | 1131 | Transcript | XM_005273032.1 | protein_coding | XM_005273032.1: c.-312-730C>G |
| | | | MODIFIER | 1131 | Transcript | XM_006711732.1 | protein_coding | XM_006711732.1: c.-185-730C>G |
| | | | MODIFIER | 1131 | Transcript | NM_000740.2 | protein_coding | NM_000740.2: c.-312-730C>G |
| 8 | rs16891561 | 42724596 | MODIFIER | 1142 | Transcript | NM_000749.3 | protein_coding | NM_000749.3: c.250-5998T>C |

Results

Participants

There were 115 CFS patients (age=48.68±1.06 years), of which 84 (73.04%) were females and 31 (26.96%) were males. There were 90 non-fatigued controls (age=46.48±1.22 years) comprising 59 (65.56%) females and 31 (34.44%) males. All participants in both groups were of European decent and were residents of Australia at the time of blood collection.

Of 81 SNPs identified in TRP ion channel and AChR genes, 29 nsSNPs were located at intron variants, as well as regulatory region variants, and up-stream and down-stream variants. A total of 12 nsSNPs for TRP ion channel genes (TRPA1, TRPC4 and TRPM3 and TRPM4) were identified in the CPS/ME group. Specifically, 7 nsSNPs featured for TRPM3, 2 nsSNPs for TRPC4, 2 nsSNPs for TRPA1 and 1 nsSNP for TRPM4. A total of 17 nsSNPs for AChR were found, where 10 nsSNPs were identified for mAChM3, 4 nsSNPs for nAChα10, 1 nsSNP for nAChα5 and 2 nsSNPs for nAChα2. Tables 3-4 and Tables 5-6 represent the nsSNPs for TRP ion channel and AChR genes, respectively.

The predominant gene where these nsSNPs for TRP ion channels were reported was gene 80036 as it had 51 significant reportable events (66%) from a total of 77 events. The remaining nsSNPs for TRP ion channels were found in genes 7223, 101927086 and 54795 where each reported 12 (15%), 2 (2%) and 5 (6%) events, respectively.

Analysis of the nsSNPs for AChRs found the gene 1131 had 44 reportable (59%) events from a total number of 74 events. The remaining nsSNPs for AChR genes were found in genes 417, 4928, 57053, 100873984, 1138 and 1142 where each reported 12 (16%), 6 (8%), 4 (5%), 2 (3%), 2 (3%) and 2 (3%) events, respectively.

Discussion

This is the first study to report the presence of nsSNP variations in TRP ion channel genes and AChR genes in CFS/ME patients. Collectively, 29 nsSNPs were identified in genes for TRP ion channels and AChRs. A total of 12 nsSNPs were identified for TRP ion channel genes (TRPA1, TRPC4, TRPM3 and TRPM4) and 17 nsSNPs were identified for AChR genes (10 nsSNPs for mAChM3, 4 nsSNPs for nAchα10, 1 nsSNP for nAchα5 and 2 nsSNPs for nAchα2).

There is limited information available on the role of nsSNPs in these AChR and TRP ion channels in disease. The inventors now report nsSNPs located in intron variants, regulatory region variants and up-stream and down-stream variants of the TRP ion channel and AChR genes in their patient cohort. These variants are likely to be critical in contributing to perturbations of TRP ion channel and AChR function mediated through altered calcium and ACh signalling and manifested as physiological system compromise. Therefore, the critical role of AChRs and TRP ion channels in $Ca^{2+}$ cell signalling suggests these nsSNPs may contribute to the clinical manifestation of CFS/ME.

Identification of the genes containing these nsSNPs for both TRP ion channels and AChRs revealed important roles in calcium cell signalling as well as acetylcholine function with additional roles in adenylate cyclase inhibition respectively. Importantly, genes 80036 and 1131 which accounted for the majority of nsSNPs influence these functions. For example, gene 80036 is associated with calcium signalling mechanisms and calcium store depletion via different isoforms which have been identified through alternative splicing [33d]. Gene 1131 codes for muscarinic cholinergic receptors which demonstrate features including binding of acetylcholine as well as adenylate cyclase inhibition, phosphoinositide degeneration, and potassium channel mediation. As noted above muscarinic receptors mediate acetylcholine activity in the central and peripheral nervous systems. The muscarinic cholinergic receptor 3 (mAChRM3), controls smooth muscle contraction and glandular secretion [34d].

The significance of the inventors' findings is supported by others who suggest that alternate splicing in the coding and also in the non-coding sequences may have significant unexpected outcomes on the splicing mechanism of the gene transcripts [10d, 11d]. Splicing genetic variants found in the exons and deep intronic variants, as well as down and up-stream variants have a role in alternative splicing mechanisms resulting in diverse protein isoforms. Such altered protein isoform expression may be an important contributing factor affecting changes in protein function. Incidentally, the human gene has the largest average number of mRNA isoforms per gene [35d] with an average of seven mRNA isoforms per gene [36d, 37d]. Furthermore, the regulatory elements in the intron sequences as well as the assembly of the spliceosome add a significant level of complexity to the splicing mechanism for the correct coding of a protein sequence. Enhancers and silencers that are located either in the exons or introns are integral in recognition of the correct exon sequence [38d]. Additionally, others have shown introns are able to generate active spliceosomes, giving rise to alternative splicing events [39d, 40d]. Importantly, the inventors' data show that the greatest proportion of intron variants as well as regulatory region variants occur in the nsSNPs in TRPM3 and mAChM3 genes and may alter the gene transcripts.

Research to date highlights the importance of such variants in affecting gene transcripts by causing alternative splicing resulting in anomalies in mRNA and translation products. Alternative splicing in TKPM3 and mAChM3 genes may result in aberrant $Ca^{2+}$ signalling because of the known secondary pathways involving $Ca^{2+}$ which mediate effects for both TRPM ion channels and AChRs. Changes in AChRs and TRP ion channel signalling may have important physiological implications for CFS/ME patients as these TRP ion channels and AChRs are located on nearly all cells in the body. The predominance of CNS symptoms in CFS/ME may result in part from TRPM3 being substantially distributed in the CNS [41d]. Calcium metabolism and signalling in the context of TRPC ion channel as well as muscarinic receptor function is vital for the function of the CNS. Memory, attention, sensory acuity, emotion, pain and motor control [42d, 43d] are critical functions localised throughout a number of regions in the brain [44d]. These CNS functions have been reported to be significantly impaired in CFS/ME patients [45d-47d]. TRPM3 ion channels also function in the roles of heat detection, nociception and transmission of pain [48d, 49d]. Dysregulation in thermoregulatory responses as well as central and peripheral pain have also been reported in CFS/ME patients [50d], suggesting the nsSNPs reported in this study may contribute to the potential CNS impairments in these patients.

Interestingly, TRPM3 is the only TRP ion channel discovered so far to have a second embedded channel or Omega pore [51d]. This pore is characterised to have features distinguishing it from the TRPM3 main channel, such as activation and current flow characteristics and permeability to $Na^+$ and $K^+$ rather than $Ca^{2+}$, which may be relevant in signalling. For example, it appears the Omega channel acts to potentiate the signal mediated via the main TRPM3 channel, thus giving TRPM3 unique qualities of magnified signalling, particularly nociception and pain transmission. As there have been a number of previous findings reporting significant changes in inflammatory cytokines from CFS/ME patients [52d-54d] the question is asked if an inflammatory mediator may act on the Omega pore to exert an effect on pore opening and promulgation of a nociceptive signal [55d]. The possibility therefore exists that the reportable nsSNPs for TRPM3 in conjunction with this omega pore may potentiate and amplify pathological signalling of TRPM3 when stimulated by inflammatory or other agents.

mAChM3 receptors have been documented in the gastrointestinal tract and are controlled in part by the parasympathetic nervous system, through the vagus nerve [56d]. ACh has been shown to mediate gut motility via the nerve fibres that make synapses within the gut wall. $Ca^{2+}$ mediated channel perturbations through excessive influx or reduction of $Ca^{2+}$ flow could cause significant changes in GI motility. It is plausible that nsSNPs' alternative splicing in intron and regulatory regions of mAChM3 genes and TRPC4 genes may cause irregular gastrointestinal motility through activating smooth muscle depolarization [57d]. Additionally, TRPC4 couples to mAChRM3 in the intestine, activating smooth muscle depolarization, inflow of $Ca^{2+}$ and smooth muscle contraction [57d]. TRPC4 may be simultaneously regulated by G protein-coupled receptors (GPCRs) [58d]. Enhanced cholinergic-mediated increase in the pro-inflammatory cytokines IL-6 and IL-8 has also been reported in patients with irritable bowel syndrome [59d]. CFS/ME patients report intestinal dysfunction or irritable bowel syndrome including diarrhoea [14d, 30d], while other researchers have reported elevated IL-6 and IL-8 in this patient group [60d].

nsSNPs of intron or regulatory regions of mAChRM3 receptors may affect metabolic and cardiac responses. mAChRM3 receptors, along with TRPM3 ion channels, play a role in regulating insulin and glucagon secretion [61d, 62d]. Muscarinic acetylcholine receptors (mAChRs) expressed by pancreatic β-cells function to maintain homeostasis of whole body glucose [61d]. nsSNPs documented in mAChM3R genes may mediate changes in $Ca^{2+}$ channels thus influencing pancreatic β-cell function and impact glucose metabolism in CFS/ME patients [63d]. Cardiac function via mAChRM3 parasympathetic control is well established [37d] and pacemaker slowing effects of muscarinic agonists are augmented by $Ca^{2+}$ transient inhibition, resulting in altered cardio-regulatory mechanisms. Importantly the nsSNPs (intron variants or regulatory regions) found in mAChM3 may alter intracellular $Ca^{2+}$ concentrations, resulting in changes in insulin response to glucose or other stimuli as well as contributing to orthostatic cardiovascular effects. Both these physiological disturbances are reported in CFS/ME patients [15d, 23d, 27d, 29d, 31d].

TRPA1 ion channels are reported on astrocytes of the CNS and contribute to calcium uptake and regulation of astrocytes [64d-67d]. TRPA1 ion channels also initiate acute headache as well as mediating pain and migraine in fibromyalgia patients [68d]. Both symptoms are identified in CFS/ME patients, suggesting nsSNPs for TRPA1 may play a role in the pathology of this illness.

Conclusion

This Example shows a high proportion of nsSNPs (i.e. non-synonymous SNPs) in intronic variants and regulatory variants for TRP ion channels and AChR genes in the inventors' CFS/ME patient cohort. Silent alternative splicing has been suggested to be involved in disease phenotypes, e.g. through exon skipping, alternative splice isoforms of the gene transcript or alternate spliceosomes. The inventors' results suggest such gene variants may result in phenotype anomalies in TRP ion channel expression and AChR expression leading to altered calcium and acetylcholine regulation in CFS/ME and provide a possible rationale for the development of, or predisposition to this debilitating illness.

Example 4: Genotype Frequencies of TRPM3 Ion Channels and mAChM3 Receptors Gene Polymorphisms in CFS/ME Patients In thee Examples above the inventors describe SNPs in genes for TRP ion channels and AChRs, which have important roles in calcium ($Ca^{2+}$) and acetylcholine (ACh) signalling. The inventors now report from this same cohort of patients additional data showing the prevalence of both melastatin TRP (TRPM3) ion channel and muscarinic acetylcholine receptor (mAChM3R) SNP genotypes in CFS/ME patients.

Genomic DNA extraction and SNP genotyping studies were performed as previously described. The PLINK v1.07 whole genome analysis toolset and IBM® SPSS® Statistics (version 21) was used to determine the genotype frequency between the CFS patients and the nonfatigued controls. A two column $\chi^2$ test was used, where the alpha level of significance was set at a p<0.05 and their consequences can be found in Table 7 for TRPM3 and mAChM3, respectively. Analysis of SNP genotype frequencies in TRPM3 family (rs12682832; rs11142508; rs3763619) and mAChM3R (rs12036141; rs589962; rs1072320; rs7543259; rs7520974; rs726169; rsrs6669810; rsrs6429157) demonstrated high prevalence in this cohort of CFS/ME patients as compared to non-fatigued controls (Table 7).

TABLE 7

Genotype frequencies of TRPM3 and mAChMS gene polymorphisms in CFS patients and nonfatigued controls.

| Gene | Chromosome | RefSNPID | Genotype | CFS (%) | Non fatigued controls (%) | $\chi^2$ | P-VALUE | OR |
| --- | --- | --- | --- | --- | --- | --- | --- | --- |
| mAchM3 | 1 | rs589962 | TT | 52 (65%) | 28 (35%) | 6.839 | 0.009 | 2.286 |
| mAchM3 | 1 | rs1072320 | AG | 47 (66.2%) | 24 (33.8%) | 6.825 | 9.009 | 2.314 |
| mAchM3 | 1 | rs7543259 | AG | 46 (65.7%) | 24 (34.3%) | 6.122 | 0.013 | 2.215 |
| mAchM3 | 1 | rs7520974 | AA | 30 (68.2%) | 14 (31.8%) | 4.515 | 0.034 | 2.178 |
| mAchM3 | 1 | rs726169 | AA | 49 (67.1%) | 24 (32.9%) | 8.345 | 0.004 | 2.528 |
| mAchM3 | 1 | rs6669810 | CC | 29 (67.4%) | 14 (32.6%) | 3.917 | 0.048 | 2.071 |
| mAchM3 | 1 | rs6429157 | GG | 25 (71.4%) | 10 (28.6%) | 5.123 | 0.024 | 2.500 |
| mAchM3 | 1 | rs12036141 | AA | 15 (75%) | 5 (25%) | 3.854 | 0.050 | 2.803 |
| TRPM3 | 9 | rs12682832 | AA | 24 (75%) | 8 (25%) | 5.501 | 0.019 | 2.703 |
| TRPM3 | 9 | rs11142508 | CC | 25 (73.5%) | 9 (26.5%) | 5.029 | 0.025 | 2.500 |
| TRPM3 | 9 | rs3763619 | AA | 25 (71.4%) | 10 (28.6%) | 4.028 | 0.045 | 2.222 |

Notes:
Data presented for gene TRPM3 (100 CFS/ME patients and 90 controls) and muscarinic M3 (91 CFS patients and 76 controls), chromosome location (CHR), reference SNP identification (Ref SNP ID), genotype, number and percentage of CFS patients and non-fatigued controls with a genotype, Pearson Chi-Square test was used for genotype frequency (ldf) and p-value for this test was set at a significance of p < 0.05, odds ratio (OR).

mAChRs are involved in autonomic function, particularly parasympathetic and exocrine function, such as in pancreas, exocrine glands and inotropic and chronotropic cardiac regulation. Given AChRs are distributed differentially around the body it is axiomatic that tissues expressing a predominance of AChRs will be affected differentially by SNPs in muscarinic vs nicotinic ACh receptors. Similarly, TRPs are distributed differentially around the body in all tissues. Adding to the complexity is the relative lack of knowledge about interactions between TRP and AChRs in humans. Interestingly, certain muscarinic ACh receptors are antagonists of TRPM3 via e.g. phospholipase C-coupled mAChM1R [21h, 22h]. Given this developing research regarding the interdependence of mAChRs and TRP families, the inventors question whether mAChM3K and TRPM3 SNP genotype combinations in CFS/ME patients contribute to the pathomechanism and phenotypes of this illness.

Even though the distribution of these receptors varies in peripheral blood mononuclear cells, SNP genotypes such as those identified in this patient cohort are likely to contribute to perturbations of TRP ion channel and AChR function mediated through altered calcium and ACh signalling and manifest as physiological system compromise. The critical role of AChRs and TRP ion channels in $Ca^{2+}$ cell signalling suggests further characterisation of TRPM3 and mAChM3R may elucidate perturbations of second messenger signalling in CFS/ME. Moreover changes in structure of these receptors may contribute to potential autoimmune responses. A recent publication by Loebel et al [23h] suggests a possible autoimmune mechanism in a subgroup of CFS patients affecting muscarinic acetylcholine receptors (mAChR) and β adrenergic receptors (βAdR). However the evidence for an autoimmune pathology is modest as only a minority (29.5%) of patients expressed antibodies against these receptors. Despite multiple Rituximab infusions only 15 of 25 patients responded. However the possibility of some autoimmune mechanisms contributing to pathomechanisms of CFS/ME could be a response to altered structure of SNP affected receptors or ion channels.

Example 5: Natural Killer Cytotoxicity and SNPs in TRP Ion Channel and AChR Genes of Isolated Natural Killer Cells in ME/CFS Patients NK cells are granular lymphocytes found in peripheral blood, bone marrow, spleen and lymph nodes [1j-4j]. In peripheral blood, NK cells comprise 15% of lymphocytes and can be grouped into four subtypes according to the surface expression and density of CD56 (neural cell adhesion molecule) and CD16 [Fey III receptor, the low-affinity receptor for immunoglobulin G (IgG)], [1j-3j, 5j, 6j]. These phenotypes include $CD56^{bright}CD16^{-/dim}$, $CD56^{dim}CD16^{bright}$, $CD56^{dim}CD16^{-}$, $CD56^{-}CD16^{bright}$ [1j-3j]. Approximately 90% of NK cells in peripheral blood are $CD56^{dim}CD16^{bright}$ and $CD56^{bright}$ comprise approximately 10% [2j-4j, 7j]. NK cell cytotoxic activity requires a number of regulated processes to ensure apoptosis of the target cell [8j].

Though little is known about calcium signaling in NK cells, it has been observed that the granule-dependent pathway of apoptosis is calcium dependent whereas the death-receptor pathway is not [9j, 10j]. In this instance lytic protein transport, exocytosis and fusion have clearly shown calcium dependence [11j-13j]. Calcium is also required for the reorientation of microtubules and actin skeleton as well as activation of cytokine gene transcription [13j]. Moreover, studies have demonstrated the relationship between calcium mobilisation and the abrogation of degranulation in NK phospholipase C (PLC)-γ2-deficient cells [13j-15j].

Transient receptor potential (TRP) ion channels are expressed on almost all cells and have a significant effect on physiological functions [16j]. Dysregulation in TRPs has been associated with pathological conditions and diseases [17j-21j]. TRP ion channels are activated in the presence of irritants, inflammatory products, and xenobiotic toxins. TRP ion channels have an important role in $Ca^{2+}$ signaling.

Acetylcholine (ACh) binds to two membrane proteins, namely the muscarinic (mAChR) and nicotinic receptors (nAChR) of which there are multiple isoforms. ACh performs non-neuronal functions, termed the non-neuronal cholinergic system (NNCS), where ACh performs endocrine and paracrine functions of tissue located on smooth muscle, β pancreatic cells, glial cells, lymphocytes, ocular lens cells and brain vascular endothelium [17j-26j] that is mediated through $Ca^{2+}$ signaling. Acetylcholine receptors (AChRs) transmit activation signals in a variety of human tissues including skeletal and smooth muscle, all preganglionic autonomic nerve fibers, post ganglionic autonomic parasympathetic nerves as well as in many locations throughout the central nervous system (CNS) [27j-29j].

CFS/ME is characterized by significant impairment in physical activity and debilitating fatigue accompanied by impairment in memory, cognition and concentration, enhanced experience of pain as well as dysregulation of the gastrointestinal, cardiovascular and immune systems [30j-42j]. Importantly, NK cell dysfunction, in particular reduced NK cell cytotoxic activity is a consistent finding in CFS/ME patients [32j-36j, 39j, 43j]. The inventors have described above SNPs in TRP ion channel genes and AChR genes, namely for TRP ion channels TRPM3, TRPA1, TRPC4, the muscarinic receptor mAChRM3 and the nicotinic alpha receptors nAChR alpha 10, alpha 5 and alpha 2 in peripheral blood mononuclear cells from CFS/ME patients. These SNP anomalies in genes for TRP ion channels and AChRs may produce altered receptor proteins, potentially changing TRP ion channel and AChR structures and also functions.

The aim of the present study was to determine NK cytotoxic activity as well as whether SNPs and their genotypes were present in TRP ion channel and AChR genes in isolated NK cells from CFS/ME patients.

Method

Subjects

CFS patients were defined in accordance with the 1994 CDC criteria for CFS [45j]. A total of 39 CFS/ME patients and 30 non-fatigued controls were recruited for this study with no medical history or symptoms of prolonged fatigue or illness of any kind [45j].

Sample Preparation and Measurements

A volume of 80 ml of blood was collected from the antecubital vein of participants into lithium heparinized and EDTA collection tubes between 9 am and 11 am. Routine blood samples were analyzed within 6 hours of collection and analyzed for red blood cell counts, lymphocytes, granulocytes and monocytes using an automated cell counter (ACT Differential Analyzer, Beckman Coulter, Miami, Fla.). Refer to Table 8.

TABLE 8

Participant Characteristics for Chronic Fatigue Syndrome and Non Fatigued Controls

| Variable | CFS n = 39 | Non-fatigued controls n = 30 | p-value |
|---|---|---|---|
| Gender (% F) | 71.80% | 23.70% | 0.228 |
| Mean Age (years) | 51.69 ± 2.00 | 47.60 ± 2.39 | 0.191 |
| Hemoglobin (g/L) | 136.05 ± 2.07 | 138.20 ± 2.24 | 0.375 |
| Hematocrit (%) | 0.41 ± 0.01 | 0.41 ± 0.01 | 0.702 |
| Red Cell Count (×$10^{12}$/L) | 4.54 ± 0.07 | 4 58 ± 0.08 | 0.697 |
| Mean Corpuscular Volume (fL) | 89.97 ± 0.55 | 90.07 ± 0.70 | 0.917 |
| White Cell Count (×$10^9$/L) | 5.95 ± 0.26 | 6.38 ± 0.31 | 0.747 |
| Neutrophils ×$10^9$/L) | 3.53 ± 0.19 | 3.96 ± 0.26 | 0.173 |
| Lymphocytes (×$10^9$/L) | 1,91 ± 0.10 | 1.97 ± 0.08 | 0.64 |
| Monocytes(×$10^9$/L) | 0 34 ± 0.02 | 0.32 ± 0.02 | 0.41 |
| Eosinophils (×$10^9$/L) | 0.33 ± 0.18 | 0.37 ± 0.23 | 0.892 |
| Basophils (×$10^9$/L) | 0.20 ± 0.18 | 0.02 ± 0.00 | 0.385 |
| Platelets (×$10^9$/L) | 262.56 ± 8.41 | 256.79 ± 9.58 | 0.653 |

NK Cell Isolation

Peripheral blood mononuclear cells were isolated from 20 mL of whole blood for NK cells using Ficoll-Hypaque (GE Healthcare, Uppsala, Sweden). Enrichment of NK was performed using NK Isolation Kit (Miltenyi Biotech, Bergisch Gladbacb, Germany) according to the manufacturer's instructions. Enriched NK purity was examined on the FACS Calibur flow cytometer (BD Bioscience, San Diego, Calif.) after staining with CD16/CD56 as previously described [35j] (BD Bioscience, San Diego, Calif.). Flow cytometry and hemoeytometer assessment were used to determine the purity of the NK cells isolated. The recovery of isolated cells was calculated based on the observation that NK represent 2% of peripheral blood lymphocytes respectively [46j]. Recovery was expressed as the ratio of percentage of the total number of NK cells isolated to the percentage of cells present in the volume of blood collected. Enriched cells were snap frozen in liquid nitrogen and stored at −80° C. until further assessment.

NK Cell Cytotoxicity

NK cytotoxic activity was conducted as previously described [36j, 39j]. Briefly, following NK lymphocytes isolation using density gradient centrifugation and labelled with 0.4% PKH-26 (Sigma, St Louis, Mo.), NK cells were incubated with K562 cells, for 4 hours at 37° C. in 95% air, 5% $CO_2$ at an effector to target ratio of 25 (NK cells):1 (K562). An E:T ratio of 25:1 has been previously been shown by the inventors and other researchers to be the most optimal ratio for assessing cytotoxic activity [36j, 39j]. NK cell lysis was determined following four hours of NK cells with K562 cells, NK lysis was calculated to determine induced tumor cell death or apoptosis [47j]. Fortessa X-20 flow cytometry (BD Bioscience, San Jose, Calif.), using Annex in V-FITC and 7-AAD reagents (BD Pharmingen, San Diego, Calif.) was employed. NK cytotoxic activity was performed within 2-4 hours upon receipt of all blood samples.

DNA Extraction

A volume of 40 mL was collected into EDTA tubes for SNP analysis. Genomic DNA was extracted from all whole blood samples using the Qiagen DNA blood mini-kit as per manufacturer's instructions (Qiagen). SNP genotyping studies were performed as previously described.

SNP Analysis

A total of 678 SNPs from isolated NK cells were examined for twenty-one mammalian TRP ion channel genes (TRPA1, TRPC1, TRPC2, TRPC3, TRPC4, TRPC6, TRPC7, TRPM1, TRPM2, TRPM3, TRPM4, TRPM5, TRPM6, TRPM7, TRPM8, TRPV1, TRPV2, TRPV3, TRPV4, TRPV5 and TRPV6) and for nine mammalian ACh receptor genes (muscarinic M1, M2, M3, M4, M5, nicotinic alpha 2, 3, 5, 7, 10 and epsilon) and were examined using MassARRAY iPLEX Gold Assay (Sequenom Inc.). Quality and quantity of the DNA extracted was determined by the Nanodrop (Nanodrop), where approximately 2 μg of genomic DNA was used to perform the SNP analysis. SNP analysis was performed as previously described. Briefly, MassARRAY (MALTI-TOF mass spectrometry platform) was employed to discriminate alleles based on single-base extension of an extension primer of known mass that is designed to attach directly next to the SNP site of interest. Custom multiplexed wells were designed in silico using Agena's Assay Design Suite. The designed multiplexes were then built using custom synthesized oligonucleotides that are pooled together for sample processing. The iPLEX Gold chemistry utilized two multiplexed oligo pools for each genotyping well. These were pooled and balanced prior to running against DNA samples. First a multiplexed PCR pool was utilized to generate short amplicons that include all the genomic markers of interest in that particular well. After PCR and clean-up steps were undertaken, a secondary PCR 'extension' step was undertaken utilizing pools of extension primers that were designed to attached directly next to the SNP sites of interest. A termination mix was added to the extension phase which allowed these extension primers to be extended by a single base only. As the molecular weight of the extension primer is known, discrimination of the allele was able to be measured using the peak heights of the unextended primer and this primer plus the possible single-base extension possibilities for the SNP.

TRP Ion Channel and AChR SNP Assays

Primers and extension primers were created for each of the SNPs using the Assay Designer (Sequenom Inc.) according to the manufacturer's instructions. DNA was amplified via polymerase chain reaction (PCR) under the following conditions: 94° C. for 2 minutes, 94° C. for 30 seconds, 56° C. for 30 seconds, and 72° C. for 1 minute. Amplification products were then heated with shrimp alkaline phosphatase at 37° C. for 40 minutes, 85° C. for 5 minutes reaction, and a final incubation at 4° C. Extension primers are optimized to control the signal-to-noise ratio where unextended primers (UEPs) are examined on the spectroCHIP and evaluated in Typer 4.0 to enable the division into low-mass UEP, medium-mass UEP, and high-mass UEP. To perform the iPLEX extension reaction, a mixture containing iPLEX Gold reaction was prepared using iPLEX Gold Buffer Plus, iPLEX termination mix, iPLEX enzyme, and primer mix. The iPLEX reaction was cycled at an initial denaturation of 94° C. for 30 seconds, annealing at 52° C. for 5 minutes, extension at 80° C. for 5 minutes (five cycles of annealing and extension were performed, but the whole reaction was performed in 40 cycles) and extension again at 72° C. for 3 minutes. Resin beads were used to rinse all iPLEX Gold reaction products. Following the iPLEX Gold reaction, MassARRAY was performed using the MassARRAY mass spectrometer, and the data generated were analyzed using the TyperAnalyzer software.

Statistical Analysis

Statistical analysis was performed using SPSS software version 22 [IBM Corp]. The experimental data represented in this study are reported as means plus/minus standard error of the mean (±SEM) while all the clinical data are reported as means plus/minus standard deviation (±SD). Comparative assessments among participants (CFS/ME and non-fatigued controls) were performed with the analysis of variance test (ANOVA) and the criterion for significance was set at $p<0.05$.

The PLINK v 1.07 (http://pngn:mgh.harvard.edu/purcell/plink/) whole genome analysis tool set was used to determine associations between the CFS patients and the non-fatigued control group. A two column $\chi 2$ test was used to examine differences where p value of <0.05 was determined to be significant and the resulting variants and their consequences can be found in Table 9 for TRP and AChR, respectively. Further genotype analysis for differences between CFS and the non-fatigued group was also completed according to a two column $\chi 2$ test with significance of $p<0.05$ and results are presented in Table 10. Analyses were performed at the Australian Genome Research Facility Ltd, The Walter and Eliza Hall Institute, Parkyille, Victoria, Australia.

TABLE 9

Analysis of the frequency, distribution and significance of SNPs in genes for TRP ion channels and AChRs in CFS/ME patients (n = 39_) and non-fatigued controls (n = 30) in rank order of significance

| Gene | CHR | SNP | BP | AL | F_A | F_U | A2 | CHISQ | OR | p- value |
|---|---|---|---|---|---|---|---|---|---|---|
| TRPM8 | 2 | rs17865678 | 2.34E+08 | A | 0.4595 | 0.1667 | G | 12.88 | 4.25 | 0.000332 |
| TRPM8 | 2 | rs11563204 | 2.34E+08 | A | 0.3553 | 0.1167 | G | 10.18 | 4.172 | 0.00142 |
| nAChRβ4 | 15 | rs12441088 | 78635922 | G | 0.1795 | 0.3793 | T | 6.824 | 0.358 | 0.008993 |
| TRPC4 | 13 | rs2985167 | 37656405 | G | 0.2821 | 0.5 | A | 6.742 | 0.3929 | 0.009418 |
| TRPM3 | 9 | rs6560200 | 71365306 | T | 0.3974 | 0.6207 | C | 6.633 | 0.4031 | 0.01001 |
| TRPM3 | 9 | rs1106948 | 71402258 | C | 0.3974 | 0.6167 | T | 6.521 | 0.41 | 0.01066 |

TABLE 9-continued

Analysis of the frequency, distribution and significance of SNPs in genes for TRP ion channels and AChRs in CFS/ME patients (n = 39_) and non-fatigued controls (n = 30) in rank order of significance

| Gene | CHR | SNP | BP | AL | F_A | F_U | A2 | CHISQ | OR | p-value |
|---|---|---|---|---|---|---|---|---|---|---|
| TRPM8 | 2 | rs6758653 | 2.34E+08 | A | 0.2436 | 0.45 | G | 6.502 | 0.3936 | 0.01078 |
| nAChRα3 | 15 | rs12914385 | 78606381 | T | 0.4872 | 0.2833 | C | 5.879 | 2.403 | 0.01532 |
| nAChRα2 | 8 | rs891398 | 27467305 | C | 0.5526 | 0.3448 | T | 5.714 | 2.347 | 0.01683 |
| TRAM3 | 9 | rs12350232 | 71417232 | G | 0.3974 | 0.6 | T | 5.571 | 0.4397 | 0.01826 |
| nAChRα2 | 8 | rs2741343 | 27468610 | C | 0.5526 | 0.35 | T | 5.537 | 2.204 | 0.01862 |
| TRPM3 | 9 | rs11142822 | 71427327 | T | 0.03346 | 0.15 | G | 5.314 | 0.2267 | 0.02115 |
| nAChRα3 | 15 | rs2869546 | 78615003 | C | 0.2763 | 0.4667 | T | 5.271 | 0.4364 | 0.02168 |
| TRPM3 | 9 | rs1891301 | 71403580 | T | 0.5769 | 0.3833 | C | 5.085 | 2.194 | 0.02414 |
| nAChRα3 | 15 | rs951266 | 78586199 | T | 0.4356 | 0.2586 | C | 4.536 | 2.215 | 0.03319 |
| TRPC2 | 11 | rs7108612 | 3628856 | T | 0.1923 | 0.06667 | G | 4.509 | 3.333 | 0.03372 |
| TRPC2 | 11 | rs6578398 | 3616831 | A | 0.3462 | 0.1833 | G | 4.506 | 2.358 | 0.00378 |
| mAChRM1 | 11 | rs6578398 | 62920797 | A | 0.2436 | 0.1034 | G | 4.354 | 2.791 | 0.03691 |
| mACbRM3 | 1 | rs4620530 | 2.4E+08 | T | 0.4744 | 0.3 | G | 4.301 | 2.106 | 0.03809 |
| mAChRM1 | 11 | rs11823728 | 62900330 | T | 0.05263 | 0.1607 | C | 4.242 | 0.2901 | 0.03943 |
| nAChRα3 | 15 | rs4243084 | 78619330 | G | 0.4359 | 0.2667 | C | 4.204 | 2.125 | 0.04034 |
| nAChRα3 | 15 | rs3743075 | 78617110 | A | 0.2821 | 0.45 | G | 4.177 | 0.4802 | 0.04097 |
| nAChRα3 | 15 | rs3743074 | 78617138 | C | 0.2821 | 0.45 | T | 4.177 | 0.4802 | 0.04097 |
| nAChRε | 17 | rs33970119 | 4901607 | A | 0.03846 | 0.1333 | G | 4.161 | 0.26 | 0.04136 |
| nAChRα5 | 15 | rs7180002 | 78581651 | T | 0.4342 | 0.2667 | A | 4.084 | 2.11 | 0.0433 |

SNPs of 39 CFS/ME patients and 30 non-fatigued controls. Data presented are included for p < 0.05. Data are presented for gene (TRPM3, TRPM8, TRPC2, TRPC4, AChRM1, M3, alpha 2, 3. 5, 10 and epsilon), chromosome location (CHR). reference SNP identification (RefSNPID), base pair (BP) location of SNP, alleles (A1 and A2), allelic frequency A (Frequency A) of this allele in CFS cases, frequency U (Frequency_U) of this allele in controls, chi-square (χ2) for basic allelic test (1 df). odds ratio (OR) and (*) P-value for this est set at a significance of <0.05.

TABLE 10

Analysis of the genotype, odds ratio and significance of SNPs in genes for TRP ion channels and AChRs in CFS/ME patients (n = 39) and non-fatigued controls (n = 30) in rank order of significance

| Gene | CHR | SNP | Genotype | CFS (n %) | Non-Fatigued Control (n %) | $\chi^2$ | OR | p-value |
|---|---|---|---|---|---|---|---|---|
| TRPM8 | 2 | rs11563204 | GA | 23 (82.1%) | 5 (17.9%) | 12.59 | 7.19 | 0 |
| nAChRα2 | 8 | rs891398 | CC | 11 (91.7%) | 1 (8.3%) | 7.31 | 11.39 | 0.007 |
| nAChRα2 | 8 | rs2741343 | CC | 11 (91.7%) | 1 (8.3%) | 7.3 | 11.39 | 0.007 |
| TRPC4 | 13 | rs2985167 | AA | 20 (76.9%) | 6 (23.1%) | 7.07 | 4.21 | 0.008 |
| TRPM3 | 9 | rs6560200 | CC | 15 (83.3%) | 3 (16.7%) | 7.12 | 5.63 | 0.008 |
| TRPC4 | 13 | rs1570612 | GG | 30 (68.2%) | 14 (31.8%) | 6.72 | 3.81 | 0.01 |
| nAChRβ4 | 15 | rs12441088 | TT | 25 (71.4%) | 10 (28.6%) | 6.42 | 3.57 | 0.011 |
| TRPM8 | 2 | rs17865678 | AG | 22 (73.3%) | 8 (26.7%) | 6.1 | 3.56 | 0.013 |
| TRPC4 | 13 | rs655207 | GG | 12 (85.7%) | 2 (14.3%) | 6.09 | 6.22 | 0.014 |
| nAChRα3 | 15 | rs12914385 | TT | 12 (85.7%) | 2 (14.3%) | 6.09 | 6.22 | 0.014 |
| TRPM3 | 9 | rs11142822 | GG | 36 (63.2%) | 21 (36.8%) | 5.87 | 5.14 | 0.015 |
| TRPM3 | 9 | rs1106948 | TT | 15 (78.9%) | 4 (21.1%) | 5.37 | 4.06 | 0.021 |
| TRPC2 | 11 | rs7108612 | GT | 15 (78.9%) | 4 (21.1%) | 5.37 | 4.06 | 0.021 |
| nAChRε | 17 | rs33970119 | GG | 36 (62.1%) | 22 (37.9%) | 4.56 | 4.36 | 0.033 |
| TRPM3 | 9 | rs1891301 | TT | 14 (77.8%) | 4 (22.2%) | 4.48 | 3.64 | 0.034 |
| TRPM3 | 9 | rs12350232 | TT | 15 (75%) | 5 (25%) | 3.91 | 3.13 | 0.048 |

Genotype with 39 CFS/ME patients and 30 non-fatigued controls.
Data presented are included for p < 0.05.
Data are presented for gene (TRPM3, TRPM8, TRPC2, TRPC4, AChRM3, alpha 2, 3, and epsilon), chromosome location (CHR), reference SNP identification (RefSNPID), genotype percentage of CFS patients with genotype (%), percentage of non-fatigued controls (5), chi-square ($\chi^2$) for basic allelic test (1 df), odds ratio (OR) and (*) P-value for this test set at a significance of <0.05.

Results

Participants

There were 39 CFS patients (age=51.69±2.00 years), of which 72% were females and 18% were males. There were 30 non-fatigued controls (age=47.60±2.39 years) comprising 24% females and 76% males. All participants in both groups were of European decent and were residents of Australia at the time of blood collection. There were no significant changes in white blood cell counts between CFS/ME patients and the non-fatigued control group. Table 8 outlines participants' characteristics.

NK Cell Purity

There was no significant difference between groups for levels of NK purity. FIG. 1 outlined the high levels of purity (>93%) of NK cells following isolation and enrichment.

NK Cell Cytotoxic Activity

Figure 2:
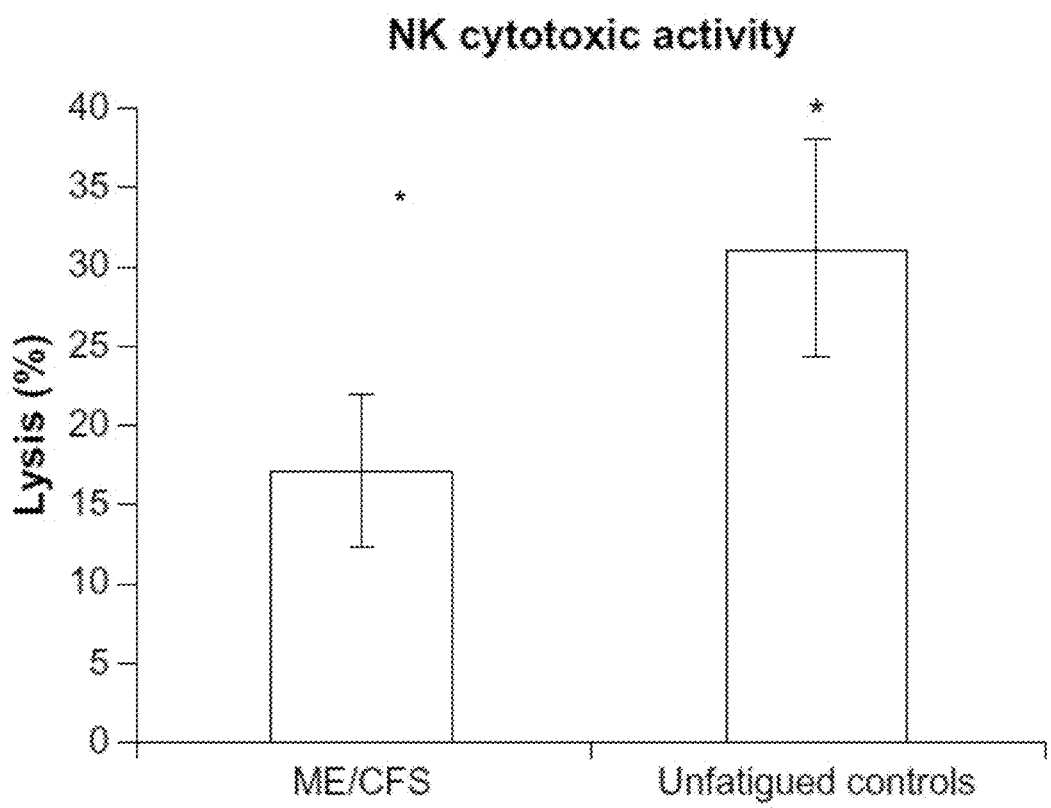
FIG. 2: Reduced NK cytotoxic activity in CFS/ME. In vivo assessment of NK cytotoxic activity of tumour cell lines K562 in CFS/ME (n=39) and unfatigued controls (n=30). Lytic activity represented by percentage lysis of target cells on the y-axis. Data presented as mean±SE*P<0.05.

There was a significant difference for NK cytotoxic activity between groups at the E:T ratio of 25:1. CFS/ME patients had a significant reduction in NK % lysis (17±4.68) compared with the control group (31±6.78) (FIG. 2).

SNP Analysis

Of 678 SNPs identified in TRP ion channel and AChR genes from isolated NK cells there were 11 SNPs for TRP ion channel genes (TRPC4, TRPC2, TRPM3 and TRPM8) significantly associated in the CFS/ME group. Five of these SNPs were associated with TRPM3 (rs rs6560200; p=0.010, rs1106948; p=0.010, rs12350232; p=0.018, rs11142822; p=0.021, rs189130); p=0.024) while the remainder were associated with TRPM8 (rs17S65678; p=0.000, rs1156320;

p=0.001), TRPC2 (rs7108612; p=0.034, rs6578398; p=0.0334) and TRPC4 (rs2985167; p=0.001, rs655207; p=0.018).

Fourteen SNPs were associated with nicotinic and muscarinic acetylcholine receptor genes, where six were nAChR alpha 3 (rs12914385; p=0.015, rs2869546; p=0.021, rs951266; p=0.033, rs4243084; p=0.040, rs3743075; p=0.041, rs3743074; p=0.041), while the remainder were associated with nAChR alpha 2 (rs891398; p=0.017, rs2741343; p=0.019), nAChR beta 4 (rs12441088; p=0.009), nAChR alpha 5 (rs7180002; p=0.043) and nAChR epsilon (rs33970U9; p=0.041). Table 9 represents the SNPs for TRP ion channel and AChR genes isolated from NK cells, respectively.

Genotype Analysis

There were sixteen genotypes identified from SNPs that were reported significant for TRPM3 (n=5), TRPM8 (n=2), TRPC4 (n=3), TRPC2 (n=1), nAChR epsilon (n=1), nAChR alpha 2 (n=2), nAChR alpha 3 (n=1) and nAChR beta 4 (n=1). Table 10 represents the genotypes for SNPs in TRP and AChR genes from isolated NK cells that were reported as statistically significant between groups. The odds ratio for specific genotypes for SNPs in TRP and AChR genes from isolated NK cells ranged between 3.13-11.39 for CFS/ME compared with the non-fatigued control group.

Discussion

Reduced NK cell cytotoxic activity has previously been reported in CFS/ME and the current investigation supports those findings. The current investigation reports novel findings for a number of SNPs in genes for AChR and TRP variants and genotypes from isolated NK cells from CFS/ME patients. A further novel finding from this investigation is the identification of SNPs in TRPM3 and TRPM8 from isolated NK cells, suggesting TRPM3 and TRPM8 receptors are located on NK cells.

This investigation reports a significant reduction in NK lysis in CFS/ME patients compared with the non-fatigued controls. TRP ion channels have an important role in $Ca^{2+}$ signaling and immune cells have been documented to express TRPC and TRPM subfamilies, mainly TRPC-1, 3, 5 and TRPM-2, 4, 7 [49j]. These channels are non-selective and permeable to calcium. In NK cells $Ca^{2+}$ plays a key role in lytic granule fusion [11j, 50j, 51j] as well as ensuring lytic granules mobilize to the immune synapse to release perforin and granzymes to kill target cells [11j, 50j, 51j]. Rho-GTPase Miro, provides a link between the mitochondria and the microtubules, where it mediates the $Ca^{2+}$ dependent arrest of mitochondrial motility [52j]. As Rho GTPase Miro modifies mitochondrial polarization, it also may alter lytic granule transport to the immune synapse as well as lytic function due to modulation by cytosolic $Ca^{2+}$ concentration through TRPM and AChR genotypes. Clearly mitochondria play a key role in NK cell function. A recent discovery that mitochondria express a range of AChR subtypes including nicotinic alpha 3, although differentially expressed according to tissue type [53j] suggests that nAChR may impact mitochondrial function and regulate oxidant stress. Interestingly the inventors have previously reported a significant decrease in respiratory bust function of neutrophils from CFS/ME patients [34j].

TRPM2 and TRPM3 mobilize $Ca^{2+}$, where the latter has been shown to mediate $Ca^{2+}$ signaling for cytolytic granule polarization and degranulation [54j]. ADPR targets TRPM2 channels on cytolytic granules resulting in TRPM2-mediated $Ca^{2+}$ signaling, subsequently inducing cytolytic granule polarization and degranulation, which results in antitumor activity. Further, NK cells treated with ADPR antagonist had reduced tumor-induced granule polarization, degranulation, granzyme B secretion, and cytotoxicity of NK cells. Interestingly similar findings for NK cell functions have been reported from previous CFS/ME research [32j-36j], potentially suggesting the genotype changes reported in this present study for TRPM3 may also play a similar role for cytolytic granule polarization and degranulation.

Out of the 678 SNPs examined, eleven variants for TRP ion channels and fourteen variants for AChRs were found to be significantly associated with CFS/ME patients compared with the non-fatigued controls. The variant TRP SNPs were located in the gene sequence of two of the canonical TRP ion channels (TRPC2 and TRPC4) and two melastatin TRP ion channels (TRPM3 and TRPM8). The inventors also report variant SNPs on genes for two of the muscarinic acetylcholine three receptors (mAChRM3), two muscarinic acetylcholine one receptors (mAChRM1), six nicotinic acetylcholine alpha three receptors (nAChRα3), three nicotinic acetylcholine alpha two receptors (nAChRα2), one nicotinic acetylcholine alpha five receptor (nAChRα5) as well as one nicotinic acetylcholine beta four receptor (nAChRβ4) and one nicotinic acetylcholine epsilon receptor (nAChRε).

The inventors' current research reports significant SNP associations of genotypes for AChRs in isolated NK cells from CFS/ME patients. Lymphocytes express both muscarinic and nicotinic acetylcholine (ACh) receptors, where T and B cells and monocytes express all five subtypes of mAChRs (M(1)-M(5)), while nAChR are found for 2-6, 2-4, and 9/10 subunits [55j-S8j]. Lymphocytes constitute a cholinergic system that is independent of cholinergic nerves, resulting in the regulation of immune function [55j, 56j]. AChR agonists have been shown to enhance lymphocyte cytotoxicity, increase their intracellular cGMP and inositol-1,4,5-triphosphate (IP3) [55j-59j], suggesting the lymphocytic cholinergic system is involved in the regulation of immune function via AChRs coupled to phospholipase-C (PLC) via changes in $[Ca^{2+}]$ [60j-65j]. Previous research has highlighted the importance of variants in affecting gene transcripts by causing alternative splicing resulting in anomalies in mRNA and translation products [66j]. The inventors have also identified SNPs and genotype in nAChRε in CFS/ME patients. Interestingly, this SNP is located in the 3' untranslated region (3'-UTR), an important coding region that often contains regulatory regions that post-transcriptionally influence gene expression. 3'-UTR is a binding site for regulatory proteins as well as microRNAs (miRNAs) [67j]. Binding to specific sites within the 3'-UTR, miRNAs can decrease gene expression of various mRNAs by either inhibiting translation or directly causing degradation of the transcript. The inventors' previous research has found significant differences in NK cytotoxic activity as well as miRNAs from isolated NK cells from CFS/ME patients [32j].

Previous investigators suggest that alternate splicing in the coding and also in the non-coding sequences may have significant unexpected outcomes on the splicing mechanism of the gene transcripts [68j, 69j]. Splicing genetic variants located in the exons, introns, as well as the assembly of the spliceosome all contribute to the splicing mechanism for the correct coding of a protein sequence. Moreover, silencers and enhancers located either in the exons or introns are integral in recognition of the correct exon sequence [70j]. Importantly introns are able to generate active spliceosomes, giving rise to alternative splicing events [71j, 72j]. Gene 80036 (TRPM3) is associated with calcium entry and calcium store depletion via different isoforms which have been identified through alternative splicing [Fruhwald, Julia, et al.

"Alternative splicing of a protein domain indispensable for function of transient receptor potential melastatin 3 (TRPM3) ion channels." Journal of Biological Chemistry 287.44 (2012): 36663-36672]. The 'indispensable for channel function' (ICF) is an 18 amino acid residue region whose absence tenders the channels functionally unable to mediate calcium entry, and is found devoid in a TRPM3 variant [73j]. Co-expression of these TRPM3 ICF variants with functional TRPM3 ion channels additionally show impaired calcium mobilization [73j]. As TRPM3 ICF variants show ubiquitous expression in many tissues and cell types and constitute 15% of all TRPM3 isoforms, expression on NK cells may provide a potential explanation for reduced cytotoxic activity in CFS/ME patients. Additionally, ion selectivity occurs through the selective splicing of exon 24 and results in two variants, TRPM3α1 and TRPM3α2 [73j, 74j]. The significance of these two isoforms is highlighted as TRPM3α1 preferentially mediates monovalent cation conduction, while TRPM3α2 shows high and specific permeability towards divalent cations, particularly calcium [73j, 74j]. This alteration in function may be attributed to the introduction of positively charged amino acid residues to the pore region [74j], resulting in increases in electrostatic repulsion of divalent cations, thus promoting increases in monovalent selectivity [74j]. Therefore, particular splice variants such as TRPM3α1 may potentially be favoured, culminating in a diminished NK cell cytotoxic response as well as heat detection including dysregulation of thermoregulatory responses, nociception and transmission of pain such as central and peripheral pain perception. Moreover, TRPM8 has also been identified to be activated by cold and noxious stimuli [75j-77j], suggesting the genotype changes reported in this investigation align to the clinical presentation of thermoregulatory responses, nociception and transmission of central and peripheral pain perception seen in CFS/ME patients [78j].

The inventors' results suggest SNP variants and genotypes reported in NK cells may not be exclusive to this immune cell type. Acetylcholine receptors and TRP ion channel receptors are located ubiquitously on multiple cell types and control other functions in body systems. $Ca^{2+}$ signaling in the context of TRP ion channels as well as AChR function is vital for the function of the CNS and there is wide variety in nicotinic receptors expressed in animal and human immune cells [58j]. Inferences regarding differential effects on function between these systems should note limitations depending on sub-types respectively expressed. The endothelium contains nicotinic receptors; nAChRα3, α5 and Γ4.α3 and α5 are found in arteries [79j-81j] and nAChR α5, α7, β2, and β3 are found in brain endothelial cells [82j], which are important components of the blood-brain barrier. Others have reported various nAChR receptors located on mitochondria, and depending upon tissues, mitochondria express several nicotinic receptor subtypes in a tissue-specific manner; brain and liver mitochondria contain α7β2, α4β2 and less α3β2 nicotinic receptors, while mitochondria from the lung express preferentially α3β4 receptor subtype [53j]. Interestingly this epsilon sub-type has been identified in thymomas from patients with myasthenia gravis [83j]. Of note, nAChRs are reported to be involved in arousal, sleep, and fatigue as well as those functions that are responsible for processing of pain, memory, and cognition all of which are clinical symptoms reported in CFS/ME patients [84j-86j].

Conclusion

In this study the inventors identified, for the first time, SNPs in genes for TRPM3 and TRPM8 ion channels on isolated NK cells. The inventors also identified numerous SNPs of nAChRs along with other TRP channels on isolated NK cells, indicating the non-neuronal acetylcholine system has an important role in NK cell function. Anomalies in genotypes for TRP ion channels and AChRs suggest altered calcium would be an important functional consequence not only for NK cells but also depending upon tissue type, susceptibility or predisposition to CFS/ME.

Example 6: SNPs and Genotypes in TRP Ion Channel and AChR Genes From Isolated B Lymphocytes in ME/CFS Patients The pathomechanism of CFS/ME is unknown. However, a small subgroup of patients has shown muscarinic antibodies and reduced symptom presentation following anti-CD20 intervention. Given the important roles in calcium ($Ca^{2+}$) and acetylcholine (ACh) signaling in B cell activation and potential antibody development, the inventors' aim in this Example was to determine SNPs and their genotypes from isolated B cells from CFS/ME patients.

Acetylcholine (Ach) is a neuronal cholinergic neurotransmitter where it performs a vital role through transmitting activation signals to receptors located in the central nervous system (CNS) as well as in skeletal and smooth muscle, all preganglionic autonomic nerve fibers and post ganglionic autonomic parasympathetic nerves as well immune cells and other tissues through the non-neuronal cholinergic system [1x-4x].

There are two types of membrane proteins that bind ACh known as muscarinic receptors (mAChRs) and nicotinic receptors (nAChRs). Importantly, both receptor proteins (mAChR and nAChR) have multiple isoforms. While muscarinic receptors are metabotropic receptors classified M1-M5, nicotinic receptors are ion channels and, with the exception of homomeric nicotinic alpha 7, are heteromers with various combinations of usually two sub-types (selected from 9 alpha and 3 beta) [5x]. The ratio of subtypes affects signal conducting speed through the receptor [6x]. Importantly one receptor subtype may impact receptor function of the other linked subtype.

ACh also functions within the non-neuronal cholinergic system (NNCS) where ACh binds AChRs that have been found on immune and other cell types. ACh is produced by lymphocytes where nAChRs have been shown to influence B lymphocyte function including development in the bone marrow as well as regulating B lymphocyte activation and autoantibody response [7x-9x]. ACh also performs endocrine and paracrine functions on tissues such as smooth muscle, beta pancreatic cells, glial cells, lymphocytes, ocular lens cells and brain vascular endothelium [10x-14x]. Calcium signaling is highly important for the activation of cell surface receptors on immune cells. Moreover, these ACh functions are mediated through $Ca^{2+}$ signaling.

Interestingly, muscarinic acetylcholine receptors have been found to be inhibited by another calcium channel [15x]. Mammalian Transient receptor potential (TRP) ion channels are $Ca^{2+}$ permeable cation channels that when open act as an excitatory signal to induce depolarisation of the cell and cause $Ca^{2+}$ influx which plays a role in intracellular signalling pathways. (TRPs) are comprised of six main groups including the TRPA (ankyrin), TRPC (canonical), TRPM (melastatin), TRPML (mucolipin), TRPP (polycystin) and TRPV (vanilloid) [16x]. TRPs are present on almost all cells and dysregulation in TRPs has been associated with pathological conditions and diseases [17x-22x].

The inventors have previously described single nucleotide polymorphisms (SNPs) in genes for receptors where $Ca^{2+}$ calcium is an important key component in their function. Additionally, the inventors have shown changes in $Ca^{2+}$ mobilization intracellularly for TRPM3 from NK cells and B lymphocytes. Hence, these SNPs and their genotypes for TRP ion channels and AChRs may produce altered receptor proteins, potentially changing TRP ion channel and AChR structures and functions. A recent study reported a subgroup of CFS/ME patients had muscarinic antibodies and a modest positive response occurred with reduced symptom presentation following anti-CD20 intervention [39x]. Given the important roles in $Ca^{2+}$ and acetylcholine (ACh) signaling in B cell activation as well as the potential for antibody development, the aim of this investigation was to determine SNPs and their genotypes for TRP and AChRs from isolated B cells from CFS/ME patients.

Method

Subjects

CFS/ME patients were defined in accordance with the 1994 CDC criteria for CFS/ME [40x]. A total of 11 CFS/ME patients and 11 non-fatigued controls were recruited for this study with no medical history or symptoms of prolonged fatigue or illness of any kind [40x].

Sample Preparation and Measurements

A volume of 40 ml of blood was collected from the antecubital vein of participants into lithium heparinized and EDTA collection tubes between 9 am and 11 am. Routine blood samples were analyzed within 6 hours of collection and analyzed for red blood cell counts, lymphocytes, granulocytes and monocytes using an automated cell counter (ACT Differential Analyzer, Beckman Coulter, Miami, Fla.). Refer to Table 11.

TABLE 11

Participant Characteristics for CFS/ME and Non Fatigued Controls.

| Descriptive | CFS/ME n = 11 | Controls n = 11 | P-VALUE |
|---|---|---|---|
| Gender (% F) | 8 (72.7%) | 7 (63.6%) | 0.497 |
| Mean Age (Years) | 31.82 (5.50) | 33.91 (5.06) | 0.783 |
| Haemoglobin (g/L) | 133 ± 2.70 | 134.70 ± 3.85 | 0.728 |
| Haematocrit (%) | 0.36 ± 0.02 | 0.30 ± 0.02 | 0.967 |
| Red Cell Count ($\times 10^{12}$/L) | 4.40 ± 0.13 | 4.50 ± 0.11 | 0.591 |
| Mean Corpuscular Volume (fL) | 89.56 ± 1.54 | 88.20 ± 0.61 | 0.406 |
| White Cell Count ($\times 10^9$/L) | 7.09 ± 0.69 | 5.80 ± 0.32 | 0.097 |
| Neutrophils ($\times 10^9$/L) | 4.15 ± 0.51 | 3.21 ± 0.21 | 0.096 |
| Lymphocytes ($\times 10^9$/L) | 2.35 ± 0.23 | 2.13 ± 0.24 | 0.549 |
| Monocytes ($\times 10^9$/L) | 0.36 ± 0.02 | 0.30 ± 0.02 | 0.043 |
| Eosinophils ($\times 10^9$/L) | 0.19 ± 0.04 | 0.14 ± 0.03 | 0.275 |
| Basophils ($\times 10^9$/L) | 0.03 ± 0.00 | 0.03 ± 0.01 | 0.752 |
| Platelets ($\times 10^9$/L) | 241.56 ± 19.55 | 248.10 ± 18.35 | 0.810 |

B Cell Isolation

A volume of 40 ml of blood was collected from the antecubital vein of participants into EDTA blood collection tubes between 8 am and 11 am. Routine blood samples were analyzed within 6 hours of collection and analyzed for red blood cell counts, lymphocytes, granulocytes and monocytes using an automated cell counter (ACT Differential Analyzer, Beckman Coulter, Miami, Fla.). Refer to Table 11.

Peripheral blood mononuclear (PBMCs) cells were isolated from 40 mL of whole blood for B cell isolation using method previously described Jamies et al. (2004) [69x]. Briefly, PBMCs were isolated by density gradient with Picoll-Paque (GE Healthcare, Uppsala, Sweden). Subsequently, cells were then washed twice with phosphate-buffered saline (PBS) (Gibco-BRL, Gaithersburg, Md.).

Cells were then resuspended in autoMACs separation buffer, which contains PBS containing bovine serum albumin, EDTA and 0.09% azide (Miltenyi Biotec. Auburn, Calif.). Immunomagnetic negative selection of B cells was performed with a B-cell isolation kit II (Miltenyi Biotec, Auburn, Calif.), according to the manufacturer's instructions. Briefly, non-B cells, such as T cells, NK cells, dendritic cells, monocytes, granulocytes, and erythroid cells, are indirectly magnetically labeled by using a cocktail of biotin conjugated antibodies against CD2, CD14, CD16, CD36, CD43 and CD235a (Glycophorin A). Consequently, isolation of B cell populations is achieved by depletion of magnetically labeled cells.

Untouched B-cells were measured with LSR Fortessa X-20 flow cytometry where cells were fluorescently stained with anti-CD19-BV421 and anti-CD3-PerCP. Cell debris and dead cells were excluded from the analysis based on scatter signals. Mean purity was 85.66%±9.6% for non-fatigued controls and 76.5%±13.1% for CFS/ME patients, where there was no significant difference between groups for levels of B lymphocytes.

DNA Extraction

A volume of 40 mL was collected into EDTA tubes for SNP analysis. Genomic DNA was extracted from all whole blood samples using the Qiagen DNA blood mini-kit as per manufacturer's instructions (Qiagen). SNP genotyping studies were performed as previously described.

SNP Analysis

A total of 661 SNPs from B cells were examined for twenty-one mammalian TRP ion channel genes (TRPA1, TRPC1, TRPC2, TRPC3, TRPC4, TRPC6, TRPC7, TRPM1, TRPM2, TRPM3, TRPM4, TRPM5, TRPM6, TRPM7, TRPM, TRPV1, TRPY2, TRPV3, TRPV4, TRPV5 and TRPV6) and for nine mammalian ACh receptor genes (muscarinic M1, M2, M3, M4, M5, nicotinic alpha 2, 3, 5, 7, 9, 10, beta 1, 4 and epsilon) and were examined using MassARRAY iPLEX Gold Assay (Sequenom Inc.).

Quality and quantity of the DNA extracted was conducted as previously described [44x, 48x]. Briefly a Nanodrop (Nanodrop) was used to quantify genomic DNA where approximately 2 μg of genomic DNA was used to perform the SNP analysis. MassARRAY (MALTI-TOF mass spectrometry platform) was employed to discriminate alleles based on single-base extension of an extension primer of known mass that is designed to attach directly next to the SNP site of interest. Custom multiplexed wells were designed in silico using Agena's Assay Design Suite. The designed multiplexes were then built using custom synthesized oligonucleotides that are pooled together for sample processing. The iPLEX Gold chemistry utilized two multiplexed oligo pools for each genotyping well. A multiplexed PCR pool was utilized to generate short amplicons that include all the genomic markers of interest in that particular well. Following PCR and clean-up steps, a secondary PCR 'extension' step was undertaken utilizing pools of extension primers that were designed to attach directly next to the SNP sites of interest. During the extension phase a termination mix was added that enabled these extension primers to be extended by a single base only. Given the molecular weight of the extension primer is known, discrimination of the allele was able to be measured using the peak heights of the unextended primer and this primer plus the possible single-base extension possibilities for the SNP.

TRP Ion Channel and AChR SNP Assays

Primers and extension primers were created for each of the SNPs using the Assay Designer (Sequenom Inc.) according to the manufacturer's instructions and previously described [44x, 45x]. Briefly, DNA was amplified via polymerase chain reaction (PCR) under the following conditions: 94° C. for 2 minutes, 94° C. for 30 seconds, 56° C. for 30 seconds, and 72° C. for 1 minute, where the amplification products were then treated with shrimp alkaline phosphatase at 37° C. for 40 minutes, 85° C. for 5 minutes reaction, and a final incubation at 4° C. Extension primers are optimized to control the signal-to-noise ratio where unextended primers (UEPs) are examined on the spectroCHIP and evaluated in Typer 4.0 to enable the division into low-mass UEP, medium-mass UEP, and high-mass UEP. A mixture containing iPLEX Gold reaction was prepared using iPLEX Gold Buffer Plus, iPLEX termination mix, iPLEX enzyme, and primer mix to perform the iPLEX extension reaction. This reaction consisted of cycling at an initial denaturation of 94° C. for 30 seconds, annealing at 52° C. for 5 minutes, extension at 80° C. for 5 minutes (five cycles of annealing and extension were performed, but the whole reaction was performed in 40 cycles) and extension again at 72° C. for 3 minutes. Resin beads were used to rinse all iPLEX Gold reaction products. Following the iPLEX Gold reaction, MassARRAY was performed using the MassARRAY mass spectrometer, and the data generated were analyzed using the Typer Analyzer software.

Statistical Analysis

Statistical analysis was performed using SPSS software version 22 [IBM Corp]. The experimental data represented in this study are reported as means plus/minus standard error of the mean (±SEM) while all the clinical data are reported as means plus/minus standard deviation (±SD). Comparative assessments among participants (CFS/ME and non-fatigued controls) were performed with the analysis of variance test (ANOVA) and the criterion for significance was set at $p<0.05$.

The PLINK v1.07 (http://pngu.mgh.harvard.edu/purcell/plink/) whole genome analysis tool set was used to determine associations between the CFS/ME patients and the non-fatigued control group. A two column $\chi 2$ test was used to examine differences where p value of <0.05 was determined to be significant and the resulting variants and their consequences can be found in Table 12 for TRP and AChR, respectively.

TABLE 12

Analysis of the frequency, distribution and significance of SNPs in B cells for TRP ion channels and AChRs in Chronic Fatigue Syndrome/Myalgic Encephalomyelitis patients and non-fatigued controls in rank order of significance

| Gene | CHR | SNP | BP | A1 | F_A | F_U | A2 | CHISQ | P | OR |
|---|---|---|---|---|---|---|---|---|---|---|
| CHRNA4 | 20 | rs11698563 | 63360932 | A | 0.2885 | 0.7083 | C | 11.88 | 0 | 0.1669 |
| CHRND | 12 | rs11674608 | 2.33E+08 | G | 0.34 | 0.7778 | C | 10.23 | 0 | 0.1472 |
| CHRNA9 | 14 | rs10009238 | 40354404 | A | 0.1786 | 0.5 | G | 8.706 | 0 | 0.2174 |
| CHRM3 | 11 | rs1867264 | 2.40E+08 | A | 0.28 | 0.6364 | T | 8.164 | 0 | 0.2222 |
| CHRNA9 | 14 | rs4861323 | 40353797 | G | 0.1786 | 0.4583 | A | 6.792 | 0.01 | 0.2569 |
| CHRNA2 | 18 | rs2741341 | 27472768 | C | 0.5179 | 0.2083 | T | 6.586 | 0.01 | 4.081 |
| TRPC6 | 11 | rs11224816 | 1.02E+08 | T | 0.5192 | 0.2083 | C | 6.511 | 0.01 | 4.104 |
| CHRND | 2 | rs12463989 | 2.33E+08 | C | 0.3571 | 0.6667 | T | 6.503 | 0.01 | 0.2778 |
| CHRND | 2 | rs2767 | 2.33E+08 | C | 0.3571 | 0.6667 | T | 6.503 | 0.01 | 0.2778 |
| CHRND | 2 | rs112001880 | 2.33E+08 | D | 0.3571 | 0.6667 | T | 6.503 | 0.01 | 0.2778 |
| CHRNB1 | 17 | rs4151134 | 7443803 | C | 0.3214 | 0.625 | T | 6.389 | 0.01 | 0.2842 |
| CHRM3 | 1 | rs1899616 | 2.40E+08 | A | 0.3269 | 0.6667 | G | 6.361 | 0.01 | 0.2429 |
| CHRNB4 | 15 | rs12440298 | 78635246 | G | 0.01786 | 0.1667 | T | 6.349 | 0.01 | 0.09091 |
| TRPV3 | 17 | rs4790519 | 3553440 | C | 0.5556 | 0.25 | T | 6.242 | 0.01 | .375 |
| TRPM3 | 9 | rs1317103 | 70580786 | C | 0.3519 | 0.08333 | T | 6.089 | 0.01 | 5.971 |
| CHRND | 2 | rs67583510 | 2.33E+08 | A | 0.1852 | 0.4545 | G | 5.849 | 0.02 | 0.2727 |
| CHRM3 | 1 | rs12093821 | 2.40E+08 | A | 0.2963 | 0.5833 | G | 5.784 | 0.02 | 0.3009 |
| CHRM3 | 1 | rs10802802 | 2.40E+08 | A | 0.375 | 0.6667 | G | 5.749 | 0.02 | 0.3 |
| CHRNA9 | 4 | rs4861065 | 40342377 | C | 0.3929 | 0.125 | T | 5.61 | 0.02 | 4.529 |
| CHRNA9 | 4 | rs7669882 | 40348633 | A | 0.3929 | 0.125 | G | 5.61 | 0.02 | 4.529 |
| CHRM3 | 1 | rs6684622 | 2.40E+08 | C | 0.38 | 0.6818 | G | 5.584 | 0.02 | 0.286 |
| CHRM3 | 1 | rs1134 | 2.40E+08 | T | 0.3462 | 0.625 | C | 5.197 | 0.02 | 0.3176 |
| CHRND | 2 | rs3762529 | 2.33E+08 | C | 0.3462 | 0.625 | T | 5.197 | 0.02 | 0.3176 |
| CHRND | 2 | rs12466358 | 2.33E+08 | G | 0.1731 | 0.4167 | T | 5.197 | 0.02 | 0.393 |
| CHRND | 2 | rs3828246 | 2.33E+08 | T | 0.1731 | 0.4167 | C | 5.197 | 0.02 | 0.393 |
| CHRM3 | 1 | rs11585281 | 2.40E+08 | T | 0.3889 | 0.6667 | C | 5.142 | 0.02 | 0.3182 |
| CHRM3 | 1 | rs12029701 | 2.40E+08 | C | 0.3889 | 0.6667 | T | 5.142 | 0.02 | 0.3182 |
| CHRND | 2 | rs13026409 | 2.33E+08 | T | 0.1786 | 0.4167 | C | 5.079 | 0.02 | 0.3043 |
| CHRNG | 2 | rs13018423 | 2.33E+08 | T | 0.1786 | 0.4167 | C | 5.079 | 0.02 | 0.3043 |
| CHRM3 | 1 | rs619214 | 2.40E+08 | G | 0.3 | 0.6111 | T | 5.021 | 0.03 | 0.2727 |
| CHRM3 | 1 | rs2165872 | 2.40E+08 | T | 0.3148 | 0.5833 | C | 5.003 | 0.03 | 0.3282 |
| CHRM3 | 1 | rs2083817 | 2.40E+08 | A | 0.3148 | 0.5833 | T | 5.003 | 0.03 | 0.3282 |
| CHRND | 3 | rs4973537 | 2.33E+08 | G | 0.3571 | 0.625 | A | 4.898 | 0.03 | 0.3333 |
| CHRND | 2 | rs3791729 | 2.33E+08 | T | 0.3571 | 0.625 | C | 4.898 | 0.03 | 0.3333 |
| TRPV2 | 17 | rs35400274 | 4900415 | A | 0.07143 | 0.25 | G | 4.898 | 0.03 | 0.2308 |
| CHRM3 | 1 | rs16838637 | 2.40E+08 | G | 0.3214 | 0.5833 | A | 4.802 | 0.03 | 0.3383 |
| CHRM3 | 1 | rs1867265 | 2.40E+08 | A | 0.3214 | 0.5833 | G | 4.802 | 0.03 | 0.3383 |
| CHRM3 | 1 | rs7551001 | 2.40E+08 | G | 0.3214 | 0.5833 | A | 4.802 | 0.03 | 0.3383 |
| CHRM3 | 15 | rs603152 | 34002435 | A | 0.4643 | 0.2083 | C | 4.637 | 0.03 | 3.293 |
| CHRM3 | 1 | rs1155612 | 2.40E+08 | G | 0.4 | 0.6667 | A | 4.616 | 0.03 | 0.3333 |
| CHRM2 | 7 | rs1424569 | 1.37E+08 | G | 0.4 | 0.6667 | A | 4.616 | 0.03 | 0.3333 |
| TRPV3 | 17 | rs3514 | 4898298 | C | 0.07407 | 0.25 | G | 4.601 | 0.03 | 0.24 |
| TRPV3 | 17 | rs12942540 | 4900777 | C | 0.07407 | 0.25 | G | 4.601 | 0.03 | 0.24 |
| TRPM4 | 19 | rs11083963 | 491602082 | G | 0.2826 | 0.5417 | A | 4.534 | 0.03 | 0.3333 |
| CHRM2 | 7 | rs1364403 | 1.37E+08 | T | 0.4107 | 0.1667 | C | 4.475 | 0.03 | 3.485 |

TABLE 12-continued

Analysis of the frequency, distribution and significance of SNPs in B cells for TRP ion channels and AChRs in Chronic Fatigue Syndrome/Myalgic Encephalomyelitis patients and non-fatigued controls in rank order of significance

| Gene | CHR | SNP | BP | A1 | F_A | F_U | A2 | CHISQ | P | OR |
|---|---|---|---|---|---|---|---|---|---|---|
| TRPM3 | 9 | rs4620343 | 71121726 | T | 0.4107 | 0.1667 | C | 4.475 | 0.03 | 3.485 |
| CHRM3 | 1 | rs12743042 | 2.40E+08 | C | 0.3704 | 0.6364 | T | 4.473 | 0.03 | 0.3361 |
| CHRM3 | 1 | rs6688537 | 2.40E+08 | A | 0.4074 | 0.6667 | C | 4.47 | 0.03 | 0.3438 |
| CHRM5 | 15 | rs646950 | 33999458 | T | 0.4615 | 0.2083 | C | 4.461 | 0.03 | 3.257 |
| CHRM3 | 1 | rs2163546 | 2.40E+08 | G | 0.5385 | 0.2727 | A | 4.396 | 0.04 | 3.111 |
| CHRM3 | 1 | rs1544170 | 2.40E+08 | A | 0.3704 | 0.635 | G | 4.355 | 0.04 | 0.3529 |
| TRPM4 | 9 | rs3812532 | 70868677 | A | 0.3704 | 0.625 | C | 4.355 | 0.04 | 0.3529 |
| CHRND | 2 | rs2853457 | 2.33E+08 | A | 0.5 | 0.25 | G | 4.297 | 0.04 | 3 |
| CHRM3 | 1 | rs6429147 | 2.40E+08 | C | 0.2963 | 0.5417 | G | 4.283 | 0.04 | 0.3563 |
| CHRM3 | 1 | rs6700643 | 2.40E+08 | C | 0.2963 | 0.5417 | T | 4.283 | 0.04 | 0.3563 |
| CHRM3 | 1 | rs10925941 | 2.40E+08 | A | 0.2963 | 0.5417 | G | 4.283 | 0.04 | 0.3563 |
| CHRM3 | 1 | rs576386 | 2.40E+08 | C | 0.5192 | 0.25 | G | 4.24 | 0.04 | 3.24 |
| CHRNA9 | 4 | rs10015231 | 40335548 | T | 0.1964 | 0.4167 | C | 4.209 | 0.04 | 0.3422 |
| TRPV2 | 17 | rs33970119 | 4901606 | A | 0.03571 | 0.1667 | G | 4.153 | 0.04 | 0.1852 |
| CHRM3 | 1 | rs1867263 | 2.40E+08 | A | 0.3036 | 0.5417 | G | 4.063 | 0.04 | 0.3688 |
| CHRM5 | 15 | rs511422 | 33990780 | C | 0.4464 | 0.2083 | T | 4.063 | 0.04 | 3.065 |
| TRPM3 | 9 | rs10780950 | 70578511 | T | 0.2885 | 0.08333 | C | 3.979 | 0.05 | 4.459 |
| TRPV2 | 17 | rs2075763 | 4899389 | T | 0.03704 | 0.1667 | C | 3.932 | 0.05 | 0.1923 |
| CHRM3 | 1 | rs685550 | 2.40E+08 | C | 0.2222 | 0.04167 | T | 3.9 | 0.05 | 6.571 |
| CHRM3 | 1 | rs6694220 | 2.40E+08 | G | 0.4231 | 0.6667 | A | 3.897 | 0.05 | 0.3667 |
| TRPV2 | 17 | rs12602006 | 16433973 | G | 0.2692 | 0.5 | A | 3.885 | 0.05 | 0.3684 |
| TRPV2 | 17 | rs7222754 | 16426430 | T | 0.4423 | 0.2083 | C | 3.863 | 0.05 | 3.014 |
| CHRNB1 | 17 | rs3829603 | 7443772 | A | 0.2593 | 0.5 | C | 3.86 | 0.05 | 0.35 |
| CHRM3 | 1 | rs10754677 | 2.40E+08 | G | 0.3845 | 0.625 | A | 3.819 | 0.05 | 0.375 |
| CHRM3 | 1 | rs7513746 | 2.40E+08 | G | 0.3889 | 0.625 | A | 3.727 | 0.05 | 0.3818 |
| CHRM3 | 1 | rs10802795 | 2.40E+08 | C | 0.3889 | 0.625 | T | 3.727 | 0.05 | 0.3818 |
| CHRM3 | 1 | rs3738436 | 2.40E+08 | A | 0.3889 | 0.625 | C | 3.727 | 0.05 | 0.3818 |
| CHRM3 | 1 | rs7511970 | 2.40E+08 | A | 0.3889 | 0.625 | G | 3.727 | 0.05 | 0.3818 |
| CHRM3 | 1 | rs1155611 | 2.40E+08 | T | 0.3889 | 0.625 | C | 3.727 | 0.05 | 0.3818 |
| CHRM3 | 1 | rs1019882 | 2.40E+08 | G | 0.3889 | 0.625 | A | 3.727 | 0.05 | 0.3818 |
| CHRM3 | 1 | rs1416789 | 2.40E+08 | G | 0.3889 | 0.625 | A | 3.727 | 0.05 | 0.3818 |
| CHRM3 | 1 | rs10925964 | 2.40E+08 | A | 0.3889 | 0.625 | T | 3.727 | 0.05 | 0.3818 |
| CHRNB1 | 17 | rs2302767 | 7447224 | C | 0.2778 | 0.5 | T | 3.725 | 0.05 | 0.3846 |

Further genotype analysis for differences between CFS/ME and the non-fatigued group was also completed according to a two column $\chi^2$ test with significance of $p<0.05$ and results are presented in Table 13. Analyses were performed at the Australian Genome Research Facility Ltd, The Walter and Eliza Hall Institute, Parkville, Victoria, Australia.

cell counts between CFS/ME patients and the non-fatigued control group. Table 11 outlines participants' characteristics.

SNP Analysis

Of 661 SNPs identified in TRP ion channel and AChR genes from B cells a total of seventy-seven SNPs were associated with nicotinic and muscarinic acetylcholine

TABLE 13

Analysis of the genotype, odds ratio and significance of SNPs in B cell genes for TRP ion channels and AChRs in Chronic Fatigue Syndrome/Myalgic Encephalomyelitis patients and non-fatigued controls in rank order of significance.

| Gene | CHRM | RefSNP | Genotype | CFS (%) | Non Fatigued Controls (%) | $\chi^2$ | OR | P-VALUE |
|---|---|---|---|---|---|---|---|---|
| CHRNB1 | 17 | rs3829603 | CC | 8 (72.7%) | 1 (9.1%) | 9.21 | 20.67 | 0.002 |
| CHRNB1 | 17 | rs4151134 | TT | 7 (63.6%) | 1 (9.1%) | 7.07 | 17.50 | 0.005 |
| CHRNB1 | 17 | rs2302767 | TT | 7 (63.6%) | 1 (9.1%) | 7.07 | 17.50 | 0.005 |
| CHRNA4 | 20 | rs11698563 | CC | 6 (54.5%) | 1 (9.1%) | 5.24 | 12.00 | 0.022 |
| CHRNB1 | 17 | rs7210231 | CA | 7 (63.6%) | 2 (18.2%) | 4.70 | 7.88 | 0.030 |
| TRPM3 | 9 | rs7038646 | AG | 9 (81.8%) | 4 (36%) | 4.70 | 7.53 | 0.030 |
| TRPC6 | 11 | rs10791504 | GG | 7 (63.6%) | 3 (27.3%) | 4.70 | 7.58 | 0.030 |
| CHRM3 | 1 | rs1867264 | TA | 8 (72.7%) | 3 (27.3%) | 4.55 | 7.11 | 0.033 |
| CHRM3 | 1 | rs6688537 | CA | 8 (72.7%) | 3 (27.3%) | 4.55 | 7.11 | 0.030 |

Results

Participants

There were 11 CFS/ME patients (age=31.82±5.50 years) of which 72.7% were females. There were 11 non-fatigued controls (age=33.91±3.06 years), comprising 63.6% females. All participants in both groups were of European decent and were residents of Australia at the time of blood collection. There were no significant changes in white blood receptor genes in CFS/ME patients. A total of thirty-five SNPs for mAChM3 featured, while the remaining predominate SNPs were identified for nAChR delta (n=12), nAChR alpha 9 (n=5), TRPV2 (n=7), TRPM3 (n=4), TRPM4 (n=1), mAChRM2 (n=2) and mAChRM5 (n=3). Table 12 represents the SNPs for TRP ion channel and AChR genes in B lymphocytes.

Genotype Analysis

Nine genotypes were identified from SNPs that reported significant for TRPM3 (n=1), TRPC6 (n=1), mAChRM3 (n=2), nAChR alpha 4 (n=1) and nAChR beta 1 (n=4). Table 13 represents the genotypes for SNPs in TRP and AChR genes from B lymphocytes that were reported as statistically significant between groups. The odds ratio for specific genotypes for SNPs in TRP and AChR genes from B lymphocytes ranged between 7.11-26.67 for CFS/ME compared with the non-fatigued control group.

Genotype with 11 CFS/ME patients and 11 non-fatigued controls. Data presented are included for p<0.05. Data are presented for gene (TRPM3, TRPC6, AChRM3, alpha 3, 4, 7 and beta 1), chromosome location (CHR), reference SNP identification (RefSNPID), genotype percentage of CFS/ME patients with genotype (%), percentage of non-fatigued controls (5), chi-square ($\chi 2$) for basic allelic test (1 df), odds ratio (OR) and (*) P-value for this test set at a significance of <0.05.

Discussion

The current investigation reports novel findings for a number of SNPs in genes for AChR and TRP variants and genotypes from B cells from CFS/ME patients. These data are consistent the inventors' findings above in PBMCs and NK cells, showing B cells of high SNP prevalence and genotypes in TRP and AChR genes in CFS/ME patients.

Intracellular $Ca^{2+}$ levels are substantially modulated by receptor induced alterations and are critical for lymphocyte differentiation and function. $Ca^{2+}$ regulates antigen receptors, co-receptors, signal transduction, mitochondrial function, transcriptional factors and gene expression [42x-45x]. For example $Ca^{2+}$ entry is regulated by plasma membrane channels, intracellular receptor channels, non-selective cation channels, specific membrane transporters and cell membrane potential [20x, 45x, 46x].

The immune system is dependent on cholinergic signaling as B and T cells express cholinergic receptors and regulate cytokines in inflammatory responses [47x, 48x] and immune function [49x]. Cholinergic signaling influences both B cell [9x] and T cell [50x] responses and has been found to initiate B cell autoimmunity [51x]. In cholinergic receptor SNPs, mAChM3R featured significantly (45%) which is consistent with the inventors' findings of SNPs and their genotype in NK cells. In this current investigation there were two SNP genotypes reported for mAChM3R. However, given the small sample number as well as noting the inventors' previous results of SNP genotypes from isolated NK cells and PBMCs, other genotypes for this receptor may be present in CFS/ME patients. A recent study has reported a subgroup of CFS/ME patients who had muscarinic antibodies (mAChM3R) and a modest positive response occurred with reduced symptom presentation following anti-CD20 intervention [39x]. As this finding was only reported in a small group of patients and genotype SNPs were not reported, the inventors' current findings, along with their previous SNP genotype findings in isolated NK cells from a larger cohort, suggest these SNP genotype changes and their combinations may play a role in B cell function. Moreover, the ubiquitous distribution of cholinergic receptors throughout the body suggests that anomalies in SNP genotypes and their heterodimer configuration and pattern may contribute to the various clinical symptoms of CFS/ME.

The inventors have identified SNPs in muscarinic and nicotinic receptors from diverse blood cells, such as PBMC and isolated natural killer cells in larger cohorts of CFS/ME patients, suggesting cholinergic signaling may be impeded in this disorder. Muscarinic signaling has a role in gastrointestinal function [52x] as antibodies to mAChM3Rs have been found to inhibit gastrointestinal motility and cholinergic neurotransmission [53x]. The mAChM3Rs are widely distributed in the heart, where they regulate intracellular phosphoinositide hydrolysis to improve cardiac contraction, haemodynamic function [54x] and provide a protective effect against ischaemia [55x]. The mAChM3Rs are located in the pancreas where they mediate acetylcholine control over insulin secretion and have other important regulatory functions [56x-58x].

Nicotinic signaling via nAChRs is widely distributed in organisms demonstrating the universal character of cholinergic signaling. Muscle-type nAChRs, such as β1, are similar in all parts of the body [7x]. In the inventors' data, there is high demonstration of SNPs and genotypes in nAChRs, suggesting the extent of SNP genotypes in cholinergic receptors may play a role in B cell function, as acetylcholine functions as a paracrine/autocrine regulator of immune and other physiological functions [59x]. The present data highlights the SNP genotypes for nAChR beta 1 where SNPs rs3829603 (C/C) and rs4151134 (T/T) are located in the 3' untranslated region and demonstrate significant odds ratio for these genotypes that range between 17.50-26.67 for the CFS/ME group. This location is a regulatory region that post-transcriptionally influences gene expression: 3'-UTR is a binding site for regulatory proteins [60x]. Binding to specific sites within the 3'-UTR may decrease gene expression of various mRNAs by either inhibiting translation or directly causing degradation of the transcript. Additionally, the agonist-binding site of nAChRs is located at the interface between adjacent subunits. Binding of the agonist that is located at the α subunit (α1, α2, α3, α4, α6, α7, or α9), and the binding of the negative agonist-binding site is composed by α10, β2, β4, δ, γ, or ε subunit. Importantly α5, β1, and β3 subunits assemble in the receptor complex assumes the fifth subunit position, where they do not directly participate in the formation of the agonist-binding site, however, they form an integral configuration for the binding agonists and ligand selectivity [61x]. Given the number of SNP genotypes for nAChR β1 that were located at the 3'UTR, the fifth subunit may alter ligand selectivity. Moreover, various subunit combinations have been shown to result in different nAChR subtypes that vary in the kinetic parameters and selectivity of the ion channels, as well as ligand specificity, signaling pathways and functions that are performed in different tissues [62x]. The density of distribution of AChRs throughout the body means that many tissues are likely to be affected where AChR expression occurs, suggesting a potential loss of function of neuronal and non-neuronal cholinergic signaling pathways in virtually all body tissues. Interestingly, the inventors and others have previously reported changes in B cell phenotypes from CFS/ME patients [26x, 63x] and in a study above the inventors reported a reduction in calcium mobilisation into B cells via TRPM3 where this receptor was identified to have 3'UTR SNP genotypes.

Cholinergic signaling in the brain is primarily focused on two main loci, the basal forebrain and the pedunculo-pontine area of the hindbrain [64x]. Acute vasoconstriction occurs after removal of the cholinergic parasympathetic input to forebrain cerebral arteries [65x], indicating the critical importance of intact cholinergic signaling in the brain. Both nicotinic and muscarinic cholinergic signaling influence hippocampal synaptic plasticity and processing cholinergic-dependent higher cognitive functions [66x]. Cholinergic and glutamatergic signaling demonstrate interdependence in cortical glial cell function in sleep/wake studies [67x]. Key CNS functions such as memory formation are associated with long term potentiation (LTP) in hippocampal synapses. This memory mechanism is $Ca^{2+}$ dependent through its association with cholinergic signaling [68x].

Conclusion

These findings of SNP genotypes in cholinergic and TRP receptor genes in B cells, and previously in PBMCs and isolated NK cells, suggest a potential contribution to widespread pathology across all organ systems of the body including immune, CNS, heart, gastrointestinal and hormonal systems. The effects of these SNP genotypes on cholinergic signaling are likely to be particularly important in the central nervous system, peripheral nervous system, autonomic nervous system as well as other organ systems. Taken together, the functional effects of these SNP genotypes and their combinations suggest they may be contributing factors in the aetiology and clinical phenotypes of CFS/ME.

Example 7—Reduction in TRPM3 Cell Surface Expression in NK Cells and B Lymphocytes from CFS/ME Patients as Well as Decreased Intracellular Calcium The inventors in the Examples above identify SNPs in TRP ion channels, namely from the TRPM3 family (rs12682832; rs11142508; rs1160742; rs4454352; rs1328153; rs3763619; rs7865858; rs1504401; rs10115622), as well as TRPA1 (rs2383844; rs4738202) and TRPC4 (rs6650469; rs655207) in CFS/ME patients, as well as SNPs in ACh receptors, mainly muscarinic M3 receptors (mAChRm3), (rs4463655; rs589962; rs1072320; rs7543259; rs6661621; rs7520974; rs726169; rsrs6669810; rsrs6429157), as well as nicotinic ACh receptors (nAChR) alpha 10 (rs2672211; rs2672214; rs2741868; rs2741870; rs2741862), alpha 5 (rs951266; rs7180002), and alpha 2 (rs2565048; P=0.01403. These ion channels and receptors are widely expressed in cells and tissues throughout the body and are strongly associated with the symptomatology often reported in CFS/ME. The inventors demonstrated that these are exhibited in 99-100% of n=115 CFS/ME patients compared to 0-1% In healthy controls of n=90 (see Table 7).

Data presented for gene (TRPM3 and mAChR3), chromosome location (CHR), reference SNP identification (Ref SNP ID), base pair (BP) location of SNP, alleles (A1 and A2), chi-square ($\chi2$) for basic allelic test (1 df), p-value for this test set at a significance of p<0.05, odds ratio (OR), percentage of CFS patients with SNP and percentage of non-fatigue controls with SNPs.

Recently others have reported muscarinic acetylcholine receptors (mAChR3) have been found to inhibit TRPM3 via the action of phospholipase C [41y]. Given the present inventors found a significant association with SNPs in TRPM3 and mAChR3 in CFS/ME patients and both these receptors mediate calcium mobilization intracellularly for cell function, such as NK lysis, the present inventors investigated TRPM3 surface expression on NK cells and B lymphocytes and determined this phenotype in CFS/ME patients compared to healthy controls.

In this Example the inventors describe, for the first time, significant reduction in TRPM3 cell surface expression in NK cells and B lymphocytes from CFS/ME patients as well as decreased intracellular calcium.

Methods

Sample preparation and other steps were carried out largely as described in Example 5.

TRPM3 Immunophenotyping Assay

PBMCs were incubated in 20 µl of PCR blocking reagent (Miltenyi Biotech) for 10 minutes at room temperature and washed with phosphate buffer saline (PBS) and centrifuged at 400 g for 5 minutes. Supernatant was removed and incubated with primary fluorochrome labelled antibodies (CD19-BV421 CD3-PerCP, CD56-BV421 and CD16-APC Cy7, BD Bioscience) for 30 minutes at room temperature in the dark. Labelled cells were washed and incubated with J10 µg final concentration of goat anti-human TRPM3 antibody for 30 minutes, followed by a wash and resuspended in a final concentration of 5% (v/v) of Bovine Serum Albumin (Sigma) for 30 minutes. Cells were washed again and incubated with 5 µg final concentration of donkey anti-goat IgG FITC (Santa Cruz) for 30 minutes. Cells were washed cells and resuspended in 200 µl of staining buffer (BD Bioscience) and acquired at 50, 000 events using LSR-Fortessa X-20 (BD Bioscience). Lymphocyte populations were identified using forward scatter and side scatter (FSC, SSC) dot plots. Exclusions were $CD3^+$ cells and only $CD3^-$ lymphocytes were further used to characterize B lymphocytes and NK cell subset populations using CD19, CD56 and CD16. Total B cells were identified as $CD19^+$, whereas NK cell subsets were characterized using the expression of $CD56^{Bright}CD16^{Dim-}$ NK cells, $CD56^{Dim}CD16^{Bright+}$ NK cells and $CD56^-CD16^+$ NK cells. NK lysis, degranulation and lytic proteins were conducted as previously described [42y].

LSRFotessa X-20 Flow cytometry was utilized for sequential determination of cytoplasmic calcium $[Ca2^+]C$ and mitochondrial $[Ca2^+]M$, to help compare cytoplasmic or mitochondrial $Ca^{2+}$ influx kinetics in B lymphocytes and NK cells. Characterizing kinetic measurements using median florescence of Fura-AM or Rhod-2 AM dye were used and smoothing curve method was applied to measure the area under the curve (AUC).

Cytoplasmic Calcium Influx Assay

Following phenotypic staining, the cells were incubated with 0.5 ml staining buffer that contained 0.02% Pluronic® F-127 and 1 µM Fura-red AM or Rhod-2 AM for 30 minutes in the incubator at 37° C. Stained cells were washed with DPBS without calcium and magnesium. Fura AM stained cells were stimulated after 30 seconds of flow cytometric acquisition in the presence of either a final concentration of 1.4 µg streptavidin, 714 ng ionomycin, 50 µg 2-APB or 14 µg Thapsigargin. Data was recorded over 4 minutes. Rhod-2 AM stain cells were incubated for a further 12 hours, prior to acquisition. Thapsigargin is a potent inhibitor for Calcium-ATPases receptors and raises cytoplasmic calcium concentration by inhibiting the ability for the cells to pump calcium into the endoplasmic reticulum (ER). 50 µg 2-aminoethoxydiphenyl borate (2-APB) was used given its inhibition of ER and $IP_3R$. NK receptors (NG2DA and NKp46) were identified for cross-linking for calcium influx for activation, co-activation, and co-stimulation of resting human NK cells, whereas, CD19 and complement receptor CR2 (CD21) responsible for signal transduction and activation of Immunoglobulin M (IgM) were identified for cross-linking for induced calcium influx to enhanced activation of CD19+ B cells.

Statistical Analysis

Statistical analysis was performed using IBM SPSS Statistics version 22 software (SPSS, Chicago, USA). Significance was tested by MANOVA (p<0.05 for significance) between healthy and CPS/ME groups using parameters including TRPM3, intracellular and calcium influx in B lymphocytes and NK cells. Flowjo was employed to analyze FCS files extracted from FACSDiva 8 software (BD Bioscience). Post Hoc test was performed to determine specifically where the significance was between groups (Control and CFS/ME). Levene test was used to analyze homogeneity of variance between groups.

Discussion

The inventors have identified, for the first time, TRPM3 on NK cells and B lymphocytes, and also report a significant reduction of TRPM3 surface expression on B lymphocytes and NK cells in CFS/ME patients compared with healthy controls (see FIG. 3A and FIG. 3B).

The inventors also report, for the first time, a significant reduction in cytoplasmic calcium ion concentration in $CD19^+$ 8 lymphocytes during cross-linking between CD21 and IgM following treatment with stepadividin or thapsigargin in CFS/ME patients (FIG. 4A) as well as $CD56^{Bright}$ NK cells also had a significant decrease in cytoplasmic calcium in the presence of 2-APB and thapsigargin in CFS/ME patients (FIG. 4B). Collectively, these findings suggest TRPM3 play a role in impaired calcium cytoplasmic influx in B lymphocytes and NK cells from CFS/ME patients.

Example 8—Other SNPs and Genotypes in TRP Ion Channel and AChR Genes from Peripheral Blood Mononuclear Cells (PBMCs), Isolated B Lymphocytes and NK Cells in CFS/ME Patients Examples above describe SNPs of TRP ion channel and AChR genes from PBMCs, isolated B lymphocytes and NK cells that scored significantly in a cohort of 115 CFS/ME patients. Using larger cohorts, the inventors believe that other identified SNPs will also score significantly, thus also being useful as probes, tools or reagents for identifying, screening, diagnosing, monitoring or treating subjects with, or predisposed to, medical conditions (or symptoms thereof), such as chronic fatigue syndrome (CFS), myalgic encephalomyelitis (ME), Gulf war syndrome (GWS), irritable bowel syndrome (IBS), multiple chemical sensitivity (MCS), fibromyalgia, and migraine, as well as some medical conditions caused by dysregulation in calcium, acetylcholine and TRP, and dysregulation in the gastrointestinal, cardiovascular, neurological, genitourinary and immune systems.

Identified SNPs that have p values of 0.05 to 0.1, which the inventors believe may score significantly in a larger cohort of patients, are listed in the tables below (Tables 14 to 17). Table 14: Analysis of the frequency distribution and significance of AChR gene SNPs in PBMCs in CFS/ME patients and non-fatigued controls that were not significant in n–115, in rank order of significance.

| Gene | Chromosome | RefSNP ID | A1 | Frequency_A | Frequency_U | A2 | $\chi 2$ | P |
|---|---|---|---|---|---|---|---|---|
| nAchα10 | 11 | rs2672215 | A | 0.4607 | 0.36 | C | 3.399 | 0.07 |
| nAchα2 | 8 | rs6474413 | C | 0.2308 | 0.1513 | T | 3.336 | 0.07 |
| nAchM3 | 3 | rs10926008 | G | 0.3722 | 0.277 | A | 3.333 | 0.07 |
| nAchα2 | 8 | rs2741343 | C | 0.5337 | 0.4324 | T | 3.317 | 0.07 |
| nAchα5 | 15 | rs7178270 | G | 0.3571 | 0.4539 | C | 3.231 | 0.07 |
| nAchα5 | 15 | rs4243084 | G | 0.3977 | 0.3026 | C | 3.227 | 0.07 |
| nAchα5 | 15 | rs601079 | A | 0.3901 | 0.4868 | T | 3.155 | 0.08 |
| nAchα5 | 15 | rs12911602 | C | 0.3901 | 0.4868 | T | 3.155 | 0.08 |
| nAchα5 | 15 | rs588765 | T | 0.3846 | 0.4803 | C | 3.095 | 0.08 |
| nAchα5 | 15 | rs680244 | A | 0.3846 | 0.4803 | G | 3.095 | 0.08 |
| nAchα5 | 15 | rs6495306 | G | 0.3895 | 0.4863 | A | 3.01 | 0.08 |
| nAchα5 | 15 | rs6495307 | T | 0.4111 | 0.5068 | C | 2.997 | 0.08 |
| mAchM3 | 3 | rs12093821 | A | 0.489 | 0.3947 | G | 2.979 | 0.08 |
| mAchM3 | 3 | rs16838637 | G | 0.4889 | 0.3947 | A | 2.957 | 0.09 |
| nAchα2 | 8 | rs6997909 | A | 0.2333 | 0.1579 | G | 2.945 | 0.09 |
| nAchα10 | 11 | rs2672216 | C | 0.4888 | 0.3947 | T | 2.934 | 0.09 |
| nAchM3 | 3 | rs6429165 | A | 0.2473 | 0.1711 | G | 2.873 | 0.09 |
| nAchα2 | 8 | rs891398 | C | 0.533 | 0.4392 | T | 2.872 | 0.09 |
| nAchα5 | 15 | rs4366683 | G | 0.3956 | 0.4868 | A | 2.802 | 0.09 |
| nAchα2 | 8 | rs6985052 | C | 0.2308 | 0.1579 | T | 2.774 | 0.10 |
| nAchα2 | 8 | rs4950 | C | 0.2308 | 0.1579 | T | 2.774 | 0.10 |

TABLE 15

Analysis of the frequency distribution and significance of TRP receptor gene SNPs in PBMCs in CFS/ME patients and non-fatigued controls that were not significant in n = 115, in rank order of significance.

| Gene | Chromosome | RefSNP ID | A1 | Frequency_A | Frequency_U | A2 | $\chi 2$ | P |
|---|---|---|---|---|---|---|---|---|
| TRPM4 | 19 | rs10403114 | G | A | 0.293 | 0.390 | 3.302 | 0.051 |
| TRPV3 | 17 | rs9909424 | G | A | 0.115 | 0.060 | 3.442 | 0.664 |
| TRPC4 | 13 | rs612308 | A | G | 0.439 | 0.537 | 3.393 | 0.065 |
| TRPM3 | 9 | rs7860377 | A | C | 0.350 | 0.262 | 3.314 | 0.069 |
| TRPC7 | 5 | rs2673930 | C | A | 0.200 | 0.280 | 3.218 | 0.073 |
| TRPC4 | 13 | rs603955 | C | T | 0.445 | 0.536 | 3.008 | 0.083 |
| TRPM3 | 9 | rs11142798 | C | G | 0.135 | 0.202 | 2.998 | 0.083 |
| TRPM3 | 9 | rs4744611 | G | A | 0.360 | 0.446 | 2.843 | 0.092 |
| TPPM2 | 21 | rs1785452 | T | C | 0.215 | 0.289 | 2.67 | 0.102 |
| TRPM3 | 9 | rs1566838 | G | T | 0.460 | 0.375 | 2.669 | 0.102 |
| TRPA1 | 8 | rs1384002 | T | C | 0.495 | 0.410 | 2.664 | 0.103 |

TABLE 15-continued

Analysis of the frequency distribution and significance of TRP receptor gene SNPs in PBMCs in CFS/ME patients and non-fatigued controls that were not significant in n = 115, in rank order of significance.

| Gene | Chromosome | RefSNP ID | A1 | Frequency_A | Frequency_U | A2 | γ2 | P |
|---|---|---|---|---|---|---|---|---|
| TRPM6 | 9 | rs2274924 | G | A | 0.115 | 0.175 | 2.652 | 0.103 |
| TRPM3 | 9 | rs1394309 | G | A | 0.030 | 0.065 | 2.608 | 0.106 |
| TRPC4 | 13 | rs2985167 | G | A | 3.340 | 0.422 | 2.577 | 0.108 |
| TRPM5 | 11 | rs2301698 | G | T | 0.530 | 0.446 | 2.551 | 0.110 |
| TRPM6 | 9 | rs944857 | C | T | 0.185 | 0.125 | 2.476 | 0.116 |
| TRPM2 | 21 | rs762426 | G | A | 0.160 | 0.223 | 2.325 | 0.127 |

TABLE 16

Analysis of the frequency distribution and significance of AChR and TRP gene SNPs in isolated NK cells in CFS/ME patients (n = 39) and non-fatigued controls (n = 30) that were not significant, in rank order of significance.

| Gene | CHR | SNP | BP | MAF | A1 | F_A | F_U | A2 | CHISQ | P | OR |
|---|---|---|---|---|---|---|---|---|---|---|---|
| CHRM5 | 15 | rs623941 | 34060377 | 0.362221 | C | 0.4211 | 0.25 | A | 3.76 | 0.05249 | 2.182 |
| CHRNA3 | 15 | rs615470 | 78593646 | 0.291134 | T | 0.2895 | 0.45 | C | 3.749 | 0.05285 | 0.4979 |
| CHRNA3 | 15 | rs7182583 | 78606868 | 0.271565 | C | 0.2895 | 0.45 | G | 3.749 | 0.05285 | 0.4979 |
| CHRM3 | 1 | rs536071 | 2.4E+08 | 0.352236 | C | 0.4615 | 0.3 | T | 3.715 | 0.05391 | 2 |
| CHRM3 | 1 | rs693948 | 2.4E+08 | 0.446486 | G | 0.4605 | 0.3 | A | 3.633 | 0.05665 | 1.992 |
| TRPM3 | 9 | rs4620343 | 71121727 | 0.428115 | T | 0.3718 | 0.5345 | C | 3.571 | 0.05879 | 0.5155 |
| CHRNA5 | 15 | rs495956 | 78577588 | 0.308307 | G | 0.2949 | 0.45 | A | 3.532 | 0.06019 | 0.5111 |
| CHRNA5 | 15 | rs692780 | 78584163 | 0.5 | G | 0.2949 | 0.45 | C | 3.532 | 0.06019 | 0.5111 |
| CHRNA5 | 15 | rs11637635 | 78384808 | 0.254593 | A | 0.2949 | 0.45 | G | 3.532 | 0.06019 | 0.5111 |
| CHRNA3 | 15 | rs17408276 | 78589276 | 0.208866 | C | 0.2949 | 0.45 | T | 3.532 | 0.06019 | 0.5111 |
| CHRNA3 | 15 | rs660652 | 78595490 | 0.256989 | A | 0.2949 | 0.45 | G | 3.532 | 0.06019 | 0.5111 |
| CHRNA3 | 15 | rs472054 | 78595652 | 0.256989 | T | 0.2949 | 0.45 | C | 3.532 | 0.06019 | 0.5111 |
| TRPC4 | 13 | rs6650469 | 17793812 | 0.399561 | T | 0.5256 | 0.3667 | C | 3.434 | 0.06308 | 1.914 |
| CHRNB4 | 15 | rs1316971 | 78638168 | 0.442492 | A | 0.141 | 0 2667 | G | 3.402 | 0.06513 | 0.4515 |
| CHRNA3 | 15 | rs4887070 | 78623845 | 0 339457 | C | 0.2692 | 0.4167 | T | 3.317 | 0.06855 | 0.5158 |
| CHRM5 | 15 | rs8035849 | 34058132 | 0.34385 | A | 0.359 | 0.2167 | C | 3.289 | 0.06976 | 2.025 |
| CHRM3 | 1 | rs606709 | 2.4E+08 | 0.347444 | T | 0.4342 | 0.2833 | C | 3.283 | 0.07 | 1.941 |
| TRPC2 | 11 | rs2898934 | 3623827 | 0 14996 | C | 0.1795 | 0.07143 | A | 3.273 | 0.07042 | 2.844 |
| TRPM8 | 2 | rs10170647 | 2.34E+08 | 0.207867 | G | 0.1053 | 0.2167 | T | 3.187 | 0.07423 | 0.4253 |
| CHRN7 | 15 | rs2337980 | 32151995 | 0.375 | T | 0.3974 | 0.55 | C | 3.174 | 0.07482 | 0.5397 |
| CHRNA3 | 15 | rs514743 | 78591885 | 0.241214 | T | 0.3026 | 0.45 | A | 3.132 | 0.07676 | 0.5304 |
| CHRND | 2 | rs2853446 | 2.33E+08 | 0.480232 | C | 0.5526 | 0.4 | T | 3.127 | 0.077 | 5 653 |
| CHRND | 2 | rs224601 | 2.33E+08 | 0.483427 | T | 0.5513 | 0.4 | C | 3.107 | 0.07795 | 1.843 |
| CHRM3 | 1 | rs6701181 | 2.4E+08 | 0.491014 | T | 0.3846 | 0.5333 | C | 3.031 | 0.08167 | 0.5469 |
| TRPV4 | 12 | rs3825394 | 1.1E+08 | 0.245607 | A | 0.3846 | 0.5333 | C | 3 031 | 0.08167 | 0.5469 |
| TRPV4 | 12 | rs1861809 | 1.1E+08 | 0.239617 | T | 0.3846 | 0.5333 | C | 3 031 | 0.08167 | 0.5469 |
| CHRND | 2 | rs2278478 | 2.33E+08 | 0.272564 | C | 0.1974 | 0.3276 | T | 2.946 | 0.0861 | 0.5047 |
| TRPC4 | 13 | rs655207 | 37793875 | 0.388179 | G | 0.5128 | 0.3664 | T | 2.928 | 0.08707 | 1.818 |
| CHRNE | 12 | rs3075763 | 4899390 | 0.10623 | T | 0.05128 | 0.1333 | C | 2.876 | 0.08993 | 0.3514 |
| TRPM3 | 9 | rs10123815 | 71068915 | 0.1248 | G | 0 | 0.03571 | A | 2.828 | 0.09264 | 0 |
| TRPC6 | 11 | rs6578397 | 3614380 | 0.427516 | T | 0.3846 | 0.25 | A | 2.797 | 0.09447 | 1.875 |
| CHRM3 | 1 | rs12036141 | 2.4E+08 | 0.173442 | A | 0.3553 | 0.5 | G | 2.779 | 0.09551 | 0.551 |
| TRPV4 | 12 | rs10850783 | 1.1E+08 | 0.273163 | A | 0.3947 | 0.5333 | C | 2.596 | 0.1071 | 0.5707 |

TABLE 17

Analysis of the frequency distribution and significance of AChR and TRP gene SNPs in isolated B lymphocytes in CFS/ME patients (n = 11) and non-fatigued controls (n = 11) that were not significant, in rank order of significance.

| Gene | CHR | SNP | BP | A1 | F_A | F_U | A2 | CHISQ | P | OR |
|---|---|---|---|---|---|---|---|---|---|---|
| CHRM3 | 1 | rs10764677 | 239669799 | G | 0.3846 | 0.625 | A | 3.819 | 0.05066 | 0.375 |
| CHRM3 | 1 | rs7513746 | 239699110 | G | 0.3889 | 0.625 | A | 3.727 | 0.05353 | 0.3818 |
| CHRM3 | 1 | rs10802795 | 239707474 | C | 0.3889 | 0.625 | T | 3.727 | 0.05353 | 0.3818 |
| CHRM3 | 1 | rs3738436 | 239709192 | A | 0.3889 | 0.625 | C | 3.727 | 0.05353 | 0.3818 |
| CHRM3 | 1 | rs7511970 | 239719954 | A | 0.3889 | 0.625 | G | 3.727 | 0.05353 | 0.3818 |
| CHRM3 | 1 | rs1155611 | 239735676 | T | 0.3889 | 0.625 | C | 3.727 | 0.05353 | 0.3818 |
| CHRM3 | 1 | rs1019882 | 239735555 | G | 0.3889 | 0.625 | A | 3.727 | 0.05353 | 0.3818 |
| CHRM3 | 1 | rs1416789 | 239738344 | G | 0.3889 | 0.625 | A | 3.727 | 0.05353 | 0.3818 |
| CHRM3 | 1 | rs10925964 | 239739213 | A | 0.3889 | 0.625 | T | 3.727 | 0.05353 | 0.3818 |
| TRPV2 | 17 | rs8079010 | 16425640 | C | 0.4815 | 0.25 | T | 3.65 | 0.05508 | 2.786 |
| CHRM3 | 1 | rs6429154 | 239713965 | G | 0.3929 | 0.625 | A | 3.642 | 0.05634 | 0.3882 |
| CHRNB1 | 17 | rs2302762 | 7447224 | C | 0.2778 | 0.5 | T | 3.625 | 0.05691 | 0.3846 |

TABLE 17-continued

Analysis of the frequency distribution and significance of AChR and TRP gene SNPs in isolated B lymphocytes in CFS/ME patients (n = 11) and non-fatigued controls (n = 11) that were not significant, in rank order of significance.

| Gene | CHR | SNP | BP | A1 | F_A | F_U | A2 | CHISQ | P | OR |
|---|---|---|---|---|---|---|---|---|---|---|
| TRPM3 | 9 | rs7038646 | 7822907 | A | 0.4808 | 0.25 | G | 3.621 | 0.05706 | 2.778 |
| CHRNA2 | 8 | rs2741342 | 27472578 | A | 0.1786 | 0.375 | G | 3.579 | 0.0585 | 0.3623 |
| CHRND | 3 | rs4973536 | 232527170 | C | 0.3571 | 0.5909 | G | 3.536 | 0.06004 | 0.3846 |
| C17orfI07 | 17 | rs33978919 | 4899033 | A | 0.07407 | 0.2273 | G | 3.514 | 0.06085 | 0.272 |
| TRPM3 | 9 | rs1891301 | 71403579 | T | 0.5577 | 0.3333 | C | 3.309 | 0.06892 | 2.522 |
| CHRM3 | 1 | rs12406493 | 239689804 | C | 0.5556 | 0.3333 | A | 3.284 | 0.06995 | 2.5 |
| CHRM3 | 1 | rs6429152 | 239690836 | G | 0.5556 | 0.3333 | A | 3.284 | 0.06995 | 2.5 |
| CHRM3 | 1 | rs2355237 | 239694223 | A | 0.5556 | 0.3333 | G | 3.284 | 0.06995 | 2.5 |
| CHRM3 | 1 | rs988231 | 239696189 | C | 0.5556 | 0.3333 | T | 3.284 | 0.06995 | 2.5 |
| CHRM3 | 1 | rs217227 | 239719298 | C | 0.5556 | 0.3333 | T | 3.284 | 0.06995 | 2.5 |
| TRPM3 | 9 | rs1106948 | 71402257 | T | 0.5556 | 0.3333 | C | 3.262 | 0.07092 | 2.48 |
| CHRNA2 | 8 | rs2565048 | 27472614 | C | 0.125 | 0.2917 | T | 3.232 | 0.0722 | 0.3469 |
| CHRNB1 | 17 | rs2302762 | 7455541 | T | 0.2778 | 0.5 | C | 3.222 | 0.07267 | 0.3846 |
| CHRM3 | 1 | rs1431719 | 239717902 | G | 0.4038 | 0.625 | A | 3.221 | 0.07268 | 0.4065 |
| AVEN | 15 | rs2702282 | 34023860 | G | 0.4643 | 0.25 | T | 3.215 | 0.073 | 2.6 |
| CHRM3 | 1 | rs6693851 | 239678896 | C | 0.3182 | 0.5455 | T | 3.173 | 0.07486 | 0.3889 |
| CHRM3 | 1 | rs2278642 | 239703842 | T | 0.4074 | 0.625 | G | 3.155 | 0.07569 | 0.4125 |
| CHRM3 | 1 | rs12751235 | 23976520 | T | 0.4074 | 0.625 | C | 3.155 | 0.07569 | 0.4125 |
| CHRM3 | 1 | rs6663633 | 239714420 | A | 0.4074 | 0.625 | C | 3.155 | 0.07569 | 0.4125 |
| CHRM3 | 1 | rs665159 | 239798701 | G | 0.4074 | 0.625 | T | 3.155 | 0.07569 | 0.4125 |
| TRPM4 | 19 | rs12461216 | 49160966 | C | 0.07143 | 0.2083 | G | 3.154 | 0.07575 | 0.2923 |
| CHRM3 | 1 | rs714803 | 239631122 | T | 0.3704 | 0.5833 | A | 3.065 | 0.08001 | 0.4202 |
| CHRM3 | 1 | rs2120241 | 239645190 | T | 0.2885 | 0.5 | A | 3.035 | 0.08146 | 0.4054 |
| AC009264.1 | 7 | rs1455858 | 136946955 | A | 0.5 | 0.2917 | G | 2.963 | 0.08519 | 2.429 |
| AC009264.1 | 7 | rs1378646 | 136950253 | G | 0.5 | 0.2917 | A | 2.963 | 0.08519 | 2.429 |
| AC009264.1 | 7 | rs1158586 | 136952388 | G | 0.5 | 0.2917 | A | 2.963 | 0.08519 | 2.429 |
| AC009264.1 | 7 | rs1455857 | 136955193 | A | 0.5 | 0.2917 | G | 2.963 | 0.08519 | 2.429 |
| CHRM3 | 1 | rs685548 | 239831605 | T | 0.5 | 0.2917 | G | 2.933 | 0.0868 | 2.429 |
| CHRM3 | 1 | rs16839070 | 239900649 | T | 0.3571 | 0.1667 | A | 2.902 | 0.08844 | 2.778 |
| CHRNG | 2 | rs2697782 | 232542805 | C | 0.3571 | 0.1667 | G | 2.902 | 0.08844 | 2.778 |
| CHRNB2 | 1 | rs2072660 | 154576244 | T | 0.1964 | 0.375 | C | 2.857 | 0.09097 | 0.4074 |
| TRPM7 | 15 | rs4775894 | 50611402 | T | 0.4375 | 0.2273 | C | 2.856 | 0.09105 | 2.644 |
| CHRM3 | 1 | rs6657343 | 239728210 | T | 0.537 | 0.3333 | A | 2.765 | 0.09634 | 2.32 |
| CHRM3 | 1 | rs891700 | 239718625 | A | 0.5457 | 0.3333 | G | 2.759 | 0.09669 | 2.308 |
| AC018890.6 | 2 | rs2600685 | 174762319 | G | 0.4464 | 0.25 | A | 2.731 | 0.09841 | 2.419 |
| AVEN | 15 | rs1685119 | 33984851 | G | 0.4464 | 0.25 | A | 2.731 | 0.09841 | 2.419 |
| AVEN | 15 | rs489832 | 33985705 | A | 0.4464 | 0.25 | G | 2.731 | 0.09841 | 2.419 |
| AC009264.1 | 7 | rs2113550 | 136881785 | G | 0.2963 | 0.5 | A | 2.657 | 0.1031 | 0.4211 |
| AC009264.1 | 7 | rs6944132 | 136885528 | T | 0.4444 | 0.25 | A | 2.654 | 0.1033 | 2.4 |
| CHRNA10 | 11 | rs2672214 | 3670281 | C | 0.4259 | 0.2273 | T | 2.651 | 0.1035 | 2.523 |
| CHRM3 | 1 | rs658842 | 239785334 | T | 0.4259 | 0.625 | A | 2.636 | 0.1045 | 0.4452 |
| TRPV2 | 17 | rs8121 | 16422653 | C | 0.375 | 0.1667 | T | 2.619 | 0.1056 | 3 |

Example 9—Exome Sequencing for Determining SNPs and Genotypes in TRP Ion Channel and AChR Genes from Isolated B Lymphocytes in CFS/ME Patients Example 6 above describes SNPs and genotypes in TRP ion channel and AChR genes from isolated B lymphocytes in ME/CFS patients. In this Example the inventors utilise exome sequencing to characterise SNPs and genotypes in TRP ion channel and AChR genes from isolated B lymphocytes in ME/CFS patients.

Methods

For details of the subjects and sample preparation, see Example 6.

DNA Extraction

Genomic DNA was extracted from all whole blood samples using the Qiagen DNA blood mini-kit as per manufacturer's instructions (Qiagen). The Nanodrop (Nanodrop) was used to assess the quality and quantity of the DNA extracted. Approximately 2 µg of genomic DNA was used in the SNP assay.

DNA Quantification and Qualification

DNA degradation and contamination was monitored on 1% agarose gels.

(1) DNA purity was checked using the NanoPhotometer® spectrophotometer (IMPLEN, Calif., USA).

(2) DNA concentration was measured using Qubit® DNA Assay Kit in Qubit® 2.0 Flurometer (Life Technologies, CA, USA).

(3) Fragment distribution of DNA library was measured using the DNA Nano 6000 Assay Kit of Agilent Bioanalyzer 2100 system (Agilent Technologies, CA, USA).

Library Preparation for Sequencing

A total amount of 1 µg genomic DNA per sample was used as input material for the DNA sample preparation. Sequencing libraries were generated using Agilent Sure Select Human All ExonV5 kit (Agilent Technologies, CA, USA) following manufacturer's recommendations and x index codes were added to attribute sequences to each sample. Briefly, fragmentation was carried out by hydrodynamic shearing system (Covaris, Massachusetts, USA) to generate 180-280 bp fragments. Remaining overhangs were converted into blunt ends via exonuclease/polymerase activities and enzymes were removed. After adenylation of 3' ends of DNA fragments, adapter oligonucleotides were ligated. DNA fragments with ligated adapter molecules on both ends were selectively enriched in a PCR reaction. After PCR reaction, the library was hybridized with Liquid phase with biotin labeled probe, then magnetic beads with streptomycin were used to capture the 334,378 exons in 20, 965 genes. Captured libraries were enriched in a PCR reaction to add index tags to prepare for hybridization. Products were purified using AMPure XP system (Beckman Coulter, Beverly, USA) and quantified using the Agilent high sensitivity DNA assay on the Agilent Bioanalyzer 2100 system.

Clustering and Sequencing

If library qualities, the clustering of the index-coded samples was performed on a cBot Cluster Generation System using TruSeq PE Cluster Kit v4-cBot-HS (Illumia, San Diego, USA) according to the manufacturer's instructions. After cluster generation, the library preparations were sequenced on an Illumina platform and 125 bp paired-end reads were generated.

Analysis Result

Raw Data

The original raw data obtained from high throughput sequencing platforms (e.g. illumina platform) was transformed to sequenced reads by base calling and recorded in FASTQ file (which contains sequence information (reads) and corresponding sequencing quality information) as explained in Section 4.1 of Novogene Bioinformatics Technology Co., Ltd's document entitled "Novogene—Cancer Project Report (2014, 11), which is accessible at www.filgen.ip/Product/Bioscience5-seq/Cancer_WGS_report_V1.1.pdf.

informatics Technology Co., Ltd's document entitled "Novogene—Cancer Project Report (2014, 11), which is accessible at www.filgen.ip/Product/Bioscience5-seq/Cancer_WGS_report_V1.1.pdf.

Sequencing Quality Distribution

Sequence quality distribution was carried out as explained in Section 4.2.4 of Novogene Bioinformatics Technology Co., Ltd's document entitled "Novogene—Cancer Project Report (2014, 11), which is accessible at www.filgen.ip/Product/Bioscience5-seq/Cancer_WGS_report_V1.1.pdf.

To ensure downstream analysis, most base quality is required to be greater than Q20. According to sequencing feature, base quality in sequence end is usually lower than that in sequence beginning.

Statistics Summary of Sequencing Quality

According to the illumina platform sequencing feature, for PE data the average percentage of Q20 was required to be above 90%, Q30 was required to be above 80%, average error rate was required to be below 0.1%. (See Section 4.2.5 of Novogene Bioinformatics Technology Co., Ltd's document entitled "Novogene—Cancer Project Report (2014, 11), which is accessible at www.filgen.ip/Product/Bioscience5-seq/Cancer_WGS_report_V1.1.pdf.

TABLE 18

Overview of data production quality

| Sample name | Library | Lane | Raw reads | Raw data (G) | Raw depth (x) | Effective (%) | Error (%) | Q20 (%) | Q30 (%) | GC (%) |
|---|---|---|---|---|---|---|---|---|---|---|
| SEV1114047 | DHE01587 | HCWL3CCXX_L6 | 25814640 | 7.74 | 153.6 | 98.92 | 0.04 | 94.23 | 86.82 | 48.55 |
| SEV1114046 | DHE01595 | HF5KJCCXX_L5 | 27668541 | 8.3 | 164.71 | 98.96 | 0.03 | 96.29 | 90.78 | 48.45 |
| SEV1114065 | DHE01585 | HCWL3CCXX_L3 | 21195532 | 6.36 | 126.21 | 98.59 | 0.04 | 94.82 | 88.25 | 48.64 |
| SEV1114064 | DHE01594 | HF5KJCCXX_L5 | 21146920 | 6.34 | 126.82 | 98.93 | 0.03 | 96.25 | 90.69 | 48.89 |
| SEV1114001 | DHE01605 | HF5KJCCXX_L4 | 27647015 | 8.29 | 164.51 | 98.87 | 0.03 | 96.36 | 90.97 | 48.77 |
| SEV1114066 | DHE01602 | HF5KJCCXX_L7 | 22154417 | 6.65 | 131.97 | 98.71 | 0.03 | 95.08 | 88.41 | 49.27 |
| SEV1114006 | DHE01584 | HCWL3CCXX_L6 | 20859072 | 6.26 | 124.23 | 98.80 | 0.04 | 94.28 | 86.84 | 48.28 |
| SEV1114049 | DHE01582 | HCWL3CCXX_L4 | 23731273 | 7.12 | 141.3 | 98.98 | 0.04 | 95.06 | 88.68 | 48.86 |
| SEV1114020 | DHE01601 | HF5KJCCXX_L5 | 25066003 | 7.52 | 149.23 | 98.37 | 0.03 | 96.44 | 91.08 | 49.22 |
| SEV1114022 | DHE01598 | HF5KJCCXX_L5 | 20484764 | 6.15 | 122.05 | 98.87 | 0.03 | 96.26 | 90.68 | 48.52 |
| SEV1114025 | DHE01591 | HF5KJCCXX_L5 | 25343055 | 7.6 | 150.82 | 98.87 | 0.03 | 96.3 | 90.8 | 49.0 |
| SEV1114026 | DHE01593 | HF5KJCCXX_L5 | 24210778 | 7.26 | 144.07 | 99.06 | 0.03 | 96.18 | 90.57 | 48.98 |
| SEV1114029 | DHE01604 | HF5KJCCXX_L4 | 22825090 | 6.85 | 135.94 | 98.77 | 0.03 | 96.22 | 90.69 | 47.81 |
| SEV1114052 | DHE01592 | HF5JCCXX_L5 | 22862429 | 6.86 | 136.14 | 98.98 | 0.03 | 96.13 | 90.41 | 48.09 |
| SEV1114054 | DHE01586 | HCWL3CCXX_L6 | 18507970 | 6.76 | 134.15 | 98.85 | 0.05 | 94.03 | 86.41 | 48.08 |
| SEV1114054 | DHE01586 | H3LLHBBXX_L2 | 4044682 | | | 98.82 | 0.03 | 95.16 | 89.02 | 47.95 |
| SEV1114055 | DHE01603 | HF5KJCCXX_L4 | 28499810 | 8.55 | 169.67 | 98.80 | 0.03 | 96.43 | 91.09 | 49.28 |
| SEV1114056 | DHE01590 | HCWL3CCXX_L3 | 22338448 | 6.7 | 132.92 | 98.92 | 0.04 | 93.91 | 86.43 | 48.62 |
| SEV1114033 | DHE01588 | HCWL3CCXX_L6 | 24351080 | 7.31 | 145.07 | 98.82 | 0.07 | 92.06 | 92.06 | 48.48 |
| SEV1114017 | DHE01560 | HCWL3CCXX_L3 | 19811998 | 6.79 | 134.75 | 98.66 | 0.04 | 94.84 | 88.22 | 48.42 |
| SEV1114017 | DHE01580 | H3LLHBBXX_L2 | 2841615 | | | 98.65 | 0.03 | 95.22 | 89.11 | 48.33 |
| SEV1114036 | DHE01599 | HF5KJCCXX_L5 | 29249682 | 8.77 | 174.04 | 98.76 | 0.03 | 96.5 | 91.19 | 49.01 |
| SEV1114013 | DHE01597 | HF5KJCCXX_L5 | 20799394 | 6.24 | 123.83 | 98.85 | 0.03 | 96.31 | 90.81 | 48.97 |
| SEV1114038 | DHE01583 | HCWL3CCXX_L6 | 22737075 | 6.82 | 135.34 | 98.35 | 0.04 | 94.27 | 86.93 | 44.61 |
| SEV1114035 | DHE01600 | HF5KJCCXX_L5 | 23864253 | 7.16 | 142.09 | 98.86 | 0.03 | 95.94 | 90.01 | 49.42 |
| SEV1114018 | DHE01596 | HF5KJCCXX_L5 | 26046285 | 7.81 | 154.99 | 98.89 | 0.03 | 96.34 | 90.87 | 48.28 |
| SEV1114019 | DHE01581 | HCWL3CCXX_L6 | 22847621 | 6.85 | 135.94 | 98.75 | 0.04 | 94.37 | 87.01 | 48.7 |
| SEV1114067 | DHE01589 | HCWL3CCXX_L6 | 29636240 | 8.89 | 176.42 | 99.09 | 0.05 | 94.06 | 86.52 | 48.18 |

Quality Control

Sequencing Data Filtration

The steps of data processing undertaken were as explained in Section 4.2.1 of Novogene Bioinformatics Technology Co., Ltd's document entitled "Novogene—Cancer Project Report (2014, 11), which is accessible at www-.filgen.ip/Product/Bioscience5-seq/Cancer_WGS_report_V1.1.pdf.

Sequencing Error Rate Distribution

A Phred score of a base (Phred score, Qphred) was calculated as explained in Section 4.2.2 of Novogene Bio- Note:

Sample name: Sample name

Library: Library name

Lane: The flowcell ID and lane number of she sequencing machine

Raw reads: The number of sequencing reads pairs; According to the format of FASTQ, four lines will be considered as one unit Raw data: The original sequence data Raw depth: The original sequence depth Effective: The percentage of clean reads in all raw reads Error: The average error rate of all bases on read1 and read2; the error rate of a base is obtained from equation No. 1

Q20, Q30: Percentage of reads with average quality>Q20 and percentage of reads with average quality>Q30

GC: Percentage of G and C in the total bases

Sequence Alignment

Sequence alignment was carried out as explained in Section 4.3 of Novogene Bioinformatics Technology Co., Ltd's document entitled "Novogene—Cancer Project Report (2014, 11), which is accessible at www.filgen.ip/Product/Bioscience5-seq/Cancer_WGS_report_V1.1.pdf.

Sequencing Depth, Coverage Distribution

Sequence depth, coverage and distribution was carried out as explained in Section 4.3.1 of Novogene Bioinformatics Technology Co., Ltd's document entitled "Novogene—Cancer Project Report (2014, 11), which is accessible at www-.filgen.ip/Product/Bioscience5-seq/Cancer_WGS_report_V1.1.pdf.

Statistics of Coverage

TABLE 19

| Mapping rate and coverage | | | | | | | |
|---|---|---|---|---|---|---|---|
| | Sample: | | | | | | |
| | SEV1114001 | SEV1114006 | SEV1114013 | SEV1114017 | SEV1114018 | SEV1114019 | SEV1114020 |
| Total:[1] | 54670194 (100%) | 41215750 (100%) | 41119412 (100%) | 44696626 (100%) | 51514900 (100%) | 45124448 (100%) | 49314848 (100%) |
| Duplicate:[2] | 4135812 (7.57%) | 3511317 (8.55%) | 2941076 (7.16%) | 3498605 (7.84%) | 3940121 (7.65%) | 4269190 (9.48%) | 4144231 (8.41%) |
| Mapped:[3] | 54602797 (99.88%) | 41065284 (99.63%) | 41086392 (99.92%) | 44649355 (99.89%) | 51477839 (99.93%) | 45047006 (99.83%) | 49279459 (99.93%) |
| Properly mapped:[4] | 54360518 (99.43%) | 40813320 (99.02%) | 40857002 (99.36%) | 44367034 (99.26%) | 51194750 (99.38%) | 44803432 (99.29%) | 49026366 (99.42%) |
| PE mapped:[5] | 54563548 (99.80%) | 41040922 (99.58%) | 41058450 (99.85%) | 44619616 (99.83%) | 51447768 (99.87%) | 45022618 (99.77%) | 49250278 (99.87%) |
| SE mapped:[6] | 78498 (0.14%) | 48724 (0.12%) | 55884 (0.14%) | 59478 (0.13%) | 60142 (0.12%) | 48776 (0.11%) | 58362 (0.12%) |
| With mate mapped to a different chr:[7] | 142924 (0.26%) | 149738 (0.36%) | 154072 (0.37%) | 170022 (0.38%) | 183192 (0.35%) | 162664 (0.36%) | 162730 (0.33%) |
| With mate mapped to a different chr ((mapQ >= 5)):[8] | 101328 (0.19%) | 112180 (0.27%) | 117932 (0.29%) | 124944 (0.28%) | 137490 (0.27%) | 118673 (0.26%) | 119873 (0.24%) |
| Initial_bases_on_target:[9] | 50390601 | 50390601 | 50390601 | 50390601 | 50390601 | 50390601 | 50390601 |
| Initial_bases_near_target:[10] | 73902222 | 73902222 | 73902222 | 73902222 | 73902222 | 73902222 | 73902222 |
| Initial_bases_on_or_near_target:[11] | 124292823 | 124292823 | 124292823 | 124292823 | 124292823 | 124292823 | 124292823 |
| Total_effective_reads:[12] | 54724346 | 41165446 | 41184155 | 44768806 | 51605973 | 45163755 | 49397515 |
| Total_effective_yield(Mb):[13] | 8135.35 | 6105.14 | 6122.14 | 6634.39 | 7670.35 | 6697.31 | 7342.94 |
| Effective_sequences_on_target(Mb):[14] | 5037.78 | 3704.62 | 3854.15 | 4072.38 | 4711.59 | 4101.86 | 4687.35 |
| Effective_sequences_near_target(Mb):[15] | 2000.96 | 1390.06 | 1452.36 | 1471.79 | 1798.55 | 1497.86 | 1721.88 |
| Effective_sequences_on_or_near_target(Mb):[16] | 7038.73 | 5094.68 | 5306.51 | 5544.17 | 6510.14 | 5599.71 | 6409.23 |
| Fraction_of_effective_bases_on_target:[17] | 61.9% | 60.7% | 63.0% | 61.4% | 61.4% | 61.2% | 63.8% |
| Fraction_of_effective_bases_on_or_near_target:[18] | 86.5% | 83.4% | 86.7% | 83.6% | 84.9% | 83.6% | 87.3% |
| Average_sequencing_depth_on_target:[19] | 99.97 | 73.52 | 76.49 | 80.82 | 93.50 | 81.40 | 93.02 |
| Average_sequencing_depth_near_target:[20] | 27.08 | 18.81 | 19.65 | 19.92 | 24.34 | 20.27 | 23.30 |
| Mismatch_rate_in_target_region:[21] | 0.42% | 0.71% | 0.42% | 0.66% | 0.42% | 0.70% | 0.41% |
| Mismatch_rate_in_all_effective_sequence:[22] | 0.36% | 0.60% | 0.37% | 0.56% | 0.36% | 0.58% | 0.36% |
| Base_covered_on_target:[23] | 50339057 | 50272295 | 50289269 | 50280756 | 50288070 | 50282958 | 50293685 |
| Coverage_of_target_region:[24] | 99.9% | 99.8% | 99.8% | 99.8% | 99.8% | 99.8% | 99.8% |
| Base_covered_near_target:[25] | 72376506 | 70567761 | 70990893 | 70387626 | 71749373 | 70491462 | 71357622 |
| Coverage_of_flanking_region:[26] | 97.9% | 95.5% | 96.1% | 95.2% | 97.1% | 95.4% | 96.6% |
| Fraction_of_target_covered_with_at_least_20×:[27] | 97.9% | 95.5% | 96.0% | 96.5% | 97.6% | 96.8% | 97.5% |
| Fraction_of_target_covered_with_at_least_10×:[28] | 99.4% | 98.8% | 99.0% | 99.1% | 99.3% | 99.2% | 99.3% |

TABLE 19-continued

| Mapping rate and coverage | | | | | | | |
|---|---|---|---|---|---|---|---|
| Fraction_of_target_covered_with_at_least_4x:[29] | 99.8% | 99.6% | 99.6% | 99.6% | 99.7% | 99.7% | 99.7% |
| Fraction_of_flanking_region_covered_with_at_least_20x:[30] | 46.1% | 33.5% | 35.3% | 34.9% | 41.8% | 35.8% | 40.2% |
| Fraction_of_flanking_region_covered_with_at_least_10x:[31] | 67.4% | 54.7% | 56.7% | 55.0% | 62.5% | 56.0% | 60.7% |
| Fraction_of_flanking_region_covered_with_at_least_4x:[32] | 87.7% | 78.6% | 80.3% | 78.0% | 84.2% | 78.7% | 82.6% |

| | Sample: | | | | | | |
|---|---|---|---|---|---|---|---|
| | SEV1114022 | SEV1114025 | SEV1114026 | SEV1114029 | SEV1114033 | SEV1114035 | SEV1114036 |
| Total:[1] | 40507428 (100%) | 50114094 (100%) | 47968266 (100%) | 45088696 (100%) | 48126088 (100%) | 47184402 (100%) | 57776330 (100%) |
| Duplicate:[2] | 2635177 (6.51%) | 4614914 (9.22%) | 3701115 (7.72%) | 3291977 (7.31%) | 4227445 (8.81%) | 3728944 (7.91%) | 5746777 (9.95%) |
| Mapped:[3] | 40477086 (99.93%) | 50074792 (99.92%) | 47924335 (99.91%) | 45031444 (99.87%) | 47995758 (99.73%) | 47143556 (99.91%) | 57736193 (99.93%) |
| Properly mapped:[4] | 40233188 (99.32%) | 49824458 (99.42%) | 47650122 (99.34%) | 44810918 (99.38%) | 47632054 (98.97%) | 46854308 (99.30%) | 57379832 (99.31%) |
| PE mapped:[5] | 40450560 (99.56%) | 50043672 (99.86%) | 47890928 (99.84%) | 44996712 (99.80%) | 47934994 (99.60%) | 47107362 (99.84%) | 57703192 (99.87%) |
| SE mapped:[6] | 53052 (0.13%) | 62240 (0.12%) | 66814 (0.14%) | 69464 (0.15%) | 121528 (0.25%) | 72388 (0.15%) | 66002 (0.11%) |
| With mate mapped to a different chr:[7] | 172036 (0.42%) | 154142 (0.31%) | 174070 (0.36%) | 134364 (0.30%) | 165888 (0.34%) | 192974 (0.41%) | 260964 (0.45%) |
| With mate mapped to a different chr ((mapQ>=5)):[8] | 135940 (0.34%) | 107675 (0.21%) | 129625 (0.27%) | 94740 (0.21%) | 119379 (0.25%) | 153442 (0.33%) | 207140 (0.36%) |
| Initial_bases_on_target:[9] | 50390601 | 50390601 | 50390601 | 50390601 | 50390601 | 50390601 | 50390601 |
| Initial_bases_near_target:[10] | 73902222 | 73902222 | 73902222 | 73902222 | 73902222 | 73902222 | 73902222 |
| Initial_bases_on_or_near_target:[11] | 124292823 | 124292823 | 124292823 | 124292823 | 124292823 | 124292823 | 12429282 |
| Total_effective_reads:[12] | 40573617 | 50203411 | 48047147 | 45141593 | 48111810 | 47249031 | 57879227 |
| Total_effective_yield(Mb):[13] | 6031.60 | 7459.36 | 7137.71 | 6707.70 | 7110.19 | 7023.35 | 8603.59 |
| Effective_sequences_on_target(Mb):[14] | 3798.41 | 4620.48 | 4367.11 | 4140.25 | 4290.55 | 4442.67 | 5487.55 |
| Effective_sequences_near_target(Mb):[15] | 1427.86 | 1747.06 | 1731.17 | 1648.62 | 1653.01 | 1657.83 | 1976.27 |
| Effective_sequences_on_or_near_target(Mb):[16] | 5226.27 | 6367.54 | 6098.28 | 5788.87 | 5943.57 | 6100.49 | 7463.82 |
| Fraction_of_effective_bases_on_target:[17] | 63.0% | 61.9% | 61.2% | 61.7% | 60.3% | 63.3% | 63.8% |
| Fraction_of_effective_bases_on_or_near_target:[18] | 86.6% | 85.4% | 85.4% | 86.3% | 83.6% | 86.9% | 86.8% |
| Average_sequencing_depth_on_target:[19] | 75.38 | 91.69 | 86.67 | 82.16 | 85.15 | 88.16 | 108.90 |
| Average_sequencing_depth_near_target:[20] | 19.32 | 23.64 | 23.43 | 22.31 | 22.37 | 22.43 | 26.74 |
| Mismatch_rate_in_target_region:[21] | 0.43% | 0.43% | 0.44% | 0.43% | 1.01% | 0.46% | 0.40% |
| Mismatch_rate_in_all_effective_sequence:[22] | 0.37% | 0.37% | 0.38% | 0.37% | 0.83% | 0.40% | 0.35% |
| Base_covered_on_target:[23] | 50278328 | 50339739 | 50283155 | 50276905 | 50280817 | 50277032 | 50287129 |
| Coverage_of_target_region:[24] | 99.8% | 99.9% | 99.8% | 99.8% | 99.8% | 99.8% | 99.8% |
| Base_covered_near_target:[25] | 70771233 | 71684433 | 72093897 | 71759095 | 71547879 | 71433493 | 71409886 |
| Coverage_of_flanking_region:[26] | 95.8% | 97.0% | 97.6% | 97.1% | 96.8% | 96.7% | 96.6% |
| Fraction_of_target_covered_with_at_least_20x:[27] | 95.8% | 97.5% | 97.3% | 96.6% | 96.7% | 97.1% | 98.3% |
| Fraction_of_target_covered_with_at_least_10x:[28] | 98.9% | 99.4% | 99.3% | 99.1% | 99.0% | 99.2% | 99.4% |

TABLE 19-continued

| Mapping rate and coverage | | | | | | | |
|---|---|---|---|---|---|---|---|
| Fraction_of_target_covered_with_at_least_4x:[29] | 99.6% | 99.8% | 99.7% | 99.6% | 99.6% | 99.7% | 99.7% |
| Fraction_of_flanking_region_covered_with_at_least_20x:[30] | 34.6% | 41.0% | 41.6% | 39.4% | 39.2% | 39.4% | 43.9% |
| Fraction_of_flanking_region_covered_with_at_least_10x:[31] | 55.9% | 61.8% | 63.6% | 61.3% | 60.7% | 60.4% | 63.1% |
| Fraction_of_flanking_region_covered_with_at_least_4x:[32] | 79.4% | 83.6% | 85.6% | 84.0% | 83.4% | 82.7% | 83.4% |

| | Sample: | | | | | | |
|---|---|---|---|---|---|---|---|
| | SEV1114038 | SEV1114046 | SEV1114047 | SEV1114049 | SEV1114052 | SEV1114054 | SEV1114055 |
| Total:[1] | 44722048 (100%) | 54763244 (100%) | 51073268 (100%) | 46978130 (100%) | 45256624 (100%) | 44582698 (100%) | 56318006 (100%) |
| Duplicate:[2] | 4541856 (10.17%) | 4641632 (8.48%) | 5291500 (10.38%) | 4883669 (10.43%) | 3251478 (7.19%) | 3336346 (7.50%) | 5175130 (9.20%) |
| Mapped:[3] | 44647068 (99.83%) | 54713303 (99.91%) | 50986163 (99.83%) | 46839975 (99.71%) | 45219271 (99.92%) | 44501053 (99.82%) | 56251245 (99.88%) |
| Properly mapped:[4] | 44425184 (99.34%) | 54394398 (99.33%) | 50684634 (99.24%) | 46541488 (99.07%) | 44983062 (99.40%) | 44216864 (99.18%) | 55974440 (99.39%) |
| PE mapped:[5] | 44622126 (99.78%) | 54675638 (99.84%) | 50956130 (99.77%) | 46808118 (99.64%) | 45187752 (99.85%) | 44470850 (99.75%) | 56212394 (99.81%) |
| SE mapped:[6] | 49884 (0.11%) | 75330 (0.14%) | 60066 (0.12%) | 63714 (0.14%) | 63038 (0.14%) | 60406 (0.14%) | 77702 (0.14%) |
| With mate mapped to a different chr:[7] | 140022 (0.31%) | 194068 (0.35%) | 192980 (0.38%) | 176660 (0.38%) | 139118 (0.31%) | 193716 (0.43%) | 163956 (0.29%) |
| With mate mapped to a different chr ((mapQ >= 5)):[8] | 103050 (0.23%) | 147351 (0.27%) | 142995 (0.28%) | 125435 (0.27%) | 100054 (0.22%) | 148414 (0.33%) | 116431 (0.21%) |
| Initial_bases_on_target:[9] | 50390601 | 50390601 | 50390601 | 50390601 | 50390601 | 50390601 | 50390601 |
| Initial_bases_near_target:[10] | 73902222 | 73902222 | 73902222 | 73902222 | 73902222 | 73902222 | 73902222 |
| Initial_bases_on_or_near_target:[11] | 124292823 | 124292823 | 124292823 | 124292823 | 124292823 | 124292823 | 124292823 |
| Total_effective_reads:[12] | 44754448 | 54844566 | 51115002 | 46965450 | 45330042 | 44616103 | 56386708 |
| Total_effective_yield(Mb):[13] | 6637.76 | 8152.46 | 7579.03 | 6959.51 | 6736.17 | 6607.26 | 8380.18 |
| Effective_sequences_on_target(Mb):[14] | 3958.17 | 5002.31 | 4621.23 | 4166.87 | 4125.72 | 4003.35 | 5238.93 |
| Effective_sequences_near_target(Mb):[15] | 1526.55 | 1924.60 | 1733.32 | 1599.32 | 1616.63 | 1519.48 | 1985.45 |
| Effective_sequences_on_or_near_target(Mb):[16] | 5484.72 | 6926.91 | 6354.55 | 5766.19 | 5742.35 | 5522.82 | 7224.38 |
| Fraction_of_effective_bases_on_target:[17] | 59.6% | 61.4% | 61.0% | 59.9% | 61.2% | 60.6% | 62.5% |
| Fraction_of_effective_bases_on_or_near_target:[18] | 82.6% | 85.0% | 83.8% | 82.9% | 85.2% | 83.6% | 86.2% |
| Average_sequencing_depth_on_target:[19] | 78.55 | 99.27 | 91.71 | 82.69 | 81.87 | 79.45 | 103.97 |
| Average_sequencing_depth_near_target:[20] | 20.66 | 26.04 | 23.45 | 21.64 | 21.88 | 20.56 | 26.87 |
| Mismatch_rate_in_target_region:[21] | 0.73% | 0.42% | 0.72% | 0.64% | 0.44% | 0.73% | 0.41% |
| Mismatch_rate_in_all_effective_sequence:[22] | 0.60% | 0.37% | 0.60% | 0.54% | 0.38% | 0.61% | 0.36% |
| Base_covered_on_target:[23] | 49862620 | 50286241 | 50283219 | 50280322 | 50284517 | 50275077 | 50282839 |
| Coverage_of_target_region:[24] | 99.0% | 99.8% | 99.8% | 99.8% | 99.8% | 99.8% | 99.8% |
| Base_covered_near_target:[25] | 67544245 | 72114359 | 71330539 | 71494431 | 71811777 | 70938898 | 72124165 |
| Coverage_of_flanking_region:[26] | 91.4% | 97.6% | 96.5% | 96.7% | 97.2% | 96.0% | 97.6% |
| Fraction_of_target_covered_with_at_least_20x:[27] | 81.7% | 98.0% | 97.4% | 96.9% | 96.8% | 96.3% | 98.2% |
| Fraction_of_target_covered_with_at_least_10x:[28] | 89.0% | 99.3% | 99.2% | 99.2% | 99.1% | 99.0% | 99.4% |

TABLE 19-continued

| Mapping rate and coverage | | | | | | | |
|---|---|---|---|---|---|---|---|
| Fraction_of_target_covered_with_at_least_4x:[29] | 95.7% | 99.7% | 99.7% | 99.7% | 99.6% | 99.6% | 99.7% |
| Fraction_of_flanking_region_covered_with_at_least_20x:[30] | 33.7% | 44.3% | 40.4% | 38.4% | 38.9% | 36.4% | 45.2% |
| Fraction_of_flanking_region_covered_with_at_least_10x:[31] | 51.2% | 65.1% | 60.8% | 59.8% | 60.9% | 57.3% | 65.9% |
| Fraction_of_flanking_region_covered_with_at_least_4x:[32] | 72.5% | 86.2% | 82.6% | 82.7% | 83.9% | 80.3% | 86.5% |

| | Sample: | | | | |
|---|---|---|---|---|---|
| | SEV1114056 | SEV1114064 | SEV1114065 | SEV1114066 | SEV1114067 |
| Total:[1] | 44192564 (100%) | 41841878 (100%) | 41792295 (100%) | 43735354 (100%) | 58732910 (100%) |
| Duplicate:[2] | 3396993 (7.69%) | 3021750 (7.23%) | 3280347 (7.81%) | 2849828 (6.53%) | 5586885 (9.53%) |
| Mapped:[3] | 44152752 (99.91%) | 41809015 (99.92%) | 41758803 (99.92%) | 43667750 (99.85%) | 58631891 (99.83%) |
| Properly mapped:[4] | 43938622 (99.43%) | 41562658 (99.33%) | 41509140 (99.32%) | 43428192 (99.30%) | 58260638 (99.20%) |
| PE mapped:[5] | 44121356 (99.84%) | 41781042 (99.85%) | 41732106 (99.86%) | 43628176 (99.75%) | 58594770 (99.76%) |
| SE mapped:[6] | 62792 (0.14%) | 55946 (0.13%) | 53394 (0.13%) | 79148 (0.18%) | 74242 (0.13%) |
| With mate mapped to a different chr:[7] | 132692 (0.30%) | 159952 (0.38%) | 164858 (0.39%) | 142734 (0.33%) | 234308 (0.40%) |
| With mate mapped to a different chr ((mapQ >= 5)):[8] | 87472 (0.20%) | 119588 (0.29%) | 125123 (0.30%) | 101128 (0.23%) | 174256 (0.30%) |
| Initial_bases_on_target:[9] | 50390601 | 50390601 | 50390601 | 50390601 | 50390601 |
| Initial_bases_near_target:[10] | 73902222 | 73902222 | 73902222 | 73902222 | 73902222 |
| Initial_bases_on_or_near_target:[11] | 124292823 | 124292823 | 124292823 | 124292823 | 124292823 |
| Total_effective_reads:[1][2] | 44266981 | 41917520 | 41865966 | 43777539 | 58787066 |
| Total_effective_yield(Mb):[13] | 6561.25 | 6228.01 | 6210.75 | 6489.11 | 8712.50 |
| Effective_sequences_on_target(Mb):[14] | 4071.61 | 3840.98 | 3757.03 | 4060.00 | 5206.35 |
| Effective_sequences_near_target(Mb):[15] | 1547.48 | 1467.33 | 1428.00 | 1561.14 | 2090.16 |
| Effective_sequences_on_or_near_target(Mb):[16] | 5619.09 | 5308.31 | 5185.03 | 5621.14 | 7296.50 |
| Fraction_of_effective_bases_on_target:[17] | 62.1% | 61.7% | 60.5% | 62.6% | 59.8% |
| Fraction_of_effective_bases_on_or_near_target:[18] | 85.6% | 85.2% | 83.5% | 86.6% | 83.7% |
| Average_sequencing_depth_on_target:[19] | 80.80 | 76.22 | 74.56 | 80.57 | 103.32 |
| Average_sequencing_depth_near_target:[20] | 20.94 | 19.85 | 19.32 | 21.12 | 28.28 |
| Mismatch_rate_in_target_region:[21] | 0.79% | 0.43% | 0.67% | 0.54% | 0.75% |
| Mismatch_rate_in_all_effective_sequence:[22] | 0.65% | 0.37% | 0.56% | 0.46% | 0.62% |
| Base_covered_on_target:[23] | 50281452 | 50330219 | 50294971 | 50336402 | 50282437 |
| Coverage_of_target_region:[24] | 99.8% | 99.9% | 99.8% | 99.9% | 99.8% |
| Base_covered_near_target:[25] | 71323056 | 71252228 | 71068079 | 71738889 | 72373869 |
| Coverage_of_flanking_region:[26] | 96.5% | 96.4% | 96.2% | 97.1% | 97.9% |

TABLE 19-continued

| Mapping rate and coverage | | | | | |
|---|---|---|---|---|---|
| Fraction_of_target_covered_with_at_least_20x:[27] | 96.8% | 96.1% | 95.9% | 96.3% | 98.0% |
| Fraction_of_target_covered_with_at_least_10x:[28] | 99.1% | 99.1% | 99.0% | 99.2% | 99.3% |
| Fraction_of_target_covered_with_at_least_4x:[29] | 99.7% | 99.7% | 99.6% | 99.8% | 99.7% |
| Fraction_of_flanking_region_covered_with_at_least_20x:[30] | 37.4% | 35.7% | 34.7% | 37.7% | 47.2% |
| Fraction_of_flanking_region_covered_with_at_least_10x:[31] | 58.6% | 57.4% | 56.3% | 59.8% | 68.0% |
| Fraction_of_flanking_region_covered_with_at_least_4x:[32] | 81.5% | 81.0% | 80.2% | 83.2% | 88.0% |

(1) Total: The number of total clean reads (2) Duplicate: The number of duplication reads (3) Mapped: The number of total reads that mapped to the reference genome (percentage)

(4) Properly mapped: The number of reads that mapped to the reference genome and the direction is right (5) PE mapped: The number of pair-end reads that mapped to the reference genome (percentage)

(6) SE mapped: The number of single-end reads that mapped to the reference genome (7) With mate mapped to a different chr: The number of mate reads that mapped to the different chromosomes (8) With mate mapped to a different chr (mapQ>=5): The number of mate reads that mapped to the different chromosomes and the MAQ>5

(9) Initial_bases_on_target: Total bases mapped to the target region (exonic region we capture)

(10) Initial_bases_near_target: Total based mapped to the flanking region (The region nearby target upstream and downstream 200 bp)

(11) Initial_bases_on_or_near_target: Total length of target region and flanking region

(12) Total_effective_reads: The number of valid reads that mapped to the reference genome

(13) Total_effective_yield(Mb): Total effective yield

(14) Effective_sequences_on_target(Mb): Total reads that mapped to the reference genome target region

(15) Effective_sequences_near_target(Mb): Total reads that mapped to the reference genome flanking region

(16) Effective_sequences_on_or_near_target(Mb): Total reads that mapped to the reference genome target region and flanking region

(17) Fraction_of_effective_bases_on_target: The percentage of the mapped reads in target region to the reads in reference genome

(18) Fraction_of_effective_bases_on_or_near_target: The percentage of the mapped reads in target region and flanking region to the reads in reference genome

(19) Average_sequencing_depth_on_target: The average sequencing depth that mapped to the reference genome target region

(20) Average_sequencing_depth_near_target: The average sequencing depth that mapped to the reference genome flanking region

(21) Mismatch_rate_in_target_region: The percentage of mismatch reads in reference genome target region

(22) Mismatch_rate_in_all_effective_sequence: The percentage of mismatch reads in reference genome

(23) Base_covered_on_target: The coverage length of target region

(24) Coverage_of_target_region: The percentage of target region coveraged

(25) Base_covered_near_target: The coverage length of flanking region

(26) Coverage_of_flanking_region: The percentage of flanking region coveraged

(27) Fraction_of_target_covered_with_at_least_20x: The percentage of bases with depth >20x in target region

(28) Fraction_of_target_covered_with_at_least_10x: The percentage of bases with depth >10x in target region

(29) Fraction_of_target_covered_with_at_least_4x: The percentage of bases with depth >4x in target region

(30) Fraction_of_flanking_region_covered_with_at_least_20x: The percentage of bases with depth >20x in flanking region

(31) Fraction_of_flanking_region_covered_with_at_least_10x: The percentage of bases with depth >10x in flanking region

(32) Fraction_of_flanking_region_covered_with_at_least_4x: The percentage of bases with depth >4x in flanking region (Source: Novogene Bioinformatics Technology Co., Ltd—www.filgen.ip/Product/Bioscience5-seq/Cancer_WGS_report_V1.1.pdf)

Variation Detection Result

SNV Detection Result

SNV Statistical Result

Generally, the whole genome of human has about 3.6 M SNV. Most (above 95%) SNVs with high frequency (the allele frequency in population is above 5%) have records in dbSNP (Sherry S T, Ward M H, Kholodov M, et al. dbSNP: the NCBI database of genetic variation[J]. Nucleic acids research, 2001, 29(1): 308-311.(dbSNP)). The ration of Ts/Tv can reflect the accuracy of sequencing. Generally, the ratio in genome is about 2.2 and in coding region is about 3.2.

GATK was used to detect SNV, and the statistics of SNVs are as follows:

TABLE 20

The number of SNV in different genomic region

| Sample | exonic | intronic | UTR3 | UTR5 | intergenic | ncRNA_exonic | ncRNA_intronic | upstream | downstream | splicing | ncRNA_UTR3 | ncRNA_UTR5 | ncRNA_splicing |
|---|---|---|---|---|---|---|---|---|---|---|---|---|---|
| SEV1114055 | 22693 | 108836 | 5125 | 3010 | 62930 | 2703 | 7604 | 4137 | 1766 | 2499 | 103 | 44 | 100 |
| SEV1114029 | 22152 | 96990 | 4598 | 2716 | 49336 | 2425 | 6679 | 3335 | 1342 | 2438 | 109 | 47 | 90 |
| SEV1114001 | 21959 | 107581 | 4943 | 2928 | 61021 | 2619 | 7373 | 3865 | 1674 | 2431 | 103 | 43 | 92 |
| SEV1114025 | 22104 | 103872 | 4819 | 2855 | 59388 | 2490 | 7256 | 3721 | 1600 | 2457 | 94 | 46 | 79 |
| SEV1114052 | 21397 | 98878 | 4689 | 2713 | 51860 | 2476 | 6558 | 3347 | 1462 | 2382 | 105 | 48 | 90 |
| SEV1114026 | 21834 | 105544 | 4910 | 2943 | 59627 | 2576 | 7014 | 3867 | 1628 | 2417 | 107 | 35 | 84 |
| SEV1114064 | 21987 | 94806 | 4651 | 2745 | 49648 | 2520 | 6280 | 3401 | 1437 | 2340 | 97 | 35 | 72 |
| SEV1114046 | 21913 | 110289 | 5051 | 2900 | 67019 | 2473 | 7607 | 3834 | 1758 | 2400 | 111 | 59 | 73 |
| SEV1114018 | 22132 | 106056 | 4890 | 2852 | 64134 | 2555 | 7639 | 3749 | 1621 | 2475 | 123 | 41 | 104 |
| SEV1114013 | 22038 | 190748 | 4549 | 2652 | 44070 | 2419 | 5745 | 3054 | 1233 | 2491 | 106 | 42 | 92 |
| SEV1114022 | 23040 | 911171 | 4521 | 2698 | 44429 | 2502 | 5940 | 3002 | 1349 | 2507 | 107 | 46 | 87 |
| SEV1114036 | 21900 | 103186 | 4820 | 2839 | 61614 | 2609 | 7300 | 3630 | 1564 | 2427 | 100 | 43 | 87 |
| SEV1114035 | 22105 | 96007 | 4666 | 2790 | 49280 | 2455 | 6280 | 3428 | 1477 | 2448 | 108 | 42 | 77 |
| SEV1114020 | 22306 | 198238 | 4682 | 2902 | 52087 | 2621 | 6606 | 3514 | 1460 | 2436 | 113 | 44 | 101 |
| SEV1114006 | 21961 | 92358 | 4428 | 2630 | 50616 | 2495 | 6364 | 3136 | 1503 | 2393 | 88 | 43 | 84 |
| SEV1114019 | 22256 | 97165 | 4501 | 2662 | 56449 | 2494 | 6485 | 3359 | 1458 | 2443 | 98 | 41 | 91 |
| SEV1114033 | 21903 | 100337 | 4680 | 2726 | 56302 | 2445 | 6731 | 3484 | 1538 | 2351 | 107 | 46 | 85 |
| SEV1114038 | 19932 | 88855 | 3826 | 1478 | 55433 | 1984 | 6182 | 1913 | 1322 | 2197 | 83 | 18 | 79 |
| SEV1114047 | 22493 | 104441 | 4784 | 2836 | 62484 | 2606 | 7244 | 3553 | 1709 | 2460 | 100 | 45 | 82 |
| SEV1114049 | 22347 | 103536 | 4741 | 2881 | 61941 | 2452 | 7110 | 3724 | 1665 | 2397 | 102 | 50 | 86 |
| SEV1114056 | 22015 | 927177 | 4662 | 2743 | 47933 | 2498 | 6141 | 3273 | 1397 | 2440 | 99 | 41 | 91 |
| SEV1114065 | 22324 | 959124 | 4985 | 2729 | 52800 | 2535 | 6526 | 3306 | 1458 | 2415 | 133 | 43 | 85 |
| SEV1114067 | 22192 | 117546 | 5170 | 2929 | 75835 | 2611 | 8118 | 4029 | 1901 | 2484 | 117 | 42 | 93 |
| SEV1114066 | 21987 | 954149 | 4521 | 2779 | 46796 | 2429 | 5993 | 3388 | 1281 | 2388 | 111 | 45 | 77 |
| SEV1114017 | 22504 | 97498 | 5357 | 2752 | 58929 | 2584 | 6815 | 3291 | 1630 | 2432 | 181 | 46 | 94 |
| SEV1114054 | 22357 | 986172 | 5001 | 2702 | 58379 | 2684 | 6810 | 3221 | 1464 | 2416 | 118 | 35 | 84 |

Note:
Sample: Sample name
exonic: The number of SNV in exonic region
intronic: The number of SNV in intronic region
UTR3: The number of SNV in 3'UTR region
UTR5: The number of SNV in 5'UTR region
intergnic: The number of SNV in intergenic region
ncRNA_exonic: The number of SNV in non-coding RNA exonic region
ncRNA_intronic: The number of SNV in non-coding RNA intronic region
upstream: The number of SNV in the 1 kb upstream region of transcription start site
downstream: The number of SNV in the 1 kb downstream region of transcription ending site
splicing: The number of SNV in 4 bp splicing junction region
ncRNA_UTR3: The number of SNV in 3'UTR of non-coding RNA
ncRNA_UTR5: The number of SNV in 5'UTR of non-coding RNA
ncRNA_splicing: The number of SNV in 4 bp splicing junction of non-coding RNA

TABLE 21

The number of SNV of different types in coding region

| Sample | synonymous_SNV | missense_SNV | stopgain | stoploss | unknown |
|---|---|---|---|---|---|
| SEV1114055 | 11508 | 10703 | 87 | 12 | 383 |
| SEV1114029 | 11321 | 10376 | 71 | 9 | 375 |
| SEV1114001 | 11228 | 10281 | 74 | 9 | 367 |
| SEV1114025 | 11277 | 10402 | 77 | 13 | 335 |
| SEV1114052 | 11076 | 9883 | 74 | 12 | 352 |
| SEV1114026 | 11164 | 10185 | 64 | 10 | 411 |
| SEV1114064 | 11267 | 10285 | 67 | 11 | 357 |
| SEV1114046 | 11145 | 10315 | 78 | 12 | 363 |
| SEV1114018 | 11353 | 10329 | 73 | 14 | 363 |
| SEV1114013 | 11349 | 10251 | 70 | 14 | 354 |
| SEV1114022 | 11776 | 10774 | 84 | 8 | 398 |
| SEV1114036 | 11200 | 10259 | 76 | 8 | 357 |
| SEV1114035 | 11280 | 10358 | 72 | 7 | 388 |
| SEV1114020 | 11415 | 10422 | 70 | 19 | 390 |
| SEV1114006 | 11330 | 10205 | 71 | 11 | 344 |
| SEV1114019 | 11471 | 10294 | 67 | 12 | 412 |
| SEV1114033 | 11298 | 10185 | 64 | 10 | 346 |
| SEV1114038 | 10235 | 9282 | 70 | 10 | 335 |
| SEV1114047 | 11492 | 10555 | 76 | 10 | 360 |
| SEV1114049 | 11425 | 10451 | 81 | 12 | 378 |
| SEV1114056 | 11364 | 10207 | 70 | 10 | 364 |
| SEV1114065 | 11436 | 10387 | 75 | 12 | 414 |
| SEV1114067 | 11357 | 10378 | 76 | 8 | 373 |
| SEVI114066 | 11248 | 10272 | 77 | 15 | 375 |
| SEV1114017 | 11769 | 10275 | 79 | 11 | 370 |
| SEV1114054 | 11398 | 10524 | 69 | 15 | 351 |

Note:
Sample: Sample name
synonymous_SNV: A single nucleotide change that does not cause an amino acid change
missense_SNV: A single nucleotide change that cause an amino acid change
stopgain: A nonsynonymous SNV that lead to the immediate creation of stop codon at the variant site
stoploss: A nonsynonymous SNV that lead to the immediate elimination of stop codon at the variant site
unknown: Unknown function (due to various errors in the gene structure definition in the database file)
InDel Detection Result
Indel Statistical Result
See Section 4.4.2 of Novogene Bioinformatics Technology Co., Ltd's document entitled "Novogene—Cancer Project Report (2014, 11), which is accessible at www.filgen.ip/

Product/Bioscience5-seq/Cancer_WGS_report_V1.1.pdf. Generally, the genome of human has about 350K InDel (insertion and deletion, less than 50 bp insertion and deletion).

The InDel in coding region or splicing site may change the protein translation. Frameshift mutation, in which the number of inserted or deleted bases is not an integral multiple of three, may lead to the change of the whole reading frame. Compared to non-flameshift mutation, frameshift mutation is more limited by selective pressure.

GATK was used to detect Indel, and obtained InDel result is as follows:

ncRNA_exonic: The number of InDel in non-coding RNA exonic region ncRNA_intronic: The number of InDel in non-coding RNA intronic region upstream: The number of InDel in the 1 kb upstream region of transcription start site downstream: The number of InDel in the 1 kb downstream region of transcription ending site splicing: The number of InDel in 4 bp splicing junction region

TABLE 22

The number of InDel in different genomic regions

| Sample | exonic | intronic | UTR3 | UTR5 | intergenic | ncRNA_intronic | ncRNA_intronic | upstream | downstream | splicing | ncRNA_UTR3 | ncRNA_UTR5 | ncRNA_splicing |
|---|---|---|---|---|---|---|---|---|---|---|---|---|---|
| SEV1114055 | 672 | 17873 | 794 | 492 | 10953 | 299 | 1306 | 780 | 288 | 558 | 9 | 9 | 13 |
| SEV1114029 | 683 | 15858 | 733 | 434 | 9117 | 269 | 1156 | 601 | 223 | 557 | 13 | 11 | 23 |
| SEV1114001 | 647 | 17626 | 813 | 459 | 10382 | 293 | 1235 | 685 | 282 | 528 | 20 | 9 | 11 |
| SEV1114025 | 691 | 16993 | 792 | 499 | 10461 | 230 | 1274 | 672 | 266 | 527 | 12 | 13 | 14 |
| SEV1114052 | 641 | 16193 | 724 | 435 | 9494 | 273 | 1111 | 612 | 258 | 525 | 14 | 13 | 14 |
| SEV1114026 | 674 | 16902 | 815 | 502 | 10158 | 285 | 1153 | 689 | 275 | 520 | 10 | 13 | 12 |
| SEV1114064 | 684 | 15395 | 712 | 433 | 8833 | 291 | 1039 | 621 | 237 | 516 | 14 | 11 | 13 |
| SEV1114046 | 669 | 17948 | 816 | 475 | 11903 | 287 | 1307 | 700 | 302 | 537 | 11 | 14 | 20 |
| SEV1114018 | 714 | 17488 | 764 | 465 | 11739 | 295 | 1318 | 636 | 289 | 523 | 15 | 19 | 19 |
| SEV1114013 | 655 | 14728 | 702 | 437 | 8107 | 283 | 982 | 592 | 202 | 546 | 9 | 12 | 12 |
| SEV1114022 | 701 | 14623 | 682 | 416 | 8114 | 270 | 1022 | 539 | 235 | 542 | 13 | 8 | 16 |
| SEV1114036 | 710 | 17213 | 773 | 458 | 11080 | 280 | 1308 | 661 | 268 | 480 | 11 | 10 | 15 |
| SEV1114035 | 694 | 15320 | 703 | 451 | 8775 | 276 | 1056 | 601 | 229 | 509 | 16 | 11 | 12 |
| SEV1114020 | 688 | 16166 | 747 | 470 | 9501 | 305 | 1124 | 675 | 278 | 531 | 14 | 12 | 10 |
| SEV1114006 | 681 | 14416 | 665 | 403 | 8968 | 265 | 1014 | 549 | 235 | 506 | 7 | 9 | 20 |
| SEV1114019 | 632 | 15739 | 669 | 445 | 10080 | 288 | 1130 | 614 | 242 | 535 | 12 | 10 | 9 |
| SEV1114033 | 646 | 14906 | 670 | 415 | 9164 | 262 | 1074 | 586 | 231 | 479 | 14 | 12 | 17 |
| SEV1114038 | 525 | 14784 | 614 | 184 | 10648 | 216 | 1120 | 306 | 239 | 475 | 16 | 3 | 17 |
| SEV1114047 | 667 | 16312 | 727 | 447 | 10515 | 293 | 1206 | 632 | 281 | 524 | 9 | 12 | 17 |
| SEV1114049 | 653 | 16413 | 716 | 451 | 10636 | 274 | 1142 | 621 | 230 | 491 | 10 | 14 | 15 |
| SEV1114056 | 642 | 14451 | 748 | 432 | 8209 | 277 | 1002 | 578 | 228 | 501 | 13 | 12 | 14 |
| SEV1114065 | 680 | 14902 | 798 | 427 | 9262 | 253 | 1051 | 590 | 255 | 521 | 14 | 11 | 13 |
| SEV1114067 | 662 | 18057 | 772 | 454 | 11955 | 276 | 1297 | 705 | 296 | 535 | 12 | 10 | 15 |
| SEV1114066 | 654 | 14929 | 728 | 495 | 8035 | 266 | 969 | 618 | 225 | 531 | 10 | 14 | 10 |
| SEV1114017 | 680 | 15847 | 932 | 432 | 10707 | 269 | 1167 | 565 | 297 | 530 | 38 | 14 | 15 |
| SEV1114054 | 661 | 15406 | 766 | 440 | 10098 | 289 | 1121 | 561 | 247 | 495 | 11 | 7 | 11 |

Note:
Sample: Sample name
exonic: The number of InDel in exonic region
intronic: The number of InDel in intronic region
UTR3: The number of InDel in 3'UTR region
UTR5: The number of InDel in 5'UTR region
intergnic: The number of InDel in intergenic region ncRNA_UTR3: The number of InDel in 3'UTR of non-coding RNA ncRNA_UTR5: The number of InDel in 5'UTR of non-coding RNA ncRNA_splicing: The number of InDel in 4 bp splicing junction of non-coding RNA

TABLE 23

The number of different type InDel in coding regions

| Sample | frameshift_deletion | frameshift_insertion | nonframeshift_deletion | nonframeshift_insertion | stoploss | stopgain | unknown |
|---|---|---|---|---|---|---|---|
| SEV1114055 | 106 | 104 | 203 | 158 | 1 | 6 | 94 |
| SEV1114029 | 131 | 101 | 196 | 155 | 1 | 7 | 92 |
| SEV1114001 | 110 | 90 | 199 | 152 | 0 | 5 | 91 |
| SEV1114025 | 123 | 100 | 203 | 168 | 0 | 11 | 86 |
| SEV1114052 | 107 | 90 | 190 | 156 | 1 | 7 | 90 |
| SEV1114026 | 119 | 84 | 204 | 169 | 2 | 5 | 91 |
| SEV1114064 | 135 | 100 | 183 | 170 | 0 | 6 | 90 |
| SEV1114046 | 117 | 94 | 192 | 168 | 0 | 10 | 88 |
| SEV1114018 | 135 | 105 | 201 | 174 | 0 | 9 | 90 |
| SEV1114013 | 123 | 87 | 192 | 157 | 1 | 6 | 89 |
| SEV1114022 | 134 | 95 | 200 | 176 | 1 | 6 | 89 |
| SEV1114036 | 125 | 110 | 207 | 166 | 0 | 10 | 91 |
| SEV1114035 | 134 | 99 | 189 | 172 | 0 | 9 | 91 |

TABLE 23-continued

The number of different type InDel in coding regions

| Sample | frameshift_deletion | frameshift_insertion | nonframeshift_deletion | nonframeshift_insertion | stoploss | stopgain | unknown |
|---|---|---|---|---|---|---|---|
| SEV1114020 | 116 | 107 | 206 | 157 | 1 | 9 | 92 |
| SEV1114006 | 120 | 103 | 200 | 157 | 1 | 10 | 90 |
| SEV1114019 | 102 | 86 | 174 | 175 | 0 | 4 | 91 |
| SEV1114033 | 113 | 84 | 193 | 161 | 1 | 7 | 87 |
| SEV1114038 | 99 | 90 | 139 | 113 | 0 | 7 | 76 |
| SEV1114047 | 126 | 89 | 196 | 158 | 0 | 6 | 92 |
| SEV1114049 | 109 | 93 | 200 | 157 | 1 | 5 | 88 |
| SEV1114056 | 114 | 89 | 183 | 160 | 1 | 7 | 87 |
| SEV1114065 | 124 | 94 | 192 | 169 | 0 | 7 | 94 |
| SEV1114067 | 115 | 88 | 196 | 166 | 0 | 7 | 90 |
| SEV1114066 | 112 | 89 | 199 | 161 | 1 | 6 | 86 |
| SEV1114017 | 119 | 97 | 200 | 167 | 1 | 7 | 89 |
| SEV1114064 | 123 | 85 | 187 | 168 | 1 | 7 | 89 |

Note:

Sample: Sample name frameshift_deletion: A deletion of one or more nucleotides that cause frameshift changes in protein coding sequence. the deletion length is not multiple of 3 frameshift_insertion: An insertion of one or more nucleotides that cause frameshift changes in protein coding sequence. the insertion length is not multiple of 3 nonframeshift_deletion: Non-frameshift deletion does not change coding protein frame deletion, the deletion length is multiple of 3 nonframeshift_insertion: Non-frameshift insertion, does not change coding protein frame insertion: the insertion length is multiple of 3 stopgain: Frameshift insertion/deletion, nonframeshift insertion/deletion or block substitution that lead to the immediate creation of stop codon at the variant site stoploss: Frameshift insertion/deletion, nonframeshift insertion/deletion or block substitution that lead to the immediate elimination of stop codon at the variant site unknown: Unknown function (due to various errors in the gene structure definition in the database file)

TABLE 24

InDel and genotype distribution

| Sample | all | genotype.Het | genotype.Hom | novel | novel_proportion |
|---|---|---|---|---|---|
| SEV1114055 | 34046 | 11817 | 22229 | 7444 | 0.218645362 |
| SEV1114029 | 29678 | 10651 | 19027 | 6444 | 0.217130534 |
| SEV1114001 | 32990 | 11595 | 21395 | 7354 | 0.222916035 |
| SEV1114025 | 32444 | 11106 | 21338 | 7158 | 0.220626310 |
| SEV1114052 | 30307 | 10586 | 19721 | 6403 | 0.211271323 |
| SEV1114026 | 32008 | 10399 | 21609 | 6806 | 0.212634341 |
| SEV1114064 | 28799 | 9604 | 19195 | 6237 | 0.216570020 |
| SEV1114046 | 34989 | 11712 | 23277 | 7625 | 0.217925634 |
| SEV1114018 | 34274 | 11635 | 22639 | 7404 | 0.216023808 |
| SEV1114013 | 27267 | 9951 | 17316 | 5958 | 0.218505886 |
| SEV1114022 | 27181 | 10092 | 17089 | 5743 | 0.211287296 |
| SEV1114036 | 33267 | 11523 | 21744 | 7358 | 0.221180148 |
| SEV1114035 | 28653 | 10361 | 18292 | 6293 | 0.219627962 |
| SEV1114020 | 30521 | 10454 | 20067 | 6567 | 0.215163330 |
| SEV1114006 | 27738 | 8998 | 18740 | 5688 | 0.205061648 |
| SEV1114019 | 30405 | 9881 | 20524 | 6407 | 0.210721921 |
| SEV1114033 | 28476 | 9479 | 18997 | 5693 | 0.199922742 |
| SEV1114038 | 29147 | 8841 | 20306 | 6029 | 0.206848046 |
| SEV1114047 | 31642 | 10710 | 20932 | 6516 | 0.205928829 |
| SEV1114049 | 31666 | 10356 | 21310 | 6603 | 0.208520179 |
| SEV1114056 | 27107 | 9451 | 17656 | 5797 | 0.213856200 |
| SEV1114065 | 28777 | 9653 | 19124 | 6094 | 0.211766341 |
| SEV1114067 | 35046 | 12015 | 23031 | 7438 | 0.212235348 |
| SEV1114066 | 27484 | 9915 | 17569 | 5826 | 0.211977878 |
| SEV1114017 | 31493 | 10055 | 21438 | 7195 | 0.228463468 |
| SEV1114054 | 30113 | 9919 | 20194 | 6486 | 0.215388703 |

Note:

Sample: Sample name all: The total number of InDel genotype.Het: The genotype of heterozygote genotype.Hom: The genotype of homoozygote novel: InDel not in dbSNP novel_proportion: Is calculated as novel Indel/total number of Indel Software Used for Analysis The softwares which were applied in the bioinformatic analysis are listed as below:

TABLE 25

The list of exome analysis software

| Analytical content | Software | Comments | Version |
|---|---|---|---|
| Quality control | in-house | Quality control | 1.0 |
| Alignment | BWA | Map the sequencing reads to the reference genome and the BAM file was obtained | 0.7.8-r455 |
| | SAMtools | Sort bam | 1.0 |
| | Picard | Merge the bam file from the same sample and mark the duplicate reads | 1.111 |
| SNP/INDEL detection | GATK | Detect and filter SNP, InDel | v3.1 |
| Functional annotation | ANNOVAR | Annotate variation site | 2013 Aug. 23 |

Analysis was conducted using association software such as PLINK.

Statistical Analysis

The PLINK v1.0721 whole genome analysis tool set was used to determine associations between the CFS patients and the non-fatigued control group. A two column $\chi 2$ test was used to determine significance where p value of <0.05 was determined to be significant. Data analysis was performed by the Australian Genome Research Facility.

Results

Exome sequencing identified SNP variants in the TRP channel and AChR genes TRPV1, TRPC6, TRPV4, TRPC1, TRPM8, TRPC4, TRPV2, TRPV5, TRPC5, TRPM6, TRPC7, TRPM5, TRPC3, PKD1, TRPV6, PKD2, TRPA1, TRPM7, TRPM2, TRPM4, TRPM3, TRPV3, and CHRNA7, CHRM3, CHRNA4, CHRNA3, CHRNB4, CHRNB2 and CHRNE. These, together with their annotated consequences, are described in Tables 26, 27 and 28 below

TABLE 26

SNP variants of TRP channel or ACh receptors (TRP family, TRPV1, TRPC6, TRPV4, TRPC1, TRPM8, TRPC4, TRPV2, TRPV5, TRPC5, TRPM6, TRPC7, TRPM5, TRPC3, PKD1, TRPV6,P KD2, TRPA1, TRPM7, TRPM2, TRPM4, TRPM3, TRPV3, and CHRNA7,CHRM3, CHRNA4, CHRNA3, CHRNB4, CHRNB2 and CHRNE) annotated with their consequences.

| Chromosome | Location | Reference allele | Alternative allele | Consequences (intronic or exonic) |
|---|---|---|---|---|
| 15 | 32322929 | G | A | ExonicFunc = synonymous_SNV |
| 1 | 240070784 | T | C | ExonicFunc = synonymous_SNV |
| 1 | 240070944 | G | A | ExonicFunc = missense_SNV |
| 2 | 61981104 | C | T | ExonicFunc = synonymous_SNV |
| 20 | 61981134 | G | A | ExonicFunc = synonymous_SNV |
| 20 | 61981253 | C | T | ExonicFunc = missense_SNV |
| 20 | 61981362 | G | A | ExonicFunc = synonymous_SNV |
| 20 | 61981411 | G | A | ExonicFunc = missense_SNV |
| 20 | 61981536 | A | G | ExonicFunc = synonymous_SNV |
| 20 | 61981554 | C | A | ExonicFunc = synonymous_SNV |
| 20 | 61982085 | A | G | ExonicFunc = synonymous_SNV |
| 20 | 61982124 | A | G | ExonicFunc = synonymous_SNV |
| 20 | 61990939 | G | A | ExonicFunc = synonymous_SNV |
| 20 | 61992467 | C | T | ExonicFunc = synonymous_SNV |
| 20 | 61992509 | T | C | ExonicFunc = synonymous_SNV |
| 15 | 78880752 | G | A | ExonicFunc = missense_SNV |
| 15 | 78882925 | G | A | ExonicFunc = missense_SNV |
| 15 | 78885574 | T | A | ExonicFunc = missense_SNV |
| 15 | 78894339 | G | A | ExonicFunc = synonymous_SNV |
| 15 | 78894357 | G | T | ExonicFunc = synonymous_SNV |
| 15 | 78909452 | T | C | ExonicFunc = synonymous_SNV |
| 15 | 78911181 | T | C | ExonicFunc = synonymous_SNV |
| 15 | 78911230 | C | T | ExonicFunc = missense_SNV |

TABLE 26-continued

SNP variants of TRP channel or ACh receptors (TRP family, TRPV1, TRPC6, TRPV4, TRPC1, TRPM8, TRPC4, TRPV2, TRPV5, TRPC5, TRPM6, TRPC7, TRPM5, TRPC3, PKD1, TRPV6,P KD2, TRPA1, TRPM7, TRPM2, TRPM4, TRPM3, TRPV3, and CHRNA7,CHRM3, CHRNA4, CHRNA3, CHRNB4, CHRNB2 and CHRNE) annotated with their consequences.

| Chromosome | Location | Reference allele | Alternative allele | Consequences (intronic or exonic) |
|---|---|---|---|---|
| 15 | 78913131 | G | A | ExonicFunc = synonymous_SNV |
| 15 | 78917399 | A | G | ExonicFunc = synonymous_SNV |
| 15 | 78921762 | G | A | ExonicFunc = synonymous_SNV |
| 15 | 78922194 | G | A | ExonicFunc = synonymous_SNV |
| 15 | 78922229 | T | C | ExonicFunc = missense_SNV |
| 15 | 78922240 | C | T | ExonicFunc = missense_SNV |
| 15 | 78923505 | G | A | ExonicFunc = missense_SNV |
| 17 | 4796274 | T | C | ExonicFunc = missense_SNV |
| 17 | 4796286 | C | T | ExonicFunc = missense_SNV |
| 17 | 4797305 | G | A | ExonicFunc = missense_SNV |
| 17 | 4797910 | G | A | ExonicFunc = missense_SNV |
| 17 | 4802317 | T | C | ExonicFunc = synonymous_SNV |
| 17 | 4802329 | G | A | ExonicFunc = synonymous_SNV |
| 17 | 4802829 | G | A | ExonicFunc = synonymous_SNV |
| 17 | 4803711 | G | A | ExonicFunc = stopgain |
| 17 | 4804902 | G | A | ExonicFunc = synonymous_SNV |
| 17 | 4805777 | C | G | ExonicFunc = missense_SNV |
| 17 | 4806052 | C | A | ExonicFunc = missense_SNV |
| 17 | 3475490 | C | T | ExonicFunc = synonymous_SNV |
| 17 | 3476990 | G | A | ExonicFunc = synonymous_SNV |
| 17 | 3480433 | G | C | ExonicFunc = missense_SNV |
| 17 | 3480447 | T | C | ExonicFunc = missense_SNV |
| 17 | 3480910 | A | G | ExonicFunc = synonymous_SNV |
| 17 | 3486702 | G | A | ExonicFunc = missense_SNV |
| 17 | 3493200 | C | G | ExonicFunc = missense_SNV |
| 17 | 3494361 | G | A | ExonicFunc = synonymous_SNV |
| 17 | 3495374 | G | A | ExonicFunc = missense_SNV |
| 17 | 3495465 | C | T | ExonicFunc = synonymous_SNV |
| 11 | 101323770 | C | T | ExonicFunc = synonymous_SNV |
| 11 | 101325788 | G | A | ExonicFunc = synonymous_SNV |
| 11 | 101342958 | G | A | ExonicFunc = synonymous_SNV |
| 11 | 101347093 | A | G | ExonicFunc = synonymous_SNV |
| 11 | 101359750 | G | A | ExonicFunc = missense_SNV |
| 11 | 101454192 | G | A | ExonicFunc = missense_SNV |
| 12 | 110222146 | C | G | ExonicFunc = synonymous_SNV |
| 12 | 110226379 | G | A | ExonicFunc = synonymous_SNV |
| 12 | 110230597 | C | T | ExonicFunc = missense_SNV |
| 12 | 110238481 | G | A | ExonicFunc = synonymous_SNV |
| 12 | 110238487 | A | G | ExonicFunc = synonymous_SNV |
| 12 | 110240838 | T | G | ExonicFunc = synonymous_SNV |
| 12 | 110240848 | G | A | ExonicFunc = synonymous_SNV |
| 12 | 110252547 | G | A | ExonicFunc = missense_SNV |
| 3 | 142443441 | G | A | ExonicFunc = missense_SNV |
| 3 | 142503605 | G | A | ExonicFunc = synonymous_SNV |
| 3 | 142523349 | G | A | ExonicFunc = synonymous_SNV |
| 3 | 142524858 | G | A | ExonicFunc = synonymous_SNV |
| 2 | 234854540 | G | C | ExonicFunc = missense_SNV |
| 2 | 234854547 | A | T | ExonicFunc = synonymous_SNV |
| 2 | 234854550 | G | C | ExonicFunc = synonymous_SNV |
| 2 | 234854552 | A | G | ExonicFunc = missense_SNV |
| 2 | 234858645 | C | T | ExonicFunc = synonymous_SNV |
| 2 | 234863788 | G | A | ExonicFunc = missense_SNV . |
| 2 | 234875354 | G | A | ExonicFunc = synonymous_SNV |
| 2 | 234905078 | C | T | ExonicFunc = synonymous_SNV |
| 2 | 234915540 | C | G | ExonicFunc = synonymous_SNV |
| 13 | 38211105 | T | C | ExonicFunc = missense_SNV |
| 13 | 38211313 | T | C | ExonicFunc = synonymous_SNV |
| 13 | 38237564 | A | G | ExonicFunc = synonymous_SNV |
| 13 | 38357384 | G | A | ExonicFunc = synonymous_SNV |
| 20 | 33585437 | C | T | ExonicFunc = synonymous_SNV |
| 20 | 33586193 | C | T | ExonicFunc = synonymous_SNV |
| 20 | 33587198 | G | C | ExonicFunc = missense_SNV |
| 20 | 33587596 | G | A | ExonicFunc = synonymous_SNV |
| 20 | 33589107 | G | A | ExonicFunc = synonymous_SNV |
| 20 | 33657126 | G | A | ExonicFunc = synonymous_SNV |
| 20 | 33665969 | C | T | ExonicFunc = synonymous_SNV |
| 17 | 16320994 | C | T | ExonicFunc = synonymous_SNV |
| 17 | 16321032 | G | C | ExonicFunc = missense_SNV |

TABLE 26-continued

SNP variants of TRP channel or ACh receptors
(TRP family, TRPV1, TRPC6, TRPV4, TRPC1, TRPM8, TRPC4,
TRPV2, TRPV5, TRPC5, TRPM6, TRPC7, TRPM5,
TRPC3, PKD1, TRPV6,P KD2, TRPA1, TRPM7, TRPM2,
TRPM4, TRPM3, TRPV3, and CHRNA7,CHRM3,
CHRNA4, CHRNA3, CHRNB4, CHRNB2 and CHRNE)
annotated with their consequences.

| Chromosome | Location | Reference allele | Alternative allele | Consequences (intronic or exonic) |
|---|---|---|---|---|
| 17 | 16325968 | A | G | ExonicFunc = synonymous_SNV |
| 17 | 16326005 | A | C | ExonicFunc = synonymous_SNV |
| 17 | 16326990 | C | G | ExonicFunc = missense_SNV |
| 17 | 16336992 | C | G | ExonicFunc = synonymous_SNV |
| 7 | 142609749 | C | T | ExonicFunc = missense_SNV |
| 7 | 142622714 | G | A | ExonicFunc = synonymous_SNV |
| 7 | 142625249 | T | C | ExonicFunc = synonymous_SNV |
| 7 | 142625258 | G | A | ExonicFunc = synonymous_SNV |
| 7 | 142625882 | G | A | ExonicFunc = synonymous_SNV |
| 7 | 142625933 | G | A | ExonicFunc = synonymous_SNV |
| 7 | 142626549 | C | T | ExonicFunc = missense_SNV |
| 7 | 142626656 | C | T | ExonicFunc = synonymous_SNV |
| 7 | 142630534 | G | A | ExonicFunc = missense_SNV |
| X | 111078236 | G | C | ExonicFunc = synonymous_SNV |
| 9 | 77376633 | A | G | ExonicFunc = synonymous_SNV |
| 9 | 77376647 | T | C | ExonicFunc = missense_SNV |
| 9 | 77376652 | A | C | ExonicFunc = synonymous_SNV |
| 9 | 77377410 | C | T | ExonicFunc missense_SNV |
| 9 | 77407636 | C | T | ExonicFunc = synonymous_SNV |
| 9 | 77415284 | A | C | ExonicFunc = synonymous_SNV |
| 9 | 77416972 | C | T | ExonicFunc = synonymous_SNV |
| 9 | 77436641 | G | A | ExonicFunc = synonymous_SNV |
| 9 | 77448950 | A | G | ExonicFunc = synonymous_SNV |
| 9 | 77502160 | G | A | ExonicFunc = missense_SNV |
| 5 | 135692575 | G | A | ExonicFunc = synonymous_SNV |
| 5 | 135692743 | C | A | ExonicFunc = synonymous_SNV |
| 11 | 2423913 | A | C | ExonicFunc = missense_SNV |
| 11 | 2424105 | A | G | ExonicFunc = missense_SNV |
| 11 | 2424541 | C | G | ExonicFunc = missense_SNV |
| 11 | 2424684 | A | C | ExonicFunc = missense_SNV |
| 11 | 2427291 | A | C | ExonicFunc = synonymous_SNV |
| 11 | 2432666 | C | T | ExonicFunc = missense_SNV |
| 11 | 2432964 | T | C | ExonicFunc = synonymous_SNV |
| 11 | 2434402 | C | T | ExonicFunc = missense_SNV |
| 11 | 2435946 | A | G | ExonicFunc = synonymous_SNV |
| 11 | 2435956 | C | T | ExonicFunc = missense_SNV |
| 11 | 2436464 | C | T | ExonicFunc = missense_SNV |
| 11 | 2438963 | C | A | ExonicFunc = missense_SNV |
| 11 | 2439542 | A | G | ExonicFunc = missense_SNV |
| 11 | 2439767 | T | C | ExonicFunc missense_SNV |
| 11 | 2442364 | G | A | ExonicFunc = synonymous_SNV |
| 11 | 2444188 | C | T | ExonicFunc = missense_SNV |
| 4 | 122800987 | T | C | ExonicFunc = synonymous_SNV |
| 4 | 122824052 | C | T | ExonicFunc = synonymous_SNV |
| 4 | 122854116 | G | C | ExonicFunc = synonymous_SNV |
| 4 | 122872719 | G | A | ExonicFunc = synonymous_SNV |
| 7 | 47835027 | A | G | ExonicFunc = missense_SNV |
| 7 | 47840310 | C | G | ExonicFunc = missense_SNV |
| 7 | 47840387 | C | T | ExonicFunc = missense_SNV |
| 7 | 47851578 | G | A | ExonicFunc = missense_SNV |
| 7 | 47851623 | C | T | ExonicFunc = missense_SNV |
| 7 | 47852837 | C | T | ExonicFunc = missense_SNV |
| 7 | 47854956 | C | T | ExonicFunc = synonymous_SNV |
| 7 | 47869038 | T | C | ExonicFunc = synonymous_SNV |
| 7 | 47872845 | A | G | ExonicFunc = synonymous_SNV |
| 7 | 47874630 | G | A | ExonicFunc = missense_SNV |
| 7 | 47876567 | G | A | ExonicFunc = synonymous_SNV |
| 7 | 47879049 | G | A | ExonicFunc = missense_SNV |
| 7 | 47892745 | A | G | ExonicFunc = missense_SNV |
| 7 | 47913560 | G | T | ExonicFunc = missense_SNV |
| 7 | 47913579 | T | C | ExonicFunc = missense_SNV |
| 7 | 47913580 | G | A | ExonicFunc = synonymous_SNV |
| 7 | 47917087 | C | T | ExonicFunc = missense_SNV |
| 7 | 47917126 | T | C | ExonicFunc = synonymous_SNV |
| 7 | 47920345 | G | A | ExonicFunc = synonymous_SNV |
| 7 | 47921682 | A | T | ExonicFunc = synonymous_SNV |
| 7 | 47925331 | C | G | ExonicFunc = missense_SNV |
| 7 | 47927744 | C | T | ExonicFunc = missense_SNV |
| 7 | 47930148 | C | T | ExonicFunc = synonymous_SNV |
| 7 | 47930280 | C | T | ExonicFunc = synonymous_SNV |
| 7 | 47968927 | C | A | ExonicFunc = missense_SNV |
| 7 | 47970707 | G | A | ExonicFunc = missense_SNV |
| 7 | 47971575 | A | G | ExonicFunc = synonymous_SNV |
| 7 | 47971626 | G | A | ExonicFunc = synonymous_SNV |
| 16 | 2138269 | T | C | ExonicFunc = synonymous_SNV |
| 16 | 2138584 | G | C | ExonicFunc = synonymous_SNV |
| 16 | 2139814 | G | A | ExonicFunc = missense_SNV |
| 16 | 2139935 | G | A | ExonicFunc = synonymous_SNV |
| 16 | 2140010 | A | G | ExonicFunc = synonymous_SNV |
| 16 | 2140321 | G | A | ExonicFunc = synonymous_SNV |
| 16 | 2140454 | T | C | ExonicFunc = synonymous_SNV |
| 16 | 2140554 | G | A | ExonicFunc = missense_SNV |
| 16 | 2140680 | T | C | ExonicFunc = missense_SNV |
| 16 | 2140912 | G | C | ExonicFunc = synonymous_SNV |
| 16 | 2141454 | G | A | ExonicFunc = synonymous_SNV |
| 16 | 2144176 | G | A | ExonicFunc = missense_SNV |
| 16 | 2144182 | G | A | ExonicFunc = missense_SNV |
| 16 | 2147421 | C | T | ExonicFunc = missense_SNV |
| 16 | 2152387 | A | G | ExonicFunc = missense_SNV |
| 16 | 2152388 | C | G | ExonicFunc = synonymous_SNV |
| 16 | 2156021 | A | G | ExonicFunc = synonymous_SNV |
| 16 | 2158871 | C | A | ExonicFunc = synonymous_SNV |
| 16 | 2159405 | C | T | ExonicFunc = synonymous_SNV |
| 16 | 2159522 | C | T | ExonicFunc = synonymous_SNV |
| 16 | 2159750 | G | A | ExonicFunc = synonymous_SNV |
| 16 | 2159996 | G | A | ExonicFunc = synonymous_SNV |
| 16 | 2160494 | C | T | ExonicFunc = synonymous_SNV |
| 16 | 2160503 | T | G | ExonicFunc = synonymous_SNV |
| 16 | 2160973 | A | G | ExonicFunc = missense_SNV |
| 16 | 2161113 | C | T | ExonicFunc = missense_SNV |
| 16 | 2161150 | G | A | ExonicFunc = missense_SNV |
| 16 | 2161489 | C | A | ExonicFunc = missense_SNV |
| 16 | 2161793 | G | A | ExonicFunc = synonymous_SNV |
| 16 | 2161796 | G | A | ExonicFunc = synonymous_SNV |
| 16 | 2162955 | A | G | ExonicFunc = missense_SNV |
| 16 | 2164808 | C | T | ExonicFunc = missense_SNV |
| 16 | 2167970 | G | A | ExonicFunc = synonymous_SNV |
| 16 | 71967886 | G | A | ExonicFunc = unknown |
| 16 | 71967927 | C | T | ExonicFunc = unknown |
| 16 | 71983772 | G | C | ExonicFunc = unknown |
| 16 | 71986946 | A | G | ExonicFunc = unknown |
| 16 | 71988106 | C | T | ExonicFunc = unknown |
| 16 | 72001110 | G | A | ExonicFunc = unknown |
| 16 | 72001136 | G | A | ExonicFunc = unknown |
| 16 | 72003952 | G | C | ExonicFunc = unknown |
| 16 | 72007232 | G | A | ExonicFunc = unknown |
| 16 | 72007399 | C | T | ExonicFunc = unknown |
| 16 | 72011162 | G | C | ExonicFunc = unknown |
| 16 | 72011181 | G | T | ExonicFunc = unknown |
| 16 | 72011193 | A | C | ExonicFunc = unknown |
| 16 | 72011261 | A | G | ExonicFunc = unknown |
| 16 | 72012239 | C | G | ExonicFunc = unknown |
| 16 | 72013797 | G | C | ExonicFunc = unknown |
| 16 | 72020134 | T | C | ExonicFunc = unknown |
| 16 | 72020294 | G | A | ExonicFunc = unknown |
| 16 | 72020323 | A | G | ExonicFunc = unknown |
| 16 | 72027191 | T | A | ExonicFunc = unknown |
| 16 | 72032221 | G | A | ExonicFunc = unknown |
| 16 | 72032231 | T | A | ExonicFunc = unknown |
| 16 | 72033801 | G | T | ExonicFunc = unknown |
| 16 | 81129822 | G | A | ExonicFunc = missense_SNV |
| 16 | 81134860 | C | G | ExonicFunc-unknown |
| 16 | 81142257 | T | C | ExonicFunc = unknown |
| 16 | 81145807 | C | G | ExonicFunc = unknown |
| 16 | 81145976 | C | T | ExonicFunc = unknown |
| 16 | 81151122 | A | C | ExonicFunc = unknown |

TABLE 26-continued

SNP variants of TRP channel or ACh receptors
(TRP family, TRPV1, TRPC6, TRPV4, TRPC1, TRPM8, TRPC4,
TRPV2, TRPV5, TRPC5, TRPM6, TRPC7, TRPM5,
TRPC3, PKD1, TRPV6, PKD2, TRPA1, TRPM7, TRPM2,
TRPM4, TRPM3, TRPV3, and CHRNA7, CHRM3,
CHRNA4, CHRNA3, CHRNB4, CHRNB2 and CHRNE)
annotated with their consequences.

| Chromosome | Location | Reference allele | Alternative allele | Consequences (intronic or exonic) |
|---|---|---|---|---|
| 16 | 81151123 | c | G | ExonicFunc = unknown |
| 16 | 81157324 | G | A | ExonicFunc = unknown |
| 16 | 81157353 | G | A | ExonicFunc = unknown |
| 16 | 81157385 | G | T | ExonicFunc = unknown |
| 16 | 81161552 | C | T | ExonicFunc = unknown |
| 16 | 81161569 | T | G | ExonicFunc = unknown |
| 16 | 81161571 | T | C | ExonicFunc = unknown |
| 16 | 81161578 | G | A | ExonicFunc = unknown |
| 16 | 81161608 | T | C | ExonicFunc = unknown |
| 16 | 81161635 | C | A | ExonicFunc = unknown |
| 16 | 81173136 | T | C | ExonicFunc = unknown |
| 16 | 81173193 | C | T | ExonicFunc = unknown |
| 16 | 81174978 | A | G | ExonicFunc = unknown |
| 16 | 81174992 | G | T | ExonicFunc = unknown |
| 16 | 81174999 | A | G | ExonicFunc = unknown |
| 16 | 81175103 | G | A | ExonicFunc = unknown |
| 16 | 81180988 | C | G | ExonicFunc = unknown |
| 16 | 81180995 | T | C | ExonicFunc = unknown |
| 16 | 81181066 | G | A | ExonicFunc = unknown |
| 16 | 81181097 | G | T | ExonicFunc = unknown |
| 16 | 81181783 | T | C | ExonicFunc = unknown |
| 16 | 81181821 | T | C | ExonicFunc = unknown |
| 16 | 81181869 | T | C | ExonicFunc = unknown |
| 16 | 81183325 | T | A | ExonicFunc = unknown |
| 16 | 81183492 | T | G | ExonicFunc = unknown |
| 16 | 81185412 | C | T | ExonicFunc = unknown |
| 16 | 81185416 | A | G | ExonicFunc = unknown |
| 16 | 81185419 | G | C | ExonicFunc = unknown |
| 16 | 81187685 | G | A | ExonicFunc = unknown |
| 16 | 81190598 | T | C | ExonicFunc = unknown |
| 16 | 81190601 | T | C, A | ExonicFunc = unknown |
| 16 | 81190613 | A | G | ExonicFunc = unknown |
| 16 | 81193321 | C | T | ExonicFunc = unknown |
| 16 | 81193358 | C | G | ExonicFunc = unknown |
| 16 | 81194382 | T | C, A | ExonicFunc = unknown |
| 16 | 81197218 | G | A | ExonicFunc = unknown |
| 16 | 81198306 | C | A | ExonicFunc = unknown |
| 16 | 81199468 | G | C | ExonicFunc = unknown |
| 16 | 81199520 | T | C | ExonicFunc-unknown |
| 16 | 81199538 | T | C | ExonicFunc = unknown |
| 16 | 81199544 | G | A | ExonicFunc = unknown |
| 16 | 81199554 | C | T | ExonicFunc = unknown |
| 16 | 81199555 | A | G | ExonicFunc = unknown |
| 16 | 81201620 | C | A | ExonicFunc = unknown |
| 16 | 81201625 | G | A | ExonicFunc = unknown |
| 16 | 81204396 | G | A | ExonicFunc = synonymous_SNV |
| 16 | 81204635 | G | C | ExonicFunc = synonymous_SNV |
| 16 | 81208515 | G | A | ExonicFunc = missense_SNV |
| 16 | 81209234 | C | T | ExonicFunc = synonymous_SNV |
| 16 | 81211496 | C | A | ExonicFunc = missense_SNV |
| 16 | 81211548 | G | A | ExonicFunc = synonymous_SNV |
| 16 | 81211587 | T | C | ExonicFunc = synonymous_SNV |
| 16 | 81213378 | A | G | ExonicFunc = missense_SNV |
| 16 | 81213381 | A | C | ExonicFunc = missense_SNV |
| 16 | 81219187 | C | T | ExonicFunc = missense_SNV |
| 16 | 81232275 | G | A | ExonicFunc = missense_SNV |
| 16 | 81232294 | T | C | ExonicFunc = missense_SNV |
| 16 | 81232336 | T | C | ExonicFunc = missense_SNV |
| 16 | 81232564 | T | G | ExonicFunc = missense_SNV |
| 16 | 81241098 | C | T | ExonicFunc = synonymous_SNV |
| 16 | 81241100 | G | C | ExonicFunc = missense_SNV |
| 16 | 81242102 | G | A | ExonicFunc = missense_SNV |
| 16 | 81242107 | C | A | ExonicFunc = missense_SNV |
| 16 | 81242151 | T | C | ExonicFunc = synonymous_SNV |
| 16 | 81242194 | T | C | ExonicFunc = missense_SNV |
| 16 | 81242198 | G | A | ExonicFunc = stopgain |
| 16 | 81248716 | C | T | ExonicFunc = missense_SNV |
| 16 | 81248745 | A | G | ExonicFunc = missense_SNV |
| 16 | 81249927 | C | T | ExonicFunc = missense_SNV |
| 16 | 81249954 | T | A | ExonicFunc = missense_SNV |
| 16 | 81253745 | C | G | ExonicFunc = missense_SNV |
| 16 | 81253759 | A | G | ExonicFunc = missense_SNV |
| 16 | 81253917 | A | G | ExonicFunc = missense_SNV |
| 7 | 142565385 | G | A | ExonicFunc = synonymous_SNV |
| 7 | 142565776 | G | A | ExonicFunc = synonymous_SNV |
| 7 | 142568070 | G | A | ExonicFunc = missense_SNV |
| 7 | 142569556 | A | G | ExonicFunc = synonymous_SNV |
| 7 | 142569596 | A | G | ExonicFunc = missense_SNV |
| 7 | 142569701 | C | T | ExonicFunc = missense_SNV |
| 7 | 142570142 | T | C | ExonicFunc = synonymous_SNV |
| 7 | 142570217 | C | T | ExonicFunc = synonymous_SNV |
| 7 | 142572304 | G | A | ExonicFunc = synonymous_SNV |
| 7 | 142572908 | T | C | ExonicFunc = missense_SNV |
| 7 | 142573263 | C | T | ExonicFunc = synonymous_SNV |
| 7 | 142573614 | G | A | ExonicFunc = missense_SNV |
| 7 | 142573644 | A | T | ExonicFunc = missense_SNV |
| 7 | 142574913 | A | G | ExonicFunc = missense_SNV |
| 4 | 88928968 | G | C | ExonicFunc = missense_SNV |
| 4 | 88929305 | G | A | ExonicFunc = synonymous_SNV |
| 4 | 88929453 | G | A | ExonicFunc = missense_SNV |
| 4 | 88964586 | C | T | ExonicFunc = synonymous_SNV |
| 5 | 137244517 | G | A | ExonicFunc = missense_SNV |
| 5 | 137259179 | T | C | ExonicFunc = missense_SNV |
| 5 | 137278682 | T | O | ExonicFunc = missense_SNV |
| 10 | 102046380 | T | G | ExonicFunc = missense_SNV |
| 10 | 102048208 | G | T | ExonicFunc = missense_SNV |
| 10 | 102050242 | C | A | ExonicFunc = missense_SNV |
| 10 | 102056745 | C | T | ExonicFunc = missense_SNV |
| 10 | 102089663 | C | T | ExonicFunc = missense_SNV |
| 8 | 72936145 | T | C | ExonicFunc = missense_SNV |
| 8 | 72948588 | C | T | ExonicFunc = synonymous_SNV |
| 8 | 72951118 | T | C | ExonicFunc = synonymous_SNV |
| 8 | 72964965 | G | A | ExonicFunc = synonymous_SNV |
| 8 | 72966002 | G | A | ExonicFunc = synonymous_SNV |
| 8 | 72975801 | T | G | ExonicFunc = missense_SNV |
| 8 | 72977703 | C | T | ExonicFunc = missense_SNV |
| 8 | 72981318 | G | A | ExonicFunc = synonymous_SNV |
| 8 | 72981327 | A | G | ExonicFunc = synonymous_SNV |
| 8 | 72984041 | C | G | ExonicFunc = missense_SNV |
| 8 | 72987638 | G | A | ExonicFunc = missense_SNV |
| 15 | 50867082 | G | A | ExonicFunc = synonymous_SNV |
| 15 | 50867142 | C | T | ExonicFunc = synonymous_SNV |
| 15 | 50878630 | G | A | ExonicFunc = missense_SNV |
| 15 | 50888568 | A | G | ExonicFunc = synonymous_SNV |
| 15 | 50897114 | A | G | ExonicFunc = synonymous_SNV |
| 21 | 45811343 | T | G | ExonicFunc = missense_SNV |
| 21 | 45820196 | C | T | ExonicFunc = missense_SNV |
| 21 | 45825799 | C | T | ExonicFunc = missense_SNV |
| 21 | 45833864 | C | T | ExonicFunc = missense_SNV |
| 21 | 45844751 | A | G | ExonicFunc = missense_SNV |
| 21 | 45855100 | G | T | ExonicFunc = missense_SNV |
| 19 | 49657613 | G | T | ExonicFunc = missense_SNV |
| 19 | 49658084 | G | A | ExonicFunc = synonymous_SNV |
| 19 | 49658209 | A | C | ExonicFunc = missense_SNV |
| 19 | 49658367 | C | T | ExonicFunc = missense_SNV |
| 19 | 49658390 | T | C | ExonicFunc = synonymous_SNV |
| 19 | 49671214 | A | G | ExonicFunc = missense_SNV |
| 19 | 49671281 | G | A | ExonicFunc = synonymous_SNV |
| 19 | 49675017 | G | T | ExonicFunc = synonymous_SNV |
| 19 | 49699866 | C | T | ExonicFunc = synonymous_SNV |
| 9 | 73150873 | T | G | ExonicFunc = missense_SNV |
| 9 | 73150918 | C | T | ExonicFunc = missense_SNV |
| 9 | 73150984 | C | T | ExonicFunc = missense_SNV |
| 9 | 73151715 | C | T | ExonicFunc = synonymous_SNV |
| 9 | 73151970 | C | T | ExonicFunc = synonymous_SNV |
| 9 | 73240431 | T | G | ExonicFunc = synonymous_SNV |

TABLE 26-continued

SNP variants of TRP channel or ACh receptors
(TRP family, TRPV1, TRPC6, TRPV4, TRPC1, TRPM8, TRPC4,
TRPV2, TRPV5, TRPC5, TRPM6, TRPC7, TRPM5,
TRPC3, PKD1, TRPV6,P KD2, TRPA1, TRPM7, TRPM2,
TRPM4, TRPM3, TRPV3, and CHRNA7,CHRM3,
CHRNA4, CHRNA3, CHRNB4, CHRNB2 and CHRNE)
annotated with their consequences.

| Chromosome | Location | Reference allele | Alternative allele | Consequences (intronic or exonic) |
|---|---|---|---|---|
| 9 | 73255554 | G | A | ExonicFunc = synonymous_SNV |
| 9 | 73461337 | T | A | ExonicFunc = synonymous_SNV |
| 17 | 3417253 | A | G | ExonicFunc = synonymous_SNV |
| 17 | 3422032 | G | A | ExonicFunc = synonymous_SNV |
| 17 | 3422073 | C | T | ExonicFunc = missense_SNV |
| 17 | 3422077 | G | A | ExonicFunc = synonymous_SNV |
| 17 | 3436080 | C | T | ExonicFunc = synonymous_SNV |
| 17 | 3436209 | T | C | ExonicFunc = synonymous_SNV |
| 17 | 3445901 | T | G | ExonicFunc = synonymous_SNV |
| 17 | 3446885 | T | C | ExonicFunc = missense_SNV |
| 17 | 3447914 | C | T | ExonicFunc = synonymous_SNV |
| 17 | 3458072 | T | C | ExonicFunc = missense_SNV |

TABLE 27

Frequency distribution and significance of Transient Receptor Potential (TRP) SNPs in CFS/ME patients (n = 14) and non-fatigued controls (n = 11) from isolated B cells in rank order of significance.

| Chr | Position | A1 | F_A | F_U | A2 | CHISQ | P | OR | ExonicFunc | Gene |
|---|---|---|---|---|---|---|---|---|---|---|
| 4 | 122,872,719 | G | 0.1 | 0.45 | A | 6.144 | 0.01318 | 0.1358 | synonymous_SNV | Gene = NM_001130698 |
| 16 | 81,253,759 | A | 0.0625 | 0.3333 | G | 3.8 | 0.05124 | 0.1333 | missense_SNV | Gene = NM_001076780, NM_052892 |
| 16 | 81,253,917 | A | 0.0625 | 0.3333 | G | 3.8 | 0.05124 | 0.1333 | missense_SNV | Gene = NM_001076780, NM_052892 |
| 9 | 73,151,715 | C | 0.2308 | 0.04545 | T | 3.285 | 0.0699 | 6.3 | synonymous_SNV | Gene = NM_001007471, NM_020952, NM_024971, NM_206944, NM_206945, NM_206946, NM_206947 |
| 11 | 2,439,542 | A | 0.3846 | 0.15 | G | 3.069 | 0.07979 | 3.542 | missense_SNV | Gene = NM_014555 |
| 11 | 2,435,946 | A | 0.2917 | 0.1111 | G | 1.992 | 0.1582 | 3.294 | synonymous_SNV | Gene = NM_014555 |
| 17 | 3,493,200 | C | 0.3077 | 0.1364 | G | 1.98 | 0.1594 | 2.815 | missense_SNV | Gene = NM_018727, NM_080704, NM_080705, NM_080706 |
| 12 | 110,226,379 | G | 0.5 | 0 | A | 1.714 | 0.1904 | NA | synonymous_SNV | Gene = NM_001177428, NM_001177431, NM_001177433, NM_021625, NM_147204 |
| 17 | 16,325,968 | A | 0.25 | 0.5 | G | 1.699 | 0.1924 | 0.3333 | synonymous_SNV | Gene = NM_016113 |
| 17 | 16,326,005 | A | 0.25 | 0.5 | C | 1.699 | 0.1924 | 0.3333 | synonymous_SNV | Gene = NM_016113 |
| 7 | 47,913,579 | T | 0.2308 | 0.09091 | C | 1.678 | 0.1951 | 3 | missense_SNV | Gene = NM_138295 |
| 16 | 81,249,954 | T | 0.125 | 0.3125 | A | 1.646 | 0.1995 | 0.3143 | missense_SNV | Gene = NM_001076780, NM_052892 |
| 17 | 3,446,885 | T | 0.5 | 0.2857 | C | 1.429 | 0.232 | 2.5 | missense_SNV | Gene = NM_001258205, NM_145068 |
| 8 | 72,975,801 | T | 0.3636 | 0.2 | G | 1.375 | 0.241 | 2.286 | missense_SNV | Gene = NM_007332 |
| 8 | 72,981,327 | A | 0.3636 | 0.2 | G | 1.375 | 0.241 | 2.286 | synonymous_SNV | Gene = NM_007332 |
| 9 | 73,150,873 | T | 0.5 | 0.25 | G | 1.25 | 0.2636 | 3 | missense_SNV | Gene = NM_001007471, NM_020952, NM_024971, NM_206944, NM_206945, NM_206946, NM_206947 |
| 9 | 73,150,918 | C | 0.5 | 0.25 | T | 1.25 | 0.2636 | 3 | missense_SNV | Gene = NM_001007471, NM_020952, NM_024971, NM_206944, NM_206945, NM_206946, NM_206947 |
| 8 | 72,966,002 | G | 0.3889 | 0.2143 | A | 1.117 | 0.2905 | 2.333 | synonymous_SNV | Gene = NM_007332 |
| 16 | 81,241,098 | C | 0.08333 | 0.1818 | T | 0.9816 | 0.3218 | 0.4091 | synonymous_SNV | Gene = NM_001076780, NM_052892 |
| 16 | 81,242,194 | T | 0.08333 | 0.1818 | C | 0.9816 | 0.3218 | 0.4091 | missense_SNV | Gene = NM_001076780, NM_052892 |
| 17 | 16,336,992 | C | 0.3125 | 0.5 | G | 0.9141 | 0.339 | 0.4545 | synonymous_SNV | Gene = NM_016113 |
| 17 | 3,480,447 | T | 0.35 | 0.5 | C | 0.765 | 0.3818 | 0.5385 | missense_SNV | Gene = NM_018727, NM_080704, NM_080705, NM_080706 |
| 11 | 101,347,093 | A | 0.5 | 0.3 | G | 0.7481 | 0.3871 | 2.333 | synonymous_SNV | Gene = NM_004621 |
| 17 | 3,422,032 | G | 0.25 | 0.3889 | A | 0.7466 | 0.3876 | 0.5238 | synonymous_SNV | Gene = NM_001258205, NM_145068 |
| 11 | 2,432,964 | T | 0.2778 | 0.4 | C | 0.6288 | 0.4278 | 0.5769 | synonymous_SNV | Gene = NM_014555 |
| 15 | 50,878,630 | G | 0.25 | 0.5 | A | 0.625 | 0.4292 | 0.3333 | missense_SNV | Gene = NM_017672 |
| 16 | 2,160,973 | A | 0.25 | 0.5 | G | 0.5333 | 0.4652 | 0.3333 | missense_SNV | Gene = NM_000296, NM_001009944 |

TABLE 27-continued

Frequency distribution and significance of Transient Receptor Potential (TRP) SNPs in CFS/ME patients (n = 14) and non-fatigued controls (n = 11) from isolated B cells in rank order of significance.

| Chr | Position | A1 | F_A | F_U | A2 | CHISQ | P | OR | ExonicFunc | Gene |
|---|---|---|---|---|---|---|---|---|---|---|
| 17 | 3,436,080 | C | 0.4375 | 0.3125 | T | 0.5333 | 0.4652 | 1.711 | synonymous_SNV | Gene = NM_001258205, NM_145068 |
| 17 | 3,494,361 | G | 0.25 | 0.5 | A | 0.5333 | 0.4652 | 0.3333 | synonymous_SNV | Gene = NM_018727, NM_080704, NM_080705, NM_080706 |
| 7 | 47,872,845 | A | 0.2083 | 0.3 | G | 0.4889 | 0.4844 | 0.614 | synonymous_SNV | Gene = NM_138295 |
| 11 | 2,427,291 | A | 0.1667 | 0.25 | C | 0.4656 | 0.495 | 0.6 | synonymous_SNV | Gene = NM_014555 |
| 16 | 81,211,496 | C | 0.1667 | 0.3333 | A | 0.4444 | 0.505 | 0.4 | missense_SNV | Gene = NM_001076780, NM_001278423, NM_001278425, NM_052892 |
| 16 | 81,211,548 | G | 0.1667 | 0.3333 | A | 0.4444 | 0.505 | 0.4 | synonymous_SNV | Gene = NM_001076780, NM_001278423, NM_001278425, NM_052892 |
| 3 | 142,443,441 | G | 0.25 | 0.5 | A | 0.375 | 0.5403 | 0.3333 | missense_SNV | Gene = NM_001251845, NM_003304 |
| 7 | 47,913,580 | G | 0.2 | 0.3333 | A | 0.3556 | 0.551 | 0.5 | synonymous_SNV | Gene = NM_138295 |
| 7 | 47,920,345 | G | 0.2 | 0.3333 | A | 0.3556 | 0.551 | 0.5 | synonymous_SNV | Gene = NM_138295 |
| 8 | 72,987,638 | G | 0.3333 | 0.5 | A | 0.3429 | 0.5582 | 0.5 | missense_SNV | Gene = NM_007332 |
| 15 | 50,888,568 | A | 0.3333 | 0.5 | G | 0.3429 | 0.5582 | 0.5 | synonymous_SNV | Gene = NM_017672 |
| 17 | 3,486,702 | G | 0.375 | 0.5 | A | 0.3429 | 0.5582 | 0.6 | missense_SNV | Gene = NM_018727, NM_080704, NM_080705, NM_080706 |
| 16 | 81,232,275 | G | 0.08333 | 0.1364 | A | 0.3332 | 0.5638 | 0.5758 | missense_SNV | Gene = NM_001076780, NM_052892 |
| 16 | 81,232,564 | T | 0.08333 | 0.1364 | G | 0.3332 | 0.5638 | 0.5758 | missense_SNV | Gene = NM_001076780, NM_052892 |
| 12 | 110,240,838 | T | 0.3 | 0.3889 | G | 0.3326 | 0.5641 | 0.6735 | synonymous_SNV | Gene = NM_001177428, NM_001177431, NM_001177433, NM_021625, NM_147204 |
| 17 | 3,422,077 | G | 0.375 | 0.5 | A | 0.3208 | 0.5711 | 0.6 | synonymous_SNV | Gene = NM_001258205, NM_145068 |
| 5 | 137,244,517 | G | 0.25 | 0.1818 | A | 0.3136 | 0.5755 | 1.5 | missense_SNV | Gene = NM_001258448, NM_014386 |
| 3 | 142,523,349 | G | 0.375 | 0.25 | A | 0.2909 | 0.5896 | 1.8 | synonymous_SNV | Gene = NM_001251845, NM_003304 |
| 3 | 142,524,858 | G | 0.375 | 0.25 | A | 0.2909 | 0.5896 | 1.8 | synonymous_SNV | Gene = NM_001251845, NM_003304 |
| 16 | 81,208,515 | G | 0.4 | 0.3 | A | 0.2871 | 0.5921 | 1.556 | missense_SNV | Gene = NM_001076780, NM_001278423, NM_001278425, NM_052892 |
| 9 | 77,415,284 | A | 0.3889 | 0.5 | C | 0.2801 | 0.5966 | 0.6364 | synonymous_SNV | Gene = NM_001177310, NM_001177311, NM_017662 |
| 2 | 234,854,550 | G | 0.375 | 0.5 | C | 0.254 | 0.6143 | 0.6 | synonymous_SNV | Gene = NM_024080 |
| 16 | 81,242,102 | G | 0.3182 | 0.25 | A | 0.2386 | 0.6252 | 1.4 | missense_SNV | Gene = NM_001076780, NM_052892 |
| 9 | 77,502,160 | G | 0.3889 | 0.3 | A | 0.2212 | 0.6381 | 1.485 | missense_SNV | Gene = NM_001177311 |
| 2 | 234,905,078 | C | 0.5 | 0.4 | T | 0.22 | 0.639 | 1.5 | synonymous_SNV | Gene = NM_024080 |
| 3 | 142,503,605 | G | 0.4 | 0.3 | A | 0.2198 | 0.6392 | 1.556 | synonymous_SNV | Gene = NM_001251845, NM_003304 |
| 7 | 47,876,567 | G | 0.5 | 0.3333 | A | 0.1778 | 0.6733 | 2 | synonymous_SNV | Gene = NM_138295 |
| 9 | 73,150,984 | C | 0.2222 | 0.1667 | T | 0.1773 | 0.6737 | 1.429 | missense_SNV | Gene = NM_001007471, NM_020952, NM_024971, NM_206944, NM_206945, NM_206946, NM_206947 |
| 2 | 234,915,540 | C | 0.375 | 0.5 | G | 0.1714 | 0.6788 | 0.6 | synonymous_SNV | Gene = NM_024080 |
| 11 | 2,438,963 | C | 0.375 | 0.5 | A | 0.1714 | 0.6788 | 0.6 | missense_SNV | Gene = NM_014555 |
| 4 | 88,928,968 | G | 0.25 | 0.3333 | C | 0.1587 | 0.6903 | 0.6667 | missense_SNV | Gene = NM_000297 |
| 7 | 47,925,331 | C | 0.35 | 0.2857 | G | 0.1555 | 0.6933 | 1.346 | missense_SNV | Gene = NM_138295 |
| 8 | 72,936,145 | T | 0.5 | 0.4 | C | 0.1524 | 0.6963 | 1.5 | missense_SNV | Gene = NM_007332 |
| 9 | 73,151,970 | C | 0.2222 | 0.2778 | T | 0.1481 | 0.7003 | 0.7429 | synonymous_SNV | Gene = NM_001007471, NM_020952, NM_024971, NM_206944, NM_206945, NM_206946, NM_206947 |
| 9 | 77,436,641 | G | 0.4 | 0.3333 | A | 0.1422 | 0.7061 | 1.333 | synonymous_SNV | Gene = NM_001177310, NM_001177311, NM_017662 |
| 11 | 2,439,767 | T | 0.4286 | 0.5 | C | 0.1327 | 0.7137 | 0.75 | missense_SNV | Gene = NM_014555 |
| 4 | 122,854,116 | C | 0.5 | 0.4 | C | 0.1167 | 0.7327 | 1.5 | synonymous_SNV | Gene = NM_001130698, NM_003305 |
| 16 | 81,242,198 | G | 0.4167 | 0.5 | A | 0.1125 | 0.7373 | 0.7143 | stopgain | Gene = NM_001076780, NM_052892 |

TABLE 27-continued

Frequency distribution and significance of Transient Receptor Potential (TRP) SNPs in CFS/ME patients (n = 14) and non-fatigued controls (n = 11) from isolated B cells in rank order of significance.

| Chr | Position | A1 | F_A | F_U | A2 | CHISQ | P | OR | ExonicFunc | Gene |
|---|---|---|---|---|---|---|---|---|---|---|
| 9 | 73,461,337 | T | 0.3333 | 0.2857 | A | 0.0928 | 0.7607 | 1.25 | synonymous_SNV | Gene = NM_001007470, NM_001007471, NM_020952, NM_024971, NM_206944, NM_206945, NM_206946, NM_206947, NM_206948 |
| 17 | 3,445,901 | T | 0.2692 | 0.3125 | G | 0.09087 | 0.7631 | 0.8105 | synonymous_SNV | Gene = NM_001258205, NM_145068 |
| 16 | 81,241,100 | G | 0.3182 | 0.2778 | C | 0.07696 | 0.7815 | 1.213 | missense_SNV | Gene = NM_001076780, NM_052892 |
| 16 | 81,242,151 | T | 0.3182 | 0.2778 | C | 0.07696 | 0.7815 | 1.213 | synonymous_SNV | Gene = NM_001076780, NM_052892 |
| 7 | 47,971,575 | A | 0.2727 | 0.3125 | G | 0.07124 | 0.7895 | 0.825 | synonymous_SNV | Gene = NM_138295 |
| 16 | 81,253,745 | C | 0.2857 | 0.3333 | G | 0.06878 | 0.7931 | 0.8 | missense_SNV | Gene = NM_001076780, NM_052892 |
| 16 | 2,140,010 | A | 0.375 | 0.4286 | G | 0.06044 | 0.8058 | 0.8 | synonymous_SNV | Gene = NM_000296, NM_001009944 |
| 16 | 2,160,503 | T | 0.375 | 0.4286 | G | 0.06044 | 0.8058 | 0.8 | synonymous_SNV | Gene = NM_000296, NM_001009944 |
| 15 | 50,867,082 | G | 0.3182 | 0.3571 | A | 0.05844 | 0.809 | 0.84 | synonymous_SNV | Gene = NM_017672 |
| 4 | 122,824,052 | C | 0.4 | 0.4375 | T | 0.05143 | 0.8206 | 0.8571 | synonymous_SNV | Gene = NM_001130698, NM_003305 |
| 16 | 81,213,378 | A | 0.08333 | 0.1 | G | 0.03667 | 0.8481 | 0.8182 | missense_SNV | Gene = NM_001076780, NM_001278423, NM_001278425, NM_052892 |
| 16 | 2,159,996 | G | 0.375 | 0.4167 | A | 0.03472 | 0.8522 | 0.84 | synonymous_SNV | Gene = NM_000296, NM_001009944 |
| 16 | 81,248,716 | C | 0.3333 | 0.3 | T | 0.02794 | 0.8673 | 1.167 | missense_SNV | Gene = NM_001076780, NM_052892 |
| 11 | 2,435,956 | C | 0.4444 | 0.4167 | T | 0.02262 | 0.8804 | 1.12 | missense_SNV | Gene = NM_014555 |
| 17 | 3,447,914 | C | 0.2308 | 0.25 | T | 0.02019 | 0.887 | 0.9 | synonymous_SNV | Gene = NM_001258205, NM_145068 |
| 16 | 2,140,454 | T | 0.4 | 0.4286 | C | 0.01959 | 0.8887 | 0.8889 | synonymous_SNV | Gene = NM_000296, NM_001009944 |
| 16 | 2,140,680 | T | 0.4 | 0.4286 | C | 0.01959 | 0.8887 | 0.8889 | missense_SNV | Gene = NM_000296, NM_001009944 |
| 7 | 47,921,682 | A | 0.375 | 0.4 | T | 0.01625 | 0.8986 | 0.9 | synonymous_SNV | Gene = NM_138295 |
| 16 | 81,248,745 | A | 0.3571 | 0.3333 | G | 0.01618 | 0.8988 | 1.111 | missense_SNV | Gene = NM_001076780, NM_052892 |
| 7 | 142,626,549 | C | 0.3571 | 0.375 | T | 0.007015 | 0.9332 | 0.9259 | missense_SNV | Gene = NM_019841 |
| 7 | 47,968,927 | C | 0.3182 | 0.3125 | A | 0.001384 | 0.9703 | 1.027 | missense_SNV | Gene = NM_138295 |
| 2 | 234,854,540 | G | 0.5 | 0.5 | C | 0 | 1 | 1 | missense_SNV | Gene = NM_024080 |
| 2 | 234,854,552 | A | 0.5 | 0.5 | G | 0 | 1 | 1 | missense_SNV | Gene = NM_024080 |
| 2 | 234,863,788 | G | 0.5 | 0.5 | A | 0 | 1 | 1 | missense_SNV | Gene = NM_024080 |
| 4 | 88,929,305 | G | 0.5 | 0.5 | A | 0 | 1 | 1 | synonymous_SNV | Gene = NM_000297 |
| 5 | 135,692,575 | G | 0.5 | 0.5 | A | 0 | 1 | 1 | synonymous_SNV | Gene = NM_001167576, NM_001167577, NM_020389 |
| 7 | 47,840,387 | C | 0.5 | 0.5 | T | 0 | 1 | 1 | missense_SNV | Gene = NM_138295 |
| 7 | 47,851,623 | C | 0.5 | 0.5 | T | 0 | 1 | 1 | missense_SNV | Gene = NM_138295 |
| 7 | 47,852,837 | C | 0.5 | 0.5 | T | 0 | 1 | 1 | missense_SNV | Gene = NM_138295 |
| 7 | 47,854,956 | C | 0.5 | 0.5 | T | 0 | 1 | 1 | synonymous_SNV | Gene = NM_138295 |
| 7 | 47,869,038 | T | 0.5 | 0.5 | C | 0 | 1 | 1 | synonymous_SNV | Gene = NM_138295 |
| 7 | 47,874,630 | G | 0.5 | 0.5 | A | 0 | 1 | 1 | missense_SNV | Gene = NM_138295 |
| 7 | 47,879,049 | G | 0.5 | 0.5 | A | 0 | 1 | 1 | missense_SNV | Gene = NM_138295 |
| 7 | 47,913,560 | G | 0.3333 | 0.3333 | T | 0 | 1 | 1 | missense_SNV | Gene = NM_138295 |
| 7 | 47,917,087 | C | 0.5 | 0.5 | T | 0 | 1 | 1 | synonymous_SNV | Gene = NM_138295 |
| 7 | 47,927,744 | C | 0.5 | 0.5 | T | 0 | 1 | 1 | missense_SNV | Gene = NM_138295 |
| 7 | 47,930,148 | C | 0.5 | 0.5 | T | 0 | 1 | 1 | synonymous_SNV | Gene = NM_138295 |
| 7 | 47,971,626 | G | 0.5 | 0.5 | A | 0 | 1 | 1 | synonymous_SNV | Gene = NM_138295 |
| 7 | 142,569,596 | A | 0.5 | 0.5 | G | 0 | 1 | 1 | missense_SNV | Gene = NM_018646 |
| 7 | 142,570,142 | T | 0.5 | 0.5 | C | 0 | 1 | 1 | synonymous_SNV | Gene = NM_018646 |
| 7 | 142,572,304 | G | 0.5 | 0.5 | A | 0 | 1 | 1 | synonymous_SNV | Genc = NM_018646 |
| 7 | 142,572,908 | T | 0.5 | 0.5 | C | 0 | 1 | 1 | missense_SNV | Gene = NM_018646 |
| 7 | 142,573,263 | C | 0.5 | 0.5 | T | 0 | 1 | 1 | synonymous_SNV | Gene = NM_018646 |
| 7 | 142,574,913 | A | 0.5 | 0.5 | G | 0 | 1 | 1 | missense_SNV | Gene = NM_018646 |
| 7 | 142,622,714 | G | 0.5 | 0.5 | A | 0 | 1 | 1 | synonymous_SNV | Gene = NM_019841 |
| 7 | 142,625,249 | T | 0.5 | 0.5 | C | 0 | 1 | 1 | synonymous_SNV | Gene = NM_019841 |
| 7 | 142,625,258 | G | 0.5 | 0.5 | A | 0 | 1 | 1 | synonymous_SNV | Gene = NM_019841 |
| 7 | 142,625,882 | G | 0.5 | 0.5 | A | 0 | 1 | 1 | synonymous_SNV | Gene = NM_019841 |
| 7 | 142,625,933 | G | 0.5 | 0.5 | A | 0 | 1 | 1 | synonymous_SNV | Gene = NM_019841 |
| 7 | 142,626,656 | C | 0.5 | 0.5 | T | 0 | 1 | 1 | synonymous_SNV | Gene = NM_019841 |
| 8 | 72,977,703 | C | 0.5 | 0.5 | T | 0 | 1 | 1 | missense_SNV | Gene = NM_007332 |
| 8 | 72,981,318 | G | 0.5 | 0.5 | A | 0 | 1 | 1 | synonymous_SNV | Gene = NM_007332 |
| 8 | 72,984,041 | C | 0.5 | 0.5 | G | 0 | 1 | 1 | missense_SNV | Gene = NM_007332 |
| 9 | 73,240,431 | T | 0.5 | 0.5 | G | 0 | 1 | 1 | synonymous_SNV | Gene = NM_024971, NM_206945 |

TABLE 27-continued

Frequency distribution and significance of Transient Receptor Potential (TRP) SNPs in CFS/ME patients (n = 14) and non-fatigued controls (n = 11) from isolated B cells in rank order of significance.

| Chr | Position | A1 | F_A | F_U | A2 | CHISQ | P | OR | ExonicFunc | Gene |
|---|---|---|---|---|---|---|---|---|---|---|
| 9 | 77,376,633 | A | 0.5 | 0.5 | G | 0 | 1 | 1 | synonymous_SNV | Gene = NM_001177310, NM_001177311, NM_017662 |
| 9 | 77,376,647 | T | 0.5 | 0.5 | C | 0 | 1 | 1 | missense_SNV | Gene = NM_001177310, NM_001177311, NM_017662 |
| 9 | 77,377,410 | C | 0.5 | 0.5 | T | 0 | 1 | 1 | missense_SNV | Gene = NM_001177310, NM_001177311, NM_017662 |
| 9 | 77,407,636 | C | 0.5 | 0.5 | T | 0 | 1 | 1 | synonymous_SNV | Gene = NM_001177310, NM_001177311, NM_017662 |
| 9 | 77,416,972 | C | 0.5 | 0.5 | T | 0 | 1 | 1 | synonymous_SNV | Gene = NM_001177310, NM_001177311, NM_017662 |
| 10 | 102,048,208 | G | 0.5 | 0.5 | T | 0 | 1 | 1 | missense_SNV | Gene = NM_001253837, NM_016112 |
| 10 | 102,050,242 | C | 0.5 | 0.5 | A | 0 | 1 | 1 | missense_SNV | Gene = NM_001253837, NM_016112 |
| 10 | 102,056,745 | C | 0.5 | 0.5 | T | 0 | 1 | 1 | missense_SNV | Gene = NM_001253837, NM_016112 |
| 10 | 102,089,663 | C | 0.5 | 0.5 | T | 0 | 1 | 1 | missense_SNV | Gene = NM_001253837, NM_016112 |
| 11 | 2,432,666 | C | 0.5 | 0.5 | T | 0 | 1 | 1 | missense_SNV | Gene = NM_014555 |
| 11 | 101,323,770 | C | 0.5 | 0.5 | T | 0 | 1 | 1 | synonymous_SNV | Gene = NM_004621 |
| 11 | 101,359,750 | G | 0.5 | 0.5 | A | 0 | 1 | 1 | missense_SNV | Gene = NM_004621 |
| 12 | 110,238,487 | A | 0.5 | 0.5 | G | 0 | 1 | 1 | synonymous_SNV | Gene = NM_001177431, NM_021625, NM_147204 |
| 13 | 38,211,105 | T | 0.5 | 0.5 | C | 0 | 1 | 1 | missense_SNV | Gene = NM_001135955, NM_001135956, NM_001135957, NM_001135958, NM_003306, NM_016179 |
| 13 | 38,357,384 | G | 0.5 | 0.5 | A | 0 | 1 | 1 | synonymous_SNV | Gene = NM_001135955, NM_001135956, NM_001135957, NM_001135958, NM_003306, NM_016179 |
| 16 | 2,140,321 | G | 0.5 | 0.5 | A | 0 | 1 | 1 | synonymous_SNV | Gene = NM_000296, NM_001009944 |
| 16 | 2,140,554 | G | 0.5 | 0.5 | A | 0 | 1 | 1 | missense_SNV | Gene = NM_000296, NM_001009944 |
| 16 | 2,144,176 | G | 0.5 | 0.5 | A | 0 | 1 | 1 | missense_SNV | Gene = NM_000296, NM_001009944 |
| 16 | 2,144,182 | G | 0.5 | 0.5 | A | 0 | 1 | 1 | missense_SNV | Gene = NM_000296, NM_001009944 |
| 16 | 2,159,405 | C | 0.5 | 0.5 | T | 0 | 1 | 1 | synonymous_SNV | Gene = NM_000296, NM_001009944 |
| 16 | 81,219,187 | C | 0.3333 | 0.3333 | T | 0 | 1 | 1 | missense_SNV | Gene = NM_001076780, NM_052892 |
| 16 | 81,232,336 | T | 0.5 | 0.5 | C | 0 | 1 | 1 | missense_SNV | Gene = NM_001076780, NM_052892 |
| 16 | 81,249,927 | C | 0.5 | 0.5 | T | 0 | 1 | 1 | missense_SNV | Gene = NM_001076780, NM_052892 |
| 17 | 3,475,490 | C | 0.5 | 0.5 | T | 0 | 1 | 1 | synonymous_SNV | Gene = NM_018727, NM_080704, NM_080705, NM_080706 |
| 17 | 3,476,990 | G | 0.5 | 0.5 | A | 0 | 1 | 1 | synonymous_SNV | Gene = NM_018727, NM_080704, NM_080705, NM_080706 |
| 17 | 3,480,910 | A | 0.5 | 0.5 | G | 0 | 1 | 1 | synonymous_SNV | Gene = NM_018727, NM_080704, NM_080705, NM_080706 |
| 17 | 3,495,374 | G | 0.5 | 0.5 | A | 0 | 1 | 1 | missense_SNV | Gene = NM_018727, NM_080704, NM_080705, NM_080706 |
| 17 | 16,321,032 | G | 0.5 | 0.5 | C | 0 | 1 | 1 | missense_SNV | Gene = NM_016113 |
| 19 | 49,671,281 | G | 0.5 | 0.5 | A | 0 | 1 | 1 | synonymous_SNV | Gene = NM_001195227, NM_017636 |
| 19 | 49,675,017 | G | 0.5 | 0.5 | T | 0 | 1 | 1 | synonymous_SNV | Gene = NM_001195227, NM_017636 |
| 19 | 49,699,866 | C | 0.5 | 0.5 | T | 0 | 1 | 1 | synonymous_SNV | Gene = NM_017636 |
| 20 | 33,657,126 | G | 0.25 | 0.25 | A | 0 | 1 | 1 | synonymous_SNV | Gene = NM_015638, NM_199368 |
| 20 | 33,665,969 | C | 0.5 | 0.5 | T | 0 | 1 | 1 | synonymous_SNV | Gene = NM_015638, NM_199368 |
| 21 | 45,811,343 | T | 0.5 | 0.5 | G | 0 | 1 | 1 | missense_SNV | Gene = NM_003307 |
| 21 | 45,820,196 | C | 0.5 | 0.5 | T | 0 | 1 | 1 | missense_SNV | Gene = NM_003307 |
| 2 | 234,854,547 | A | 0.5 | NA | T | NA | NA | NA | synonymous_SNV | Gene = NM_024080 |
| 2 | 234,858,645 | C | 0.5 | NA | T | NA | NA | NA | missense_SNV | Gene = NM_024080 |

TABLE 27-continued

Frequency distribution and significance of Transient Receptor Potential (TRP) SNPs in CFS/ME patients (n = 14) and non-fatigued controls (n = 11) from isolated B cells in rank order of significance.

| Chr | Position | A1 | F_A | F_U | A2 | CHISQ | P | OR | ExonicFunc | Gene |
|---|---|---|---|---|---|---|---|---|---|---|
| 2 | 234,875,354 | G | NA | 0.5 | A | NA | NA | NA | synonymous_SNV | Gene = NM_024080 |
| 4 | 88,929,453 | 0 | NA | 0 | A | NA | NA | NA | missense_SNV | Gene = NM_000297 |
| 4 | 88,964,586 | C | NA | 0.5 | T | NA | NA | NA | synonymous_SNV | Gene = NM_000297 |
| 4 | 122,800,987 | T | 0.5 | NA | C | NA | NA | NA | synonymous_SNV | Gene = NM_001130698, NM_003305 |
| 5 | 135,692,743 | C | 0.5 | NA | A | NA | NA | NA | synonymous_SNV | Gene = NM_001167576, NM_001167577, NM_020389 |
| 5 | 137,259,179 | 0 | 0 | 0 | C | NA | NA | NA | missense_SNV | Gene = NM_001258448, NM_001258449, NM_014386 |
| 7 | 47,840,310 | C | 0.5 | NA | G | NA | NA | NA | missense_SNV | Gene = NM_138295 |
| 7 | 47,851,578 | G | 0.5 | NA | A | NA | NA | NA | missense_SNV | Gene = NM_138295 |
| 7 | 47,892,745 | A | 0.5 | NA | G | NA | NA | NA | missense_SNV | Gene = NM_138295 |
| 7 | 47,917,126 | T | NA | 0.5 | C | NA | NA | NA | synonymous_SNV | Gene = NM_138295 |
| 7 | 47,930,280 | C | 0.5 | NA | T | NA | NA | NA | synonymous_SNV | Gene = NM_138295 |
| 7 | 47,970,707 | G | 0.5 | NA | A | NA | NA | NA | missense_SNV | Gene = NM_138295 |
| 7 | 142,569,556 | A | 0.5 | NA | G | NA | NA | NA | synonymous_SNV | Gene = NM_018646 |
| 7 | 142,569,701 | C | NA | 0.5 | T | NA | NA | NA | missense_SNV | Gene = NM_018646 |
| 7 | 142,570,217 | C | 0.5 | NA | T | NA | NA | NA | synonymous_SNV | Gene = NM_018646 |
| 7 | 142,573,614 | G | NA | 0.5 | A | NA | NA | NA | missense_SNV | Gene = NM_018646 |
| 7 | 142,573,644 | A | NA | 0.5 | T | NA | NA | NA | missense_SNV | Gene = NM_018646 |
| 7 | 142,609,749 | C | 0.5 | NA | T | NA | NA | NA | missense_SNV | Gene = NM_019841 |
| 7 | 142,630,534 | G | 0.5 | NA | A | NA | NA | NA | missense_SNV | Gene = NM_019841 |
| 8 | 72,948,588 | C | 0.5 | NA | T | NA | NA | NA | synonymous_SNV | Gene = NM_007332 |
| 8 | 72,951,118 | T | NA | 0.5 | C | NA | NA | NA | synonymous_SNV | Gene = NM_007332 |
| 8 | 72,964,965 | G | 0.5 | NA | A | NA | NA | NA | synonymous_SNV | Gene = NM_007332 |
| 9 | 73,255,554 | G | 0.5 | NA | A | NA | NA | NA | synonymous_SNV | Gene = NM_001007471, NM_020952, NM_024971, NM_206944, NM_206945, NM_206946, NM_206947 |
| 9 | 77,376,652 | A | NA | 0.5 | C | NA | NA | NA | missense_SNV | Gene = NM_001177310, NM_001177311, NM_017662 |
| 9 | 77,448,950 | A | 0.5 | NA | G | NA | NA | NA | synonymous_SNV | Gene = NM_001177310, NM_001177311, NM_017662 |
| 11 | 2,434,402 | C | 0.5 | NA | T | NA | NA | NA | synonymous_SNV | Gene = NM_014555 |
| 11 | 2,436,464 | C | 0.5 | NA | T | NA | NA | NA | missense_SNV | Gene = NM_014555 |
| 11 | 2,442,364 | G | 0.5 | NA | A | NA | NA | NA | synonymous_SNV | Gene = NM_014555 |
| 11 | 2,444,188 | C | 0.5 | NA | T | NA | NA | NA | missense_SNV | Gene = NM_014555 |
| 11 | 101,325,788 | G | NA | 0.5 | A | NA | NA | NA | synonymous_SNV | Gene = NM_004621 |
| 11 | 101,342,958 | G | NA | 0.5 | A | NA | NA | NA | synonymous_SNV | Gene = NM_004621 |
| 11 | 101,454,192 | G | NA | 0.5 | A | NA | NA | NA | missense_SNV | Gene = NM_004621 |
| 12 | 110,222,146 | C | 0.5 | NA | G | NA | NA | NA | synonymous_SNV | Gene = NM_001177428, NM_001177431, NM_001177433, NM_021625, NM_147204 |
| 12 | 110,230,597 | C | 0.5 | NA | T | NA | NA | NA | missense_SNV | Gene = NM_001177428, NM_001177431, NM_001177433, NM_021625, NM_147204 |
| 12 | 110,238,481 | G | NA | 0.5 | A | NA | NA | NA | synonymous_SNV | Gene = NM_001177431, NM_021625, NM_147204 |
| 12 | 110,240,848 | G | NA | 0.5 | A | NA | NA | NA | synonymous_SNV | Gene = NM_001177428, NM_001177431, NM_001177433, NM_021625, NM_147204 |
| 12 | 110,252,547 | G | NA | 0.5 | A | NA | NA | NA | missense_SNV | Gene = NM_001177428, NM_001177431, NM_001177433, NM_021625, NM_147204 |
| 13 | 38,211,313 | T | 0.5 | NA | C | NA | NA | NA | synonymous_SNV | Gene = NM_001135955, NM_001135956, NM_001135957, NM_001135958, NM_003306, NM_016179 |
| 13 | 38,237,564 | A | NA | 0.5 | G | NA | NA | NA | synonymous_SNV | Gene = NM_001135955, NM_001135956, NM_001135957, NM_001135958, NM_003306, NM_016179 |
| 15 | 50,867,142 | C | 0.5 | NA | T | NA | NA | NA | synonymous_SNV | Gene = NM_017672 |
| 15 | 50,897,114 | A | 0.5 | NA | G | NA | NA | NA | synonymous_SNV | Gene = NM_017672 |
| 16 | 2,139,814 | G | NA | 0.5 | A | NA | NA | NA | missense_SNV | Gene = NM_000296, NM_001009944 |
| 16 | 2,139,935 | G | 0.5 | NA | A | NA | NA | NA | synonymous_SNV | Gene = NM_000296, NM_001009944 |

TABLE 27-continued

Frequency distribution and significance of Transient Receptor Potential (TRP) SNPs in CFS/ME patients (n = 14) and non-fatigued controls (n = 11) from isolated B cells in rank order of significance.

| Chr | Position | A1 | F_A | F_U | A2 | CHISQ | P | OR | ExonicFunc | Gene |
|---|---|---|---|---|---|---|---|---|---|---|
| 16 | 2,140,912 | G | 0.5 | NA | C | NA | NA | NA | synonymous_SNV | Gene = NM_000296, NM_001009944 |
| 16 | 2,141,454 | G | NA | 0.5 | A | NA | NA | NA | synonymous_SNV | Gene = NM_000296, NM_001009944 |
| 16 | 2,152,387 | 0 | NA | 0 | G | NA | NA | NA | missense_SNV | Gene = NM_000296, NM_001009944 |
| 16 | 2,152,388 | 0 | NA | 0 | G | NA | NA | NA | synonymous_SNV | Gene = NM_000296, NM_001009944 |
| 16 | 2,156,021 | A | 0.5 | NA | G | NA | NA | NA | synonymous_SNV | Gene = NM_000296, NM_001009944 |
| 16 | 2,158,871 | C | NA | 0.5 | A | NA | NA | NA | synonymous_SNV | Gene = NM_000296, NM_001009944 |
| 16 | 2,159,522 | C | 0.5 | NA | T | NA | NA | NA | synonymous_SNV | Gene = NM_000296, NM_001009944 |
| 16 | 2,159,750 | G | 0.5 | NA | A | NA | NA | NA | synonymous_SNV | Gene = NM_000296, NM_001009944 |
| 16 | 2,160,494 | C | 0.5 | NA | T | NA | NA | NA | synonymous_SNV | Gene = NM_000296, NM_001009944 |
| 16 | 2,161,113 | C | 0.5 | NA | T | NA | NA | NA | missense_SNV | Gene = NM_000296, NM_001009944 |
| 16 | 2,161,150 | G | NA | 0.5 | A | NA | NA | NA | missense_SNV | Gene = NM_000296, NM_001009944 |
| 16 | 2,161,489 | C | NA | 0.5 | A | NA | NA | NA | missense_SNV | Gene = NM_000296, NM_001009944 |
| 16 | 2,161,793 | G | NA | 0.5 | A | NA | NA | NA | synonymous_SNV | Gene = NM_000296, NM_001009944 |
| 16 | 2,161,796 | G | NA | 0.5 | A | NA | NA | NA | synonymous_SNV | Gene = NM_000296, NM_001009944 |
| 16 | 2,162,955 | G | 0 | NA | G | NA | NA | NA | missense_SNV | Gene = NM_000296, NM_001009944 |
| 16 | 2,164,808 | C | 0.5 | NA | T | NA | NA | NA | missense_SNV | Gene = NM_000296, NM_001009944 |
| 16 | 2,167,970 | G | 0.5 | NA | A | NA | NA | NA | synonymous_SNV | Gene = NM_000296, NM_001009944 |
| 16 | 81,204,396 | G | 0.5 | NA | A | NA | NA | NA | synonymous_SNV | Gene = NM_001076780, NM_001278423 |
| 16 | 81,204,635 | G | 0.5 | NA | C | NA | NA | NA | synonymous_SNV | Gene = NM_001076780, NM_001278423, NM_001278425, NM_052892 |
| 16 | 81,209,234 | C | NA | 0.5 | T | NA | NA | NA | synonymous_SNV | Gene = NM_001076780, NM_001278423, NM_001278425, NM_052892 |
| 16 | 81,211,587 | T | 0.5 | NA | C | NA | NA | NA | synonymous_SNV | Gene = NM_001076780, NM_001278423, NM_001278425, NM_052892 |
| 16 | 81,213,381 | A | NA | 0.5 | C | NA | NA | NA | missense_SNV | Gene = NM_001076780, NM_001278423, NM_001278425, NM_052892 |
| 16 | 81,232,294 | T | 0.5 | NA | C | NA | NA | NA | missense_SNV | Gene = NM_001076780, NM_052892 |
| 16 | 81,242,107 | T | 0.5 | NA | C | NA | NA | NA | missense_SNV | Gene = NM_001076780, NM_052892 |
| 17 | 3,417,253 | A | NA | 0.5 | G | NA | NA | NA | synonymous_SNV | Gene = NM_001258205, NM_145068 |
| 17 | 3,422,073 | C | NA | 0.5 | T | NA | NA | NA | missense_SNV | Gene = NM_001258205, NM_145068 |
| 17 | 3,436,209 | T | NA | 0.5 | C | NA | NA | NA | synonymous_SNV | Gene = NM_001258205, NM_145068 |
| 17 | 3,458,072 | 0 | 0 | 0 | C | NA | NA | NA | missense_SNV | Gene = NM_001258205, NM_145068 |
| 17 | 3,480,433 | G | NA | 0.5 | C | NA | NA | NA | missense_SNV | Gene = NM_018727, NM_080704, NM_080705, NM_080706 |
| 17 | 3,495,465 | C | NA | 0.5 | T | NA | NA | NA | synonymous_SNV | Gene = NM_018727, NM_080704, NM_080705, NM_080706 |
| 17 | 16,320,994 | C | NA | 0.5 | T | NA | NA | NA | synonymous_SNV | Gene = NM_016113 |
| 17 | 16,326,990 | C | 0.5 | NA | G | NA | NA | NA | missense_SNV | Gene = NM_016113 |
| 19 | 49,671,214 | A | NA | 0.5 | G | NA | NA | NA | missense_SNV | Gene = NM_001195227, NM_017636 |
| 21 | 45,825,799 | C | NA | 0.5 | T | NA | NA | NA | missense_SNV | Gene = NM_003307 |
| 21 | 45,833,864 | C | NA | 0.5 | T | NA | NA | NA | missense_SNV | Gene = NM_003307 |
| 21 | 45,844,751 | 0 | 0 | 0 | G | NA | NA | NA | missense_SNV | Gene = NM_003307 |
| 21 | 45,855,100 | G | NA | 0.5 | T | NA | NA | NA | missense_SNV | Gene = NM_003307 |

TABLE 28

Frequency distribution and significance of AChR SNPs in CFS/ME (n = 14) patients and non-fatigued controls (n = 11) from isolated B cells in rank order of significance.

| Chr | Position | A1 | F_A | F_U | A2 | CHISQ | P | OR | ExonicFunc | Gene |
|---|---|---|---|---|---|---|---|---|---|---|
| 20 | 61981554 | C | 0.04167 | 0.1818 | A | 2.327 | 0.1271 | 0.1957 | synonymous_SNV | Gene = NM_000744, NM_001256573 |
| 20 | 61982124 | A | 0.04167 | 0.1818 | G | 2.327 | 0.1271 | 0.1957 | synonymous_SNV | Gene = NM_000744, NM_001256573 |
| 20 | 61981134 | G | 0.2727 | 0.4 | A | 0.7636 | 0.3822 | 0.5625 | synonymous_SNV | Gene = NM_000744, NM_001256573 |
| 15 | 78909452 | T | 0.2083 | 0.3182 | C | 0.7183 | 0.3967 | 0.5639 | synonymous_SNV | Gene = NM_000743, NM_001166694 |
| 20 | 61981104 | C | 0.2917 | 0.4 | T | 0.5698 | 0.4503 | 0.6176 | synonymous_SNV | Gene = NM_000744, NM_001256573 |
| 15 | 78894339 | G | 0.3889 | 0.3 | A | 0.2212 | 0.6381 | 1.485 | synonymous_SNV | Gene = NM_000743, NM_001166694 |
| 15 | 78911181 | T | 0.4 | 0.3333 | C | 0.181 | 0.6706 | 1.333 | synonymous_SNV | Gene = NM_000743, NM_001166694 |
| 20 | 61982085 | A | 0.07692 | 0.09091 | G | 0.03051 | 0.8613 | 0.8333 | synonymous_SNV | Gene = NM_000744, NM_001256573 |
| 20 | 61981536 | A | 0.03846 | 0.04545 | G | 0.01459 | 0.9038 | 0.84 | synonymous_SNV | Gene = NM_000744, NM_001256573 |
| 15 | 78917399 | A | 0.2083 | 0.2222 | G | 0.01178 | 0.9136 | 0.9211 | synonymous_SNV | Gene = NM_001256567 |
| 15 | 32322929 | G | 0.5 | 0.5 | A | 0 | 1 | 1 | synonymous_SNV | Gene = NM_001190455 |
| 15 | 78911230 | C | 0.5 | 0.5 | T | 0 | 1 | 1 | missense_SNV | Gene = NM_000743, NM_001166694 |
| 15 | 78923505 | G | 0.5 | 0.5 | A | 0 | 1 | 1 | missense_SNV | Gene = NM_000750, NM_001256567 |
| 17 | 4802329 | G | 0.5 | 0.5 | A | 0 | 1 | 1 | synonymous_SNV | Gene = NM_000080 |
| 17 | 4806052 | C | 0.5 | 0.5 | A | 0 | 1 | 1 | missense_SNV | Gene = NM_000080 |
| 20 | 61990939 | G | 0.5 | 0.5 | A | 0 | 1 | 1 | synonymous_SNV | Gene = NM_000744 |
| 1 | 240070784 | T | 0.5 | NA | C | NA | NA | NA | synonymous_SNV | Gene = NM_000740 |
| 1 | 240070944 | G | 0.5 | NA | A | NA | NA | NA | missense_SNV | Gene = NM_000740 |
| 15 | 78894357 | G | 0.5 | NA | T | NA | NA | NA | synonymous_SNV | Gene = NM_000743, NM_001166694 |
| 15 | 78913131 | G | NA | 0.5 | A | NA | NA | NA | synonymous_SNV | Gene = NM_000743, NM_001166694 |
| 15 | 78921762 | G | NA | 0.5 | A | NA | NA | NA | synonymous_SNV | Gene = NM_000750 |
| 15 | 78922194 | 0 | 0 | NA | A | NA | NA | NA | synonymous_SNV | Gene = NM_000750 |
| 15 | 78922229 | T | NA | 0.5 | C | NA | NA | NA | missense_SNV | Gene = NM_000750 |
| 15 | 78922240 | C | 0.5 | NA | T | NA | NA | NA | missense_SNV | Gene = NM_000750 |
| 17 | 4802317 | T | NA | 0.5 | C | NA | NA | NA | synonymous_SNV | Gene = NM_000080 |
| 17 | 4802829 | G | 0.5 | NA | A | NA | NA | NA | synonymous_SNV | Gene = NM_000080 |
| 17 | 4804902 | G | NA | 0.5 | A | NA | NA | NA | synonymous_SNV | Gene = NM_000080 |
| 17 | 4805777 | C | NA | 0.5 | G | NA | NA | NA | missense_SNV | Gene = NM_000080 |
| 20 | 61981253 | C | NA | 0.5 | T | NA | NA | NA | missense_SNV | Gene = NM_000744, NM_001256573 |
| 20 | 61981362 | G | 0.5 | NA | A | NA | NA | NA | synonymous_SNV | Gene = NM_000744, NM_001256573 |
| 20 | 61981411 | G | 0.5 | NA | A | NA | NA | NA | missense_SNV | Gene = NM_000744, NM_001256573 |
| 20 | 61992467 | C | 0.5 | NA | T | NA | NA | NA | synonymous_SNV | Gene = NM_000744 |
| 20 | 61992509 | T | 0.5 | NA | C | NA | NA | NA | synonymous_SNV | Gene = NM_000744 |

Further information on these SNPs can be found at http://www.ocbi.nlm.nih.gov/projects/SNP/.

The SNPs and genotypes of Tables 26, 27 and 28 are consistent with those identified for isolated B lymphocytes in Example 6.

PLINK analysis highlighted missense, synonomous and genes for SNPs of the TRP families and PKD1L2.

81,253,759 and 81,253,917 SNPs were identified as missense SNPs for the exon sequence for PKD1L2: NM_001076780:exon1:e.T217C:p.W73R and PKD1L2: NM_001076780:exon1:c.T59C:p.V20A. SNP 122,872,719, a TRPC3 receptor, was also found to be significantly associated with CSF/ME patients compared to controls from isolated B cells.

These finds are significant as TRPC3 has shown a direct association with PKCbeta that is required for downstream activation in B cells [43y]. Additionally, TRPP subunits can be divided into two subcategories depending on structural similarity. The first group, polycystic kidney disease 1 (PKD1)-like, contains polycystic 1 (Previously known as TRPP1), PKDREJ, PKD1L1, PKD1L2, and PKD1L3.

Example 10—ERK1/2, MEK1/2 and p38 Downstream Signalling Molecules Impaired in $CD56^{dim}CD16^+$ and $CD56^{bright}CD16^{dim/-}$ Natural Killer Cells in Chronic Fatigue Syndrome/Myalgic Encephalomyelitis Patients Natural Killer (NK) cells are innate immune cells which comprise approximately 10-15% of lymphocytes circulating in the peripheral blood [1m]. Two predominant NK cell phenotypes identified by the surface expression of cluster of differentiation (CD) 56 and CD16 and an absence of CD3 provide host immunity through the production of immunoregulatory cytokines and the cytotoxic lysis of target cells [2m-4m].

Ten percent of peripheral NK cells are $CD56^{bright}CD16^{dim/-}$ NK cells which constitutively express receptors for monocyte derived cytokines (monokines) [5m, 6m]. Monokine receptor ligation rapidly stimulates $CD56^{bright}CD16^{dim/-}$ NK cells to produce cytokines including interferon gamma (IFN-$\gamma$), tumour necrosis factor alpha and beta (TNF-$\alpha$ and $\beta$), granulocyte-macrophage colony-stimulating factor (GM-CSF), interleukin (IL)-10 and IL-13 [5m, 6m]. $CD56^{bright7}CD16^{dim/-}$ NK cell cytokine production provides an early source of cytokines which augments NK cell cytotoxic activity and regulates the function of other lymphocytes [2m, 5m, 4m]. Approximately 90% of peripheral NK cells are cytotoxic $CD56^{dim}CD16^+$ NK cells [7m, 5m]. Cytotoxic NK cells contain high numbers of secretory granules which constitutively express apoptotic inducing lytic proteins perforin, Granzyme A and Granzyme B [3m, 8m].

Following $CD56^{dim}CD16^+$ NK cell recognition of a target cell, the lytic proteins are released by a process known as degranulation to induce cytotoxic lysis and subsequent removal of target cells infected with viruses, bacteria or cells which have been malignantly transformed [9m, 10m].

Unlike T and B lymphocytes, the effector function of NK cells is governed by a myriad of surface receptors which integrate activating or inhibiting signals into intracellular signalling cascades [11m-13m]. After NK cell receptor ligation, intracellular activation signals are propagated through protein phosphorylation cascades by mitogen-activated protein kinases (MAPKs) [14m-16m]. Three main subgroups of MAPKs include extracellular signal-regulated kinases (ERK) 1/2, p38 MAPK (p38) and the c-Jun N-terminal kinase (JNK) [14m-16m]. In response to extra cellular stimuli, the MAPK signalling pathways transduce signals to specific intracellular targets to mediate cellular responses including gene expression, mitosis, motility, cell survival, apoptosis and differentiation [17m]. Within the NK cells, phosphorylation of MEK1/2 and p38 regulate cytokine production and ERK1/2 phosphorylation polarises the secretory granule towards the immune synapse for degranulation [16m, 18m]. In addition to MAPK signalling for normal cellular responses, impairments in MAPK signalling have been suggested to contribute to the pathology of disease processes relating to leukaemia, diabetes, Alzheimer's and Parkinson's disease, atherosclerosis, arthritis and airway inflammation [19m-25m].

Longitudinal reports of significantly reduced NK cell cytotoxic activity in Chronic Fatigue Syndrome/Myalgic Encephalomyelitis (CFS/ME) patients suggests the presence of an NK cell functional deficiency which may contribute to the illness pathogenesis [26m-34m]. Current investigations into NK cell phenotypes, receptors and lytic proteins in CFS/ME have reported equivocal findings and importantly, intracellular signalling by MAPKs in NK cells remains to be examined [27m, 35m, 36m]. Therefore, the purpose of the present study was to investigate NK cell phosphorylation of the MAPK signalling cascade, including signalling via the MAPK kinase (MAPKK/MEK1/2) and extracellular signal-regulated kinase (ERK)1/2 as well as p38, cytotoxic activity, degranulation, lytic proteins and cytokine production in $CD56^{dim}CD16^+$ and $CD56^{bright}CD16^{dim/-}$ NK cells from CFS/ME patients.

Methods

Participant Recruitment and Inclusion Criteria

CFS/ME patients and non-fatigued controls (NFC) were recruited from a participant database at the National Centre for Neuroimmunology and Emerging Diseases, Menzies Health Institute Queensland. All participants completed an online questionnaire based on the 1994 Fukuda definition for fatigue and symptom presentation to determine suitability for study inclusion [37m]. From the questionnaire responses, CFS/ME patients meeting the 1994 Fukuda definition and NFC were included. All participants were screened for exclusionary conditions such as epilepsy, thyroid conditions, psychosis, diabetes, cardiac disorders, smoking, pregnant or breastfeeding and immunological, inflammatory or autoimmune diseases.

Blood Collection and Cell Isolation

Forty millilitres of sodium heparin blood was collected by venepuncture from the antecubital vein of each participant. To avoid the influence of circadian variation, all blood samples were collected in the morning between 7:30-10 am. Laboratory analysis commenced within four hours of blood collection to maintain cell viability. Routine blood parameters including a full blood count, erythrocyte sedimentation rate, electrolytes and high sensitivity C-reactive protein were assessed on each participant sample by Queensland Pathology. The whole blood samples were diluted with unsupplemented Roswell Park Memorial Institute medium (RPM1I 1640 media (Life Technologies, Carlsbad, USA) and peripheral blood mononuclear cells (PBMCs) were isolated by density gradient centrifugation with Ficoll-Hypaque (GE Health Care, Uppsala, UP).

NK Cell MAPK Phosphorylation

Phosphorylation of signalling proteins in the MAPK pathway including signalling via the MAPK kinase (MAPKK/MEK1/2) and extracellular signal-regulated kinase (ERK)1/2 as well as p38, was examined under two stimulatory conditions using phospho-specific antibodies as previously described [38m-40m]. Following isolation, the PBMCs in RPMI 1640 media supplemented with ten percent FBS were incubated for a minimum of two hours at 37° C. with five percent $CO_2$ to reduce background phosphorylation. After resting, the PBMCs were stained with mAbs for CD56-APC (Miltenyi Biotech, Cologne, BG) or CD56-phycoerythrin-cyanine (PE-Cy)7, CD16-brilliant violet (BV)711 and CD3-BV510 (BD Biosciences, San Diego, USA) for 25 minutes and subsequently washed. The PBMCs were stimulated with either K562 cells (E:T of 25:1) or PMA (50 ng/ml) plus ionomycin (1, 0.5 µg/ml) as a positive control for 15 minutes in a water bath at 37° C. A parallel sample of unstimulated (US) cells in RPMI media alone was used to determine basal levels of phosphorylation. BD Phosflow fix buffer 1 (San Diego, USA) containing 4.2% formaldehyde was pre-warmed to 37° C. and added to the PBMCs, incubated for ten minutes at 37° C. and subsequently washed off. The cells were then incubated in BD perm/wash buffer 1 (San Diego, USA) containing FBS and saponin for ten minutes which was followed by staining with phosospecific mAbs including signal transducer and activator of transcription (Stat)-3 (pS727)-alexa fluor (AF) 488, MEK1 (pS218)/MEK2 (pS222)-AF488, p38 (pT180/pY182)-PerCP Cy5.5, ERK1/2 (pT202/pY204)-BV421, nuclear factor kappa beta (NF-κβ, pS529)-AF488, inhibitory kappa beta (Iκβ)-AF647, PKCα (pT497)-AF488 and JNK (pT183/pY185)-AF647 for 30 minutes and subsequent flow cytometry analysis.

NK Cell Cytotoxic Activity

Flow cytometry was used to measure NK cell cytotoxic activity against the human chronic myelogenous leukaemia K562 cell line as previously described [41m, 29m]. Briefly, K562 ceils (Sigma-Aldrich, St Louis, USA) were cultured in RPMI 1640 media (Life Technologies, Carlsbad, USA) supplemented with ten percent fetal bovine serum (FBS) (Life Technologies, Carlsbad, USA). Following isolation, the PBMCs were stained with Paul Karl Horan-26 fluorescent cell linker dye (Sigma-Aldrich, St Louis, USA) and washed with RPMI supplemented with ten percent FBS. The concentrations of the PBMCs and K562 cells were adjusted to $2.5 \times 10^6$ cells/ml and $1 \times 10^5$ cells/ml respectively and combined at three effector to target (E:T) ratios including 25:1, 12.5:1 and 6.25:1. A control sample of only K562 cells was also included to determine K562 cells undergoing apoptosis not induced by NK cell cytotoxic activity. The PBMCs and K562 cells were incubated for four hours at 37° C. with five percent $CO_2$ and then stained with fluorescein isothiocyanate (FITC) annexin V and 7-aminoactinomycin (Becton Dickinson [BD] Pharminogen, San Diego, USA) for flow cytometric analysis on a BD Calibur (BD Biosciences, San Diego, USA) dual laser four colour flow cytometer. NK cytotoxic activity was calculated as percent specific death of the K562 cells for the three E:T ratios as previously described [41m].

NK Cell Degranulation

NK cell surface expression of CD107a and CD107b was measured as a marker for NK cell degranulation as previously reported [9m]. PBMCs in the presence of mAbs for CD107a-PE and CD107b-FITC (BD Biosciences, San Diego, USA) were stimulated with either K562 cells (E:T of 25:1) or PMA (50 ng/ml) plus ionomycin (0.5 µg/ml) for one hour at 37° C. with five percent $CO_2$. Monensin (BD Biosciences, San Diego, USA) was added to the PBMCs and the cells were then incubated for an additional three hours. An unstimulated control sample included PBMCs incubated in only RPMI 1640 media. Post four hours incubation, the cells were washed and incubated with mAbs against CD56-APC, CD16-BV711 and CD3-BV510 (BD Biosciences, San Diego, USA) for 25 minutes which was followed by flow cytometric analysis.

NK Cell Lytic Proteins and Maturation Marker

Intracellular staining was used to measure the lytic proteins perforin, granzyme A and granzyme B contained within the secretory granules of NK cells [27m, 42m]. Surface expression of CD57 was measured as a marker for NK cell maturation [43m]. The PBMCs were incubated with mAbs for CD56-PE-Cy7, CD16-BV711, CD3-BV510 and CD57-PE-cyanin-based fluorescent dye (CF)594 for 23 minutes. The PBMCs were then permeabilised with BD fixation/permeabilisation solution for 20 minutes, washed in BD perm/wash buffer and then incubated with mAbs including perforin-APC (Miltenyi Biotec, Cologne, BG), granzyme A-FITC and granzyme B-V450 (BD Biosciences, San Diego, USA) for 30 minutes which was followed by flow cytometric analysis.

NK Cell Cytokines

NK cell production of the cytokines IFN-$\gamma$, TNF-$\alpha$ and GM-CSF was determined by intracellular staining under two stimulatory conditions as described previously [9m, 44m]. After isolation, PBMCs were incubated in the presence of either K562 cells (E:T of 25:1) or phorbol-12-myristate-13-acelate (PMA, 50 ng/ml) (Sigma-Aldrich, St Louis, USA) plus ionomycin (1, 0.5 µg/ml) (Sigma-Aldrich, St Louis, USA) for one hour at 37° C. with five percent $CO_2$. Brefeldin A (BD Biosciences, San Diego, USA) was added to prevent cytokine secretion during stimulation and the cells were incubated for an additional five hours [9m, 44m]. PBMCs incubated in RPMI 1640 media alone served as the unstimulated control sample. Following six hours incubation, the PBMCs were washed and incubated with monoclonal antibodies (mAbs) for CD56-PE-Cy7, CD16-BV711 and CD3-BV510 (BD Biosciences, San Diego, USA) for 25 minutes. The PBMCs were subsequently washed, incubated in BD fixation/permeabilisation solution (BD Biosciences, San Diego, USA) for 20 minutes, washed in BD perm/wash buffer (BD Biosciences, San Diego, USA) and then incubated for 30 minutes with mAbs against IFN-$\gamma$-allophycocyanin (APC), TNF-$\alpha$-peridinin chlorophyll protein-cyanine (PerCP-Cy)-5.5 (BD Biosciences, San Diego, USA) and GM-CSF-PE (Biolegend, San Diego, USA) for flow cytometric detection of intracellular cytokines.

Multiparametric Flow Cytometry Analysis

Data were collected on a 14-parameter LSR-Fortessa X20 flow cytometer (BD Biosciences, San Diego, USA). Cell signalling technology beads (BD Biosciences, San Diego, USA) were run on a daily basis to ensure optimal flow cytometry performance and application settings were employed to standardise target values for the duration of the experiments. A total of 2500 to 5000 CD56 positive events were acquired. Data generated for NK cell cytokines, degranulation, lytic proteins and cell maturation was analysed on FlowJo (version 10.0.8) and phosphorylation data were analysed on Cytobank (version 5.0) [45m]. NK cell analysis was performed on cells which fell within the lymphocyte population according to forward and side scatter properties. CD56$^+$CD3$^-$ NK cells were gated to determine total NK cells which was extrapolated to a plot of CD56 and CD16 to identify CD56$^{bright}$CD16$^{dim/-}$ and CD56$^{dim}$CD16$^+$ NK cells for the analysis of each marker for cytokines, degranulation, phosphorylation, lytic proteins and cell maturation. A combination of appropriate fluorescence minus one controls, isotype controls matched to antibody concentrations and unstimulated samples were used to determine NK cell gating for each analysis.

Statistical Analysis

Statistical analysis of the data was performed on the Statistical Package for the Social Sciences (version 22) and GraphPad Prism (version 6). All data sets were tested for normality using the Shapiro-Wilk test. The independent Mann-Whitney U-test was used to identify any significant differences in the NK cell parameters between the CFS/ME and NFC groups. A Kruskal-Wallis multiple comparisons test was used to identify significant differences in NK cell parameters before and after stimulation within the CFS/ME and NFC cohorts. Significance was set at p<0.05 and the data is presented as median±interquartile range unless otherwise stated.

Abbreviations

APC: allophycocyanin, AF: alexa fluor, BD: Becton Dickinson, BV: brilliant violet, CD: cluster of differentiation, CF: cyanin-based fluorescent dye, ERK: extracellular signal-regulated kinases, E:T: effector to target, FBS: fetal bovine serum, FITC: fluorescein isothiocyanate, GM-CSF: granulocyte-macrophage colony-stimulating factor, I$\kappa\beta$: inhibitory kappa beta, I: ionomycin , IFN-$\gamma$: interferon gamma, IL: interleukin, JNK: Jun N-terminal kinase, mABs: monoclonal antibodies, MAPK: mitogen-activated protein kinase, MFI: median fluorescence intensity, NK: Natural killer, NFC: non-fatigued control, NF-$\kappa\beta$: nuclear factor kappa beta, PBMCs: peripheral, blood mononuclear cells, PE: phycoerythrin, PE-Cy: phycoerythrin-cyanine, PerCP-Cy: peridinin chlorophyll protein-cyanine, PMA: phorbol-12-myristate-13-acetate, p38: p38 mitogen-activated protein kinase, RPMI: Roswell Park Memorial Institute, Stat: signal transducer and activator of transcription, TNF: tumour necrosis factor, US: unstimulated.

Results

Participant Inclusion, Blood Parameters and NK cell Phenotypes

14 CFS/ME patients meeting the 1994 Fukuda definition (mean age [years]±standard error of the mean (SEM) =53.5±2.17) and 11 NFC (mean age [years] ±SEM=48.82±3.46) were included in this study. Comparison of the group ages and blood parameters including erythrocyte sedimentation rate, high sensitivity C-reactive protein and full blood counts of white and red blood ceils between CFS/ME and the NFC revealed no significant differences (Table 29). Total NK cells were compared according to two phenotype populations, which were CD56$^{dim}$CD16$^+$ and CD56$^{bright}$CD16$^{dim/-}$—between CFS/ME and NFC cohorts and no significant differences were observed (See FIG. 5).

TABLE 29

CFS/ME and NFC blood parameters.

| | | CFS/ME (n = 14) | NFC (n = 11) | P value |
|---|---|---|---|---|
| | ESR (mm/Hr) | 7.85 ± 0.77 | 8.45 ± 1.44 | 0.700 |
| | High sensitivity C-reactive protein (mg/L) | 0.99 ± 0.30 | 0.91 ± 0.41 | 0.873 |
| White and red | White blood cells (10$^9$/L) | 5.16 ± 0.38 | 5.26 ± 0.41 | 0.860 |
| | Lymphocytes (10$^9$/L) | 1.67 ± 0.15 | 1.67 ± 0.13 | 1.000 |
| | Monocytes (10$^9$/L) | 0.32 ± 0.03 | 0.27 ± 0.03 | 0.258 |

TABLE 29-continued

CFS/ME and NFC blood parameters.

| | | CFS/ME (n = 14) | NFC (n = 11) | P value |
|---|---|---|---|---|
| blood cells | Neutrophils ($10^9$/L) | 2.96 ± 0.24 | 3.15 ± 0.28 | 0.610 |
| | Eosinophils ($10^9$/L) | 0.17 ± 0.03 | 0.15 ± 0.03 | 0.647 |
| | Basophils ($10^9$/L) | 0.03 ± 0.001 | 0.03 ± 0.001 | 1.000 |
| | Platelets ($10^9$/L) | 238.54 ± 15.50 | 248.00 ± 18.01 | 0.693 |
| | Red blood cells ($10^{12}$/L) | 4.55 ± 0.12 | 4.61 ± 0.15 | 0.755 |
| | Haemoglobin (g/L) | 138.85 ± 3.82 | 138.82 ± 4.26 | 0.996 |
| | Haematocrit | 0.42 ± 0.01 | 0.41 ± 0.01 | 0.493 |
| | Mean cell volume (fL) | 91.62 ± 0.94 | 89.27 ± 0.93 | 0.094 |
| Electrolytes | Sodium (mmol/L) | 137.92 ± 0.46 | 137.09 ± 0.53 | 0.249 |
| | Potassium (mmol/L) | 4.10 ± 0.10 | 4.16 ± 0.12 | 0.702 |
| | Chloride (mmol/L) | 100.69 ± 0.61 | 101.64 ± 0.65 | 0.301 |
| | Bicarbonate (mmol/L) | 28.62 ± 0.63 | 27.27 ± 0.45 | 0.112 |
| | Anion gap (mmol/L) | 8.54 ± 0.63 | 8.36 ± 0.64 | 0.845 |

Figure 6:
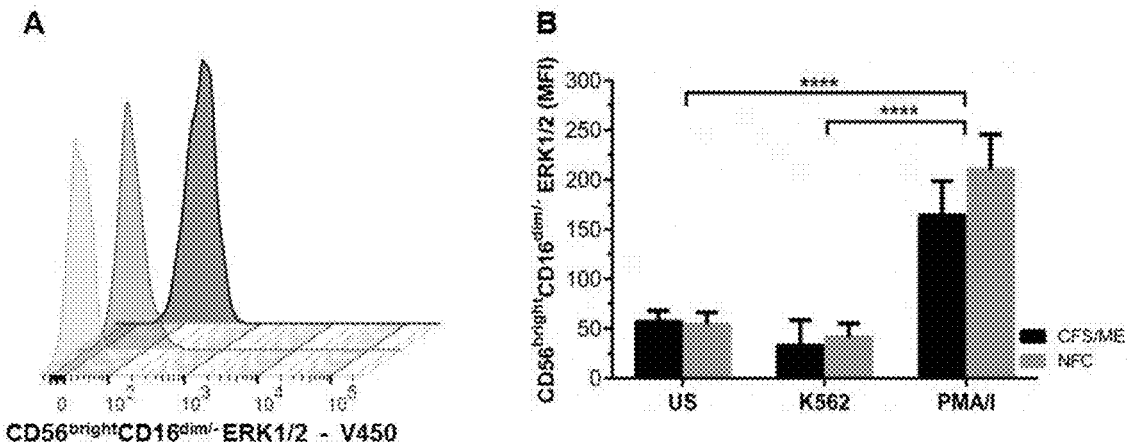
FIG. 6: $CD56^{bright}CD16^{dim/-}$ NK cell ERK1/2 flow cytometric plot for a representative individual (A). ERK1/2 in $CD56^{bright}CD16^{dim/-}$ NK cells were compared between CFS/ME and NFC groups and no significant differences were observed. PMA/I stimulation caused a significant increase in ERK1/2 phosphorylation compared to US (*p<0.001) and K562 cells (**p<0.0001) in both CFS/ME and NFC. Data are presented as MFI with interquartile range.

ERK1/2 Significantly Reduced in $CD56^{dim}CD16^+$ NK Cells from CFS/ME Patients After incubation with K562 cells at an E:T ratio of 25:1, ERK 1/2 was significantly reduced in $CD56^{dim}CD16^+$ NK cells from CFS/ME patients when compared to NFC. (See FIG. 5.) PMA/I induced a significant increase in ERK1/2 phosphorylation in $CD56^{dim}CD16^+$ NK cells compared to the US and K562 stimulated cells from CFS/ME and NFC participants. Comparison of ERK1/2 in $CD56^{bright}CD16^{dim/-}$ NK cells revealed no significant differences between CFS/ME and NFCs. (See FIG. 6.)

Figure 7:
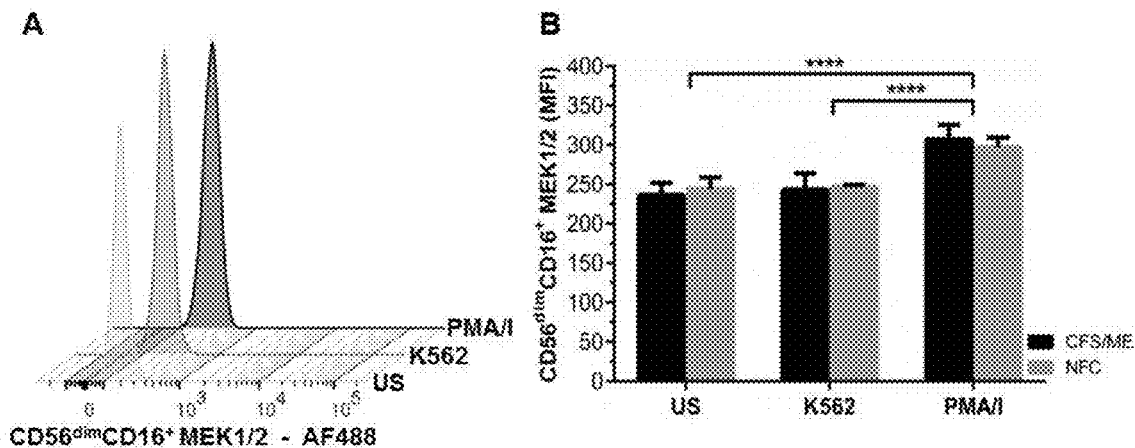
FIG. 7: Representative flow cytometric plot for MEK1/2 in $CD56^{dim}CD16^+$ NK cells (A). No significant differences were observed when MEK1/2 was compared between CFS/ME and NFC (B). In both CFS/ME and NFC, PMA/I stimulation resulted in a significant increase in phosphorylated MEK1/2 compared to US (**p<0.0001) and K562 stimulation (**p<0.0001). Data are presented as MFI with interquartile range.
Figure 8:
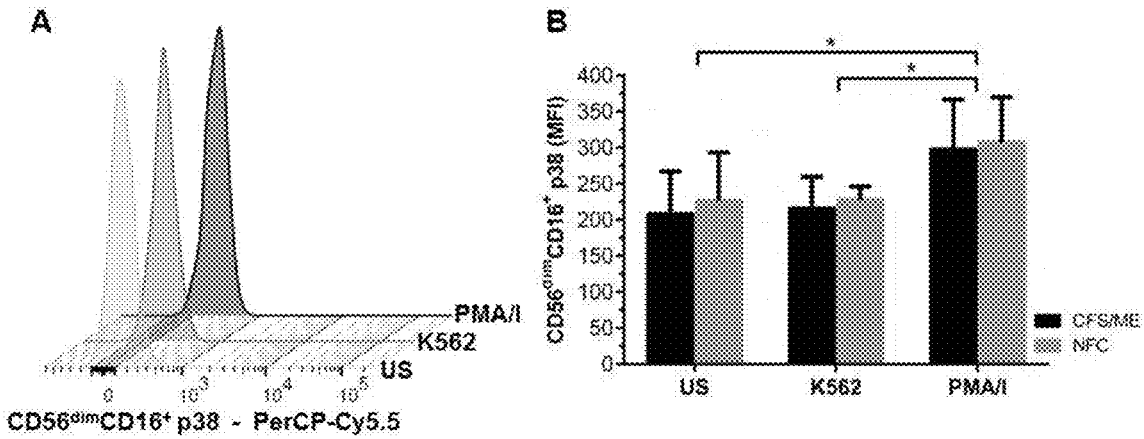
FIG. 8: p38 representative flow cytometric plot in $CD56^{dim}CD16^+$ NK cells (A). p38 was compared between CFS/ME and NFC and no significant differences were observed (B). Stimulation with PMA/I caused a significant increase in phosphorylated p38 when compared to US and K562 incubated cells (*p<0.05). Data are presented as MFI with interquartile range.
Figure 9:
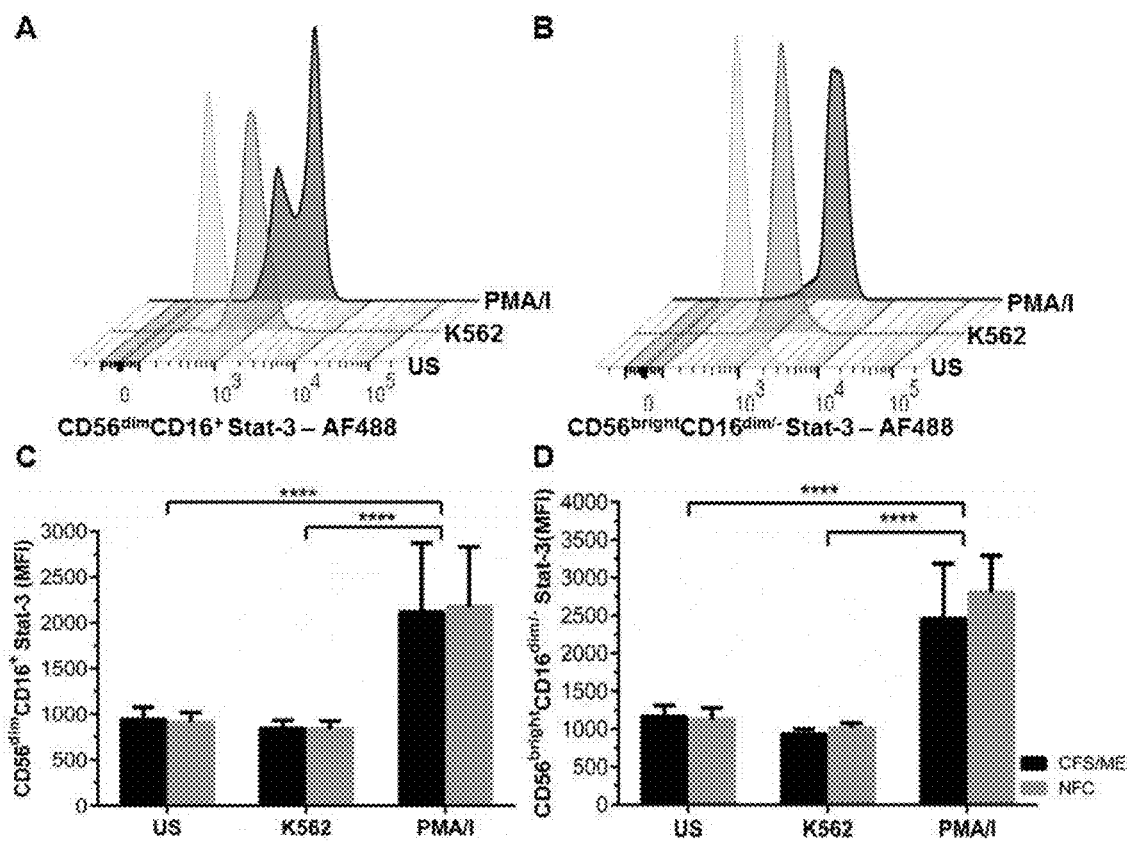
FIG. 9: Representative Stat-3 flow cytometric plots in $CD56^{dim}CD16^+$ (A) and $CD56^{bright}CD16^{dim/-}$ (B) NK cells. Comparison of Stat-3 in $CD56^{dim}CD16^+$ (C) and $CD56^{bright}CD16^{dim/-}$ (D) NK cells between CFS/ME and NFC revealed no significant differences. In $CD56^{dim}CD16^+$ and $CD56^{bright}CD16^{dim/-}$ NK cells, stimulation with PMA/I caused a significant increase in Stat-3 when compared to US (**p<0.0003) and K562 (**p<0.0001) in both CFS/ME and NFC.
Figure 10:
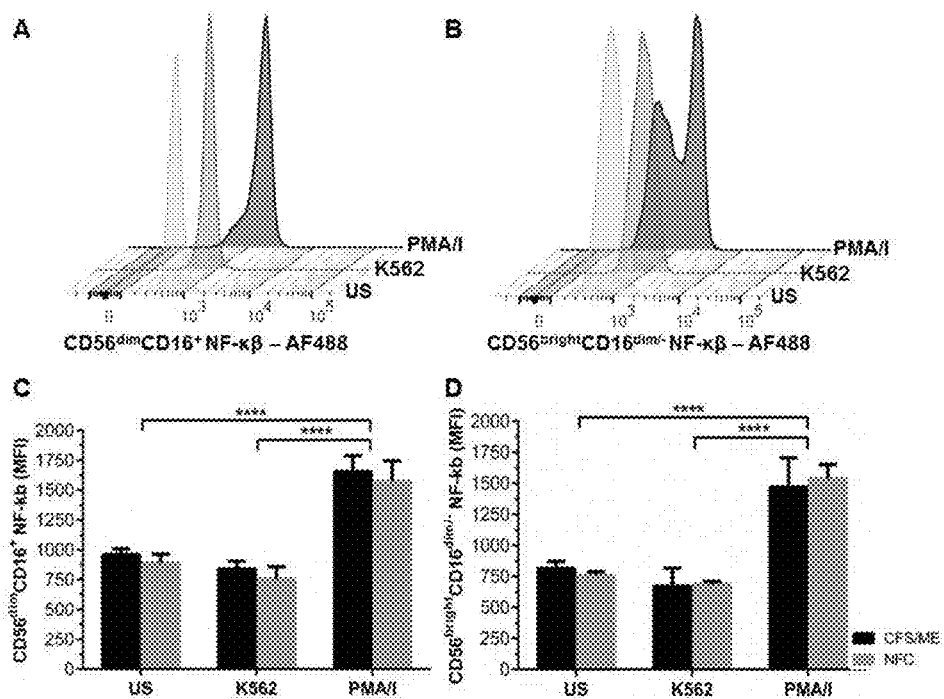
FIG. 10: Representative flow cytometric analysis of NF-κβ in $CD56^{dim}CD16^+$ (A) and $CD56^{bright}CD16^{dim/-}$ (B) NK cells. No significant differences were observed when NF-κβ was compared between CFS/ME and NFC in $CD56^{dim}CD16^+$ (C) and $CD56^{bright}CD16^{dim/-}$ (D) NK cells. Phosphorylated NF-κβ significantly increased after PMA/I stimulation in both $CD56^{dim}CD16^+$ (C) and $CD56^{bright}CD16^{dim/-}$ (D) NK cells compared to US (**p<0.0001) and K562 (**p<0.0001) in CFS/ME and NFC. Data are presented as MFI with interquartile range.
Figure 11:
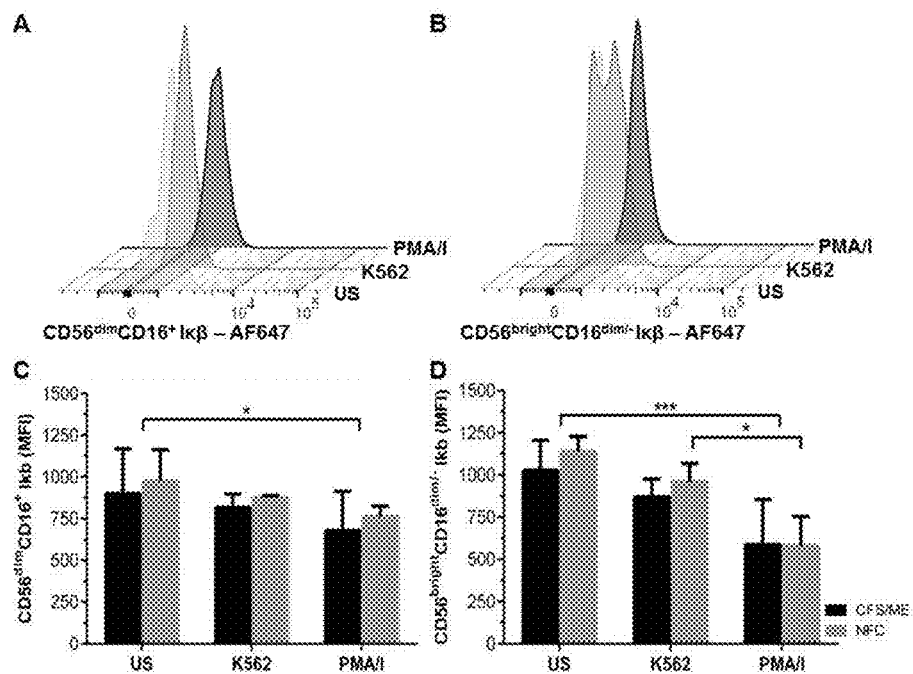
FIG. 11: Iκβ representative flow cytometric plots in $CD56^{dim}CD16^+$ (A) and $CD56^{bright}CD16^{dim/-}$ (B) NK cells. Iκβ was compared in $CD56^{dim}CD16^+$ (C) and $CD56^{bright}CD16^{dim/-}$ (D) NK ceils from CFS/ME and NFC and no significant differences were observed. Stimulation with PMA/I caused a significant reduction in Iκβ in both $CD56^{dim}CD16^+$ (*p<0.05) and $CD56^{bright}CD16^{dim/-}$ (***p<0.001) NK cells from CFS/ME and NFC. Incubation with PMA/I also caused a significant reduction (*p<0.05) in IκB in CD56$^{bright}$CD16$^{dim/-}$ NK cells from CFS/ME patients.
Figure 12:
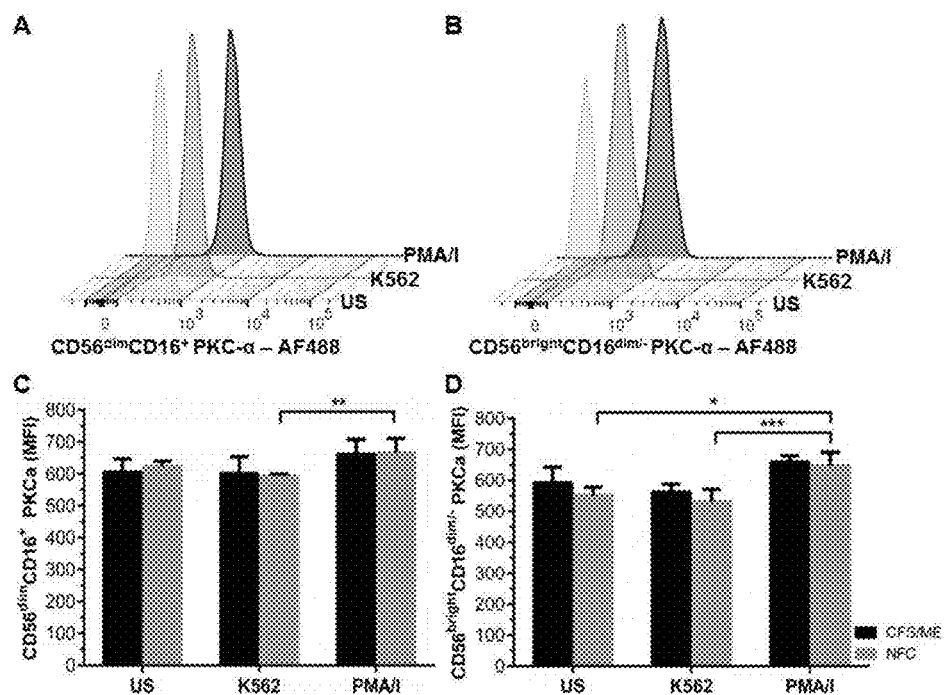
FIG. 12: Representative flow cytometric plots for the analysis of PKC-α in CD56$^{dim}$CD16$^+$ (A) and CD56$^{bright}$CD16$^{dim/-}$ (B) NK cells. PKC-α was compared in CD56$^{dim}$CD16$^+$ (C) and CD56$^{bright}$CD16$^{dim/-}$ (D) NK cells from CFS/ME and NFC and no significant differences were observed. In CD56$^{dim}$CD16$^+$ NK cells from NFC, stimulation with PMA/I caused a significant increase (**p<0.01) in PKC-α phosphorylation compared to K562 cells. PKC-α was significantly increased in CD56$^{bright}$CD16$^{dim/-}$ NK cells after PMA/I stimulation when compared to US (*p<0.05) and K562 (***p<0.001) in NFC.
Figure 13:
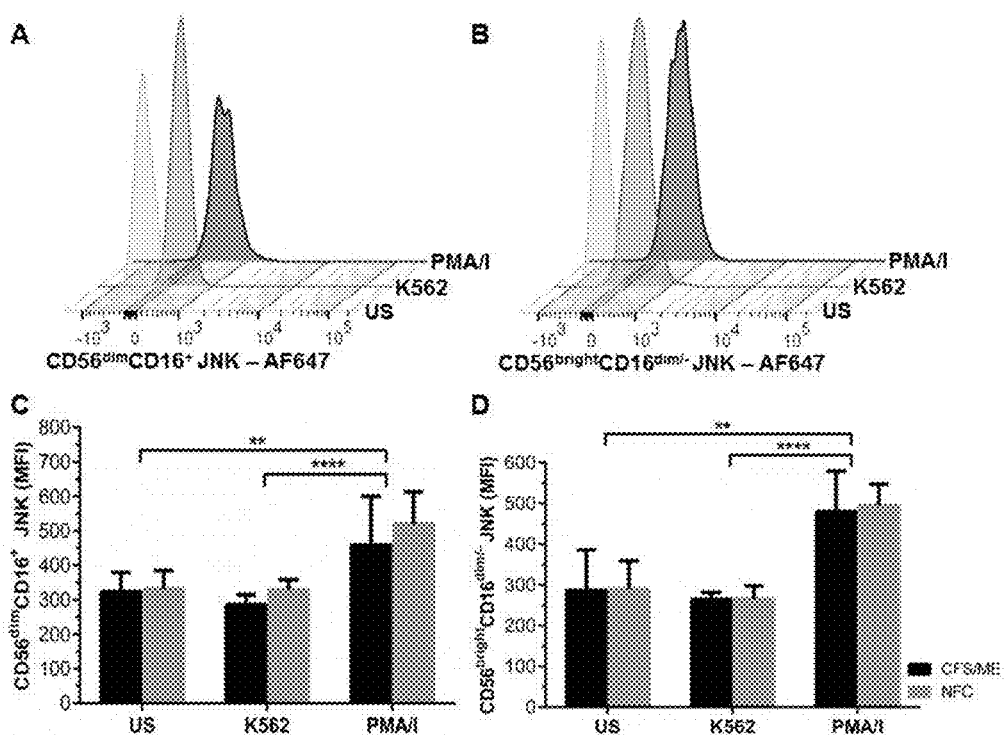
FIG. 13: Flow cytometric analysis of JNK in CD56$^{dim}$CD16$^+$ (A) and CD56$^{bright}$CD16$^{dim/-}$ (B) NK cells. No significant differences were observed when JNK was compared in CD56$^{dim}$CD16$^+$ (C) and CD56$^{bright}$CD16$^{dim/-}$ (D) NK cells from CFS/ME and NFC. Significant increases in phosphorylated JNK were observed in both CD56$^{dim}$CD16$^+$ (C) and CD56$^{bright}$CD16$^{dim/-}$ (D) NK cells after PMA/I stimulation when compared to US (p<0.01) and K562 (*p<0.001) in CFS/ME and NFC.

MEK1/2 and p38 Significantly Increased $CD56^{bright}CD16^{dim/-}$ NK Cells from CFS/ME Patients In CFS/ME patients, phosphorylation of MEK1/2 and p38 was significantly increased in $CD56^{bright}CD16^{dim/-}$ cells following incubation with K562 cells at an E:T ratio of 25:1 compared to the NFC. (See FIG. 6.) Stimulation with PMA/I induced a significant increase in MEK1/2 and p38 compared to US and K562 stimulated cells in both CFS/ME and NFC cohorts. Comparison of MEK1/2 and p38 in $CD56^{dim}CD16^+$ NK cells from CFS/ME and NFC revealed no significant differences. (See FIGS. 7 and 8.) Measurement of additional MAPK proteins including Stat-3, NF-κβ, Iκβ, protein kinase c-α and JNK revealed no significant differences between CFS/ME and the NFC cohorts. (See FIGS. 9-13.)

NK Cell Cytotoxic Activity Reduced in CFS/ME

Figure 14:
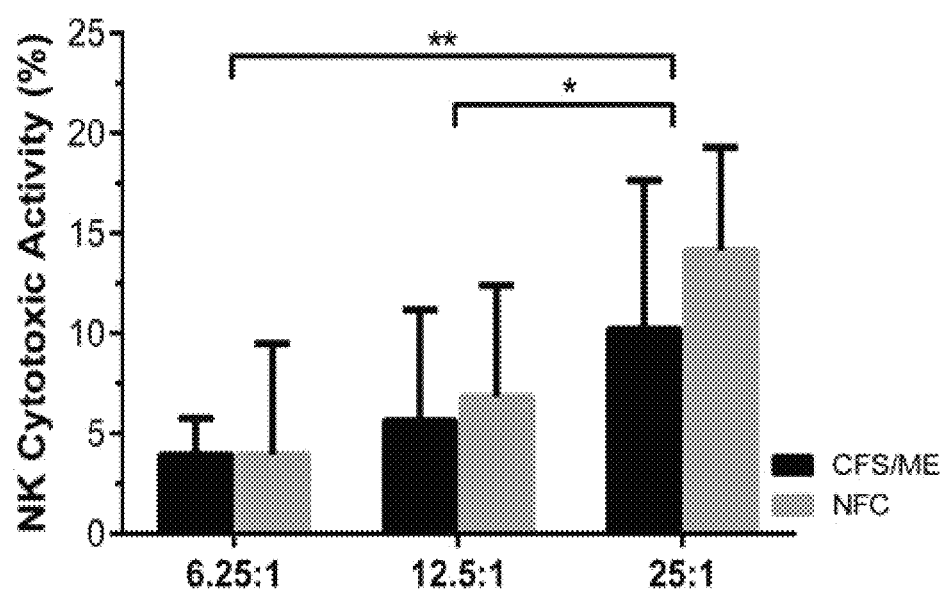
FIG. 14: NK cell cytotoxic activity in CFS/ME and NFC at three E:T ratios.

In both CFS/ME patients and NFC, NK cell cytotoxic activity at 2.5:1 was significantly increased compared to 12.5:1 and 6.25:1 ratios. Compared to NFC, CFS/ME was reduced at 25:1 and 12.5 ratios, although this was not statistically significant. (See FIG. 14.)

CD107a and CD107b Increased on $CD56^{dim}CD16^+$ NK Cells After Stimulation

Figure 15:
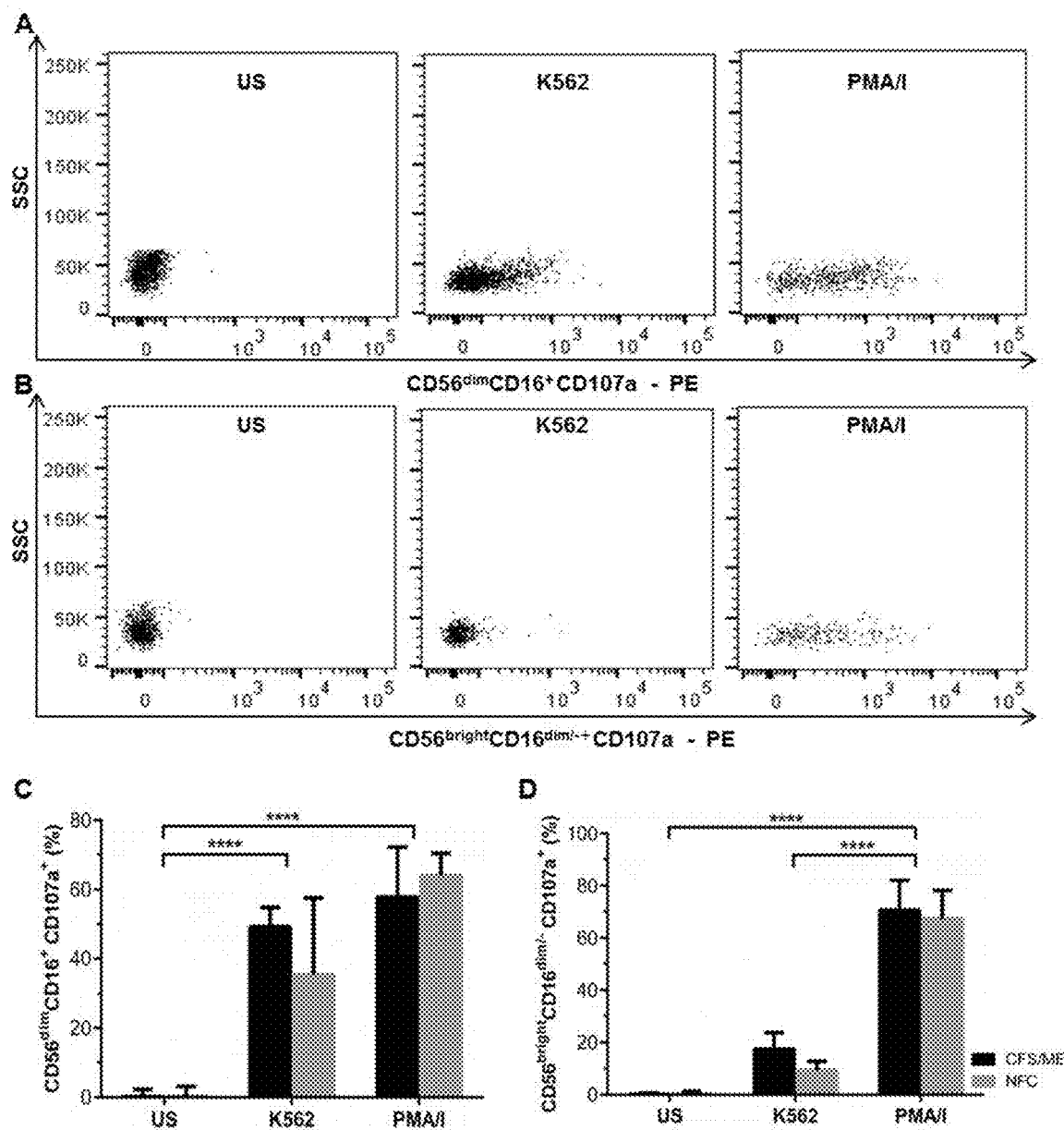
FIG. 15: Representative flow cytometry plots for CD107a in CD56$^{dim}$CD16$^+$ (A) and CD56$^{bright}$CD16$^{dim/-}$ (B) NK cells. CD107a was measured in US cells and after stimulation with either K562 cells or PMA/I. Comparison of CD107a on CD56$^{dim}$CD16$^+$ (C) and CD56$^{bright}$CD16$^{dim/-}$ (D) NK cells between CFS/ME and NFC revealed no significant differences. CD107a expression significantly increased after K562 and PMA/I (**p<0.0001) stimulation in CD56$^{dim}$CD16$^+$ NK cells from both CFS/ME and NFC. In CD56$^{bright}$CD16$^{dim/-}$ NK cells, PMA/I stimulation significantly increased expression of CD107a when compared to K562 and US cells (**p<0.0001) from CFS/ME and NFC.
Figure 16:
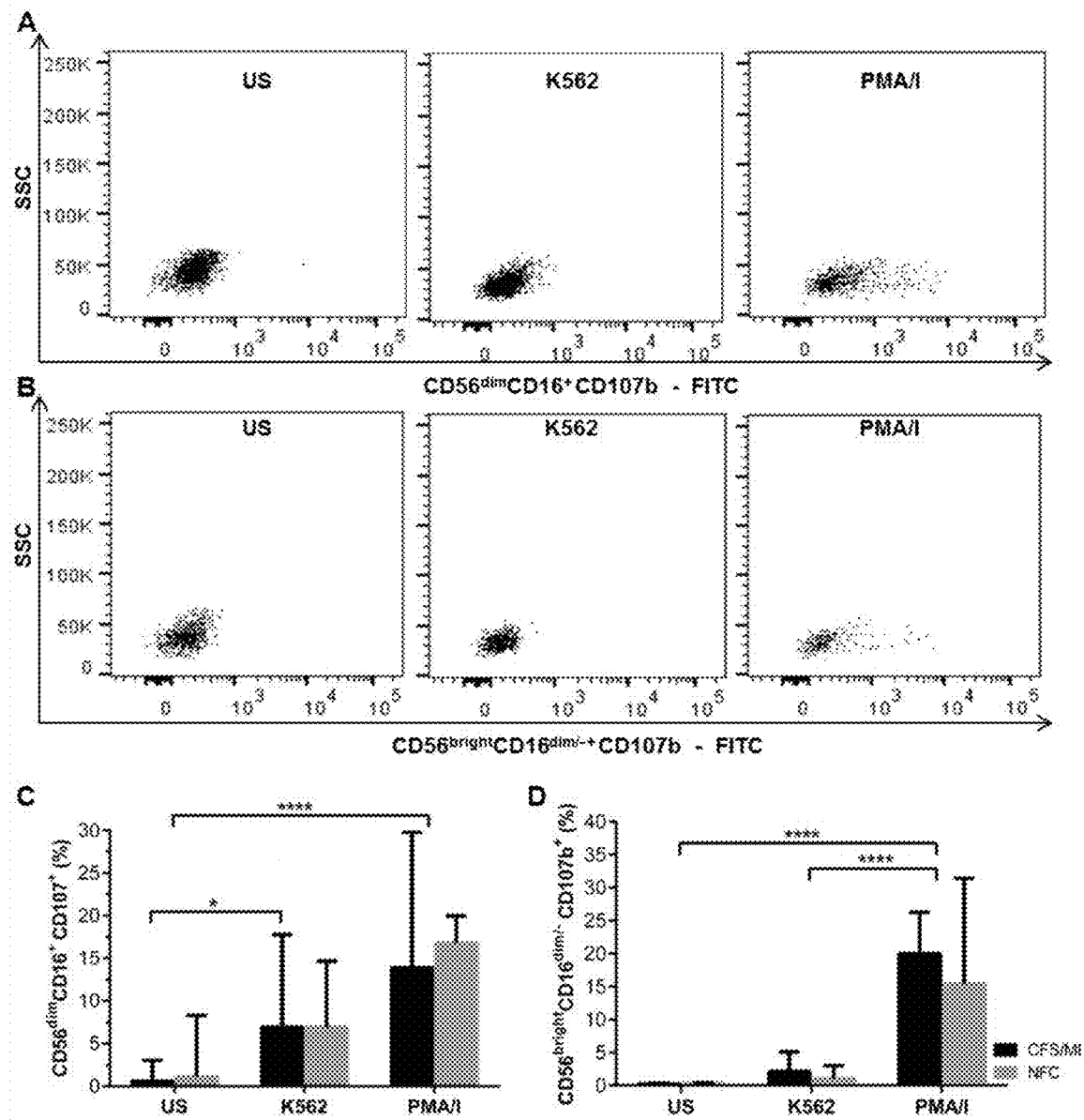
FIG. 16: Flow cytometric analysis of CD107b on CD56$^{dim}$CD16$^+$ (A) and CD56$^{bright}$CD16$^{dim/-}$ (B) NK cells. No significant differences were observed when CD107b expression was compared between CFS/ME and NFC on CD56$^{dim}$CD16$^+$ (C) and CD56$^{bright}$CD16$^{dim/-}$ (D) NK cells. In CD56$^{dim}$CD16$^+$ NK cells, stimulation with K562 cells (*p<0.05) and PMA/I (**p<0.0001) caused a significant increase in CD107b expression in both CFS/ME and NFC compared to US. PMA/I stimulation significantly increased CD107b expression on CD56$^{bright}$CD16$^{dim/-}$ NK cells from CFS/ME and NFC when compared to K562 and US (**p<0.0001).

Surface expression of CD107a and CD107b on $CD56^{dim}CD16^+$ and $CD56^{bright}CD16^{dim/-}$ NK cells was significantly increased following stimulation with PMA/I and K562 cells in both CFS/ME and NFC. (See FIGS. 15 and 16.) Comparison of CD107a and CD107b expression between CFS/ME and the NFC under each stimulatory condition revealed no significant differences. $CD56^{dim}CD16^+$ NK cells from CFS/ME patients displayed increased CD107a following K562 stimulation, although this increase was not significant.

No Significant Differences in NK Cell Lytic Proteins from CFS/ME Patients

Figure 17:
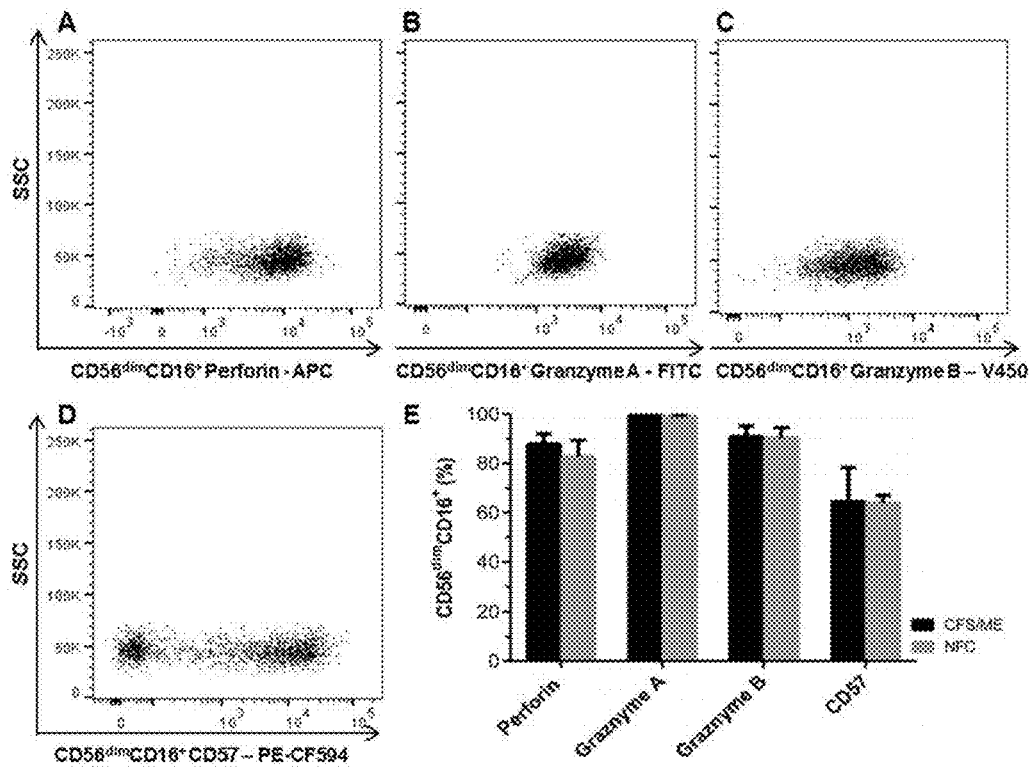
FIG. 17: Perforin, Granzymes A and B and CD57 from CD56$^{dim}$CD16$^+$ NK cells from CFS/ME patients.
Figure 18:
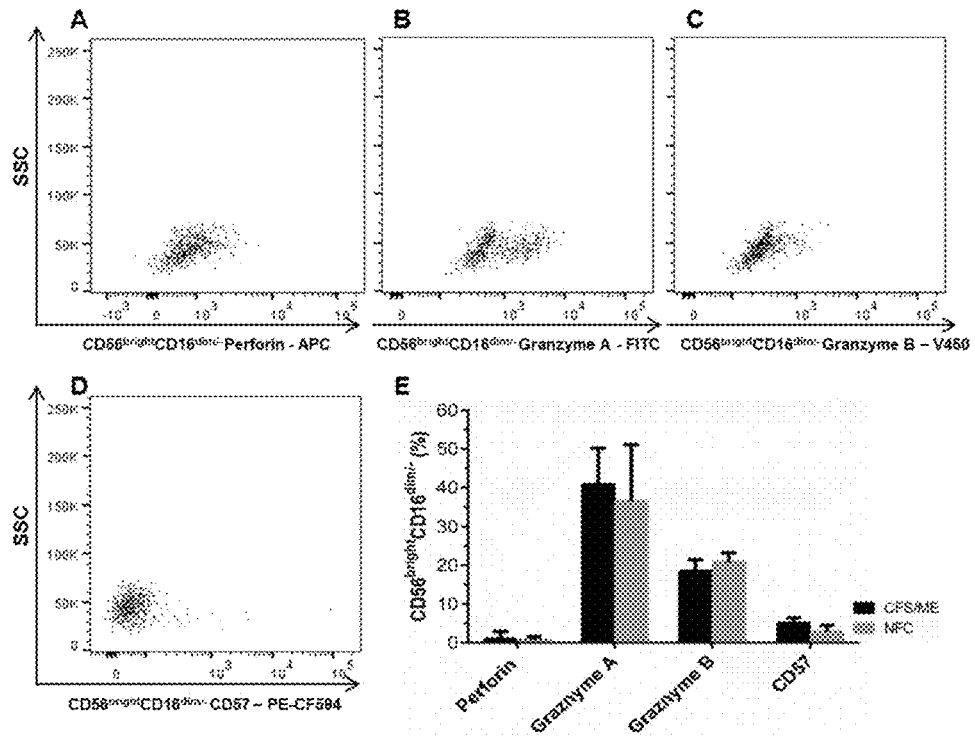
FIG. 18: Perforin, Granzymes A and B and CD57 from CD56$^{bright}$CD16$^{dim/-}$ NK cells from CFS/ME patients.

NK cell lytic proteins perforin, granzyme A and granzyme B were measured in $CD56^{dim}CD16^+$ and $CD56^{bright}CD16^{dim/-}$ NK cells from CFS/ME patients and NFC. Comparison between the two groups revealed no significant differences. Surface expression of CD57 was measured as a marker for NK cell maturation on $CD56^{dim}CD16^+$ and $CD56^{bright}CD16^{dim/-}$ NK cells and no significant differences were observed between the CFS/ME patients and the NFC. (See FIGS. 17 and 18.)

Figure 19:
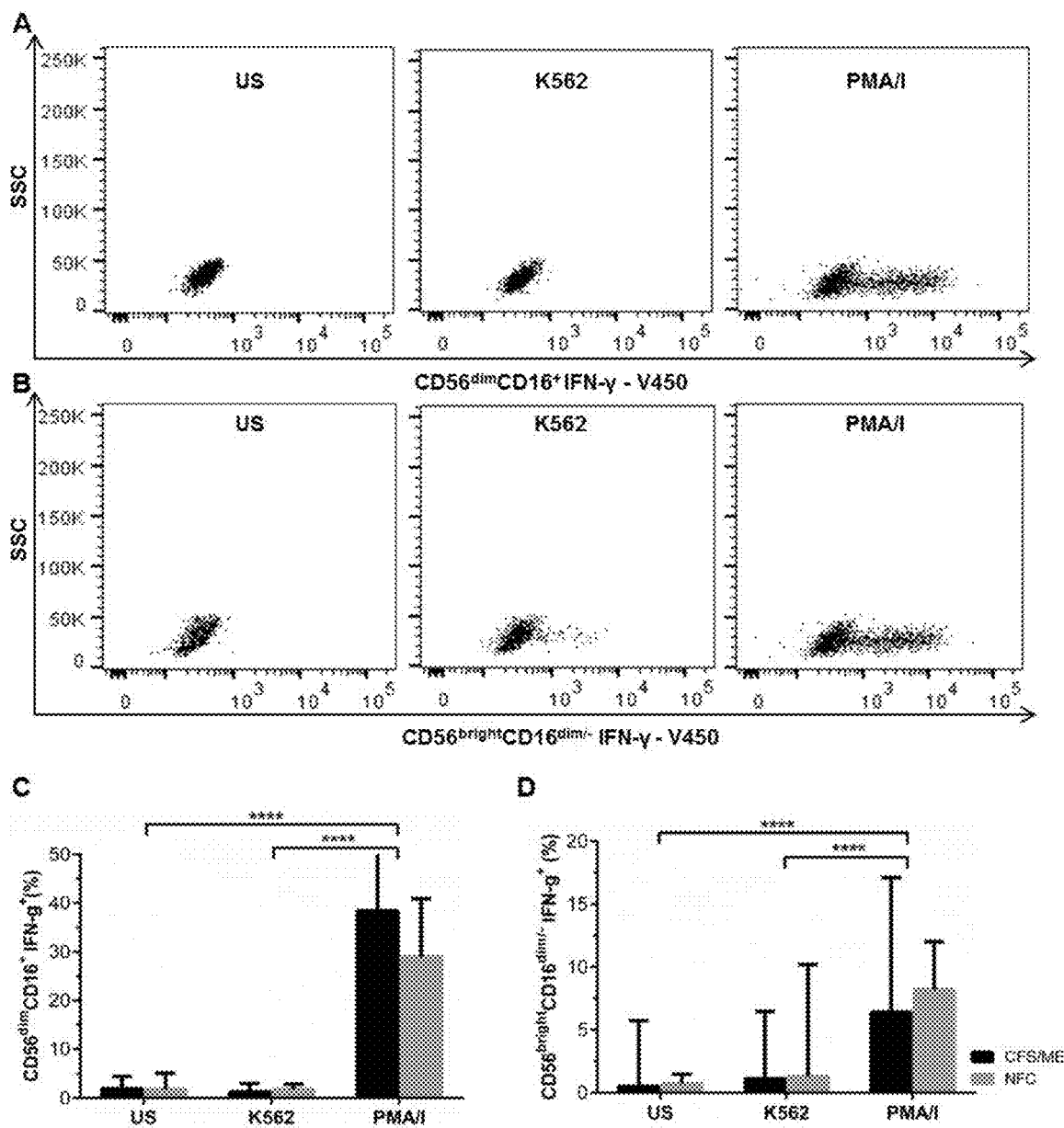
FIG. 19: Representative flow cytometric plots for CD56$^{dim}$CD16$^+$ (A) and CD56$^{bright}$CD16$^{dim/-}$ (B) NK cell production of IFN-γ. Comparison of IFN-γ production in CD56$^{dim}$CD16$^+$ (C) and CD56$^{bright}$CD16$^{dim/-}$ (D) NK cells between CFS/ME and NFC revealed no significant differences. IFN-γ production significantly increased after PMA/I stimulation in both CD56$^{dim}$CD16$^+$ and CD56$^{bright}$CD16$^{dim/-}$ NK cells when compared to US and K562 (****p<0.0001).
Figure 20:
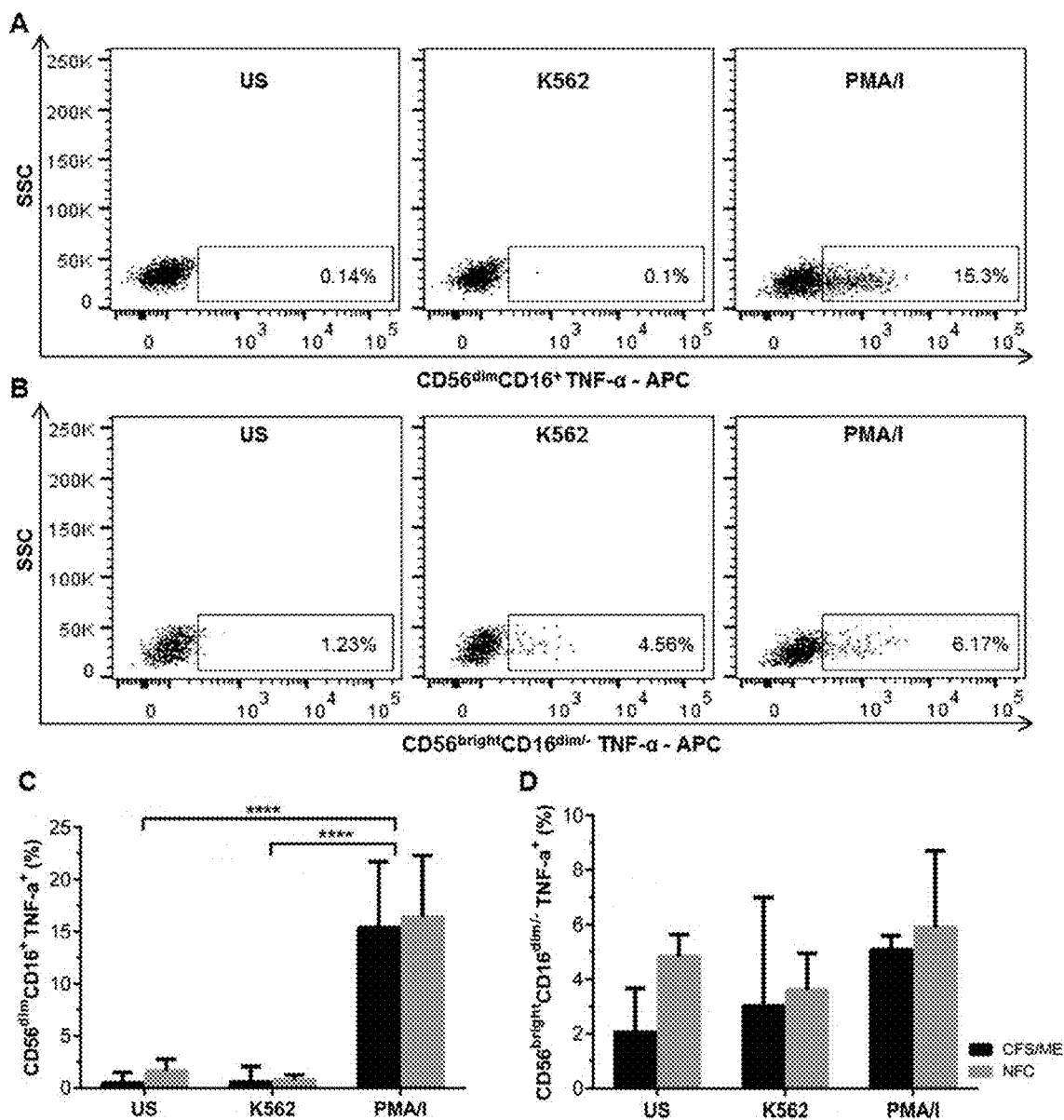
FIG. 20: Flow cytometric plots for TNF-α in CD56$^{dim}$CD16$^+$ (A) and CD56$^{bright}$CD16$^{dim/-}$ (B) NK cells. Between CFS/ME and NFC cohorts, TNF-α production in CD56$^{dim}$CD16$^+$ (C) and CD56$^{bright}$CD16$^{dim/-}$ (D) NK cells were not significantly different. In CD56$^{dim}$CD16$^+$ NK cells, PMA/I stimulation significantly increased TNF-α production when compared to US and K562 incubated cells (****p<0.0001) in both CFS/ME and NFC.
Figure 21:
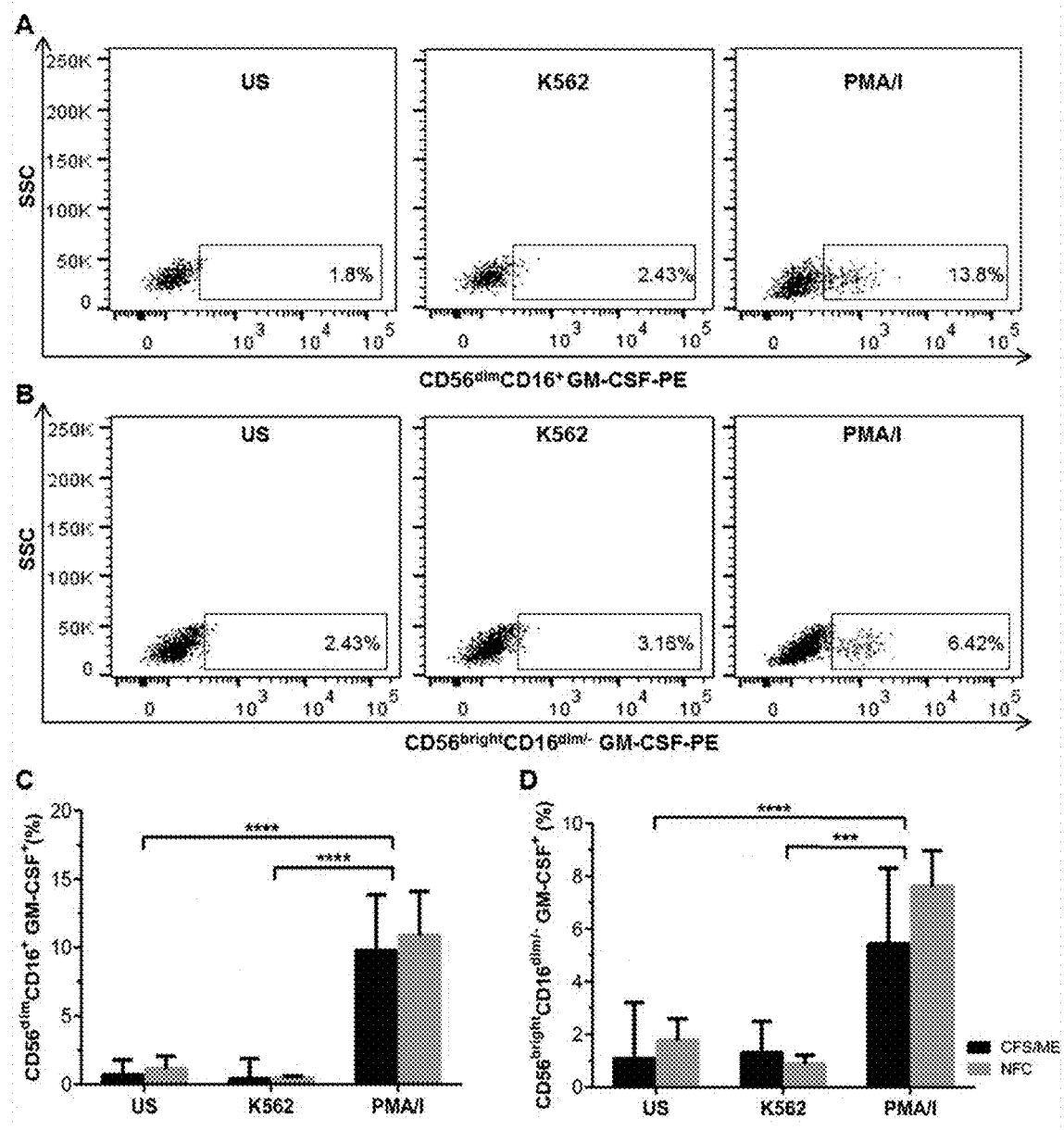
FIG. 21: Flow cytometric analysis of GM-CSF production in CD56$^{dim}$CD16$^+$ (A) and CD56$^{bright}$CD16$^{dim/-}$ (B) NK cells. Production of GM-CSF in CD56$^{dim}$CD16$^+$ (C) and CD56$^{bright}$CD16$^{dim/-}$ (D) NK cells were not significantly different when compared between CFS/ME and NFC cohorts. Stimulation with PMA/I caused a significant increase in CD56$^{dim}$CD16$^+$ and CD56$^{bright}$CD16$^{dim/-}$ GM-CSF production in both CFS/ME and NFC compared to US and K562 incubated cells (**p<0.0001, *p<0.001).

$CD56^{dim}CD16^+$ and $CD56^{bright}CD16^{dim/-}$ NK Cell Cytokine Production Increased After PMA/I Stimulation $CD56^{dim}CD16^+$ and $CD56^{bright}CD16^{dim/-}$ NK cell cytokine production was measured under two stimulatory conditions with PMA/I or K562 cells. INF-γ, TNF-α and GM-CSF production in $CD56^{dim}CD16^+$ and $CD56^{bright}CD16^{dim/-}$ NK cells increased following stimulation with PMA/I in both the NFC and CFS/ME patients. (See FIGS. 19-21.) Comparisons of $CD56^{dim}CD16^+$ and $CD56^{bright}CD16^{dim/-}$ NK cell cytokine production between CFS/ME patients and the NFC under the different stimulatory conditions revealed no significant differences between groups.

Discussion

This is the first study to investigate ERK1/2 and MEK1/2 MARK intracellular signalling in $CD56^{dim}CD16^+$ and $CD56^{bright}CD16^{dim/-}$ NK cell phenotypes in CFS/ME. The inventors report novel and significant findings of reduced ERK1/2 in $CD56^{dim}CD16^+$ NK cells in conjunction with increased MEK1/2 and p38 in $CD56^{bright}CD16^{dim/-}$ NK cells. Further investigation of other extracellular signal regulated kinases will contribute to the understanding of the role of dysregulated MAPK signalling and reduced cytotoxic function of NK cells in CFS/ME. The synergistic functions of both $CD56^{dim}CD16^+$ and $CD56^{bright}CD16^{dim/-}$ NK cells are required for clearance of target cells and dysfunctional signalling through the MAPK pathway in CFS/ME patients may compromise efficient removal of target cells.

$CD56^{dim}CD16^+$ NK cells from CFS/ME patients had a significant decrease in ERK1/2 which has been identified as an important component for cytotoxic activity due to substrate targeting of paxillin, a cytoskeletal protein kinase [46m, 47m]. Downstream activation of ERK1/2 is the result of intracellular signalling networks propagating activating signals through phosphorylation cascades [48m, 49m]. Sequential phosphorylation of MAPK kinase kinase (MAPKKK) and MAPK kinase (MAPKK/MEK1/2) activates ERK1/2 through dual phosphorylation of threonine and tyrosine residues [48m, 49m]. Phosphorylation of ERK1/2 induces a significant conformational change which is required for NK cell cytotoxic activity as it increases substrate accessibility to phosphorylate paxillin [50m, 51m]. Paxillin is an adaptor protein which provides a docking site for regulatory proteins such as ERK1/2 and structural proteins including microtubules and actin cytoskeleton [50m, 51m]. Colocalisation of phosphorylated ERK2 and paxillin to the microtubules and the microtubule organising centre (MTOC) facilitates polarisation of the secretory granules towards the immune synapse [14m, 15m, 46m, 51m, 52m]. In CFS/ME patients, abnormal signalling through ERK1/2 may interfere with and delay release of the lytic proteins to induce cytotoxic lysis of target cells NK cell cytotoxic activity was reduced in the CFS/ME cohort compared to the NFC. The significant reduction of ERK1/2 in $CD56^{dim}CD16^+$ NK cells may disrupt intracellular signalling required for secretory granule polarisation through the MAPK pathway. As the MAPK cascade integrates signals received from the cell surface, the pathway is subject to complex regulatory and feedback mechanisms which may contribute to the reduction observed in ERK1/2 from CFS/ME patients [46m, 53m]. ERK1/2 is under constant regulation which also functions to determine specificity of ERK1/2 to target the secretory granules in cytotoxic NK cells [14m, 15m, 46m, S3m]. Regulatory mechanisms of ERK1/2 include phosphatases MKP3 and MKPX which dephosphorylate protein tyrosine kinases to inhibit activation [46m, 53m]. Receptor desensitisation and dissociation of the receptor-ligand interaction changes the strength and duration of activation signals [46m, 53m]. Scaffold proteins and subcellular localisation of the cascade regulate phosphorylation by directing ERK1/2 to target substrates in the cytoplasm or nucleus [46m, 53m]. The integration and crosstalk of ERK1/2 with other signalling pathways also acts as a feedback mechanism to regulate phosphorylation levels [46m, 53m]. As ERK1/2 is subject to a number of distinct mechanisms of regulation, further investigations in $CD56^{dim}CD16^+$ NK cells from CFS/ME patients are required to determine if these regulatory mechanisms contribute to reduce ERK1/2 phosphorylation.

Degranulation of cytotoxic NK cells was measured to investigate if potential impairments in intracellular signalling through ERK1/2 contribute to reduced cytotoxic activity in CFS/ME patients. Whilst no significant differences were observed in NK cell surface expression of CD107a and CD 107b, $CD56^{dim}CD16^+$ NK cells from CFS/ME patients displayed increased CD107a following K562 stimulation. In support of this current finding, the inventors previously reported a significant increase in CD107a on NK cells following K562 stimulation in a larger cohort of CFS/ME patients [27m]. This finding suggests that the reduction in ERK1/2 may delay movement of the secretory granule and MTOC towards the immune synapse but does not prevent degranulation [14m, 15m]. Increased degranulation of $CD56^{dim}CD16^+$ NK cells from CFS/ME patients suggests the cells may be under a continuum of activation due to an inability to induce cytotoxic lysis and subsequent removal of the target cells [27m].

Continual activation of NK cells in CFS/ME patients may be the result of prolonged contact with target cells. Kinetic priming facilitated by sustained NK cell contact with target cells retains convergence of the secretory granules and the MTOC at the plasma membrane [54m]. This mechanism is known as 'serial killing' as subsequent lysis of target cells is more rapid due to pre-docking of the secretory granules, bypassing the need for ERK1/2 to initiate polarisation of the secretory granules towards the immune synapse for degranulation [55m]. Further investigations are required to determine if the secretory granule completely fuses with the NK cell membrane to release the entire lytic protein content or if deficiencies in the lytic proteins may contribute to reduced target cell lysis in CFS/ME patients [27m, 36m, 56m]. Reduced perforin and granzyme B has been reported in NK cells from CFS/ME patients which may be a consequence of 'serial killing' [27m, 36m]. Whilst it has been identified that NK cells from CFS/ME patients are degranulating, the inability of NK cells to eliminate target cells by cytotoxic activity suggests that the NK cells may be highly activated through a potential mechanism of inefficient 'serial killing'.

NK cell production of cytokines including IFN-γ and TNF-α has been identified as an integral part of NK cell cytotoxic activity and increased production of IFN-γ has previously been reposted in CFS/ME [27m, 29m, 57m]. NK cells differentiate and mature from $CD56^{bright}CD16^{dim/-}$ to $CD56^{dim}CD16^+$ NK cells with predominant cytokine or cytotoxic effector function [6m, S8m-60m]. This differentiation process suggests that together $CD56^{bright}CD16^{dim/-}$ and $CD56^{dim}CD16^+$ NK cells function to optimise an efficient NK cell response which may be impaired in CFS/ME patients [6m, 58m-60m]. NK cell production of IFN-γ has been reported to augment cytotoxic activity by up-regulating expression of the adhesion molecule ICAM-1 on tumour target cells through the NF-κβ pathway which improves conjugate formation and adherence with cytotoxic NK cells [60m]. Conversely, it has also been reported that IFN-γ treatment of tumour cells with high basal levels of ICAM-1, such as K562 cells, up-regulates major histocompatibility class I which acts as a ligand for inhibitory receptors on NK cells and reduces NK cytotoxic activity [61m, 62m, 60m]. In CFS/ME patients, further investigations are required to determine if increased IFN-γ may contribute to the proposed inefficient mechanism of 'serial killing' resulting in increased degranuiation or if IFN-γ desensitises K562 cells to NK cell mediated cytotoxic activity.

Phosphorylation of MEK1/2 and p38 has been implicated in the pathogenesis of many chronic inflammatory diseases and increased production of IFN-γ may be a result of increased MEK1/2 and p38 in $CD56^{bright}CD16^{dim/-}$ NK cells from CFS/ME patients [27m, 46m, 63m]. Receptor ligation through environmental stress or innate proinflammatory cytokines including IL-12 and IL-18 initiate MAPK intracellular signalling cascades [17m, 64m-67m]. Similar to ERK1/2 activation, phosphorylation of MEK1/2 and p38 is the result of a tiered protein phosphorylation cascade [17m, 64m-67m]. Activated MEK1/2 in turn phosphorylates ERK1/2, resulting in the formation of ERK2-MEK1 chimera [46m, 66m, 67m]. This chimera is released from its cytoplasmic anchors to undergo a cyto-nuclear shift to initiate IFN-γ production in the nucleus [46m, 66m, 67m]. The phosphorylated ERK2-MEK1 chimera activates c-Fos transcription factor and the activating protein (AP)-1 heterodimer which regulates the IFN-γ gene promoter and subsequent cytokine production [66m, 67m]. Increased phosphorylation of MEK1/2 may therefore result in increased production of IFN-γ from NK cells in CFS/ME patients as we have previously repotted [27m, 29m, 57m]. In contrast to targeting IFN-γ transcription factors, phosphorylated p38 translocates into the nucleus to mediate cytokine production by regulating the half-life of adenylate/uridylate (AU)-rich IFN-γ gene which stabilises and prevents degradation of IFN-γ mRNA [64m, 65m]. In $CD56^{bright}CD16^{dim/-}$ NK cells from CFS/ME patients, an increase in p38 may prolong transcription and translation of IFN-γ [27m, 65m, 64m].

Cytokine synthesis by MEK1/2 and p38 is tightly controlled and each tier of the MAPK signalling cascade is subject to regulation which may be impaired in CFS/ME patients [46m, 53m]. Phosphatase MKP1 is located in the nucleus and downregulates MEK1/2 and p38 activity by dephosphorylating threonine and tyrosine residues, attenuating cytokine production [53m, 46m]. Further investigations into the regulation of MEK1/2 and p38 in $CD56^{bright}CD16^{dim/-}$ NK cells from CFS/ME patients are required to determine if a regulatory mechanism such as MPK1 may contribute to increased MEK1/2 and p38 activity and IFN-γ cytokine production.

Investigations into the MAPK intracellular signalling pathway in NK cells from CFS/ME patients has revealed novel findings which may explain previous reports of reduced NK cell cytotoxic activity and increased cytokine production. To the inventors' knowledge, this is the first study to report significant differences in $CD56^{dim}CD16^+$ NK cell ERK1/2 from CFS/ME patients. $CD56^{dim}CD16^+$ NK cell cytotoxic activity is dependent on synergistic action of $CD56^{bright}CD16^{dim/-}$ NK cell cytokine production. Consequently, increased MEK1/2 and p38 may increase IFN-γ production which in turn may desensitise K562 cells against NK cell cytotoxic activity in CFS/ME patients. The novel, preliminary findings of this study provide a rationale for further investigations into a larger cohort and into particular clinical subgroups of CFS/ME including severity to elucidate the cause of reduced NK cytotoxic activity.

Conclusions

The results from this study highlight the importance of intracellular signalling through the MAPK pathway for synergistic function of $CD56^{dim}CD16^+$ and $CD56^{bright}CD16^{dim/-}$ NK cells to ensure efficient clearance of target cells in CFS/ME patients. Importantly, this intracellular signalling through the MAPK pathway is likely to be a mechanism operating in other cell/tissue types, including peripheral blood mononuclear cells.

Example 11—Dysregulation of $Ca^{2+}$ Dependent Protein Kinase Gene Expression in NK Cells from Chronic Fatigue Syndrome/Myalgic Encephalomyelitis Patients In this Example, mRNA expression of 528 $Ca^{2+}$ dependent protein kinase genes in isolated NK cells was analysed from moderate and severe CFS/ME patients. The expression of 92 $Ca^{2+}$ dependent protein kinase genes was significantly different in the severe CFS/ME group compared with con-fatigued controls. Among these, 37 $Ca^{2+}$ dependent protein kinase genes were significantly upregulated and 55 $Ca^{2+}$ dependent protein kinase genes were significantly downregulated in severe CFS/ME patients compared to non-fatigued controls. In severe CFS/ME patients, dysfunction in $Ca^{2+}$ dependent protein kinase genes may contribute to impairments in NK cell intracellular signalling and effector function. Similar changes in $Ca^{2+}$ dependent protein kinase genes may be present in other cells, potentially contributing to the pathomechanism of this illness.

Introduction

Calcium ($Ca^{2+}$) ions play an integral role in intracellular signalling. Calcium controls a diverse range of cellular processes, such as gene transcription, muscle contraction and cell proliferation [1u]. The effects of $Ca^{2+}$ ions are mediated by the $Ca^{2+}$ binding protein calmodulin, which activates a number of different protein kinases. $Ca^{2+}$/calmodulin-dependent protein kinase includes myosin light chain kinase which signals muscle contraction and members of the CaM kinase family which phosphorylate a number of different proteins, including metabolic enzymes, ion channels, and transcription factors [2u].

In natural killer (NK) cells, $Ca^{2+}$ signaling plays an important role in the granule dependent pathway of apoptosis [3u]. $Ca^{2+}$ is required for inducing cytolytic granule polarization, cytokine gene transcription and degranulation in NK cells [4u, 5u]. $Ca^{2+}$ also regulates lytic granule fusion [5u-7u] as well as lytic granule mobilization to the immune synapse to release perforin and granzymes to kill target cells [3u, 8u, 9u]. Furthermore, the downstream intracellular signals that occur in NK cells upon target cell ligation to trigger target lysis are governed by the $Ca^{2+}$ regulated mitogen-activated protein kinase (MAPK) pathway [10u]. Intracellular $Ca^{2+}$ concentrations can either stimulate or inhibit the MAPK cascade, and thereby play an important role in the regulation of MAPK dependent cellular process. The effector functions of NK cells are regulated by three specific MAPK subgroups [11u, 13u] which include the p38 MAPK (p38) and the C-Jun terminal kinase (JNK) which regulate cytokine production and extracellular signal regulated kinases (ERK1/2). These kinases regulate the mobilization and redistribution of cytoplasmic perforin and grartzyme B towards the contact zone with target cells [14u]. Interestingly, the inventors' earlier findings (described in Example 10) demonstrate impairments in MAPK signalling as well as decreased intracellular $Ca^{2+}$ concentration in NK cells as well as isolated B cells from CFS/ME patients. Collectively, these anomalies may contribute to NK cell dysfunction in particular the reduced NK cell cytotoxic activity which is consistently reported in CFS/ME patients [17u-25u].

Given the importance of $Ca^{2+}$ signalling in regulating NK cell function, the present study aimed to examine the role of $Ca^{2+}$ dependent protein kinase genes in isolated NK cells from CFS/ME patients. This investigation explores the association of functionally important NK intracellular signalling alterations with CFS/ME.

Methodology

Participants

Participants were recruited from the National Centre for Neuroimmunology and Emerging Diseases (NCNED) research database for CFS/ME. All participants completed an online questionnaire regarding their medical history and symptoms based on the 2011 International Consensus Criteria (ICC) to determine suitability for the study [26u]. This requires the presence of debilitating post-exertional fatigue, accompanied further by neurological, immune, and autonomic symptoms. CFS/ME patients meeting the 2011 ICC symptoms and non-fatigued healthy controls were included in this study. Severity of CFS/ME was defined according to the Dr Bell's diability scale that ranges from 100% (no symptoms) to 0% (severe symptoms) [27u]. Patients categorized as moderate CFS/ME scored >30%. Severe CFS/ME scored <30% and were considered housebound or bedridden. Patients disability was further characterized by self-reporting scales which included the Fatigue Severity Scale (FSS), and the SF-36 [28u, 29u]. Participants were excluded if they were previously diagnosed or had a history of any alternative disease that would explain symptoms including autoimmune disorder, multiple sclerosis, psychosis, major depression, heart disease or thyroid-related disorders or if they were pregnant, breast feeding, smokers.

Blood Collection

Forty millilitres of EDTA blood was collected from the antecubital vein of participants into EDTA blood collection tubes. All the laboratory analysis was performed within six hours of blood collection to maintain the cell viability. Routine pathology testing parameters including full blood count, erythrocyte sedimentation rate, electrolytes and high sensitivity C reactive protein were also assessed on each participant sample by Queensland pathology.

NK Cell Isolation

Figure 22:
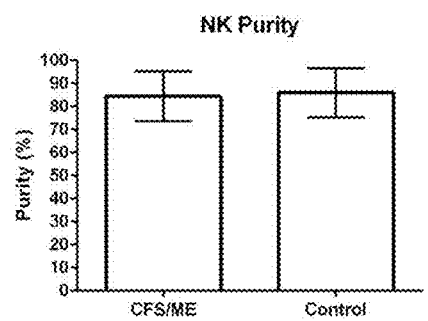
FIG. 22. Natural Killer cell purity. NK cell purity measurements are represented as total % of CD3$^-$CD56$^+$ cells. Data are presented as mean±SD for CFS/ME group (n=24) and control group (n=11).

NK cells were isolated from 40 mL of whole blood using negative selection with RosetteSep Human Natural Killer Cell Enrichment Cocktail (STEMCELL Technologies Australia Pty. Ltd, Victoria, Australia) according to manufacturer instructions. The isolated NK cells were incubated in unsupplemented Rosewell Park Memorial Institute (RPMI)-1640 culture media (Life technologies, Carlsbad, USA) and were counted using Trypan blue. Briefly following NK cell isolation (FIG. 22), the NK cell purity was also assessed on the LSR-Fortessa X-20 flow cytometer (BD Biosciences, San Diego, USA) after labelling with CD3 and CD56 as previously described (BD Biosciences, San Diego, USA). The isolated NK cells were lysed at a concentration 10,000 cells/μl of RLT buffer (Cat No: 79216, QIAGEN, Australia)

and were snap-frozen in liquid nitrogen and stored at −80° C. until further $Ca^{2+}$ dependent protein kinase genes assessment.

$Ca^{2+}$ Dependent Protein Kinase Gene Expression

Gene expression was directly measured via counts of corresponding messenger RNA (mRNA) in each sample using an nCounter (Nanostring, Seattle, Wash.) GX human kinase kit v2 (XT), which is a multiplex assay for 528 genes known to be differentially expressed in the human kinome [31u]. The nCounter system allows for direct detection and counting of nucleic acid via reporter probes appended with multiple fluorophore barcodes and biotinylated capture-probes that attach to microscopic beads, which are then affixed to lanes in a translucent cartridge and read in an optical scanner. Batches of 12 separate samples at one time were prepared as per manufacturer's instructions, with NK cell lysate hybridized with probes at 65° C. for 16-18 hours before being placed into the automated nCounter Prep Station (Nanostring) in which samples were affixed to cartridges. Cartridges were then immediately placed into the nCounter Digital Analyzer (Nanostring) optical scanner and read at a goal resolution of 550 Fields of View (FOV), which is the maximum resolution for this instrument.

Statistical Analysis

Statistical analysis was performed using SPSS software version 22 and GraphPad Prism version 6. Data were compared among the three participant groups (control, moderate CFS/ME and severe CFS/ME) with statistical analysis performed based on the distribution. Shapiro-Wilk normality tests were performed on all the data sets to test for Gaussian distribution. ANOVA was used to examine parametric data and the Kruskal Wallis test of independent was performed for non-parametric data when appropriate, with statistical significance set at an alpha criterion at p<0.05. Gene expression was directly measured via counts of corresponding messenger RNA (mRNA) in each sample using DESeq R package software [32u], where alpha level of significance was set at a p value of <0.05.

Results

Participants

Table 30 summarises participant clinical characteristics. The study included 11 moderate CFS/ME (age 54.9±10.3; 83.3% female) and 12 severe CFS/ME (age 47.5±8.0; 75.0% female), and 11 non-fatigued controls (age 50.0±12.3 years; 72.5 % female). There was no significant difference between mean age and sex between groups. All participants in the study were of European decent and were residents of Australia at the time of blood collection. Fatigue severity was highest among severe CFS/ME compared with moderate CFS/ME and non-fatigued controls (p<0.05). Furthermore, severe CFS/ME reported significantly greater impairment across all SF-36 scales compared with moderate CFS/ME and non-fatigued controls (p<0.05), except for general mental health (p=0.11). Comparison of the group age and blood parameters including erythrocyte sedimentation rate, high sensitivity C-reactive protein and full blood counts for white and red blood cells between participant groups showed no significant difference. Table 30 outlines participant characteristics.

TABLE 30

Clinical characteristics between non-fatigued controls, moderate CFS/ME and severe CFS/ME

| Variable | Moderate CFS/ME n = 11 | Severe CFS/ME n = 12 | Control n = 11 | P-value |
|---|---|---|---|---|
| Mean age (years) | 54.9 ± 10.3 | 47.5 ± 8.0 | 50.0 ± 12.3 | 0.286 |
| Sex (% Female) | 83.3 | 75 | 72.5 | 0.813 |
| FSS | 5.2 ± 1.3 | 7.0 ± 0.3 | 2.1 ± 1.4 | <0.05 |
| SF-36 | | | | |
| Physical functioning | 47.5 ± 27.8 | 15.3 ± 12.3 | 98.2 ± 4.8 | <0.05 |
| Physical role | 15.9 ± 29.4 | 3.3 ± 8.8 | 98.7 ± 5.7 | <0.05 |
| Bodily pain | 48.3 ± 28.1 | 36.0 ± 22.6 | 94.2 ± 13.0 | <0.05 |
| General health | 31.1 ± 20.5 | 19.7 ± 10.8 | 83.9 ± 4.5 | <0.05 |
| Vitality | 25.2 ± 10.6 | 7.2 ± 6.3 | 80.2 ± 4.3 | <0.05 |
| Emotional role | 96.3 ± 5.4 | 92.3 ± 6.4 | 100 ± 0 | <0.05 |
| Social functioning | 47.5 ± 24.8 | 25.0 ± 17.6 | 96.9 ± 5.4 | <0.05 |
| Mental health | 85.6 ± 22.0 | 72.8 ± 18.6 | 87.0 ± 6.8 | 0.11 |
| Pathology | | | | |
| White Cell Count (×10^9/L) | 5.8 ± 1.9 | 5.3 ± 1.2 | 6.2 ± 0.9 | 0.362 |
| Neutrophils (×10^9/L) | 3.4 ± 1.5 | 3.2 ± 1.0 | 3.7 ± 0.8 | 0.738 |
| Lymphocytes (×10^9/L) | 2.0 ± 0.5 | 1.7 ± 0.4 | 2.0 ± 0.5 | 0.147 |
| Monocytes (×10^9/L) | 0.3 ± 0.1 | 0.3 ± 0.6 | 0.3 ± 0.1 | 0.926 |
| Eosinophils (×10^9/L) | 0.1 ± 0.14 | 0.1 ± 0.1 | 0.2 ± 0.2 | 0.375 |
| Basophils (×10^9/L) | 0.03 ± 0.01 | 0.02 ± 0.01 | 0.02 ± 0.01 | 0.707 |
| Platelets (×10^9/L) | 262.0 ± 67.5 | 242.6 ± 50.0 | 257.5 ± 43.0 | 0.537 |
| Haemoglobin (g/L) | 136.3 ± 9.6 | 135.6 ± 13.1 | 137.6 ± 16.2 | 0.975 |
| Haematocrit ( | 0.4 ± 0.02 | 0.8 ± 1.2 | 0.4 ± 0.03 | 0.844 |
| Red Cell Count (×10^12/L) | 4.3 ± 1.1 | 4.6 ± 0.5 | 4.7 ± 0.5 | 0.775 |
| MCV (fL) | 90.1 ± 4.3 | 88.5 ± 3.4 | 87.3 ± 2.8 | 0.446 |
| Sodium (mmol/L) | 137.3 ± 3.04 | 138.0 ± 2.1 | 137.6 ± 1.3 | 0.769 |
| Potassium (mmol/L) | 4.2 ± 0.4 | 3.9 ± 0.2 | 4.1 ± 0.1 | 0.357 |
| Chloride (mmol/L) | 102.4 ± 3.3 | 102.9 ± 2.5 | 102.2 ± 2.7 | 0.730 |
| Bicarbonate (mmol/L) | 27.4 ± 2.2 | 26.5 ± 1.9 | 27.5 ± 2.4 | 0.303 |
| Anion Gap (mmol/L) | 7.3 ± 1.4 | 7.3 ± 1.4 | 7.8 ± 1.4 | 0.546 |
| ESR (mm/Hr) | 19.0 ± 17.1 | 14.5 ± 15.2 | 11.1 ± 4.2 | 0.341 |
| C-Reactive Protein (mg/L) | 3.8 ± 4.5 | 2.8 ± 6.4 | 1.0 ± 0.6 | 0.188 |

Data represented as mean±standard deviation, CFS, Chronic fatigue syndrome; ME, myalgic encephalomyelitis; FSS; Fatigue severity scale; SF-36, Short form 36 item health survey, WHODAS, World health organisation disability adjustment schedule.

$Ca^{2-}$ Dependent Protein Kinase Gene Expression

Figure 23:
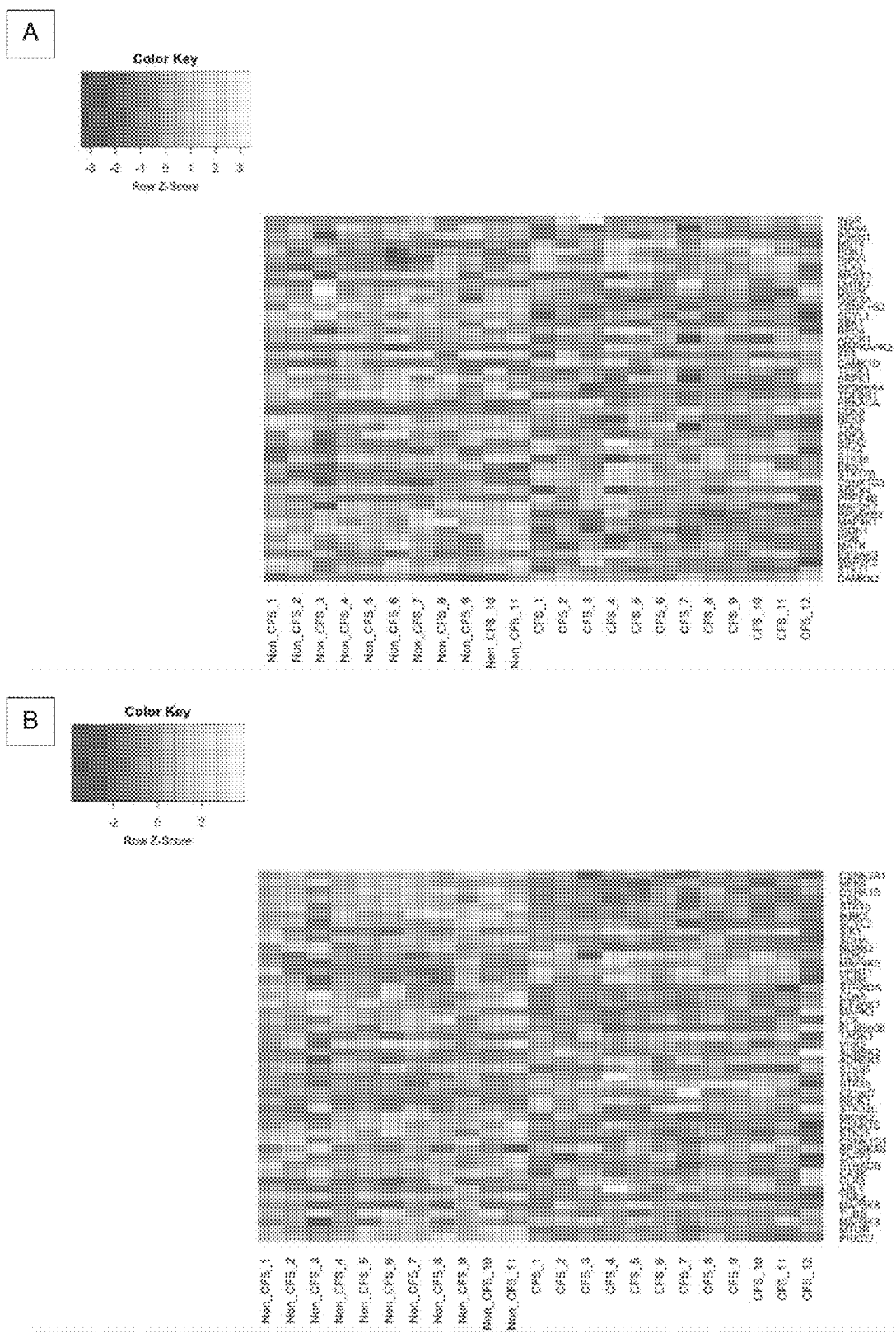
FIG. 23. Heat map of kinase gene expression showing (A) significantly upregulated and (B) significantly downregulated genes from severe CFS/ME patients compared with non-fatigued controls.

Microarray analysis of the 528 kinase genes revealed there were 92 genes which were significantly associated with severe CF5/ME patients compared with non-fatigued controls. Of the 92 genes, 37 genes were significantly upregulated (Table 31) and 55 genes were significantly downregulated (Table 32) in severe CFS/ME patients compared to non-fatigued controls. A heat map of gene expression with clustering using spearman correlation in severe CFS/ME patients and non-fatigued controls is shown in FIG. 23. There was no significant alteration in the expression of kinase genes in moderate CFS/ME patients compared with non-fatigued controls.

TABLE 31

List of calcium-dependent kinase genes significantly upregulated in severe CFS/ME group compared with non-fatigued controls.

| Gene name | Log2 (fold change) | P value |
|---|---|---|
| CDK9 | 0.418505235 | 1.44786E−09 |
| MAPKAPK2 | 0.458988465 | 3.17148E−08 |
| CSNK1G3 | 0.354351365 | 1.68531E−06 |
| CAMK1D | 0.322970895 | 1.65639E−05 |
| MST4 | 0.281702517 | 2.2541E−05 |

TABLE 31-continued

List of calcium-dependent kinase genes significantly upregulated in severe CFS/ME group compared with non-fatigued controls.

| Gene name | Log2 (fold change) | P value |
|---|---|---|
| PRKACA | 0.294878003 | 3.20405E−05 |
| STK39 | 0.316411907 | 6.97134E−05 |
| ADRBK1 | 0.233462724 | 7.80645E−05 |
| MAP4K5 | 0.325434189 | 0.000148478 |
| EIF2AK3 | 0.548932354 | 0.000156029 |
| YES1 | 0.586095547 | 0.00019027 |
| PRPF4B | 0.330804207 | 0.00024688 |
| CAMKK2 | 0.459516611 | 0.000307664 |
| TAOK3 | 0.207997286 | 0.000476049 |
| CDK7 | 0.500189253 | 0.000494901 |
| RIPK2 | 0.484439203 | 0.0006405 |
| RIOK3 | 0.550401811 | 0.000630622 |
| STK4 | 0.261572944 | 0.000663088 |
| CLK3 | 0.257415278 | 0.000730866 |
| CLK4 | 0.249497083 | 0.000975821 |
| ADRBK2 | 0.75043569 | 0.000997031 |
| MAP3K8 | 0.474587427 | 0.001133225 |
| LMTK2 | 0.414585483 | 0.001318789 |
| BRD4 | 0.161675211 | 0.001674596 |
| RPS6KA5 | 0.300257315 | 0.001883647 |
| HPRT1 | 0.235063603 | 0.002985669 |
| ABL1 | 0.473436245 | 0.00506836 |
| INSR | 0.625855881 | 0.005335724 |
| SNRK | 0.249400839 | 0.005940401 |
| ERN1 | 0.414439855 | 0.006022066 |
| MAP3K3 | 0.191248184 | 0.006262361 |
| PDK1 | 0.281715195 | 0.006628024 |
| C21orf7 | 0.611100452 | 0.006700917 |
| SIK1 | 0.593133707 | 0.006828076 |
| RIPK1 | 0.235813317 | 0.00781539 |
| STK32C | 0.571056394 | 0.010416118 |

TABLE 32

List of calcium-dependent kinase genes significantly downregulated in severe CFS/ME group compared with non-fatigued controls.

| Gene name | Log2 (fold change) | P value |
|---|---|---|
| TNK2 | −0.5929763 | 7.8935E−17 |
| TGFBR1 | −0.951662 | 4.4321E−15 |
| CSNK1G2 | −0.5948012 | 2.5963E−13 |
| STK11 | −0.6196713 | 8.9479E−12 |
| CSK | −0.5855852 | 5.6434E−10 |
| STK10 | −0.3506819 | 5.5896E−09 |
| CSNK2A1 | −0.5130831 | 2.1444E−08 |
| PRKD2 | −0.5883312 | 5.7048E−08 |
| DYRK1B | −0.6287082 | 8.4794E−08 |
| SBK1 | −0.7100798 | 1.2219E−07 |
| FES | −0.9457073 | 1.4352E−07 |
| STK25 | −0.4783125 | 1.4354E−07 |
| SDHA | −0.5258195 | 2.5036E−07 |
| ADCK4 | −0.571751 | 8.0054E−07 |
| TUBB | −0.4055129 | 1.0585E−06 |
| NEK9 | −0.3498812 | 2.1641E−06 |
| STK35 | −0.6132598 | 3.9862E−06 |
| IKBKE | −0.6077292 | 5.3859E−06 |
| EIF2AK1 | −0.4001172 | 6.3883E−06 |
| VRK3 | −0.32799 | 2.4521E−05 |
| RIOK1 | −0.558951 | 2.8792E−05 |
| MTOR | −0.389873 | 3.1103E−05 |
| NEK6 | −0.5891655 | 5.3333E−05 |
| RPS6KA4 | −0.4077403 | 6.6127E−05 |
| STRADA | −0.3801652 | 6.9352E−05 |
| SCYL2 | −0.2888867 | 7.9998E−05 |
| CDK5 | −0.6222848 | 8.9234E−05 |
| MATK | −0.4030913 | 0.00012599 |
| MKNK2 | −0.3089365 | 0.00018668 |
| IRAK4 | −0.2873769 | 0.00024716 |
| MAP4K1 | −0.3408634 | 0.00023847 |
| FGR | −0.4531449 | 0.0002525 |
| STRADB | −0.4698047 | 0.00041397 |
| PDK2 | −0.3431478 | 0.00074842 |
| STK38 | −0.3263961 | 0.00076823 |
| CSNK1G1 | −0.3344949 | 0.00075652 |
| LCK | −0.3682158 | 0.00084175 |
| RPS6KB2 | −0.3343033 | 0.00087291 |
| ADCK1 | −0.5383807 | 0.00103763 |
| PSKH1 | −0.3536634 | 0.00137302 |
| DMPK | −0.6344797 | 0.00173864 |
| ZAP70 | −0.2369642 | 0.00217501 |
| CASK | −0.613404 | 0.00231632 |
| SCYL1 | −0.2825376 | 0.00258513 |
| CSNK1E | −0.2937711 | 0.00270961 |
| SRPK1 | −0.2377855 | 0.0037189 |
| GSK3A | −0.2383325 | 0.00476715 |
| MAPK3 | −0.3200085 | 0.0048246 |
| MAP2K7 | −0.2578818 | 0.00538244 |
| FLJ25006 | −0.4910571 | 0.00567251 |
| NUAK2 | −0.4855813 | 0.0061345 |
| MAP2K2 | −0.1521624 | 0.00689828 |
| TESK1 | −0.3332313 | 0.00752948 |
| TLK2 | −0.1859512 | 0.00846469 |
| MAST3 | −0.3216447 | 0.00968208 |

Ninety-two genes associated with severe CFS/ME patients were analysed using MetaCore pathway analysis. The gene signatures were associated with seventy-seven significant process networks including NK cytotoxicity, IFN-γ, IL-17 of immune cells, immune cell function, physiological processes, signal transduction and translation in CFS/ME patients (Table 33).

TABLE 32-continued

| Gene name | Log2 (fold change) | P value |
|---|---|---|
| RPS6KB2 | -0.3343033 | 0.00087291 |
| ADCK1 | -0.5383807 | 0.00103763 |
| PSKH1 | -0.3536634 | 0.00137302 |
| DMPK | -0.6344797 | 0.00173864 |
| ZAP70 | -0.2369642 | 0.00217501 |
| CASK | -0.613404 | 0.00231632 |
| SCYL1 | -0.2825376 | 0.00258513 |
| CSNK1E | -0.2937711 | 0.00270961 |
| SRPK1 | -0.2377855 | 0.0037189 |
| GSK3A | -0.2383325 | 0.00476715 |
| MAPK3 | -0.3200085 | 0.0048246 |
| MAP2K7 | -0.2578818 | 0.00538244 |
| FLJ25006 | -0.4910571 | 0.00567251 |
| NUAK2 | -0.4855813 | 0.0061345 |
| MAP2K2 | -0.1521624 | 0.00689828 |
| TESK1 | -0.3332313 | 0.00752948 |
| TLK2 | -0.1859512 | 0.00846469 |
| MAST3 | -0.3216447 | 0.00968208 |

Discussion

This study reports, for the first time, the differential expression of $Ca^{2+}$ dependent protein kinase genes from isolated NK cells in severe CFS/ME patients compared with non-fatigued controls. Thirty seven $Ca^{2+}$ dependent protein kinase genes were significantly upregulated and 55 $Ca^{2+}$ dependent protein kinase genes were significantly downregulated in severe CFS/ME patients compared to non-fatigued controls. As this current investigation was undertaken in isolated NK cells, the $Ca^{2+}$ dependent protein kinase genes that are reported will be discussed in the context of intracellular pathways involved in JNK, STAT and NFkappa beta (NF-κβ) activity and NK cell lysis.

The results from this current investigation highlight significant down regulation of $Ca^{2+}$ dependent protein kinases, namely Lck and ZAP70, between the severe CFS/ME patients compared to non-fatigued controls. NK cells contain a zeta chain, associated to the Fc receptor CDI6 (FcgRIIIA), where Zap-70 phosphorylates as well as the associated transducing gamma chain [33u]. The cytoplasmic tails of adhesion molecules and activating receptors of the NK cells recruit Src family of kinases to phosphorylate ITAMs or ITSMs [34u-37u]. Subsequently the signalling molecules including Lck, Zap70, linker activation for T cells (LAT) and SH2 domain-containing Leukocyte Protein of 76 kDa (SLP-76) are phosphorylated which continue to phosphorylate and mobilize multiple downstream signalling proteins which results in the activation of NK cells and the initiation of granule dependent exocytosis [38u-40u]. The significant reduction in ZAP70 and Lck expression may affect the phosphorylation of NK cell activating receptors that contain immunoreceptor tyrosine-based activation motifs (ITAMs) to phosphorylate and mobilize multiple downstream signalling proteins which results in the activation of NK cells and the initiation of granule dependent exocytosis. Given the significant reduction of both ZAP70 and Lck, these being $Ca^{2+}$ dependent protein kinases, the intracellular downstream effect may be significant for effector functions of NK cells. The present inventors and others have previously described significant reduction in NK lysis, changes in cytokine production and mobilization and redistribution of cytoplasmic perforin and granzyme B towards the contact zone with target cells [14u, 20u, 41u-45u].

The significant reduction in $Ca^{2+}$ dependent protein kinases ERK1/2 and MEK1/2 reported in this current study aligns to the inventors' previous investigation that reported a significant decrease in ERK1/2 in $CD56^{dim}CD16^+$ NK cells compared to the non-fatigued controls [see the Example above]. A significant reduction in MEK1/2 suggests further compromises in the effector NK cell functions. Following the activation of triggers, a signalling cascade via sequential phosphorylation of MAPK, MEK and ERK results in the lytic granule polarization mediated by TUBB [47u] which regulates the reorientation of the microtubule and microtubule organizing centre (MTOC) towards the target cells to release perforin and granzymes. Activation of ERK1/2 facilitates polarisation of cytotoxic granules towards the microtubule organising centre (MTOC) [48u, 49u]. MAPK intracellular signals activate reorganisation and polarisation of the actin cytoskeleton which facilitates movement of the cytotoxic granules along the MTOC microtubules towards the immune synapse [48u, 49u]. As a critical threshold of signalling of MAPK, MEK and ERK are required for NK cells to mount an effector cell response. A significant reduction in the expression of MEK2, ERK1 and TUBB, as reported in this current investigation, may disrupt these distal events that lead ultimately to reduced NK cytotoxicity. This reduced NK cytotoxicity may be due to a reduction in the ERK1/2 phosphorylation, reducing the polarisation of the secretory granule towards the immune synapse for degranulation [3u, 50u] in severe CFS/ME patients. Importantly, the inventors have reported reduced ERK1/2 from isolated NK cells. Also, the inventors and other researchers have reported a significant reduction in lytic granules, such as granzyme B from CFS/ME patients [14u, 20u, 41u-45u].

Binding of NK cells to target cells triggers phosphatidylinositol (PI)-3 kinase (PI3K) to be rapidly activated by Src-family tyrosine kinases (SETKs) and/or SYK leading to calcium influx [51u] and protein kinase C (PKC) activation. In this present investigation the inventors report significant increases in PKC alpha in the severe CFS/ME group compared with the non-fatigued control group. Importantly, PKC-alpha, a member of protein kinase C (PKC) family of $Ca^{2+}$ and/or lipid-activated serine/threonine kinases, functions downstream of many membrane-associated signal transduction pathways [52u]. The activation of PKC alpha triggers a signalling cascade via sequential phosphorylation of MAPK, MEK, ERK and JNK pathways. Calcium ions, magnesium ions, and diacylglycerols (DAGs) are the most important molecules for regulating PKC-α activity as low concentrations of these molecules increase the PKC-alpha activity. Hence the present study highlights the importance of $Ca^{2+}$ transport ion channels in this context.

As described in earlier Examples, the inventors investigated the role of transient receptor potential melastatin 3 (TRPM3) cation channels and intracellular calcium levels in isolated NK and B cells and found significant reductions in intracellular calcium from each of the cell types as well as significant reduction in cell surface TRPM3 receptors. These findings suggest that the significant reduction in intracellular calcium from these cell types may result in significant increases in calcium-dependent kinase PKC-alpha. Consequently, the downstream effect of this increased gene expression suggest increased p38 and subsequently NF-κβ activation and the production of inflammatory mediators [54u]. Interestingly, the inventors have reported in an earlier Example a significant increase in isolated NK cells, of MAPK (p38) from CFS/ME patients. Other researchers have reported significantly increased NF-κβ production as well as increased pro-inflammatory factors, such as IL-6, IFN gamma, and anti-inflammatory IL10 products from CFS/ME patients [56u-62u].

Moreover, activation of C-Jun terminal kinase (JNK) is activated by PKC-alpha, where JNK modifies the activity of numerous proteins located in the mitochondria or activates inflammation and pro-inflammatory cytokines such as IL-2, IL-6 and TNF-α. Increased activation of PKC alpha may provide possible explanation for the increase in JNK along p38, resulting in proinflammatory cytokine production such as IFNγ, TNF alpha, IL-2 and IL-6, from NK cells [63u]. The significant increase in PKC-alpha may suggest a shift towards a Th1/pro-inflammatory immune response. Previous researchers report significant increases in IFN gamma, IL-2, TNF alpha and IL-6 in CFS/ME patients [56u-62u]. Moreover, anti-inflammatory IL-10 exerts inhibitory effects on cytokine secretion and impedes pro-inflammatory cytokine secretion by multiple cells including NK cells (IFN-γ and TNF-α) [63u]. A decrease in IL-10 favours an increase in pro-inflammatory responses and this may increase the prevalence of Th1-like cytokines. Importantly the inventors and others have reported significant reductions in IL-10 from CFS/ME patients [64u, 65u].

During inflammation, NK cells are recruited to lymph nodes where they are activated by trans-presentation of IL-15 by IL-15Rα expressed on dendritic cells [66u]. Engagement of IL-15R on NK cells causes auto-phosphorylation and activation of Janus kinases (JAK1 and JAK3). Subsequently this induces Ras-Raf-MEK, PI3K-AKT-mTOR, and signal transduction and activation of transcription (STAT) 5 pathways [67u, 68u]. Studies have shown that IL-15 activates NK cells to become equipped with cytotoxic granules and sensitize them to secondary stimuli. Furthermore, previous researchers have reported mTOR pathway is central to the IL-15-induced activation of vital NK cell functions. Hence a significant reduction in mTOR reported in this investigation suggests reduced NK effector function of the production of lytic granules and reduced cell lysis as previously described in CFS/ME patients [14u, 20u, 41u-45u]. Stat5 proteins are activated by a wide variety of cytokines and growth factors, including IL-2, IL-3, IL-5, IL-7, IL-9, IL-15 and granulocyte-macrophage colony-stimulating factors. Importantly previous investigations found IL-2, IL-4 and IL-15 were tightly associated in CFS/ME and less centred about any individual cytokine. Importantly the authors also highlight IL-2, 4 and 15 belong to a family of cytokines that also includes IL-7, IL-9 and are initiated by STAT5 [69u].

The kinase genes identified in this study control a large number of process networks within cells affecting synaptic function, signal transduction, inflammation pathways, apoptosis, muscle contraction, microtubule cytoskeleton spindle assembly, circadian rhythm, calcium transport and nitric oxide signalling. Metabolic effects, predominantly insulin gene expression pathways were identified. Protein phosphorylation and protein modification pathways predominated in gene association analysis. Thus this study revealed multiple gene, metabolic and signalling pathway perturbations manifest in calcium-sensitive kinase genes. Kinase pathways control or regulate numerous physiologies including cardiovascular, urogenital, gastrointestinal, neurological, and respiratory systems. Kinase perturbations suggest the likely demonstration of an inflammatory profile along with other dysregulated physiological mechanisms, adding to widespread inflammation mechanism dysregulation in virtually all cells [70u]. Furthermore, $Ca^{2+}$ dysregulation is an important consequence of altered membrane receptor signalling and likely to have effects in neuronal function, such as impulse transmission [71u], as well as muscle contraction [72u]. Impaired neurological and motor control are common symptoms associated with CFS/ME [26u]. Therefore, it is suggested that $Ca^{2+}$ and kinase signalling dysregulation be further investigated in the central nervous system given the high dependence on $Ca^{2+}$ signalling for glial and neuronal cell functioning and their potential role in the pathomechanism of CFS/ME.

Conclusion

This study identifies, for the first time, 92 calcium-dependent kinase genes differentially regulated in NK cells of CFS/ME patients compared with healthy non-fatigued controls. Specifically 37 genes were upregulated and 55 genes were downregulated that are involved in numerous cell signalling and metabolic pathways including inflammation. While primarily indicating functional impairment in NK cytotoxic activity and immunological dysfunction, kinases are located throughout cells in the body and may be associated with other clinical manifestations reported in CFS/ME.

Example 12—A Targeted Genome Association Study Examining Transient Receptor Potential (TRP) Ion Channels, Acetylcholine Receptors (AChRs), and Adrenergic Receptors (ADRs) in Chronic Fatigue Syndrome/Myalgic Encephalomyelitis (CFS/ME)

In this Example the inventors identify and characterise a SNP in adrenergic receptor α1 (ADRA1A) that is a potential cellular marker for CFS/ME.

Introduction

Biological processes responsible for the varied symptoms reported for CFS/ME may involve several ion channels and receptors that are located on cells throughout the body. Transient receptor potential ion channels (TRPs) are widely expressed on tissues and cells and are activated and regulated by various stimuli in the cellular environment such as pain, temperature, taste, pressure, and vision [5p]. There are six subfamilies including TRPA (ankyrin), TRPC (canonical), TRPM (meiastatin), TRPML (mucolipin), TRPP (polycystin), and TRPV (vanilioid) [6p]. Most consist of non-selective channels permeable to cations such as calcium ($Ca^{2+}$), sodium ($Na^+$), and magnesium ($Mg^+$). This has an important role in maintaining homeostasis for a number of physiological requirements. Accordingly, dysregulation of these channels has been found to have a role in pathological conditions such as chronic pain, overactive bladder, diabetes, chronic obstructive pulmonary disease, cardiac hypertrophy, familial Alzheimer's disease, skin diseases, skeletal dysplasia's, neuropathy, and cancer [7p-12p].

In addition to TRPs, acetylcholine receptors (AChRs) are of particular interest due to their role in neurological and neuromuscular transmission [13p, 14p]. Their function may have a role in difficulties processing information and short term memory loss reported in CFS/ME [1p, 15p]. AChRs consist of two types that bind with acetylcholine and transmit its signal. Nicotinics (nAChRs) are ligand-gated ion channels and are involved in fast synaptic interactions of neurotransmitters [16p]. Muscarinics (mAChRs) consist of 17 different subunits and are G-protein coupled receptors that facilitate slow metabolic responses through secondary messenger cascades [17p].

Moreover, adrenergic receptors (ADRs) are another class of G-protein coupled receptors which have catecholamine ligands [18p]. This binding is associated with stimulation of the sympathetic nervous system, commonly known for the fight or flight response in which energy is mobilised and blood flow is diverted from non-essential organs to skeletal muscle. There are 3 types of receptor; α1, which is primarily involved in intracellular $Ca^{2+}$ and subsequent smooth muscle contractions [19p]. The α2 receptors have a role in inhibition of neurotransmitters, decreased cAMP and decreased smooth muscle contraction. Beta receptors have 3 subtypes and alternatively increase cAMP activity resulting in heart muscle contractions, smooth muscle relaxation and glycogenolysis [20p, 21p].

In the earlier Examples the inventors identified significant SNPs and genotypes in TRPs and AChRs in peripheral blood mononuclear cells in CFS/ME patients compared with healthy controls. Specifically, 13 significant SNPs in TRPs and 17 significant SNPs in AChRs were identified (9 mAChRs; 8 nAChRs). CFS/ME is largely characterised as a heterogeneous illness. The above ion channels and receptors were chosen as targets in a genome-wide association study due to their wide expression in cells and their involvement in numerous physiological processes. Hence, the purpose of this investigation was to identify whether association between SNPs for TRPs, AChRs, and ADRs are observed in patients with CFS/ME compared with healthy controls.

Methodology

Participants

Participants were from the National Centre for Neuroimmunology and Emerging Diseases (NCNED) research database for CFS/ME. Participants aged between 18 and 65 years were recruited from community support networks in the South East Queensland and Northern New South Wales region of Australia. All participants completed a screening questionnaire reporting their sociodemographic details, medical history, and symptoms. CFS/ME patients were classified according to Fukuda criteria (1). This required the presence of fatigue that significantly impacts with daily activities for at least 6 months. This should not be due to ongoing exertion or other medical conditions and accompanied by at least four of the following symptoms: post-exertional malaise, unrefreshing sleep, impairment of short-term memory or concentration, muscle pain, joint pain, headaches, tender lymph nodes, and/or sore throat. Healthy controls reported no evidence of disease. Exclusions were participants not meeting the above criteria or with other medical diagnoses that would exclude CFS/ME for example autoimmune disorder, multiple sclerosis, psychosis, major depression, cardiovascular disease. Participants were also excluded if they were pregnant, breast feeding, smokers or had a history of substance abuse.

DNA Extraction

Peripheral blood mononuclear cells were collected into ethylenadiaminetetraacetic acid tubes. Routine pathology was performed for screening of any abnormal parameters including full blood count, erythrocyte sedimentation rate, and high sensitivity C reactive protein by Pathology Queensland. The Qiagen DNA blood mini-kit was used to extract approximately 2 μg of genomic DNA as per manufacturer instructions. To assess the quality and quantity of DNA, the nCounter Digital Analyzer (Nanostring, United States of America) optical scanner was used. Whole genome genotyping was performed using the HumansOmniExpress BeadChip array (Illumina, South Korea).

Statistical Analysis

Statistical analysis was performed using PLINK v1.07 (http://pngu.mgh.harvard.edu/purcell/plink/) whole genome analysis software [Purcell, 2007p] to identify the frequency of SNPs. For quality control, a major allele frequency filter of <1% was applied. Further, SNPs with a variance lower than 2% were removed. Sample heterozygosity was also applied as a quality control measure and calculated as the proportion of heterozygous genotypes in relation to all genotypes at the SNP and sample levels. Data were compared between CFS/ME patients and healthy controls using R (R Core Team, 2013). Fisher's exact probability test was used to examine significant genotype association for each individual SNP, and a Bonferroni correction for multiple test correction was applied as post hoc analysis ($p<0.05$).

Results

Demographic Characteristics

The majority of participants in this study were of Caucasian descent (97.8%). Of the 172 participants, 95 met criteria for CFS/ME and 77 met criteria for healthy controls, and the mean age and proportion female was 45.8±8.9 (69% female) and 42.3±10.3 (63% female) respectively. Potential confounding factors for analysis such as age, sex and ethnicity were analysed for interaction with genes of interest and no outliers were identified, hence no adjustments were required.

SNP Association Study

A total of 950 SNPs were included for analysis after quality control measures were applied. These are listed in Table 34a below.

TABLE 34a

26: SNP variants of TRP channel, ACh receptors or ADR annotated with their consequence.

| SNP | Location | Consequence | Gene |
| --- | --- | --- | --- |
| rs2072660 | 1:154576245-154576245 | 3_prime_UTR_variant | CHRNB2 |
| rs3811450 | 1:154578556-154578556 | 3_prime_UTR_variant | CHRNB2 |
| rs726168 | 1:239631064-239631064 | intron_variant | CHRM3 |
| rs12037424 | 1:239635112-239635112 | intron_variant | CHRM3 |
| rs1867263 | 1:239644620-239644620 | intron_variant | CHRM3 |
| rs16832152 | 1:239648409-239648409 | intron_variant | CHRM3 |
| rs6691263 | 1:239648803-239648803 | intron_variant | CHRM3 |
| rs10925941 | 1:239649238-239649238 | intron_variant | CHRM3 |
| rs12090480 | 1:239650653-239650653 | intron_variant | CHRM3 |
| rs4659550 | 1:239656203-239656203 | intron_variant | CHRM3 |
| rs12021900 | 1:239661754-239661754 | intron_variant | CHRM3 |
| rs10802789 | 1:239669380-239669380 | intron_variant | CHRM3 |
| rs10754677 | 1:239669800-239669800 | intron_variant | CHRM3 |
| rs1867266 | 1:239676005-239676005 | intron_variant | CHRM3 |
| rs6692711 | 1:239683080-239683080 | intron_variant | CHRM3 |
| rs12406493 | 1:239689805-239689805 | intron_variant | CHRM3 |
| rs4145784 | 1:239694692-239694692 | intron_variant | CHRM3 |
| rs2278642 | 1:239703843-239703843 | intron_variant | CHRM3 |
| rs10802794 | 1:239707321-239707321 | intron_variant | CHRM3 |

TABLE 34a-continued

26: SNP variants of TRP channel, ACh receptors or ADR annotated with their consequence.

| SNP | Location | Consequence | Gene |
|---|---|---|---|
| rs6663632 | 1:239714421-239714421 | intron_variant | CHRM3 |
| rs1431718 | 1:239716253-239716253 | intron_variant | CHRM3 |
| rs12143018 | 1:239726189-239726189 | intron_variant | CHRM3 |
| rs12124903 | 1:239752715-239752715 | intron_variant | CHRM3 |
| rs12126146 | 1:239754487-239754487 | intron_variant | CHRM3 |
| rs685475 | 1:239761043-239761043 | intron_variant | CHRM3 |
| rs685550 | 1:239761108-239761108 | intron_variant | CHRM3 |
| rs685960 | 1:239761186-239761186 | intron_variant | CHRM3 |
| rs843030 | 1:239761505-239761505 | intron_variant | CHRM3 |
| rs6703930 | 1:239761570-239761570 | intron_variant | CHRM3 |
| rs7533134 | 1:239761809-239761809 | intron_variant | CHRM3 |
| rs17657156 | 1:239763709-239763709 | intron_variant | CHRM3 |
| rs532718 | 1:239768318-239768318 | intron_variant | CHRM3 |
| rs2841037 | 1:239771241-239771241 | intron_variant | CHRM3 |
| rs663927 | 1:239772051-239772051 | intron_variant | CHRM3 |
| rs481036 | 1:239773282-239773282 | intron_variant | CHRM3 |
| rs534615 | 1:239781857-239781857 | intron_variant | CHRM3 |
| rs626694 | 1:239782776-239782776 | intron_variant | CHRM3 |
| rs693948 | 1:239792376-239792376 | intron_variant | CHRM3 |
| rs665159 | 1:239798702-239798702 | intron_variant | CHRM3 |
| rs2790336 | 1:239799386-239799386 | intron_variant | CHRM3 |
| rs12059546 | 1:239806797-239806797 | intron_variant | CHRM3 |
| rs558438 | 1:239808619-239808619 | intron_variant | CHRM3 |
| rs6690809 | 1:239810706-239810706 | intron_variant | CHRM3 |
| rs7543259 | 1:239815886-239815886 | intron_variant | CHRM3 |
| rs6429157 | 1:239818343-239818343 | intron_variant | CHRM3 |
| rs1578180 | 1:239819338-239819338 | intron_variant | CHRM3 |
| rs4523505 | 1:239820613-239820613 | intron_variant | CHRM3 |
| rs10802807 | 1:239820751-239820751 | intron_variant | CHRM3 |
| rs1934349 | 1:239821625-239821625 | intron_variant | CHRM3 |
| rs12072181 | 1:239822576-239822576 | intron_variant | CHRM3 |
| rs589962 | 1:239826664-239826664 | intron_variant | CHRM3 |
| rs621060 | 1:239828986-239828986 | intron_variant | CHRM3 |
| rs685548 | 1:239831606-239831606 | intron_variant | CHRM3 |
| rs1304352 | 1:239839119-239839119 | intron_variant | CHRM3 |
| rs602117 | 1:239843485-239843485 | intron_variant | CHRM3 |
| rs1594513 | 1:239848453-239848453 | intron_variant | CHRM3 |
| rs10925994 | 1:239852008-239852008 | intron_variant | CHRM3 |
| rs497576 | 1:239862677-239862677 | intron_variant | CHRM3 |
| rs682355 | 1:239867099-239867099 | intron_variant | CHRM3 |
| rs536477 | 1:239882608-239882608 | intron_variant | CHRM3 |
| rs2217533 | 1:239884998-239884998 | intron_variant | CHRM3 |
| rs10495447 | 1:239888040-239888040 | intron_variant | CHRM3 |
| rs16839034 | 1:239897028-239897028 | intron_variant | CHRM3 |
| rs16839045 | 1:239898428-239898428 | intron_variant | CHRM3 |
| rs10926008 | 1:239898823-239898823 | intron_variant | CHRM3 |
| rs16839051 | 1:239900066-239900066 | intron_variant | CHRM3 |
| rs10926009 | 1:239900399-239900399 | intron_variant | CHRM3 |
| rs4620530 | 1:239900521-239900521 | intron_variant | CHRM3 |
| rs10399860 | 1:239901238-239901238 | intron_variant | CHRM3 |
| rs12036109 | 1:239902578-239902578 | intron_variant | CHRM3 |
| rs7520974 | 1:239903960-239903960 | intron_variant | CHRM3 |
| rs6701181 | 1:239906887-239906887 | intron_variant | CHRM3 |
| rs11195419 | 10:111079610-111079610 | 3_prime_UTR_variant | ADRA2A |
| rs553668 | 10:111079821-111079821 | 3_prime_UTR_variant | ADRA2A |
| rs800345 | 11:2408503-2408503 | intron_variant | TRPM5 |
| rs2074234 | 11:2411734-2411734 | synonymous_variant | TRPM5 |
| rs2301698 | 11:2416195-2416195 | intron_variant | TRPM5 |
| rs886277 | 11:2418537-2418537 | missense_variant | TRPM5 |
| rs757091 | 11:2419759-2419759 | intron_variant | TRPM5 |
| rs2271581 | 11:3626837-3626837 | splice_region_variant, intron_variant, non_coding_transcript_variant | TRPC2 |
| rs11028621 | 11:3627501-3627501 | intron_variant, non_coding_transcript_variant | TRPC2 |
| rs2271584 | 11:3635291-3635291 | downstream_gene_variant | ART5 |
| rs1514690 | 11:3635817-3635817 | downstream_gene_variant | ART5 |
| rs1514691 | 11:3636206-3636206 | downstream_gene_variant | ART5 |
| rs2672215 | 11:3670419-3670419 | intron_variant | CHRNA10 |
| rs11823728 | 11:62909330-62909330 | 3_prime_UTR_variant | CHRM1 |
| rs2067477 | 11:62910834-62910834 | synonymous_variant | CHRM1 |
| rs544978 | 11:62917758-62917758 | intron_variant | CHRM1 |
| rs2075748 | 11:62920797-62920797 | intron_variant | CHRM1 |
| rs11822237 | 11:101459359-101459359 | intron_variant | TRPC6 |
| rs10895111 | 11:101462443-101462443 | intron_variant | TRPC6 |
| rs7935581 | 11:101470508-101470508 | intron_variant | TRPC6 |
| rs7948300 | 11:101473968-101473968 | intron_variant | TRPC6 |

TABLE 34a-continued

26: SNP variants of TRP channel, ACh receptors or ADR annotated with their consequence.

| SNP | Location | Consequence | Gene |
| --- | --- | --- | --- |
| rs11224783 | 11:101479107-101479107 | intron_variant | TRPC6 |
| rs12791865 | 11:101480818-101480818 | intron_variant | TRPC6 |
| rs17673079 | 11:101481460-101481460 | intron_variant | TRPC6 |
| rs10895115 | 11:101481696-101481696 | intron_variant | TRPC6 |
| rs12361641 | 11:101482750-101482750 | intron_variant | TRPC6 |
| rs7924551 | 11:101484237-101484237 | intron_variant | TRPC6 |
| rs7942339 | 11:101484395-101484395 | intron_variant | TRPC6 |
| rs10895118 | 11:101493494-101493494 | intron_variant | TRPC6 |
| rs10501979 | 11:101496481-101496481 | intron_variant | TRPC6 |
| rs10501986 | 11:101504818-101504818 | intron_variant | TRPC6 |
| rs10501982 | 11:101517985-101517985 | intron_variant | TRPC6 |
| rs4272759 | 11:101523810-101523810 | intron_variant | TRPC6 |
| rs4481994 | 11:101524579-101524579 | intron_variant | TRPC6 |
| rs11224816 | 11:101525555-101525555 | intron_variant | TRPC6 |
| rs7106968 | 11:101530713-101530713 | intron_variant | TRPC6 |
| rs7106085 | 11:101535964-101535964 | intron_variant | TRPC6 |
| rs10895131 | 11:101537138-101537138 | intron_variant | TRPC6 |
| rs7118839 | 11:101538747-101538747 | intron_variant | TRPC6 |
| rs11224827 | 11:101539171-101539171 | intron_variant | TRPC6 |
| rs7112255 | 11:101540477-101540477 | intron_variant | TRPC6 |
| rs11224829 | 11:101542144-101542144 | intron_variant | TRPC6 |
| rs4492784 | 11:101545871-101545871 | intron_variant | TRPC6 |
| rs4237603 | 11:101554211-101554211 | intron_variant | TRPC6 |
| rs11224855 | 11:101559088-101559088 | intron_variant | TRPC6 |
| rs10219300 | 11:101560391-101560391 | intron_variant | TRPC6 |
| rs9326314 | 11:101562430-101562430 | intron_variant | TRPC6 |
| rs4394815 | 11:101577066-101577066 | intron_variant | TRPC6 |
| rs4326755 | 11:101578627-101578627 | intron_variant | TRPC6 |
| rs3742037 | 12:109788574-109788574 | synonymous_variant | TRPV4 |
| rs10735104 | 12:109790160-109790160 | intron_variant | TRPV4 |
| rs1861812 | 12:109790878-109790878 | intron_variant | TRPV4 |
| rs3742035 | 12:109796853-109796853 | intron_variant | TRPV4 |
| rs3825396 | 12:109796893-109796893 | intron_variant | TRPV4 |
| rs12579553 | 12:109797827-109797827 | intron_variant | TRPV4 |
| rs3825394 | 12:109803033-109803033 | missense_variant | TRPV4 |
| rs10850783 | 12:109805128-109805128 | intron_variant | TRPV4 |
| rs1861809 | 12:109807783-109807783 | intron_variant | TRPV4 |
| rs11147662 | 13:37639679-37639679 | intron_variant | TRPC4 |
| rs9547994 | 13:37645311-37645311 | intron_variant | TRPC4 |
| rs9566245 | 13:37650994-37650994 | intron_variant | TRPC4 |
| rs7332871 | 13:37656850-37656850 | intron_variant | TRPC4 |
| rs2025407 | 13:37661974-37661974 | intron_variant | TRPC4 |
| rs1570612 | 13:37668344-37668344 | intron_variant | TRPC4 |
| rs9548010 | 13:37670760-37670760 | intron_variant | TRPC4 |
| rs2147124 | 13:37672492-37672492 | intron_variant | TRPC4 |
| rs1924303 | 13:37673369-37673369 | intron_variant | TRPC4 |
| rs1924304 | 13:37674518-37674518 | intron_variant | TRPC4 |
| rs7329459 | 13:37677502-37677502 | intron_variant | TRPC4 |
| rs9532095 | 13:37677552-37677552 | intron_variant | TRPC4 |
| rs9532096 | 13:37677661-37677661 | intron_variant | TRPC4 |
| rs9576336 | 13:37680202-37680202 | intron_variant | TRPC4 |
| rs9532099 | 13:37681051-37681051 | intron_variant | TRPC4 |
| rs9576338 | 13:37682477-37682477 | intron_variant | TRPC4 |
| rs17056448 | 13:37691055-37691055 | intron_variant | TRPC4 |
| rs17056451 | 13:37691402-37691402 | intron_variant | TRPC4 |
| rs1413005 | 13:37694300-37694300 | intron_variant | TRPC4 |
| rs17056462 | 13:37695783-37695783 | intron_variant | TRPC4 |
| rs7332772 | 13:37696027-37696027 | intron_variant | TRPC4 |
| rs1413002 | 13:37699627-37699627 | intron_variant | TRPC4 |
| rs7319926 | 13:37706293-37706293 | intron_variant | TRPC4 |
| rs9548026 | 13:37708333-37708333 | intron_variant | TRPC4 |
| rs9532107 | 13:37715824-37715824 | intron_variant | TRPC4 |
| rs1360623 | 13:37716203-37716203 | intron_variant | TRPC4 |
| rs1360624 | 13:37716537-37716537 | intron_variant | TRPC4 |
| rs2991010 | 13:37716874-37716874 | intron_variant | TRPC4 |
| rs17056501 | 13:37720342-37720342 | intron_variant | TRPC4 |
| rs11147666 | 13:37722946-37722946 | intron_variant | TRPC4 |
| rs1360625 | 13:37729884-37729884 | intron_variant | TRPC4 |
| rs1556541 | 13:37731277-37731277 | intron_variant | TRPC4 |
| rs17203175 | 13:37731368-37731368 | intron_variant | TRPC4 |
| rs2025402 | 13:37743884-37743884 | intron_variant | TRPC4 |
| rs9603254 | 13:37752578-37752578 | intron_variant | TRPC4 |
| rs4399429 | 13:37761202-37761202 | intron_variant | TRPC4 |
| rs11147670 | 13:37767832-37767832 | intron_variant | TRPC4 |
| rs17056604 | 13:37769649-37769649 | intron_variant | TRPC4 |

TABLE 34a-continued

26: SNP variants of TRP channel, ACh receptors or ADR annotated with their consequence.

| SNP | Location | Consequence | Gene |
| --- | --- | --- | --- |
| rs11147671 | 13:37771058-37771058 | intron_variant | TRPC4 |
| rs7327037 | 13:37774169-37774169 | intron_variant | TRPC4 |
| rs9315512 | 13:37778933-37778933 | intron_variant | TRPC4 |
| rs4943538 | 13:37781807-37781807 | intron_variant | TRPC4 |
| rs12869943 | 13:37782110-37782110 | intron_variant | TRPC4 |
| rs12875527 | 13:37783247-37783247 | synonymous_variant | TRPC4 |
| rs3904512 | 13:37783334-37783334 | upstream_gene_variant | TRPC4 |
| rs12583681 | 13:37783357-37783357 | upstream_gene_variant | TRPC4 |
| rs9594231 | 13:37783463-37783463 | upstream_gene_variant | TRPC4 |
| rs9576354 | 13:37788657-37788657 | intron_variant | TRPC4 |
| rs9532117 | 13:37788910-37788910 | intron_variant | TRPC4 |
| rs9548050 | 13:37789313-37789313 | intron_variant | TRPC4 |
| rs6650469 | 13:37793812-37793812 | intron_variant | TRPC4 |
| rs655207 | 13:37793875-37793875 | intron_variant | TRPC4 |
| rs7337719 | 13:37796561-37796561 | intron_variant | TRPC4 |
| rs9566255 | 13:37804227-37804227 | intron_variant | TRPC4 |
| rs9566257 | 13:37807531-37807531 | intron_variant | TRPC4 |
| rs2184129 | 13:37818198-37818198 | intron_variant | TRPC4 |
| rs612701 | 13:37833682-37833682 | intron_variant | TRPC4 |
| rs2093812 | 13:37834053-37834053 | intron_variant | TRPC4 |
| rs9548066 | 13:37838874-37838874 | intron_variant | TRPC4 |
| rs9576386 | 13:37842343-37842343 | intron_variant | TRPC4 |
| rs9548074 | 13:37843946-37843946 | intron_variant | TRPC4 |
| rs9548075 | 13:37844095-37844095 | intron_variant | TRPC4 |
| rs9548078 | 13:37848698-37848698 | intron_variant | TRPC4 |
| rs861005 | 13:37849947-37849947 | downstream_gene_variant | RNA5SP26 |
| rs651451 | 13:37854139-37854139 | downstream_gene_variant | RNA5SP26 |
| rs1415601 | 13:37866431-37866431 | intron_variant | TRPC4 |
| rs17273171 | 13:37866516-37866516 | intron_variant | TRPC4 |
| rs4144140 | 13:37868903-37868903 | intron_variant | TRPC4 |
| rs1924379 | 13:37869575-37869575 | intron_variant | TRPC4 |
| rs17227989 | 15:31001571-31001571 | 3_prime_UTR_variant | TRPM1 |
| rs3784588 | 15:31002451-31002451 | missense_variant | TRPM1 |
| rs17227996 | 15:31002948-31002948 | missense_variant | TRPM1 |
| rs10152819 | 15:31003839-31003839 | intron_variant | TRPM1 |
| rs7182547 | 15:31005469-31005469 | intron_variant | TRPM1 |
| rs2113946 | 15:31009544-31009544 | intron_variant | TRPM1 |
| rs964925 | 15:31013776-31013776 | intron_variant | TRPM1 |
| rs16956447 | 15:31015464-31015464 | intron_variant | TRPM1 |
| rs12915504 | 15:31020416-31020416 | intron_variant | TRPM1 |
| rs7161812 | 15:31025182-31025182 | intron_variant | TRPM1 |
| rs13380246 | 15:31026364-31026364 | intron_variant | TRPM1 |
| rs10519726 | 15:31029672-31029672 | intron_variant | TRPM1 |
| rs16955797 | 15:31030362-31030362 | intron_variant | TRPM1 |
| rs12904035 | 15:31034586-31034586 | intron_variant | TRPM1 |
| rs12914747 | 15:31036292-31036292 | intron_variant | TRPM1 |
| rs2911853 | 15:31036325-31036325 | intron_variant | TRPM1 |
| rs12911350 | 15:31037741-31037741 | synonymous_variant | TRPM1 |
| rs2288242 | 15:31038077-31038077 | synonymous_variant | TRPM1 |
| rs12913672 | 15:31038110-31038110 | stop_gained | TRPM1 |
| rs17815774 | 15:31042159-31042159 | missense_variant | TRPM1 |
| rs2338834 | 15:31045522-31045522 | intron_variant | TRPM1 |
| rs3743234 | 15:31047470-31047470 | intron_variant | TRPM1 |
| rs3784594 | 15:31049870-31049870 | intron_variant | TRPM1 |
| rs1035705 | 15:31050541-31050541 | synonymous_variant | TRPM1 |
| rs4779809 | 15:31051828-31051828 | intron_variant | TRPM1 |
| rs11070767 | 15:31057918-31057918 | intron_variant | TRPM1 |
| rs12902840 | 15:31060780-31060780 | intron_variant | TRPM1 |
| rs2278133 | 15:31061185-31061185 | intron_variant | TRPM1 |
| rs4779814 | 15:31064222-31064222 | intron_variant | TRPM1 |
| rs919001 | 15:31064935-31064935 | intron_variant | TRPM1 |
| rs2241493 | 15:31070149-31070149 | missense_variant | TRPM1 |
| rs17815804 | 15:31070451-31070451 | intron_variant | TRPM1 |
| rs2241494 | 15:31076401-31076401 | intron_variant | TRPM1 |
| rs2241495 | 15:31076469-31076469 | intron_variant | TRPM1 |
| rs4779816 | 15:31076920-31076920 | missense_variant | TRPM1 |
| rs7180591 | 15:31077295-31077295 | intron_variant | TRPM1 |
| rs4779503 | 15:31080131-31080131 | intron_variant | TRPM1 |
| rs9944230 | 15:31086256-31086256 | intron_variant | TRPM1 |
| rs6493454 | 15:31101742-31101742 | intron_variant | TRPM1 |
| rs3809579 | 15:31102119-31102119 | intron_variant | TRPM1 |
| rs3809578 | 15:31102334-31102334 | intron_variant | TRPM1 |
| rs4779824 | 15:31112091-31112091 | intron_variant | TRPM1 |
| rs6493462 | 15:31112651-31112651 | intron_variant | TRPM1 |
| rs11070816 | 15:31114132-31114132 | intron_variant | TRPM1 |

TABLE 34a-continued

26: SNP variants of TRP channel, ACh receptors or ADR annotated with their consequence.

| SNP | Location | Consequence | Gene |
| --- | --- | --- | --- |
| rs10467996 | 15:31118568-31118568 | intron_variant | TRPM1 |
| rs10467997 | 15:31118640-31118640 | intron_variant | TRPM1 |
| rs4779829 | 15:31126563-31126563 | intron_variant | TRPM1 |
| rs783024 | 15:31128582-31128582 | intron_variant | TRPM1 |
| rs16956564 | 15:31129126-31129126 | intron_variant | TRPM1 |
| rs783026 | 15:31129473-31129473 | intron_variant | TRPM1 |
| rs7178742 | 15:31129667-31129667 | intron_variant | TRPM1 |
| rs2077321 | 15:31131274-31131274 | intron_variant | TRPM1 |
| rs783033 | 15:31132571-31132571 | intron_variant | TRPM1 |
| rs8028220 | 15:31135189-31135189 | intron_variant | TRPM1 |
| rs803534 | 15:31136053-31136053 | intron_variant | TRPM1 |
| rs8033503 | 15:31144120-31144120 | intron_variant | TRPM1 |
| rs12148879 | 15:31145728-31145728 | intron_variant | TRPM1 |
| rs12148567 | 15:31145764-31145764 | intron_variant | TRPM1 |
| rs813299 | 15:31146100-31146100 | intron_variant | TRPM1 |
| rs1672407 | 15:31147601-31147601 | intron_variant | TRPM1 |
| rs1672408 | 15:31148494-31148494 | intron_variant | TRPM1 |
| rs1580141 | 15:31152567-31152567 | intron_variant | TRPM1 |
| rs8035624 | 15:31153995-31153995 | intron_variant | TRPM1 |
| rs8025178 | 15:31157425-31157425 | intron_variant | TRPM1 |
| rs12913209 | 15:31159295-31159295 | intron_variant | TRPM1 |
| rs11635209 | 15:32041794-32041794 | intron_variant | CHRNA7 |
| rs11071503 | 15:32042753-32042753 | intron_variant | CHRNA7 |
| rs11637923 | 15:32058572-32058572 | intron_variant | CHRNA7 |
| rs2175886 | 15:32063744-32063744 | intron_variant | CHRNA7 |
| rs8033518 | 15:32089406-32089406 | intron_variant | CHRNA7 |
| rs6494212 | 15:32092916-32092916 | intron_variant | CHRNA7 |
| rs8036104 | 15:32097159-32097159 | intron_variant | CHRNA7 |
| rs4779565 | 15:32097867-32097867 | intron_variant | CHRNA7 |
| rs8035668 | 15:32099143-32099143 | intron_variant | CHRNA7 |
| rs12440480 | 15:32099188-32099188 | intron_variant | CHRNA7 |
| rs6494223 | 15:32104256-32104256 | intron_variant | CHRNA7 |
| rs8028396 | 15:32104520-32104520 | intron_variant | CHRNA7 |
| rs10438342 | 15:32109845-32109845 | intron_variant | CHRNA7 |
| rs11858834 | 15:32110720-32110720 | intron_variant | CHRNA7 |
| rs13329490 | 15:32116030-32116030 | intron_variant | CHRNA7 |
| rs904951 | 15:32125837-32125837 | intron_variant | CHRNA7 |
| rs1909884 | 15:32147097-32147097 | intron_variant | CHRNA7 |
| rs2611605 | 15:32149432-32149432 | intron_variant | CHRNA7 |
| rs7178176 | 15:32151612-32151612 | intron_variant | CHRNA7 |
| rs480616 | 15:33977774-33977774 | intron_variant | AVEN |
| rs558160 | 15:33979037-33979037 | intron_variant | AVEN |
| rs557225 | 15:33980113-33980113 | intron_variant | AVEN |
| rs527834 | 15:33981076-33981076 | intron_variant | AVEN |
| rs8038713 | 15:33984788-33984788 | intron_variant | AVEN |
| rs8042524 | 15:33989422-33989422 | intron_variant | AVEN |
| rs12050692 | 15:33997997-33997997 | intron_variant | AVEN |
| rs603152 | 15:34002436-34002436 | intron_variant | AVEN |
| rs602302 | 15:34002591-34002591 | intron_variant | AVEN |
| rs6495442 | 15:34004223-34004223 | intron_variant | AVEN |
| rs9806373 | 15:34015756-34015756 | intron_variant | AVEN |
| rs6495459 | 15:34022365-34022365 | intron_variant | AVEN |
| rs12903907 | 15:34029780-34029780 | intron_variant | AVEN |
| rs2339352 | 15:34035620-34035620 | intron_variant | AVEN |
| rs8035849 | 15:34058132-34058132 | intron_variant | CHRM5 |
| rs623941 | 15:34060377-34060377 | intron_variant | CHRM5 |
| rs2630 | 15:50557202-50557202 | 3_prime_UTR_variant | TRPM7 |
| rs11070795 | 15:50561175-50561175 | 3_prime_UTR_variant | TRPM7 |
| rs616256 | 15:50561374-50561374 | 3_prime_UTR_variant | TRPM7 |
| rs3105591 | 15:50576845-50576845 | intron_variant | TRPM7 |
| rs1060599 | 15:50582435-50582435 | intron_variant | TRPM7 |
| rs8042919 | 15:50586433-50586433 | missense_variant | TRPM7 |
| rs543821 | 15:50596371-50596371 | synonymous_variant | TRPM7 |
| rs11634859 | 15:50600748-50600748 | intron_variant | TRPM7 |
| rs615835 | 15:50604141-50604141 | intron_variant | TRPM7 |
| rs4775894 | 15:50611403-50611403 | intron_variant | TRPM7 |
| rs11635045 | 15:50629095-50629095 | intron_variant | TRPM7 |
| rs8023644 | 15:50644926-50644926 | intron_variant | TRPM7 |
| rs9806676 | 15:50652392-50652392 | intron_variant | TRPM7 |
| rs11636576 | 15:50654564-50654564 | intron_variant | TRPM7 |
| rs16963844 | 15:50660713-50660713 | intron_variant | TRPM7 |
| rs667282 | 15:78571130-78571130 | intron_variant | CHRNA5 |
| rs680244 | 15:78578946-78578946 | intron_variant | CHRNA5 |
| rs11637635 | 15:78584808-78584808 | intron_variant | CHRNA5 |
| rs951266 | 15:78586199-78586199 | intron_variant | CHRNA5 |

TABLE 34a-continued

26: SNP variants of TRP channel, ACh receptors or ADR annotated with their consequence.

| SNP | Location | Consequence | Gene |
|---|---|---|---|
| rs16969968 | 15:78590583-78590583 | missense_variant | CHRNA5 |
| rs615470 | 15:78593646-78593646 | 3_prime_UTR_variant | CHRNA5 |
| rs660652 | 15:78595490-78595490 | 3_prime_UTR_variant | CHRNA3 |
| rs578776 | 15:78596058-78596058 | 3_prime_UTR_variant | CHRNA3 |
| rs6495307 | 15:78597979-78597979 | intron_variant | CHRNA3 |
| rs1051730 | 15:78601997-78601997 | synonymous_variant | CHRNA3 |
| rs3743077 | 15:78602554-78602554 | intron_variant | CHRNA3 |
| rs12914385 | 15:78606381-78606381 | intron_variant | CHRNA3 |
| rs6495308 | 15:78615314-78615314 | intron_variant | CHRNA3 |
| rs3743074 | 15:78617138-78617138 | splice_region_variant, intron_variant | CHRNA3 |
| rs8040868 | 15:78618839-78618839 | synonymous_variant | CHRNA3 |
| rs8192475 | 15:78618888-78618888 | missense_variant | CHRNA3 |
| rs1948 | 15:78625057-78625057 | 3_prime_UTR_variant | CHRNB4 |
| rs950776 | 15:78633676-78633676 | intron_variant | CHRNB4 |
| rs1316971 | 15:78638168-78638168 | intron_variant | CHRNB4 |
| rs7208811 | 17:3513261-3513261 | 3_prime_UTR_variant | TRPV3 |
| rs7219780 | 17:3515260-3515260 | intron_variant | TRPV3 |
| rs9909424 | 17:3515304-3515304 | intron_variant | TRPV3 |
| rs8081785 | 17:3516395-3516395 | intron_variant | TRPV3 |
| rs7217270 | 17:3518181-3518181 | intron_variant | TRPV3 |
| rs17763099 | 17:3520145-3520145 | intron_variant | TRPV3 |
| rs7212403 | 17:3526009-3526009 | intron_variant | TRPV3 |
| rs4790145 | 17:3528392-3528392 | intron_variant | TRPV3 |
| rs395357 | 17:3532786-3532786 | synonymous_variant | TRPV3 |
| rs401643 | 17:3536160-3536160 | intron_variant | TRPV3 |
| rs322942 | 17:3540949-3540949 | intron_variant | TRPV3 |
| rs11078458 | 17:3542607-3542607 | synonymous_variant | TRPV3 |
| rs1039519 | 17:3544620-3544620 | synonymous_variant | TRPV3 |
| rs9911213 | 17:3545140-3545140 | intron_variant | TRPV3 |
| rs12453105 | 17:3548453-3548453 | intron_variant | TRPV3 |
| rs1699138 | 17:3549024-3549024 | intron_variant | TRPV3 |
| rs322962 | 17:3555838-3555838 | intron_variant | TRPV3 |
| rs4790522 | 17:3566559-3566559 | 3_prime_UTR_variant | TRPV1 |
| rs16953163 | 17:3567945-3567945 | intron_variant | TRPV1 |
| rs224546 | 17:3569577-3569577 | intron_variant | TRPV1 |
| rs11655540 | 17:3570651-3570651 | intron_variant | TRPV1 |
| rs877610 | 17:3572196-3572196 | synonymous_variant | TRPV1 |
| rs9902581 | 17:3579005-3579005 | intron_variant | TRPV1 |
| rs150908 | 17:3581074-3581074 | intron_variant | TRPV1 |
| rs224534 | 17:3583408-3583408 | missense_variant | TRPV1 |
| rs17706630 | 17:3583848-3583848 | intron_variant | TRPV1 |
| rs222745 | 17:3585577-3585577 | intron_variant | TRPV1 |
| rs150846 | 17:3591574-3591574 | intron_variant | TRPV1 |
| rs222749 | 17:3592080-3592080 | missense_variant | TRPV1 |
| rs7217945 | 17:3594276-3594276 | intron_variant | TRPV1 |
| rs2277675 | 17:3597216-3597216 | intron_variant | TRPV1 |
| rs17707155 | 17:3601939-3601939 | intron_variant | TRPV1 |
| rs161373 | 17:3602749-3602749 | intron_variant | TRPV1 |
| rs222741 | 17:3605586-3605586 | intron_variant | TRPV1 |
| rs460716 | 17:3608514-3608514 | 5_prime_UTR_variant | TRPV1 |
| rs1053754 | 17:4897993-4897993 | 3_prime_UTR_variant | CHRNE |
| rs4790235 | 17:4902757-4902757 | missense_variant | CHRNE |
| rs2302767 | 17:7447225-7447225 | intron_variant | CHRNB1 |
| rs2302765 | 17:7447656-7447656 | splice_region_variant, intron_variant | CHRNB1 |
| rs12452047 | 17:7448517-7448517 | intron_variant | CHRNB1 |
| rs2302761 | 17:7455201-7455201 | intron_variant | CHRNB1 |
| rs2302763 | 17:7455958-7455958 | intron_variant | CHRNB1 |
| rs2302764 | 17:7456791-7456791 | 3_prime_UTR_variant | CHRNB1 |
| rs3855924 | 17:7457004-7457004 | 3_prime_UTR_variant | CHRNB1 |
| rs3813769 | 17:16415618-16415618 | 5_prime_UTR_variant | TRPV2 |
| rs8079271 | 17:16419050-16419050 | intron_variant | TRPV2 |
| rs8121 | 17:16422654-16422654 | synonymous_variant | TRPV2 |
| rs4792742 | 17:16428506-16428506 | intron_variant | TRPV2 |
| rs12602006 | 17:16433974-16433974 | intron_variant | TRPV2 |
| rs12979689 | 19:49160532-49160532 | intron_variant | TRPM4 |
| rs3760666 | 19:49164094-49164094 | intron_variant | TRPM4 |
| rs1477363 | 19:49171238-49171238 | intron_variant | TRPM4 |
| rs2287923 | 19:49171976-49171976 | intron_variant | TRPM4 |
| rs909010 | 19:49188565-49188565 | intron_variant | TRPM4 |
| rs1175803 | 19:49193800-49193800 | intron_variant | TRPM4 |
| rs1716274 | 19:49203479-49203479 | intron_variant | TRPM4 |
| rs2229169 | 2:96114968-96114968 | synonymous_variant | ADRA2B |
| rs2646165 | 2:174756754-174756754 | intron_variant, non_coding_transcript_variant | AC018890.6 |
| rs1376865 | 2:174759869-174759869 | intron_variant, non_coding_transcript_variant | AC018890.6 |
| rs2245601 | 2:232526227-232526227 | synonymous_variant | CHRND |

TABLE 34a-continued

26: SNP variants of TRP channel, ACh receptors or ADR annotated with their consequence.

| SNP | Location | Consequence | Gene |
| --- | --- | --- | --- |
| rs2767 | 2:232535364-232535364 | 3_prime_UTR_variant | CHRND |
| rs2289080 | 2:232541468-232541468 | missense_variant | CHRNG |
| rs1881492 | 2:232542288-232542288 | intron_variant | CHRNG |
| rs2853462 | 2:232542410-232542410 | intron_variant | CHRNG |
| rs2099489 | 2:232545584-232545584 | upstream_gene_variant | EIF4E2 |
| rs17862921 | 2:233920475-233920475 | intron_variant | TRPM8 |
| rs1003757 | 2:233921224-233921224 | intron_variant | TRPM8 |
| rs1003756 | 2:233921255-233921255 | intron_variant | TRPM8 |
| rs6431648 | 2:233924812-233924812 | intron_variant | TRPM8 |
| rs10803665 | 2:233925989-233925989 | intron_variant | TRPM8 |
| rs11563220 | 2:233926525-233926525 | splice_region_variant, intron_variant | TRPM8 |
| rs11563219 | 2:233926795-233926795 | intron_variant | TRPM8 |
| rs735552 | 2:233928621-233928621 | intron_variant | TRPM8 |
| rs758277 | 2:233929092-233929092 | intron_variant | TRPM8 |
| rs12473889 | 2:233936301-233936301 | intron_variant | TRPM8 |
| rs7577157 | 2:233940259-233940259 | intron_variant | TRPM8 |
| rs17868387 | 2:233945908-233945908 | missense_variant | TRPM8 |
| rs12466401 | 2:233948374-233948374 | intron_variant | TRPM8 |
| rs10169266 | 2:233952992-233952992 | intron_variant | TRPM8 |
| rs4663990 | 2:233953396-233953396 | intron_variant | TRPM8 |
| rs10490013 | 2:233954593-233954593 | intron_variant | TRPM8 |
| rs7593557 | 2:233955144-233955144 | missense_variant | TRPM8 |
| rs917435 | 2:233958869-233958869 | intron_variant | TRPM8 |
| rs10929320 | 2:233959741-233959741 | intron_variant | TRPM8 |
| rs11563212 | 2:233960714-233960714 | intron_variant | TRPM8 |
| rs28948671 | 2:233963105-233963105 | intron_variant | TRPM8 |
| rs12185625 | 2:233966789-233966789 | intron_variant | TRPM8 |
| rs13401339 | 2:233967393-233967393 | intron_variant | TRPM8 |
| rs28902187 | 2:233970784-233970784 | intron_variant | TRPM8 |
| rs6719311 | 2:233974736-233974736 | intron_variant | TRPM8 |
| rs13414162 | 2:233975300-233975300 | intron_variant | TRPM8 |
| rs11685673 | 2:233976386-233976386 | intron_variant | TRPM8 |
| rs10803667 | 2:233977209-233977209 | intron_variant | TRPM8 |
| rs17864755 | 2:233977719-233977719 | intron_variant | TRPM8 |
| rs10207672 | 2:233979517-233979517 | intron_variant | TRPM8 |
| rs4663992 | 2:233980533-233980533 | intron_variant | TRPM8 |
| rs6708995 | 2:233981747-233981747 | intron_variant | TRPM8 |
| rs4663995 | 2:233983483-233983483 | intron_variant | TRPM8 |
| rs1016062 | 2:233986249-233986249 | intron_variant | TRPM8 |
| rs12692252 | 2:233988700-233988700 | intron_variant | TRPM8 |
| rs17864768 | 2:233989074-233989074 | intron_variant | TRPM8 |
| rs11563057 | 2:233989825-233989825 | intron_variant | TRPM8 |
| rs28901881 | 2:233990523-233990523 | intron_variant | TRPM8 |
| rs11695247 | 2:233990629-233990629 | intron_variant | TRPM8 |
| rs2362294 | 2:233991869-233991869 | intron_variant | TRPM8 |
| rs11563056 | 2:233992526-233992526 | intron_variant | TRPM8 |
| rs28948673 | 2:233992780-233992780 | intron_variant | TRPM8 |
| rs11563208 | 2:233996434-233996434 | synonymous_variant | TRPM8 |
| rs2362295 | 2:233997882-233997882 | intron_variant | TRPM8 |
| rs6723922 | 2:233999852-233999852 | intron_variant | TRPM8 |
| rs6746331 | 2:234001155-234001155 | intron_variant | TRPM8 |
| rs11682848 | 2:234002284-234002284 | intron_variant | TRPM8 |
| rs7560562 | 2:234003571-234003571 | intron_variant | TRPM8 |
| rs6721761 | 2:234004017-234004017 | intron_variant | TRPM8 |
| rs6712962 | 2:234004389-234004389 | intron_variant | TRPM8 |
| rs11563204 | 2:234008733-234008733 | intron_variant | TRPM8 |
| rs10490018 | 2:234009088-234009088 | intron_variant | TRPM8 |
| rs17864777 | 2:234010474-234010474 | intron_variant | TRPM8 |
| rs17865678 | 2:234010670-234010670 | intron_variant | TRPM8 |
| rs17865679 | 2:234010944-234010944 | intron_variant | TRPM8 |
| rs3732214 | 2:234014480-234014480 | intron_variant | TRPM8 |
| rs11562973 | 2:234015590-234015590 | intron_variant | TRPM8 |
| rs17865681 | 2:234018106-234018106 | 3_prime_UTR_variant | TRPM8 |
| rs709024 | 20:4221337-4221337 | 3_prime_UTR_variant | ADRA1D |
| rs3787441 | 20:4224413-4224413 | intron_variant | ADRA1D |
| rs6084664 | 20:4227283-4227283 | intron_variant | ADRA1D |
| rs8183794 | 20:4229801-4229801 | intron_variant | ADRA1D |
| rs6116268 | 20:4230793-4230793 | intron_variant | ADRA1D |
| rs946188 | 20:4234669-4234669 | intron_variant | ADRA1D |
| rs4815670 | 20:4236217-4236217 | intron_variant | ADRA1D |
| rs4815675 | 20:4242807-4242807 | intron_variant | ADRA1D |
| rs6052456 | 20:4244926-4244926 | intron_variant | ADRA1D |
| rs946189 | 20:4246877-4246877 | intron_variant | ADRA1D |
| rs1058003 | 20:35002614-35002614 | downstream_gene_variant | MYH7B |
| rs6060151 | 20:35006423-35006423 | downstream_gene_variant | MYH7B |

TABLE 34a-continued

26: SNP variants of TRP channel, ACh receptors or ADR annotated with their consequence.

| SNP | Location | Consequence | Gene |
|---|---|---|---|
| rs3736802 | 20:35016239-35016239 | intron_variant | TRPC4AP |
| rs6579211 | 20:35018054-35018054 | intron_variant | TRPC4AP |
| rs6088678 | 20:35019748-35019748 | intron_variant | TRPC4AP |
| rs6142280 | 20:35034439-35034439 | intron_variant | TRPC4AP |
| rs13042358 | 20:35046676-35046676 | intron_variant | TRPC4AP |
| rs8117847 | 20:35054677-35054677 | intron_variant | TRPC4AP |
| rs1998233 | 20:35069323-35069323 | synonymous_variant | TRPC4AP |
| rs6090378 | 20:63344026-63344026 | 3_prime_UTR_variant | CHRNA4 |
| rs1044394 | 20:63350733-63350733 | synonymous_variant | CHRNA4 |
| rs762426 | 21:44367367-44367367 | intron_variant | TRPM2 |
| rs1556314 | 21:44391460-44391460 | missense_variant | TRPM2 |
| rs1785469 | 21:44398726-44398726 | intron_variant | TRPM2 |
| rs9974831 | 21:44401646-44401646 | intron_variant | TRPM2 |
| rs2238722 | 21:44420722-44420722 | intron_variant | TRPM2 |
| rs2003775 | 21:44434503-44434503 | intron_variant | TRPM2 |
| rs1403725 | 3:142725291-142725291 | intron_variant | TRPC1 |
| rs13094259 | 3:142725783-142725783 | intron_variant | TRPC1 |
| rs953239 | 3:142727363-142727363 | intron_variant | TRPC1 |
| rs2177398 | 3:142768058-142768058 | intron_variant | TRPC1 |
| rs9836269 | 3:142772883-142772883 | intron_variant | TRPC1 |
| rs13086677 | 3:142784353-142784353 | intron_variant | TRPC1 |
| rs7621642 | 3:142784763-142784763 | synonymous_variant | TRPC1 |
| rs16852615 | 3:142797984-142797984 | intron_variant | TRPC1 |
| rs3821647 | 3:142804507-142804507 | synonymous_variant | TRPC1 |
| rs4627 | 3:142807752-142807752 | downstream_gene_variant | TRPC1 |
| rs10022491 | 4:40335891-40335891 | synonymous_variant | CHRNA9 |
| rs10021263 | 4:40340601-40340601 | intron_variant | CHRNA9 |
| rs4861065 | 4:40342378-40342378 | intron_variant | CHRNA9 |
| rs4861307 | 4:40343222-40343222 | intron_variant | CHRNA9 |
| rs10029313 | 4:40348130-40348130 | intron_variant | CHRNA9 |
| rs7669882 | 4:40348634-40348634 | intron_variant | CHRNA9 |
| rs10029872 | 4:40348746-40348746 | intron_variant | CHRNA9 |
| rs10009228 | 4:40354405-40354405 | missense_variant | CHRNA9 |
| rs10518290 | 4:121884717-121884717 | intron_variant | TRPC3 |
| rs11726196 | 4:121885073-121885073 | intron_variant | TRPC3 |
| rs12502635 | 4:121892304-121892304 | intron_variant | TRPC3 |
| rs2135976 | 4:121895026-121895026 | intron_variant | TRPC3 |
| rs11732666 | 4:121902897-121902897 | synonymous_variant | TRPC3 |
| rs17517624 | 4:121903436-121903436 | intron_variant | TRPC3 |
| rs3762839 | 4:121904209-121904209 | intron_variant | TRPC3 |
| rs884701 | 4:121909251-121909251 | intron_variant | TRPC3 |
| rs13127488 | 4:121909645-121909645 | intron_variant | TRPC3 |
| rs906496 | 4:121912159-121912159 | intron_variant | TRPC3 |
| rs4292355 | 4:121921112-121921112 | intron_variant | TRPC3 |
| rs6841843 | 4:121936413-121936413 | intron_variant | TRPC3 |
| rs950574 | 4:121943086-121943086 | intron_variant | TRPC3 |
| rs970349 | 4:121950477-121950477 | intron_variant | TRPC3 |
| rs6596299 | 5:136234879-136234879 | intron_variant | TRPC7 |
| rs10463951 | 5:136238423-136238423 | intron_variant | TRPC7 |
| rs13157486 | 5:136243734-136243734 | intron_variant | TRPC7 |
| rs11740657 | 5:136245971-136245971 | intron_variant | TRPC7 |
| rs2042243 | 5:136248224-136248224 | intron_variant | TRPC7 |
| rs7724982 | 5:136254004-136254004 | intron_variant | TRPC7 |
| rs2546651 | 5:136269662-136269662 | intron_variant | TRPC7 |
| rs6868895 | 5:136275754-136275754 | intron_variant | TRPC7 |
| rs17762209 | 5:136278044-136278044 | intron_variant | TRPC7 |
| rs1909544 | 5:136287330-136287330 | intron_variant | TRPC7 |
| rs1392171 | 5:136295761-136295761 | intron_variant | TRPC7 |
| rs1392172 | 5:136295900-136295900 | intron_variant | TRPC7 |
| rs6894680 | 5:136298053-136298053 | intron_variant | TRPC7 |
| rs4976485 | 5:136314610-136314610 | intron_variant | TRPC7 |
| rs2277052 | 5:136315555-136315555 | intron_variant | TRPC7 |
| rs2881486 | 5:136327904-136327904 | intron_variant | TRPC7 |
| rs10053931 | 5:136332836-136332836 | intron_variant | TRPC7 |
| rs4976489 | 5:136343269-136343269 | intron_variant | TRPC7 |
| rs950715 | 5:136344551-136344551 | intron_variant | TRPC7 |
| rs2673930 | 5:136355990-136355990 | intron_variant | TRPC7 |
| rs2546661 | 5:136356887-136356887 | synonymous_variant | TRPC7 |
| rs2649693 | 5:136364165-136364165 | intron_variant | TRPC7 |
| rs1042713 | 5:148826877-148826877 | missense_variant | ADRB2 |
| rs1042718 | 5:148827354-148827354 | synonymous_variant | ADRB2 |
| rs3729604 | 5:159917454-159917454 | synonymous_variant | ADRA1B |
| rs2030373 | 5:159920474-159920474 | intron_variant | ADRA1B |
| rs6884105 | 5:159921436-159921436 | intron_variant | ADRA1B |
| rs17455628 | 5:159921891-159921891 | intron_variant | ADRA1B |

TABLE 34a-continued

26: SNP variants of TRP channel, ACh receptors or ADR annotated with their consequence.

| SNP | Location | Consequence | Gene |
|---|---|---|---|
| rs756275 | 5:159924453-159924453 | intron_variant | ADRA1B |
| rs11952941 | 5:159927768-159927768 | intron_variant | ADRA1B |
| rs6892282 | 5:159933478-159933478 | intron_variant | ADRA1B |
| rs10515805 | 5:159938560-159938560 | intron_variant | ADRA1B |
| rs4921242 | 5:159939691-159939691 | intron_variant | ADRA1B |
| rs6888306 | 5:159940107-159940107 | intron_variant | ADRA1B |
| rs7718362 | 5:159940858-159940858 | intron_variant | ADRA1B |
| rs11743425 | 5:159941279-159941279 | intron_variant | ADRA1B |
| rs7737796 | 5:159942422-159942422 | intron_variant | ADRA1B |
| rs34467921 | 5:159950714-159950714 | intron_variant | ADRA1B |
| rs13171967 | 5:159951152-159951152 | intron_variant | ADRA1B |
| rs3896275 | 5:159954519-159954519 | intron_variant | ADRA1B |
| rs12653825 | 5:159956264-159956264 | intron_variant | ADRA1B |
| rs952037 | 5:159963870-159963870 | intron_variant | ADRA1B |
| rs7636 | 7:100892456-100892456 | upstream_gene_variant | UFSP1 |
| rs1799805 | 7:100893176-100893176 | upstream_gene_variant | UFSP1 |
| rs3735028 | 7:136873411-136873411 | intron_variant | CHRM2 |
| rs10954565 | 7:136875501-136875501 | intron_variant | CHRM2 |
| rs11771119 | 7:136879066-136879066 | intron_variant | CHRM2 |
| rs2113550 | 7:136881786-136881786 | intron_variant | CHRM2 |
| rs1424569 | 7:136884669-136884669 | intron_variant | CHRM2 |
| rs17494846 | 7:136885565-136885565 | intron_variant | CHRM2 |
| rs10242108 | 7:136886960-136886960 | intron_variant | CHRM2 |
| rs4475425 | 7:136890452-136890452 | intron_variant | CHRM2 |
| rs889934 | 7:136892602-136892602 | intron_variant | CHRM2 |
| rs12537962 | 7:136894261-136894261 | intron_variant | CHRM2 |
| rs1424386 | 7:136895738-136895738 | intron_variant | CHRM2 |
| rs10228048 | 7:136897646-136897646 | intron_variant | CHRM2 |
| rs12535371 | 7:136899328-136899328 | intron_variant | CHRM2 |
| rs6963819 | 7:136903362-136903362 | intron_variant | CHRM2 |
| rs1364403 | 7:136904080-136904080 | intron_variant | CHRM2 |
| rs7810473 | 7:136911710-136911710 | intron_variant | CHRM2 |
| rs10267949 | 7:136912518-136912518 | intron_variant | CHRM2 |
| rs10488600 | 7:136920711-136920711 | intron_variant | CHRM2 |
| rs1364405 | 7:136923412-136923412 | intron_variant | CHRM2 |
| rs1364407 | 7:136925178-136925178 | intron_variant | CHRM2 |
| rs10256854 | 7:136927567-136927567 | intron_variant | CHRM2 |
| rs7806357 | 7:136935405-136935405 | intron_variant | CHRM2 |
| rs7800170 | 7:136939573-136939573 | intron_variant | CHRM2 |
| rs10271552 | 7:136939912-136939912 | intron_variant | CHRM2 |
| rs10225215 | 7:136946065-136946065 | intron_variant | CHRM2 |
| rs1455858 | 7:136946956-136946956 | intron_variant | CHRM2 |
| rs1378646 | 7:136950254-136950254 | intron_variant | CHRM2 |
| rs1455857 | 7:136955194-136955194 | intron_variant | CHRM2 |
| rs1824024 | 7:136958947-136958947 | intron_variant | CHRM2 |
| rs324576 | 7:136963375-136963375 | intron_variant | CHRM2 |
| rs324588 | 7:136967391-136967391 | intron_variant | CHRM2 |
| rs324594 | 7:136970576-136970576 | intron_variant | CHRM2 |
| rs2113545 | 7:136977994-136977994 | intron_variant | CHRM2 |
| rs12707339 | 7:136986594-136986594 | intron_variant | CHRM2 |
| rs2350786 | 7:136991823-136991823 | intron_variant | CHRM2 |
| rs17414604 | 7:136997441-136997441 | intron_variant | CHRM2 |
| rs10242859 | 7:137001224-137001224 | intron_variant | CHRM2 |
| rs420817 | 7:137002656-137002656 | intron_variant | CHRM2 |
| rs324640 | 7:137004249-137004249 | intron_variant | CHRM2 |
| rs10488602 | 7:137005756-137005756 | intron_variant | CHRM2 |
| rs4987682 | 7:142871843-142871843 | downstream_gene_variant | EPHB6 |
| rs4987668 | 7:142874896-142874896 | downstream_gene_variant | EPHB6 |
| rs4987667 | 7:142875155-142875155 | downstream_gene_variant | EPHB6 |
| rs4987665 | 7:142875510-142875510 | downstream_gene_variant | EPHB6 |
| rs4252499 | 7:142912583-142912583 | missense_variant | TRPV5 |
| rs4252460 | 7:142920130-142920130 | intron_variant | TRPV5 |
| rs4252448 | 7:142922613-142922613 | intron_variant | TRPV5 |
| rs4252435 | 7:142925619-142925619 | synonymous_variant | TRPV5 |
| rs4252424 | 7:142927238-142927238 | intron_variant | TRPV5 |
| rs4252417 | 7:142928163-142928163 | synonymous_variant | TRPV5 |
| rs4252416 | 7:142928322-142928322 | intron_variant | TRPV5 |
| rs4252407 | 7:142929561-142929561 | synonymous_variant | TRPV5 |
| rs4252402 | 7:142930043-142930043 | intron_variant | TRPV5 |
| rs4252381 | 7:142932278-142932278 | intron_variant | TRPV5 |
| rs1442341 | 8:26752910-26752910 | intron_variant | ADRA1A |
| rs4732853 | 8:26753134-26753134 | intron_variant | ADRA1A |
| rs17055923 | 8:26754329-26754329 | intron_variant | ADRA1A |
| rs2036109 | 8:26759267-26759267 | intron_variant | ADRA1A |
| rs12674917 | 8:26759612-26759612 | intron_variant | ADRA1A |

TABLE 34a-continued

26: SNP variants of TRP channel, ACh receptors or ADR annotated with their consequence.

| SNP | Location | Consequence | Gene |
|---|---|---|---|
| rs4236678 | 8:26760849-26760849 | intron_variant | ADRA1A |
| rs10110905 | 8:26761908-26761908 | intron_variant | ADRA1A |
| rs3802241 | 8:26765867-26765867 | intron_variant | ADRA1A |
| rs17333700 | 8:26765884-26765884 | intron_variant | ADRA1A |
| rs17055954 | 8:26766351-26766351 | intron_variant | ADRA1A |
| rs4236679 | 8:26769040-26769040 | intron_variant | ADRA1A |
| rs3739216 | 8:26769732-26769732 | intron_variant | ADRA1A |
| rs1048101 | 8:26770511-26770511 | missense_variant | ADRA1A |
| rs13261597 | 8:26770801-26770801 | intron_variant | ADRA1A |
| rs13277287 | 8:26771248-26771248 | intron_variant | ADRA1A |
| rs7842829 | 8:26771819-26771819 | intron_variant | ADRA1A |
| rs12543356 | 8:26776280-26776280 | intron_variant | ADRA1A |
| rs6557946 | 8:26777072-26777072 | intron_variant | ADRA1A |
| rs10086077 | 8:26778227-26778227 | intron_variant | ADRA1A |
| rs11135955 | 8:26781393-26781393 | intron_variant | ADRA1A |
| rs2055195 | 8:26783508-26783508 | intron_variant | ADRA1A |
| rs13248896 | 8:26785674-26785674 | intron_variant | ADRA1A |
| rs4732874 | 8:26788095-26788095 | intron_variant | ADRA1A |
| rs11135957 | 8:26794493-26794493 | intron_variant | ADRA1A |
| rs7835853 | 8:26804729-26804729 | intron_variant | ADRA1A |
| rs12547707 | 8:26805409-26805409 | intron_variant | ADRA1A |
| rs2036108 | 8:26805583-26805583 | intron_variant | ADRA1A |
| rs7816340 | 8:26808070-26808070 | intron_variant | ADRA1A |
| rs13261054 | 8:26809528-26809528 | intron_variant | ADRA1A |
| rs7817265 | 8:26809549-26809549 | intron_variant | ADRA1A |
| rs4732897 | 8:26813278-26813278 | intron_variant | ADRA1A |
| rs12681695 | 8:26813612-26813612 | intron_variant | ADRA1A |
| rs7017961 | 8:26815412-26815412 | intron_variant | ADRA1A |
| rs13257637 | 8:26816385-26816385 | intron_variant | ADRA1A |
| rs11779546 | 8:26817419-26817419 | intron_variant | ADRA1A |
| rs13282836 | 8:26820689-26820689 | intron_variant | ADRA1A |
| rs4732902 | 8:26822061-26822061 | intron_variant | ADRA1A |
| rs11781115 | 8:26823933-26823933 | intron_variant | ADRA1A |
| rs7820633 | 8:26826275-26826275 | intron_variant | ADRA1A |
| rs17334323 | 8:26831309-26831309 | intron_variant | ADRA1A |
| rs526302 | 8:26833178-26833178 | intron_variant | ADRA1A |
| rs2322333 | 8:26837738-26837738 | intron_variant | ADRA1A |
| rs10503800 | 8:26838100-26838100 | intron_variant | ADRA1A |
| rs574647 | 8:26839540-26839540 | intron_variant | ADRA1A |
| rs577366 | 8:26839848-26839848 | intron_variant | ADRA1A |
| rs1079078 | 8:26840530-26840530 | intron_variant | ADRA1A |
| rs556793 | 8:26841550-26841550 | intron_variant | ADRA1A |
| rs3102087 | 8:26842420-26842420 | intron_variant | ADRA1A |
| rs2036107 | 8:26843927-26843927 | intron_variant | ADRA1A |
| rs13274679 | 8:26844301-26844301 | intron_variant | ADRA1A |
| rs498194 | 8:26845704-26845704 | intron_variant | ADRA1A |
| rs10093667 | 8:26847358-26847358 | intron_variant | ADRA1A |
| rs558455 | 8:26848064-26848064 | intron_variant | ADRA1A |
| rs12541572 | 8:26851469-26851469 | intron_variant | ADRA1A |
| rs2046186 | 8:26853697-26853697 | intron_variant | ADRA1A |
| rs544104 | 8:26854473-26854473 | intron_variant | ADRA1A |
| rs544215 | 8:26854511-26854511 | intron_variant | ADRA1A |
| rs11782159 | 8:26855464-26855464 | intron_variant | ADRA1A |
| rs13278849 | 8:26857357-26857357 | intron_variant | ADRA1A |
| rs489790 | 8:26859105-26859105 | intron_variant | ADRA1A |
| rs17426222 | 8:26860300-26860300 | intron_variant | ADRA1A |
| rs10503801 | 8:26862932-26862932 | intron_variant | ADRA1A |
| rs580644 | 8:26862973-26862973 | intron_variant | ADRA1A |
| rs17056112 | 8:26862998-26862998 | intron_variant | ADRA1A |
| rs573514 | 8:26863764-26863764 | intron_variant | ADRA1A |
| rs2280375 | 8:27459820-27459820 | downstream_gene_variant | PTK2B |
| rs2292974 | 8:27460874-27460874 | downstream_gene_variant | PTK2B |
| rs735421 | 8:27461775-27461775 | downstream_gene_variant | PTK2B |
| rs9314347 | 8:27462288-27462288 | downstream_gene_variant | PTK2B |
| rs11778371 | 8:27462388-27462388 | downstream_gene_variant | PTK2B |
| rs2163177 | 8:27466343-27466343 | intron_variant | CHRNA2 |
| rs891398 | 8:27467305-27467305 | missense_variant | CHRNA2 |
| rs747111 | 8:27467956-27467956 | intron_variant | CHRNA2 |
| rs2741343 | 8:27468610-27468610 | intron_variant | CHRNA2 |
| rs2565065 | 8:27470504-27470504 | intron_variant | CHRNA2 |
| rs2472553 | 8:27470994-27470994 | missense_variant | CHRNA2 |
| rs2741342 | 8:27472579-27472579 | intron_variant | CHRNA2 |
| rs7819756 | 8:27473420-27473420 | intron_variant | CHRNA2 |
| rs2565067 | 8:27473602-27473602 | intron_variant | CHRNA2 |
| rs2741339 | 8:27477452-27477452 | intron_variant | CHRNA2 |

TABLE 34a-continued

26: SNP variants of TRP channel, ACh receptors or ADR annotated with their consequence.

| SNP | Location | Consequence | Gene |
|---|---|---|---|
| rs4998 | 8:37963968-37963968 | 3_prime_UTR_variant | ADRB3 |
| rs4994 | 8:37966280-37966280 | missense_variant | ADRB3 |
| rs4950 | 8:42697490-42697490 | 5_prime_UTR_variant | CHRNB3 |
| rs1530848 | 8:42697765-42697765 | intron_variant | CHRNB3 |
| rs7815274 | 8:42727440-42727440 | intron_variant | CHRNB3 |
| rs4952 | 8:42731922-42731922 | synonymous_variant | CHRNB3 |
| rs2196128 | 8:42763143-42763143 | intron_variant | CHRNA6 |
| rs10109429 | 8:42763247-42763247 | intron_variant | CHRNA6 |
| rs16891604 | 8:42763570-42763570 | intron_variant | CHRNA6 |
| rs6996413 | 8:72021286-72021286 | 3_prime_UTR_variant | TRPA1 |
| rs6996723 | 8:72021397-72021397 | 3_prime_UTR_variant | TRPA1 |
| rs7827617 | 8:72021797-72021797 | 3_prime_UTR_variant | TRPA1 |
| rs959974 | 8:72023604-72023604 | intron_variant | TRPA1 |
| rs959976 | 8:72023910-72023910 | missense_variant, splice_region_variant | TRPA1 |
| rs4738202 | 8:72028626-72028626 | intron_variant | TRPA1 |
| rs10100108 | 8:72031276-72031276 | intron_variant | TRPA1 |
| rs13259803 | 8:72032802-72032802 | intron_variant | TRPA1 |
| rs12545839 | 8:72035077-72035077 | intron_variant | TRPA1 |
| rs13280644 | 8:72036353-72036353 | synonymous_variant | TRPA1 |
| rs1025926 | 8:72040923-72040923 | intron_variant | TRPA1 |
| rs6982184 | 8:72046917-72046917 | intron_variant | TRPA1 |
| rs2383844 | 8:72049017-72049017 | intron_variant | TRPA1 |
| rs1025927 | 8:72050900-72050900 | intron_variant | TRPA1 |
| rs1025928 | 8:72051023-72051023 | intron_variant | TRPA1 |
| rs1025929 | 8:72051061-72051061 | intron_variant | TRPA1 |
| rs3735942 | 8:72053738-72053738 | intron_variant | TRPA1 |
| rs3735943 | 8:72053767-72053767 | synonymous_variant | TRPA1 |
| rs7825042 | 8:72057642-72057642 | intron_variant | TRPA1 |
| rs10101155 | 8:72059782-72059782 | intron_variant | TRPA1 |
| rs10109581 | 8:72062094-72062094 | intron_variant | TRPA1 |
| rs16937961 | 8:72064762-72064762 | intron_variant | TRPA1 |
| rs920829 | 8:72065468-72065468 | missense_variant | TRPA1 |
| rs10091093 | 8:72069264-72069264 | intron_variant | TRPA1 |
| rs13268757 | 8:72075403-72075403 | missense_variant | TRPA1 |
| rs17535963 | 9:70535957-70535957 | missense_variant | TRPM3 |
| rs7033976 | 9:70536799-70536799 | synonymous_variant | TRPM3 |
| rs3739776 | 9:70537054-70537054 | synonymous_variant | TRPM3 |
| rs12338410 | 9:70546638-70546638 | intron_variant | TRPM3 |
| rs1414850 | 9:70547320-70547320 | intron_variant | TRPM3 |
| rs1889915 | 9:70549796-70549796 | intron_variant | TRPM3 |
| rs10780947 | 9:70550162-70550162 | intron_variant | TRPM3 |
| rs6560143 | 9:70553764-70553764 | intron_variant | TRPM3 |
| rs10511984 | 9:70555379-70555379 | intron_variant | TRPM3 |
| rs10746847 | 9:70555466-70555466 | intron_variant | TRPM3 |
| rs4352910 | 9:70557885-70557885 | intron_variant | TRPM3 |
| rs10746850 | 9:70568365-70568365 | intron_variant | TRPM3 |
| rs13290576 | 9:70576813-70576813 | intron_variant | TRPM3 |
| rs10868854 | 9:70578455-70578455 | intron_variant | TRPM3 |
| rs10780950 | 9:70578512-70578512 | intron_variant | TRPM3 |
| rs1317103 | 9:70580787-70580787 | intron_variant | TRPM3 |
| rs17458750 | 9:70581750-70581750 | intron_variant | TRPM3 |
| rs4744604 | 9:70584567-70584567 | intron_variant | TRPM3 |
| rs11790957 | 9:70585991-70585991 | intron_variant | TRPM3 |
| rs10735599 | 9:70588696-70588696 | intron_variant | TRPM3 |
| rs7865858 | 9:70589515-70589515 | intron_variant | TRPM3 |
| rs11142498 | 9:70595386-70595386 | intron_variant | TRPM3 |
| rs4744607 | 9:70598819-70598819 | intron_variant | TRPM3 |
| rs4615645 | 9:70603740-70603740 | intron_variant | TRPM3 |
| rs10114679 | 9:70609644-70609644 | intron_variant | TRPM3 |
| rs3763619 | 9:70610886-70610886 | intron_variant | TRPM3 |
| rs11142508 | 9:70616746-70616746 | intron_variant | TRPM3 |
| rs11142515 | 9:70624146-70624146 | intron_variant | TRPM3 |
| rs10868861 | 9:70624689-70624689 | intron_variant | TRPM3 |
| rs11142518 | 9:70630284-70630284 | intron_variant | TRPM3 |
| rs11142521 | 9:70633607-70633607 | intron_variant | TRPM3 |
| rs4322073 | 9:70635121-70635121 | intron_variant | TRPM3 |
| rs7849603 | 9:70646944-70646944 | intron_variant | TRPM3 |
| rs7027906 | 9:70666442-70666442 | intron_variant | TRPM3 |
| rs7854748 | 9:70669274-70669274 | intron_variant | TRPM3 |
| rs4465028 | 9:70672160-70672160 | intron_variant | TRPM3 |
| rs1011308 | 9:70673340-70673340 | intron_variant | TRPM3 |
| rs1934474 | 9:70678583-70678583 | intron_variant | TRPM3 |
| rs12345213 | 9:70679994-70679994 | intron_variant | TRPM3 |
| rs4617221 | 9:70690807-70690807 | intron_variant | TRPM3 |
| rs10780959 | 9:70692574-70692574 | intron_variant | TRPM3 |

TABLE 34a-continued

26: SNP variants of TRP channel, ACh receptors or ADR annotated with their consequence.

| SNP | Location | Consequence | Gene |
|---|---|---|---|
| rs7023662 | 9:70694951-70694951 | intron_variant | TRPM3 |
| rs7860377 | 9:70697213-70697213 | intron_variant | TRPM3 |
| rs11142556 | 9:70700856-70700856 | intron_variant | TRPM3 |
| rs11142561 | 9:70742751-70742751 | intron_variant | TRPM3 |
| rs12335434 | 9:70754585-70754585 | intron_variant | TRPM3 |
| rs7849151 | 9:70754771-70754771 | intron_variant | TRPM3 |
| rs4745035 | 9:70760089-70760089 | intron_variant | TRPM3 |
| rs10868882 | 9:70763974-70763974 | intron_variant | TRPM3 |
| rs12003443 | 9:70774003-70774003 | intron_variant | TRPM3 |
| rs879857 | 9:70775018-70775018 | intron_variant | TRPM3 |
| rs10868885 | 9:70776168-70776168 | intron_variant | TRPM3 |
| rs1328148 | 9:70778067-70778067 | intron_variant | TRPM3 |
| rs10435960 | 9:70783532-70783532 | intron_variant | TRPM3 |
| rs1831143 | 9:70784834-70784834 | intron_variant | TRPM3 |
| rs7040905 | 9:70787285-70787285 | intron_variant | TRPM3 |
| rs11142594 | 9:70790328-70790328 | intron_variant | TRPM3 |
| rs10118380 | 9:70790948-70790948 | intron_variant | TRPM3 |
| rs1028879 | 9:70791635-70791635 | intron_variant | TRPM3 |
| rs10868890 | 9:70793602-70793602 | intron_variant | TRPM3 |
| rs11142598 | 9:70793734-70793734 | intron_variant | TRPM3 |
| rs7048454 | 9:70794420-70794420 | intron_variant | TRPM3 |
| rs17055833 | 9:70797246-70797246 | intron_variant | TRPM3 |
| rs1328153 | 9:70801146-70801146 | intron_variant | TRPM3 |
| rs17055851 | 9:70801357-70801357 | intron_variant | TRPM3 |
| rs1410373 | 9:70801881-70801881 | intron_variant | TRPM3 |
| rs13285335 | 9:70802759-70802759 | intron_variant | TRPM3 |
| rs7863403 | 9:70806255-70806255 | intron_variant | TRPM3 |
| rs995903 | 9:70808009-70808009 | intron_variant | TRPM3 |
| rs10868894 | 9:70812317-70812317 | intron_variant | TRPM3 |
| rs17554439 | 9:70813150-70813150 | intron_variant | TRPM3 |
| rs7022747 | 9:70820112-70820112 | intron_variant | TRPM3 |
| rs4526420 | 9:70822055-70822055 | intron_variant | TRPM3 |
| rs7038646 | 9:70822908-70822908 | intron_variant | TRPM3 |
| rs7863095 | 9:70825789-70825789 | intron_variant | TRPM3 |
| rs7862322 | 9:70825897-70825897 | intron_variant | TRPM3 |
| rs10117842 | 9:70826521-70826521 | intron_variant | TRPM3 |
| rs1034538 | 9:70827808-70827808 | intron_variant | TRPM3 |
| rs17470402 | 9:70830004-70830004 | intron_variant | TRPM3 |
| rs10081686 | 9:70831457-70831457 | intron_variant | TRPM3 |
| rs1890017 | 9:70838129-70838129 | intron_variant | TRPM3 |
| rs7022926 | 9:70847868-70847868 | intron_variant | TRPM3 |
| rs11142623 | 9:70855695-70855695 | intron_variant | TRPM3 |
| rs1337026 | 9:70855840-70855840 | intron_variant | TRPM3 |
| rs10868916 | 9:70857444-70857444 | intron_variant | TRPM3 |
| rs1415225 | 9:70857902-70857902 | intron_variant | TRPM3 |
| rs17555916 | 9:70858680-70858680 | intron_variant | TRPM3 |
| rs11142627 | 9:70859717-70859717 | intron_variant | TRPM3 |
| rs10511988 | 9:70861581-70861581 | intron_variant | TRPM3 |
| rs17556165 | 9:70862225-70862225 | intron_variant | TRPM3 |
| rs12553375 | 9:70863297-70863297 | intron_variant | TRPM3 |
| rs12003687 | 9:70865324-70865324 | intron_variant | TRPM3 |
| rs1337024 | 9:70865710-70865710 | intron_variant | TRPM3 |
| rs1415221 | 9:70865802-70865802 | intron_variant | TRPM3 |
| rs12378024 | 9:70867524-70867524 | intron_variant | TRPM3 |
| rs3812530 | 9:70870132-70870132 | intron_variant | TRPM3 |
| rs7856482 | 9:70870530-70870530 | intron_variant | TRPM3 |
| rs13293998 | 9:70873648-70873648 | intron_variant | TRPM3 |
| rs9792446 | 9:70875255-70875255 | intron_variant | TRPM3 |
| rs9792690 | 9:70875368-70875368 | intron_variant | TRPM3 |
| rs4532663 | 9:70877591-70877591 | intron_variant | TRPM3 |
| rs1890016 | 9:70878812-70878812 | intron_variant | TRPM3 |
| rs11142635 | 9:70879522-70879522 | intron_variant | TRPM3 |
| rs13283806 | 9:70880023-70880023 | intron_variant | TRPM3 |
| rs17471974 | 9:70882051-70882051 | intron_variant | TRPM3 |
| rs7021176 | 9:70882602-70882602 | intron_variant | TRPM3 |
| rs11142636 | 9:70885565-70885565 | intron_variant | TRPM3 |
| rs7851915 | 9:70885941-70885941 | intron_variant | TRPM3 |
| rs10780982 | 9:70887508-70887508 | intron_variant | TRPM3 |
| rs1361028 | 9:70887720-70887720 | intron_variant | TRPM3 |
| rs13285568 | 9:70889229-70889229 | intron_variant | TRPM3 |
| rs1337033 | 9:70892141-70892141 | intron_variant | TRPM3 |
| rs10511992 | 9:70892180-70892180 | intron_variant | TRPM3 |
| rs11142639 | 9:70893581-70893581 | intron_variant | TRPM3 |
| rs7046928 | 9:70893636-70893636 | intron_variant | TRPM3 |
| rs13287493 | 9:70893777-70893777 | intron_variant | TRPM3 |

TABLE 34a-continued

26: SNP variants of TRP channel, ACh receptors or ADR annotated with their consequence.

| SNP | Location | Consequence | Gene |
| --- | --- | --- | --- |
| rs17472220 | 9:70894761-70894761 | intron_variant | TRPM3 |
| rs2993013 | 9:70895964-70895964 | intron_variant | TRPM3 |
| rs7868945 | 9:70900042-70900042 | intron_variant | TRPM3 |
| rs10868926 | 9:70900855-70900855 | intron_variant | TRPM3 |
| rs4143736 | 9:70902189-70902189 | intron_variant | TRPM3 |
| rs10868928 | 9:70910599-70910599 | intron_variant | TRPM3 |
| rs1337036 | 9:70912542-70912542 | intron_variant | TRPM3 |
| rs9696174 | 9:70917613-70917613 | intron_variant | TRPM3 |
| rs3010419 | 9:70921500-70921500 | intron_variant | TRPM3 |
| rs7849064 | 9:70923238-70923238 | intron_variant | TRPM3 |
| rs3010421 | 9:70924449-70924449 | intron_variant | TRPM3 |
| rs1337009 | 9:70925353-70925353 | intron_variant | TRPM3 |
| rs1415219 | 9:70932192-70932192 | intron_variant | TRPM3 |
| rs1337013 | 9:70932857-70932857 | intron_variant | TRPM3 |
| rs12347867 | 9:70942253-70942253 | intron_variant | TRPM3 |
| rs1981161 | 9:70948181-70948181 | intron_variant | TRPM3 |
| rs12377705 | 9:70949480-70949480 | intron_variant | TRPM3 |
| rs2993000 | 9:70952818-70952818 | intron_variant | TRPM3 |
| rs2993001 | 9:70952866-70952866 | intron_variant | TRPM3 |
| rs945688 | 9:70959944-70959944 | intron_variant | TRPM3 |
| rs1108226 | 9:70960746-70960746 | intron_variant | TRPM3 |
| rs2993003 | 9:70962410-70962410 | intron_variant | TRPM3 |
| rs7863158 | 9:70968623-70968623 | intron_variant | TRPM3 |
| rs2993008 | 9:70971440-70971440 | intron_variant | TRPM3 |
| rs3010434 | 9:70971643-70971643 | intron_variant | TRPM3 |
| rs7857794 | 9:70972604-70972604 | intron_variant | TRPM3 |
| rs12351733 | 9:70975207-70975207 | intron_variant | TRPM3 |
| rs10868934 | 9:70975460-70975460 | intron_variant | TRPM3 |
| rs3010438 | 9:70978950-70978950 | intron_variant | TRPM3 |
| rs1558924 | 9:70983392-70983392 | intron_variant | TRPM3 |
| rs10868936 | 9:70983512-70983512 | intron_variant | TRPM3 |
| rs1558926 | 9:70983549-70983549 | intron_variant | TRPM3 |
| rs10868937 | 9:70984034-70984034 | intron_variant | TRPM3 |
| rs7857162 | 9:70984585-70984585 | intron_variant | TRPM3 |
| rs719788 | 9:70985514-70985514 | intron_variant | TRPM3 |
| rs1558928 | 9:70987712-70987712 | intron_variant | TRPM3 |
| rs12554003 | 9:70995372-70995372 | intron_variant | TRPM3 |
| rs11142667 | 9:70999821-70999821 | intron_variant | TRPM3 |
| rs2909292 | 9:71000458-71000458 | intron_variant | TRPM3 |
| rs13298352 | 9:71006206-71006206 | intron_variant | TRPM3 |
| rs978790 | 9:71017328-71017328 | intron_variant | TRPM3 |
| rs495259 | 9:71017548-71017548 | intron_variant | TRPM3 |
| rs12551768 | 9:71018489-71018489 | intron_variant | TRPM3 |
| rs11142672 | 9:71029900-71029900 | intron_variant | TRPM3 |
| rs1411164 | 9:71040156-71040156 | intron_variant | TRPM3 |
| rs6560173 | 9:71041161-71041161 | intron_variant | TRPM3 |
| rs672801 | 9:71059440-71059440 | intron_variant | TRPM3 |
| rs523734 | 9:71065317-71065317 | intron_variant | TRPM3 |
| rs11142684 | 9:71076267-71076267 | intron_variant | TRPM3 |
| rs552849 | 9:71080844-71080844 | intron_variant | TRPM3 |
| rs13285838 | 9:71082970-71082970 | intron_variant | TRPM3 |
| rs656875 | 9:71088032-71088032 | intron_variant | TRPM3 |
| rs667136 | 9:71094663-71094663 | intron_variant | TRPM3 |
| rs7026563 | 9:71096739-71096739 | intron_variant | TRPM3 |
| rs1329748 | 9:71103891-71103891 | intron_variant | TRPM3 |
| rs972386 | 9:71107200-71107200 | intron_variant | TRPM3 |
| rs17056295 | 9:71113442-71113442 | intron_variant | TRPM3 |
| rs1759831 | 9:74734929-74734929 | intron_variant | TRPM6 |
| rs877809 | 9:74743052-74743052 | intron_variant | TRPM6 |
| rs2254229 | 9:74743514-74743514 | intron_variant | TRPM6 |
| rs476673 | 9:74746468-74746468 | intron_variant | TRPM6 |
| rs11787707 | 9:74751283-74751283 | intron_variant | TRPM6 |
| rs12002738 | 9:74758213-74758213 | intron_variant | TRPM6 |
| rs2274925 | 9:74761717-74761717 | synonymous_variant | TRPM6 |
| rs2274924 | 9:74761731-74761731 | missense_variant | TRPM6 |
| rs3750425 | 9:74762494-74762494 | missense_variant | TRPM6 |
| rs11144082 | 9:74778773-74778773 | intron_variant | TRPM6 |
| rs6560408 | 9:74781739-74781739 | intron_variant | TRPM6 |
| rs11144083 | 9:74788287-74788287 | intron_variant | TRPM6 |
| rs11144085 | 9:74789519-74789519 | intron_variant | TRPM6 |
| rs2151424 | 9:74791365-74791365 | intron_variant | TRPM6 |
| rs4145894 | 9:74792720-74792720 | synonymous_variant | TRPM6 |
| rs7859201 | 9:74800368-74800368 | synonymous_variant | TRPM6 |
| rs11144089 | 9:74802056-74802056 | synonymous_variant | TRPM6 |
| rs7848706 | 9:74802573-74802573 | intron_variant | TRPM6 |

TABLE 34a-continued

26: SNP variants of TRP channel, ACh receptors or ADR annotated with their consequence.

| SNP | Location | Consequence | Gene |
|---|---|---|---|
| rs17060535 | 9:74808814-74808814 | intron_variant | TRPM6 |
| rs12551151 | 9:74810041-74810041 | intron_variant | TRPM6 |
| rs4745361 | 9:74826221-74826221 | intron_variant | TRPM6 |
| rs7045949 | 9:74827700-74827700 | intron_variant | TRPM6 |
| rs17060568 | 9:74828508-74828508 | intron_variant | TRPM6 |
| rs7867868 | 9:74831958-74831958 | intron_variant | TRPM6 |
| rs1475717 | 9:74839224-74839224 | intron_variant | TRPM6 |
| rs12378991 | 9:74857150-74857150 | intron_variant | TRPM6 |
| rs6560417 | 9:74860672-74860672 | intron_variant | TRPM6 |
| rs2184118 | 9:74861470-74861470 | intron_variant | TRPM6 |
| rs9650770 | 9:74871543-74871543 | intron_variant | TRPM6 |
| rs7858012 | 9:74879240-74879240 | intron_variant | TRPM6 |
| rs1333343 | 9:74887406-74887406 | intron_variant | TRPM6 |
| rs3027744 | X:111822103-111822103 | intron_variant | TRPC5 |
| rs10521536 | X:111894324-111894324 | intron_variant | TRPC5 |
| rs7050529 | X:111912005-111912005 | intron_variant | TRPC5 |
| rs4893416 | X:111913443-111913443 | intron_variant | TRPC5 |
| rs2238999 | X:111916179-111916179 | intron_variant | TRPC5 |
| rs5985655 | X:111917973-111917973 | intron_variant | TRPC5 |
| rs5943223 | X:111922316-111922316 | intron_variant | TRPC5 |
| rs767034 | X:111925601-111925601 | intron_variant | TRPC5 |
| rs5943226 | X:111935514-111935514 | intron_variant | TRPC5 |
| rs7876872 | X:111943013-111943013 | intron_variant | TRPC5 |
| rs17222629 | X:111972464-111972464 | intron_variant | TRPC5 |
| rs7063059 | X:111972495-111972495 | intron_variant | TRPC5 |
| rs1009560 | X:111991013-111991013 | intron_variant | TRPC5 |
| rs16986729 | X:112005891-112005891 | intron_variant | TRPC5 |
| rs6642976 | X:112025020-112025020 | intron_variant | TRPC5 |
| rs16986741 | X:112027326-112027326 | intron_variant | TRPC5 |
| rs16986742 | X:112030800-112030800 | intron_variant | TRPC5 |
| rs7060180 | X:112042274-112042274 | intron_variant | TRPC5 |
| rs16986746 | X:112042431-112042431 | intron_variant | TRPC5 |

Figure 24:
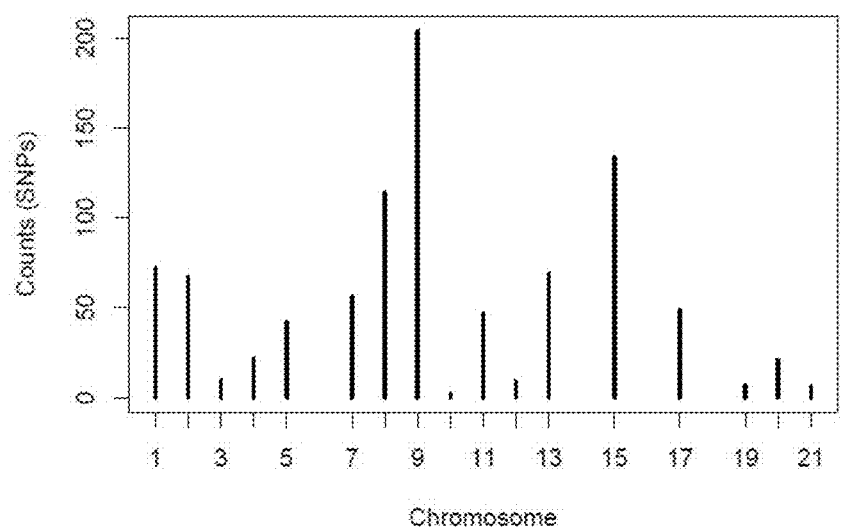
FIG. 24: Frequency of SNPs per chromosome.

The distribution of these SNPs per chromosome is summarised in FIG. 24. Accordingly, the majority of SNPs were observed on chromosome 9 (204 SNPs).

Figure 25:
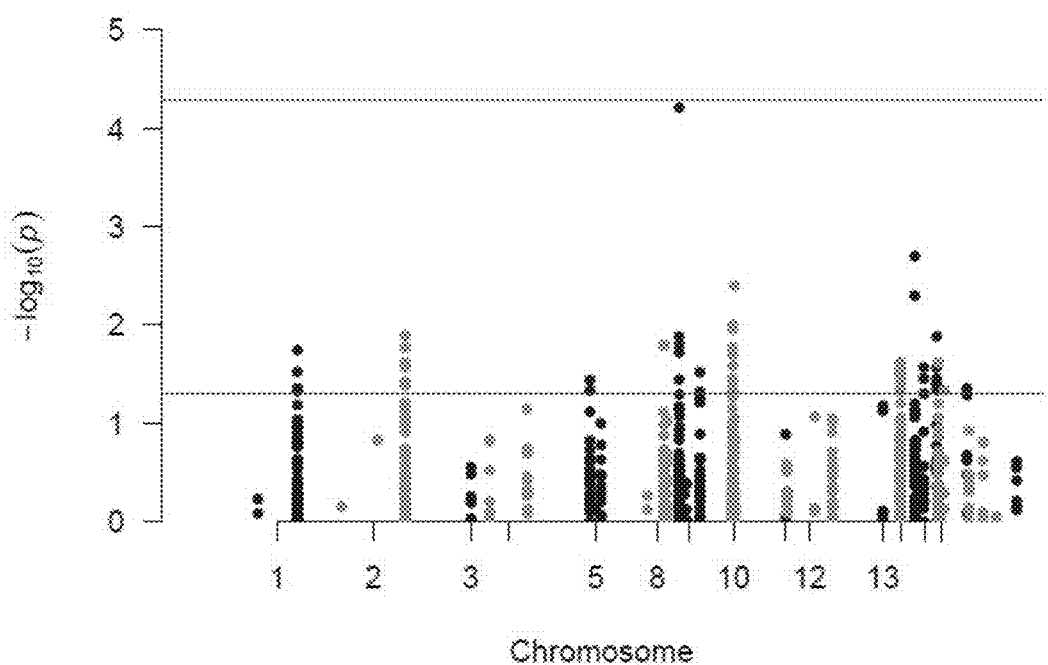
FIG. 25: Manhattan plot of Fisher's exact test on 950 SNPs.

FIG. 25 demonstrates a Manhattan plot of results of Fisher's exact test. Blue line (ie. the lower line between 3 and 2 on the log axis) corresponds to the significant threshold without any adjustment (raw p-values). Prior to Bonferroni correction, 60 significant SNPs were associated with CFS/ME compared with healthy controls. The red line (ie. the upper line between four and five on the log axis) corresponds to the significant threshold after Bonferroni correction.

Figure 26:
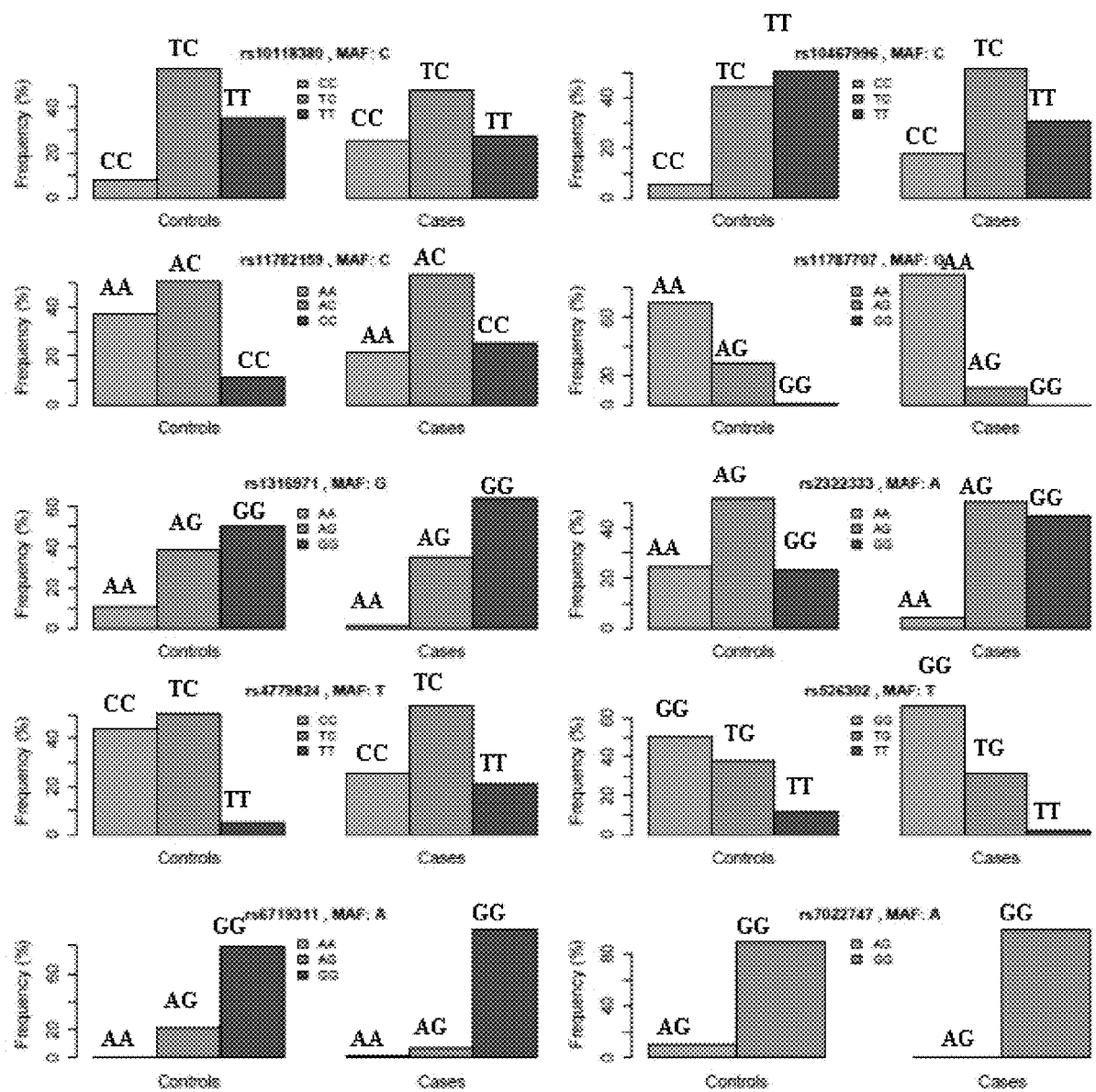
FIG. 26: Frequency of top 10 SNPs from Fisher's exact test. Cases: CFS/ME group; Controls: Healthy control group; MAF: Minor allele.

The raw p-values of the top 10 SNPs identified are summarised in Table 34b. The corresponding frequencies in CFS/ME compared with healthy controls are shown in FIG. 26.

TABLE 34b

Results of Fisher's exact test for top 10 SNPs prior to Bonferroni corrections

| SNP name | raw p-value | padj FDR | padj Bonferroni |
|---|---|---|---|
| "rs2322333" | "6.2e−05" | "0.059" | "0.059" |
| "rs4779824" | "0.002" | "0.788" | "1" |
| "rs11787707" | "0.004" | "0.788" | "1" |
| "rs10467996" | "0.005" | "0.788" | "1" |
| "rs10118380" | "0.01" | "0.788" | "1" |
| "rs7022747" | "0.011" | "0.788" | "1" |
| "rs1316971" | "0.013" | "0.788" | "1" |
| "rs526302" | "0.013" | "0.788" | "1" |
| "rs6719311" | "0.013" | "0.788" | "1" |
| "rs11782159" | "0.016" | "0.788" | "1" |

Figure 27:
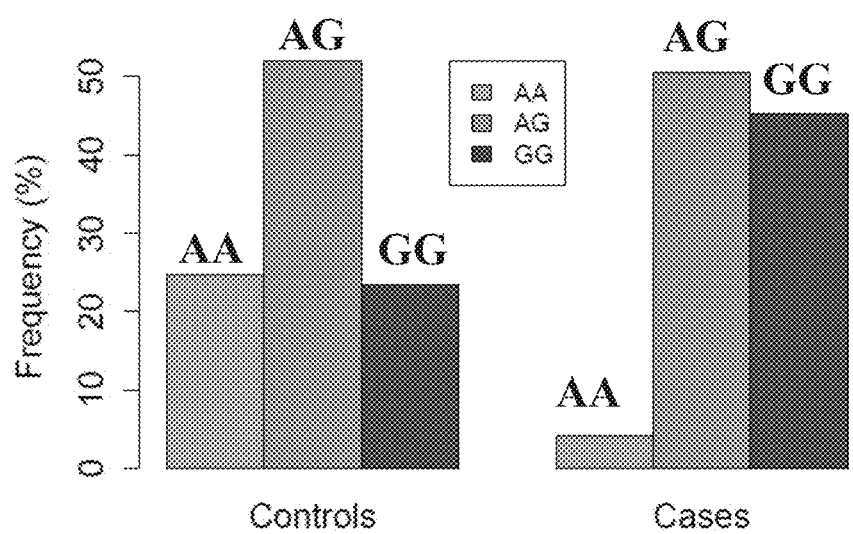
FIG. 27: Proportion of CFS/ME patients ("Cases") and healthy control group ("Controls") being homozygous major (GG), heterozygous (AG) or homozygous minor (AA) for adrenergic α1A (ADRA1A) SNP rs2322333.

Following adjustment using Bonferroni correction, the association with adrenergic α1A (ADRA1A) SNP rs2322333 located on chromosome 8 was almost significant (p=0.058) (FIG. 27). The proportion of CFS/ME patients being homozygous major (GG) for this SNP was higher compared with healthy controls. Moreover, the genotype class that was homozygous minor (AA) was much lower in CFS/ME patients compared with healthy controls (4.2% vs. 24.7) (FIG. 27).

Discussion

This study is the first to identify ADRA1A as a novel candidate gene for CFS/ME according to whole genome analysis. After stringent corrections for multiple testing were applied, the ADRA1A SNP remained predominant. Moreover, the proportion of patients that were homozygous minor, AA was much lower in CFS/ME compared with healthy controls. These results specifically suggest that patients exhibiting this allele marker may have a decreased risk of development of CFS/ME.

The specific physiological implications of ADRA1A are mainly involved in smooth muscle contraction [20p]. This is required for vasoconstriction of blood vessels throughout the body including the skin, gastrointestinal system, genitourinary system, kidney and brain. It is also involved in the glyogenolysis and gluconeogenesis of adipose tissue in the liver, in addition to secretions from sweat glands [24p, 25p, 26p]. These above processes have been commonly reported in the symptomatology of CFS/ME [3p, 4p]. Hence, the differential expression of ADRA1A may explain particular clinical phenotypes of CFS/ME.

ADRA1A are members of the superfamily for G protein-coupled receptors [27p]. When activated, heterotrimeric G protein ($G_g$) in turn activates phospholipase (PLC). PLC cleaves phosphatidylinositol 4,5-biphosphate (PIP2), which leads to an increase in inositol triphosphate (IP3) and diacyglycerol (DAG) (REFS). IP3 acts as a secondary messenger and is a soluble molecule that is able to diffuse through the cytoplasm to the endoplasmic reticulum of cells (or sarcoplasmic reticulum in muscle cells) to stimulate $Ca^{2+}$ influx. This involves the binding of IP3 ligand to IP3 sensitive $Ca^{2+}$ channels that result in the release of $Ca^{2+}$ into the cytoplasm [28p, 29p]. This contributes to a number of cellular processes, including a slow after depolarizing current (sADP) in neurons [30p].

As described in an earlier Example, the inventors investigated the dysregulation of $Ca^{2+}$ dependent kinase genes in isolated Natural Killer (NK) cells from CFS/ME patients [Chacko et al. 2016p]. Compared with healthy controls, reduced NK cytotoxic activity is consistently reported in CFS/ME patients [31p-39p]. In NK cells, $Ca^{2+}$ signaling has a vital role in the granule dependent pathway of apoptosis [40p]. $Ca^{2+}$ is required for inducing cytolytic granule polarisation, cytokine gene transcription and degranulation in NK cells [41p, 42p]. The inventors found that 92 significant $Ca^{2+}$ dependent protein kinase genes were differentially expressed in a clinically severe (housebound or bedridden) CFS/ME group compared with non-fatigued controls. These may contribute downstream to impairments in intracellular signalling networks and effector function. Accordingly, the inventors have also demonstrated significant impairments in the MAPK signalling pathway, as well as observed decreased intracellular $Ca^{2+}$ concentration in NK cells as well as isolated B cells from CFS/ME patients.

In addition to adrenergic receptors, this study selected genes for TRPs, AChRs, and acetylcholinesterase due their role in neurological, sensory and motor function that feature as symptoms of CFS/ME. Although these did not remain significant following post-hoc analysis, additional genes that were observed at a higher frequency in CFS/ME patients included TRPC1, TRPM1, TRPM3, TRPM6, TRPM8 and CHRNB4. Previously in the Examples above, the inventors examined 678 SNPs in isolated NK cells in CFS/ME patients and identified 11 significant TRP ion channel genes for TRPC4, TRPC2, TRPM3, and TRPM8, as well as 14 significant AChR genes including CHRNA2, CHRNA2, CHRNB4, CHRNA5, and CHRNE ($p<0.05$). Importantly the present study examined an additional 950 SNP in which there were only 80 overlapping with the previous studies in the earlier Examples. TRPM3 in particular is known to have a vital role in $Ca^{2+}$ signalling and was prominent across the inventors' analyses. Hence, the inventors have also previously investigated and reported a significantly decreased surface expression of TRPM3 on NK and B cells.

It is not known whether the associations observed in this study may be involved in the underlying biological mechanism of CFS/ME. Of particular interest is if the functional role of the SNP rs2322333 identified in this study is involved in the regulation of further genes. This SNP is located within the intron of ADRA1A, some GWAS studies have indicated that intronic genes may regulate the transcription of a nearby gene by specific chromatin looping [47p]. Furthermore, the results of this study are indicative that a larger cohort should be examined to determine if being homozygous minor for various allele markers have a protective effect from CFS/ME.

This study is the first genome-wide association study conducted on an Australian cohort with CFS/ME. A particular strength of this study was a considerable association with ADRA1A being detected among a preliminary cohort of patients, when strict statistical considerations were applied.

Conclusion

In conclusion, this study demonstrated that ADRA1A is a potential cellular marker for CFS/ME. It is recommended that future studies examine their functional role in the variation of further genes to further elucidate whether these allele markers have a potential protective role against CFS/ME.

Example 13—AchR, TRP and ADR Gene and Gene Product-Based Probes, Tools and Reagents as Well as Other Types of Tools and Reagents The Examples above explain how TRP, AchR and ADR SNPs can be used as "tools" for identifying subjects with, or predisposed to, CFS/ME as well as other medical conditions or symptoms thereof. This key SNP finding enables the inventors to develop TRP ion channel, ACh receptor or ADR gene/allele-based and gene product-based probes, tools, reagents, methods and assays for identifying, screening, diagnosing, monitoring and/or treating subjects with, or predisposed to, those medical conditions/symptoms.

One of skill in the art could readily design, produce or manufacture a wide range of TRP ion channel, ACh receptor or ADR gene/allele-based and gene product-based probes, tools, reagents, methods and assays based on the information of Tables 1 to 7, 9, 10, 12 to 17, 26 to 28, and 34.

Generally speaking, such TRP ion channel, ACh receptor or ADR gene/allele-based or gene product-based probes, tools, reagents, methods and assays can be used for identifying, screening, diagnosing, monitoring or treating/managing subjects with, or predisposed to, those medical conditions.

Generally speaking, such probes, tools or reagents based on or developed from a TRP ion channel, ACh receptor or ADR gene or gene product can, for example, specifically bind, detect, identify, characterise or quantify the gene or part of the gene, the RNA gene product or part of the RNA gene product, the polypeptide gene product or part of the polypeptide gene product.

Generally speaking, such probe, tool or reagent can be for detection of a polymorphism at the genomic level, at the transcription level or polypeptide level.

Generally speaking, such probe, tool or reagent can be for quantitative or qualitative measurement of RNA transcription or translation.

Generally speaking, such probe, tool or reagent can also be an antibody or other type of molecule or chemical entity capable of detecting the gene or gene product (RNA or polypeptide).

More specifically, probes, tools and reagents of particular interest include, but are not limited to, the following:

1. An isolated, purified, synthetic or recombinant form of TRP, AchR or ADR, or a fragment thereof, including a fragment containing a SNP of interest—single stranded or double stranded.

2. A non-naturally occurring polynucleotide, recombinant polynucleotide, oligonucleotide or cDNA form of TRP, AchR or ADR, or a fragment thereof, including a fragment containing a SNP of interest—single stranded or double stranded.

3. An expression product (mRNA) of TRP, AchR or ADR, or a fragment thereof, including a fragment containing a SNP of interest. Depending on the SNP, the mRNA may differ from an expression product in a healthy individual. The expression product may be unlabelled or labelled with a detectable moiety.

4. A polynucleotide, oligonucleotide, probe or primer (unlabelled or labelled with a detectable moiety) for specifically binding to, annealing to, detecting, isolating or amplifying (eg. by PCR) TRP, AchR or ADR, or a fragment thereof, including a SNP of Interest.

5. A polynucleotide, oligonucleotide, probe or primer (unlabelled or labelled with a detectable moiety) for specifically binding to, annealing to, detecting, isolating or amplifying (eg. by PCR) the expression product of 3.

6. An expression vector, recombinant cell or biological sample comprising the nucleic acid or polynucleotide of 1, 2, 3, 4 or 5.

7. An expression product (polypeptide/protein) of TRP, AchR or ADR, or a fragment thereof, including a fragment containing a SNP of interest. Depending on the SNP, the polypeptide may differ from a polypeptide in a healthy individual. The polypeptide may be unlabelled or labelled with a detectable moiety or for isolation (eg. tagged at the C- or N-terminus).

8. A monoclonal or polyclonal antibody capable of binding to the expression product of 7.

Yet other probes, tools and reagents are described in the specification section entitled "Detailed Description".

The key SNP finding also enables the inventors to develop kits, assays, microarrays, biochips and methods for identifying, screening, diagnosing, monitoring and/or treating subjects with, or predisposed to, the medical conditions/symptoms described in this specification.

Generally speaking, the kit, assay, microarray, biochip or method for identifying, screening, diagnosing, monitoring and/or treating subjects with, or predisposed to, the medical conditions/symptoms, can comprise one or more materials of any one of 1-8. This may be, for example, for genotyping, or identifying or measuring gene product expression or lack of expression.

Yet other kits, assays, microarrays, biochips and methods are described in the specification section entitled "Detailed Description".

Examples of preferred polynucleotides, oligonucleotides, probes or primers for specifically binding to, annealing to, detecting, isolating or amplifying (eg. by PCR) the SNPs of TRP or AchR are shown in Table 35. An example of a preferred polynucleotide, oligonucleotide, probe or primer for specifically binding to, annealing to, detecting, isolating or amplifying (eg. by PCR) a SNP of ADR is shown in Table 36.

TABLE 35

Preferred polynucleotides, oligonucleotides, probes or primers for detecting the SNPs of TRP or AChR. (On next page.)

| Gene | RefSNP ID | SNP ID | Forward Primer ID | Forward Primer Sequence | Reverse Primer ID | Reverse Primer Sequence | Extended Primer ID | Extended Primer Sequence |
|---|---|---|---|---|---|---|---|---|
| TRPM3 | rs12682832 | rs12682832_W3 | rs12682832_W3_F | ACGTTGGATGAGCCTCCTTCTGACTTGAAC (SEQ ID No. 1) | rs12682832_W3_R | ACGTTGGATGCATTTCACCTACAAGTGATG (SEQ ID No. 2) | rs12682832_W3_E | cGRATGGAATTTGACCCAAC (SEQ ID No. 3) |
| TRPM3 | rs11142508 | rs11142508_W3 | rs11142508_W3_F | ACGTTGGATGGCTCCGTATGTGCTGAGAG (SEQ ID No. 4) | rs11142508_W3_R | ACGTTGGATGAGAAATACAGCGCTGGCTTC (SEQ ID No. 5) | rs11142508_W3_E | aGGGGCTTGTGTGTAA (SEQ ID No. 6) |
| TRPM3 | rs1160742 | rs1180742_W9 | rs1180742_W9_F | ACGTTGGATGTTCTCACAGTTAAGGCCTTG (SEQ ID No. 7) | rs1160742_W9_R | ACGTTGGATGGCTGCTAATGATAGAGGCTC (SEQ ID No. 8) | rs1160742_W9_E | TACATGGGGATTTACATAGACTA (SEQ ID No. 9) |
| TRPM3 | rs4454352 | rs1160742_W6 | rs1160742_W6_F | ACGTTGGATGTTCTCACAGTTAAGGCCTTG (SEQ ID No. 10) | rs1160742_W6_R | ACGTTGGATGGCTGCTAATGATAGAGGCTG (SEQ ID No. 11) | rs1160742_W6_E | TACATGGGGATTTACATAGACTA (SEQ ID No. 12) |
| TRPM3 | rs1328153 | rs1160742_W6 | rs1160742_W6_F | ACGTTGGATGTTCTCACAGTTAAGGCCTTG (SEQ ID No. 13) | rs1160742_W6_R | ACGTTGGATGGCTGCTAATGATAGAGGCTG (SEQ ID No. 14) | rs1160742_W6_E | TACATGGGGATTTACATAGACTA (SEQ ID No. 15) |
| TRPM3 | rs3763619 | rs3763619_W9 | rs3763619_W9_F | ACGTTGGATGCTCAOGCAAAGGTATTCAC (SEQ ID No. 16) | rs3763619_W9_R | ACGTTGGATGAGAACCTAAGAACCAAGGC (SEQ ID No. 17) | rs3763619_W9_E | gggaAGAGATTAGAGGTTGTACC (SEQ ID No. 18) |
| TRPC4 | rs6650469 | rs6650469_W4 | rs6650469_W4_F | ACGTTGGATGTTGCTGGTGGTGGCTTAAAC (SEQ ID No. 19) | rs6650469_W4_R | ACGTTGGATGCTAGGGTGAACAACTTGAAC (SEQ ID No. 20) | rs6650469_W4_E | ggggACCTTTCAAAAGAGTGATAC (SEQ ID No. 21) |
| TRPM3 | rs655207 | rs655207_W3 | rs655207_W3_F | ACGTTGGATGAAGGTTCAAGTTGTTCACCC (SEQ ID No. 22) | rs655207_W3_R | ACGTTGGATGTTACCTGCCTTTTACCACAC (SEQ ID No. 23) | rs655207_W3_E | cCCTCCTTCCAGGAACTAC (SEQ ID No. 24) |
| TRPA1 | rs4738202 | rs4738202_W8 | rs4738202_W8_F | ACGTTGGATGAGTGTTCCAATCGCTCTGTG (SEQ ID No. 25) | rs4738202_W8_R | ACGTTGGATGAATCAACTGAGAACCATTG (SEQ ID No. 26) | rs4738202_W8_E | cttcTAATATACAGCCATGTCATAGA (SEQ ID No. 27) |
| TRPM3 | rs7765858 | rs7865856_W7 | rs7865858_W7_F | ACGTTGGATGGGAAAAACAATTCTTGGGG (SEQ ID No. 28) | rs7865858_W7_R | ACGTTGGATGCCCACCTATGACCATTTCC (SEQ ID No. 29) | rs7855656_W7_E | GACCATTTTCCTCAGAGA (SEQ ID No. 30) |
| TRPA1 | rs2383844 | rs2383844_W7 | rs2383844_W7_F | ACGTTGGATGCATCAAGACAGATTTCAAC (SEQ ID No. 31) | rs2383844_W7_R | ACGTTGGATGCCTACATCTCATCAAAGGAC (SEQ ID No. 32) | rs2383844_W7_E | ggTACAGAATAAGAAAAGTTTGAGATTA (SEQ ID No. 33) |
| TRPM3 | rs1504401 | rs1504401_W6 | rs1504401_W6_F | ACGTTGGATGCGTTTGTGTTTATGCCCTC (SEQ ID No. 34) | rs1504401_W6_R | ACGTTGGATGGGAGTTTGCTATATATTCCC (SEQ ID No. 35) | rs1504401_W6_E | ggggcACCATTACAGGTAATTCCA (SEQ ID No. 36) |
| TRPM3 | rs10115622 | rs10115622_W4 | rs10115622_W4_F | ACGTTGGATGTTTTCCCTTATTCTCCCAC (SEQ ID No. 37) | rs10115622_W4_R | ACGTTGGATGACCCTCTAGCCTCTGAATTGC (SEQ ID No. 38) | rs10115622_W4_E | GGAGGAGAAACAAACTCCA (SEQ ID No. 39) |
| TRPM4 | rs10403114 | rs10403114_W7 | rs10403114_W7_F | ACGTTGGATGAAAGTGGGCGGGACATAG (SEQ ID No. 40) | rs10403114_W7_R | ACGTTGGATGAAAACACGCCCCATTGCTC (SEQ ID No. 41) | rs10403114_W4_E | AAGTCACGCCCCTTC (SEQ ID No. 42) |
| TRPV3 | rs9909424 | rs9909424_W6 | rs9909424_W6_F | ACGTTGGATGGAAATGATGCTTTCCACGGG (SEQ ID No. 43) | rs9909424_W6_R | ACGTTGGATGAACTGCCTGAGCCTACAGAC (SEQ ID No. 44) | rs9909424_W6_E | ctgcaTGAGCCTACAGACCACCTTCT (SEQ ID No. 45) |
| TRPC4 | rs612308 | rs612308_W8 | rs612308_W8_F | ACGTTGGATGGAGGCTTTTAATCAACTCCC (SEQ ID No. 46) | rs612308_W8_R | ACGTTGGATGGATAAATTTTCTGTGACAGAC (SEQ ID No. 47) | rs612308_W8_E | gacacTGTCTTTCATTTGACTTGT (SEQ ID No. 48) |
| TRPC4 | rs7860377 | rs7860377_W9 | rs7860377_W9_F | ACGTTGGATGCTGGTGGGAGAAATGCAAGTC (SEQ ID No. 49) | rs7860377_W9_R | ACGTTGGATGGCTAATAGTCCCTTTACC (SEQ ID No. 50) | rs7860377_W9_E | gggGTCATGTTTTTCCATTGTCA (SEQ ID No. 51) |
| TRPM3 | rs2673930 | rs2673930_W6 | rs2673930_W6_F | ACGTTGGATGTGTCAACCTAGTAGACGAGC (SEQ ID No. 52) | rs2673630_W6_F | ACGTTGGATGTGGAGATGCATCCTCTAGGC (SEQ ID No. 53) | r2673930_W6_E | AGGCGAAAGCTCTAATT (SEQ ID No. 54) |
| TRPC7 | rs603955 | rs603955_W9 | rs603955_W9_F | ACGTTGGATGACCATCTGCAGGACTTTAGG (SEQ ID No. 55) | rs603955_W9_R | ACGTTGGATGCTTTTGGGGCTGAGTTTAAG (SEQ ID No. 56) | rs603955_W9_E | ccccgCTCTTCCTTCAAAACTATCTTG (SEQ ID No. 57) |
| TRPC4 | rs11142798 | rs11142798_W9 | rs11142798_W9_F | ACGTTGGATGGGGTAAAAGAATTACACAAG (SEQ ID No. 58) | rs11142798_W9_R | ACGTTGGATGTGCCTGAATTATGCAATAG (SEQ ID No. 59) | rs11142799_W9_E | TATGCAATAGAATCACTTGGT (SEQ ID No. 60) |
| TRPM3 | rs4744611 | rs4744611_W9 | rs4744611_W9_F | ACGTTGGATGTCTTCTCCAGTGTCTAAGGG (SEQ ID No. 61) | rs4744611_W9_R | ACGTTGGATGCCCAATGTTACATGGCTTCC (SEQ ID No. 62) | rs4744611_W9_E | AGGGCTACAAGAGCTGA (SEQ ID No. 63) |

TABLE 36

A preferred polynucleotide, oligonucleotide,
probe or primer for detecting a SNP of ADR.

Gene: ADRA1A
Sequence: CTCATCCTGTCTTTGCAGGAGATTCTGGGTATATAGTTCCTCCAGAGACA
(SEQ ID No. 64)

One or more Examples above explain how calcium metabolism testing can be used for identifying, screening, diagnosing or monitoring a subject having, or at risk of developing, a medical condition or symptom thereof—particularly CFS/ME. This key finding by the inventors allows one of skill in the art to develop probes, tools, reagents, methods and assays for calcium metabolism testing, as also described elsewhere.

Example 11 above explains how a differentially regulated calcium-dependent kinase gene can be used as an indicator of a medical condition or symptom thereof—particularly severe CFS/ME. This key finding by the inventors allows one of skill in the art to develop probes, tools, reagents, methods and assays for detecting the differentially regulated calcium-dependent kinase gene, as also described elsewhere.

Example 10 above explains how Natural Killer (NK) cells (and other cell types or tissues) can be tested in a subject for dysfunctional signalling through the Mitogen-Activated Protein Kinase (MARK) pathway, including signalling via the MAPK kinase (MAPKK/MEK1/2) and extracellular signal-regulated kinase (ERK)1/2 as well as p38, whereby dysfunctional signalling indicates that the subject has the medical condition or symptom thereof—particularly CFS/ME. This key finding by the inventors allows one of skill in the art to develop probes, tools, reagents, methods and assays for assaying or characterising the cell Mitogen-Activated Protein Kinase pathway, as also described elsewhere.

Example 14—AchR, TRP and ADR SNPs;
Differentially Regulated Calcium-Dependent Kinase
Genes; and Dysfunctional Signalling Through the
MAPK Pathway, as Indicators of Medical
Conditions Based on Examples 1 to 9 and 12, the skilled person will appreciate that the SNPs listed in the earlier Tables, such as Tables 1 to 7, 9, 10, 12 to 17, 26 to 28 and 34, can be used for identifying, screening, diagnosing, monitoring or treating/managing subjects with, or predisposed to, CFS or specific symptoms thereof as well as ME or specific symptoms thereof.

The skilled person will also appreciate that the SNPs listed in the earlier Tables, such as Tables 1 to 7, 9, 10, 12 to 17, 26 to 28 and 34, can be used for identifying, screening, diagnosing, monitoring or treating/managing subjects with, or predisposed to, other medical conditions or specific symptoms thereof, such as: IBS; MCS; non-allergic rhinitis; fibromyalgia; migraine; rheumatoid arthritis.

The skilled person will also appreciate that the SNPs listed in the earlier Tables, such as Tables 1 to 7, 9, 10, 12 to 17, 26 to 28 and 34, can be used for identifying, screening, diagnosing, monitoring or treating/managing subjects with, or predisposed to, other medical conditions or specific symptoms thereof: caused by dysregulation in calcium (especially in respect of CPS, ME, GWS, IBS, MCS, fibromyalgia or migraine); caused by dysregulation in acetylcholine (especially in respect of CFS, ME, GWS, IBS, MCS, fibromyalgia or migraine); caused by dysregulation in TRP (especially in respect of CFS, ME, GWS, IBS, MCS, fibromyalgia or migraine); caused by dysregulation in ADR; caused by dysregulation of the gastrointestinal, cardiovascular, neurological and immune systems (especially in respect of CFS, ME, GWS, IBS, MCS, non-allergic rhinitis, fibromyalgia or migraine).

Specific symptoms of CFS or ME include: neuromuscular fatigue, particularly fatigue upon exertion; memory and concentration difficulties; muscle and joint pain; altered blood pressure, particularly postural orthorstatic tachycardia syndrome; headache; immunological dysregulation; sore throat; swollen lymph nodes/glands; gastrointestinal symptoms including IB, diarrhoea, constipation and abdominal pain; chemical sensitives; and intolerances to drugs and chemicals.

MCS conditions/symptoms include: headache; fatigue; confusion; depression; shortness of breath; arthralgia; myalgia; nausea; dizziness; memory problems; gastrointestinal symptoms; or respiratory symptoms.

Medical conditions caused by dysregulation in calcium, (especially in respect of CFS, ME, GWS, IBS, MCS, fibromyalgia or migraine), are typified by specific symptoms or dysregulation such as: significant impairment in physical activity; debilitating fatigue accompanied by impairment in memory, cognition and concentration; enhanced experience of pain; dysregulation of the gastrointestinal, cardiovascular and immune systems; headache; fatigue; confusion; depression; shortness of breath; arthralgia; myalgia; nausea; dizziness; memory problems; gastrointestinal symptoms; respiratory symptoms; and immunological "allergic" sensitivities.

Medical conditions caused by dysregulation in acetylcholine, (especially in respect of CFS, ME, GWS, IBS, MCS, fibromyalgia or migraine), are typified by specific symptoms or dysregulation such as: significant impairment in physical activity; debilitating fatigue accompanied by impairment in memory, cognition and concentration; enhanced experience of pain; dysregulation of the gastrointestinal, cardiovascular and immune systems; headache; fatigue; confusion; depression; shortness of breath; arthralgia; myalgia; nausea; dizziness; memory problems; gastrointestinal symptoms; respiratory symptoms; and deregulation of the gastrointestinal, cardiovascular and immune systems (immunological "allergic" sensitivities).

Medical conditions caused by dysregulation in TRP are typified by specific symptoms or dysregulation, including: significant impairment in physical activity; debilitating fatigue accompanied by impairment in memory, cognition and concentration; enhanced experience of pain; dysregulation of the gastrointestinal, cardiovascular and immune systems; headache; fatigue; confusion; depression; shortness of breath; arthralgia; myalgia; nausea; dizziness; memory problems; gastrointestinal symptoms; respiratory symptoms; and dysregulation of the gastrointestinal, cardiovascular and immune systems (immunological "allergic" sensitivities).

Medication conditions caused by dysregulation in ADR are typified by specific symptoms such as respiratory difficulties including shortness or breath, air hunger, colds and nasalpharynx congestion, cardiovascular conditions such as hypertension, and palpitations, gastrointestinal illness, kidney disease, diabetes, and autonomic function including sweating episodes.

Medical conditions caused by dysregulation of the gastrointestinal, cardiovascular and immune systems, (especially in respect of CFS, ME, GWS, IBS, MCS, fibromyalgia or migraine), are typified by specific symptoms or dysregulation, including: significant impairment in physical activity; debilitating fatigue accompanied by impairment in memory, cognition and concentration; enhanced experience of pain; headache; fatigue; confusion; depression; shortness of breath; arthralgia; myalgia; nausea; dizziness; memory problems; gastrointestinal symptoms; respiratory symptoms; and immunological "allergic" sensitivities.

The inventors note that up to 45% of patients with CFS have IBS. M3 muscarinic drugs are being used to target IBS. The inventors have identified abnormalities in the Ach receptors in patients with CFS.

The inventors also note that many patients with CFS have headache and chemical smell sensitivity. The TRPV1 receptor has been reported to be increased in this condition.

Based on Example 10, the skilled person will appreciate that testing cells (such as NK cells) for dysfunctional signalling through the Mitogen-Activated Protein Kinase (MAPK) pathway, including signalling via the MAPK kinase (MAPKK/MEK1/2) and extracellular signal-regulated kinase (ERK)1/2 as well as p38, can be used for identifying, screening, diagnosing, monitoring or treating/managing subjects with, or predisposed to a medical condition described above.

Based on Example 11, the skilled person will appreciate that one or more differentially regulated calcium-dependent kinase genes as listed in Tables 31 and 32 can be used for identifying, screening, diagnosing, monitoring or treating/managing subjects with, or predisposed to a medical condition described above.

In the present specification and claims, the word 'comprising' and its derivatives including 'comprises' and 'comprise' include each of the stated integers but do not exclude the inclusion of one or more further integers.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

The articles 'a' and 'an' are used herein to refer to one or to more than one of the article.

The term 'about' is to be understood as referring to a range of numbers that a person of skill in the art would consider equivalent to the recited value in the context of achieving the same function or result.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims appropriately interpreted by those skilled in the art.

CITATION LIST

[The entire contents of which are incorporated herein by way of cross-reference.]

1a. Prins J B, van der Meer J W, Bleijeriberg G (2006) Chronic fatigue syndrome. Lancet 367: 346-355.

2a. Johnston S, Brenu E W, Staines D, Marshall-Gradisnik S (2013) The prevalence of chronic fatigue syndrome/myalgic encephalomyelitis: a meta-analysis. Clin Epidemiol 5: 105-110.

3a. Fukuda K, Straus S E, Hickie I, Sharpe M C, Dobbins J G, et al. (1994) The chronic fatigue syndrome: a comprehensive approach to its definition and study. International Chronic Fatigue Syndrome Study Group. Ann Intern Med 121: 953-959.

4a. Brenu E W, Ashton K J, van Driel M, Staines D R, Peterson D, et al. (2012) Cytotoxic lymphocyte microRNAs as prospective biomarkers for Chronic Fatigue Syndrome/Myalgic Encephalomyelitis. J Affect Disord 141: 261-269.

5a. Brenu E W, van Driel M L, Staines D R, Ashton K J, Hardcastle S L, et al. (2012) Longitudinal investigation of natural killer cells and cytokines in chronic fatigue syndrome/myalgic encephalomyelitis. J Transl Med 10: 88.

6a. Brenu E W, Staines D R, Baskurt O K, Ashton K J, Ramos S B, et al. (2010) Immune and hemorheological changes in chronic fatigue syndrome. J Transl Med 8: 1.

7a. Kaushik N, Fear D, Richards S C, McDermott C R, Nuwaysir E F, et al. (2005) Gene expression in peripheral blood mononuclear cells from patients with chronic fatigue syndrome. J Clin Pathol 58: 826-832.

8a. Frampton D, Kerr J, Harrison T J, Kellam P (2011) Assessment of a 44 gene classifier for the evaluation of chronic fatigue syndrome from peripheral blood mononuclear cell gene expression. PLoS One 6: e16872.

9a. Kerr J R (2008) Gene profiling of patients with chronic fatigue syndrome/myalgic encephalomyelitis. Curr Rheumatol Rep 10: 482-491.

10a. Kerr J R, Petty R, Burke B, Gough J, Fear D, et al. (2008) Gene expression subtypes in patients with chronic fatigue syndrome/myalgic encephalomyelitis. J Infect Dis 197: 1171-1184.

11a. Kerr J R, Burke B, Petty R, Gough J, Fear D. et al. (2008) Seven genomic subtypes of chronic fatigue syndrome/myalgic encephalomyelitis: a detailed analysis of gene networks and clinical phenotypes. J Clin Pathol 61: 730-739.

12a. Brenu E W, van Driel M L, Staines D R, Ashton K J, Ramos S B, et al. (2011) Immunological abnormalities as potential biemarkers in Chronic Fatigue Syndrome/Myalgic Encephalomyelitis. J Transl Med 9: 81.

13a. Sun W, Julie Li Y S, Huang H D, Shyy J Y, Chien S (2010) microRNA: a master regulator of cellular processes for bioengineering systems. Annu Rev Biomed Eng 12: 1-27.

14a. Xiao C, Rajewsky K. (2009) MicroRNA control in the immune system: basic principles. Cell 136: 26-36.

15a. Chen C Z, Schaffert S, Fragoso R, Loh C (2013) Regulation of immune responses and tolerance: the microRNA perspective. Immunol Rev 253: 112-128.

16a. Long J M, Lahiri D K (2012) Advances in microRNA experimental approaches to study physiological regulation of gene products implicated in CNS disorders. Exp Neurol 235: 402-418.

17a. Nakamoto M, Jin P, O'Donnell W T, Warren S T (2005) Physiological identification of human transcripts transiationally regulated by a specific microRNA. Hum Mol Genet 14: 3813-3821.
18a. Janssen M D, Lund A H (2012) MicroRNA and cancer. Mol Oncol 6: 590-610.
19a. Mo Y Y (2012) MicroRNA regulatory networks and human disease. Cell Mol Life Sci 69: 3529-3531.
20a. Shafi G, Aliya N, Munshi A (2010) MicroRNA signatures in neurological disorders. Can J Neurol Sci 37: 177-185.
21a. Qin C, Chen G, Cui Q (2012) Towards the understanding of microRNA and environmental factor interactions and their relationships to human diseases. Sci Rep 2:318.
26a. Adachi T, Nakanishi M, Otsuka Y, Nishimura K, Hirokawa G, et al. (2010) Plasma microRNA 499 as a biomarker of acute myocardial infarction. Clin Chem 56: 1183-1185.
27a. Stocks M B, Moxon S, Mapleson D, Woolfenden H C, Mohorianu I, et al. (2012) The UEA sRNA workbench: a suite of tools for analysing and visualizing next generation sequencing microRNA and small RNA datasets. Bioinformatics 28: 2059-2061.
28a. Hackenberg M, Sturm M, Langenberger D, Falcon-Perez J M, Aransay A M (2009) miRanalyzer: a microRNA detection and analysis tool for next-generation sequencing experiments. Nucleic Acids Res 37: W68-76.
29a. Anders S, Huber W (2010) Differential expression analysis for sequence count data. Genome Biol 11: R106.
30a. Carruthers B M, van de Sande M I, De Meirleir K L, Klimas N G, Broderick G, et al. (2011) Myaiglc encephalomyelitis: International Consensus Criteria. J Intern Med 270: 327-338.
31a. Pritchard C C, Cheng H H, Tewari M (2012) MicroRNA profiling: approaches and considerations. Nat Rev Genet 13: 358-369.
32a. Duttagupta R, Jiang R, Gollub J, Getts R C, Jones K W (2011) Impact of cellular miRNAs on circulating miRNA biomarker signatures. PLoS One 6: e20769.
33a. Turchinovich A, Weiz L, Langheinz A, Burwinkel B (2011) Characterization of extracellular circulating microRNA. Nucleic Acids Res 39: 7223-7233.
34a. D'Alessandra Y, Devanna P, Limana F, Straino S, Di Carlo A, et al. (2010) Circulating microRNAs are new and sensitive biomarkers of myocardial infarction. Eur Heart J 31: 2765-2773.
35a. Robertus J L, Harms G, Blokzijl T, Booman M, de Jong D, et al. (2009) Specific expression of miR-17-5p and miR-127 in testicular and central nervous system diffuse large B-cell lymphoma. Mod Pathol 22: 547-555.
36a. Zhang Y, Wang Z, Chen M, Peng L, Wang X, et al. (2012) MicroRNA-143 targets MACC1 to inhibit cell invasion and migration in colorectal cancer. Mol Cancer 11: 23.
37a. Ansel K M (2013) RNA regulation of the immune system. Immunol Rev 253: 5-11.
38a. Mas V R, Dumur C I, Scian M J, Gehrau R C, Maluf D G (2013) MicroRNAs as biomarkers in solid organ transplantation. Am J Transplant 13: 11-19.
39a. Saito Y, Suzuki H, Tsugawa H, Imaeda H, Matsuzaki J, et al. (2012) Overexpression of miR-142-5p and miR-155 in gastric mucosa-associated lymphoid tissue (MALT) lymphoma resistant to *Helicobacter pylori* eradication. PLoS One 7: e47396.
40a. Merkerova M, Belickova M, Bruchova H (2008) Differential expression of microRNAs in hematopoietic cell lineages. Eur J Haematol 81: 304-310.
41a. Ding S, Liang Y, Zhao M, Liang G, Long H, et al. (2012) Decreased microRNA-142-3p/5p expression causes CD4+ T cell activation and B cell hyperstimulation in systemic lupus erythematosus. Arthritis Rheum 64: 2953-2963.
42a. Cannons J L, Qi H, Lu K T, Dutta M, Gomez-Rodriguez J, et al. (2010) Optimal germinal center responses require a multistage T cell:B cell adhesion process involving integrins, SLAM-associated protein, and CD84. Immunity 32: 253-265.
43a. Slaby O, Svoboda M, Fabian P, Smerdova T, Knoflickova D, et al. (2007) Altered expression of miR-21, miR-31, miR-143 and miR-143 is related to clinicopathologic features of colorectal cancer. Oncology 72: 397-402.
44a. Chen X, Guo X, Zhang H, Xiang Y, Chen J, et al. (2009) Role of miR-143 targeting KRAS in colorectal tumorigenesis. Oncogene 28: 1385-1392.
45a. Peschiaroli A, Giacobbe A, Formosa A, Markert E K, Bongiorno-Borbone L, et al. (2013) miR-143 regulates hexokinase 2 expression in cancer cells. Oncogene 32: 797-802.
46a. Liu L, Yu X, Guo X, Tian Z, Su M, et al. (2012) miR-143 is downregulated in cervical cancer and promotes apoptosis and inhibits tumor formation by targeting Bcl-2. Mol Med Rep 5: 753-760.
47a. Slezak S, Jin P, Caruccio L, Ren J, Bennett M, et al. (2009) Gene and microRNA analysis of neutrophils from patients with polycythemia vera and essential thrombocytosis: down-regulation of micro RNA-1 and -133a. J Transl Med 7: 39.
48a. Allantaz F, Cheng D T, Bergauer T, Ravindran P, Rossier M F, et al. (2012) Expression profiling of human immune cell subsets identifies miRNA-mRNA regulatory relationships correlated with cell type specific expression. PLoS One 7: e29979.
49a. Kennedy G, Spence V, Underwood C, Belch J J (2004) Increased neutrophil apoptosis in chronic fatigue syndrome. J Clin Pathol 57: 891-893.
50a. See D M, Cimoch P, Chou S, Chang J, Tilles J (1998) The in vitro immunomodulatory effects of glyconutrients on peripheral blood mononuclear cells of patients with chronic fatigue syndrome. Integr Physiol Behav Sci 33: 280-287.
51a. Vojdani A, Mordechai E, Brautbar N (1997) Abnormal apoptosis and cell cycle progression in humans exposed to methyl tertiary-butyl ether and benzene contaminating water. Hum Exp Toxicol 16: 485-494.
52a. Mosakhani N, Sarhadi V K, Borze I, Karjalainen-Lindsberg M L, Sundstrom J, et al. (2012) MicroRNA profiling differentiates colorectal cancer according to KRAS status. Genes Chromosomes Cancer 51: 1-9.
53a. Parpart S, Wang X W (2013) microRNA Regulation and Its Consequences In Cancer. Curr Pathohiol Rep 1: 71-79.
54a. Saito Y, Liang G, Egger G, Friedman J M, Chuang J C, et al. (2006) Specific activation of microRNA-127 with downregulation of the proto-oncogene BCL6 by chromatin-modifying drugs in human cancer cells. Cancer Cell 9: 435-443.
55a. Crotiy S, Johnston R J, Schoenberger S P (2010) Effectors and memories: Bcl-6 attd Blimp-1 in T and B lymphocyte differentiation. Nat Immunol 11: 114-120.
56a. Nurieva R I, Chung Y, Martinez G J, Yang X O, Tanaka S, et al. (2009) Bcl6 mediates the development of T follicular helper cells. Science 325: 1001-1005.

57a. Johnston R J, Poholek A C, DiToro D, Yusuf iI Eto D, et al. (2009) Bcl6 and Blimp-1 are reciprocal and antagonistic regulators of T follicular helper cell differentiation. Science 325: 1006-1010.

58a. Klein U, Dalla-Favera R (2008) Germinal centres: role in B-cell physiology and malignancy. Nat Rev Immunol 8:22-33.

59a. Lerner M R, Boyle J A, Hardin J A, Steitz J A (1981) Two novel classes of small ribonucleoproteins detected by antibodies associated with lupus erythematosus. Science 211: 400-402.

60a. Verhagen A P, Pruijn G J (2011) Are the Ro RNP-associated Y RNAs concealing microRNAs? Y RNA-derived miRNAs may be involved in autoimmunity. Bioessays 33: 674-682.

61a. O'Neil D, Glowatz H, Schlumpberger M (2013) Ribosomal RNA Depletion for Efficient Use of RNA-Seq Capacity. Curr Protoc Mol Biol Chapter 4: Unit4 19.

62a. Kirschner M B, Edelman J J, Kao S C, Vallely M P, van Zandwijk N, et al. (2013) The Impact of Hemolysis on Cell-Free microRNA Blomarkers. Front Genet 4: 94.

63a. Kirschner M B, van Zandwijk N, Reid G (2013) Cell-free microRNAs: potential biomarkers in need of standardized reporting. Front Genet 4: 56.

64a. Cheng H H, Yi H S, Kim Y, Kroh E M, Chien J W, et al. (2013) Plasma Processing Conditions Substantially Influence Circulating microRNA Biomarker Levels. PLoS One 8: e64795.

65a. McAlexander M A, Phillips M J, Witwer K W (2013) Comparison of Methods for miRNA Extraction from Plasma and Quantitative Recovery of RNA from Cerebrospinal Fluid. Front Genet 4: 83.

66a. Pritchard C C, Kroh E, Wood B, Arroyo J D, Dougherty K J, et al. (2012) Blood cell origin of circulating microRNAs: a cautionary note for cancer biomarker studies. Cancer Prev Res (Phila) 5: 492-497.

67a. Boeri M, Verri C, Conte D, Roz L, Modena P, et al. (2013) MicroRNA signatures in tissues and plasma predict development and prognosis of computed tomography detected lung cancer. Proc Natl Acad Sci USA 108: 3713-3718.

68a. Duttagupta R, Jones K W (2013) The curious case of miRNAs in circulation: potential diagnostic biomarkers? Wiley Interdiscip Rev RNA 4: 129-138.

69a. De Guire V, Robitaille R, Tetreault N, Guerin R, Menard C, et al. (2013) Circulating miRNAs as sensitive and specific biomarkers for the diagnosis and monitoring of human diseases: promises and challenges. Clin Biochem 46: 846-860.

70a. Chen X, Ba Y, Ma L, Cai X, Yin Y, et al. (2008) Characterization of microRNAs in serum: a novel class of biomarkers for diagnosis of cancer and other diseases. Cell Res 18: 997-1006.

75a. 1988 Centres for Disease Control and Prevention: Holmes G P, Kaplan J E, Gantz N M, Komaroff A L, Schonberger L B, Straus S E, et al. Chronic fatigue syndrome: a working case definition. Annals of internal medicine. 1988;108(3):387-9.

76a. Australian definition: Lloyd A R, Hickie I, Boughton C R, Spencer O, Wakefield D. Prevalence of chronic fatigue syndrome in an Australian population. The Medical journal of Australia. 1990;153(9):522-8.

77a. HO-yen definition: Ho-Yen D O. Patient management of post-viral fatigue syndrome. The British journal of general practice: the journal of the Royal College of General Practitioners. 1990;40(330):37-9.

78a. 1991 Oxford definition: Sharpe M C, Archard L C, Banatvala J E, Borysiewicz L K, Clare A W, David A, et al. A report-chronic fatigue syndrome: guidelines for research. Journal of the Royal Society of Medicine. 1991;84(2):118-21.

79a. 1994 CDC: Fukuda K, Straus S E, Hickie I, Sharpe M C, Dobbins J G, Komaroff A. The chronic fatigue syndrome: a comprehensive approach to its definition and study. International Chronic Fatigue Syndrome Study Group. Annals of internal medicine. 1994;121(12):953-9.

80a. CDC empirical definition: Reeves W C, Wagner D, Nisenbaum R, Jones J F, Gurbaxani B, Solomon L, et al. Chronic fatigue syndrome—a clinically empirical approach to its definition and study. BMC medicine. 2005;3:19.

81a. Canadian Consensus Criteria: Carruthers B M, Jain A K, de Meirleir K, Paterson D L, Klimas N, Lerner A M, et al. Myalgic encephalomyelitis/chronic fatigue syndrome: Clinical working case definition, diagnostic and treatment protocols. Journal of Chronic Fatigue Syndrome. 2003;11(1):7-36.

82a. International Consensus Criteria: Carruthers B M, van de Sande M I, De Meirleir K L, Klimas N G, Broderick G, Mitchell T, et al. Myalgic encephalomyelitis: International Consensus Criteria. Journal of internal medicine. 2011;270(4):327-38.

89a. Chiang V S-C. Post-harvest consideration factors for microRNA research in cellular, tissue, serum and plasma samples. 2034. Cell Biology International.

90a. Friedlander MR, Chen W, Adamidi C, Maaskola J, Einspanier R, Knespel S, Rajewsky N. Discovering microRNAs from deep sequencing data using miRDeep. Nat. Biotechnol. 2008;26:407-415.

91a. Friedlander M R, Mackowiak S D, Li N, Chen W, Rajewsky N. miRDeep2 accurately identifies known and hundreds of novel microRNA genes in seven animal clades. Nucleic Acids Res. 2012;40:37-52.

92a. An J, Lai J, Lehman M L, Nelson C C. miRDeep*: an integrated application tool for miRNA identification from RNA sequencing data. Nucleic Acids Res. 2013;41:727-737.

93a. Mathelier A, Carbone A. MIReNA: finding microRNAs with high accuracy and no learning at genome scale and from deep sequencing data. Bioinformatics. 2010;26: 2226-2234].

94a. Hackenberg M, Rodriguez-Ezpeleta N, Aransay A M. miRanalyzer: an update on the detection and analysis of microRNAs in high-throughput sequencing experiments. Nucleic Acids Res. 2011;39:W132-W138.

95a. Hackenberg M, Sturm M, Langenberger D, Falcon-Perez J M, Aransay A M. miRanalyzer: a microRNA detection and analysis tool for next-generation sequencing experiments. Nucleic Acids Res. 2009;37:W68-W76.

96a. Jones-Rhoades M W, Bartel D P. Computational identification of plant microRNAs and their targets, including a stress-induced miRNA. Mol. Cell. 2004;14:787-799.

97a. Wang X, Zhang J, Li F, Gu J, He T, Zhang X, Li Y. MicroRNA identification based on sequence and structure alignment. Bicinformatics. 2005;21:3610-3614].

98a. Nam J W, Shin K R, Han J J, Lee Y, Kim V N, Zhang B T. Human microRNA prediction through a probabilistic co-learning model of sequence and structure. Nucieic Acids Res. 2005;33:3570-3581.

99a. Kirtzou K, Tsainardinos I, Tsakalides P, Poirazi P. MatureBayes: a probabilistic algorithm for identifying the mature miRNA within novel precursors. PLoS One. 2010; 5:e11843.

100a. Xuan P, Guo M Z, Huang Y C, Li W B, Huang Y F. MaturePred: efficient identification of microRNAs within novel plant pre-miRNAs. PLoS One. 2011;6:e27422.

101a. He C, Li Y X, Zhang G, Gu Z, Yang R, Li J, Lu Z J, Zhou Z H, Zhang C, Wang J. MiRmat: mature microRNA sequence prediction. PLoS One. 2012;7:e51673.

102a. Leciercq M, Diallo AB, Blanchette. Computational prediction of the localization of microRNAs within their pre-miRNA. Nucleric Acids Res. 2013; 41(15):7200-7211.

103a. Pall G S, Codony-Servat C, Byrne J, Ritchie L, Hamilton A (2007) Carbodiimide-mediated cross-linking of RNA to nylon membranes improves the detection of siRNA, miRNA and piRNA by northern blot. Nucieic Acids Res 35:e60.

104a. Varallyay E, Burgyan J, Haveida Z (2007) Detection of microRNAs by Northern blot analyses using LNA probes. Methods 43:140-145.

105a. Git A, Dvinge H, Salmon-Divon M, Osborne M, Kutter C, Hadfield J, Bertone P, Caldas C (2010) Systematic comparison of microarray profiling, real-time PCR, and next-generation sequencing technologies for measuring differential microRNA expression. RNA 16:991-1006.

106a. Ambros V, Lee R C (2004) Identification of microRNAs and other tiny noncoding RNAs by cDNA cloning. Methods Mol Biol 265:131-138.

107a. Friedlander M R, Chen W, Adamidi C, Maaskola J, Einspanier R, Knespel S, Rajewsky N (2008) Discovering microRNAs from deep sequencing data using miRDeep. Nat Biotechnol 26:407-415.

110a. Maroney P A, Chamnongpol S, Souret F, Nilsen T W (2008) Direct detection of small RNAs using splinted ligation. Nat Protoc 3:279-287;

111a. Maroney P A, Chamnongpol S, Souret F, Nilsen T W (2007) A rapid, quantitative assay for direct detection of microRNAs and other small RNAs using splinted ligation. RNA 13:930-936.

1b. Clapham D E. TRP channels as cellular sensors. Nature. 2003;426(6966):517-24. doi: 10.1038/nature02196. PubMed PMID: 14654832.

2b. Nilius B, Owsianik G, Voets T, Peters J A. Transient receptor potential cation channels in disease. Physiological reviews. 2007;87(1):165-217. doi: 10.1152/physrev.00021.2006. PubMed PMID: 17237345.

3b. Nilius B, Owsianik G. The transient receptor potential family of ion channels. Genome biology. 2011;12(3):218. doi: 10.1186/gb-2011-12-3-218. PubMed PMID: 21401968; PubMed Central PMCID: PMC3129667.

4b. Nilius 8, Szallasi A. Transient receptor potential channels as drug targets: from the science of basic research to the art of medicine. Pharmacological reviews. 2014;66 (3):676-814. doi: 10.1124/pr.113.008268. PubMed PMID: 24951385.

5b. Nilius B, Biro T, Owsianik G. TRPV3: time to decipher a poorly understood family member! The Journal of physiology. 2014;592(Pt 2):295-304. doi: 10.1113/jphysiol.2013.255968. PubMed PMID: 23836684; PubMed Central PMCID: PMC3922494.

6b. Nilius B, Biro T TRPV3: a 'more than skinny' channel. Experimental dermatology. 2013;22(7):447-52. doi: 10.1111/exd.12163. PubMed PMID: 23800054.

7b. Nilius B, Voets T. The puzzle of TRPV4 channelopathies. EMBO reports. 2013;14(2):152-63. doi: 10.1038/embor.2012.219. PubMed PMID: 23306656; PubMed Central PMCID: PMC3566843.

8b. Vennekens R, Menigoz A, Nilius B. TRPs in the Brain. Reviews of physiology, biochemistry and pharmacology. 2012;163:27-64. doi: 10.1007/112_2012_8. PubMed PMID: 23184016.

9b. Moran M M, McAlexander M A, Biro T, Szallasi A. Transient receptor potential channels as therapeutic targets. Nature reviews Drug discovery. 2011;10(8):601-20. doi: 10.1038/nrd3456. PubMed PMID: 21804597.

10b. Nieto-Posadas A, Jara-Oseguera A, Rosenbaum T. TRP channel gating physiology. Current topics in medicinal chemistry. 2011;11(17):2J31-50. PubMed PMID: 21671880.

11b. Fernandez-Sola J, Lluis Padierna M, Nogue Xarau S, Munne Mas P. [Chronic fatigue syndrome and multiple chemical hypersensitivity after insecticide exposure]. Medicina clinica. 2005;124(12):451-3. PubMed PMID: 15826581.

12b. Lavergne M R, Cole D C, Kerr K, Marshall L M. Functional impairment in chronic fatigue syndrome, fibromyalgia, and multiple chemical sensitivity. Canadian family physician Medecin de familJe canadien. 2010;56 (2):e57-65. PubMed PMID: 20154232; PubMed Central PMCID: PMC2821254.

13b. Brown M M, Jason L A. Functioning in individuals with chronic fatigue syndrome: increased impairment with co-occurring multiple chemical sensitivity and fibromyalgia. Dynamic medicine: D M. 2007;6:6. doi: 10.1186/1476-5918-6-6. PubMed PMID: 17540028: PubMed Central PMCID: PMC1890280.

14b. Lind R, Berstad A, Hatlebakk J, Valcur J, Chronic fatigue in patients with unexplained self-reported food hypersensitivity and irritable bowel syndrome: validation of a Norwegian translation of the Fatigue Impact Scale. Clinical and experimental gastroenterology. 2013;6:101-7. doi: 10.2147/CEG.545760. PubMed PMID: 23869173; PubMed Central PMCID: PMC3706251.

15b. Aboudiab T, Leke L, Skonieczny M, Chouraki J P. [Are IgE-independent food hypersensitivity and chronic fatigue syndrome related?]. Archives de pediatric: organc officiel de la Societe francaise de pediatric. 2004;11(8): 975-7. doi: 10.1016/j.arcpcd.2004.05.012. PubMed PMID: 15288095.

16b. Brunet J L, Fatoohi F, Liaudet A P, Cozon G J. [Role of pathological delayed-type hypersensitivity in chronic fatigue syndrome: importance of the evaluation of lymphocyte activation by flow cytometry and the measurement of urinary nroptrrin]. Allergie et immunologie. 2002;34(2):38-44. PubMed PMID: 11933752.

17b. Light A R, Bateman L, Jo D, Hughen R W, Vanhaitsma T A, White A T, et al. Gene expression alterations at baseline and following moderate exercise in patients with Chronic Fatigue Syndrome and Fibromyalgia Syndrome. Journal of internal medicine. 2012;271(1):64-81. doi: 10.1111/j.1365-2796.2011.02405.x. PubMed PMID: 21615807: PubMed Central PMCID: PMC3175315.

18b. Gees M, Owsianik G, Nilius B, Voets T. TRP channels. Comprehensive Physiology. 2012:2(1):563-608. doi: 10.1002/cphy.c110026. PubMed PMID: 23728980.

19b. Nilius B, Owsianik G. Transient receptor potential channelopathies. Pflugers Archiv: European journal of physiology. 2010;460(2):437-50. doi: 10.1007/s00424-010-0788-2. PubMed PMID: 20127491.

20b. Fukuda K, Straus S E, Hickie I, Sharpe M C, Dobbins J G, Komaroff A. The chronic fatigue syndrome: a comprehensive approach to its definition and study. International Chronic Fatigue Syndrome Study Group. Ann Intern Med. 1994; 121(12):953-9. Epub 1994 Dec. 15. PubMed PMID: 7978722.

21b. Harvard. PLINK. Whole genome association analysis toolset 2014. Available from: http://pngu.mgh.harvard.edu/purcell/plink/.

22b. Freichel M, Tsvilovskyy V, Camacho-Londono J E. TRPC4- and TRPC4-containing channels. Handbook of experimental pharmacology. 2014;222:85-128. doi: 10.1007/978-3-642-54215-2_5. PubMed PMID: 24756704.

23b. Lewis R S. Calcium signaling mechanisms in T lymphocytes. Annual review of immunology. 2001;19:497-521. doi: 10.1146/annurev.immunol.19.1.497. PubMed PMID: 11244045.

24b. Brenu E W, Huth T K, Hardcastle S L, Fuller K, Kaur M, Johnston S, et al. Role of adaptive and innate immune cells in chronic fatigue syndrome/myalgic encephalomyelitis. International immunology. 2014;26(4):233-42. doi: 10.1093/intimm/dxt068. PubMed PMID: 24343819.

25b. Brenu E W, Ashton K J, van Driel M, Staines D R, Peterson D, Atkinson G M, et al. Cytotoxic lymphocyte microRNAs as prospective biomarkers for Chronic Fatigue Syndrome/Myalgic Encephalomyelitis. Journal of affective disorders. 2012;141(2-3):261-9. doi: 10.1016/j.jad.2012.03.037. PubMed PMID: 22572093.

26b. Brenu E W, van Driel M L, Staines D R, Ashton K J, Hardcastle S L, Keane J. et al. Longitudinal investigation of natural killer cells and cytokines in chronic fatigue syndrome/myalgic encephalomyelitis. Journal of translational medicine. 2012;10:88. doi: 10.1186/1479-5876-10-88. PubMed PMID: 22571715; PubMed Central PMCID: PMC3464733.

27b. Brenu E W, van Driel M L, Staines D R, Ashton K J, Ramos S B, Keane J, et al. Immunological abnormalities as potential biomarkers in Chronic Fatigue Syndrome/Myalgic Encephalomyelitis. Journal of translational medicine. 2011;9:81. doi: 10.1186/1479-5876-9-81. PubMed PMID: 21619669; PubMed Central PMCID: PMC3120691.

28b. Brenu E W, Staines D R, Baskurt O K, Ashton K J, Ramos S B, Christy R M, et al. Immune and hemorheological changes in chronic fatigue syndrome. Journal of translational medicine. 2010;8:1. doi: 10.1186/1479-5876-8-1. PubMed PMID: 20064266: PubMed Central PMCID: PMC2829521.

29b. Barker E, Fujimura S F, Fadem M B, Landay AL, Levy J A. Immunologic abnormalities associated with chronic fatigue syndrome. Clinical infectious diseases: an official publication of the Infectious Diseases Society of America. 1994;18 Suppl 1:S136-41. PubMed PMID: 8148441.

30b. Zhang Z, Seguela P. Metabotropic induction of persistent activity in layers II/III of anterior cingulate cortex. Cerebral cortex. 2010;20(12):2948-57. doi: 10.1093/cercor/bhq043. PubMed PMID: 20348157.

31b. Zhang Z, Reboreda A, Alonso A, Barker P A, Seguela P. TRPC channels underlie cholinergic plateau potentials and persistent activity in entorhinal cortex. Hippocampus. 2011;21(4):386-97. doi: 10.1002/hipo.20755. PubMed PMID: 20082292.

32b. Rainville P. Brain mechanisms of pain affect and pain modulation. Current opinion in neurobiology. 2002;12(2): 195-204. PubMed PMID: 12015237.

33b. Sewards T V, Sewards M A. The medial pain system: neural representations of the motivational aspect of pain. Brain research bulletin. 2002;59(3):163-80. PubMed PMID: 12431746.

34b. Yan H D, Villalobos C, Andrade R. TRPC Channels Mediate a Muscarinic Receptor-Induced Afterdepolarization in Cerebral Cortex. The Journal of neuroscience: the official journal of the Society for Neuroscience. 2009:29 (32): 10038-46. doi: 10.1523/JNEUROSCI.1042-09.2009. PubMed PMID: 19675237; PubMed Central PMCID: PMC2747319.

35b. Cascras X, Mataix-Cols D, Giampietro V, Rimes K A, Brammer M, Zelaya F, et al. Probing the working memory system in chronic fatigue syndrome: a functional magnetic resonance imaging study using the n-back task. Psychosomatic medicine. 2006;68(6):947-55. doi: 10.1097/01.psy.0000242770.50979.5f. PubMed PMID: 17079703.

36b. Caseras X, Mataix-Cols D, Rimes K A, Giampictro V, Brammer M, Zelaya F, et al. The neural correlates of fatigue: an exploratory imaginal fatigue provocation study in chronic fatigue syndrome. Psychological medicine. 2008;38(7):941-51. doi: 10.1017/S0033291708003450. PubMed PMID: 18447963.

37b. Nakatomi Y, Mizuno K, Ishii A, Wada Y, Tanaka M, Tazawa S, et al. Neuroinflammation in Patients with Chronic Fatigue Syndrome/Myalgic Encephalomyelitis: An 11C-(R)-PK11195 PET Study. Journal of nuclear medicine: official publication, Society of Nuclear Medicine. 2014;55(6):945-50. doi: 10.2967/jnumed.113.131045. PubMed PMID: 24665088.

38b. Tsvilovskyy V V, Zholos A V, Aberle T, Philipp S E, Dietrich A, Zhu M X, et al. Deletion of TRPC4 and TRPC6 in mice impairs smooth muscle contraction and intestinal motility in vivo. Gastroenterology. 2009;137(4): 1415-24. doi: 10.1053/j.gastro.2009.06.046. PubMed PMID: 19549525; PubMed Central PMCID: PMC2757464.

39b. Lakhan S E, Kirchgessner A. Gut inflammation in chronic fatigue syndrome. Nutrition & metabolism. 2010: 7:79. doi: 10.1186/1743-7075-7-79. PubMed PMID: 20939923: PubMed Central PMCID: PMC2964729.

40b. Kim H, Kim J, Jeon J P, Mycong J, Wie J, Hong C, et al. The roles of G proteins in the activation of TRPC4 and TRPC5 transient receptor potential channels. Channels. 2012;6(5):333-43. doi: 10.4161/chan.21198. PubMed PMID: 22878724; PubMed Central PMCID: PMC3508772.

41b. Bautista D M, Pellegrino M, Tsunozaki M. TRPA1: A gatekeeper for inflammation. Annual review of physiology. 2013;75:181-200. doi: 10.1146/annurev-physiol-030212-183811. PubMed PMID: 23020579; PubMed Central PMCID: PMC4041114.

42b. Wang S. Dai Y, Fukuoka T, Yamanaka H, Kobayashi K, Obata K, et al. Phospholipase C and proicin kinase A mediate bradykinin sensitization of TRPA1: a molecular mechanism of inflammatory pain. Brain: a journal of neurology. 2008;131(Pt 5):1241-51. doi: 10.1093/brain/awn060. PubMed PMID: 18356188.

43b. Wilson S R, Gerhold K A, Bifolck-Fisher A, Liu Q, Patel KN, Dong X, et al. TRPA1 is required for histamine-independent. Mas-related G protein-coupled receptor-mediated itch. Nature neuroscience. 2011;14(5):595-602. doi: 10.1038/nn.2789. PubMed PMID: 21460831; PubMed Central PMCID: PMC3181150.

44b. Nilius B, Prenen J, Owsianik G. Irritating channels: the case of TRPA1. The Journal of physiology. 2011;589(Pt 7):1543-9. doi: 10.1113/jphysiol.2010.200717. PubMed PMID: 21078588; PubMed Central PMCID: PMC3099014.

45b. Wagner T F, Loch S, Lambert S, Straub I, Mannebach S, Mathar I, et al. Transient receptor potential M3 channels are ionotropic steroid receptors in pancreatic beta cells. Nature cell biology. 2008;10(12):1421-30. doi: 10.1038/ncb1801. PubMed PMID: 18978782.

46b. Schutz M, Oertel B G, Heimann D, Doehring A, Walter C, Dimova V, et al. Consequences of a human TRPA1 genetic variant on the perception of nociceptive and olfactory stimuli. PloS one. 2014;9(4):e95592. doi: 10.1371/journal.pone.0095592. PubMed PMID: 24752136; PubMed Central PMCID: PMC4005389.

47b. Shigetomi E, Tong X, Kwan K Y, Corey D P, Khakh B S. TRPA1 channels regulate astrocyte resting calcium and inhibitory synapse efficacy through GAT-3. Nature neuroscience. 2012;15(1):70-80. doi: 10.1038/nn.3000. PubMed PMID: 22158513; PubMed Central PMCID: PMC3282183.

48b. Nassini R, Materazzi S, Vriens J, Prenen J, Benemei S, De Siena G, et al. The 'headache tree' via umbellulone and TRPA1 activates the trigeminovascular system. Brain: a journal of neurology. 2012;135(Pt 2):376-90. doi: 10.1093/brain/awr272. PubMed PMID: 22036959.

49b. Garrison S R, Stucky C L. The dynamic TRPA1 channel: a suitable pharmacological pain target? Current pharmaceutical biotechnology. 2011;12(10):1689-97. PubMed PMID: 21466445; PubMed Central PMCID: PMC3884818.

50b. Garrison S R, Stucky C L. Contribution of transient receptor potential ankyrin 1 to chronic pain in aged mice with complete Freund's adjuvant-induced arthritis. Arthritis & rheumatology. 2014;66(9):2380-90. doi: 10.1002/art.38724. PubMed PMID: 24891324; PubMed Central PMCID: PMC4149259.

51b. Fischer M J, Balasuriya D, Jeggle P, Goetze T A, McNaughton P A, Reeh P W, et al. Direct evidence for functional TRPV1/TRPA1 heteromers. Pflugers Archiv: European journal of physiology. 2014:466(12):2229-41. doi: 10.1007/s00424-014-1497-z. PubMed PMID: 24643480.

52b. Marincsak R, Toth B I, Czifra G, Szabo T, Kovacs L, Biro T. The analgesic drug, tramadol, acts as an agonist of the transient receptor potential vanilloid-1. Anesthesia and analgesia. 2008;106(6):1890-6. doi: 10.1213/ane.0b013e318172fefc. PubMed PMID: 18499628.

53b. Andersson D A, Gentry C, Alenmyr L, Killander D, Lewis S E, Andersson A, et al. TRPA1 mediates spinal antinociception induced by acetaminophen and the cannabinoid Delta(9)-tetrahydrocannabiorcol. Nature communications. 2011;2:551. doi: 10.1038/ncomms1559. PubMed PMID: 22109525.

54b. De Petrocellis L, Vellani V, Schiano-Moriello A, Marini P, Magherini P C, Orlando P, et al. Plant-derived cannabinoids modulate the activity of transient receptor potential channels of ankyrin type-1 and melastatin type-8. The Journal of pharmacology and experimental therapeutics. 2008;325(3):1007-15. doi: 10.1124/jpet.107.134809. PubMed PMID: 18354058.

55b. Oberwinkler J, Philipp S E. Trpm3. Handbook of experimental pharmacology. 2014;222:427-59. doi: 10.1007/978-3-642-54215-2_17. PubMed PMID: 24756716.

56b. Thiel G, Muller I, Rossler O G. Signal transduction via TRPM3 channels in pancreatic beta-cells. Journal of molecular endocrinology. 2013;50(3):R75-83. doi: 10.1530/JME-12-0237. PubMed PMID: 23511953.

57b. Colsoul B, Vennekens R, Nilius B. Transient receptor potential cation channels in pancreatic beta cells. Reviews of physiology, biochemistry and pharmacology. 2011; 161:87-110. doi: 10.1007/112_2011_2. PubMed PMID: 21744203.

58b. Wagner T F, Drews A, Loch S, Mohr F, Philipp S E, Lambert S, et al. TRPM3 channels provide a regulated influx pathway for zinc in pancreatic beta cells. Pflugers Archiv: European journal of physiology. 2010;460(4): 755-65. doi: 10.1007/s00424-010-0838-9. PubMed PMID: 20401728.

59b. Wyller V B, Godang K, Morkrid L, Saul J P, Thaulow E, Walloe L. Abnormal thermoregulatory responses in adolescents with chronic fatigue syndrome: relation to clinical symptoms. Pediatrics. 2007;120(1):e129-37. doi: 10.1542/peds.2006-2759. PubMed PMID: 17606539.

60b. Meeus M, Nijs J. Central sensitization: a biopsychosocial explanation for chronic widespread pain in patients with fibromyalgia and chronic fatigue syndrome. Clinical rheumatology. 2007;26(4):465-73. doi: 10.1007/s10067-006-0433-9. PubMed PMID: 17115100: PubMed Central PMCID: PMC1820749.

61b. Nilius B, Vocts T. A TRP channel-steroid marriage. Nature cell biology. 2008;10(12):1383-4. doi: 10.1038/ncb1208-1383. PubMcd PMID: 19043430.

62b. Drews A, Mohr F, Rizun O, Wagner T F, Dembla S, Rudolph S, et al. Structural requirements of steroidal agonists of transient receptor potential melastatin 3 (TRPM3) cation channels. British journal of pharmacology. 2014;171(4):1019-32. doi: 10.1111/bph.12521. PubMed PMID: 24251620; PubMed Central PMCID: PMC3925040.

63b. Zamudio-Bulcock P A, Everett J, Harteneck C, Valenzuela C F. Activation of steroid-sensitive TRPM3 channels potentiates glutamatergic transmission at cerebellar Purkinje neurons from developing rats. Journal of neurochemistry. 2011;119(3):474-85. doi: 10.1111/j.1471-4159.2011.07441.x. PubMed PMID: 21955047; PubMed Central PMCID: PMC3192925.

1c. Beckmann J, Lips K S. The Non-Neuronal Cholinergic System in Health and Disease. Pharmacology. 2013;92 (5-6):286-302. doi:Doi 10.1159/000355835.

2c. Elhussciny A, Hamel E. Muscarinic—but not nicotinic—acctylcholine receptors mediate a nitric oxide-dependent dilation in brain cortical arterioles: a possible role for the M5 receptor subtype. Journal of cerebral blood flow and metabolism: official journal of the International Society of Cerebral Blood Flow and Metabolism. 2000;20(2):298-305. doi: 10.1097/00004647-200002000-00011.

3c. Felder C C, Bymaster F P, Ward J, DeLapp N. Therapeutic opportunities for muscarinic receptors in the central nervous system. Journal of medicinal chemistry. 2000;43(23):4333-53.

4c. Oki T, Takagi Y, Inagaki S, Taketo M M, Manabe T, Matsui M et al. Quantitative analysis of binding parameters of [3H]N-mcthylscopolamine in central nervous system of muscarinic acetylcholine receptor knockout mice. Brain research Molecular brain research. 2005;133 (1):6-11. doi: 10.1016/j.molbrainres.2004.09.012.

5c. Sharma G, Vijayaraghavan S. Nicotinic cholinergic signaling in hippocampal astrocytes involves calcium-induced calcium release from intracellular stores. Proceedings of the National Academy of Sciences of the United States of America. 2001;98(7):4148-53. doi: 10.1073/pnas.071540198.

6c. Wess J, Duttaroy A, Zhang W, Gomeza J, Cui Y, Miyakawa T et al. M1-M5 muscarinic receptor knockout 7c. Lanzafame A A, Christopoulos A, Mitchelson F. Cellular signaling mechanisms for muscarinic acetylcholine receptors. Receptors & channels. 2003;9(4):241-60.

8c. Wess J. Molecular biology of muscarinic acetylcholine receptors. Critical reviews in neurobiology. 1996;10(1):69-99.

9c. Veldhuis N A, Poole D P, Grace M, McIntyre P, Bunnett N W. The G protein-coupled receptor-transient receptor potential channel axis: molecular insights for targeting disorders of sensation and inflammation. Pharmacological reviews. 2015;67(1):36-73. doi:10.1124/pr.114.009555.

10c. Nilius B, Szallasi A. Transient receptor potential channels as drug targets: from the science of basic research to the art of medicine. Pharmacological reviews. 2014;66(3):676-814. doi:10.1124/pr.113.008268.

11c. Hurst R, Rollema H, Bertrand D. Nicotinic acetylcholine receptors: from basic science to therapeutics. Pharmacology & therapeutics. 2013; 137(1):22-54. doi: 10.1016/j.pharmthera.2012.08.012.

12c. Aaron L A, Burke M M, Buchwald D. Overlapping conditions among patients with chronic fatigue syndrome, fibromyalgia, and temporomandibular disorder. Archives of internal medicine. 2000;160(2):221-7.

13c. Allen J, Murray A,. Di Maria C, Newton J L. Chronic fatigue syndrome and impaired peripheral pulse characteristics on orthostasis—a new potential diagnostic biomarker. Physiological measurement. 2012;33(2):231-41. doi 10.1088/0967-3334/33/2/231.

14c. Brenu E W, Ashton K J, van Driel M, Staines D R, Peterson D, Atkinson G M et al. Cytotoxic lymphocyte microRNAs as prospective biomarkers for Chronic Fatigue Syndrome/Myalgic Encephalomyelitis. Journal of affective disorders. 2012;141(2-3):261-9. doi:10.1016/j.jad.2012.03.037.

15c. Brenu E W. Huth T K, Hardcastle S L, Fuller K, Kaur M, Johnston S et al. Role of adaptive and innate immune cells in chronic fatigue syndrome/myalgic encephalomyelitis. International immunology. 2014;26(4):233-42. doi: 10.1093/intimm/dxt068.

16c. Brenu E W, Staines D R, Baskurt O K, Ashton K J, Ramos S B, Christy R M et al. Immune and hemorheological changes in chronic fatigue syndrome. Journal of translational medicine. 2010;8:1. doi:10.1186/1479-5876-8-1.

17c. Brenu E W, van Driel M L, Staines D R, Ashton K J, Hardcastle S L, Keane J et al. Longitudinal investigation of natural killer cells and cytokines in chronic fatigue syndrome/myalgic encephalomyelitis. Journal of translational medicine. 2012;10:88. doi:10.1186/1479-5876-10-88.

18c. Brenu E W, van Driel M L, Staines D R, Ashton K J, Ramos S B, Keane J et al. Immunological abnormalities as potential biomarkers in Chronic Fatigue Syndrome/Myalgic Encephalomyelitis. Journal of translational medicine. 2011;9:81. doi:10.1186/1479-5876-9-81.

19c. DeLuca J, Johnson S K, Beldowicz D, Natelson B H. Neuropsychological impairments in chronic fatigue syndrome, multiple sclerosis, and depression. Journal of neurology, neurosurgery, and psychiatry. 1995;58(1):38-43.

20c. Grafman J, Schwartz V, Dale J K, Scheffers M, Houser C, Straus S E. Analysis of neuropsychological functioning in patients with chronic fatigue syndrome. Journal of neurology, neurosurgery, and psychiatry. 1993;56(6):684-9.

21c. Hoad A, Spickett G, Elliott J, Newton J. Postural orthostatic tachycardia syndrome is an under-recognized condition in chronic fatigue syndrome. QJM: monthly journal of the Association of Physicians. 2008:101(12): 961-5. doi:10.1093/qjmed/hcn123.

22c. Joyce E, Blumenthal S, Wessely S. Memory, attention, and executive function in chronic fatigue syndrome. Journal of neurology, neurosurgery, and psychiatry. 1996;60(5):495-503.

23c. Klimas N G, Salvato F R, Morgan R, Fletcher M A. Immunologic abnormalities in chronic fatigue syndrome. Journal of clinical microbiology. 1990;28(6):1403-10.

24c. Krupp L B, Sliwinski M, Masur D M, Friedberg F, Coyle P K. Cognitive functioning and depression in patients with chronic fatigue syndrome and multiple sclerosis. Archives of neurology. 1994;51(7):705-10.

25c. Lewis I, Pairman J, Spickett G, Newton J L. Clinical characteristics of a novel subgroup of chronic fatigue syndrome patients with postural orthostatic tachycardia syndrome. Journal of internal medicine. 2013;273(5):501-10. doi:10.1111/joim.12022.

26c. McDonald E, Cope H, David A. Cognitive impairment in patients with chronic fatigue: a preliminary study. Journal of neurology, neurosurgery, and psychiatry. 1993; 56(7):812-5.

27c. Mcdow M S, Stewart JM. The postural tachycardia syndrome. Cardiology in review. 2007:15(2):67-75. doi: 10.1097/01.crd.0000233768.68421.40.

28c. Nisenbaum R, Reyes M, Mawle A C, Reeves W C. Factor analysis of unexplained severe fatigue and inter-related symptoms: overlap with criteria for chronic fatigue syndrome. American journal of epidemiology. 1998;148(1):72-7.

29c. Ocon A J, Medow M,S, Taneja I, Clarke D, Stewart J M. Decreased upright cerebral blood flow and cerebral autoregulation in normocapnic postural tachycardia syndrome. American journal of physiology Heart and circulatory physiology. 2009:297(2):H664-73. doi:10.1152/ajpheart.00138.2009.

30c. Khan F, Kennedy G, Spence V A, Newton D J, Belch J J. Peripheral cholinergic function in humans with chronic fatigue syndrome. Gulf War syndrome and with illness following organophosphate exposure. Clinical science. 2004;106(2):183-9. doi:10.1042/CS20030246.

31c. Spence V A, Khan F, Kennedy G, Abbot N C, Belch J J. Acetylcholine mediated vasodilatation in the microcirculation of patients with chronic fatigue syndrome. Prostaglandins, leukotrienes, and essential fatty acids. 2004; 70(4):403-7. doi:10.1016/j.plefa.2003.12.016.

32c. Kawashima K, Fujii T, Moriwaki Y, Misawa H. Critical roles of acetylcholine and the muscarinic and nicotinic acetylcholine receptors in the regulation of immune function. Life sciences. 2012;91(21-22):1027-32. doi: 10.1016/j.lfs.2012.05.006.

33c. Kawashima K, Fujii T. Extraneuronal cholinergic system in lymphocytes. Pharmacology & therapeutics. 2000: 86(1):29-48. doi:Doi 10.1016/S0163-7258(99)00071-6.

34c. Kawashima K, Fujii T. The lymphocytic cholinergic system and its biological function. Life sciences. 2003; 72(18-19):2101-9.

35c. Sato K Z, Fujii T, Watanabe Y, Yamada S, Ando T, Kazuko F et al. Diversity of mRNA expression for muscarinic acetylcholine receptor subtypes and neuronal nicotinic acetylcholine receptor subunits in human mononuclear leukocytes and leukemic cell lines. Neuroscience letters. 1999;266(1):17-20.
36c. Fukuda K, Straus S E, Hickie I, Sharpe M C, Dobbins J G, Komaroff A. The chronic fatigue syndrome: a comprehensive approach to its definition and study. International Chronic Fatigue Syndrome Study Group. Ann Intern Med. 1994;121(12):953-9.
37c. Oeth P, Beaulieu M, Park C, Kosman D, del Mistro G, van den Boom D et al. iPLEX™ assay: increased plexing efficiency and flexibility for MassARRAY® system through single base primer extension with mass-modified terminators. Sequenom application note. 2005:8876-006.
39c. Harvard. PLINK whole genome association analysis toolset. 2014. http://pngu.mgh.harvard.edu/purcell/pink/.
40c. Phelan K D, Shwe U T, Abramowitz J, Wu H, Rhee S W, Howell M D et al. Canonical transient receptor channel 5 (TRPC5) and TRPC1/4 contribute to seizure and excitotoxicity by distinct cellular mechanisms. Molecular pharmacology. 2013;83(2):429-38. doi:10.1124/mol.112.082271.
41c. Phelan K D, Mock M M, Kretz O, Shwe U T, Kozhemyakin M, Greenfield L J et al. Heteromeric canonical transient receptor potential 1 and 4 channels play a critical role in epileptiform burst firing and seizure-induced neurodegeneration. Molecular pharmacology. 2012;81(3): 384-92. doi:10.1124/mol.111.075341.
42c. von Spiczak S, Muhle H, Helbig I, de Kovel C G, Hampe J, Gaus V et al. Association study of TRPC4 as a candidate gene for generalized epilepsy with photosensitivity. Neuromolecular medicine. 2010;12(3):292-9. doi: 10.1007/s12017-010-8122-x.
43c. Conti-Fine B M, Navaneetham D, Lei S, Maus A D. Neuronal nicotinic receptors in non-neuronal cells: new mediators of tobacco toxicity? European journal of pharmacology. 2000:393(1-3):279-94.
44c. Elwary S M A, Hasse S, Schallreuter K U. M2 muscarinic acetylcholine receptor (mAchR) subtype is present in human epidermal keratinocytes in situ and in vitro. Journal of Investigative Dermatology. 2004:123(6): 1206-7. doi:DOI 10.1111/j.0022-202X.2004.23493.x.
45c. Gahring L C, Rogers S W. Neuronal nicotinic acetylcholine receptor expression and function on nonneuronal cells. The AAPS journal. 2005:7(4):E885-94. doi: 10.1208/aapsj070486.
46c. Gupta V, Thompson E B, Stock-Novack D, Salmon S E, Pierce H I, Bonnet J D et al. Efficacy of prednisone in refractory multiple myeloma and measurement of glucocorticoid receptors. A Southwest Oncology Group study. Investigational new drugs. 1994:12(2):121-8.
47c. Kurzen H, Wessler I, Kirkpatrick C J, Kawashima K, Grando S A. The non-neuronal cholinergic system of human skin. Hormone and metabolic research=Hormon- und Stoffwechselforschung=Hormones et metabolisme. 2007;39(2):125-35. doi:10.1055/s-2007-961816.
48c. Macklin KD, Maus A D, Pereira E F, Albuquerque E X, Conti-Fine B M. Human vascular endothelial cells express functional nicotinic acetylcholine receptors. The Journal of pharmacology and experimental therapeutics. 1998;287(1):435-9.
49c. Maus A D, Pereira E F, Karachunski P I, Horton R M, Navaneetham D, Macklin K et al. Human and rodent bronchial epithelial cells express functional nicotinic acetylcholine receptors. Molecular pharmacology. 1998;54 (5):779-88.
50c. Mayerhofer A, Fritz S. Ovarian acetylcholine and muscarinic receptors: hints of a novel intrinsic ovarian regulatory system. Microscopy research and technique. 2002;59(6):503-8. doi:10.1002/jemt.10228.
51c. Ndoye A, Buchli R, Greenberg B, Nguyen V T, Zia S, Rodriguez J G et al. Identification and mapping of keratinocyte muscarinic acetylcholine receptor subtypes in human epidermis. The Journal of investigative dermatology. 1998;111(3):410-6. doi:10.1046/j.1523-1747.1998.00299.x.
52c. Pamavelas J G, Mione M C, Lavdas A. The cell lineage of neuronal subtypes in the mammalian cerebral cortex. Ciba Foundation symposium. 1995;193:41-58; discussion 9-70.
53c. Fujii T, Takada-Takatori Y, Kawashima K. Regulatory mechanisms of acetylcholine synthesis and release by T cells. Life sciences. 2012;91(21-22):981-5. doi:10.1016/j.lfs.2012.04.031.
54c. Paldiharis P, Szelenyi J G, Nguyen T H, Hollan S R. Changes in the Expression of the Cholinergic Structures of Human Lymphocytes-T Due to Maturation and Stimulation. Thymus. 1990:16(2):119-22.
55c. Benhammou K, Lee M, Strook M, Sullivan B, Logel J, Raschen K et al. [H-3]nicotine binding in peripheral blood cells of smokers is correlated with the number of cigarettes smoked per day. Neuropharmacology. 2000;39 (13):2818-29. doi:Doi 10.1016/S0028-3908(00)00153-2.
56c. Kuo Y P, Lucero L, Michaels J, DeLuca D, Lukas R J. Differential expression of nicotinic acetylcholine receptor subunits in fetal and neonatal mouse thymus. Journal of neuroimmunology. 2002:130(1-2):140-54. doi:Pii S0165-5728(02)00220-5 Doi 10.1016/S0165-5728(02)00220-5.
57c. Middlebrook A J, Martina C, Chang Y, Lukas R J, DeLuca D. Effects of nicotine exposure on T cell development in fetal thymus organ culture: Arrest of T cell maturation. Journal of immunology. 2002;169(6):2915-24.
58c. Richman D P, Amason B G W. Nicotinic Acetylcholine-Receptor—Evidence for a Functionally Distinct Receptor on Human-Lymphocytes. Proceedings of the National Academy of Sciences of the United States of America. 1979;76(9):4632-5. doi:DOI 10.1073/pnas.76.9.4632.
59c. Skok M V, Kalashnik E N, Koval L N, Tsetlin V I, Utkin Y N, Changeux J P et al. Functional nicotinic acetylcholine receptors are expressed in B lymphocyte-derived cell lines. Molecular pharmacology. 2003;64(4):885-9. doi: Doi 10.1124/Mol.64.4.885.
60c. Matteoli G, Boeckxstaens G E. The vagal innervation of the gut and immune homeostasis. Gut. 2013;62(8) 1214-22. doi:DOI 10.1136/gutjnl-2012-302550.
61c. Richardson C E, Morgan J M, Jasani B, Green J T, Rhodes J, Williams G T et al. Effect of smoking and transdermal nicotine on colonic nicotinic acetylcholine receptors in ulcerative colitis. Qjm-Int J Med. 2003;96 (1):57-65. doi:Doi 10.1093/Qjmed/Hcg007.
62c. Gautam D, Han S J, Hamdan F F, Jeon J, Li B, Li J H et al. A critical role for beta cell M3 muscarinic acetylcholine receptors in regulating insulin release and blood glucose homeostasis in vivo. Cell metabolism. 2006;3(6): 449-61. doi: 10.1016/j.cmet.2006.04.009.
63c. Gromada J, Hughes T E. Ringing the dinner bell for insulin: muscarinic M3 receptor activity in the control of pancreatic beta cell function. Cell metabolism. 2006;3(6): 390-2. doi:10.1016/j.cmet.2006.05.004.
64c. Morris G, Maes M. Mitochondrial dysfunctions in Myalgic Encephalomyelitis/chronic fatigue syndrome explained by activated immuno-inflammatory, oxidative and nitrosative stress pathways. Metab Brain Dis. 2014; 29(1):19-36. doi:DOI 10.1007/s11011-013-9435-x.

65c. Hellman B, Dansk H, Grapengiesser E. Activation of alpha adrenergic and muscarinic receptors modifies early glucose suppression of cytoplasmic Ca(2+) in pancreatic beta-cells. Biochemical and biophysical research communications. 2014;445(3):629-32. doi:10.1016/j.bbrc.2014.02.056.

66c. Wang H, Lu Y, Wang Z. Function of cardiac M3 receptors. Autonomic & autacoid pharmacology. 2007;27(1):1-11. doi:10.1111/j.1474-8673.2006.00381.x.

67c. van Borren M M, Verkerk A O, Wilders R, Hajji N, Zegers J G, Bourier J et al. Effects of muscarinic receptor stimulation on Ca2+ transient, cAMP production and pacemaker frequency of rabbit sinoatrial node cells. Basic research in cardiology. 2010;105(1):73-87. doi:10.1007/s00395-009-0048-9.

68c. Bruggmann D, Lips K S, Pfwil U, Haberberger R V, Kummer W. Rat arteries contain multiple nicotinic acetylcholine receptor alpha-subunits. Life sciences. 2003;72(18-19):2095-9.

69c. Wang Y, Pereira E F, Maus A D, Ostlic N S, Navaneetham D, Lei S et al. Human bronchial epithelial and endothelial cells express alpha7 nicotinic acetylcholine receptors. Molecular pharmacology. 2001;60(6):1201-9.

70c. Abbruscato T J, Lopez S P, Mark K S, Hawkins B T, Davis T P. Nicotine and cotinine modulate cerebral microvascular permeability and protein expression of ZO-1 through nicotinic acetylcholine receptors expressed on brain endothelial cells. Journal of pharmaceutical sciences. 2002;91(12):2525-38. doi: 10.1002/jps.10256.

71c. Girod R, Crabtree G, Ernstrom G, Ramirez-Latorre J, McGehee D, Turner J et al. Heteromeric complexes of alpha 5 and/or alpha 7 subunits. Effects of calcium and potential role in nicotine-induced presynaptic facilitation. Annals of the New York Academy of Sciences. 1999:868: 578-90.

72c. Yu C R, Role L W. Functional contribution of the alpha5 subunit to neuronal nicotinic channels expressed by chick sympathetic ganglion neurones. The Journal of physiology. 1998:509 ( Pt 3):667 81.

73c. Wang N, Orr-Urtreger A, Chapman J, Ergun Y, Rabinowitz R, Korczyn A D. Hidden function of neuronal nicotinic acetylcholine receptor beta2 subunits in ganglionic transmission: comparison to alpha5 and beta4 subunits. Journal of the neurological sciences. 2005;228(2): 167-77. doi: 10.1016/j.jns.2004.11.050.

74c. Wang Z Z, Hardy S F, Hall Z W. Assembly of the nicotinic acetylcholine receptor. The first transmembrane domains of truncated alpha and delta subunits are required for heterodimer formation in vivo. The Journal of biological chemistry. 1996;271(44):27575-84.

75c. Changeux J, Edelstein S J. Allosteric mechanisms in normal and pathological nicotinic acetylcholine receptors. Current opinion in neurobiology. 2001:11(3):369-77.

76c. Gotti C, Moretti M, Maggi R, Longhi R, Hanke W, Klinke N et al. Alpha7 and alpha8 nicotinic receptor subtypes immunopurified from chick retina have different immunological, pharmacological and functional properties. The European journal of neuroscience. 1997:9(6): 1201-11.

77c. Hogg R C, Raggenbass M, Bertrand D. Nicotinic acetylcholine receptors: from structure to brain function. Reviews of physiology, biochemistry and pharmacology. 2003:147:1-46. doi: 10.1007/s10254-003-0005-1.

78c. Mattick P, Parrington J, Odia E, Simpson A, Collins T, Terrar D. Ca2+-stimulated adenylyl cyclase isofomi AC1 is preferentially expressed in guinea-pig sino-atrial node cells and modulates the I(f) pacemaker current. The Journal of physiology. 2007:582(Pt 3):1195-203. doi: 10.1113/jphysiol.2007.133439.

79c. Sanchez G, Colettis N, Vazquez P, Cervenansky C, Aguirre A, Quillfeldt J A et al. Muscarinic inhibition of hippocampal and striatal adenylyl cyclase is mainly due to the M(4) receptor. Neurochemical research. 2009:34(8): 1363-71. doi:10.1007/s11064-009-9916-9.

80c. Merriam L A, Roman C W, Baran C N, Girard B M, May V, Parsons R L. Pretreatment with nonselective cationic channel inhibitors blunts the PACAP-induced increase in guinea pig cardiac neuron excitability. Journal of molecular neuroscience: MN. 2012;48(3):721-9. doi: 10.1007/s12031-012-9763-z.

81c. Harfi I, Corazza F, D'Hondt S, Sariban E. Differential calcium regulation of proinflammatory activities in human neutrophils exposed to the neuropeptide pituitary adenylate cyclase-activating protein. Journal of immunology. 2005;175(6):4091-102.

82c. Fukuchi M, Tabuchi A, Tsuda M. Transcriptional regulation of neuronal genes and its effect on neural functions: cumulative mRNA expression of PACAP and BDNF genes controlled by calcium and cAMP signals in neurons. Journal of pharmacological sciences. 2005;98(3): 212-8.

1d. Nilius B, Owsianik G. The transient receptor potential family of ion channels. Genome biology. 2011;12(3):218. doi:10.1186/gb-2011-12-3-218.

2d. Nilius B, Szallasi A. Transient receptor potential channels as drug targets: from the science of basic research to the art of medicine. Pharmacological reviews. 2014;66 (3):676-814. doi:10.1124/pr.113.008268.

3d. Nilius B, Biro T, Owsianik G. TRPV3: time to decipher a poorly understood family member! The Journal of physiology. 2014;592(Pt 2):295-304. doi:10.1113/jphysiol.2013.255968.

4d. Nilius B, Biro T. TRPV3: a 'more than skinny' channel. Experimental dermatology. 2013;22(7):447-52. doi: 10.1111/exd.12163.

5d. Nilius B, Voets T. The puzzle of TRPV4 channelopathies. EMBO reports. 2013;14(2):152-63. doi:10.1038/embor.2012.219.

6d. Vennckens R, Menigoz A, Nilius B. TRPs in the Brain. Reviews of physiology, biochemistry and pharmacology. 2012:163:27-64. doi 10.1007/112_2012_8.

7d. Beckmann J, Lips K S. The non-neuronal cholinergic system in health and disease. Pharmacology. 2013;92(5-6):286-302. doi:10.1159/000355835.

8d. Lanzafame A A, Christopoulos A, Mitchelson F. Cellular signaling mechanisms for muscarinic acetylcholine receptors. Receptors & channels. 2003;9(4):241-60.

9d. Wess J. Molecular biology of muscarinic acetylcholine receptors. Critical reviews in neurobiology. 1996;10(1): 69-99.

10d. Cartegni L, Krainer A R. Correction of disease-associated exon skipping by synthetic exon-specific activators. Nature structural biology. 2003:10(2):120-5. doi: 10.1038/nsb887.

11d. Pagani F, Baralle F E. Genomic variants in exons and introns: identifying the splicing spoilers. Nature reviews Genetics. 2004;5(5):389-96. doi:10.1038/nrg1327.

14d. Aaron L A, Burke M M, Buchwald D. Overlapping conditions among patients with chronic fatigue syndrome, fibromyalgia, and temporomandibular disorder. Archives of internal medicine. 2000;160(2):221-7.

15d. Allen J, Murray A, Di Maria C, Newton J L. Chronic fatigue syndrome and impaired peripheral pulse characteristics on orthostasis—a new potential diagnostic biomarker. Physiological measurement. 2012;33(2):231-41. doi:10.1088/0967-3334/33/2/231.

16d. Brenu E W, Ashton K J, van Driel M, Staines D R, Peterson D, Atkinson G M et al. Cytotoxic lymphocyte microRNAs as prospective biomarkers for Chronic Fatigue Syndrome/Myalgic Encephalomyelitis. Journal of affective disorders. 2012;141(2-3):261-9. doi:10.1016/j.jad.2012.03.037.

17d. Brenu E W, Huth T K, Hardcastle S L, Fuller K, Kaur M, Johnston S et al. Role of adaptive and innate immune cells in chronic fatigue syndrome/myalgic encephalomyelitis. International immunology. 2014;26(4):233-42. doi: 10.1093/intimm/dxt068.

18d. Brenu E W, Staines D R, Baskurt O K, Ashton K J, Ramos S B, Christy R M et al. Immune and hemorheological changes in chronic fatigue syndrome. Journal of translational medicine. 2010:8:1. doi:10.1186/1479-5876-8-1.

19d. Brenu E W, van Driel M L, Staines D R, Ashton K J, Hardcastle S L, Keane J et al. Longitudinal investigation of natural killer cells and cytokines in chronic fatigue syndrome/myalgic encephalomyelitis. Journal of translational medicine. 2012;10:88. doi:10.1186/1479-5876-10-88.

20d. Brenu E W, van Driel M L, Staines D R, Ashton K J, Ramos S B, Keane J et al. Immunological abnormalities as potential biomarkers in Chronic Fatigue Syndrome/Myalgic Encephalomyelitis. Journal of translational medicine. 2011;9:81. doi:10.1186/1479-5876-9-81.

21d. DeLuca J, Johnson S K, Beldowicz D, Natelson B H. Neuropsychological impairments in chronic fatigue syndrome, multiple sclerosis, and depression. Journal of neurology, neurosurgery, and psychiatry. 1995;58(1):38-43.

22d. Cirafman J, Schwartz V, Dale J K, Scheffers M, Houser C, Straus S E. Analysis of neuropsychological functioning in patients with chronic fatigue syndrome. Journal of neurology, neurosurgery, and psychiatry. 1993;56(6):684-9.

23d. Hoad A, Spickett G, Elliott J, Newton J. Postural orthostatic tachycardia syndrome is an under-recognized condition in chronic fatigue syndrome. QJM: monthly journal of the Association of Physicians. 2008:101(12): 961-5. doi:10.1093/qjmed/hcn123.

24d. Joyce E, Blumenthal S, Wessely S. Memory, attention, and executive function in chronic fatigue syndrome. Journal of neurology, neurosurgery, and psychiatry. 1996;60 (5):495-503.

25d. Klimas N G, Salvato F R, Morgan R, Fletcher M A. Immunologic abnormalities in chronic fatigue syndrome. Journal of clinical microbiology. 1990;28(6):1403-10.

26d. Krupp L B, Sliwinski M, Masur D M, Friedberg F, Coyle P K. Cognitive functioning and depression in patients with chronic fatigue syndrome and multiple sclerosis. Archives of neurology. 1994;51(7):705-10.

27d. Lewis I, Pairman J, Spickett G, Newton J L. Clinical characteristics of a novel subgroup of chronic fatigue syndrome patients with postural orthostatic tachycardia syndrome. Journal of internal medicine. 2013:273(5):501-10. doi:10.1111/joim.12022.

28d. McDonald E, Cope H, David A. Cognitive impairment in patients with chronic fatigue: a preliminary study. Journal of neurology, neurosurgery, and psychiatry. 1993; 56(7):812-5.

29d. Medow M S, Stewart J M. The postural tachycardia syndrome. Cardiology in review. 2007;15(2):67-75. doi: 10.1097/01.crd.0000233768.68421.40.

30d. Nisenbaum R, Reyes M, Mawle A C, Reeves W C. Factor analysis of unexplained severe fatigue and inter-related symptoms: overlap with criteria for chronic fatigue syndrome. American journal of epidemiology. 1998:148(1):72-7.

31d. Ocon A J, Medow M S, Taneja I, Clarke D, Stewart J M. Decreased upright cerebral blood flow and cerebral autoregulation in normocapnic postural tachycardia syndrome. American journal of physiology Heart and circulatory physiology. 2009;297(2):H664-73. doi:10.1152/ajphcart.00138.2009.

32d. Fukuda K, Straus S E, Hickie I, Sharpe M C, Dobbins J G, Komaroff A. The chronic fatigue syndrome: a comprehensive approach to its definition and study. International Chronic Fatigue Syndrome Study Group. Ann Intern Med. 1994;121(12):953-9.

33d. NCBI. TRPM3 transient receptor potential catial channel, subfamily M, member 3. 2015. http://www.ncbi.nlm.nih.gov/gene/?term=80036.

34d. NCBI. CHRM3 cholinergic receptor, muscarinic 3. 2015. http://www.ncbi.nlm.nih.gov/gene/?term=1131. Accessed Apr. 17 2015.

35d. Ensembl. Human assembly and gene annotation. 2015. http://uswest.ensembl.org/Homo_sapiens/Info/Annotation. Accessed 17 Apr. 2015.

36d. Pan Q, Shai O, Lee L J, Frey B J, Blencowe B J. Deep surveying of alternative splicing complexity in the human transcriptome by high-throughput sequencing. Nature genetics. 2008;40(12):1413-5. doi:10.1038/ng.259.

37d. Wang H, Lu Y, Wang Z. Function of cardiac M3 receptors. Autonomic & autacoid pharmacology. 2007;27 (1):1-11. doi:10.1111/j.1474-8673.2006.00381.x.

38d. Fedor M J. Alternative splicing minireview series: combinatorial control facilitates splicing regulation of gene expression and enhances genome diversity. The Journal of biological chemistry. 2008;283(3):1209-10. doi:10.1074/jbc.R700046200.

39d. Crawford D J, Hoskins A A, Friedman L J, Gelles J, Moore MJ . Single-molecule colocalization FRET evidence that spliceosome activation precedes stable approach of 5' splice site and branch site. Proceedings of the National Academy of Sciences of the United States of America. 2013;110(17):6783-8. doi:10.1073/pnas.1219305110.

40d. Shcherbakova I, Hoskins A A, Friedman L J, Serebrov V, Correa I R, Jr., Xu M Q et al. Alternative spliceosome assembly pathways revealed by single-molecule fluorescence microscopy. Cell reports. 2013;5(1):151-65. doi: 10.1016/j.celrep.2013.08.026.

41d. Oberwinkler J, Philipp S E. Trpm3. Handbook of experimental pharmacology. 2014;222:427-59. doi 10.1007/978-3-642-54215-2_17.

42d. Rainville P. Brain mechanisms of pain affect and pain modulation. Current opinion in neurobiology. 2002;12(2): 195-204.

43d. Sewards T V, Sewards M A. The medial pain system: neural representations of the motivational aspect of pain. Brain research bulletin. 2002;59(3):163-80.

44d. Yan H D, Villalobos C, Andrade R. TRPC Channels Mediate a Muscarinic Receptor-Induced Afterdepolarization in Cerebral Cortex. The Journal of neuroscience: the official journal of the Society for Neuroscience. 2009:29 (32):10038-46. doi:10.1523/JNEUROSCI.1042-09.2009.

45d. Caseras X, Mataix-Cols D, Giampietro V, Rimes K A, Brammer M, Zelaya F et al. Probing the working memory system in chronic fatigue syndrome: a functional magnetic resonance imaging study using the n-back task.

Psychosomatic medicine. 2006;68(6):947-55. doi: 10.1097/01.psy.0000242770.50979.5f.
46d. Caseras X, Mataix-Cols D, Rimes K A, Giampietro V, Brammer M, Zelaya F et al. The neural correlates of fatigue: an exploratory imaginal fatigue provocation study in chronic fatigue syndrome. Psychological medicine. 2008;38(7):941-51. doi:10.1017/S0033291708003450.
47d. Nakatomi Y, Mizuno K, Ishii A, Wada Y, Tanaka M, Tazawa S et al. Neuroinflammation in Patients with Chronic Fatigue Syndrome/Myalgic Encephalomyelitis: An 11C-(R)-PK11195 PET Study. Journal of nuclear medicine: official publication. Society of Nuclear Medicine. 2014;55(6):945-50. doi:10.2967/jnumed.113.131045.
48d. Held K, Kichko T, De Clercq K, Klaassen H, Van Bree R, Vanherck J C et al. Activation of TRPM3 by a potent synthetic ligand reveals a role in peptide release. Proceedings of the National Academy of Sciences of the United States of America. 2015; 112(11):E 1363-72. doi:10.1073/pnas.1419845112.
49d. Vriens J, Owsianik G, Hofmann T, Philipp S E, Stab J, Chen X et al. TRPM3 is a nociceptor channel involved in the detection of noxious heat. Neuron. 2011;70(3):482-94. doi:10.1016/j.neuron.2011.02.051.
50d. Wyller V B, Godang K, Morkrid L, Saul J P, Thaulow E, Walloe L. Abnormal thermoregulatory responses in adolescents with chronic fatigue syndrome: relation to clinical symptoms. Pediatrics. 2007;120(1):e129-37. doi: 10.1542/peds.2006-2759.
51d. Vriens J, Held K, Janssens A, Toth B I, Kerselaers S, Nilius B et al. Opening of an alternative ion permeation pathway in a nociceptor TRP channel. Nature chemical biology. 2014;10(3):188-95. doi:10.1038/nchembio.1428.
52d. Broderick G, Fuite J, Kreitz A, Vernon S D, Klimas N, Fletcher M A. A formal analysis of cytokine networks in chronic fatigue syndrome. Brain, behavior, and immunity. 2010;24(7):1209-17. doi:10.1016/j.bbi.2010.04.012.
53d. Maes M, Twisk F N, Kubera M, Ringel K. Evidence for inflammation and activation of cell-mediated immunity in Myalgic Encephalomyelitis/Chronic Fatigue Syndrome (ME/CFS): increased interleukin-1, tumor necrosis factor-alpha, PMN-elastase, lysozyme and neopterin. Journal of affective disorders. 2012;136(3):933-9. doi:10.1016/j.jad.2011.09.004.
54d. Maher K J, Klimas N G, Fletcher M A. Chronic fatigue syndrome is associated with diminished intracellular perforin. Clinical and experimental immunology. 2005;142(3):505-11. doi:10.1111/j.1365-2249.2005.02935.x.
55d. Liman E R. TRP Channels: Pain enters through the side door. Nature chemical biology. 2014;10(3):171-2. doi: 10.1038/nchembio.1470.
56d. Matteoli G, Boeckxstaens G E. The vagal innervation of the gut and immune homeostasis. Gut. 2013:62(8): 1214-22. doi:DOI 10.1136/gutjnl-2012-302550.
57d. Tsvilovskyy V V, Zholos A V, Aberle T, Philipp S E, Dietrich A, Zhu M X et al. Deletion of TRPC4 and TRPC6 in mice impairs smooth muscle contraction and intestinal motility in vivo. Gastroenterology. 2009;137(4):1415-24. doi:10.1053/j.gastro.2009.06.046.
58d. Kim H, Kim J, Jeon J P, Myeong J, Wie J, Hong C et al. The roles of G proteins in the activation of TRPC4 and TRPC5 transient receptor potential channels. Channels. 2012;6(5):333-43. doi:10.4161/chan.21198.
59d. Dinan T G, Clarke G, Quigley E M, Scott L V, Shanahan F, Cryan J et al. Enhanced cholinergic-mediated increase in the pro-inflammatory cytokine IL-6 in irritable bowel syndrome: role of muscarinic receptors. The American journal of gastroenterology. 2008;103(10): 2570-6. doi:10.1111/j.1572-0241.2008.01871.x.
60d. Scully P, McKeman D P, Keohane J, Groeger D, Shanahan F, Dinan T G et al. Plasma cytokine profiles in females with irritable bowel syndrome and extra-intestinal co-morbidity. The American journal of gastroenterology. 2010;105(10):2235-43. doi:10.1038/ajg.2010.159.
61d. Gautam D, Han S J, Hamdan F F, Jeon J, Li B, Li J H et al. A critical role for beta cell M3 muscarinic acetylcholine receptors in regulating insulin release and blood glucose homeostasis in vivo. Cell metabolism. 2006;3(6): 449-61. doi:10.1016/j.cmet.2006.04.009.
62d. Gromada J, Hughes T E. Ringing the dinner bell for insulin: muscarinic M3 receptor activity in the control of pancreatic beta cell function. Cell metabolism. 2006;3(6): 390-2. doi:10.1016/j.cmet.2006.05.004.
63d. Morris G, Maes M. Mitochondrial dysfunctions in Myalgic Encephalomyelitis/chronic fatigue syndrome explained by activated immuno-inflammatory, oxidative and nitrosative stress pathways. Metab Brain Dis. 2014; 29(1):19-36. doi:DOI 10.1007/s11011-013-9435-x.
64d. Kimura H. Physiological role of hydrogen sulfide and polysulfide in the central nervous system. Neurochemistry international. 2013:63(5):492-7. doi:10.1016/j.neuint.2013.09.003.
65d. Nilius B, Appendino G, Owsianik G. The transient receptor potential channel TRPA1: from gene to pathophysiology. Pflugers Archiv: European journal of physiology. 2012;464(5):425-58. doi:10.1007/s00424-012-1158-z.
66d. Shigetomi E, Jackson-Weaver O, Huckstepp R T, O'Dell T J, Khakh B S. TRPA1 channels are regulators of astrocyte basal calcium levels and long-term potentiation via constitutive D-scrine release. The Journal of neuroscience: the official journal of the Society for Neuroscience. 2013;33(24):10143-53. doi:10.1523/JNEUROSCI.5779-12.2013.
67d. Shigetomi E, Tong X, Kwan K Y, Corey D P, Khakh B S. TRPA1 channels regulate astrocyte resting calcium and inhibitory synapse efficacy through GAT-3. Nature neuroscience. 2012;15(1):70-80. doi 10.1038/nn.3000.
68d. Nassini R, Materazzi S, Vriens J, Prencn J, Benemei S, De Siena G et al. The 'headache tree' via umbellulone and TRPA1 activates the trigeminovascular system. Brain: a journal of neurology. 2012;135(Pt 2):376-90. doi: 10.1093/brain/awr272.
1e. Gulf War Illness and the Gulf War Veterans, Scientific findings and recommendations. Research Advisory Committee on Gulf War Illness, USA. Washington D.C., 2008.
2e. A SCIENTIFIC REVIEW OF MULTIPLE CHEMICAL SENSITIVITY: IDENTIFYING KEY RESEARCH NEEDS Report prepared by the National Industrial Chemicals Notification and Assessment Scheme (NICNAS) and the Office of Chemical Safety and Environmental Health (OCSEH) November 2010.
3e. Straus, S. E. (1992). Defining the chronic fatigue syndrome. Archives of internal medicine, 752(8), 1569.
4e. Carruthers, B. M., van de Sande, M. I., De Meirleir, K. L., Klimas, N. G., Broderick, G., Mitchell, T., Staines, D., Powles, A. P., Marshall-Gradisnik, S., Speight, N., & Vallings, R. (2011). Myalgic encephalomyelitis: international consensus criteria. Journal of internal medicine, 270(A), 327-33
1f. Barbado M, Fablet K, Ronjat M, De Waard M. Gene regulation by voltage-dependent calcium channels- .Biochim Biophys Acta. 2009 June; 793(6):1096-104. doi: 10.1016/j.bbamer.2009.02.004. Epub 2009 Feb. 27. Review.

2f. Feske S[1], Wulff H, Skolnik E Y. Ion channels in innate and adaptive immunity. Annu Rev Immunol. 2015 Mar. 21;33:291-353. doi: 10.1146/annurev-immunol-032414-112212.

3f. Strehler E E. Plasma membrane calcium ATPases as novel candidates for therapeutic agent development. J Pharm Pharm Sci. 2013:16(2):190-206. Review.

4f. ADRIANO SENATORE, J. DAVID SPAFFORD Calcium Channels: Regulation of GeneTranscription Title: Encyclopedia of Neuroscience.

5f. Macian F. NFAT proteins: key regulators of T-cell development and function. Nat Rev Immunol. 2005 June; 5(6):472-84. Review.

6f. Naranjo J R, Mellström B. Ca2+-dependent transcriptional control of Ca2+ homeostasis. J Biol Chem. 2012 Sep. 14;287(38):31674-80. doi: 10.1074/jbc.R112.384982. Epub 2012 Jul. 20. Review.

1h. Aaron L A, Burke M M, Buchwald D. Overlapping conditions among patients with chronic fatigue syndrome, fibromyalgia, and temporomandibular disorder. Archives of internal medicine. 2000;160(2):221-227.

2h. Allen J, Murray A, Di Maria C, Newton J L. Chronic fatigue syndrome and impaired peripheral pulse characteristics on orthostasis—a new potential diagnostic biomarker. Physiological measurement. 2012;33(2):231-241.

3h. Brenu E W, Ashton K J, van Driel M, et al. Cytotoxic lymphocyte microRNAs as prospective biomarkers for Chronic Fatigue Syndroine/Myalgic Encephalomyelitis. Journal of affective disorders. 2012:141(2-3):261-269.

4h. Brenu E W, Huth T K, Hardcastle S L, et al. Role of adaptive and innate immune cells in chronic fatigue syndrome/myalgic encephalomyelitis. International immunology. 2014;26(4):233-242.

5h. Brenu E W, Staines D R, Baskurl O K, et al. Immune and hemorheological changes in chronic fatigue syndrome. Journal of translational medicine. 2010;8:1.

6h. Brenu E W, van Driel M L, Staines D R, et al. Longitudinal investigation of natural killer cells and cytokines in chronic fatigue syndrome/myalgic encephalomyelitis. Journal of translational medicine. 2012;10:88.

7h. Brenu E W, van Driel M L, Staines D R, et al. Immunological abnormalities as potential biomarkers in Chronic Fatigue Syndromc/Myalgic Encephalomyelitis. Journal of translational medicine. 2011;9:81.

8h. DeLuca J, Johnson S K, Beldowicz D, Natelson B H. Neuropsychological impairments in chronic fatigue syndrome, multiple sclerosis, and depression. Journal of neurology, neurosurgery, and psychiatry. 1995;58(1):38-43.

9h. Grafman J, Schwartz V, Dale J K, Scheffers M, Houser C, Straus S E. Analysis of neuropsychological functioning in patients with chronic fatigue syndrome. Journal of neurology, neurosurgery, and psychiatry. 1993;56(6):684-689.

10h. Hoad A, Spickett G, Elliott J, Newton J. Postural orthostatic tachycardia syndrome is an under-recognized condition in chronic fatigue syndrome. QJM: monthly journal of the Association of Physicians. 2008; 101(12): 961-965.

11h. Joyce E, Blumenthal S, Wessely S. Memory, attention, and executive function in chronic fatigue syndrome. Journal of neurology, neurosurgery, and psychiatry. 1996;60 (5):495-503.

12h. Klimas N G, Salvato F R, Morgan R, Fletcher M A. Immunologic abnormalities in chronic fatigue syndrome. Journal of clinical microbiology. 1990:28(6);1403-1410.

13h. Krupp L B, Sliwinski M, Masur D M, Friedberg F, Coyle P K. Cognitive functioning and depression in patients with chronic fatigue syndrome and multiple sclerosis. Archives of neurology. 1994:51(7):705-710.

14h. Lewis I, Pairman J, Spickett G, Newton J L. Clinical characteristics of a novel subgroup of chronic fatigue syndrome patients with postural orthostatic tachycardia syndrome. Journal of internal medicine. 2013;273(5): 501-510.

15h. McDonald E, Cope H, David A. Cognitive impairment in patients with chronic fatigue: a preliminary study. Journal of neurology, neurosurgery, and psychiatry. 1993; 56(7):812-815.

16h. Medow M S, Stewart J M. The postural tachycardia syndrome. Cardiology in review. 2007;15(2):67-75.

17h. Nisenbaum R, Reyes M, Mawle A C, Reeves W C. Factor analysis of unexplained severe fatigue and inter-related symptoms: overlap with criteria for chronic fatigue syndrome. American journal of epidemiology. 1998;148(1):72-77.

18h. Ocon A J, Medow M S, Tancja I, Clarke D, Stewart J M. Decreased upright cerebral blood flow and cerebral autoregulation in normocapnic postural tachycardia syndrome. American journal of physiology. Heart and circulatory physiology. 2009;297(2):H664-673.

21h. Toth B I, Konrad M, Ghosh D, et al. Regulation of the transient receptor potential channel TRPM3 by phosphoinositides. The Journal of general physiology. 2015:146 (1):51-63.

22h. Badheka D, Borbiro I, Rohacs T. Transient receptor potential melastatin 3 is a phosphoinositide-dependent ion channel. The Journal of general physiology. 2015;146(1): 65-77.

23h. Loebel M, Grabowski P, Heidecke H, et al. Antibodies to beta adrenergic and muscarinic cholinergic receptors in patients with Chronic Fatigue Syndrome. Brain, behavior, and immunity. 2015.

1j. Caligiuri M A. Human natural killer cells. Blood. 2008: 112(3):461-469.

2j. Cooper M A, Fehniger T A, Caligiuri M A. The biology of human natural killer-cell subsets. Vol 22. England: Elsevier Ltd; 2001:633-640.

3j. Sun J C, Lanier L L. NK cell development, homeostasis and function: parallels with CD8+ T cells. Nature Reviews Immunology. 2011;11(10):645-657.

4j. Möller M J, Kammener R, von Kleist S. A distinct distribution of natural killer cell subgroups in human tissues and blood. International Journal of Cancer. 1998; 78(5):533-538.

5j. Bryceson Y T, March M E, Ljunggren H-G, Long E O. Activation, coactivation, and costimulation of resting human natural killer cells. Immunological reviews. 2006; 214(1):73-91.

6j. Fan Y-y, Yang B-y, Wu C-y. Phenotypically and functionally distinct subsets of natural killer cells in human PBMCs. Cell Biology International. 2008;32(2):188-197.

7j. Cooper M A, Fehniger T A, Turner S C, et al. Human natural killer cells: a unique innate immunoregulatory role for the CD56bright subset. Vol 972001.

8j. Bryceson Y T, March M E, Ljunggren H G, Long E O. Synergy among receptors on resting NK cells for the activation of natural cytotoxicity and cytokine secretion. Blood. Jan. 1 2006; 107(1): 159-166.

9j. Dustin M L, Long E O. Cytotoxic immunological synapses. *Immunological reviews.* 2010;235(1):24-34.

10j. Rouvier E, Luciani M, Golstein P. Fas involvement in Ca (2+)-independent T cell-mediated cytotoxicity. *The Journal of experimental medicine.* 1993;177(1):195-200.

11j. Maul-Pavicic A, Chiang S C, Rensing-Ehl A, et al. ORAI1-mediated calcium influx is required for human cytotoxic lymphocyte degranulation and target cell lysis. *Proceedings of the National Academy of Sciences.* 2011; 108(8):3324-3329.

12j. Pores-Femando A T, Zweifach A. Calcium influx and signaling in cytotoxic T-lymphocyte lytic granule exocytosis. *Immunological reviews.* 2009;231(1):160-173.

13j. Tassi I, Presti R, Kim S, Yokoyama W M, Gilfillan S, Colonna M. Phospholipase C-γ2 is a critical signaling mediator for murine NK cell activating receptors. *Journal of Immunology.* 2005; 175(2):749-754.

14j. Caraux A, Kim N, Bell S E, et al. Phospholipase C-{gamma}2 is essential for NK cell cytotoxicity and innate immunity to malignant and virally infected cells. *Blood.* 2006;107(3):994-1002.

15j. Zanovello P, Rosato A, Bronte V, et al. Interaction of lymphokine-activated killer cells with susceptible targets does not induce second messenger generation and cytolytic granule exocytosis. *The Journal of Experimental Medicine.* Sep. 1, 1989 1989;170(3):665-677.

16j. Nilius B, Owsianik G. The transient receptor potential family of ion channels. *Genome biology.* 2011;12(3):218.

17j. Nilius B, Biro T. TRPV3: a 'more than skinny' channel. *Experimental dermatology.* July 2013;22(7):447-452.

18j. Nilius B, Biro T, Owsianik G. TRPV3: time to decipher a poorly understood family member! *The Journal of physiology.* Jan. 15, 2014;592(Pt 2):295-304.

19j. Nilius B, Szallasi A. Transient receptor potential channels as drug targets: from the science of basic research to the art of medicine. *Pharmacological reviews.* July 2014; 66(3):676-814.

20j. Nilius B, Voets T. The puzzle of TRPV4 channclopathies. *EMBO reports.* February 2013;14(2):152-163.

21j. Vennekens R, Menigoz A, Nilius B. TRPs in the Brain. *Reviews of physiology, biochemistry and pharmacology.* 2012;163:27-64.

22j. Elhusseiny A, Hamel E. Muscarinic—but not nicotinic—acetylcholine receptors mediate a nitric oxide-dependent dilation in brain cortical arterioles: a possible role for the M5 receptor subtype. *Journal of cerebral blood flow and metabolism : official journal of the International Society of Cerebral Blood Flow and Metabolism.* February 2000:20(2):298-305.

23j. Felder C C, Bymaster F P, Ward J, DeLapp N. Therapeutic opportunities for muscarinic receptors in the central nervous system. *Journal of medicinal chemistry.* Nov. 16, 2000;43(23):4333-4353.

24j. Oki T, Takagi Y, Inagaki S. et al. Quantitative analysis of binding parameters of [3H]N-methylscopolamine in central nervous system of muscarinic acetylcholine receptor knockout mice. *Brain research. Molecular brain research.* Jan. 5, 2005:133(1):6-11.

25j. Sharma G, Vijayaraghavan S. Nicotinic cholinergic signaling in hippocampal astrocytes involves calcium-induced calcium release from intracellular stores. *Proceedings of the National Academy of Sciences of the United States of America.* Mar. 27, 2001:98(7):4148-4153.

26j. Wess J, Duttaroy A, Zhang W. et al. M1-M5 muscarinic receptor knockout mice as novel tools to study the physiological roles of the muscarinic cholinergic system. *Receptors & channels.* 2003;9(4):279-290.

27j. Beckmann J, Lips K S. The Non-Neuronal Cholinergic System in Health and Disease. *Pharmacology.* 2013;92 (5-6):286-302.

28j. Lanzafame A A, Christopoulos A, Mitchelson F. Cellular signaling mechanisms for muscarinic acetylcholine receptors. *Receptors & channels.* 2003:9(4):241-260.

29j. Wess J. Molecular biology of muscarinic acetylcholine receptors. *Critical reviews in neurobiology.* 1996;10(1): 69-99.

30j. Aaron L A, Burke M M, Buchwald D. Overlapping conditions among patients with chronic fatigue syndrome, fibromyalgia, and temporomandibular disorder. *Archives of internal medicine.* Jan. 24, 2000:160(2):221-227.

31j. Allen J, Murray A, Di Maria C, Newton J L. Chronic fatigue syndrome and impaired peripheral pulse characteristics on orthostasis—a new potential diagnostic biomarker. *Physiological measurement.* February 2012:33 (2):231-241.

32j. Brenu E W, Ashton K J, van Driel M, et al. Cytotoxic lymphocyte microRNAs as prospective biomarkers for Chronic Fatigue Syndrome/Myalgic Encephalomyelitis. *Journal of affective disorders.* Dec. 10, 2012:141(2-3): 261-269.

33j. Brenu E W, Huth T K, Hardcastle S L, et al. Role of adaptive and innate immune cells in chronic fatigue syndrome/myalgic encephalomyelitis. *International immunology.* April 2014;26(4):233-242.

34j. Brenu E W, Staines D R, Baskurt O K, et al. Immune and hemorheological changes in chronic fatigue syndrome. *Journal of translational medicine.* 2010;8:1.

35j. Brenu E W, van Driel M L, Staines D R, et al. Longitudinal investigation of natural killer cells and cytokines in chronic fatigue syndrome/myalgic encephalomyelitis. *Journal of translational medicine.* 2012:10:88.

36j. Brenu E W, van Driel M L, Staines D R, et al. Immunological abnormalities as potential biomarkers in Chronic Fatigue Syndrome/Myalgic Encephalomyelitis. *Journal of translational medicine.* 2011;9:81.

37j. DeLuca J, Johnson S K, Beldowicz D, Natelson B H. Neuropsychological impairments in chronic fatigue syndrome, multiple sclerosis, and depression. *Journal of neurology, neurosurgery, and psychiatry.* January 1995; 58(1):38-43.

38j. Hoad A, Spickett G, Elliott J, Newton J. Postural orthostatic tachycardia syndrome is an under-recognized condition in chronic fatigue syndrome. *QJM: monthly journal of the Association of Physicians.* December 2008; 101(12):961-965.

39j. Klimas N G, Salvato F R, Morgan R, Fletcher M A. Immunologic abnormalities in chronic fatigue syndrome. *Journal of clinical microbiology.* June 1990:28(6):1403-1410.

40j. Lewis I, Pairman J, Spickett G, Newton J L. Clinical characteristics of a novel subgroup of chronic fatigue syndrome patients with postural orthostatic tachycardia syndrome. *Journal of internal medicine.* May 2013;273 (5):501-510.

41j. Medow M S, Stewart J M. The postural tachycardia syndrome. *Cardiology in review.* Mar-April 2007;15(2): 67-75.

42j. Nisenbaum R, Reyes M, Mawle A C, Reeves W C. Factor analysis of unexplained severe fatigue and inter-related symptoms: overlap with criteria for chronic fatigue syndrome. *American journal of epidemiology.* Jul. 1, 1998;148(1):72-77.

43j. Maher K J, Klimas N G, Fletcher M A. Chronic fatigue syndrome is associated with diminished intracellular perforin. *Clinical and experimental immunology*. December 2005;142(3):505-511.

45j. Fukuda K, Straus S E, Hickie I, Sharpe M C, Dobbins J G, Komaroff A. The chronic fatigue syndrome: a comprehensive approach to its definition and study. International Chronic Fatigue Syndrome Study Group. *Ann Intern Med*. Dec. 15, 1994;121(12):953-959.

46j. Bancerjee K, Biswas P S, Rouse B T. Elucidating the protective and pathologic T cell species in the virus-induced corneal immunoinflammatory condition herpetic stromal keratitis. *Journal of leukocyte biology*. January 2005;77(1):24-32.

47j. Caligiuri M A. Human natural killer cells. *Blood*. Aug. 1, 2008; 112(3):461-469.

49j. Nilius B, Owsianik G, Voets T, Peters J A. Transient receptor potential cation channels in disease. *Physiological reviews*. January 2007;87(1):165-217.

50j. Pores-Fernando A T, Zweifach A. Calcium influx and signaling in cytotoxic T-lymphocyte lytic granule exocytosis. *Immunological reviews*. September 2009;231(1): 160-173.

51j. Lyubchenko T A, Wurth G A, Zweifach A. Role of calcium influx in cytotoxic T lymphocyte lytic granule exocytosis during target cell killing. *Immunity*. November 2001;15(5):847-859.

52j. Wang X, Schwarz T L. The mechanism of Ca2+-dependent regulation of kinesin-mediated mitochondrial motility. *Cell*. Jan. 9, 2009;136(1):163-174.

53j. Lykhmus O, Gergalova G, Koval L, Zhmak M, Komisarenko S, Skok M. Mitochondria express several nicotinic acetylcholine receptor subtypes to control various pathways of apoptosis induction. *The international journal of biochemistry & cell biology*. August 2014;53:246-252.

54j. Rah S Y, Kwak J Y, Chung Y J, Kim U H. ADP-ribose/TRPM2-mediated Ca2+ signaling is essential for cytolytic degranulation and antitumor activity of natural killer cells. *Scientific reports*. 2015;5:9482.

55j. Kawashima K, Fujii T. Extraneuronal cholinergic system in lymphocytes. *Pharmacology & therapeutics*. April 2000;86(1):29-48.

56j. Kawashima K, Fujii T. The lymphocytic cholinergic system and its biological function. *Life sciences*. Mar. 28, 2003;72(18-19):2101-2109.

57j. Kawashima K, Fujii T. Basic and clinical aspects of non-neuronal acetylcholine: overview of non-neuronal cholinergic systems and their biological significance. *Journal of pharmacological sciences*. February 2008;106 (2):167-173.

58j. Kawashima K, Fujii T, Moriwaki Y, Misawa H. Critical roles of acetylcholine and the muscarinic and nicotinic acetylcholine receptors in the regulation of immune function. *Life sciences*. Nov. 27, 2012;91(21-22):1027-1032.

59j. Maslinski W. Cholinergic receptors of lymphocytes. *Brain, behavior, and immunity*. March 1989;3(1):1-14.

60j. Fujii T, Kawashima K. Calcium signaling and c-Fos gene expression via M3 muscarinic acetylcholine receptors in human T- and B-cells. *Japanese journal of pharmacology*. October 2000;84(2):124-132.

61j. Fujii T, Kawashima K. YM905, a novel M3 antagonist, inhibits Ca2+ signaling and c-fos gene expression mediated via muscarinic receptors in human T cells. *General pharmacology*. August 2000;35(2):71-75.

62j. Fujii T, Harada H, Koyama T, Nakajima Y, Kawashima K. Effects of physostigmine and calcium on acetylcholine efflux from the hippocampus of freely moving rats as determined by in vivo microdialysis and a radioimmunoassay. *Neuroscience letters*. Aug. 11, 2000;289(3):181-184.

63j. Fujii T, Kawashima K. An independent non-neuronal cholinergic system in lymphocytes. *Japanese journal of pharmacology*. January 2001;85(1):11-15.

64j. Kimura R, Ushiyama N, Fujii T, Kawashima K. Nicotine-induced Ca2+ signaling and down-regulation of nicotinic acetylcholine receptor subunit expression in the CEM human leukemic T-cell line. *Life sciences*. Mar. 28, 2003;72(18-19):2155-2158.

65j. Kawashima K, Fujii T. Expression of non-neuronal acetylcholine in lymphocytes and its contribution to the regulation of immune function. *Front Biosci*. 2004;9(2): 063.

66j. Pagani F, Baralle F E. Genomic variants in exons and introns: identifying the splicing spoilers. *Nature Reviews Genetics*. 2004;5(5):389-396.

67j. Kuersten S, Goodwin E B. The power of the 3' UTR: translational control and development. *Nature reviews. Genetics*. August 2003;4(8):626-637.

68j. Cartegni L, Krainer A R. Correction of disease-associated exon skipping by synthetic exon-specific activators. *Nature structural biology*. February 2003:10(2):120-125.

69j. Pagani F, Baralle F E. Genomic variants in exons and introns: identifying the splicing spoilers. *Nature reviews. Genetics*. May 2004;5(5):389-396.

70j. Fedor M J. Alternative splicing minireview series: combinatorial control facilitates splicing regulation of gene expression and enhances genome diversity. *Journal of Biological Chemistry*. 2008;283(3):1209-1210.

71j. Crawford M H, Banerjee P, Demarchi D A, et al. Applications of pooled DNA samples to the assessment of population affinities: short tandem repeats. *Human biology*. December 2005;77(6):723-733.

72j. Shcherbakova I, Hoskins A A, Friedman L I, et al. Alternative spliceosome assembly pathways revealed by single-molecule fluorescence microscopy. *Cell reports*. Oct. 17, 2013;5(1):151-165.

73j. Frühwald J, Camacho Londoño J, Dembla S. et al. Alternative splicing of a protein domain indispensable for function of transient receptor potential melastatin 3 (TRPM3) ion channels. *The Journal of biological chemistry*. 2012;287(44):36663-36672.

74j. Oberwinkler J, Lis A, Giehl K M, Flockerzi V, Philipp S E. Alternative splicing switches the divalent cation selectivity of TRPM3 channels. *Journal of Biological Chemistry*. 2005;280(23):22540-22548.

75j. Liu B, Qin F. Functional control of cold- and menthol-sensitive TRPM8 ion channels by phosphatidylinositol 4,5-bisphosphate. *The Journal of neuroscience: the official journal of the Society for Neuroscience*. Feb. 16, 2005;25(7):1674-1681.

76j. McKemy D D. How cold is it? TRPM8 and TRPA1 in the molecular logic of cold sensation. *Molecular pain*. 2005;1:16.

77j. Park C-K, Kim M S, Fang Z, et al. Functional Expression of Thermo-transient Receptor Potential Channels in Dental Primary Afferent Neurons IMPLICATION FOR TOOTH PAIN. *Journal of Biological Chemistry*. 2006: 281(25):17304-17311.

78j. Mecus M, Nijs J. Central sensitization: a biopsychosocial explanation for chronic widespread pain in patients with fibromyalgia and chronic fatigue syndrome. *Clinical rheumatology*. April 2007;26(4):465-473.

79j. Bruggmann D, Lips K S, Pfeil U, Haberberger R V, Kummer W. Rat arteries contain multiple nicotinic acetylcholine receptor alpha-subunits. *Life sciences*. Mar. 28, 2003;72(18-19):2095-2099.

80j. Macklin K D, Maus A D, Pereira E F, Albuquerque E X, Conti-Fine B M. Human vascular endothelial cells express functional nicotinic acetylcholine receptors. *The Journal of pharmacology and experimental therapeutics*. October 1998:287(1):435-439.

81j. Wang Y, Pereira E F, Maus A D, et al. Human bronchial epithelial and endothelial cells express alpha7 nicotinic acetylcholine receptors. *Molecular pharmacology*. December 2001:60(6):1201-1209.

82j. Abbruscato T J, Lopez S P, Mark K S. Hawkins B T, Davis T P. Nicotine and cotinine modulate cerebral microvascular permeability and protein expression of ZO-1 through nicotinic acetylcholine receptors expressed on brain endothelial cells. *Journal of pharmaceutical sciences*. December 2002:91(12):2525-2538.

83j. Maclennan C A, Vincent A, Marx A, et al. Preferential expression of AChR epsilon-subunit in thymomas from patients with myasthenia gravis. *J Neuroimmunol*. Sep. 15, 2008;201-202:28-32.

84j. Cascras X, Mataix-Cols D, Giampietro V, et al. Probing the working memory system in chronic fatigue syndrome: a functional magnetic resonance imaging study using the n-back task. *Psychosomatic medicine*. November-December 2006:68(6):947-955.

85j. Caseras X, Mataix-Cols D, Rimes K A, et al. The neural correlates of fatigue: an exploratory imaginal fatigue provocation study in chronic fatigue syndrome. *Psychological medicine*. July 2008;38(7):941-951.

86j. Nakatomi Y, Mizuno K, Ishii A, et al. Neuroinflammation in Patients with Chronic Fatigue Syndrome/Myalgic Encephalomyelitis: An 11C-(R)-PK11195 PET Study. *Journal of nuclear medicine: official publication, Society of Nuclear Medicine*. Mar. 24, 2014;55(6):945-950.

1x. Lendvai B and Vizi E S. Nonsynaptic chemical transmission through nicotinic acetylcholine receptors. *Physiological reviews*. 2008; 88: 333-49.

2x. Court J A, Martin-Ruiz C, Graham A and Perry E. Nicotinic receptors in human brain: topography and pathology. *Journal of chemical neuroanatomy*. 2000; 20: 281-98.

3x. Felder C C. Muscarinic acetylcholine receptors: signal transduction through multiple effectors. *FASEB journal: official publication of the Federation of American Societies for Experimental Biology*. 1995; 9: 619-25.

4x. Brann M R, Ellis J, Jrgensen H, Hill-Eubanks D and Jones S P. Muscarinic acetylcholine receptor subtypes: localization and structure/function. *Progress in brain research*. 1993; 98: 121-.

5x. Shen J X and Yakel J L. Nicotinic acetylcholine receptor-mediated calcium signaling in the nervous system. *Acta pharrnacologica Sinica*. 2009; 30: 673-80.

6x. d'Incamps B L and Ascher P. High affinity and low affinity heteromeric nicotinic acetylcholine receptors at central synapses. *The Journal of physiology*. 2014; 592: 4131-6.

7x. Skok M, Grailhe R and Changeux J P. Nicotinic receptors regulate B lymphocyte activation and immune response. *European journal of pharmacology*. 2005; 517: 246-51.

8x. Fujii Y X, Fujigaya H, Moriwaki Y, et al. Enhanced serum antigen-spccific IgG1 and proinflammatory cytokine production in nicotinic acetylcholine receptor alpha7 subunit gene knockout mice. *J Neuroimmunol*. 2007; 189: 69-74.

9x. Koval L, Lykhmus O, Zhmak M, et al. Differential involvement of alpha4bcta2, alpha7 and alpha9alpha10 nicotinic acetylcholine receptors in B lymphocyte activation in vitro. *The international journal of biochemistry & cell biology*. 2011; 43: 516-24.

10x. Beckmann J and Lips K S. The Non-Neuronal Cholinergic System in Health and Disease. *Pharmacology*. 2013; 92: 286-302.

11x. Elhusseiny A and Hamel E. Muscarinic—but not nicotinic—acetylcholine receptors mediate a nitric oxide-dependent dilation in brain cortical arterioles: a possible role for the M5 receptor subtype. *Journal of cerebral blood flow and metabolism: official journal of the International Society of Cerebral Blood Flow and Metabolism*. 2000; 20: 298-305.

12x. Felder C C, Bymaster F P, Ward J and DeLapp N. Therapeutic opportunities for muscarinic receptors in the central nervous system. *Journal of medicinal chemistry*. 2000; 43: 4333-53.

13x. Sharma G and Vijayaraghavan S. Nicotinic cholinergic signaling in hippocampal astrocytes involves calcium-induced calcium release from intracellular stores. *Proceedings of the National Academy of Sciences of the United Stales of America*. 2001; 98: 4148-53.

14x. Wess J, Duttaroy A, Zhang W, et al. M1-M5 muscarinic receptor knockout mice as novel tools to study the physiological roles of the muscarinic cholinergic system. *Receptors & channels*. 2003; 9: 279-90.

15x. Badheka D, Borbiro I and Rohacs T. Transient receptor potential melastatin 3 is a phosphoinositide-dependcnt ion channel. *The Journal of General Physiology*. 2015; 146: 65-77.

16x. Nilius B, Owsianik G, Voets T and Peters J A. Transient receptor potential cation channels in disease. *Physiological reviews*. 2007; 87: 165-217.

17x. Nilius B and Biro T. TRPV3: a 'more than skinny' channel. *Experimental dermatology*. 2013; 22: 447-52.

18x. Nilius B, Biro T and Owsianik G. TRPV3: time to decipher a poorly understood family member! *The Journal of physiology*. 2014; 592: 295-304.

19x. Nilius B and Owsianik G. The transient receptor potential family of ion channels. *Genome biology*. 2011; 12: 218.

20x. Nilius B and Szallasi A. Transient receptor potential channels as drug targets: from the science of basic research to the art of medicine. *Pharmacological reviews*. 2014; 66: 676-814.

21x. Nilius B and Voets T. The puzzle of TRPV4 channelopathies. *EMBO reports*. 2013; 14: 152-63.

22x. Vennekens R, Mcnigoz A and Nilius B. TRPs in the Brain. *Reviews of physiology, biochemistry and pharmacology*. 2012; 163: 27-64.

23x. Aaron L A, Burke M M and Buchwald D. Overlapping conditions among patients with chronic fatigue syndrome, fibromyalgia, and temporomandibular disorder. *Archives of internal medicine*. 2000: 160: 221-7.

24x. Allen J, Murray A, Di Maria C and Newton J L. Chronic fatigue syndrome and impaired peripheral pulse characteristics on oithostasis—a new potential diagnostic biomarker. *Physiological measurement*. 2012; 33: 231-41.

25x. Brenu E W, Ashton K J, van Driel M, et al. Cytotoxic lymphocyte microRNAs as prospective biomarkers for Chronic Fatigue Syndrome/Myalgic Encephalomyelitis. *Journal of affective disorders*. 2012; 141: 261-9.

26x. Brenu E W, Huth T K, Hardcastle S L, et al. Role of adaptive and innate immune cells in chronic fatigue syndrome/myalgic encephalomyelitis. *International immunology.* 2014; 26: 233-42.

27x. Brenu E W, Staines D R, Baskurt O K, et al. Immune and hemorheological changes in chronic fatigue syndrome. *Journal of translational medicine.* 2010; 8: 1.

28x. Brenu E W, van Driel M L, Staines D R, et al. Longitudinal investigation of natural killer cells and cytokines in chronic fatigue syndrome/myalgic encephalomyelitis. *Journal of translational medicine.* 2012; 10: 88.

29x. Brenu E W, van Driel M L, Staines D R, et al. Immunological abnormalities as potential biomarkers in Chronic Fatigue Syndrome/Myalgic Encephalomyelitis. *Journal of translational medicine.* 2011; 9: 81.

30x. DeLuca J, Johnson S K, Beldowicz D and Natelson B H. Neuropsychological impairments in chronic fatigue syndrome, multiple sclerosis, and depression. *Journal of neurology, neurosurgery, and psychiatry.* 1995; 58: 38-43.

31x. Hoad A, Spickett G, Elliott J and Newton J. Postural orthostatic tachycardia syndrome is an under-recognized condition in chronic fatigue syndrome. *QJM: monthly journal of the Association of Physicians.* 2008; 101: 961-5.

32x. Klimas N G, Salvato F R, Morgan R and Fletcher M A. Immunologic abnormalities in chronic fatigue syndrome. *Journal of clinical microbiology.* 1990; 28: 1403-10.

33x. Lewis I, Pairman J, Spickett G and Newton J L. Clinical characteristics of a novel subgroup of chronic fatigue syndrome patients with postural orthostatic tachycardia syndrome. *Journal of internal medicine.* 2013; 273: 501-10.

34x. Medow M S and Stewart J M. The postural tachycardia syndrome. *Cardiology in review.* 2007; 15: 67-75.

35x. Nisenbaum R, Reyes M, Mawle A C and Reeves W C. Factor analysis of unexplained severe fatigue and interrelated symptoms: overlap with criteria for chronic fatigue syndrome. *American journal of epidemiology.* 1998; 148: 72-7.

39x. Loebel M, Grabowski P, Heidecke H, et al. Antibodies to β adrenergic and muscarinic cholinergic receptors in patients with Chronic Fatigue Syndrome. *Brain, behavior, and immunity.* 2015.

40x. Fukuda K, Straus S E, Hickie I, Sharpe M C, Dobbins J G and Komaroff A. The chronic fatigue syndrome: a comprehensive approach to its definition and study. International Chronic Fatigue Syndrome Study Group. *Ann Intern Med.* 1994; 121: 953-9.

42x. Kang S W, Wahl M I, Chu J, et al. PKCbeta modulates antigen receptor signaling via regulation of Btk membrane localization. *The EMBO journal.* 2001; 20: 5692-702.

43x. Su T T, Guo B, Kawakami Y, et al. PKC-beta controls I kappa B kinase lipid raft recruitment and activation in response to BCR signaling. *Nature immunology.* 2002; 3: 780-6.

44x. Li W, Llopis J, Whitney M, Zlokarnik G and Tsien R Y. Cell-permeant caged InsP3 ester shows that Ca2+ spike frequency can optimize gene expression. *Nature.* 1998; 392: 936-41.

45x. Dolmetsch R E, Xu K and Lewis R S. Calcium oscillations increase the efficiency and specificity of gene expression. *Nature.* 1998; 392: 933-6.

46x. Negulescu P A, Shastri N and Cahalan M D. Intracellular calcium dependence of gene expression in single T lymphocytes. *Proceedings of the National Academy of Sciences of the United States of America.* 1994; 91: 2873-7.

47x. Kawashima K, Fujii T, Moriwaki Y, Misawa H and Horiguchi K. Reconciling neuronally and nonneuronally derived acetylcholine in the regulation of immune function. *Annals of the New York Academy of Sciences.* 2012; 1261: 7-17.

48x. Kawashima K, Fujii T, Moriwaki Y and Misawa H. Critical roles of acetylcholine and the muscarinic and nicotinic acetylcholine receptors in the regulation of immune function. *Life sciences.* 2012; 91: 1027-32.

49x. Wessler I K and Kirkpatrick C J. Activation of muscarinic receptors by non-neuronal acetylcholine. *Handbook of experimental pharmacology.* 2012: 469-91.

50x. Fujii T, Takada-Takatori Y and Kawashima K. Regulatory mechanisms of acetylcholine synthesis and release by T cells. *Life sciences.* 2012; 91: 981-5.

51x. Huijbers M G, Lipka A F, Plomp J J, Niks E H, van der Maarel S M and Verschuuren J J. Pathogenic immune mechanisms at the neuromuscular synapse: the role of specific antibody-binding epitopes in myasthenia gravis. *Journal of internal medicine.* 2014; 275: 12-26.

52x. Tobin G, Giglio D and Lundgren O. Muscarinic receptor subtypes in the alimentary tract. *Journal of physiology and pharmacology: an official journal of the Polish Physiological Society.* 2009; 60: 3-21.

53x. Park K, Haberberger R V, Gordon T P and Jackson M W. Antibodies interfering with the type 3 muscarinic receptor pathway inhibit gastrointestinal motility and cholinergic neurotransmission in Sjogren's syndrome. *Arthritis and rheumatism.* 2011; 63: 1426-34.

54x. Wang H, Lu Y and Wang Z. Function of cardiac M3 receptors. *Autonomic & autacoid pharmacology.* 2007; 27: 1-11.

55x. Wang S, Han H M, Jiang YN, et al. Activation of cardiac M3 muscarinic acetylcholine receptors has cardioprotective effects against ischaemia-induced arrhythmias. *Clinical and experimental pharmacology & physiology.* 2012; 39: 343-9.

56x. Molina J, Rodriguez-Diaz R, Fachado A, Jacques-Silva M C, Berggren P O and Caicedo A. Control of insulin secretion by cholinergic signaling in the human pancreatic islet. *Diabetes.* 2014; 63: 2714-26.

57x. de Azua I R, Gautam D, Jain S, Guettier J-M and Wess J. Critical metabolic roles of β-cell M3 muscarinic acetylcholine receptors. *Life sciences.* 2012; 91: 986-91.

58x. Gautam D, Han S J, Hamdan F F, et al. A critical role for beta cell M3 muscarinic acetylcholine receptors in regulating insulin release and blood glucose homeostasis in vivo. *Cell metabolism.* 2006; 3: 449-61.

59x. Racké K, Juergens U R and Matthiesen S. Control by cholinergic mechanisms. *European journal of pharmacology.* 2006; 533: 57-68.

60x. Kuersten S and Goodwin E B. The power of the 3' UTR: translational control and development. *Nature reviews Genetics.* 2003; 4: 626-37.

61x. Albuquerque E X, Pereira E F, Alkondon M and Rogers S W. Mammalian nicotinic acetylcholine receptors: from structure to function. *Physiological reviews.* 2009; 89: 73-120.

62x. Changeux J P. The nicotinic acetylcholine receptor: the founding father of the pentameric ligand-gated ion channel superfamily. *The Journal of biological chemistry.* 2012; 287: 40207-15.

63x. Hardcastle S L, Brenu E, Johnston S, et al. Analysis of the relationship between immune dysfunction and symptom severity in patients with Chronic Fatigue Syndrome/Myalgic Encephalomyelitis (CFS/ME). *J Clin Cell Immunol.* 2014; 5: 4172.

64x. Vijayaraghavan S and Sharma G. Editorial: Brain cholinergic mechanisms. *Frontiers in synaptic neuroscience.* 2015; 7: 14.

65x. Boysen N C, Dragon D N and Talman W T. Parasympathetic tonic dilatory influences on cerebral vessels. *Autonomic neuroscience: basic & clinical.* 2009; 147; 101-4.

66x. Gu Z and Yakel J L. Timing-dependent septal cholinergic induction of dynamic hippocampal synaptic plasticity. *Neuron.* 2011; 71: 155-65.

67x. Seigneur J, Kroeger D, Nita D A and Amzica F. Cholinergic action on cortical glial cells in vivo. *Cerebral cortex.* 2006; 16: 655-68.

68x. Navarrete M, Perea G, de Sevilla D F, et al. Astrocytes mediate in vivo cholinergic-induced synaptic plasticity. *PLoS-Biology.* 2012; 10: 402.

69x. Jaimes M et al (2004) Maturation and Trafficking Markers on Rotavirus-Specific B Cells during Acute Infection and Convalescence in Children. J. Virol. 78: 10967-10976.

41y. Badheka D, Borhiro I, Rohacs T (2015) Phosphoinositides as Co-Factors for the Ion Channel TRPM3. Biophysical Journal 108: 283a.

42y. Brenu E W, van Driel M L, Staines D R, Ashton K J, Hardcastle S L, et al. (2012) Longitudinal investigation of natural killer cells and cytokines in chronic fatigue syndrome/myalgic encephalomyelitis. J Transl Med 10: 88.

43y. Numaga T I, Nishida M, Kiyonaka S, Kato K, Katano M, Mori E, Kurosaki T, Inoue R, Hikida M, Putney J W Jr, Mori Y. Ca2+ influx and protein scaffolding via TRPC3 sustain PKCbeta and ERK activation in B cells. J Cell Sci. 2010 Mar. 15;123(Pt 6):927-38. doi: 10.1242/jcs.061051. Epub 2010 Feb. 23. Article I.

1u. Colomer J, Means A R. Physiological roles of the Ca2+/CaM-dependent protein kinase cascade in health and disease. *Sub-cellular biochemistry.* 2007;45:169-214.

2u. Nairn A C, Picciotto M R. Calcium/calmodulin-dependent protein kinases. *Seminars in cancer biology.* August 1994;5(4):295-303.

3u. Dustin M L, Long E O. Cytotoxic immunological synapses. *Immunological reviews.* May 2010;235(1):24-34.

4u. Maul-Pavicic A, Chiang S C, Rensing-Ehl A, et al. ORAI1-mediated calcium influx is required for human cytotoxic lymphocyte degranulation and target cell lysis. *Proceedings of the National Academy of Sciences of the United States of America.* Feb. 22, 2011;108(8):3324-3329.

5u. Pores-Fernando A T, Zweifach A. Calcium influx and signaling in cytotoxic T-lymphocyte lytic granule exocytosis. *Immunological reviews.* September 2009;231(1): 160-173.

6u. Maul-Pavicic A, Chiang S C, Rensing-Ehl A, et al. ORAI1-mediated calcium influx is required for human cytotoxic lymphocyte degranulation and target cell lysis. *Proceedings of the National Academy of Sciences.* 2011; 108(8):3324-3329.

7u. Lyubchenko T A, Wurth G A, Zweifach A. Role of calcium influx in cytotoxic T lymphocyte lytic granule exocytosis during target cell killing. *Immunity.* November 2001;15(5):847-859.

8u. Rouvier E, Luciani M F, Golstein P. Fas involvement in Ca(2+)-independent T cell-mediated cytotoxicity. *The Journal of experimental medicine.* Jan. 1, 1993;177(1): 195-200.

9u. Tassi I, Presti R, Kim S, Yokoyama W M, Gilfillan S, Colonna M. Phospholipase C-gamma 2 is a critical signaling mediator for murine NK cell activating receptors. *Journal of immunology* (Baltimore, Md.: 1950). Jul. 15, 2005;175(2):749-754.

10u. Chuderland D, Seger R. Calcium regulates ERK signaling by modulating its protein-protein interactions. *Communicative & Integrative Biology.* 2008;1(1):4-5.

11u. Chen X, Trivedi P P, Ge B, Krzewski K, Strominger J L. Many NK cell receptors activate ERK2 and JNK1 to trigger microtubule organizing center and granule polarization and cytotoxicity. *Proceedings of the National Academy of Sciences of the United States of America.* Apr. 10, 2007;104(15):6329-6334.

12u. Li C, Ge B, Nicotra M, et al. JNK MAP kinase activation is required for MTOC and granule polarization in NKG2D-mediated NK cell cytotoxicity. *Proceedings of the National Academy of Sciences of the United States of America.* Feb. 26, 2008;105(8):3017-3022.

13u. Trotta R, Fettucciari K, Azzoni L, et al. Differential role of p38 and c-Jun N-terminal kinase 1 mitogen-activated protein kinases in NK cell cytotoxicity. *Journal of immunology* (Baltimore, Md.: 1950). Aug. 15, 2000:165(4): 1782-1789.

14u. Wei S, Gamero A M, Liu J H, et al. Control of Lytic Function by Mitogen-activated Protein Kinase/Extracellular Regulatory Kinase 2 (ERK2) in a Human Natural Killer Cell Line: Identification of Perforin and Granzyme B Mobilization by Functional ERK2. *The Journal of experimental medicine.* Jun. 1, 1998 1998; 187(11):1753-1765.

17u. Brenu E W, Hardcastle S L, Atkinson G M, et al. Natural killer cells in patients with severe chronic fatigue syndrome. *Autoimmunity Highlights.* 2013:4(3):69-80.

18u. Brenu E W, Huth T K, Hardcastle S L, et al. The Role of Adaptive and Innate Immune Cells in Chronic Fatigue Syndrome/Myalgic Encephalomyelitis. *International immunology.* Dec. 16, 2013.

19u. Brenu E W, Staines D R, Baskurt O K, et al. Immune and hemorheological changes in chronic fatigue syndrome. *Journal of translational medicine.* 2010;8:1.

20u. Brenu E W, van Driel M L, Staines D R, et al. Longitudinal investigation of natural killer cells and cytokines in chronic fatigue syndrome/myalgic encephalomyelitis. *Journal of translational medicine.* 2012;10:88.

21u. Brenu E W, van Driel M L, Staines D R, et al. Immunological abnormalities as potential biomarkers in Chronic Fatigue Syndrome/Myalgic Encephalomyelitis. *Journal of translational medicine.* 2011;9:81.

22u. Levine P H, Whiteside T L, Friberg D, Bryant J, Colclough G, Herberman R B. Dysfunction of natural killer activity in a family with chronic fatigue syndrome. *Clinical immunology and immunopathology.* July 1998; 88(1):96-104.

23u. Ojo-Amaize E A, Conley E J, Peter J B. Decreased natural killer cell activity is associated with severity of chronic fatigue immune dysfunction syndrome. *Clinical infectious diseases an official publication of the Infectious Diseases Society of America.* January 1994;18 Suppl 1:S157-159.

24u. Ornstein B W, Hill E B, Geurs T L, French A R. Natural Killer Cell Functional Defects in Pediatric Patients With Severe and Recurrent Herpesvirus Infections. *The Journal of Infectious Diseases.* 2013;207(3):458-468.

25u. Whiteside T L, Friberg D. Natural killer cells and natural killer cell activity in chronic fatigue syndrome. *The American journal of medicine.* Sep. 28, 1998;105(3a):27s-34s.

26u. Carruthers B M, van de Sande M I, De Meirleir K L, et al. Myalgic encephalomyelitis: International Consensus Criteria. *Journal of internal medicine.* October 2011;270(4):327-338.

27u. Bell D S. *The doctor's guide to chronic fatigue syndrome: understanding, treating, and living with CFIDS.* Da Capo Press; 1995.

28u. Üstün T. Measuring health and disability: Manual for WHO disability assessment schedule WHODAS 2.0. In: World Health Organization. 2010.

29u. Ware Jr J E, CD. S. The MOS 36-item short-form health survey (SF-36): I. Conceptual framework and item selection. In: Medical care. 1992. p. 473-83.

31u. Manning G, Whyte D B, Martinez R, Hunter T, Sudarsanam S. The protein kinase complement of the human genome. *Science* (New York, N.Y.). Dec. 6, 2002; 298(5600):1912-1934.

32u. Love M I, Huber W, Anders S. Moderated estimation of fold change and dispersion for RNA-seq data with DESeq2. *Genome Biology.* 2014;15(12):1-21.

33u. Sanchez-Mejorada G, Rosales C. Signal transduction by immunoglobulin Fc receptors. *Journal of leukocyte biology.* May 1998;63(5):521-533.

34u. Yu T K, Caudell E G, Smid C, Grimm E A. IL-2 activation of NK cells: involvement of MKK1/2/ERK but not p38 kinase pathway. *Journal of immunology* (Baltimore; Md.: 1950). Jun. 15, 2000;164(12):6244-6251.

35u. Zheng X, Wang Y, Wei H, Sun R, Tian Z. LFA-1 and CD2 synergize for the Erk1/2 activation in the Natural Killer (NK) cell immunological synapse. *J Biol Chem.* Aug. 7, 2009;284(32):21280-21287.

36u. Mocsai A, Abram C L, Jakus Z, Hu Y, Lanier L L, Lowell C A. Integrin signaling in neutrophils and macrophages uses adaptors containing immunoreceptor tyrosine-based activation motifs. *Nature immunology.* December 2006;7(12):1326-1333.

37u. March M E, Long E O. beta2 integrin induces TCRzeta-Syk-phospholipase C-gamma phosphorylation and paxillin-dependent granule polarization in human NK cells. *Journal of immunology* (Baltimore, Md.: 1950). Mar. 1, 2011;186(5):2998-3005.

38u. Barber D F, Faure M, Long E O. LFA-1 contributes an early signal for NK cell cytotoxicity. *Journal of immunology* (Baltimore, Md.: 1950). Sep. 15, 2004:173(6):3653-3659.

39u. Lanier L L. NK cell recognition. *Annual review of immunology.* 2005;23:225-274.

40u. Lanier L L. Up on the tightrope: natural killer cell activation and inhibition. *Nature immunology.* May 2008: 9(5):495-502.

41u. Hardcastle S L, Brenu E W, Johnston S, et al. Longitudinal analysis of immune abnormalities in varying severities of Chronic Fatigue Syndrome/Myalgic Encephalomyelitis patients. *Journal of translational medicine.* 2015;13:299.

42u. Hardcastle S L, Brenu E W, Johnston S. et al. Characterisation of cell functions and receptors in Chronic Fatigue Syndrome/Myalgic Encephalomyelitis (CFS/ME). *BMC Immunol.* 2015;16:35.

43u. Brenu E W, Hardcastle S L, Atkinson G M, et al. Natural killer cells in patients with severe chronic fatigue syndrome. *Auto-immunity highlights.* December 2013;4(3):69-80.

44u. Huth T, Brenu E W, Nguyen T, et al. Characterization of natural killer cell phenotypes in chronic fatigue syndrome/myalgic encephalomyelitis. *J Clin Cell Immunol.* 2014;5(3).

45u. Maher K J, Klimas N G, Fletcher M A. Chronic fatigue syndrome is associated with diminished intracellular perforin. *Clinical & Experimental Immunology.* 2005;142(3):505-511.

47u. Oakley B R, Paolillo V, Zheng Y. gamma-Tubulin complexes in microtubule nucleation and beyond. *Molecular biology of the cell.* Sep. 1, 2015;26(17):2957-2962.

48u. Shaul Y D, Seger R. The MEK/ERK cascade: from signaling specificity to diverse functions. *Biochimica et biophysica acta.* August 2007;1773(8):1213-1226.

49u. Zhang M, March M E, Lane W S, Long E O. A signaling network stimulated by beta2 integrin promotes the polarization of lytic granules in cytotoxic cells. *Science signaling.* Oct. 7, 2014;7(346):ra96.

50u. Wei S, Gamero A M, Liu J H, et al. Control of lytic function by mitogen-activated protein kinase/extracellular regulatory kinase 2 (ERK2) in a human natural killer cell line: identification of perforin and granzyme B mobilization by functional ERK2. *The Journal of experimental medicine.* Jun. 1, 1998;187(11):1753-1765.

51u. Rah S-Y, Kwak J-Y, Chung Y-J, Kim U-H. ADP-ribose/TRPM2-mediated Ca2+ signaling is essential for cytolytic degranulation and antitumor activity of natural killer cells. *Scientific Reports.* March 25/online 2015;5:9482.

52u. Dorn G W, 2nd, Force T. Protein kinase cascades in the regulation of cardiac hypertrophy. *The Journal of clinical investigation.* March 2005;115(3):527-537.

54u. Olson C M, Hedrick M N, Izadi H, Bates T C, Olivera E R, Anguita J. p38 mitogen-activated protein kinase controls NF-kappaB transcriptional activation and tumor necrosis factor alpha production through RelA phosphorylation mediated by mitogen- and stress-activated protein kinase 1 in response to Borrclia burgdorferi antigens. *Infection and immunity.* January 2007;75(l):270-277.

56u. Blundell S, Ray K K, Buckland M, White P D. Chronic fatigue syndrome and circulating cytokines: A systematic review. *Brain, behavior, and immunity.* November 2015; 50:186-195.

57u. Khaiboullina S F, DeMeirleir K L, Rawat S, et al. Cytokine expression provides clues to the pathophysiology of Gulf War illness and myalgic encephalomyelitis. *Cytokine.* March 2015;72(1):1-8.

58u. Neu D, Mairesse O, Montana X, et al. Dimensions of pure chronic fatigue: psychophysical, cognitive and biological correlates in the chronic fatigue syndrome. *European journal of applied physiology.* September 2014;114(9):1841-1851.

59u. Lattie E G, Antoni M H, Fletcher M A, et al. Stress management skills, neuroimmune processes and fatigue levels in persons with chronic fatigue syndrome. *Brain, behavior, and immunity.* August 2012;26(6):849-858.

60u. Maes M, Twisk F N, Ringel K. Inflammatory and cell-mediated immune biomarkers in myalgic encephalomyelitis/chronic fatigue syndrome and depression: inflammatory markers are higher in myalgic encephalomyelitis/chronic fatigue syndrome than in depression. *Psychotherapy and psychosomatics.* 2012;81(5):286-295.

61u. Maes M, Twisk F N, Kubera M, Ringel K. Evidence for inflammation and activation of cell-mediated immunity in Myalgic Encephalomyelitis/Chronic Fatigue Syndrome (ME/CFS): increased interleukin-1, tumor necrosis factor-alpha, PMN-elastase, lysozyme and neopterin. *Journal of affective disorders*. February 2012;136(3):933-939.

62u. Fletcher M A, Zeng X R, Barnes Z, Levis S, Klimas N G. Plasma cytokines in women with chronic fatigue syndrome. *Journal of translational medicine*. 2009;7:96.

63u. Commins S P, Borish L, Sleinke J W. Immunologic messenger molecules: cytokines, interferons, and chemokines. *The Journal of allergy and clinical immunology*. February 2010;125(2 Suppl 2):S53-72.

64u. Hornig M, Gottschalk G, Peterson D L, et al. Cytokine network analysis of cerebrospinal fluid in myalgic encephalomyelitis/chronic fatigue syndrome. *Molecular psychiatry*. February 2016;21(2):261-269.

65u. Peterson D, Brenu E W, Gottschalk G, et al. Cytokines in the cerebrospinal fluids of patients with chronic fatigue syndrome/myalgic encephalomyelitis. *Mediators of inflammation*. 2015;2015:929720.

66u. Lucas M, Schachterle W, Oberle K, Aichele P, Diefenbach A. Dendritic cells prime natural killer cells by trans-presenting interleukin 15. *Immunity*. April 2007;26(4):503-517.

67u. Ma A, Koka R, Burkett P. Diverse functions of IL-2, IL-15, and IL-7 in lymphoid homeostasis. *Annual review of immunology*. 2006;24:657-679.

68u. Kovanen P E, Leonard W J. Cytokines and immunodeficiency diseases: critical roles of the gamma(c)-dependent cytokines interleukins 2, 4, 7, 9, 15, and 21, and their signaling pathways. *Immunological reviews*. December 2004;202:67-83.

69u. Broderick G, Fuite J, Kreitz A, Vernon S D, Klimas N, Fletcher M A. A formal analysis of cytokine networks in chronic fatigue syndrome. *Brain, behavior, and immunity*. October 2010;24(7):1209-1217.

70u. Griendling K K, Sorescu D, Lassdgue B, Ushio-Fukai M. Modulation of protein kinase activity and gene expression by reactive oxygen species and their role in vascular physiology and pathophysiology. *Arteriosclerosis, thrombosis, and vascular biology*. 2000;20(10):2175-2183.

71u. Nedergaard M, Verkhratsky A. Calcium dyshomeostasis and pathological calcium signalling in neurological diseases. *Cell calcium*. 2010;47(2):101.

72u. Berridge M J. Elementary and global aspects of calcium signalling. *The Journal of physiology*. 1997;499(2): 291-306.

1p. Fukuda K, Straus S E, Hickie I, Sharpe M C, Dobbins J G, Komaroff A. The chronic fatigue syndrome: a comprehensive approach to its definition and study. International Chronic Fatigue Syndrome Study Group. Annals of internal medicine. 1994 Dec. 15;121(12):953-9. PubMed PMID: 7978722.

2p. Carruthers B M. Definitions and aetiology of myalgic encephalomyelitis: how the Canadian consensus clinical definition of myalgic encephalomyelitis works. Journal of clinical pathology. 2007 February;60(2):117-9. PubMed PMID: 16935963. Pubmed Central PMCID: 1860613.

3p. Carruthers B M, van de Sande M I, De Meirleir K L, Klimas N G, Broderick G, Mitchell T, et al. Myalgic encephalomyelitis: International Consensus Criteria. Journal of internal medicine. 2011 October;270(4):327-38. PubMed PMID: 21777306. Pubmed Central PMCID: 3427890.

4p. Johnston S, Staines D, Marshall-Gradisnik S. Epidemiological characteristics of Chronic Fatigue Syndrome/ Myalgic Encephalomyelitis in Australian patients Clinical epidemiology. 2016;( Accepted).

5p. Nilius B, Flockerzi V. Mammalian transient receptor potential (TRP) cation channels. Preface. Handbook of experimental pharmacology. 2014;223:v-vi. PubMed PMID: 25296415.

6p. Nilius B, Owsianik G. The transient receptor potential family of ion channels. Genome Biol. 2011;12(3):218. PubMed PMID: 21401968. Pubmed Central PMCID: 3129667.

7p. Nilius B, Owsianik G, Vocts T, Peters J A. Transient receptor potential cation channels in disease. Physiological reviews. 2007 January;87(1):165-217. PubMed PMID: 17237345.

8p. Nilius B, Appendino G, Owsianik G. The transient receptor potential channel TRPA1: from gene to pathophysiology. Pflugers Arch. 2012 November;464(5):425-58. PubMed PMID: 23001121.

9p. Li Q, Li L, Wang F, Chen J, Zhao Y, Wang P, et al. Dietary capsaicin prevents nonalcoholic fatty liver disease through transient receptor potential vanilloid 1-mediated peroxisome proliferator-activated receptor delta activation. Pflugers Arch. 2013 September;465(9):1303-16. PubMed PMID: 23605066.

10p. Colsoul B, Vennekens R, Nilius B. Transient receptor potential cation channels in pancreatic beta cells. Rev Physiol Biochem Pharmacol. 2011;161:87-110. PubMed PMID: 21744203.

11p. Colsoul B, Nilius B, Vennckens R. Transient receptor potential (TRP) cation channels in diabetes. Curr Top Med Chem. 2013;13(3):258-69. PubMed PMID: 23432059.

12p. Colsoul B, Nilius B, Vennekens R. On the putative role of transient receptor potential cation channels in asthma. Clinical and experimental allergy: journal of the British Society for Allergy and Clinical Immunology. 2009 October;39(10):1456-66. PubMed PMID: 19624522.

13p. Hasselmo M E. The role of acetylcholine in learning and memory. Current opinion in neurobiology. 2006;16(6):710-5.

14p. McGehee D S, Role L W. Physiological diversity of nicotinic acetylcholine receptors expressed by vertebrate neurons. Annual review of physiology. 1995;57(1):521-46.

15p. Lindstrom J M. Acetylcholine receptors and myasthenia. Muscle & nerve. 2000;23(4):453-77.

16p. Lukas R J, Changeux J-P, le Novére N, Albuquerque E X, Balfour D J, Berg D K, et al. International Union of Pharmacology. XX. Current status of the nomenclature for nicotinic acetylcholine receptors and their subunits. Pharmacol Rev. 1999;51(2):397-401.

17p. Ishii M, Kurachi Y. Muscarinic acetylcholine receptors. Current pharmaceutical design. 2006;12(28):3573-81.

18p. Furchgott R F. The classification of adrenoceptors (adrenergic receptors). An evaluation from the standpoint of receptor theory. Catecholamines: Springer; 1972. p. 283-335.

19p. Minneman K P. Alpha 1-adrenergic receptor subtypes, inositol phosphates, and sources of cell Ca2+. Pharmacol Rev. 1988;40(2):87-119.

20p. Berthelsen S, Pettinger W A. A functional basis for classification of α-adrenergic receptors. Life sciences. 1977;21(5):595-606.

21p. Chen-Izu Y, Xiao R-P, Izu L T, Cheng H, Kuschel M, Spurgeon H, et al. G i-dependent localization of β 2-adrenergic receptor signaling to L-type Ca 2+ channels. Biophysical journal. 2000;79(5):2547-56.

24p. Tanoue A, Koshimizu T-a, Shibata K, Nasa Y, Takeo S, Tsujimoto G. Insights into α 1 adrenoceptor function in health and disease from transgenic animal studies. Trends in Endocrinology & Metabolism. 2003;14(3):107-13.

25p. MINNEMAN K P. Recent progress in α1-adrenergic receptor research. Acta pharmacologica Sinica. 2005;26(11):1281-7.

26p. Price D T, Lefkowitz R J, Caron M G, Berkowitz D, Schwinn D A. Localization of mRNA for three distinct alpha 1-adrenergic receptor subtypes in human tissues: implications for human alpha-adrenergic physiology. Molecular pharmacology. 1994;45(2):171-5.

27p. Lomasney J W, Cotecchia S, Lorenz W, Leung W Y, Schwinn D A, Yang-Feng T L, et al. Molecular cloning and expression of the cDNA for the alpha 1A-adrenergic receptor. The gene for which is located on human chromosome 5. Journal of Biological Chemistry. 1991;266(10):6365-9.

28p. Berridge M J, Bootman M D, Roderick H L. Calcium signalling: dynamics, homeostasis and remodelling. Nature reviews Molecular cell biology. 2003;4(7):517-29.

29p. Knowlton K U, Michel M, Itani M, Shubeita H, Ishihara K, Brown J, et al. The alpha 1A-adrenergic receptor subtype mediates biochemical, molecular, and morphologic features of cultured myocardial cell hypertrophy. Journal of Biological Chemistry. 1993;268(21):15374-80.

30p. Smith R S, Weitz C J, Arancda R C. Excitatory actions of noradrenaline and mctabotropic glutamate receptor activation in granule cells of the accessory olfactory bulb. Journal of neurophysiology. 2009;102(2):1103-14.

31p. Brenu E W, Hardcastle S L, Atkinson G M, Driel M L, Kreijkamp-Kaspers S, Ashton K J, et al. Natural killer cells in patients with severe chronic fatigue syndrome. Autoimmunity Highlights. 2013;4(3):69-80.

32p. Brenu E W, Huth T K, Hardcastle S L, Fuller K, Kaur M. Johnston S, et al. The Role of Adaptive and Innate Immune Cells in Chronic Fatigue Syndrome/Myalgic Encephalomyelitis. International immunology. 2013 Dec. 16. PubMed PM ID: 24343819.

33p. Brenu E W, Staines D R, Baskurt O K, Ashton K J, Ramos S B, Christy R M, et al. Immune and hemorheological changes in chronic fatigue syndrome. Journal of translational medicine. 2010;8:1. PubMed PMID: 20064266. Pubmed Central PMCID: 2829521.

34p. Brenu E W, van Driel M L, Staines D R, Ashton K J, Hardcastle S L, Keane J, et al. Longitudinal investigation of natural killer cells and cytokines in chronic fatigue syndrome/myalgic encephalomyelitis. Journal of translational medicine. 2012;10:88. PubMed PMID: 22571715. Pubmed Central PMCID: 3464733.

35p. Brenu E W, van Driel M L, Staines D R, Ashton K J, Ramos S B, Keane J, et al. Immunological abnormalities as potential biomarkers in Chronic Fatigue Syndrome/Myalgic Encephalomyelitis. Journal of translational medicine. 2011;9:81. PubMed PMID: 21619669. Pubmed Central PMCID: 3120691.

36p. Levine P H, Whiteside T L, Friberg D, Bryant J, Colclough G, Hcrberman R B. Dysfunction of natural killer activity in a family with chronic fatigue syndrome. Clinical immunology and immunopathology. 1998 July; 88(1):96-104. PubMed PMID: 9683556. Epub 1998 Jul. 31. eng.

37p. Ojo-Amaize E A, Conley E J, Peter J B. Decreased natural killer cell activity is associated with severity of chronic fatigue immune dysfunction syndrome. Clinical infectious diseases: an official publication of the Infectious Diseases Society of America. 1994 January;18 Suppl 1:S157-9. PubMed PMID: 8148445. Epub 1994 Jan. 1. eng.

38p. Ornstein B W, Hill E B, Geurs T L, French A R. Natural Killer Cell Functional Defects in Pediatric Patients With Severe and Recurrent Herpesvirus Infections. The Journal of Infectious Diseases. 2013;207(3):458-68. PubMed PMID: PMC3693586.

39p. Whiteside T L, Friberg D. Natural killer cells and natural killer cell activity in chronic fatigue syndrome. The American journal of medicine. 1998 Sep. 28;105(3a):27s-34s. PubMed PMID: 9790479. Epub 1998 Oct. 28. eng.

40p. Dustin M L, Long E O. Cytotoxic immunological synapses. Immunological reviews. 2010 May;235(1):24-34. PubMed PMID: 20536553. Pubmed Central PMCID: Pmc2950621. Epub 2010 Jun. 12. eng.

41p. Maul-Pavicic A, Chiang S C, Rensing-Ehl A, Jessen B, Fauriat C, Wood S M, et al. ORAI1-mediated calcium influx is required for human cytotoxic lymphocyte degranulation and target cell lysis. Proceedings of the National Academy of Sciences of the United States of America. 2011 Feb. 22;108(8):3324-9. PubMed PMID: 21300876. Pubmed Central PMCID: Pmc3044412. Epub 2011 Feb. 9. eng.

42p. Pores-Fernando A T, Zweifach A. Calcium influx and signaling in cytotoxic T-lymphocytc lytic granule exocytosis. Immunological reviews. 2009 September;231(1):160-73. PubMed PMID: 19754896. Epub 2009 Sep. 17. eng.

47p. Visser M, Kayser M, Palstra R J. HERC2 rs12913832 modulates human pigmentation by attenuating chromatin-loop formation between a long-range enhancer and the OCA2 promoter. Genome research. 2012 March;22(3):446-55. PubMed PMID: 22234890. Pubmed Central PMCID: 3290780.

1m. Freud A G, Caligiuri M A. Human Natural Killer Cell Development. Immunological Reviews. 2006:214(1):56-72.

2m. Cooper M A, Fehniger T A, Turner S C, Chen K S, Ghaheri B A, Ghayur T et al. Human natural killer cells: a unique innate immunoregulatory role for the CD56 (bright) subsett. Blood. 2001;97(10):3146-51.

3m. Lieberman J. Anatomy of a Murder: How Cytotoxic T cells and NK Cells are Activated. Develop, and Eliminate their Targets. Immunol Rev. 2010;235(1):5-9. doi:10.1111/j.0105-2896.2010.00914.x.

4m. Vivier E, Tomasello E, Baratin M, Walzer T, Ugolini S. Functions of Natural Killer Cells. Nat Immunol. 2008;9(5):503-10. doi:10.1038/ni1582.

5m. Cooper M A, Fehniger T A, Caligiuri M A. The Biology of Human Natural Killer-Cell Subsets. Trends Immunol. 2001;22(11):633-40. doi:S1471-4906(01)02060-9 [pii].

6m. Poli A, Michel T, Thcresine M, Andres E, Hentges F, Zimmer J. CD56bright natural killer (NK) cells: an important NK cell subset. Immunology. 2009;126(4):458-65. doi:10.1111/j.1365-2567.2008.03027.x.

7m. Caligiuri M A. Human Natural Killer Cells. Blood. 2008;112(3):461-9.

8m. Trapani J A. Granzymes: A Family of Lymphocyte Granule Serine Protcases. Genome Biol. 2001;2(12):3014.1-7.

9m. Alter G, Malenfant J M, Altfeld M. CD107a as a functional marker for the identification of natural killer cell activity. Journal of Immunological Methods. 2004:294(1-2):15-22. doi:10.1016/j.jim.2004.08.008.

10m. Bryceson Y T, March M E, Barber D F, Ljunggren H G, Long E O. Cytolytic granule polarization and degranulation controlled by different receptors in resting NK cells. The Journal of Experimental Medicine. 2005;202(7): 1001-12. doi:10.1084/jem.20051143.

11m. Bryceson Y T, Chiang S C, Darmanin S, Fauriat C, Schlums H, Theorell J el al. Molecular mechanisms of natural killer cell activation. J Innate Immun. 2011;3(3): 216-26. doi:10.1159/000325265.

12m. Lanier L L. Up on the Tightrope: Natural Killer Cell Activation and Inhibition. Nat Immunol. 2008;9(5):495-502. doi:10.1038/ni1581.

13m. Moretta A, Bottino C, Vitale M, Pende D, Cantoni C, Mingari M C et al. Activating receptors and coreceptors involved in human natural killer cell-mediated cytolysis. Annu Rev Immunol. 2001;19:197-223. doi:10.1146/annurev.immunol.19.1.197.

14m. Chen X, Trivedi P P, Ge B, Krzewski K, Strominger J L. Many NK cell receptors activate ERK2 and JNK1 to trigger microtubule organizing center and granule polarization and cytotoxicity. Proc Natl Acad Sci USA. 2007; 104(15):6329-34. doi:10.1073/pnas.0611655104.

15m. Li C, Ge B, Nicotra M, Stem J N, Kopcow H D, Chen X et al. JNK MAP kinase activation is required for MTOC and granule polarization in NKG2D-mcdiated NK cell cytotoxicity. Proc Natl Acad Sci USA. 2008;105(8):3017-22. doi:10.1073/pnas.0712310105.

16m. Trotta R, Fettucciari K, Azzoni L, Abebe B, Puorro K A, Eisenlohr L C et al. Differential role of p38 and c-Jun N-terminal kinase 1 mitogen-activated protein kinases in NK cell cytotoxicity. Journal of Immunology. 2000;165 (4):1782-9.

17m. Roux P P, Blenis J. ERK and p38 MAPK-activated protein kinases: a family of protein kinases with diverse biological functions. Microbiol Mol Biol Rev. 2004;68 (2):320-44. doi:10.1128/MMBR.68.2.320-344.2004.

18m. Wei S, Gamero A M, Liu J H, Daulton A A, Valkov N I, Trapani J A et al. Control of lytic function by mitogen-activated protein kinase/extracellular regulatory kinase 2 (ERK2) in a human natural killer cell line: identification of perforin and granzyme B mobilization by functional ERK2. The Journal of Experimental Medicine. 1998;187 (11):1753-65.

19m. Jha S K, Jha N K, Kar R, Ambasta R K, Kumar P. p38 MAPK and PI3K/AKT Signalling Cascades in Parkinson's Disease. International journal of molecular and cellular medicine. 2015;4(2):67-86.

20m. Correa S A, Eales K L. The Role of p38 MAPK and Its Substrates in Neuronal Plasticity and Neurodegencrative Disease. Journal of signal transduction. 2012,2012: 649079. doi:10.1155/2012/649079.

21m. Jones C L, Gearheart C M, Fosmire S, Delgado-Martin C, Evensen N A, Bride K et al. MAPK signaling cascades mediate distinct glucocorticoid resistance mechanisms in pediatric leukemia. Blood. 2015. doi:10.1182/blood-2015-04-639138.

22m. Hirosumi J, Tuncman G, Chang L, Gorgun C Z, Uysal K T, Maeda K et al. A central role for JNK in obesity and insulin resistance. Nature. 2002;420(6913):333-6. doi: 10.1038/nature01137.

23m. Ricci R, Sumara G, Sumara I, Rozenberg I, Kurrer M, Akhrbeov A et al. Requirement of JNK2 for scavenger receptor A-mediated foam cell formation in atherogenesis. Science. 2004;306(5701):1558-61. doi:10.1126/science.1101909.

24m. Han Z, Boyle D L, Chang L. Bennett B, Karin M, Yang L et al. c-Jun N-terminal kinase is required for metalloproteinase expression and joint destruction in inflammatory arthritis. The Journal of clinical investigation. 2001: 108(1):73-81. doi:10.1172/JCI12466.

25m. Gu W, Song L, Li X M, Wang D, Guo X J, Xu W G. Mesenchymal stem cells alleviate airway inflammation and emphysema in COPD through down-regulation of cyclooxygenase-2 via p38 and ERK MAPK pathways. Scientific reports. 2015:5:8733. doi:10.1038/srep08733.

26m. Brenu E W, Hardcastle S L, Atkinson G M, Driel M L, Kreijkamp-Kaspers S, Ashton K J et al. Natural killer cells in patients with severe chronic fatigue syndrome. Autoimmun Highlights. 2013:1-12. doi 10.1007/s13317-013-0051-x.

27m. Brenu E W, Huth T K, Hardcastle S L, Fuller K, Kaur M, Johnston S et al. Role of adaptive and innate immune cells in chronic fatigue syndrome/myalgic encephalomyelitis. International immunology. 2014. doi:10.1093/intimm/dxt068.

28m. Brenu F W, Staines D R, Baskurt O K, Ashton K J, Ramos S B, Christy R M et al. Immune and hemorheological changes in chronic fatigue syndrome. Journal of translational medicine. 2010;8(1):1-10. doi:10.1186/1479-5876-8-1.

29m. Brenu E W, van Driel M L, Staines D R, Ashton K J, Hardcastle S L, Keane J et al. Longitudinal investigation of natural killer cells and cytokines in chronic fatigue syndrome/myalgic encephalomyelitis. Journal of translational medicine. 2012;10:88. doi:10.1186/1479-5876-10-88.

30m. Brenu E W, van Driel M L, Staines D R, Ashton KJ, Ramos S B, Keane J et al. Immunological abnormalities as potential biomarkers in Chronic Fatigue Syndromc/Myalgic Encephalomyelitis. Journal of translational medicine. 2011;9:81. doi:10.1186/1479-5876-9-81.

31m. Levine P H, Whiteside T L, Friberg D, Bryant J, Colclough G, Herberman R B. Dysfunction of natural killer activity in a family with chronic fatigue syndrome. Clinical immunology and immunopathology. 1998;88(1): 96-104.

32m. Ojo-Amaize E A, Conley E J, Peter J B. Decreased natural killer cell activity is associated with severity of chronic fatigue immune dysfunction syndrome. Clinical infectious diseases: an official publication of the Infectious Diseases Society of America. 1994:18 Suppl 1:S157-9.

33m. Omstein B W, Hill E B, Geurs T L, French A R. Natural killer cell functional defects in pediatric patients with severe and recurrent herpesvirus infections. The Journal of infectious diseases. 2013;207(3):458-68. doi:10.1093/infdis/jis701.

34m. Whiteside T L, Friberg D. Natural killer cells and natural killer cell activity in chronic fatigue syndrome. The American journal of medicine. 1998;105(3A):27S-34S.

35m. Curriu M, Carrillo J, Massanella M, Rigau J, Alegre J, Puig J et al. Screening NK-, B- and T-cell phenotype and function in patients suffering from Chronic Fatigue Syndrome. Journal of translational medicine. 2013;11:68. doi:10.1186/1479-5876-11-68.

36m. Maher K J, Klimas N G, Fletcher M A. Chronic fatigue syndrome is associated with diminished intracellular perforin. Clinical and experimental immunology. 2005;142 (3):505-11. doi:10.1111/j.1365-2249.2005.02935.x.

37m. Fukuda ,. Straus S E, Hickie I, Sharpe M C, Dobbins J G, Komaroff A. The chronic fatigue syndrome: a comprehensive approach to its definition and study International Chronic Fatigue Syndrome Study Group. Annals of internal medicine. 1994;121(12):953-9.

38m. Krulzik P O, Irish J M, Nolan G P, Perez O D. Analysis of protein phosphorylation and cellular signaling events by flow cytometry: techniques and clinical applications. Clin Immunol. 2004;110(3):206-21. doi:10.1016/j.dim.2003.11.009.

39m. Montag D T, Lotze M T. Successful simultaneous measurement of cell membrane and cytokine induced phosphorylation pathways [CIPP] in human peripheral blood mononuclear cells. J Immunol Methods. 2006;313(1-2):48-60. doi:10.1016/j.jim.2006.03.014.

40m. Wu S, Jin L, Vence L, Radvanyi L G. Development and application of 'phosphoflow' as a tool for immunomonitoring. Expert Rev Vaccines. 2010;9(6):631-43. doi: 10.1586/erv.10.59.

41m. Aubry J P, Blaecke A, Lecoanet-Henchoz S, Jeannin P, Herbault N, Caron G et al. Annexin V used for measuring apoptosis in the early events of cellular cytotoxicity. Cytometry. 1999:37(3):197-204.

42m. Grossman W J, Verbsky J W, Tollefsen B L, Kemper C, Atkinson J P, Ley T J. Differential expression of granzymes A and B in human cytotoxic lymphocyte subsets and T regulatory cells. Blood. 2004;104(9):2840-8. doi:10.1182/blood-2004-03-0859.

43m. Chattopadhyay P K, Betts M R, Price D A, Gostick E, Horton H, Roederer M et al. The cytolytic enzymes granzyme A, granzyme B, and perforin: expression patterns, cell distribution, and their relationship to cell maturity and bright CD57 expression. Journal of leukocyte biology. 2009;85(1):88-97. doi:10.1189/jlb.0208107.

44m. Reefman E, Kay J G, Wood S M, Offenhauser C, Brown D L, Roy S et al. Cytokine secretion is distinct from secretion of cytotoxic granules in NK cells. J Immunol. 2010;184(9):4852-62. doi: 10.4049/jimmunol.0803954.

45m. Kotecha N, Krulzik P O, Irish J M. Web-based analysis and publication of flow cytometry experiments. Current protocols in cytometry/editorial board. J Paul Robinson, managing editor [et al]. 2010;Chapter 10:Unit10 7. doi:10.1002/0471142956.cy1017s53.

46m. Shaul Y D, Seger R. The MEK/ERK cascade: from signaling specificity to diverse functions. Biochimica et biophysica acta. 2007;1773(8):1213-26. doi:10.1016/j.bbamer.2006.10.005.

47m. Zhang M, March M E, Lane W S, Long E O. A signaling network stimulated by beta2 integrin promotes the polarization of lytic granules in cytotoxic cells. Sci Signal. 2014;7(346):ra96. doi:10.1126/scisignal.2005629.

48m. Manna P R, Stocco D M. The role of specific mitogen-activated protein kinase signaling cascades in the regulation of steroidogenesis. Journal of signal transduction. 2011;2011:821615. doi:10.1155/2011/821615.

49m. Sacks D B. The role of scaffold proteins in MEK/ERK signalling. Biochemical Society transactions. 2006;34(Pt 5):833-6. doi:10.1042/BST0340833.

50m. Herreros L, Rodriguez-Fernandez J L, Brown M C, Alonso-Lebrero J L, Cabanas C, Sanchez-Madrid F et al. Paxillin localizes to the lymphocyte microtubule organizing center and associates with the microtubule cytoskeleton. The Journal of biological chemistry. 2000;275(34):26436-40. doi:10.1074/jbc.M003970200.

51m. Robertson L K, Ostergaard H L. Paxillin associates with the microtubule cytoskeleton and the immunological synapse of CTL through its leucine-aspartic acid domains and contributes to microtubule organizing center reorientation. J Immunol. 2011;187(1):5824-33. doi:10.4049/jimmunol.1003690.

52m. Mace E M, Dongre P, Hsu H T, Sinha P, James A M, Mann S S et al. Cell biological steps and checkpoints in accessing NK cell cytotoxicity. Immunol Cell Biol. 2014; 92(3):245-55. doi:10.1038/icb.2013.96.

53m. Liu Y, Shepherd E G, Nelin L D. MAPK phosphatases-regulating the immune response. Nature reviews Immunology. 2007;7(3):202-12. doi 10.1038/nri2035.

54m. Mentlik A N, Sanborn K B, Holzbaur E L, Orange J S. Rapid lytic granule convergence to the MTOC in natural killer cells is dependent on dynein but not cytolytic commitment. Molecular biology of the cell. 2010;21(13): 2241-56. doi:10.1091/mbc.E09-11-0930.

55m. Liu D, Xu L, Yang F, Li D, Gong F, Xu T. Rapid biogenesis and sensitization of secretory lysosomes in NK cells mediated by target-cell recognition. Proc Natl Acad Sci USA. 2005;102(1) 123-7. doi:10.1073/pnas.0405737102.

56m. Liu D, Martina J A, Wu X S, Hammer J A. 3rd, Long E O. Two modes of lytic granule fusion during degranulation by natural killer cells. Immunol Cell Biol. 2011;89 (6):728-38. doi:10.1038/icb.2010.167.

57m. Hardcastle S L, Brenu E, Wong N, Johnston S, Nguyen T, Huth T et al. Serum cytokines in patients with moderate and severe Chronic Fatigue Syndrome/Myalgic Encephalomyelitis (CFS/ME). Cytokine. 2014;70(1):45. doi: 10.1016/j.cyto.2014.07081.

58m. Chan A, Hong D L, Atzberger A, Kollnberger S, Filer A D, Buckley C D et al. CD56bright human NK cells differentiate into CD56dim cells: role of contact with peripheral fibroblasts. J Immunol. 2007;179(1):89-94.

59m. Domaica C I, Fuertes M B, Uriarte I, Girart M V, Sardanons J, Comas D I et al. Human natural killer cell maturation defect supports in vivo CD56(bright) to CD56 (dim) lineage development. PLoS one. 2012;7(12): e51677. doi:10.1371/journal.pone.0051677.

60m. Wang R, Jaw J J, Stutzman N C, Zou Z, Sun P D. Natural killer cell-produced IFN-gamma and TNF-alpha induce target cell cytolysis through up-regulation of ICAM-1. Journal of leukocyte biology. 2012;91(2):299-309. doi:10.1189/jlb.0611308.

61m. Gronberg A, Ferm M T, Ng J, Reynolds C W, Ortaldo J R. IFN-gamma treatment of K562 cells inhibits natural killer cell triggering and decreases the susceptibility to lysis by cytoplasmic granules from large granular lymphocytes. J Immunol. 1988;140(12):4397-402.

62m. Reiter Z. Interferon—a major regulator of natural killer cell-mediated cytotoxicity. Journal of interferon research. 1993:13(4):247-57.

63m. Cuenda A, Rousseau S. p38 MAP-kinases pathway regulation, function and role in human diseases. Biochimica et biophysica acta. 2007;1773(8):1358-75. doi:10.1016/j.bbamer.2007.03.010.

64m. Frevel M A, Bakhect T, Silva A M, Hissong J G, Khabar K S, Williams B R. p38 Mitogen-activated protein kinase-dependent and -independent signaling of mRNA stability of AU-rich element-containing transcripts. Mol Cell Biol. 2003;23(2):425-36.

65m. Mavropoulos A, Sully G, Cope A P, Clark A R. Stabilization of IFN-gamma mRNA by MAPK p38 in IL-12- and IL-18-stimulated human NK cells. Blood. 2005;105(1):282-8. doi:10.1182/blood-2004-07-2782.

66m. Kalina U, Kauschat D, Koyama N, Nuemberger H, Balias K, Koschmieder S et al. IL-18 activates STAT3 in the natural killer cell line 92, augments cytotoxic activity, and mediates IFN-gamma production by the stress kinase p38 and by the extracellular regulated kinases p44erk-1 and p42erk-21. J Immunol. 2000;165(3):1307-13.

67m. Mainiero F, Gismondi A, Soriani A, Cippitelli M, Palmieri G, Jacabelli J et al. Integrin-mediated ras-extracellular regulated kinase (ERK) signaling regulates interferon gamma production in human natural killer cells. The Journal of Experimental Medicine. 1998;188(7):1267-75.

The invention claimed is:

1. A method of treating a subject having or at risk of developing chronic fatigue syndrome (CFS) or myalgic encephalomyelitis (ME) comprising the steps of:
   (a) obtaining a biological sample from the subject;
   (b) carrying out an assay on the biological sample to detect the allele of one or more single nucleotide polymorphisms (SNPs) in at least one transient receptor potential (TRP) ion channel gene, wherein the allele of the one more SNPs is selected from the group consisting of an A allele in rs12682832, a C allele in rs11142508, an A allele in rs1160742, a C allele in rs4454352, a C allele in rs1328153, an A allele in rs3763619, an A allele in rs7865858, a T allele in rs1504401, an A allele in rs10115622, a G allele in rs2383844, an A allele in rs4738202, a T allele in rs6650469, a G allele in rs655207, and combinations thereof;
   (c) identifying the subject as having or at risk of developing CFS or ME when the allele of the one or more SNPs is detected using the assay; and
   (d) administering an effective amount of a therapeutic compound to the identified subject so as to alleviate symptoms of CFS or ME.

* * * * *

SEQUENCE LISTING

```
<160> NUMBER OF SEQ ID NOS: 64

<210> SEQ ID NO 1
<211> LENGTH: 30
<212> TYPE: DNA
<213> ORGANISM: Artificial Sequence
<220> FEATURE:
<223> OTHER INFORMATION: Single stranded oligonucleotide

<400> SEQUENCE: 1
acgttggatg agcctccttc tgacttgaac                                30

<210> SEQ ID NO 2
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 2
acgttggatg catttcacct acaagtgatg                                30

<210> SEQ ID NO 3
<211> LENGTH: 19
<212> TYPE: DNA
<213> ORGANISM: Artificial Sequence
<220> FEATURE:
<223> OTHER INFORMATION: Oligonucleotide for detecting SNP

<400> SEQUENCE: 3
cgatggaatt tgacccaac                                            19

<210> SEQ ID NO 4
<211> LENGTH: 29
<212> TYPE: DNA
<213> ORGANISM: Artificial Sequence
<220> FEATURE:
<223> OTHER INFORMATION: Oligonucleotide for detecting SNP

<400> SEQUENCE: 4
acgttggatg gctccgtatg tgctgagag                                 29

<210> SEQ ID NO 5
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 5
acgttggatg agaaatacag cgctggcttc                                30

<210> SEQ ID NO 6
<211> LENGTH: 16
<212> TYPE: DNA
<213> ORGANISM: Artificial Sequence
<220> FEATURE:
<223> OTHER INFORMATION: Oligonucleotide for detecting SNP

<400> SEQUENCE: 6
```
aggggcttgt gtgtaa                                                    16

<210> SEQ ID NO 7
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 7
acgttggatg ttctcacagt taaggccttg                                     30

<210> SEQ ID NO 8
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 8
acgttggatg gctgctaatg atagaggctg                                     30

<210> SEQ ID NO 9
<211> LENGTH: 23
<212> TYPE: DNA
<213> ORGANISM: Artificial Sequence
<220> FEATURE:
<223> OTHER INFORMATION: Oligonucleotide for detecting SNP

<400> SEQUENCE: 9
tacatgggga tttacataga cta                                            23

<210> SEQ ID NO 10
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 10
acgttggatg ttctcacagt taaggccttg                                     30

<210> SEQ ID NO 11
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 11
acgttggatg gctgctaatg atagaggctg                                     30

<210> SEQ ID NO 12
<211> LENGTH: 23
<212> TYPE: DNA
<213> ORGANISM: Artificial Sequence
<220> FEATURE:
<223> OTHER INFORMATION: Oligonucleotide for detecting SNP

<400> SEQUENCE: 12
tacatgggga tttacataga cta                                            23

<210> SEQ ID NO 13
<211> LENGTH: 30
<212> TYPE: DNA

```
<213> ORGANISM: Artificial Sequence
<220> FEATURE:
<223> OTHER INFORMATION: Oligonucleotide for detecting SNP

<400> SEQUENCE: 13
acgttggatg ttctcacagt taaggccttg                                    30

<210> SEQ ID NO 14
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 14
acgttggatg gctgctaatg atagaggctg                                    30

<210> SEQ ID NO 15
<211> LENGTH: 23
<212> TYPE: DNA
<213> ORGANISM: Artificial Sequence
<220> FEATURE:
<223> OTHER INFORMATION: Oligonucleotide for detecting SNP

<400> SEQUENCE: 15
tacatgggga tttacataga cta                                           23

<210> SEQ ID NO 16
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 16
acgttggatg ctcaggcaaa gggtattcac                                    30

<210> SEQ ID NO 17
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 17
acgttggatg agaacctaag aacccaaggc                                    30

<210> SEQ ID NO 18
<211> LENGTH: 24
<212> TYPE: DNA
<213> ORGANISM: Artificial Sequence
<220> FEATURE:
<223> OTHER INFORMATION: Oligonucleotide for detecting SNP

<400> SEQUENCE: 18
gggaagagat ttagaggttg tacc                                          24

<210> SEQ ID NO 19
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 19
acgttggatg ttgctggtgg tggcttaaac                                    30
```

```
<210> SEQ ID NO 20
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 20
acgttggatg ctagggtgaa caacttgaac                                    30

<210> SEQ ID NO 21
<211> LENGTH: 24
<212> TYPE: DNA
<213> ORGANISM: Artificial Sequence
<220> FEATURE:
<223> OTHER INFORMATION: Oligonucleotide for detecting SNP

<400> SEQUENCE: 21
ggggaccttt caaagagtg atac                                           24

<210> SEQ ID NO 22
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 22
acgttggatg aaggttcaag ttgttcaccc                                    30

<210> SEQ ID NO 23
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 23
acgttggatg ttacctgcct tttaccacac                                    30

<210> SEQ ID NO 24
<211> LENGTH: 20
<212> TYPE: DNA
<213> ORGANISM: Artificial Sequence
<220> FEATURE:
<223> OTHER INFORMATION: Oligonucleotide for detecting SNP

<400> SEQUENCE: 24
ccctccttcc aggaacttac                                               20

<210> SEQ ID NO 25
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 25
acgttggatg agtgttccaa tcgctctgtg                                    30

<210> SEQ ID NO 26
<211> LENGTH: 29
<212> TYPE: DNA
<213> ORGANISM: Artificial Sequence
<220> FEATURE:
```

```
<223> OTHER INFORMATION: Oligonucleotide for detecting SNP

<400> SEQUENCE: 26
acgttggatg aatcaactga gaaccattc                                        29

<210> SEQ ID NO 27
<211> LENGTH: 26
<212> TYPE: DNA
<213> ORGANISM: Artificial Sequence
<220> FEATURE:
<223> OTHER INFORMATION: Oligonucleotide for detecting SNP

<400> SEQUENCE: 27
cttctaatat acagccatgt cataga                                           26

<210> SEQ ID NO 28
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 28
acgttggatg ggaaaaacaa tttcttgggg                                       30

<210> SEQ ID NO 29
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 29
acgttggatg cccacctatg accattttcc                                       30

<210> SEQ ID NO 30
<211> LENGTH: 18
<212> TYPE: DNA
<213> ORGANISM: Artificial Sequence
<220> FEATURE:
<223> OTHER INFORMATION: Oligonucleotide for detecting SNP

<400> SEQUENCE: 30
gaccattttc ctcagaga                                                    18

<210> SEQ ID NO 31
<211> LENGTH: 29
<212> TYPE: DNA
<213> ORGANISM: Artificial Sequence
<220> FEATURE:
<223> OTHER INFORMATION: Oligonucleotide for detecting SNP

<400> SEQUENCE: 31
acgttggatg catcaagaca gatttcaac                                        29

<210> SEQ ID NO 32
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 32
acgttggatg cctacatctc atcaaaggac                                       30
```

```
<210> SEQ ID NO 33
<211> LENGTH: 27
<212> TYPE: DNA
<213> ORGANISM: Artificial Sequence
<220> FEATURE:
<223> OTHER INFORMATION: Oligonucleotide for detecting SNP

<400> SEQUENCE: 33
ggtacagaat aagaaagttt gagatta                                            27

<210> SEQ ID NO 34
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 34
acgttggatg cgtttgtgtt tatgcccctc                                         30

<210> SEQ ID NO 35
<211> LENGTH: 31
<212> TYPE: DNA
<213> ORGANISM: Artificial Sequence
<220> FEATURE:
<223> OTHER INFORMATION: Oligonucleotide for detecting SNP

<400> SEQUENCE: 35
acgttggatg ggagtttgct atattattcc c                                       31

<210> SEQ ID NO 36
<211> LENGTH: 25
<212> TYPE: DNA
<213> ORGANISM: Artificial Sequence
<220> FEATURE:
<223> OTHER INFORMATION: Oligonucleotide for detecting SNP

<400> SEQUENCE: 36
ggggcaccat tacaggtaat ttcca                                              25

<210> SEQ ID NO 37
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 37
acgttggatg ttttccctta ttcctcccac                                         30

<210> SEQ ID NO 38
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 38
acgttggatg acctctagcc tctgaattgc                                         30

<210> SEQ ID NO 39
<211> LENGTH: 20
<212> TYPE: DNA
<213> ORGANISM: Artificial Sequence
<220> FEATURE:
<223> OTHER INFORMATION: Oligonucleotide for detecting SNP
```

<400> SEQUENCE: 39
ggaggagaaa caaactccag                                              20

<210> SEQ ID NO 40
<211> LENGTH: 29
<212> TYPE: DNA
<213> ORGANISM: Artificial Sequence
<220> FEATURE:
<223> OTHER INFORMATION: Oligonucleotide for detecting SNP

<400> SEQUENCE: 40
acgttggatg aaagtgggcg gggacatag                                    29

<210> SEQ ID NO 41
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 41
acgttggatg aaaacacgc cccattgctc                                    30

<210> SEQ ID NO 42
<211> LENGTH: 15
<212> TYPE: DNA
<213> ORGANISM: Artificial Sequence
<220> FEATURE:
<223> OTHER INFORMATION: Oligonucleotide for detecting SNP

<400> SEQUENCE: 42
aagtcacgcc ccttc                                                   15

<210> SEQ ID NO 43
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 43
acgttggatg gaaatgatgc tttccacggg                                   30

<210> SEQ ID NO 44
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 44
acgttggatg aactgcctga gcctacagac                                   30

<210> SEQ ID NO 45
<211> LENGTH: 26
<212> TYPE: DNA
<213> ORGANISM: Artificial Sequence
<220> FEATURE:
<223> OTHER INFORMATION: Oligonucleotide for detecting SNP

<400> SEQUENCE: 45
ctgcatgagc ctacagacca ccttct                                       26

<210> SEQ ID NO 46
<211> LENGTH: 30

<212> TYPE: DNA
<213> ORGANISM: Artificial Sequence
<220> FEATURE:
<223> OTHER INFORMATION: Oligonucleotide for detecting SNP

<400> SEQUENCE: 46
acgttggatg gaggctttta atcaactccc      30

<210> SEQ ID NO 47
<211> LENGTH: 31
<212> TYPE: DNA
<213> ORGANISM: Artificial Sequence
<220> FEATURE:
<223> OTHER INFORMATION: Oligonucleotide for detecting SNP

<400> SEQUENCE: 47
acgttggatg gataattttt ctgtgacaga c      31

<210> SEQ ID NO 48
<211> LENGTH: 24
<212> TYPE: DNA
<213> ORGANISM: Artificial Sequence
<220> FEATURE:
<223> OTHER INFORMATION: Oligonucleotide for detecting SNP

<400> SEQUENCE: 48
gacactgtct ttcatttgac ttgt      24

<210> SEQ ID NO 49
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 49
acgttggatg ctggtgggag aatgcaagtc      30

<210> SEQ ID NO 50
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 50
acgttggatg ggctaatagt cccttttacc      30

<210> SEQ ID NO 51
<211> LENGTH: 23
<212> TYPE: DNA
<213> ORGANISM: Artificial Sequence
<220> FEATURE:
<223> OTHER INFORMATION: Oligonucleotide for detecting SNP

<400> SEQUENCE: 51
ggggtcatgt ttttccattg tca      23

<210> SEQ ID NO 52
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 52
acgttggatg tgtcaaccta gtagacgagc                                    30

<210> SEQ ID NO 53
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 53
acgttggatg tggagatgca tcctctaggc                                    30

<210> SEQ ID NO 54
<211> LENGTH: 17
<212> TYPE: DNA
<213> ORGANISM: Artificial Sequence
<220> FEATURE:
<223> OTHER INFORMATION: Oligonucleotide for detecting SNP

<400> SEQUENCE: 54
aggcgaaagc tctaatt                                                  17

<210> SEQ ID NO 55
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 55
acgttggatg accatctgca ggactttagg                                    30

<210> SEQ ID NO 56
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 56
acgttggatg cttttggggc tgagtttaag                                    30

<210> SEQ ID NO 57
<211> LENGTH: 27
<212> TYPE: DNA
<213> ORGANISM: Artificial Sequence
<220> FEATURE:
<223> OTHER INFORMATION: Oligonucleotide for detecting SNP

<400> SEQUENCE: 57
ccccgctctt ccttcaaaac tatcttg                                       27

<210> SEQ ID NO 58
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 58
acgttggatg gggtaaaaga attacacaag                                    30

<210> SEQ ID NO 59
<211> LENGTH: 29
<212> TYPE: DNA
<213> ORGANISM: Artificial Sequence

```
<220> FEATURE:
<223> OTHER INFORMATION: Oligonucleotide for detecting SNP

<400> SEQUENCE: 59
acgttggatg tgcctgaatt atgcaatag                                29

<210> SEQ ID NO 60
<211> LENGTH: 21
<212> TYPE: DNA
<213> ORGANISM: Artificial Sequence
<220> FEATURE:
<223> OTHER INFORMATION: Oligonucleotide for detecting SNP

<400> SEQUENCE: 60
tatgcaatag aatcacttgg t                                        21

<210> SEQ ID NO 61
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 61
acgttggatg tcttctccag tgtctaaggg                               30

<210> SEQ ID NO 62
<211> LENGTH: 30
<212> TYPE: DNA
<213> ORGANISM: Artificial Sequence
<220> FEATURE:
<223> OTHER INFORMATION: Oligonucleotide for detecting SNP

<400> SEQUENCE: 62
acgttggatg cccaatgtta catggcttcc                               30

<210> SEQ ID NO 63
<211> LENGTH: 15
<212> TYPE: DNA
<213> ORGANISM: Artificial Sequence
<220> FEATURE:
<223> OTHER INFORMATION: Oligonucleotide for detecting SNP

<400> SEQUENCE: 63
aggctacaga gctga                                               15

<210> SEQ ID NO 64
<211> LENGTH: 50
<212> TYPE: DNA
<213> ORGANISM: Artificial Sequence
<220> FEATURE:
<223> OTHER INFORMATION: Single standed polynucleotide

<400> SEQUENCE: 64
ctcatcctgt ctttgcagga gattctgggt atatagttcc tccagagaca          50
```